United States Patent
Nicolaou et al.

(10) Patent No.: US 6,441,186 B1
(45) Date of Patent: Aug. 27, 2002

(54) EPOTHILONE ANALOGS

(75) Inventors: Kyriacos C. Nicolaou, La Jolla; Yun He, San Diego; Sacha Ninkovic, San Diego; Joaquin Pastor, San Diego; Frank Roschangar, San Diego, all of CA (US); Francisco Sarabia, Torre de Benagalbón (ES); Hans Vallberg, Huddinge (SE); Dionisios Vourloumis, San Diego, CA (US); Nicolas Winssinger, La Jolla, CA (US); Zhen Yang, San Diego, CA (US); N. Paul King, San Diego, CA (US); M. Ray Finlay, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/923,869

(22) Filed: Sep. 4, 1997

Related U.S. Application Data

(63) Continuation-in-part of application No. 08/856,533, filed on May 14, 1997, now abandoned.
(60) Provisional application No. 60/032,864, filed on Dec. 13, 1996.

(51) Int. Cl.$^7$ .............................................. C07D 417/14
(52) U.S. Cl. ....................................... 548/204; 548/204
(58) Field of Search .......................... 549/562; 548/204, 548/236

(56) References Cited

FOREIGN PATENT DOCUMENTS

| DE | 4138042 | * | 5/1993 |
|---|---|---|---|
| WO | WO93/10121 | | 5/1993 |
| WO | 9719086 | | 5/1997 |
| WO | 9808849 | | 3/1998 |
| WO | 9822461 | | 5/1998 |
| WO | 9825929 | | 6/1998 |
| WO | 9838192 | | 9/1998 |
| WO | 9901124 | | 1/1999 |
| WO | 9902514 | | 1/1999 |
| WO | 9907692 | | 2/1999 |

OTHER PUBLICATIONS

Winkler et al., Bioorg. Med. Chem. Lett., 6(24), 2963–2966, 1996.*
Schinzer, et al., "Total Synthesis of (–) Epothilone A", Angew. Chem. Int. Ed. Engl., 36:523–524 (1997).
Yang, et al., "Total Synthesis of Epothilone A: The Olefin Metathesis Approach", Angew, Chem. Int. Ed. Engl., 36:166–168 (1997).
Bollag, et al., "Epothilones, a New Class of Microtubule–stabilizing Agents with a Taxol–like Mechanism of Action", Cancer Research, 55:2325–2333 (1995).
Meng, et al., "Remote Effects in Macrolide Formation through Ring–Forming Olefin Metathesis: . . . ", J. Am. Chem. Soc., 119:2733–2734 (1997).

Grever, et al., "The National Cancer Institute: Cancer Drug Discovery and Development Program", Seminars in Oncology, 19:622–638 (1992).
Mulzer, et al., "Synthesis of the C(1)–C(9) Segment of the Cytotoxic Macrolides Epothilon A and B", Tetrahedron Letters, 37:9179–9182 (1996).
Claus, et al, "Synthesis of the C1–C9 Segment of Epothilons", Tetrahedron Letters, 38:1359–1362 (1997).
Gabriel, et al, "The Chromium–Reformatsky Reaction: Asymmetric Synthesis . . . " Tetrahedron Letters, 38:1363–1366 (1997).
Meng, et al., "Studies toward a Synthesis of Epothilone A: Use of Hydropyran Templates . . . ", J. Org. Chem., 61:7998–7999 (1996).
Bertinato, et al, "Studies toward a Synthesis of Epothilone A: Stereo–controlled Assembly . . . ", J. Org. Chem., 61:8000–8001 (1996).
Kowalski, et al., "Activities of theMicrotubule–stabilizing Agents Epothilones A and B . . . ", Journ. Biol. Chem., 272:2534–2541 (1997).
Schiff, et al., "Promotion of Microtubule Assembly in vitro by Taxol", Nature, 277:665–667 (1979).
Balog, et al., "Total Synthesis of (–)–Epothilone A", Angew. Chem. Int. Ed. Eng., 35:2801–2803 (1996).
Hofle, et al., "Epothilone A and B–Novel 16–Membered Macrolides with Cytotoxid Activity: . . . ", Angew. Chem. Int. Ed. Engl., 35:1567–1569 (1996).
Nicolaou et al., "An Approach to Epothilones Based on Olefin Metathesis", Angew. Chem. Int. Ed. Engl., 35:2399–2401 (1996).
Nicolaou, et al., "Total Synthesis of Epothilone A: The Macrolactonization Approach", Angew. Chem. Int. Ed. Engl., 36:525–527 (1997).
Nicolaou, et al., "Chemistry and Biology Taxol", Angew. Chem. Int. Ed. Engl., 33:15–44 (1994).
Winkler, et al., "A Model for the Taxol (Paclitaxel)/Epothilone Pharmacophore", Bioorg. Med. Chem. Int. Ed. Engl. 33: 2963–2966 (1996).
Nicolaou, et al., "Designed Epothilones: Combinatorial Synthesis, Tubulin Assembly Properties, and Cytotoxic Action against Taxol–Resistant Tumor Cells", Ang. Chem. Int. Ed. Engl. 36 (19): 2097–2103 (1997).
Nicolaou, et al., "The Olefin Metathesis Approach to Epothilone A and its Analogues", J. Amer. Chem. Soc. 119 : 7960–7973 (1997).

* cited by examiner

Primary Examiner—Laura L. Stockton
(74) Attorney, Agent, or Firm—Donald G. Lewis

(57) ABSTRACT

Epothilone A, epothilone B, analogs of epothilone and libraries of epothilone analogs are synthesized. Epothilone A and B are known anticancer agents that derive their anticancer activity by the prevention of mitosis through the induction and stabilization of microtubulin assembly. The analogs of epothilone are novel. Several of the anlogs are demonstrated to have a superior cytotoxic activities as compared to epothilone A or epothilone B as demonstrated by their enhanced ability to induce the polymerization and stabilization of microtubules.

1 Claim, 74 Drawing Sheets

1: R = H, epothilone A

2: R = Me, epothilone B

A)
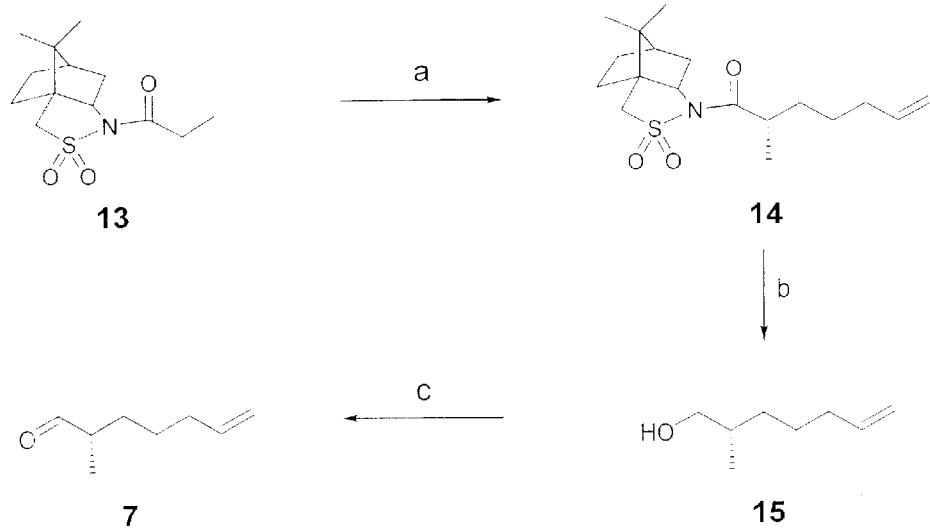
B)
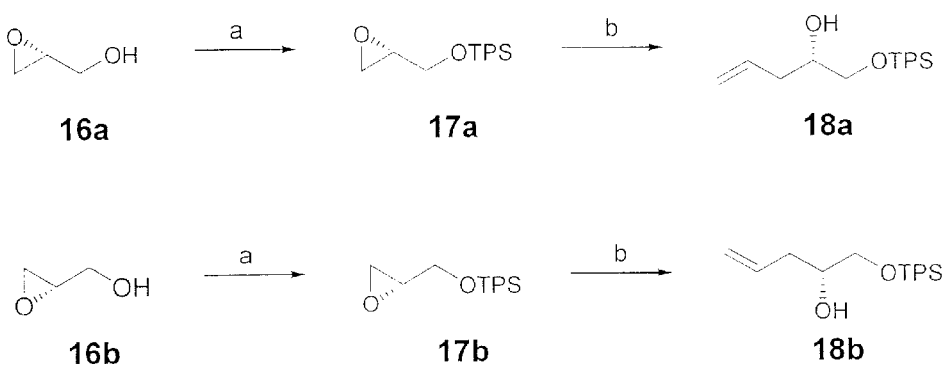
C)
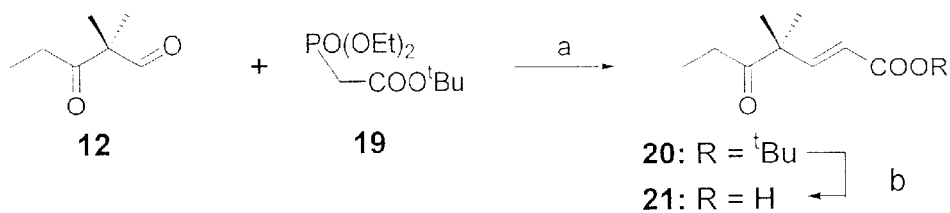
FIGURE 3

A)
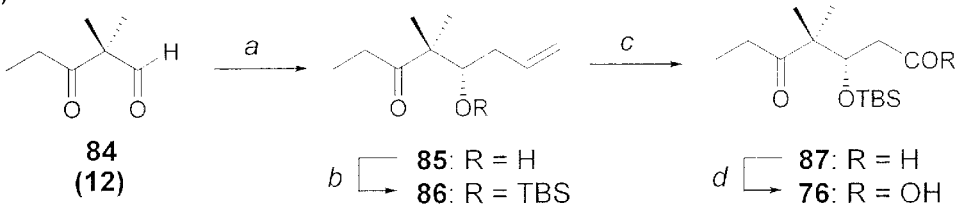
B)
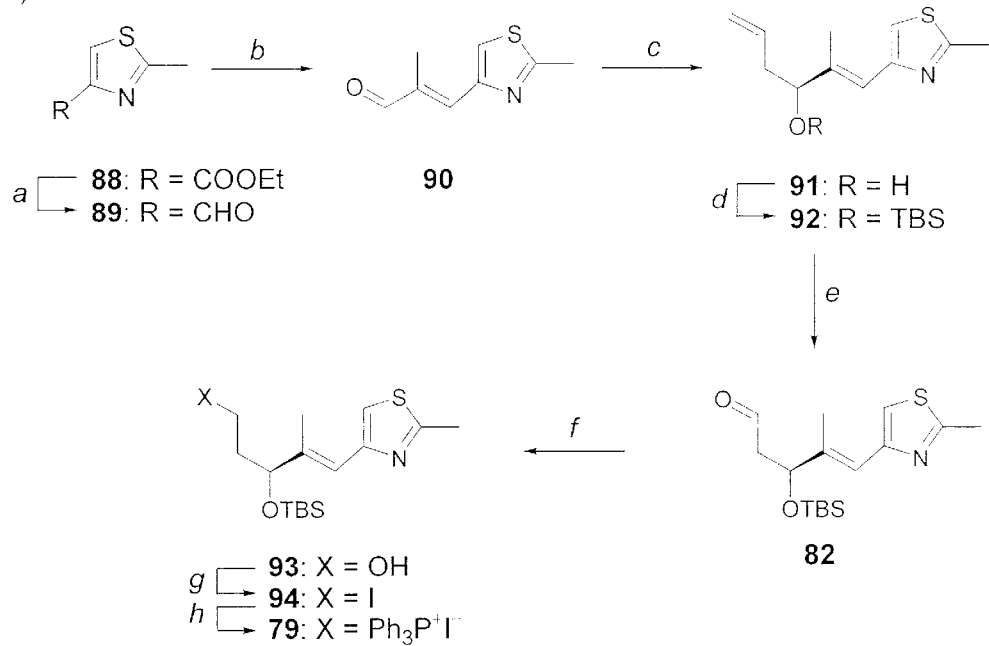
Figure 12

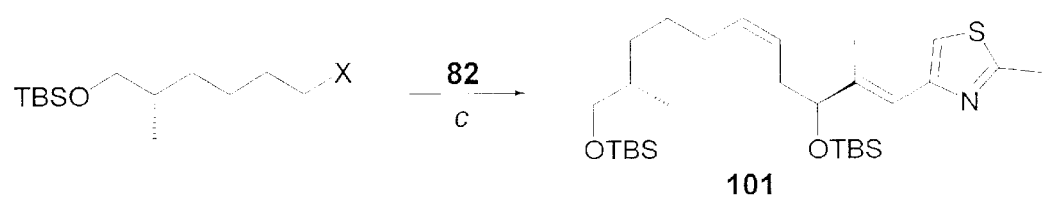
a ⎡— 99: X = OH
b ⎣— 113: X = I
  ⎣— 114: X = Ph₃P⁺I⁻
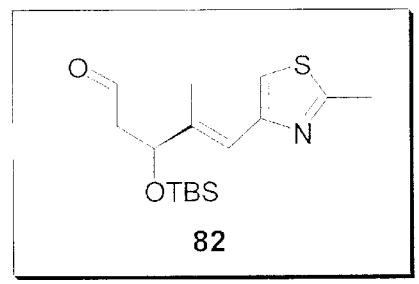
Figure 15

| Compound | Induction of tubulin assembly[a] EC$_{50}$ (mM) ± s.d. | Inhibition of human ovarian carcinoma cell growth[b] | | | |
|---|---|---|---|---|---|
| | | Parental | Taxol-resistant β-tubulin mutants | | MDR-line |
| | | 1A9 | 1A9PTX10 | 1A9PTX22 | A2780AD |
| | | IC$_{50}$ nM (relative resistance) | | | |
| 1 | 14 ±0.4 | 2.0 | 19 (9.5) | 4.2 (2.1) | 2.4 (1.2) |
| 2 | 4.0 ±0.1 | 0.040 | 0.035 (0.88) | 0.045 (1.1) | 0.040 (1.0) |
| 71 | 3.3 ±0.2 | 2.0 | 33 (17) | 3.5 (1.8) | 1.5 (0.80) |
| 158 | 25 ±1 | 25 | >100 (>4) | 75 (3.8) | 22 (0.88) |
| 123 | 39 ±2 | 48 | >100 (>2) | 75 (1.6) | 24 (0.50) |
| 125 | 22 ±0.9 | 3.5 | 30 (8.6) | 5.5 (1.6) | 3.0 (0.86) |
| Taxol | 15 ±2 | 2.0 | 50 (25) | 43 (22) | >100 (>50) |

Figure 23

1: X = S, epothilone A

161: X = O, epoxalone A

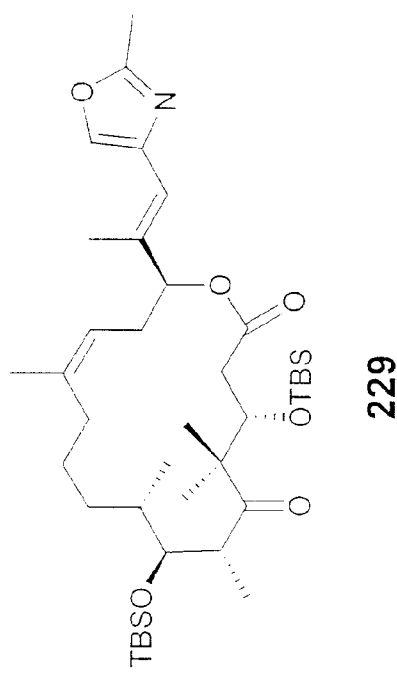
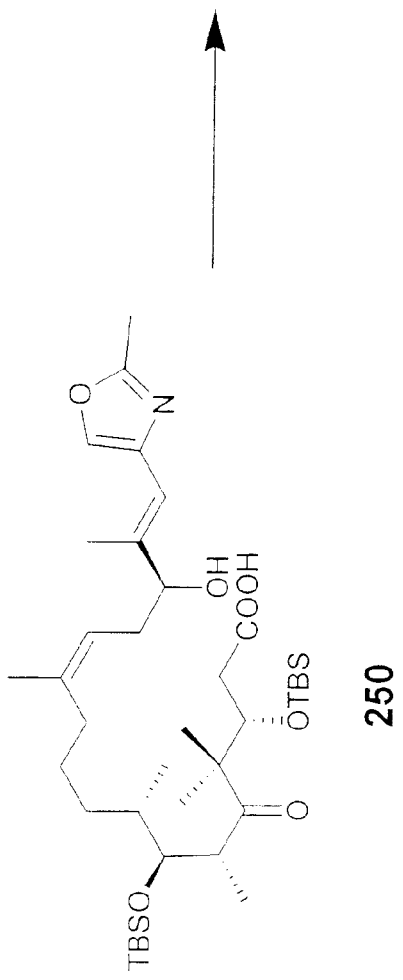
Figure 36

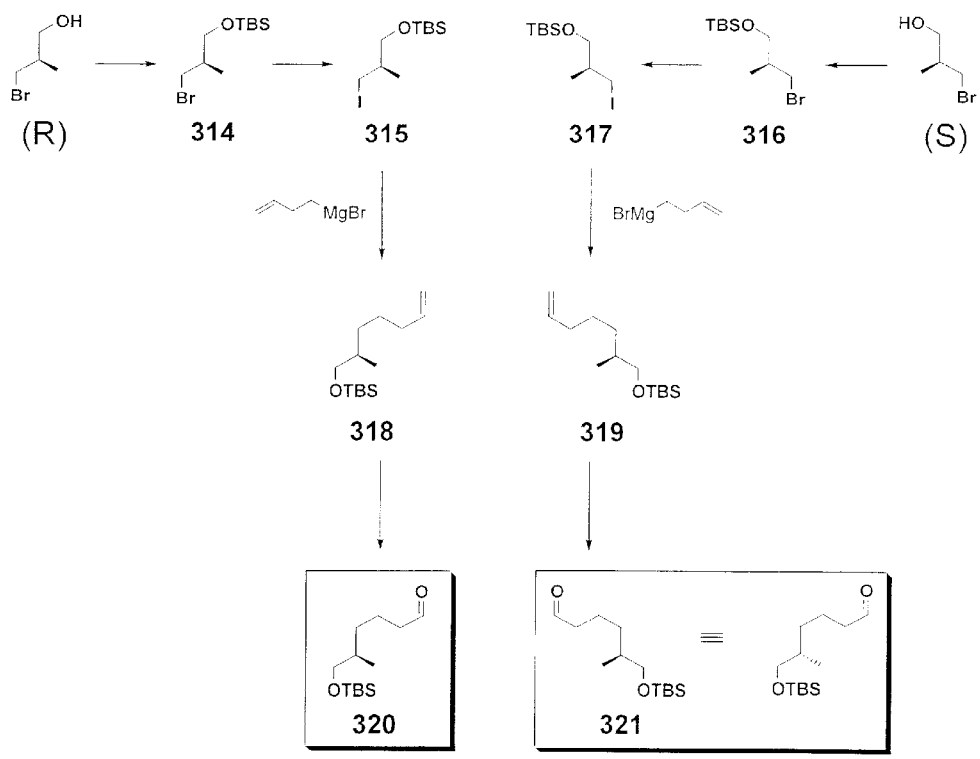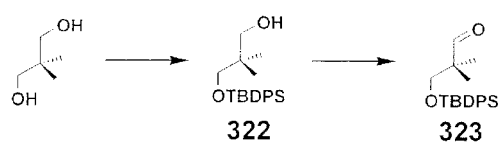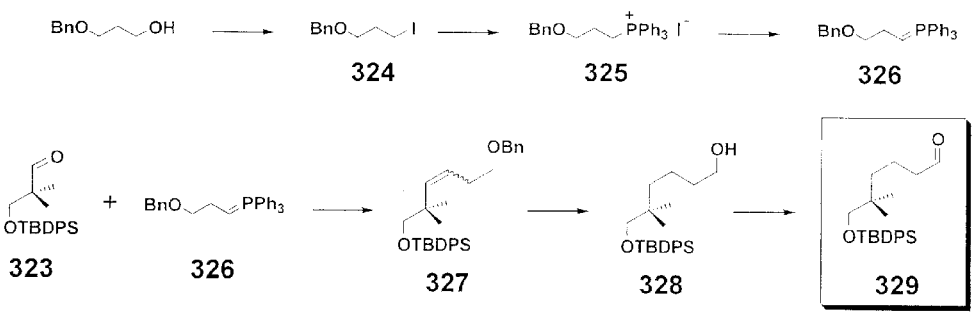
Figure 49

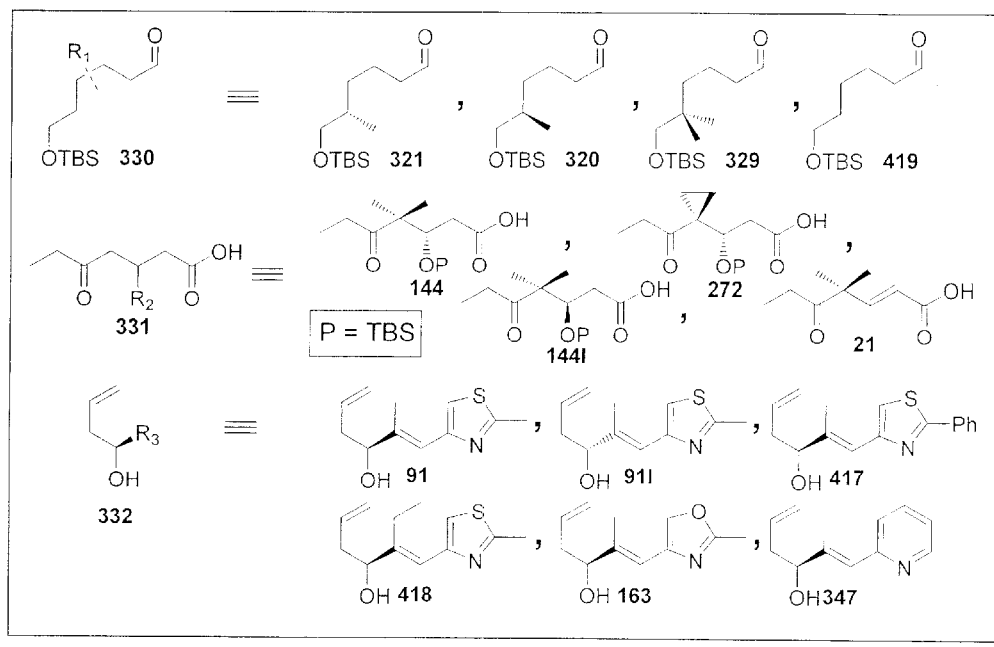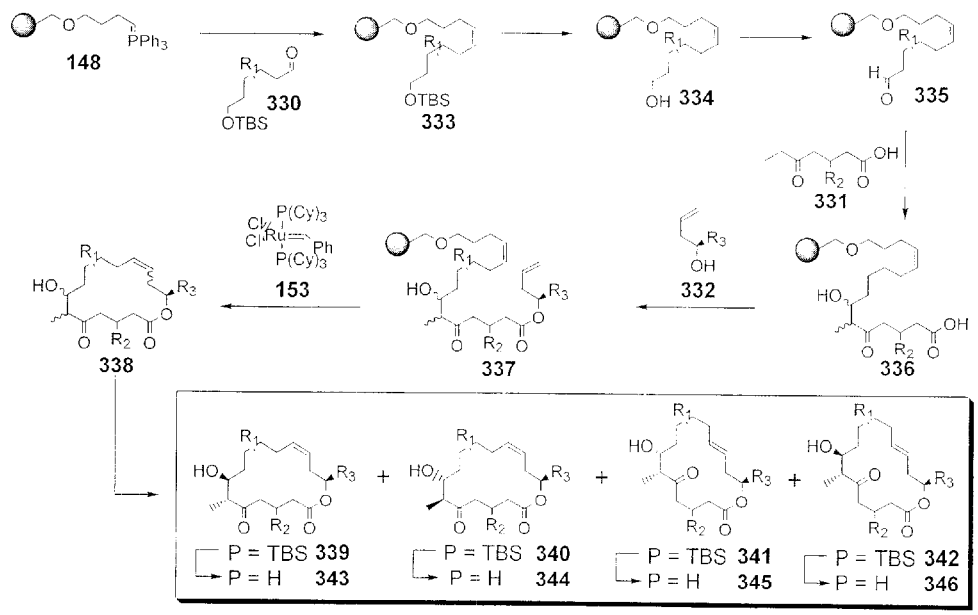
Figure 50

| Entry | Procedure[a] | 356 | Yield(%) | 357 | Yield(%) |
|---|---|---|---|---|---|
| 6 | 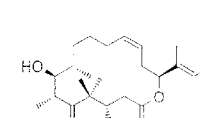 373 | A | 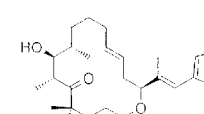 f | 55 | 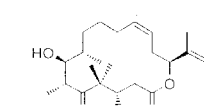 f | 75 |
| 7 | 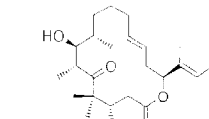 375 | A | 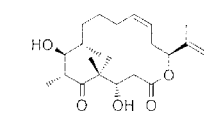 g | 45 | 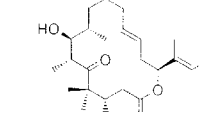 g | 72 |
| 8 | 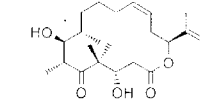 376 | B | 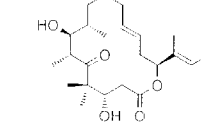 h | 87 | 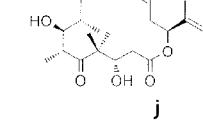 h | 92 |
| 9 | 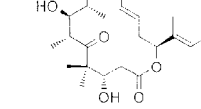 377 | B | i | 88 | i | 94 |
| 10 | 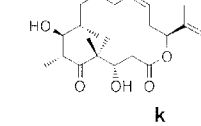 378 | B | j | 86 | j | 89 |
| 11 | 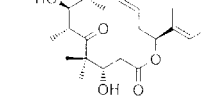 379 | A | k | 42 | k | 46 |
Figure 54b

| Entry | Procedure[a] | 356 | Yield(%) | 357 | Yield(%) |
|---|---|---|---|---|---|
| 12 | 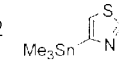 A <br> 381 | 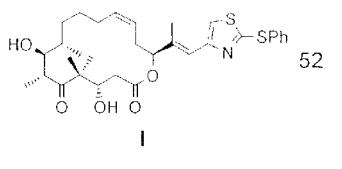 <br> l | 52 | 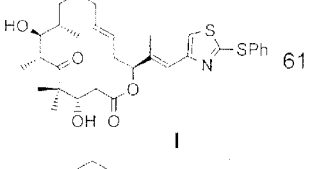 <br> l | 61 |
| 13 |  A <br> 384 | 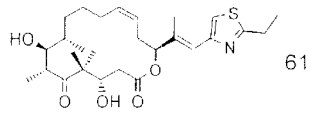 <br> m | 61 | 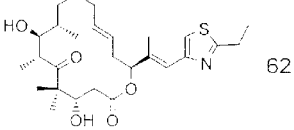 <br> m | 62 |
| 14 | 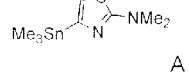 A <br> 386 | 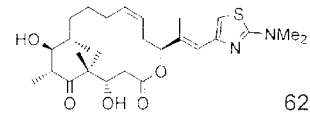 <br> n | 62 | 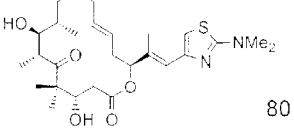 <br> n | 80 |
| 15 | 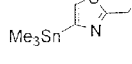 A <br> 388 | 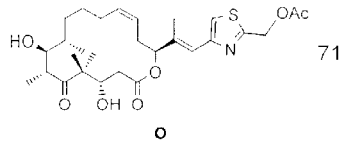 <br> o | 71 | 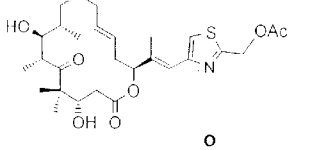 <br> o | 87 |
| 16 | 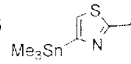 A <br> 390 | 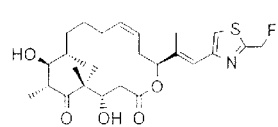 <br> p | 58 | 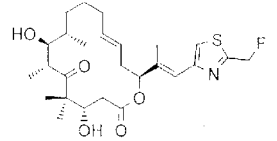 <br> p | 64 |
| 17 |  A <br> 391 | 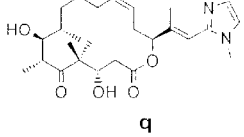 <br> q | 49 | 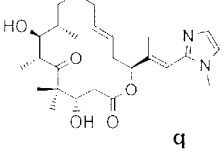 <br> q | 66 |
Figure 55

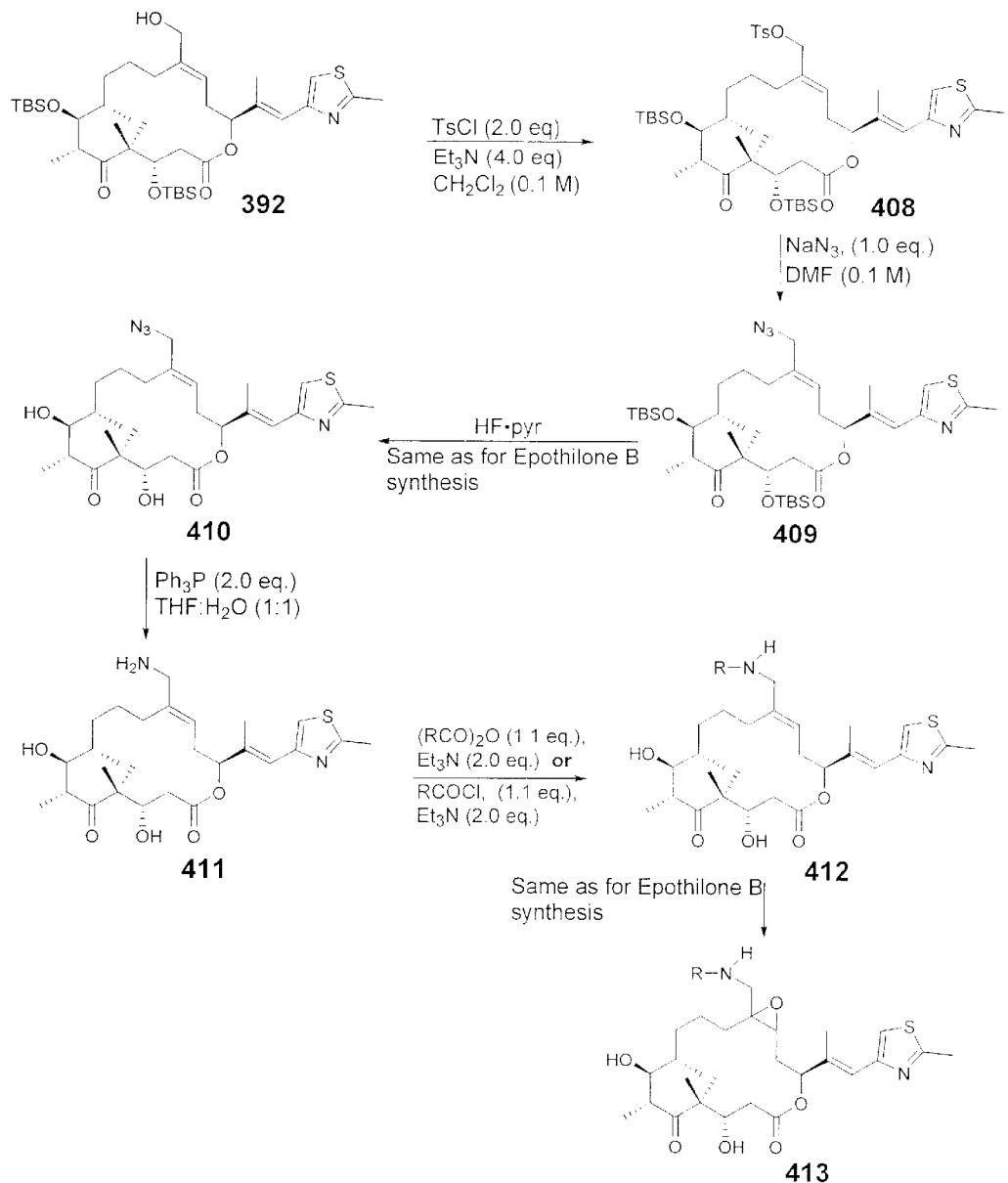

(RCO)₂O = acetic anhydride, chloroacetic anhydride, propionic anhydride, trifluoroacetic anhydride, isobutyric anhydride,
RCOCl = pivaloyl chloride, cyclopropanecarbonyl chloride, cyclohexanecarbonyl chloride, acryloyl chloride, benzoyl chloride, 2-furoyl chloride, N-benzoyl-(2R,3S)-3-phenylisoserine, cinnamoyl chloride, phenylacetyl chloride, 2-thiophenesulfonyl chloride.

FIGURE 61

XH = methanol, t-butanol, i-propanol, phenol, benzyl alcohol, furfurylamine N-benzoyl-(2R,3S)-3-phenylisoserine, dimethyl amine, diethyl amine, benzyl amine

| | Induction of tubulin polymerization | | Inhibition of carcinoma cell growth[c] | | | |
| --- | --- | --- | --- | --- | --- | --- |
| | | | Ovarian[d] | | | Breast[e] |
| | Screening assay[a] | Quantitative glutamate assay[b] | Parental IA9 | β-tubulin mutations | | MCF7 |
| Cmpd | % polymer formed with compound relative to that formed with GTP | EC$_{50}$ (μM) | IC$_{50}$(nM) | 1A9PTX10 | 1A9PTX22 | |
| | | | | [RELATIVE RESISTANCE][F] | | |
| Taxol™ | 50 | 4.7 | 1.4 | 32 [23] | 38 [27] | 4.2 |
| 1 | 76 | 4.6 | 2.2 | 20 [9.1] | 5.9 [2.7] | 5.1 |
| 2 | 98 | 3.4 | 0.13 | 1.0 [7.7] | 0.31 [2.4] | 1.0 |
| 161 | 58 | 5.3 | 3.0 | 25 [8.3] | 8.0 [2.7] | 6.1 |
| 233 | 93 | – | – | 1.1 | 0.9 | – |
| 234 | 71 | 6.1 | 1.5 | 11 [7.3] | 3.0 [2.0] | 6.2 |
| 58 | 92 | 6.2 | 2.0 | 18 [9.0] | 3.0 [1.5] | 5.4 |
| 125 | 84 | 5.6 | 1.0 | 8.5 [8.5] | 1.0 [1.0] | 1.8 |
| 171 | 64 | 7.8 | 3.5 | 32 [9.1] | 9.5 [2.7] | >100 |
| 126 | 63 | 13 | 6.0 | 30 [5.0] | 6.5 [1.1] | 14 |
| 172 | 46 | 8.1 | 4.8 | 34 [7.1] | 9.0 [1.9] | 5.7 |
| 49 | 72 | 8.3 | 32 | >100 | 100 | 38 |
| 71 | 94 | 3.9 | 6.5 | 23 [3.5] | 9.0 [1.4] | 9.3 |
| 168 | 75 | 6.1 | 68 | >100 | 90 | 74 |
| 231 | 93 | 3.3 | 8.0 | 30 [3.8] | 12 [1.5] | >100 |
| 50 | 76 | 9.8 | 60 | >100 | 100 | >100 |
| 123 | 84 | 7.5 | 61 | >100 | 85 | 75 |
| 169 | 43 | 13 | >100 | – | – | >100 |
| 232 | 54 | 6.0 | 32 | >100 | >100 | 68 |
| 461 | 34 | 17 | >100 | – | – | >100 |
| 465 | 51 | 7.6 | 32 | >100 | 70 | 57 |
| 466 | 61 | 11 | 82 | >100 | >100 | 78 |

FIGURE 66

EPOTHILONE ANALOGS

This application is a CIP of Ser. No. 08/856,533 filed May 14, 1997, now abandoned which is a CIP of U.S. Provisional No. 60/032,864 filed Dec. 13, 1996.

This invention was made with government support under Grants No. CA 46446 awarded and CA 58336 awarded by the National Institutes of Health. The U.S. government has certain rights in the invention.

TECHNICAL FIELD OF THE INVENTION

The present invention relates to epothilone A, epothilone B, epothilone analogs, libraries of epothilone analogs, and methods for producing such compounds using solid phase and solution phase chemistries.

BACKGROUND OF THE INVENTION

Epothilone A (1, FIG. 1) and epothilone B (2, FIG. 1) are natural substances isolated from myxobacteria Sorangium cellulosum strain 90. These natural substances exhibit cytotoxicity against taxol-resistant tumor cells and may prove to have a clinical utility comparable or superior to Taxol. (For Taxol references see: Horwitz et al. Nature 277, 665–667 (1979); Nicolaou et al. Angew. Chem. Int. Ed. Engl. 33, 15–44 (1994).) Like taxol, the epothilones are thought to exert their cytotoxicity by induction of microtubule assembly and stabilization. (Bollag et al. Cancer Res. 55, :2325–2333 (1995); Kowalski et al. J. Biol. Chem. 272, 2534–2541 (1997).) Epothilones are reported to be about 2000–5000 times more potent than Taxol with respect to the stabilization of microtubules. Despite the marked structural differences between the epothilones and Taxol™, the epothilones were found to bind to the same region on microtubules and to displace Taxol™ from its binding site. (Grever et al. Seminars in Oncology 1992, 19, 622–638; Bollag et al. Cancer Res. 1995, 55, 2325–2333; Kowalski et al. J. Biol. Chem. 1997, 272, 2534–2541; Horwitz et al. Nature 1979, 277, 665–667; Nicolaou et al. Angew. Chem. Int. Ed. Engl. 1994, 33, 15–44.) Epothilones A and B have generated intense interest amongst chemists, biologists and clinicians due to their novel molecular architecture, important biological action and intriguing mechanism of action. (Höfle et al. Angew. Chem. Int. Ed. Engl. 35, 1567–1569 (1996); Grever et al. Semin. Oncol. 19, 622–638 (1992); Bollag et al. Cancer Res. 55, 2325–2333 (1995); Kowalski et al. J. Biol. Chem. 272, 2534–2541 (1997); Nicolaou et al. Angew. Chem. Int. Ed. Engl. 35, 2399–2401 (1996); Meng et al. J. Org. Chem. 61, 7998–7999 (1996); Bertinato et al. J. Org. Chem. 61, 8000–8001 (1996); Schinzer et al. Chem. Eur. J. 2, 1477–1482 (1996); Mulzer et al. Tetrahedron Lett. 37, 9179–9182 (1996); Claus et al. Tetrahedron Lett. 38, 1359–1362 (1997); Gabriel et al. Tetrahedron Lett. 38, 1363–1366 (1997); Balog et al. Angew. Chem. Int. Ed. Engl. 35, 2801–2803 (1996); Yang et al. Angew. Chem. Int. Ed. Engl. 36, 166–168 (1997); Nicolaou et al. Angew. Chem. Int. Ed. Engl. 36, 525–527 (1997); Schinzer et al. Angew. Chem. Int. Ed. Engl. 36, 523–524 (1997); Meng et al. J. Am. Chem. Soc. 119, 2733–2734 (1997).)

What is needed are analogs of epothilone A and B and libraries of analogs of epothilone A and B that exhibit superior pharmacological properties in the area of microtubule stabilizing agents.

What is needed are methods for producing synthetic epothilone A, epothilone B, analogs of epothilone A and B, and libraries of epothilone analogs, including epothilone analogs possessing both optimum levels of microtubule stabilizing effects and cytotoxicity.

BRIEF SUMMARY OF THE INVENTION

The invention is directed to epothilone analogs and processes and intermediates for making same.

One aspect of the invention is directed to an epothilone analog represented by the following structure:

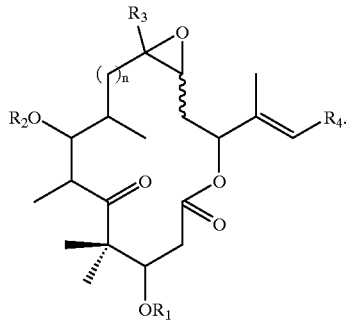

In a preferred embodiment, n is one. However, in alternative embodiments n may be as large as five. $R_1$ is a radical selected from the group consisting of hydrogen, tert-butyldimethylsilyl, trimethylsilyl, methyl, acetyl, benzoyl, and tert-butoxycarbonyl. $R_2$ is a radical selected from the group consisting of hydrogen, tert-butyldimethylsilyl, trimethylsilyl, methyl, acetyl, benzoyl, and tert-butoxycarbonyl. $R_3$ is a radical selected from the group consisting of hydrogen, methyl, —CHO, —COOH, —$CO_2$Me, —$CO_2$ (tert-butyl), —$CO_2$ (iso-propyl), —$CO_2$ (phenyl), —$CO_2$ (benzyl), —CONH(furfuryl), —$CO_2$ (N-benzo-(2R, 3S)-3-phenylisoserine), —CONH(methyl)$_2$, —CONH(ethyl)$_2$, —CONH(benzyl), and —$CH_2R_5$. $R_5$ is a radical selected from the group consisting of —OH, —O-Trityl, —O—($C_1$-$C_6$ alkyl), —O-benzyl, —O-allyl, —O—COCH$_3$, —O—COCH$_2$Cl, —O— COCH$_2$CH$_3$, —O—COCF$_3$, —O—COCH (CH$_3$)$_2$, —O—COC(CH$_3$)$_3$, —O—CO(cyclopropane), —OCO(cyclohexane), —O—COCH=CH$_2$, —O—CO-Phenyl, —O-(2-furoyl), —O-(N-benzo-(2R,3S)-3-phenylisoserine), —O-cinnamoyl, —O-(acetyl-phenyl), —O-(2-thiophenesulfonyl), —S—($C_1$-$C_6$ alkyl), —SH, —S-Phenyl, —S-Benzyl, —S-furfuryl, —NH$_2$, —N$_3$, —NHCOCH$_3$, —NHCOCH$_2$Cl, —NHCOCH$_2$CH$_3$, —NHCOCF$_3$, —NHCOCH(CH$_3$)$_2$, —NHCOC(CH$_3$)$_3$, —NHCO(cyclopropane), —NHCO(cyclohexane), —NHCOCH=CH$_2$, —NHCO-Phenyl, —NH(2-furoyl), —NH-(N-benzo-(2R,3S)-3-phenylisoserine), —NH-(cinnamoyl), —NH-(acetyl-phenyl), —NH-(2-thiophenesulfonyl), —F, —Cl, and —CH$_2$CO$_2$H. $R_4$ is a radical selected from the group represented by the formulas:

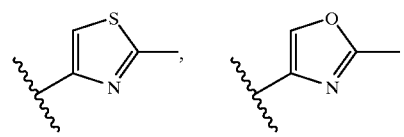

However, there is a proviso that if $R_3$ is either methyl or hydrogen and $R_4$ is represented by the following formula:

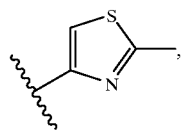

then $R_1$ and $R_2$ cannot be simultaneously hydrogen. Preferred epothilone analogs of this aspect of the invention include compounds represented by the following structures:

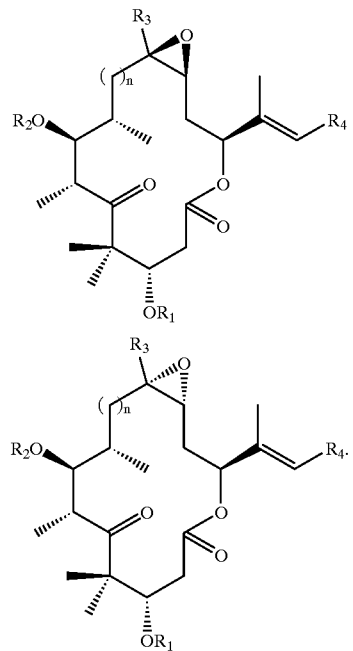

Another aspect of the invention is directed to an epothilone analog represented by the following structure:

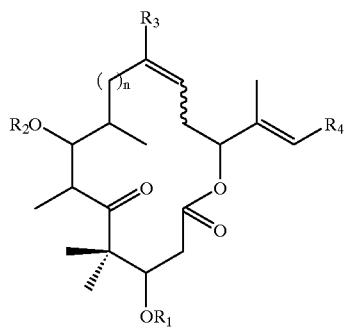

In a preferred embodiment, n is one. However, in alternative embodiments n may be as large as five. $R_1$ is a radical selected from the group consisting of hydrogen, tert-butyldimethylsilyl, trimethylsilyl, methyl, acetyl, benzoyl, and tert-butoxycarbonyl. $R_2$ is a radical selected from the group consisting of hydrogen, tert-butyldimethylsilyl, trimethylsilyl, methyl, acetyl, benzoyl, and tert-butoxycarbonyl. $R_3$ is a radical selected from the group consisting of hydrogen, methyl, —CHO, —COOH, —CO$_2$Me, —CO$_2$(tert-butyl), —CO$_2$(iso-propyl), —CO$_2$(phenyl), —CO$_2$(benzyl), —CONH(furfuryl), —CO$_2$(N-benzo-(2R,3S)-3-phenylisoserine), —CONH(methyl)$_2$, —CONH(ethyl)$_2$, —CONH(benzyl), and —CH$_2$R$_5$. $R_5$ is a radical selected from the group consisting of —OH, —O-Trityl, —O-(C$_1$–C$_6$ alkyl), —O-benzyl, —O-allyl, —O—COCH$_3$, —O—COCH$_2$Cl, —O—COCH$_2$CH$_3$, —O—COCF$_3$, —O—COCH(CH$_3$)$_2$, —O—COC (CH$_3$)$_3$, —O—CO(cyclopropane), —OCO(cyclohexane), —O—COCH=CH$_2$, —O—CO-Phenyl, —O-(2-furoyl), —O-(N-benzo-(2R,3S)-3-phenylisoserine), —O-cinnamoyl, —O-(acetyl-phenyl), —O-(2-thiophenesulfonyl), —S-(C$_1$–C$_6$ alkyl), —SH, —S-Phenyl, —S-Benzyl, —S-furfuryl, —NH$_2$, —N$_3$, —NHCOCH$_3$, —NHCOCH$_2$Cl, —NHCOCH$_2$CH$_3$, —NHCOCF$_3$, —NHCOCH(CH$_3$)$_2$, —NHCOC(CH$_3$)$_3$, —NHCO(cyclopropane), —NHCO(cyclohexane), —NHCOCH=CH$_2$, —NHCO-Phenyl, —NH(2-furoyl), —NH-(N-benzo-(2R,3S)-3-phenylisoserine), —NH-(cinnamoyl), —NH-(acetyl-phenyl), —NH-(2-thiophenesulfonyl), —F, —Cl, and —CH$_2$CO$_2$H. $R_4$ is a radical selected from the group represented by the formulas:

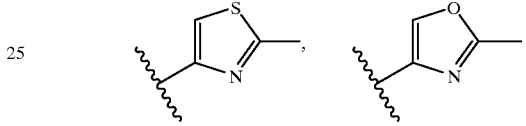

However, there is a proviso that, if $R_3$ is selected from the group consisting of methyl and hydrogen and $R_4$ is represented by the following formula:

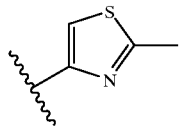

Then $R_1$ and $R_2$ cannot be simultaneously hydrogen. Preferred embodiments of this aspect of the invention include epothilone analogs represented by the following structure:

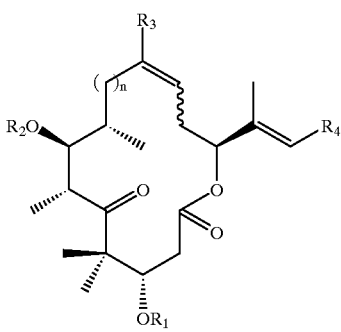

Another aspect of the invention is directed to an epothilone analog represented by the following structure:

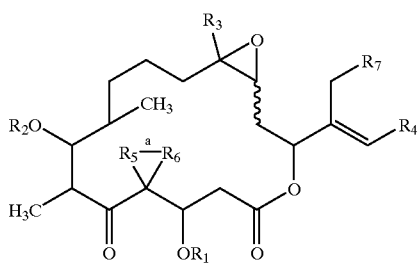

In the above structure, $R_1$ is a radical selected from the group consisting of hydrogen, tert-butyldimethylsilyl, trimethylsilyl, methyl, acetyl, benzoyl, and tert-butoxycarbonyl. $R_2$ is a radical selected from the group consisting of hydrogen, tert-butyldimethylsilyl, trimethylsilyl, methyl, acetyl, benzoyl, and tert-butoxycarbonyl. $R_3$ is a radical selected from the group consisting of hydrogen and methyl. $R_4$ is a radical selected from the group represented by the formulas:

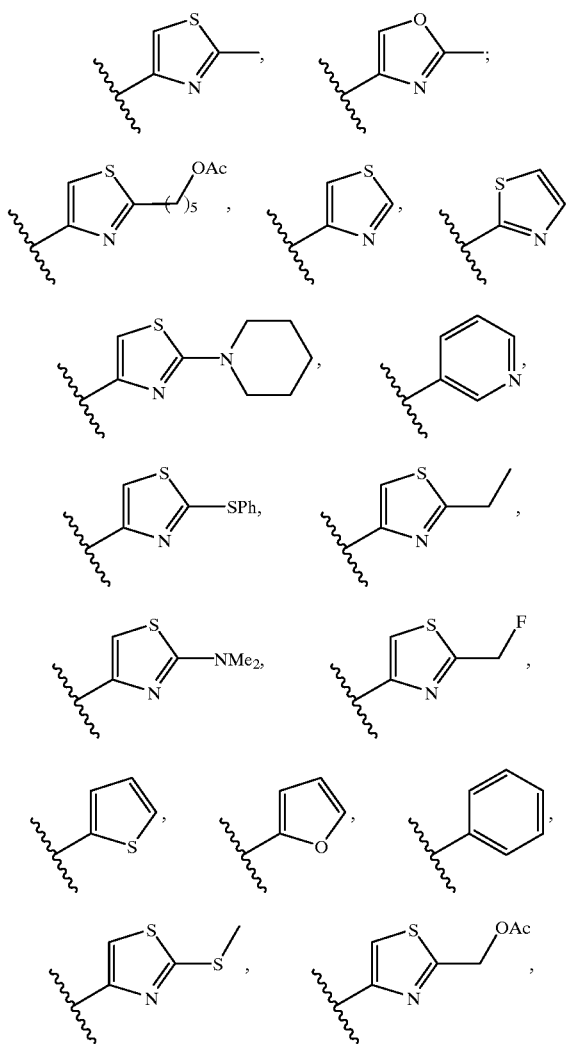

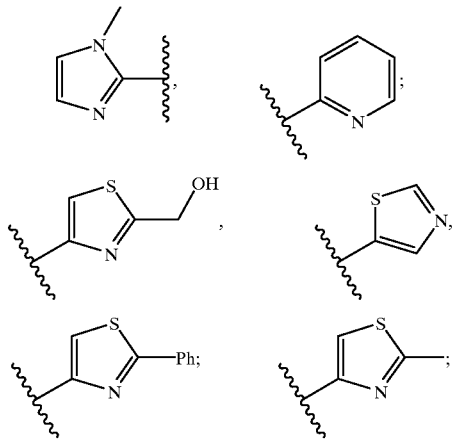

-continued $R^5$ is a radical selected from the group consisting of hydrogen, methylene and methyl. $R^6$ is a radical selected from the group consisting of hydrogen, methylene and methyl. $R_7$ is a radical selected from the group consisting of hydrogen and methyl. However, there are several provisos. If $R_5$ is methylene, then $R_6$ is methylene. If $R_5$ and $R^6$ are methylene, then $R_5$ and $R_6$ are chemically bonded to each other through a single bond "a". If $R_5$ and $R_6$ are selected from the group consisting of hydrogen and methyl, then the single bond "a" is absent. If $R_3$ is selected from the group consisting of methyl and hydrogen and $R_4$ is represented by the formula:

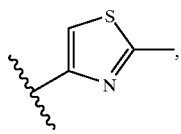

then $R_1$ and $R_2$ cannot be simultaneously hydrogen.

Another aspect of the invention is directed to an epothilone analog represented by the following structure:

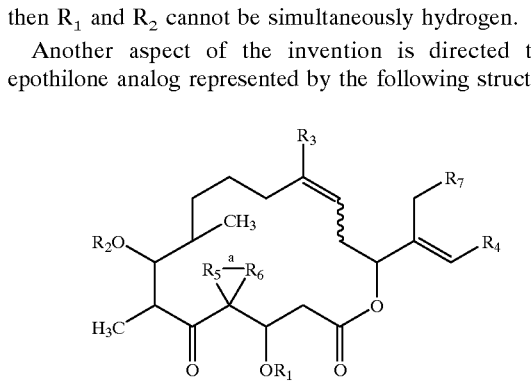

In this embodiment, $R_1$ is a radical selected from the group consisting of hydrogen, tert-butyldimethylsilyl, trimethylsilyl, methyl, acetyl, benzoyl, and tert-butoxycarbonyl. $R_2$ is a radical selected from the group consisting of hydrogen, tert-butyldimethylsilyl, trimethylsilyl, methyl, acetyl, benzoyl, and tert-butoxycarbonyl. $R_3$ is a radical selected from the group consisting of hydrogen and methyl. $R_4$ is a radical selected from the group represented by the formulas:

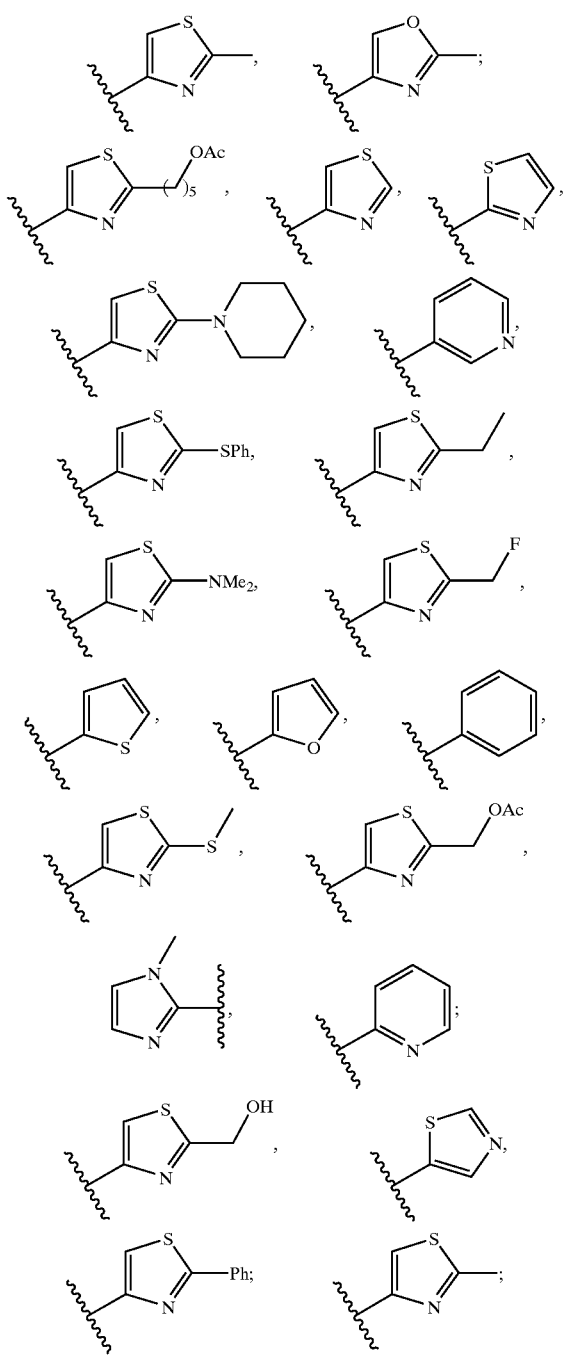

$R_5$ is a radical selected from the group consisting of hydrogen, methylene and methyl. $R_6$ is a radical selected from the group consisting of hydrogen, methylene and methyl. $R_7$ is a radical selected from the group consisting of hydrogen and methyl. However, there are several provisos. If $R_5$ is methylene, then $R_6$ is methylene. If $R_5$ and $R_6$ are methylene, then $R_5$ and $R_6$ are chemically bonded to each other through a single bond "a". If $R_5$ and $R_6$ are selected from the group consisting of hydrogen and methyl then the single bond "a" is absent. If $R_3$ is selected from the group consisting of methyl and hydrogen and $R_4$ is represented by the formula:

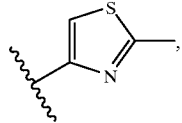

then $R_1$ and $R_2$ cannot be simultaneously hydrogen. Preferred embodiments of this aspect of the invention include compounds represented by the following structures:

Another aspect of the invention is directed to a macrolactonization procedure for synthesizing epothilone and epothilone analogs represented by the following structure:

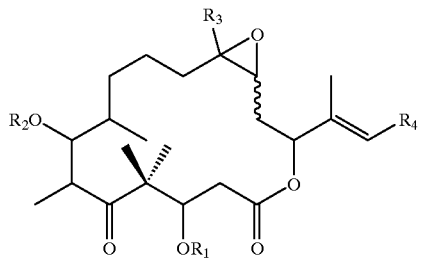

wherein $R_1$ may be hydrogen, tert-butyldimethylsilyl, trimethylsilyl, methyl, acetyl, benzoyl, or tert-butoxycarbonyl; wherein $R_2$ may be hydrogen, tert-butyldimethylsilyl, trimethylsilyl, methyl, acetyl, benzoyl, or tert-butoxycarbonyl; wherein $R_3$ may be hydrogen, methyl, —$CH_2OH$, —$CH_2Cl$, or —$CH_2CO_2H$; wherein $R_4$ is one of the radicals represented by the following formulas:

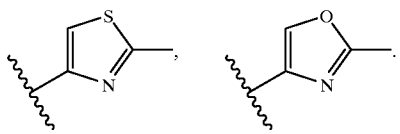

The synthesis may be initiated by condensing a keto acid represented by the following structure:

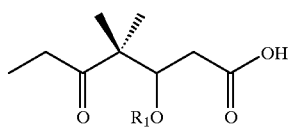

with an aldehyde represented by the following structure:

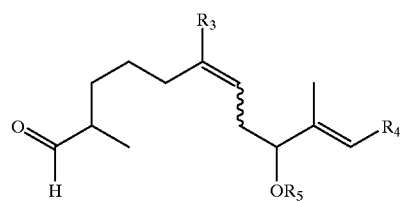

wherein $R_5$ may be tert-butyldimethylsilyl or trimethylsilyl, for producing a carboxylic acid with a free hydroxyl moiety represented by the following structure:

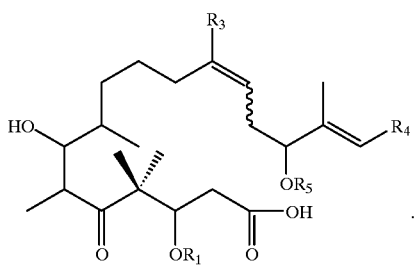

The synthesis is then continued by derivatizing the free hydroxyl moiety of the above carboxylic acid with a derivatizing agent represented by the formula $R_2$—X wherein $R_2$—X may be tert-butyldimethylsilyl chloride, tert-butyldimethylsilyl triflate, trimethylsilyl chloride, trimethylsilyl triflate, methyl iodide, methyl sulfate, acetic anhydride, acetic acid, acetyl chloride, benzoic acid, benzoyl chloride, or 2-(tert-butoxycarbonyloxyimino)-2-phenylacetonitrile for producing a derivatized carboxylic acid represented by the following structure:

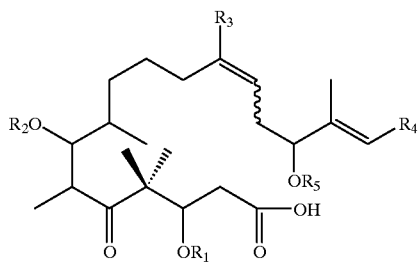

The $R_5$ protected hydroxyl moiety of the above derivatized carboxylic acid is then regioselectively deprotected for producing a hydroxy acid with the following structure:

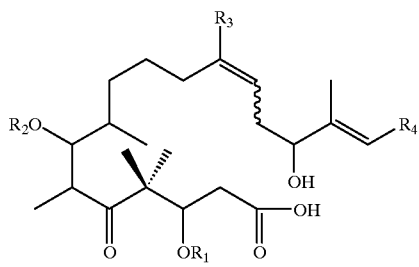

The above hydroxy acid is then macrolactonized for producing a macrolide with the following structure:

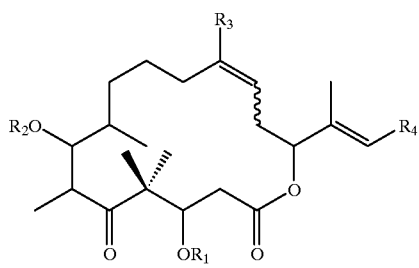

The synthesis is then completed by epoxidizing the above macrolide for producing the epothilone or epothilone analog.

Further modes of this aspect of the invention are directed to each of the individual steps of the above synthetic macrolactionization procedure and to each of the chemical intermediates employed therein.

Another aspect of the invention is directed to a metathesis approach to synthesizing epothilone and epothilone analogs represented by the following structure:

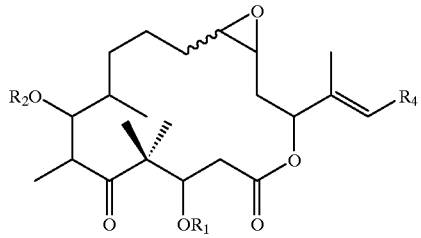

wherein $R_1$ may be hydrogen, tert-butyldimethylsilyl, trimethylsilyl, methyl, acetyl, benzoyl, or tert-butoxycarbonyl; wherein $R_2$ may be hydrogen, tert-butyldimethylsilyl, trimethylsilyl, methyl, acetyl, benzoyl, or tert-butoxycarbonyl; wherein $R_4$ is one of the radicals represented by the following formulas:

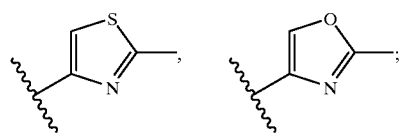

The synthetic protocol is initiated by condensing a keto acid represented by the following structure:

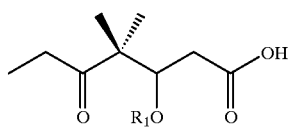

with an aldehyde represented by the following structure:

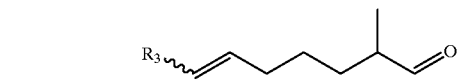

wherein $R_3$ may be hydrogen or $(CH_2)_n$-(solid phase support), for producing a carboxylic acid with a free hydroxyl moiety represented by the following structure:

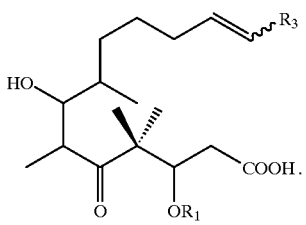

Alternative preferred solid supports include Merrifield resin, PEG-polystyrene, hydroxymethyl polystyrene, formyl polystyrene, aminomethyl polystyrene, or phenolic polystyrene.

The above carboxylic acid is then esterified with a secondary alcohol represented by the following structure:

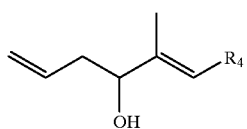

for producing an ester with a free hydroxyl moiety represented by the following structure:

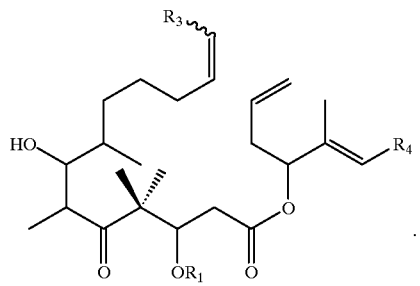

The synthesis is then continued by derivatizing the free hydroxyl moiety of the above ester with a derivatizing agent represented by the formula R$_2$—X wherein R$_2$—X may be tert-butyldimethylsilyl chloride, tert-butyldimethylsilyl triflate, trimethylsilyl chloride, trimethylsilyl triflate, methyl iodide, methyl sulfate, acetic anhydride, acetic acid, acetyl chloride, benzoic acid, benzoyl chloride, or 2-(tert-butoxycarbonyloxyimino)-2-phenylacetonitrile for producing a derivatized ester represented by the following structure:

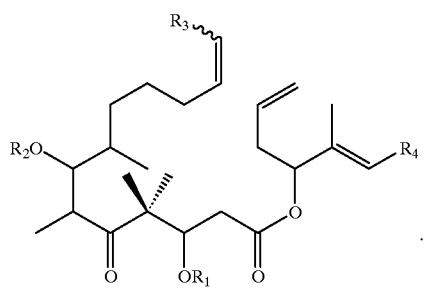

The above derivatized ester is then metathesized with an organo-metallic catalyst for producing a macrolide with the following structure:

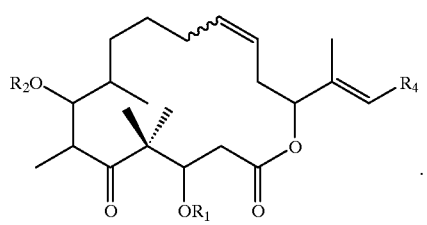

Preferred organo-metallic catalyst include bis(tricyclohexylphosphine)benzylidine ruthenium dichloride or 2,6-diisopropylphenylimido neophylidenemolybdenum bis(hexafluoro-t-butoxide).

The above macrolide is then epoxidized for producing the epothilone analog.

Further modes of this aspect of the invention are directed to each of the individual steps of the above synthetic metathesis procedure and to each of the chemical intermediates employed therein.

Another aspect of the invention is directed to a metathesis approach to synthesizing an epothilone analog represented by the following structure:

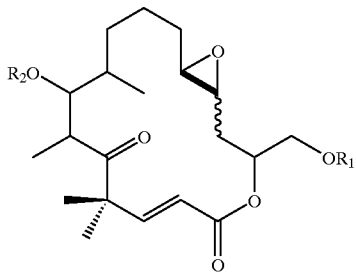

wherein R$_1$ may be hydrogen, tert-butyldiphenylsilyl, tert-butyldimethylsilyl, trimethylsilyl, methyl, acetyl, benzoyl, tert-butoxycarbonyl or a radical represented by the following formulas:

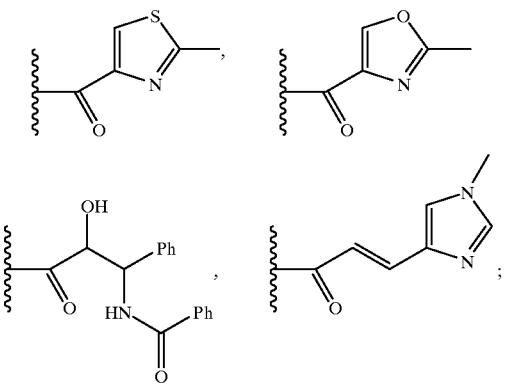

and wherein R$_2$ may be hydrogen, tert-butyldimethylsilyl, trimethylsilyl, methyl, acetyl, benzoyl, or tert-butoxycarbonyl.

The synthesis is initiated by esterifying a keto acid presented by the following structure:

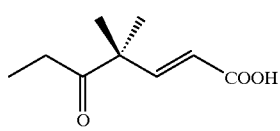

with an alcohol represented by the following structure:

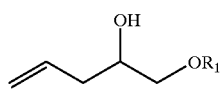

for producing an ester represented by the following structure:

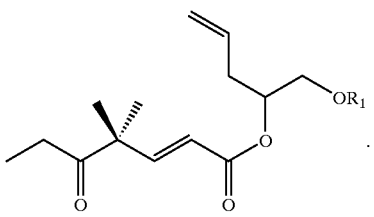

Then, the above ester is condensed with an aldehyde represented by the following structure:

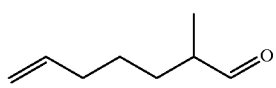

for producing a bis-terminal olefin with the following structure:

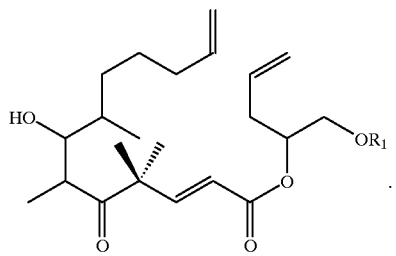

The synthesis is then continued by metathesizing the above bis-terminal olefin with an organo-metallic catalyst for producing a macrocyclic lactone with a free hydroxyl moiety represented by the following structure:

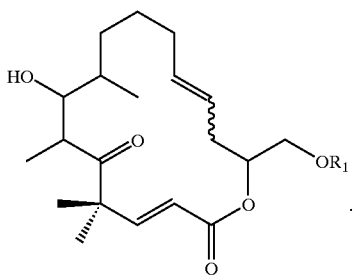

Preferred organo-metallic catalysts include bis (tricyclohexylphosphine)benzylidine ruthenium dichloride, or 2,6-diisopropylphenylimido neophylidenemolybdenum bis (hexafluoro-t-butoxide).

The free hydroxyl of the above macrocyclic lactone is then derivatized with a derivatizing agent represented by the formula $R_2$—X wherein $R_2$—X may be hydrogen, tert-butyldimethylsilyl chloride, tert-butyldimethylsilyl triflate, trimethylsilyl chloride, trimethylsilyl triflate, methyl iodide, methyl sulfate, acetic anhydride, acetic acid, acetyl chloride, benzoic acid, benzoyl chloride, or 2-(tert-butoxycarbonyloxyimino)-2-phenylacetonitrile for producing a derivatized macrolide with the following structure:

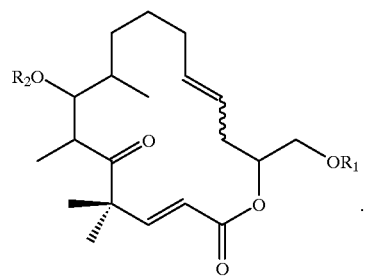

The synthesis is then completed by epoxidizing the above derivatized macrolide for producing the epothilone analog.

Further modes of this aspect of the invention are directed to each of the individual steps of the above synthetic metathesis procedure and to each of the chemical intermediates employed therein.

Another aspect of the invention is directed to a method employing a metathesis approach for synthesizing an epothilone analog represented by the following structure:

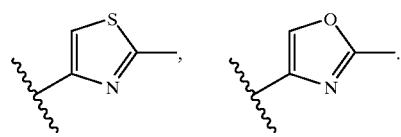

wherein $R_1$ may be hydrogen, tert-butyldimethylsilyl, trimethylsilyl, methyl, acetyl, benzoyl, or tert-butoxycarbonyl; wherein $R_2$ is one of the radicals represented by the following structures:

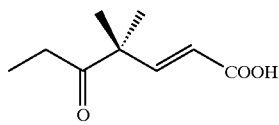

The synthesis is initiated by condensing a keto acid represented by the following structure:

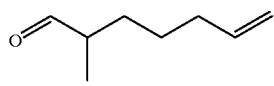

with an aldehyde represented by the following structure:

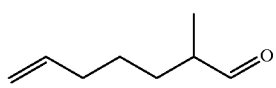

for producing a carboxylic acid with a free hydroxyl moiety represented by the following structure:

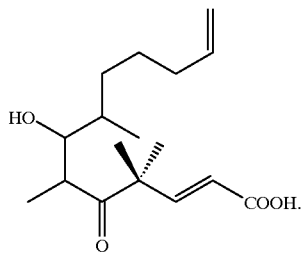

The free hydroxyl moiety of the above carboxylic acid is then derivatized with a derivatizing agent represented by the formula $R_1$—X wherein $R_1$—X may be tert-butyldimethylsilyl chloride, tert-butyldimethylsilyl triflate, trimethylsilyl chloride, trimethylsilyl triflate, methyl iodide, methyl sulfate, acetic anhydride, acetic acid, acetyl chloride, benzoic acid, benzoyl chloride, or 2-(tert-butoxycarbonyloxyimino)-2-phenylacetonitrile for producing a derivatized carboxylic acid represented by the following structure:

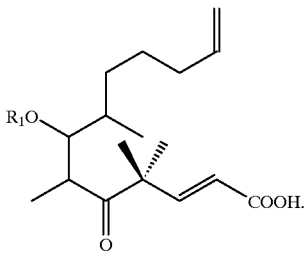

The synthesis is then continued by esterifying the derivatized carboxylic acid of said Step B with an alcohol represented by the following structure:

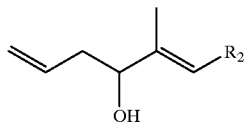

for producing a bis-terminal olefin with the following structure:

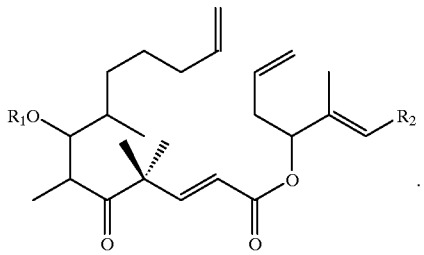

The above bis-terminal olefin is then metathesized with an organo-metallic catalyst for producing a macrocyclic lactone with the following structure:

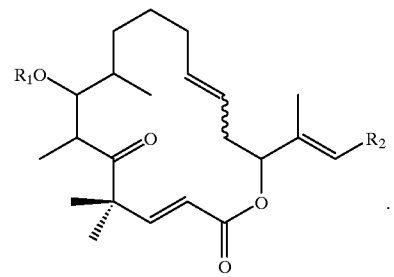

Preferred organo-metallic catalysts include bis(tricyclohexylphosphine)benzylidine ruthenium dichloride, or 2,6-diisopropylphenylimido neophylidenemolybdenum bis(hexafluoro-t-butoxide).

The synthesis is then completed by epoxidizing the above macrocyclic lactone for producing the epothilone analog.

Further modes of this aspect of the invention are directed to each of the individual steps of the above synthetic metathesis procedure and to each of the chemical intermediates employed therein.

Another aspect of the invention is directed to a method employing a macrolatonization approach for synthesizing an epothilone analog represented by the following structure:

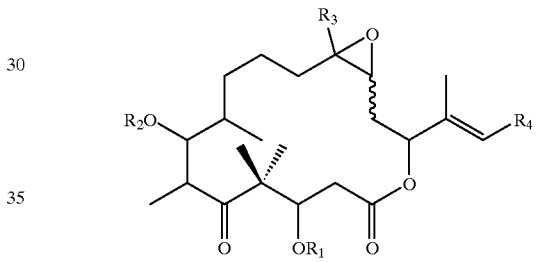

wherein $R_1$ may be hydrogen, tert-butyldimethylsilyl, trimethylsilyl, methyl, acetyl, benzoyl, or tert-butoxycarbonyl; wherein $R_2$ may be hydrogen, tert-butyldimethylsilyl, trimethylsilyl, methyl, acetyl, benzoyl, or tert-butoxycarbonyl; wherein $R_3$ may be hydrogen, methyl, —$CH_2OH$, —$CH_2Cl$, or —$CH_2CO_2H$; wherein $R_4$ is one of the radicals represented by the following formulas:

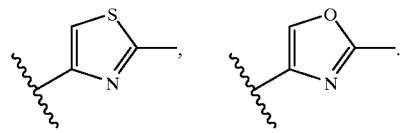

The synthesis is initiated by condensing a keto acid represented by the following structure:

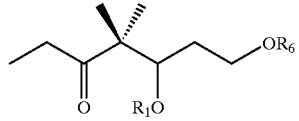

wherein $R_6$ may be tert-butyldimethylsilyl, trimethylsilyl, tert-butyldiphenylsilyl, methyl, hydrogen, triethylsilyl, or benzyl; with an aldehyde represented by the following structure:

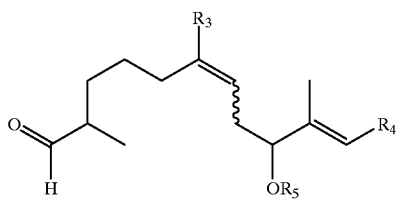

wherein $R_5$ may be tert-butyldimethylsilyl or trimethylsilyl, for producing a β-hydroxy ketone with a free hydroxyl moiety and a $R_6$ protected hydroxyl moiety represented by the following structure:

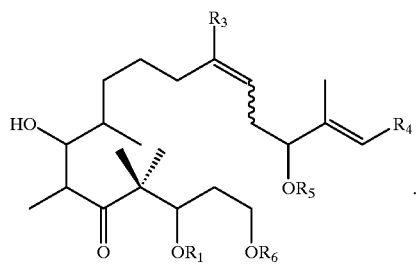

The free hydroxyl moiety of the above β-hydroxy ketone is then derivatized with a derivatizing agent represented by the formula $R_2$—X wherein $R_2$—X may be tert-butyldimethylsilyl chloride, tert-butyldimethylsilyl triflate, trimethylsilyl chloride, trimethylsilyl triflate, methyl iodide, methyl sulfate, acetic anhydride, acetic acid, acetyl chloride, benzoic acid, benzoyl chloride, or 2-(tert-butoxycarbonyloxyimino)-2-phenylacetonitrile for producing a derivatized β-hydroxy ketone represented by the following structure:

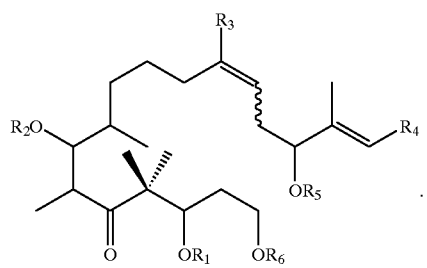

The $R_6$ protected hydroxyl moiety of the above derivatized β-hydroxy ketone is then regioselectively deprotected for producing a terminal alcohol with the following structure:

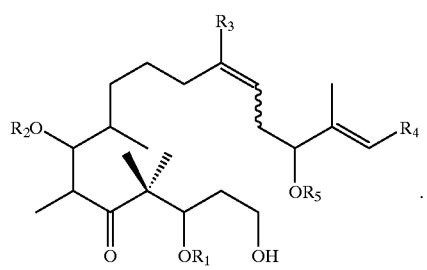

The above terminal alcohol is then oxidized for producing a derivatized carboxylic acid with a $R_5$ protected hydroxyl moiety with the following structure:

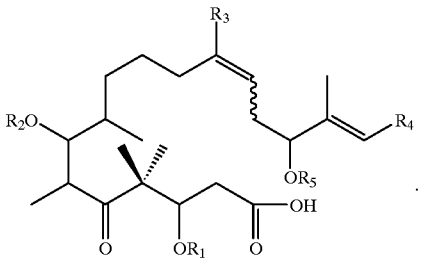

The synthesis is then continued by regioselectively deprotecting the $R_5$ protected hydroxyl moiety of the derivatized carboxylic acid of-said step D for producing a hydroxy acid with the following structure:

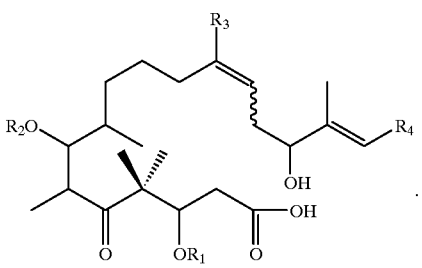

The above hydroxy acid is then macrolactonized for producing a macrolide with the following structure:

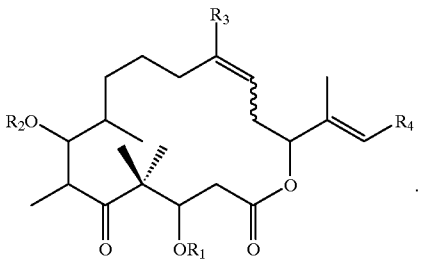

The synthesis is then completed by epoxidizing the above macrolide for producing the epothilone analog.

Further modes for this aspect of the invention are directed to each of the individual steps of the above synthetic macrolactonization procedure and to each of the chemical intermediates employed therein.

Another aspect of the invention is directed to a process for synthesizing an epothilone analog having an epoxide and an aromatic substituent. In the first step of this process, a first epothilone intermediate and an aromatic stannane are coupled by means of a Stille coupling reaction to produce a second epothilone intermediate. The first epothilone intermediate has a vinyl iodide moiety to which the aromatic stannane is coupled for producing the second epothilone intermediate. Preferred embodiments of the first epothilone intermediate are represented by the following structure:

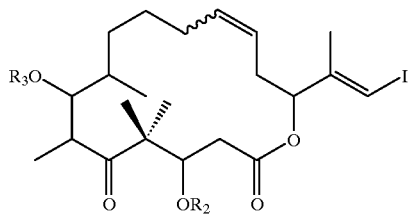

In the above structure, R₂ is a radical selected from hydrogen, tert-butyldimethylsilyl, trimethylsilyl, methyl, acetyl, benzoyl, or tert-butoxycarbonyl. R₃ is a radical selected from hydrogen, tert-butyldimethylsilyl, trimethylsilyl, methyl, acetyl, benzoyl, or tert-butoxycarbonyl. In a preferred embodiment, the aromatic stannane is a compound represented by one of the following structures:

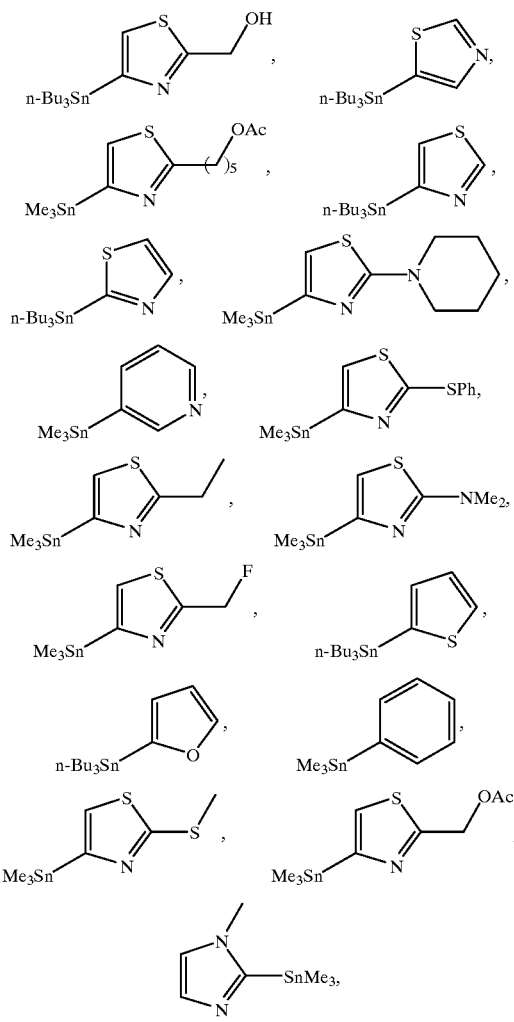

The second epothilone intermediate has the aromatic substituent and a cis olefin. In a preferred embodiment, the second epothilone intermediate is represented by the following structure:

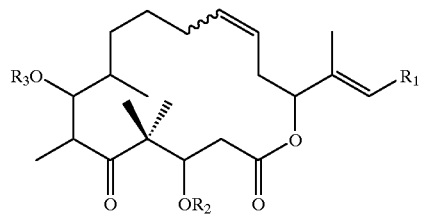

$R_1$ is one of the radicals represented by the following formulas:

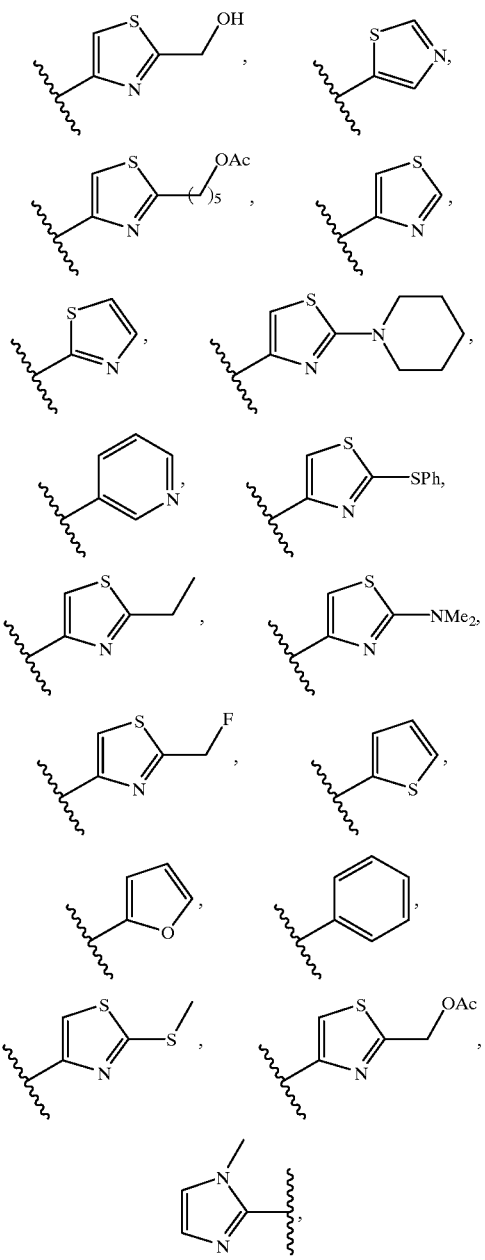

In the second step of this process, the cis olefin of the second epothilone intermediate is epoxidized to produce the epothilone analog. In a preferred embodiment, the epothilone analog is represented by the following structure:

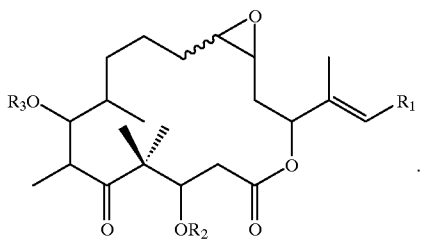

In a preferred mode of the above process for synthesizing an epothilone analog, there are several additional steps that are performed prior to the Stille coupling step. The first of the additional steps involves the condensation of a keto acid represented by the following structure:

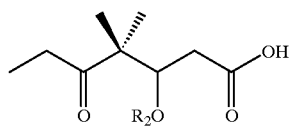

with an aldehyde represented by the following structure:

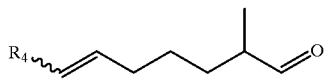

wherein $R_4$ may be hydrogen or $(CH_2)_n$-(solid phase support) for producing a carboxylic acid represented by the following structure:

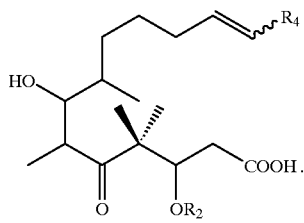

Then, the above carboxylic acid is esterified with a secondary alcohol represented by the following structure:

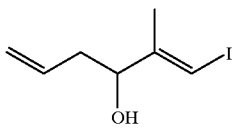

for producing an ester with a free hydroxyl moiety represented by the following structure:

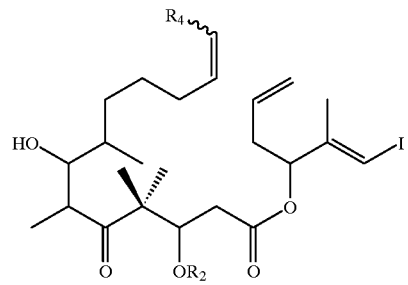

Then, there is an optional step. The free hydroxyl moiety of the above ester may be derivatized with a derivatizing agent. Preferred derivatizing agents include tert-butyldimethylsilyl chloride, tert-butyldimethylsilyl triflate, trimethylsilyl chloride, trimethylsilyl triflate, methyl iodide, methyl sulfate, acetic anhydride, acetic acid, acetyl chloride, benzoic acid, benzoyl chloride, or 2-(tert-butoxycarbonyloxyimino)-2-phenylacetonitrile for producing an optionally derivatized ester represented by the following structure:

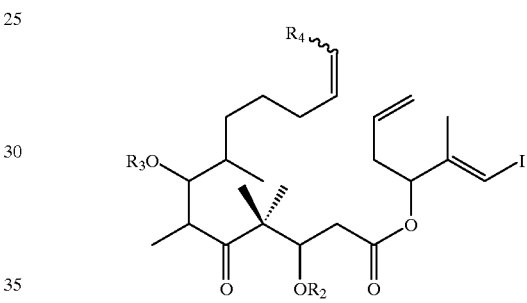

Finally, the above optionally derivatized ester is metathesized with an organo-metallic catalyst for producing the above indicated first epothilone analog.

Another aspect of the invention is directed to the use of each of the above metathesis approaches for synthesizing libraries of epothilone analogs. In this mode, a combinatorial approach is employed for synthesizing libraries of epothilone analogs having various combinations of the preferred R groups.

BRIEF DESCRIPTION OF THE DRAWINGS

FIG. 3 illustrates the synthesis of 3 building block substrates wherein A) represents the synthesis of aldehyde 7 with reagents and conditions as follows: (a) 1.05 equivalents of NaHMDS, 2.0 equivalents of n-C5H9I, 3.0 equivalents HMPA, −78 to 25° C., 5 hours; (b)1.1 equivalents of LiAlH$_4$, THF, −78° C., 15 minutes, 60% (2 steps); (c) 1.5 equivalents of NMO, 5 mol % of TPAP, Methylene chloride, 4 Å MS, 25° C., 0.5 hour, 95%. NaHMD =sodium bis(trimethylsilyl) amide; HMPA=hexamethylphosphoramide, NMO=4-methylmorpholine-N-oxide; TPAP=tetrapropyl ammonium perruthenate; B) represents the synthesis of alcohols 18a and 18b. Reagents and conditions: (a) 1.3 equivalents of TPSCl, 2.0 equivalents of imidazole, DMF, 0 to 25° C., 1.5 hours (90% of 17a, 94% of 17b); (b) 1.25 equivalents of tetravinyltin, 5.0 equivalents of n-BuLi, THF, −78° C., 45 minutes, then 2.5 equivalents of CuCN in THF, −78 to −30° C.; then 17a or 17b in THF, −30° C., 1 hour, 18a (86%), 18b (83%) (TPS =SiPh$_2$tBu); C) represents the synthesis of ketoacid 21. Reagents and conditions: (a) 1.2 equivalents of 19, 1.6 equivalents of NaH, THF, 0→25° C., 1 hour, 99%; (b) CF$_3$COOH:Methylene chloride (1:1), 25° C., 0.5 hour, 99%.

Figure 4:
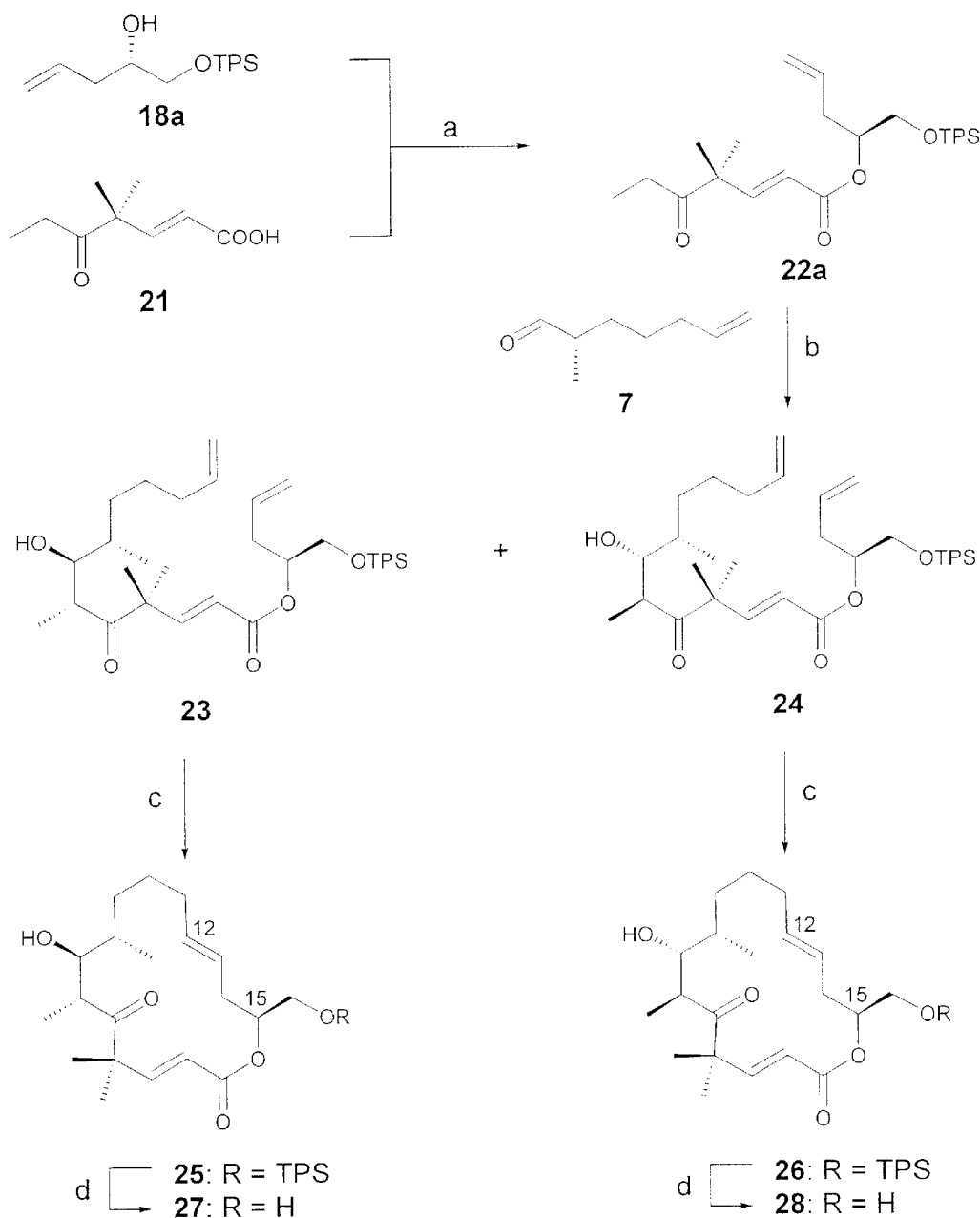

FIG. 4 illustrates the synthesis of the epothilone cyclic framework via olefin metathesis: the 15S series. Reagents and conditions: (a) 1.2 equivalents of EDC, 0.1 equivalent of 4-DMAP, Methylene chloride, 0→25° C., 12 hours, 86%; (b) 21, 1.2 equivalents of LDA, −78° C.→−40° C., THF, 45 minutes; then 1.6 equivalents of 7 in THF, −78→−40° C., 0.5 hour, 23 (42%), 24 (33%); (c) 0.1 equivalent of RuCl$_2$(═CHPh) (PCy$_3$)$_2$, Methylene chloride, 25° C., 12 hours, 25 (85%), 26 (79%); (d) 2.0 equivalents of TBAF, 5.0 equivalents of AcOH, 25° C., 36 hours, 27 (92%), 28 (95%). DCC =dicyclohexylcarbodiimide, 4-DMAP=4-dimethylaminopyridine, LDA=lithium diisopropylamide.

Figure 5:
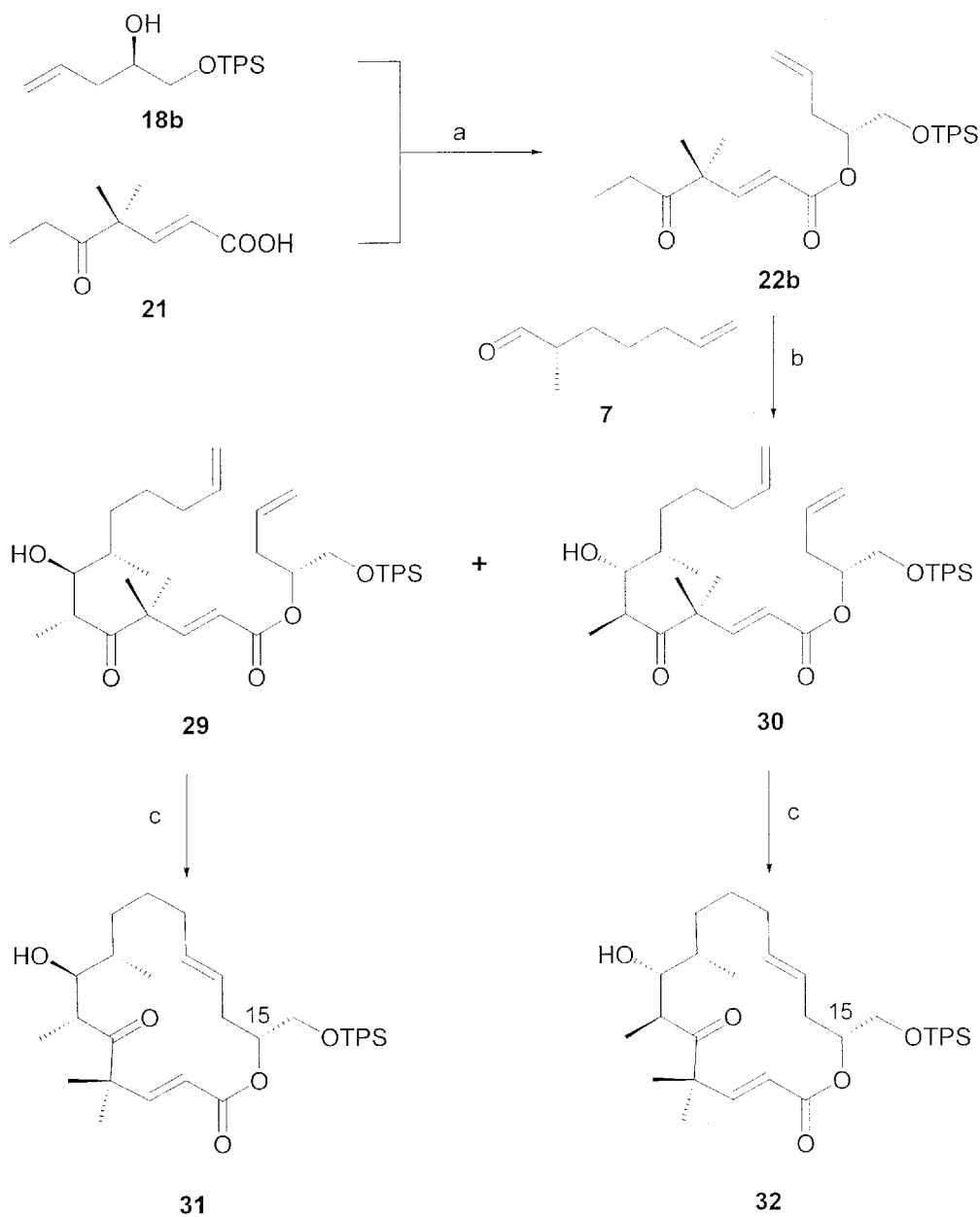

FIG. 5 illustrates the synthesis of the epothilone cyclic framework via olefin metathesis: the 15R series. Reagents and conditions: (a) 1.4 equivalents of DCC, 1.4 equivalents of 4-DMAP, toluene, 25° C., 12 hours, 95%; (b) 21, 1.2 equivalents of LDA, −78° C.→−40° C., THF, 45 minutes; then 1.6 equivalents of 7 in THF, −78→−40° C., 0.5 hour, 29 (54%), 30 (24%); (c) 0.1 equivalent of RuCl$_2$(═CHPh) (PCy$_3$)$_2$, Methylene chloride, 25° C., 12 hours, 31 (80%), 32 (81%).

Figure 6:
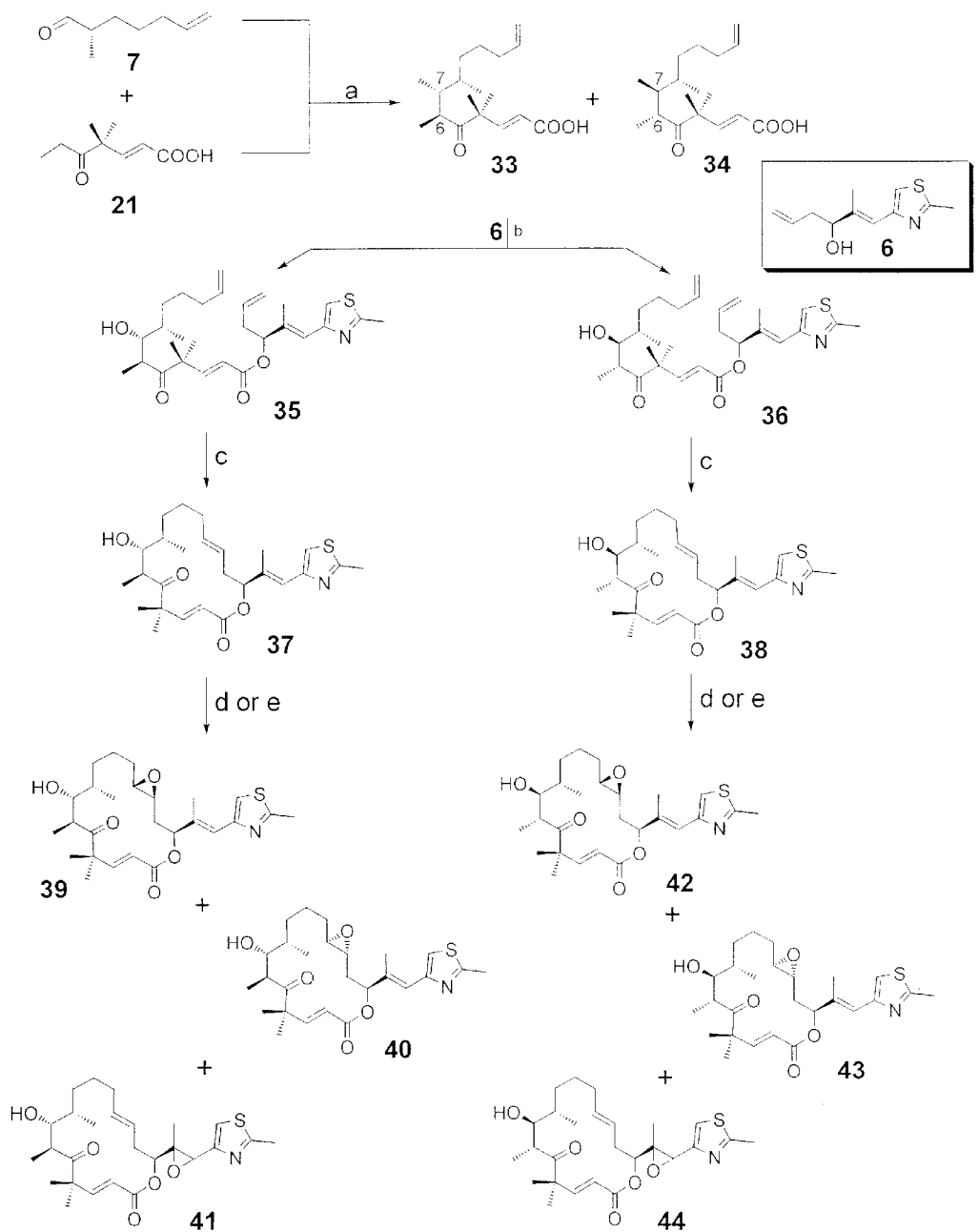

FIG. 6 illustrates the metathesis approach and epoxidation in the presence of thiazole: synthesis of epothilone analogs 39–44. Metathesis and epoxidation in the presence of thiazole: synthesis of epothilone analogs 39–44. Reagents and conditions: (a) 21, 2.3 equivalents of LDA, −78→−30° C., THF, 1.5 hours; then 1.6 equivalents of 7 in THF, −78→−40° C., 1 hour (33:34, 2:3); (b) ca 2.0 equivalents of 6, ca 1.2 equivalents of EDC, ca 0.1 equivalent of 4-DMAP, Methylene chloride, 0→25° C., 12 hours, 35 (29%), 6 (44%) (2 steps); (c) 0.1 equivalent of RuCl$_2$(═CHPh) (PCy$_3$)$_2$, Methylene chloride, 25° C., 12 hours, 7 (86%), 38 (66%); (d) 0.9–1.2 equivalents of mCPBA, CHCl$_3$, −20→0° C., 12 hours, 37→39 (or 40) (40%), 40 (or 39) (25%), 41 (18%); 38→42 (or 43) (22%), 43 (or 42) (11%), 44 (7%); (e) excess of CF$_3$COCH$_3$, 8.0 equivalents of NaHCO$_3$, 5.0 equivalents of Oxone®, CH$_3$CN/Na$_2$EDTA (2:1), 0° C., 37→39 (or 40) (45%), 40 (or 39) (28%); 38–42 (or 43) (60%), 43 (or 42) (15%). mCPBA=meta-Chloroperbenzoic acid.

Figure 7:
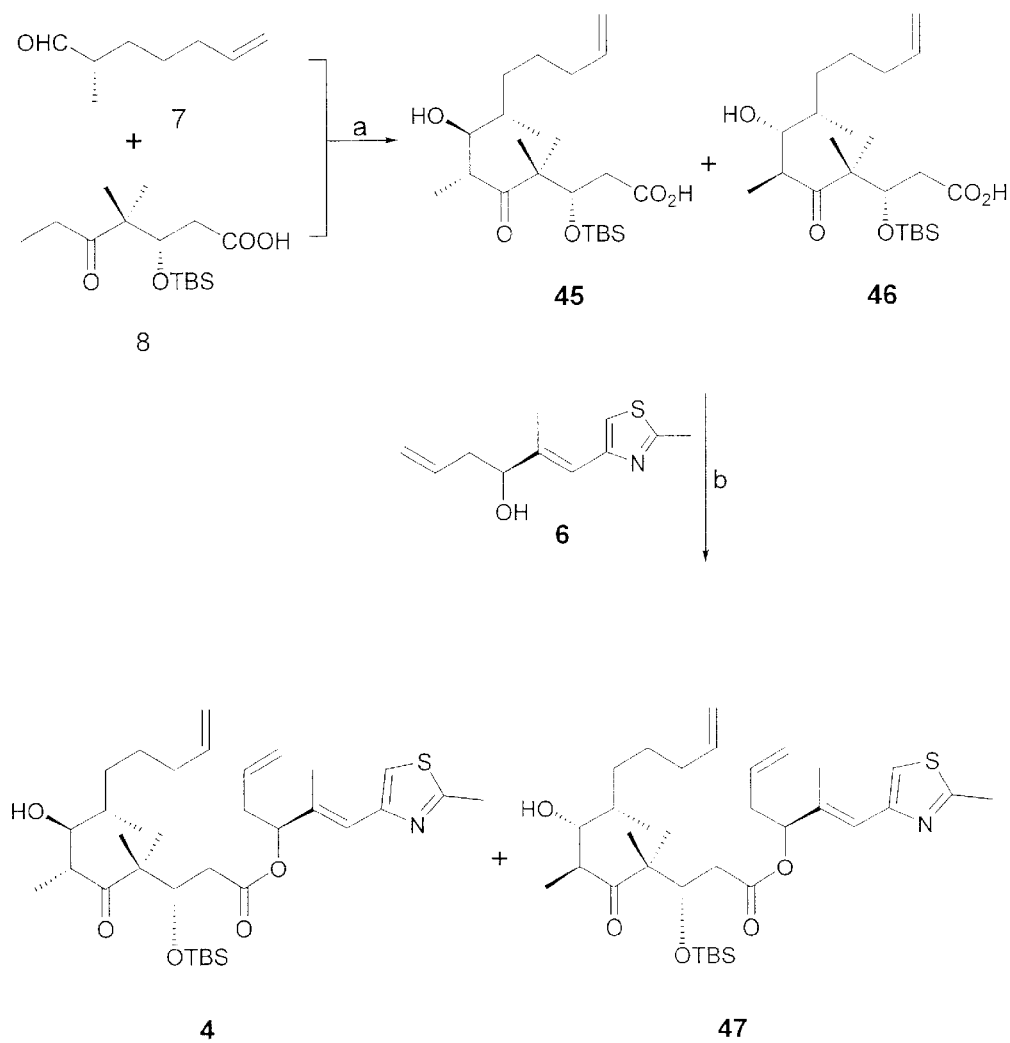

FIG. 7 illustrates the coupling of building blocks 6–8. Reagents and conditions: (a) 8, 2.3 equivalents of LDA, −78→−30° C., THF, 1.5 hours; then 1.6 equivalents of 7 in THF, −78→−40° C., 1 hour (45:46, 3:2); (b) ca 2.0 equivalents of 6, ca 1.2 equivalents of EDC, ca 0.1 equivalent of 4-DMAP, Methylene chloride, 0→25° C., 12 hours, 4 (52%), 47 (31%). (2 steps).

Figure 8:
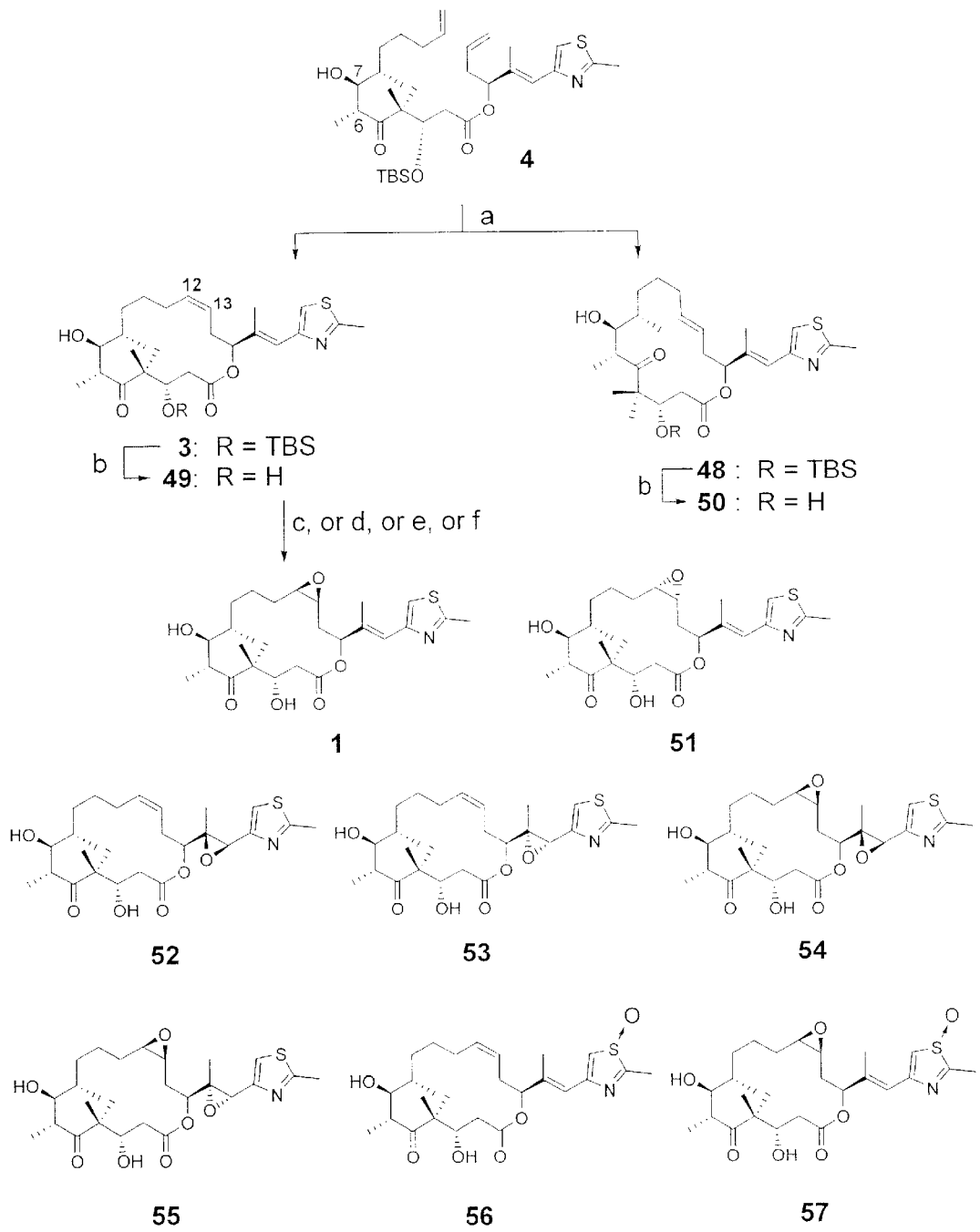

FIG. 8 illustrates the epoxidation of epothilone framework: total synthesis of epothilone A (1) and analogs 51–57. Epoxidation of epothilone framework: total synthesis of epothilone A (1) and analogs 51–57. (a) 0.1 equivalent of RuCl$_2$(═CHPh) (PCy$_3$)$_2$, Methylene chloride, 25° C., 20 hours, 3 (46%), 48 (39%); (b) 20% CF$_3$COOH in Methylene chloride, 0° C., 3 hours, 3→49 (90%); 48→50 (92%); (c) 0.8–1.2 equivalents of mCPBA, CHCl$_3$, −20→0° C., 12 hours, 49→1 (35%), 51 (13%), 52 (or 53) (9% ), 53 (or 52) (7%), 54 (or 55) (5%), 55 (or 54) (5%); 1→54 (or 55) (35%%), 55 (or 54) (33%), 57 (6%); (d) 1.3–2.0 equivalents of MCPBA, CHCl$_3$, −20→0° C., 12 hours, 1 (15%), 51 (10%), 52 (or 53) (10% ), 53 (or 52) (8%), 54 (or 55) (8%), 55 (or 54) (7%), 56 (5%), 57 (5%); (e) 1.0 equivalent of dimethyldioxirane, CH$_2$Cl$_2$/acetone, 0° C., 1 (50%), 51 (15%), 52 (or 53) (5%), 53 (or 52) (5%); (f) excess of CF$_3$COCH$_3$, 8.0 equivalents of NaHCO$_3$, 5.0 equivalents of Oxone®, CH$_3$CN/Na$_2$EDTA (2:1), 0° C., 1 (62%), 51 (13%).

Figure 9:
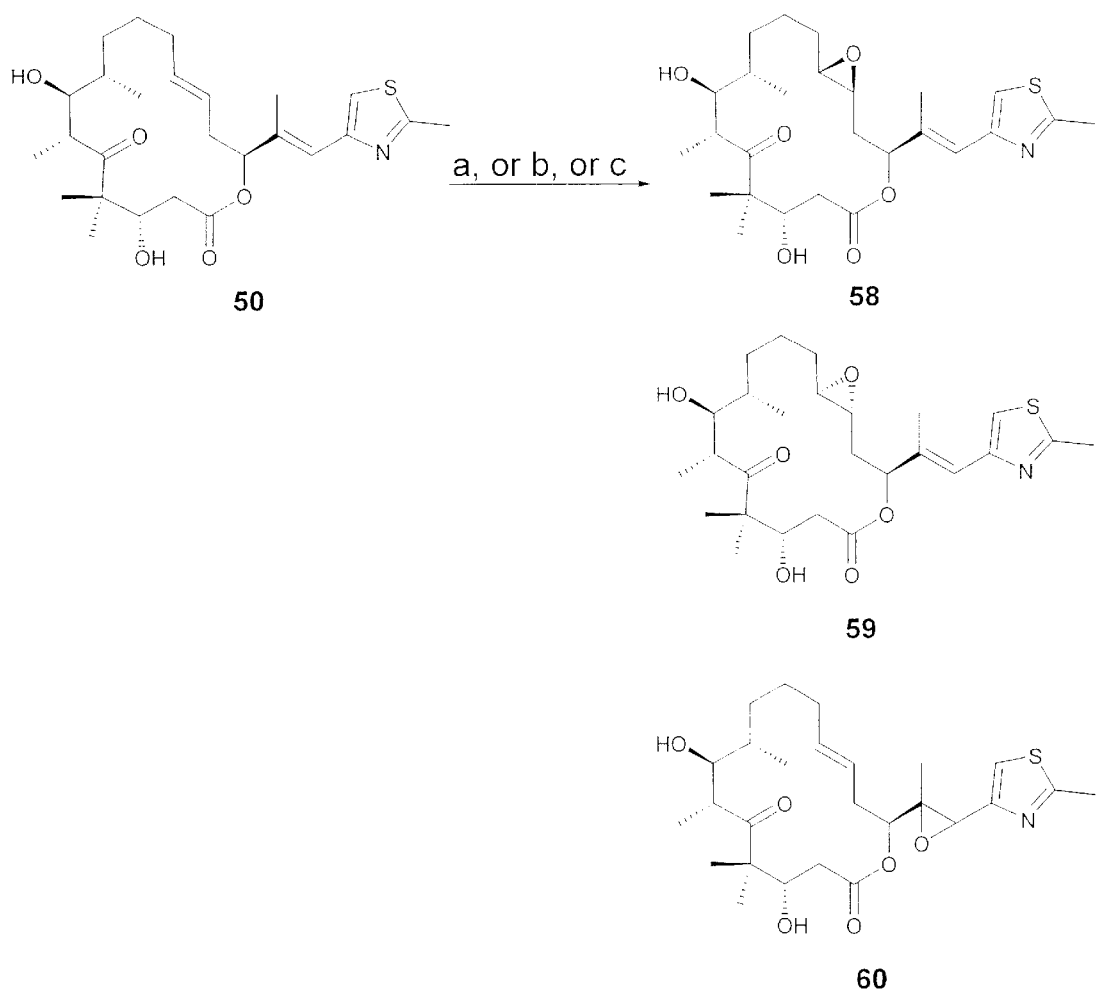

FIG. 9 illustrates the synthesis of epothilones 58–60. Reagents and conditions: (a) 0.9–1.3 equivalents of mCPBA, CHCl$_3$, −20→0° C., 12 hours, 58 (or 59) (5%), 59 (or 58) (5%), 60 (60%); (b) 1.0 equivalent of dimethyldioxirane, Methylene chloride/acetone, 0° C., 58 (or 59) (10%), 59 (or 58) (10%), 60 (40%); (c) excess of CF$_3$COCH$_3$, 8.0 equivalents of NaHCO$_3$, 5.0 equivalents of Oxone®, MeCN/Na$_2$EDTA (2:1), 0° C., 58 (or 59) (45%), 59 (or 58) (35%).

Figure 10:
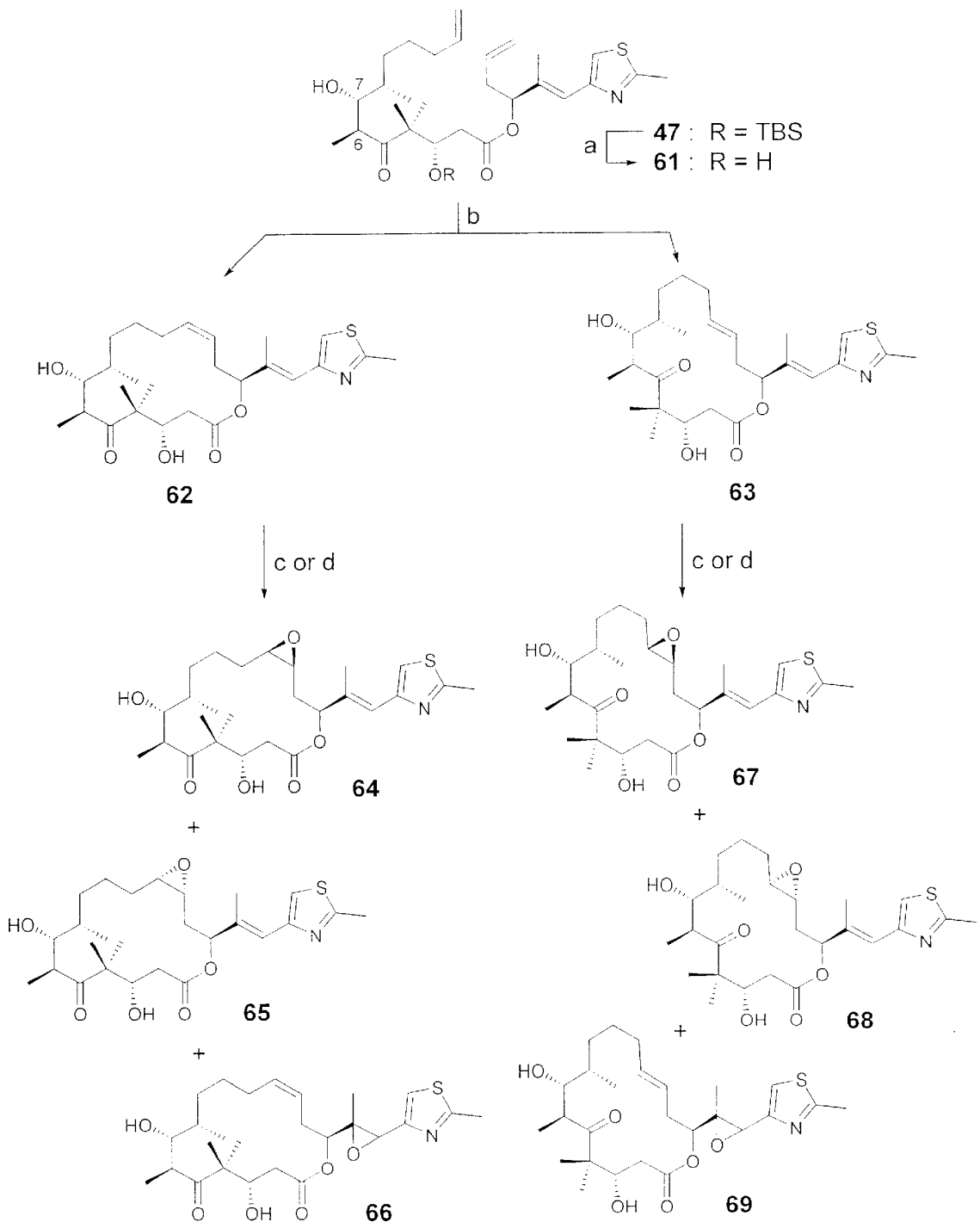

FIG. 10 illustrates the synthesis of epothilones 64–69. (a) 20% CF$_3$COOH in Methylene chloride, 0° C., 3 hours, 90%; (b) 0.1 equivalent of RuCl$_2$(═CHPh) (PCy$_3$)$_2$, Methylene chloride, 25° C., 20 hours, 62 (20%), 63 (69%); (c) 0.8–1.2 equivalents of mCPBA, CHCl$_3$, −20→0° C., 12 hours, 62→64 (or 65) (25%), 65 (or 64) (23%); 63→67 (or 68) (24%), 68 (or 67) (19%), 69 (31%); (d) excess of CF$_3$COCH$_3$, 8.0 equivalents of NaHCO$_3$, 5.0 equivalents of Oxone®, CH$_3$CN/Na$_2$EDTA (2:1), 0° C., 62→64 (or 65) (58%), 65 (or 64) (29%); 63→67 (or 68) (44%), 68 (or 67) (21%).

Figure 11:
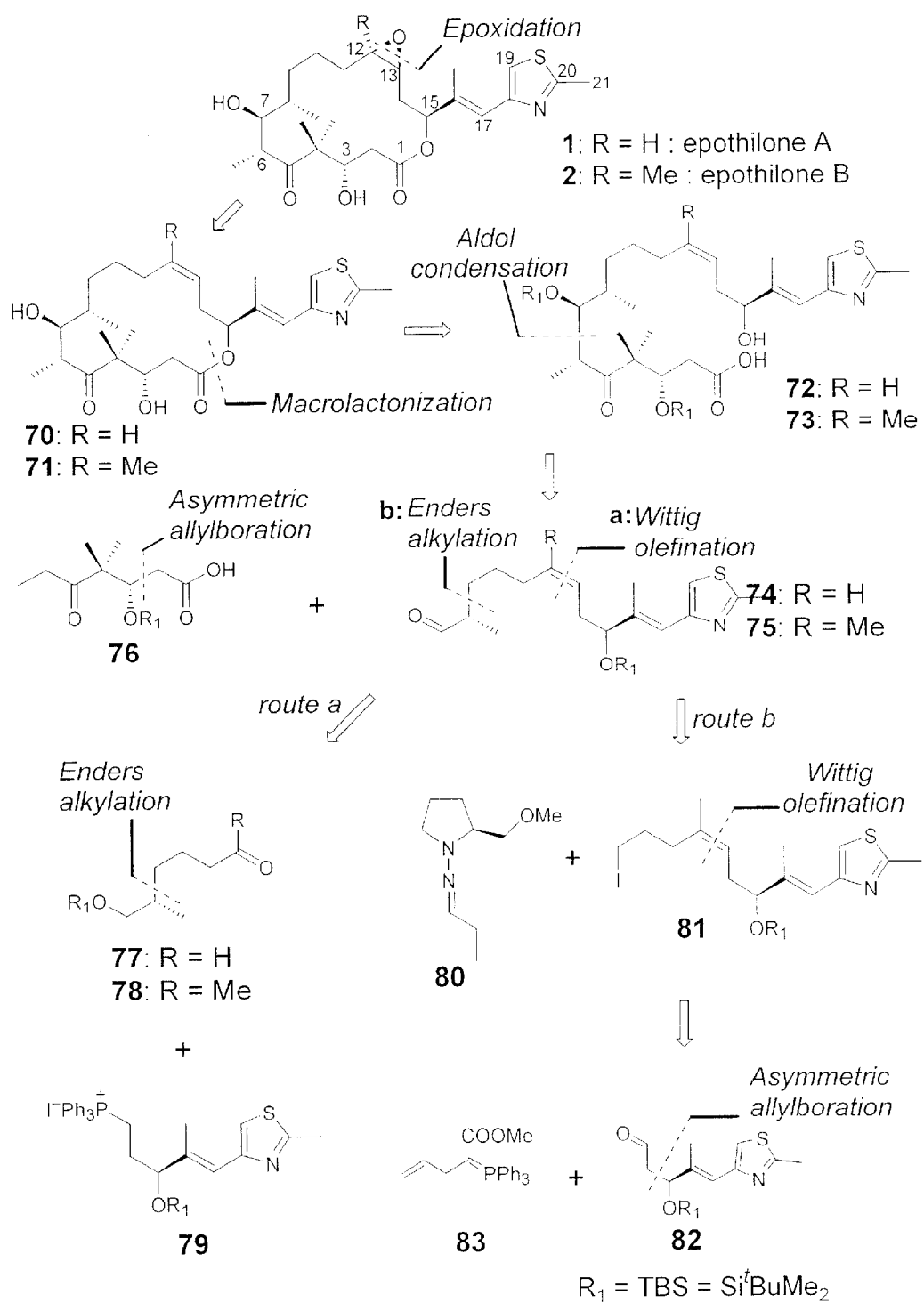

FIG. 11 illustrates the molecular structures and retrosynthetic analysis of epothilones A(1) and B(2) using the macrolactonization approach.

FIG. 12 illustrates the synthesis of 2 building block substrates wherein A) represents the synthesis of keto acid 76. Reagents and conditions: (a) 1.2 equivalents of (+)-Ipc$_2$B(allyl), Et$_2$O, −100° C., 0.5 hour, 74% (ee>98% by Mosher ester analysis); (b) 1.1 equivalents TBSOTf, 1.2 equivalents of 2,6-lutidine, Methylene chloride, 25° C., 98% ; (c) O$_3$, Methylene chloride, −78° C., 0.5 hour; then 1.2 equivalents Ph$_3$P, −78→25° C., 1 hour, 90%; (d) 3.0 equivalents of NaClO$_2$, 4.0 equivalents of 2-methyl-2-butene, 1.5 equivalents of NaH$_2$PO$_4$, tBuOH:H$_2$O (5:1), 25° C., 2 hours, 93%; B) represents the synthesis of phosphonium salt 79 and aldehyde 82. Reagents and conditions: (a) 1.6 equivalents of DIBAL, Methylene chloride, −78° C., 2 hours, 90%; (b) Ph$_3$P═C(CH$_3$)CHO, benzene, reflux, 98%; (c) 1.5 equivalents of (+)-Ipc$_2$B(allyl), Et$_2$O, −100° C., 0.5 hour, 96% (ee>97% by Mosher ester analysis); (d) 1.2 equivalents TBSCl, 1.5 equivalents of imidazole, DMF, 0→25° C., 2 hours, 99%; (e) i. 1.0 mol % OsO$_4$, 1.1 equivalents of 4-methylmorpholine N-oxide (NMO), THF:tBuOH:H$_2$O (1:1:0.1), 0→25° C., 12 hours, 95%; ii. 1.3 equivalents of Pb(OAc)$_4$, EtOAc, 0° C., 0.5 hour, 98%; (f) 2.5 equivalents of NaBH$_4$, MeOH, 0° C., 15 minutes, 96%; (g) 1.5 equivalents of I$_2$, 3.0 equivalents of imidazole, 1.5 equivalents of Ph$_3$P, Et$_2$O:MeCN (3:1), 0° C., 0.5 hour, 89%; g. 1.1 equivalents Ph$_3$P, neat, 100° C., 2 hours, 98%.

Figure 13:
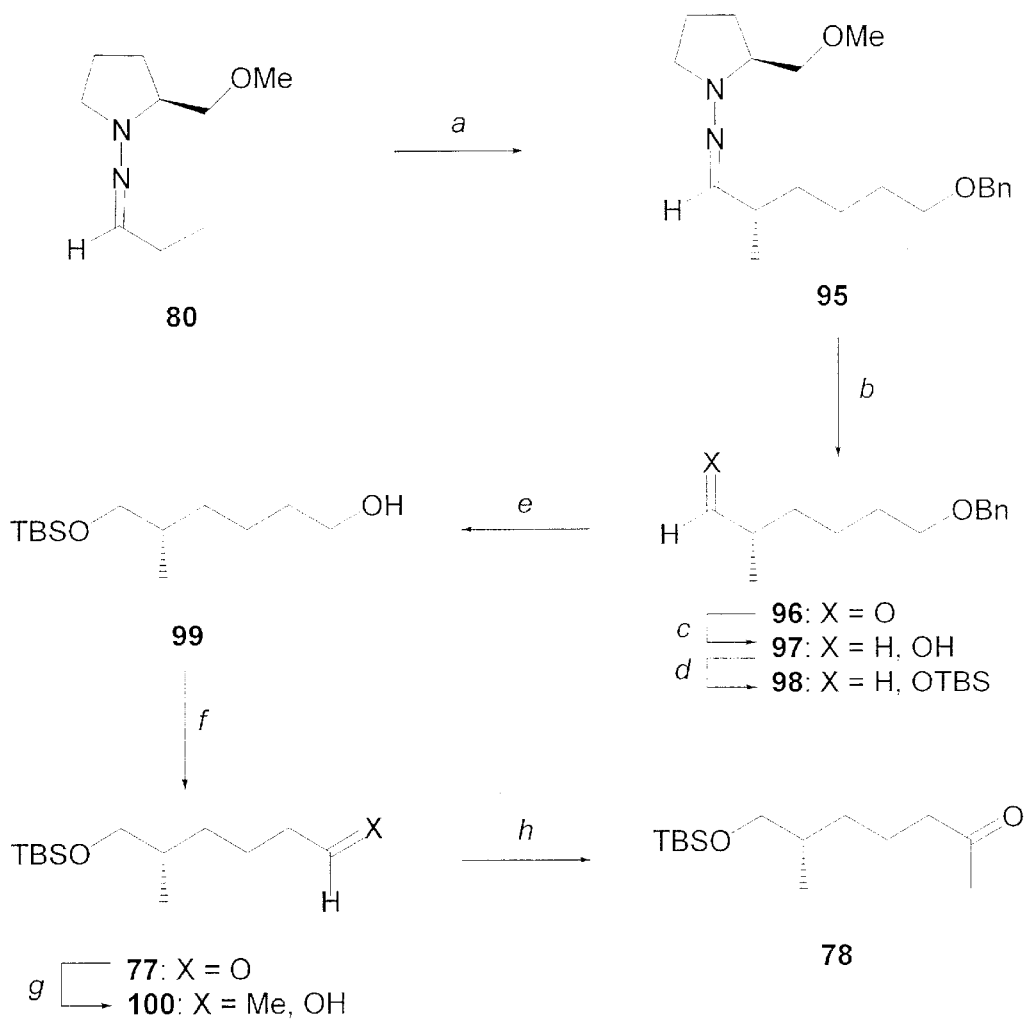

FIG. 13 illustrates the synthesis of aldehyde 77 and ketone 78. Reagents and conditions: (a) 1.1 equivalents of LDA, THF, 0° C., 8 hours; then 1.5 equivalents of 4-iodo-1-benzyloxybutane in THF, at −100→0° C., 6 hours, 92% (de >98% by $^1$H NMR); (b) O$_3$, Methylene chloride, −78° C., 77% or MeI, 60° C., 5 hours; then 3 N aq HCl, n-pentane, 25° C., 1 hour, 86%; (c) 3.0 equivalents of NaBH$_4$, MeOH, 0° C., 15 minutes, 98%; (d) 1.5 equivalents of TBSCl, 2.0 equivalents of Et$_3$N, Methylene chloride, 0→25° C., 12 hours, 95%; (e) H$_2$, Pd(OH)$_2$ cat., THF, 50 psi, 25° C., 15 minutes, 95%; (f) 2.0 equivalents of (COCl)$_2$, 4.0 equivalents of DMSO, 6.0 equivalents of Et$_3$N, Methylene chloride, −78→0° C., 1.5 hours, 98%; (g) 1.5 equivalents of MeMgBr, THF, 0° C., 15 minutes, 84%; (h) 1.5 equivalents of NMO, 0.05 equivalent of tetra-i-propylammonium perruthenate (TPAP), 4 Å MS, Methylene chloride, 25° C., 45 minutes, 96%.

Figure 14:
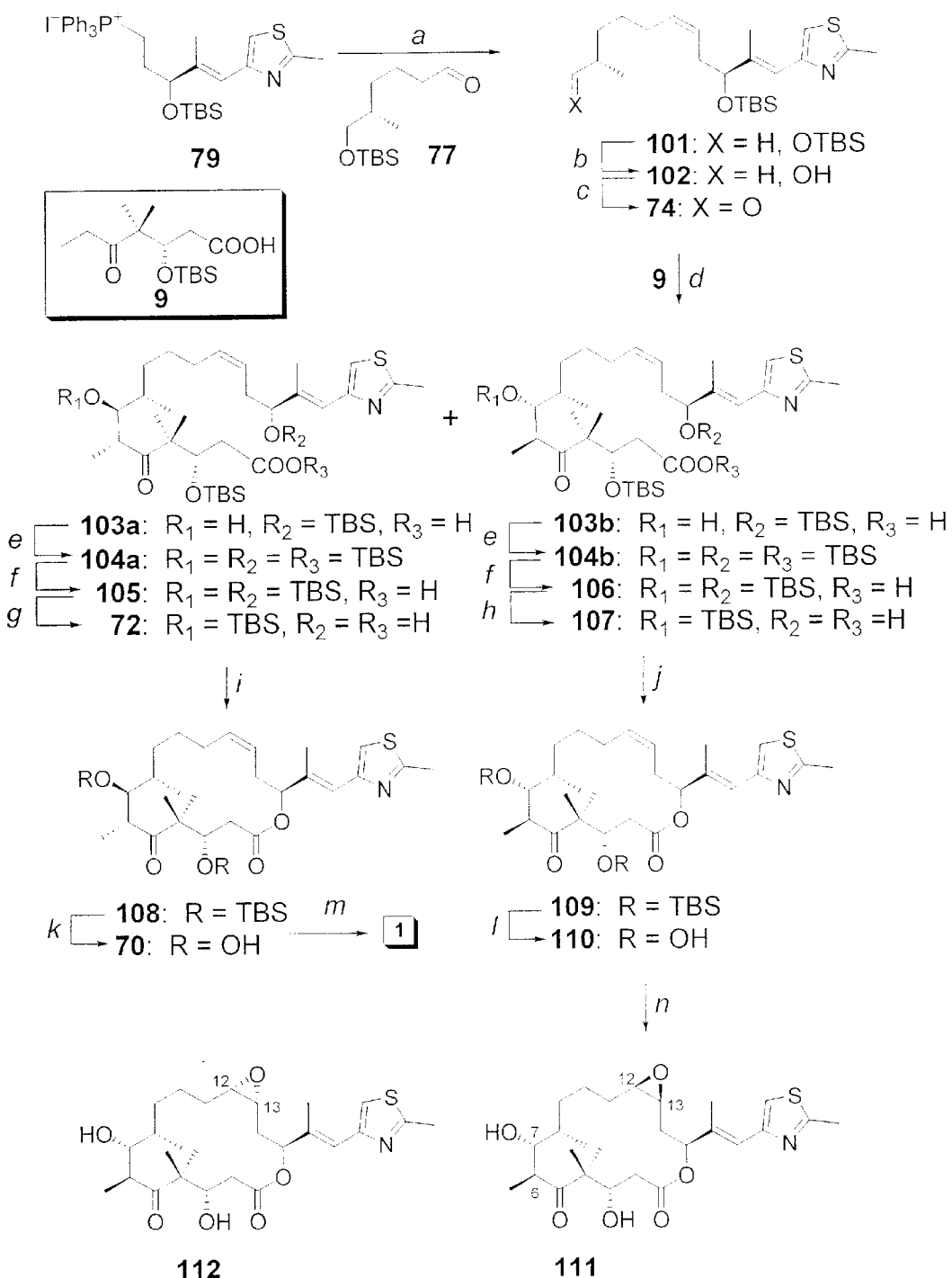

FIG. 14 illustrates the total synthesis of epothilone A (1) and its 6S,7R-diastereoisomers (111 and 112). Reagents and conditions: (a) 1.2 equivalents of 79, 1.2 equivalents of NaHMDS, THF, 0° C., 15 minutes, then add 1.0 equivalent of aldehyde 77, 0° C., 15 minutes, 77% (Z:E ca. 9:1); (b) 1.0 equivalent of CSA portionwise over 1 hour, Methylene chloride:MeOH (1:1), 0→25° C., 0.5 hour, 86%; (c) 2.0 equivalents of $SO_3$.pyr., 10.0 equivalents of DMSO, 5.0 equivalents of $Et_3N$, Methylene chloride, 25° C., 0.5 hour, 94%; (d) 3.0 equivalents of LDA, THF, 0° C., 15 minutes; then 1.2 equivalents of 76 in THF, −78→−40° C., 0.5 hour; then 1.0 equivalent of 74 in THF at −78° C., high yield of 103a and its $^6$S,7R-diastereoisomer 103b (ca. 1:1 ratio); (e) 3.0 equivalents of TBSOTf, 5.0 equivalents of 2,6-lutidine, Methylene chloride, 0° C., 2 hours; (f) 2.0 equivalents of $K_2CO_3$, MeOH, 25° C., 15 minutes, 31% of 105 and 30% of 6S,7R-diastereoisomer 106 from 74; (g) 6.0 equivalents of TBAF, THF, 25° C., 8 hours, 78%; (h) same as g, 82%; (i) 5.0 equivalents of 2,4,6-trichlorobenzoylchloride, 6.0 equivalents of $Et_3N$, THF, 25° C., 15 minutes; then add to a solution of 40.0 equivalents of 4-DMAP in toluene (0.002 M based on 72), 25° C., 0.5 hour, 90%; (j) same as i, 85%; (k) 20% $CF_3COOH$ (by volume) in Methylene chloride, 0° C., 1 hour, 92%; (l) saine as k, 95%; (m) methyl (trifluoromethyl)dioxirane, MeCN, 0° C., 75% (ca 5:1 ratio of diastereoisomers); (n) same as m, 87% (111:112 ca 2:1 ratio of diastereoisomers, tentative stereochemistry).

FIG. 15 illustrates the synthesis of compound 101. Reagents and conditions: (a) 1.5 equivalents of 12, 3.0 equivalents of imidazole, 1.5 equivalents of $Ph_3P$, $Et_2O$:MeCN (3:1), 0° C., 0.5 hour, 91%; (b) 1.1 equivalents $Ph_3P$, neat, 100° C., 2 hours, 91%; (c) 1.2 equivalents of 114, 1.2 equivalents of NaHMDS, THF, 0° C., 15 minutes; then add 1.0 equivalent of aldehyde 82, 0° C., 15 minutes, 69% (Z:E ca 9:1).

Figure 16:
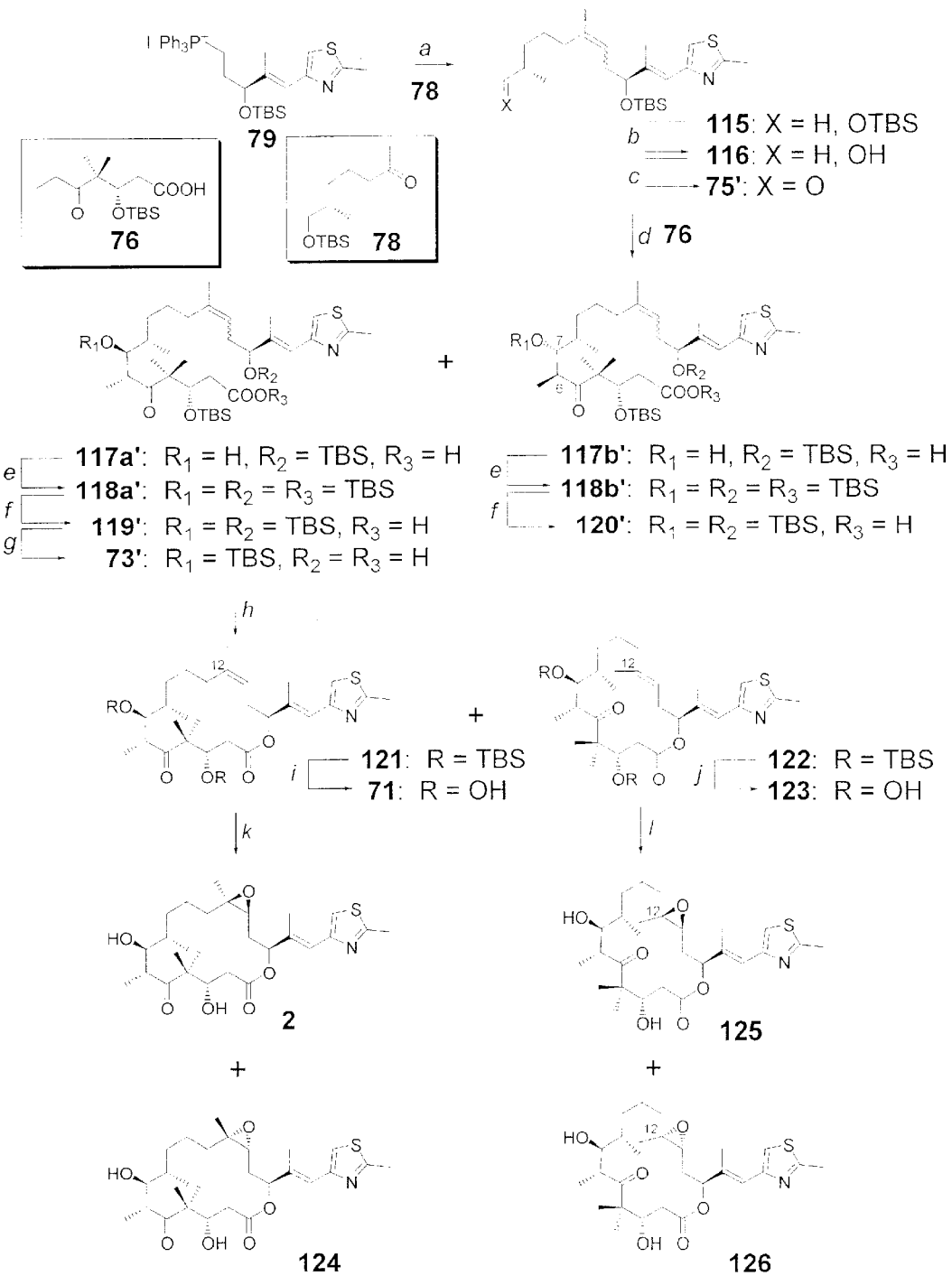

FIG. 16 illustrates the total synthesis of epothilone B (2) and analogs. Reagents and conditions: (a) 1.5 equivalents of 79, 1.5 equivalents of NaHMDS, THF, 0° C., 15 minutes, then add 1.0 equivalent of ketone 78, −20° C., 12 hours, 73% (Z:E ca 1:1); (b) 1.0 equivalent of CSA portionwise over 1 hour, Methylene chloride:MeOH (1:1), 0° C.; then 25° C., 0.5 hour, 97%; (c) 2.0 equivalents of $SO_3$.pyr., 10.0 equivalents of DMSO, 5.0 equivalents of $Et_3N$, Methylene chloride, 25° C., 0.5 hour, 95%; (d) 3.0 equivalents of LDA, THF, 0° C., 15 minutes; then 1.2 equivalents of 76 in THF, −78→−40° C., 0.5 hour; then 1.0 equivalent of 75' in THF at −78° C., high yield of 117a' and its 6S,7R-diastereoisomer 117b' (ca 1:1 ratio); (e) 3.0 equivalents of TBSOTf, 5.0 equivalents of 2,6-lutidine, Methylene chloride, 0° C., 2 hours; (f) 2.0 equivalents of $K_2CO_{31}$ MeOH, 25° C., 15 minutes, 31% of 119' and 30% of 6S,7R-diastereoisomer 120' from 75'; (g) 6.0 equivalents of TBAF, THF, 25° C., 8 hours, 75%; (h) 1.3 equivalents of 2,4,6-trichlorobenzoylchloride, 2.2 equivalents of $Et_3N$, THF, 0° C., 1 hour; then add to a solution of 10.0 equivalents of 4-DMAP in toluene (0.002 M based on 73'), 25° C., 12 hours, 37% of 121; and 40% of 122; (i) 20% $CF_3COOH$ (by volume) in Methylene chloride, −10→0° C., 1 hour, 91%; (j) same as i, 89%; (k) dimethyldioxirane, Methylene chloride, −50° C., 75% (2:124 ca 5:1 ratio of diastereoisomers) or 1.5 equivalents of mCPBA, benzene, 3° C., 2 hours, 66% (2:124 ca 5:1 ratio of diastereoisomers) or methyl(trifluoromethyl) dioxirane, MeCN, 0° C., 85% (2:124 ca 5:1 ratio of diastereoisomers); (1) 1.5 equivalents mCPBA, benzene. 3° C., 2 hours, 73% (125:126 ca 4:1 ratio of stereoisomers) or methyl(trifluoromethyl)dioxirane, MeCN, 0° C., 86% (125:126 ca 1:1 ratio of diastereoisomers).

Figure 17:
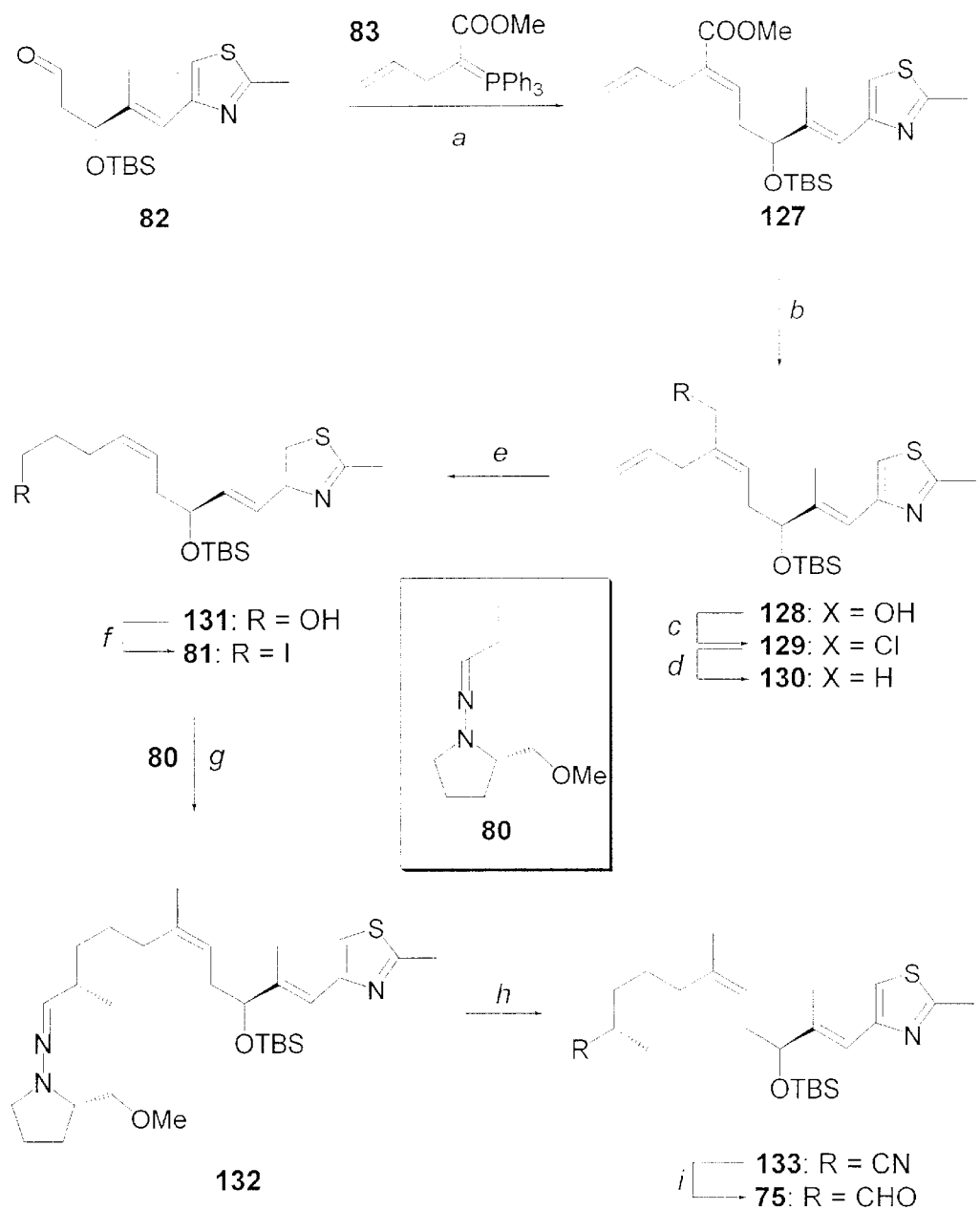

FIG. 17 illustrates the stereoselective synthesis of aldehyde 75 for epothilone B (2). Reagents and conditions: (a) 1.5 equivalents of 83, benzene, reflux, 5 hours, 95%; (b) 3.0 equivalents of DIBAL, Methylene chloride, −78° C., 2 hours, 98%; (c) 2.0 equivalents of $Ph_3P$, $CCl_4$, reflux, 24 hours, 83%; (d) 2.0 equivalents of $LiEt_3BH$, THF, 0° C., 1 hour, 99%; (e) 1.2 equivalents of 9-BBN, THF, 0° C., 2 hours, 91%; (f) 1.5 equivalents of $I_2$, 3.0 equivalents of imidazole, 1.5 equivalents of $Ph_3P$, $Et_2O$:MeCN (3:1), 0° C., 0.5 hour, 92%; (g) 1.5 equivalents of 80, 1.5 equivalents of LDA, THF, 0° C., 8 hours; then 1.0 equivalent of 81 in THF, −100→−20° C., 10 hours, 70%; (h) 2.5 equivalents of monoperoxyphthalic acid, magnesium salt (MMPP), MeO-H:phosphate buffer pH7 (1:1), 0° C., 1 hour , 80%; (i) 2.0 equivalents DIBAL, toluene, −78° C., 1 hour, 82%.

Figure 18:
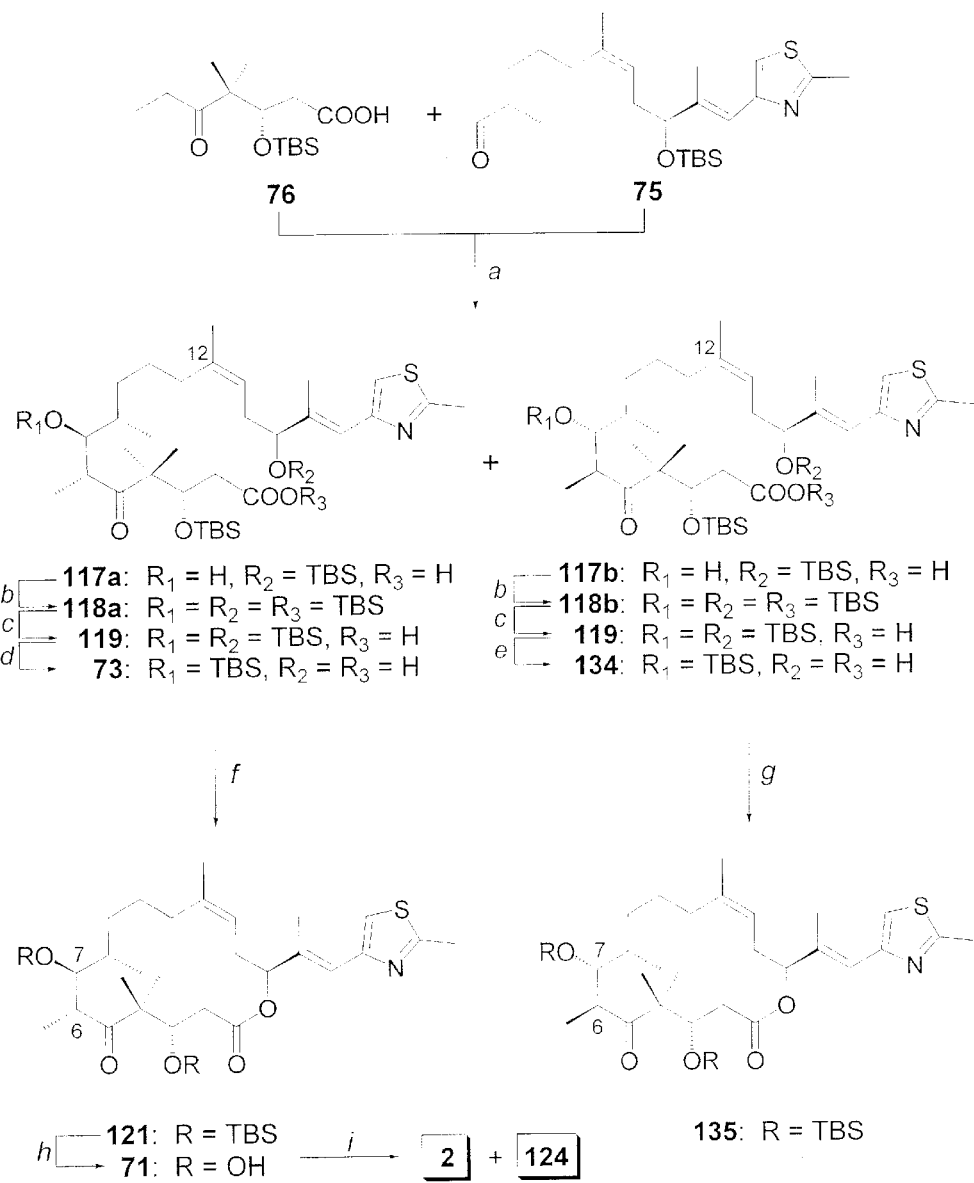

FIG. 18 illustrates the first stereoselective total synthesis of epothilone B (2). Reagents and conditions: (a) 3.0 equivalents of LDA, THF, 0° C., 15 minutes; then 1.2 equivalents of 76 in THF, −78→−40° C., 0.5 hour, then 1.0 equivalent of 75 in THF at −78° C., high yield of 117a and 6S,7R-diastereoisomer 117b (ca 1.3:1.0 ratio of diastereoisomers); (b) 3.0 equivalents of TBSOTf, 5.0 equivalents of 2,6-lutidine, Methylene chloride, 0° C., 2 hours; (c) 2.0 equivalents of $K_2CO_3$, MeOH, 25° C., 15 minutes, 32% of 119 and 28% of 6S,7R-diastereoisomer 119 from 75; (d) 6.0 equivalents of TBAF, THF, 25° C., 8 hours, 73%; (e) same as d, 71%; (f) 5.0 equivalents of 2,4,6-trichlorobenzoylchloride, 6.0 equivalents of $Et_3N$, THF, 25° C., 15 minutes, then add to a solution of 10.0 equivalents of of 4-DMAP in toluene (0.002 M based on 73), 25° C., 12 hours, 77%; (g) same as f, 76%; (h) 20% $CF_3COOH$ (by volume) in Methylene chloride, 0° C., 1 hour, 91%; (i) see FIG. 16.

Figure 19:
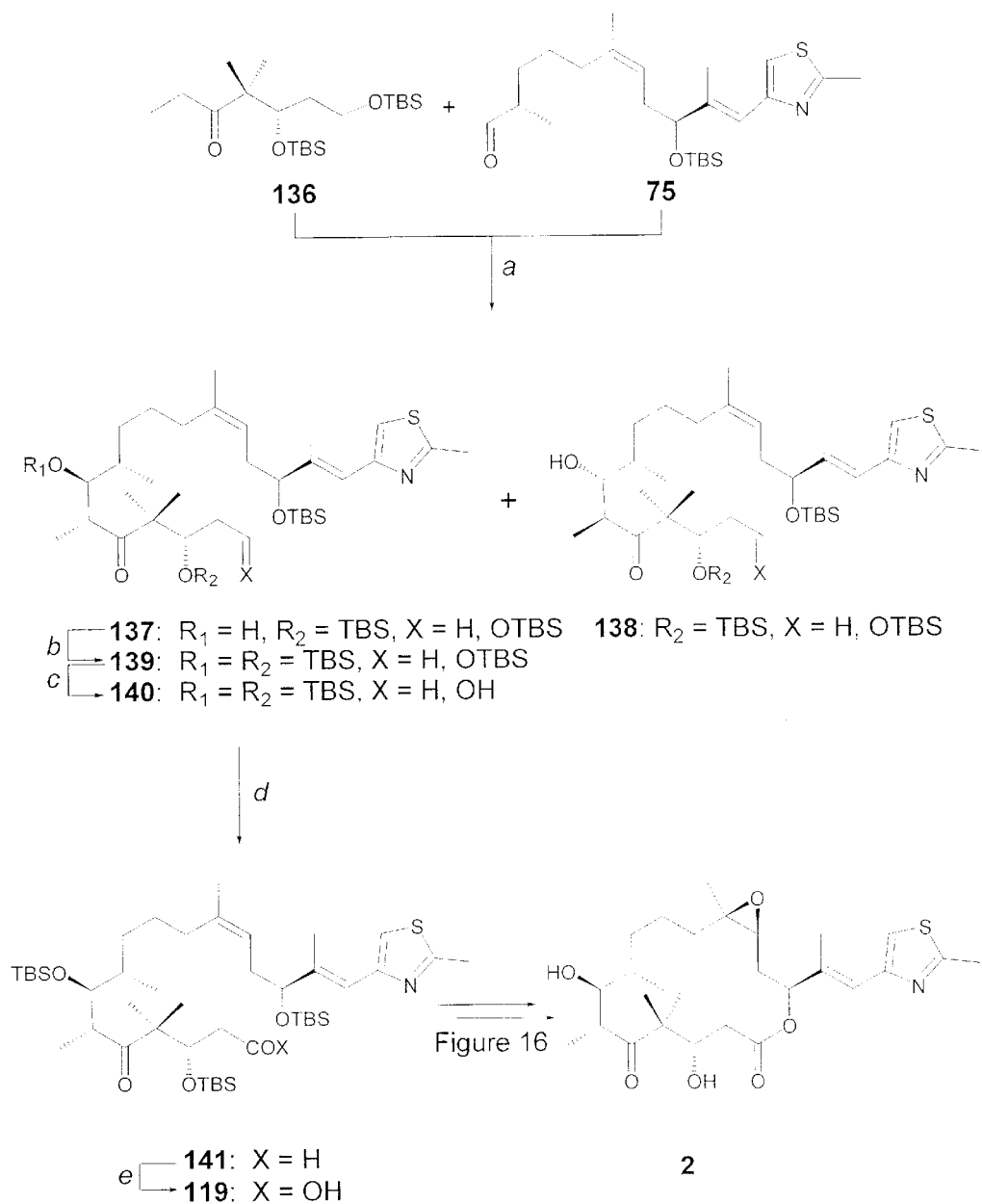

FIG. 19 illustrates the second stereoselective synthesis of epothilone B (2). Reagents and conditions: (a) 1.2 equivalents of LDA, THF, 0° C., 15 minutes; then 1.2 equivalents of 136 in THF, −78→−40° C., 1 hour; then 1.0 equivalent of 75 in THF at −78° C., 85% of 137 and 6S, 7R-diastereoisomer 138 (ca 3:1 ratio); (b) 1.2 equivalents of TBSOTf, 2.0 equivalents of 2,6-lutidine, Methylene chloride, 0° C., 2 hours, 96%; (c) 1.0 equivalent of CSA portionwise over 1 hour, Methylene chloride:MeOH (1:1), 0→25° C., 0.5 hour, 85%; (c) 2.0 equivalents of $(COCl)_2$, 4.0 equivalents of DMSO, 6.0 equivalents of $Et_3N$, Methylene chloride, −78→0° C., 1.5 hours, 95%; (d) 3.0 equivalents of $NaClO_2$, 4.0 equivalents of 2-methyl-2-butene, 1.5 equivalents of $NaH_2PO_4$, tBuOH:$H_2O$ (5:1), 25° C., 2 hours, 90%.

Figure 20:
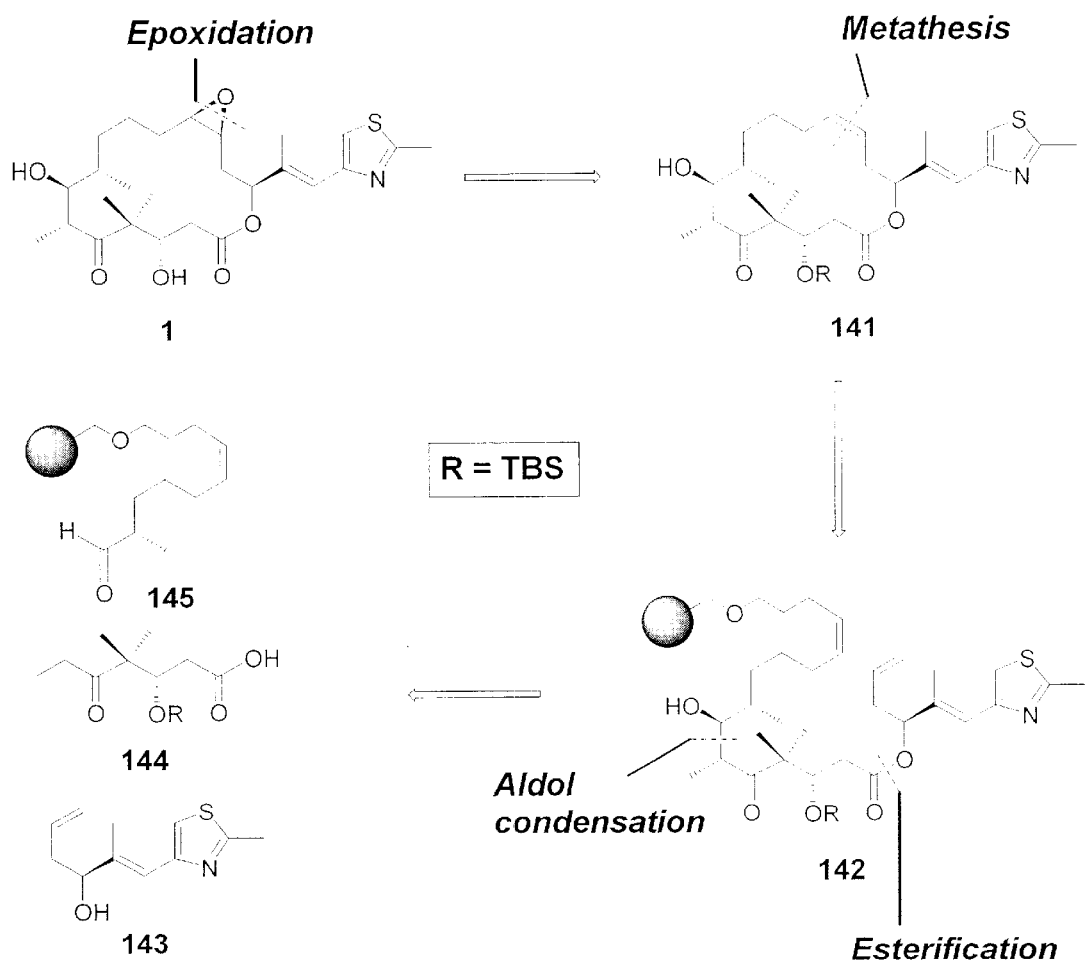

FIG. 20 illustrates the retrosynthetic analysis of epothilone A (1) by a solid phase olefin metathesis strategy wherein TBS=t-$BuMe_2Si$; filled circle=polystyrene.

Figure 21:
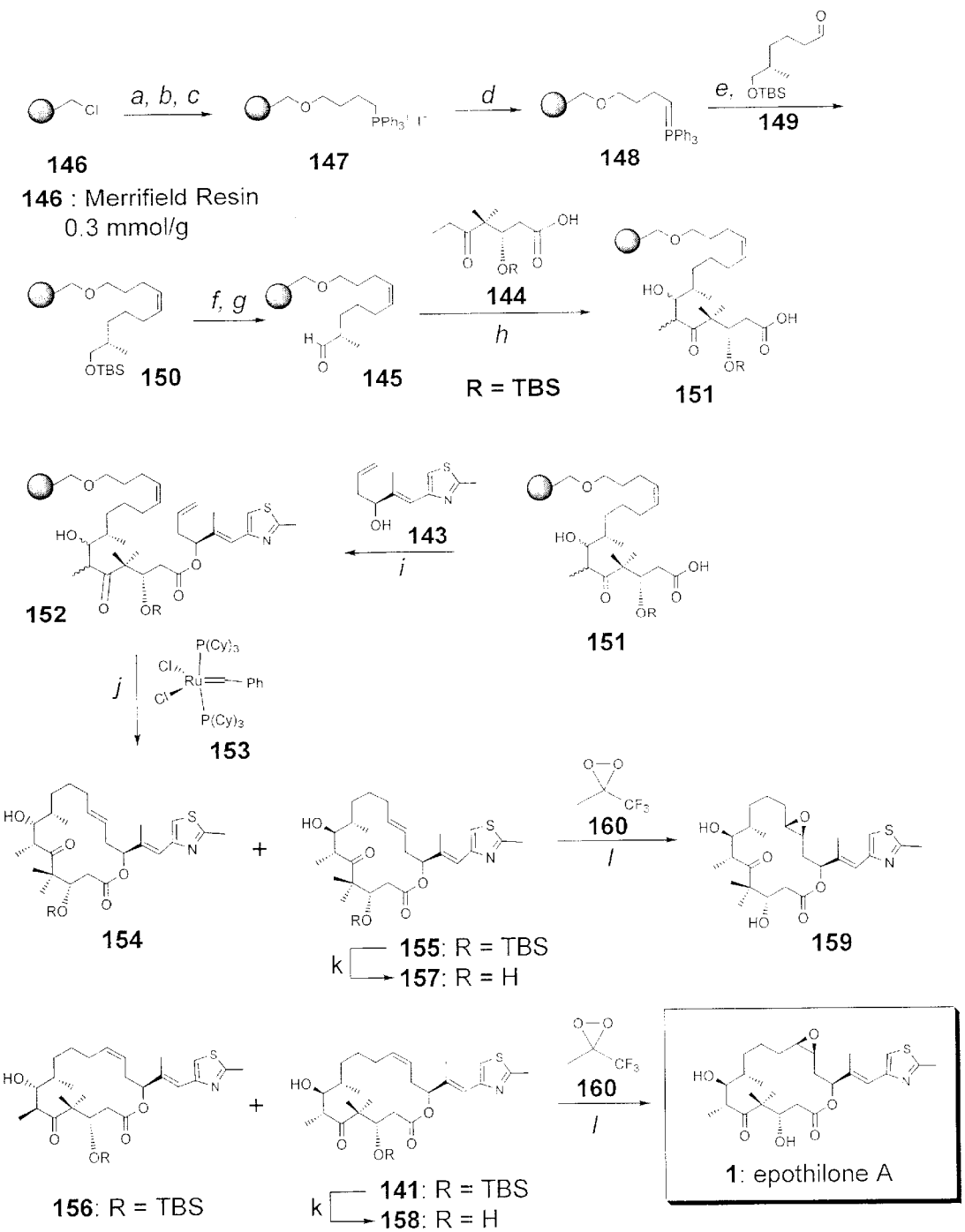

FIG. 21 illustrates the solid phase synthesis of epothilone a wherein: (a) 1,4-butanediol (5.0 eq.), NaH (5.0 eq.), n-$Bu_4NI$ (0.1 eq.), DMF, 25° C., 12 hours; (b) $Ph_3P$ (4.0 eq.), $I_2$ (4.0 eq.), imidazole (4.0 eq.), Methylene chloride, 25° C., 3 hours; (c) $Ph_3P$ (10 eq.), 90° C., 12 hours (>90% for 3 steps based on mass gain of polymer); (d) NaHMDS (3.0 eq.), THF:DMSO (1:1), 25° C., 12 hours; (e) 149 (2.0 eq.), THF, 0° C., 3 hours (>70% based on aldehyde recovered from ozonolysis); (f) 10% HF·pyridine in THF, 25° C., 12 hours; (g) $(COCl)_2$ (4.0 eq.), DMSO (8.0 eq.), $Et_3N$ (12.5 eq.), −78→25° C. (ca. 95% for 2 steps)*; (h) 144 (2.0 eq.), LDA (2.2 eq), THF, −78→−40° C., 1 hour; then add resulting enolate to the resin suspended in a ZnCl$_2$ (2.0 eq.) solution in THF, −78→−40° C., 2.0 hours (ca. 90%)*; (i) 143 (5.0 eq.), DCC (5.0 eq), 4-DMAP (5.0 eq.), 25° C., 15 h (80% yield as determined by recovered heterocycle fragments obtained by treatment with NaOMe); (j) 153 (0.75 eq.), Methylene chloride, 25° C., 48 hours (52%; 154:155:156:141=ca. 3:3:1:3); (k) 20% TFA in Methylene chloride (v/v), 92% for 157 and 90% for 158; (l) 160 [methyl(trifluoromethyl)dioxirane], MeCN, 0° C., 2 hours (70% for 1, 45% for 159; in addition to these products, the corresponding a-epoxides were also obtained). NaHMDS= sodium bis(trimethylsilyl)amide; DMSO=dimethyl sulfoxide; LDA=lithium diisopropylamide; TBS=t-BuMe$_2$Si; 4-DMAP=4-dimethylaminopyridine. * Estimated yield. The reaction was monitored by infrared (IR) analysis of polymer-bound material and by TLC analysis of the products obtained by ozonolysis.

Figure 22:
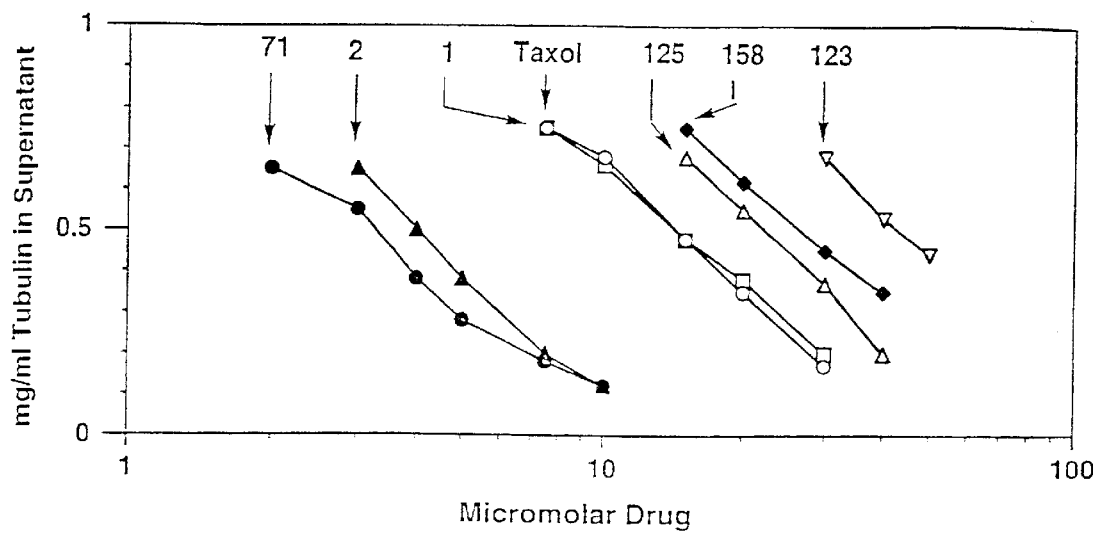

FIG. 22 illustrates activity of epothilones on tubulin assembly. Reaction mixtures contained purified tubulin at 1.0 mg/ml, 0.4 M monosodium glutamate, 5% dimethyl sulfoxide, and varying drug concentrations. Each compound was evaluated in three different experiments and average values are shown. Samples were incubated, centrifuged, and processed at room temperature (dark circle=71, EC$_{50}$= 3.3±0.2 μM; dark triangle=2, EC$_{50}$=4.0±0.1 μM; open circle=1, EC$_{50}$=14±0.4 μM; open square=taxol, EC$_{50}$=15±2 μM; open triangle=125, EC$_{50}$=22±0.9 μM; dark square=158, EC$_{50}$=25±1 μM; open upside down triangle=123, EC$_{50}$= 39±2 μM. The EC$_{50}$ is defined as the drug concentration that causes 50% of the tubulin to assemble into polymer. In the absence of drug, less than 5% of the tubulin was removed by centrifugation, while with high concentrations of the most active drugs, over 95% of the protein formed polymer. This suggests that at least 90% of the tubulin had the potential to interact with epothilones and taxoids. Although the EC$_{50}$ value obtained for Taxol was higher than that obtained in an alternate assay as described in Hofle et al. *Angew. Chem. Int. Ed. Engl* 35, 1567–1569 (1996), the agent's role in these experiments was only as a control.

FIG. 23 provides a table of results from cytotoxicity experiments with 1A9, 1A9PTX10 (β-tubulin mutant), 1A9PTX22 (β-tubulin mutant) and A2780AD cell lines showing relative activities of epothilones A (1) and B (2) as compared with synthetic analogues 71, 158, 123 and 125 as inducers of tubulin assembly and inhibitors of human ovarian carcinoma cell growth. (a) See FIG. 22; (b) The growth of all cells lines was evaluated by quantitation of the protein in microtiter plates. The parental cell line 1A9, a clone of the A2780 cell line, was used to select two Taxo'-resistant sublines (1A9PTX10 and 1A9PTX22). These sublines were selected by growth in the presence of Taxol and verapamil, a P-glycoprotein modulator. Two distinct point mutations in the β-tubulin isotype M40 gene were identified. In 1A9PTX10 amino acid residue 270 was changed from Phe (TTT) to Val (GTT), and in 1A9PTX22 residue 364 was changed from Ala (GCA) to Thr (ACA). The A2780AD line is a multidrug resistant (MDR) line expressing high levels of P-glycoprotein. Relative resistance refers to the ratio of the IC$_{50}$ value obtained with a resistant cell line to that obtained with the parental cell line.

Figure 24:
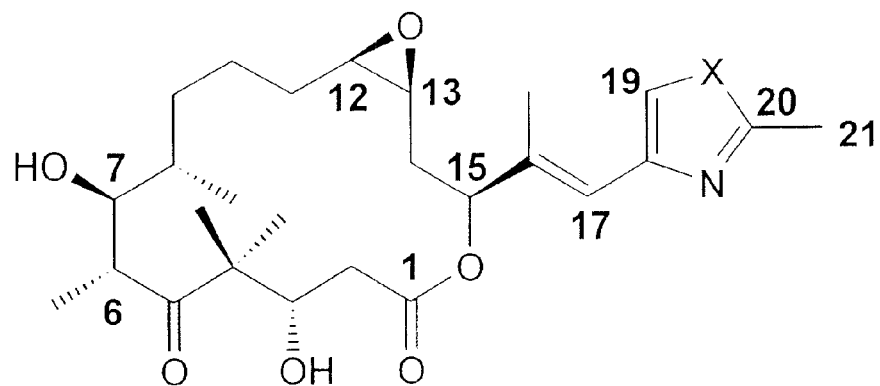

FIG. 24 illustrates the structure and numbering of epothilone A (1) and epoxalone A (2).

Figure 25:
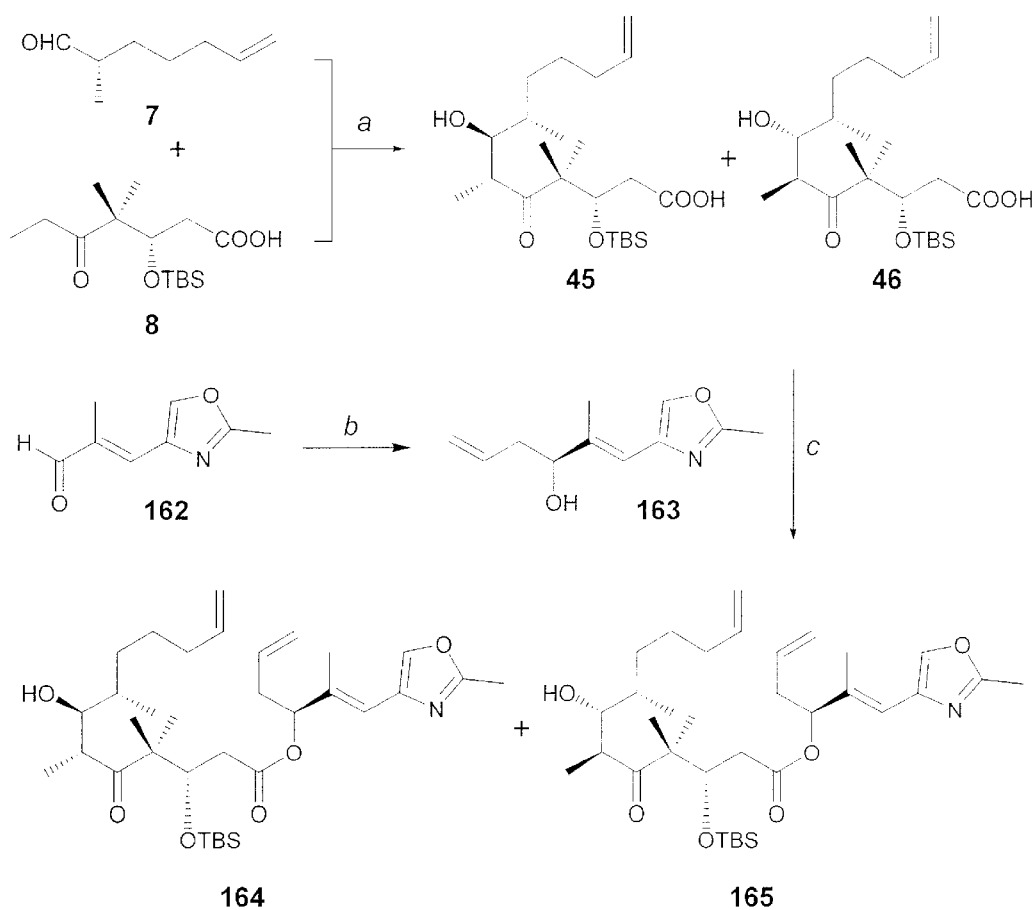

FIG. 25 illustrates the coupling of building blocks and construction of precursors 164 and 165. Reagents and conditions: (a) 2.4 equivalents of LDA, −40° C., THF, 1.5 hours, then 7 in THF, −40° C., 0.5 hour; 94% (45:46 ca 5:3); (b) 1.2 equivalents of (+)-Ipc$_2$B(allyl), Et$_2$O, −100° C., 0.5 hour, 91%; (c) 2.0 equivalents of 163, 1.5 equivalents of DCC, 1.5 equivalents of 4-DMAP, toluene, 25° C., 12 hours, 49% (164) plus 33% (165) for two steps. TBS=tert-butyldimethylsilyl; Ipc$_2$B(allyl)=diisopinocampheylallyl borane; LDA=lithium diisopropylamide; DCC= dicyclohexylcarbodiimide; 4-DMAP=4-dimethylaminopyridine.

Figure 26:
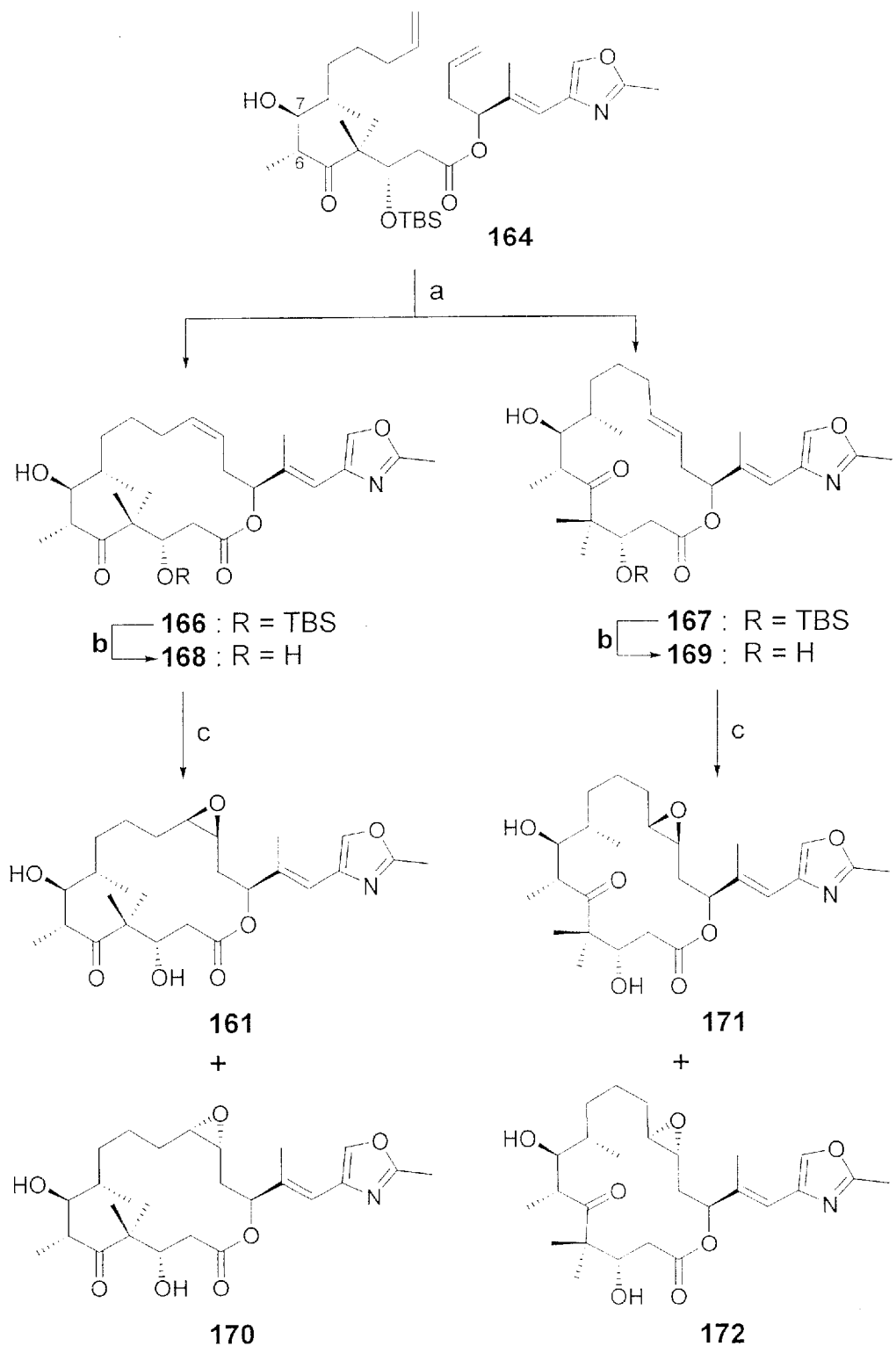

FIG. 26 illustrates the olefin metathesis of precursor 164 and synthesis of epoxalones 161, 171, 170 and 172. Reagents and conditions: (a) 20 mol % of RuCl$_2$(=CHPh) (PCy$_3$)$_2$ cat., CH$_2$Cl$_2$, 25° C., 20 hours, 40% (166) plus 29% (167); (b) 20% TFA in CH$_2$Cl$_2$, 25° C., 2 hours, 89% (168), 95% (169); (c) CH$_3$CN/Na$_2$EDTA (2:1), 10.0 equivalents of CF$_3$COCH$_3$, 8.0 equivalents of NaHCO$_3$, 3.0 equivalents of Oxone®, 0° C., 34% (161) plus 15% (170), 25% (171) plus 20% (172). TFA=trifluoroacetic acid. The tentative stereochemical assignments of epoxides 161, 171, 168, 169, 170 and 172 were based on the higher potencies at 161 and 171 in the tubulin polymerization assay as compared to those of 170 and 172 respectively (see FIG. 28).

Figure 27:
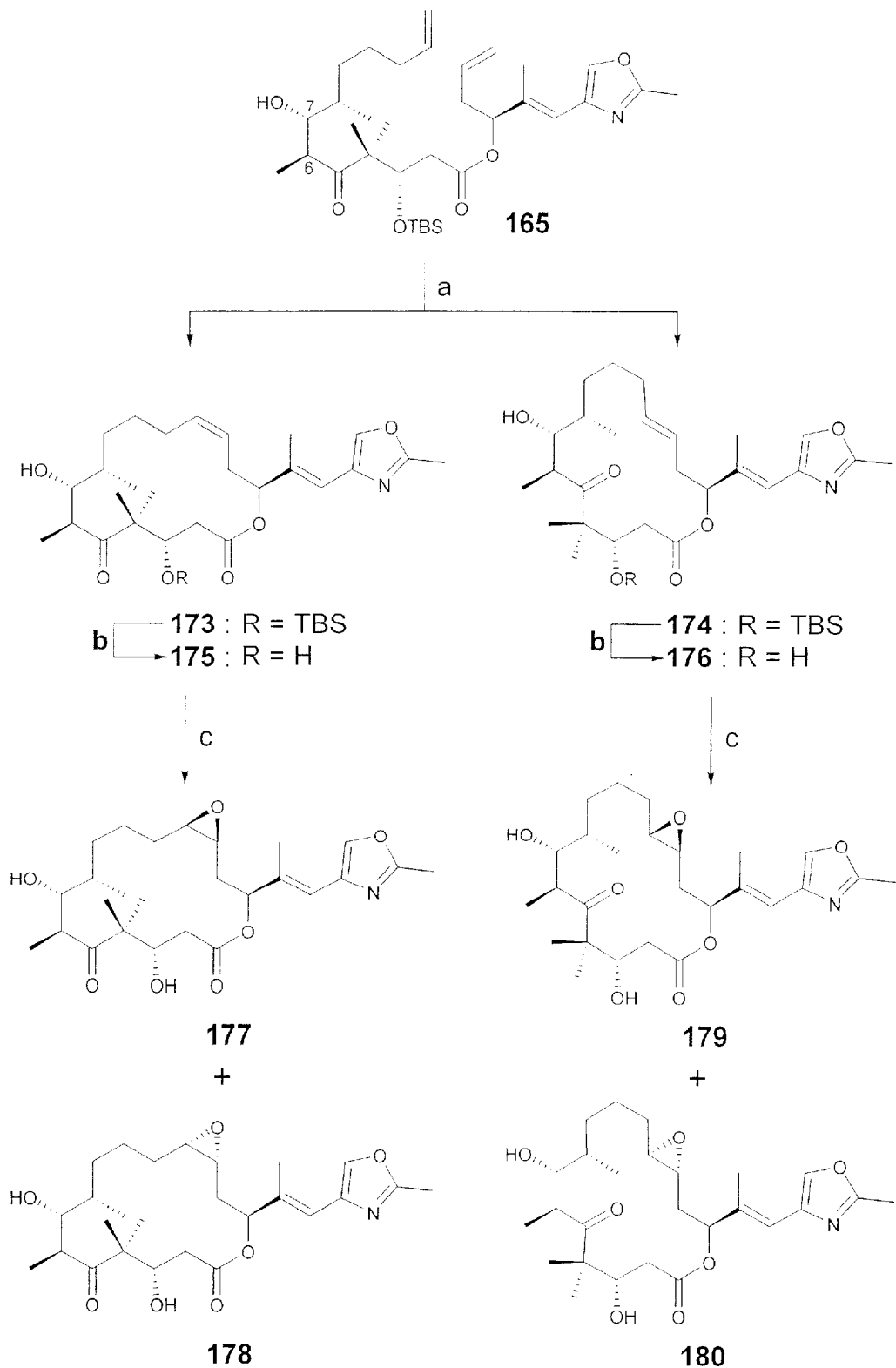

FIG. 27 illustrates the olefin metathesis of C6–7 diastereomeric precursor 165 and synthesis of epoxalones 175–180. Reagents and conditions. (a) 20 mol % of RuCl$_2$ (=CHPh) (PCy$_3$)$_2$ cat., CH$_2$Cl$_2$, 25° C., 20 hours, 25% (173) plus 63% (174); (b) 20% TFA in CH$_2$Cl$_2$, 25° C., 2 hours, 75% (175), 72% (176) (c) CH$_3$CN/Na$_2$EDTA (2:1), 10.0 equivalents of CF$_3$COCH$_3$, 8.0 equivalents of NaHCO$_3$, 3.0 equivalents of Oxone®, 0° C., 38% (177) plus 17% (178), 22% (179) plus 13% (180).

Figure 28:
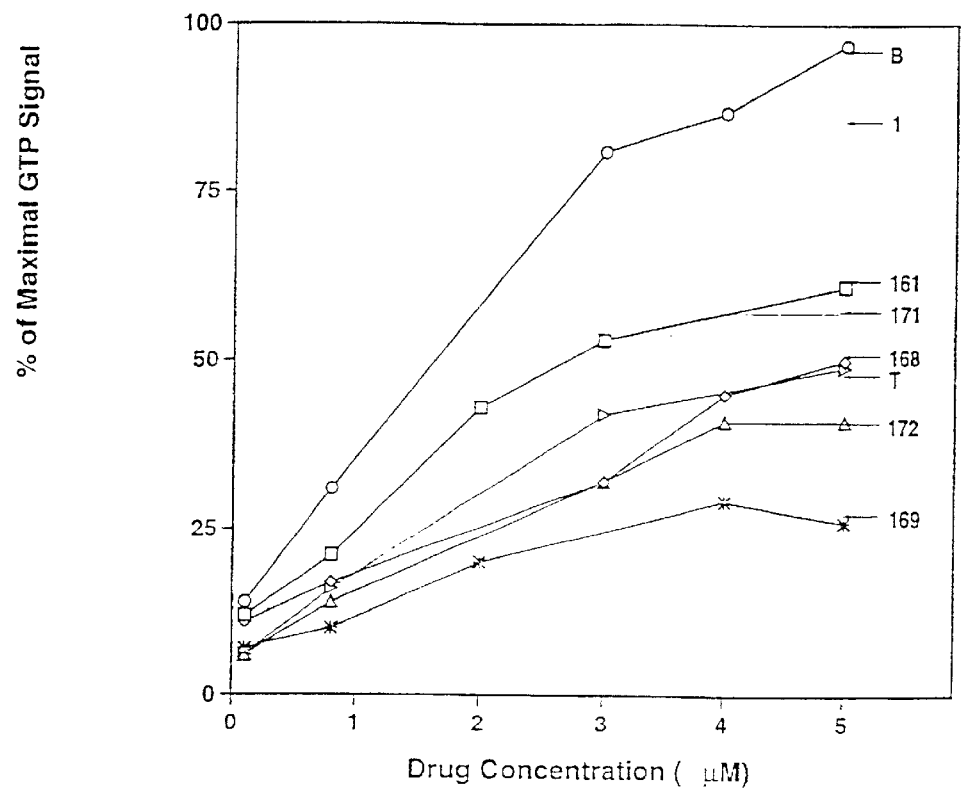

FIG. 28 illustrates the effect of epoxalones, epothilones and Taxol on tubulin polymerization. The Filtration-Colorimetric Assay was used for epothilones A and B except for the 30° C. incubation temperature (instead of 37° C.) and the pure tubulin (instead of microtubule protein). After initial screening of all epoxalones (161, 168, 169, 170, 171, 172, 175, 176, 177, 178, 179, and 180) at 20 mM concentrations, the most potent ones (161, 168, 169, 171 and 172) were tested together with epothilones A (1) and B and Taxol at 01, 1.0, 2.0, 3.0, 4.0 and 5.0 mM. B=epothilone B; T=Taxol.

Figure 29:
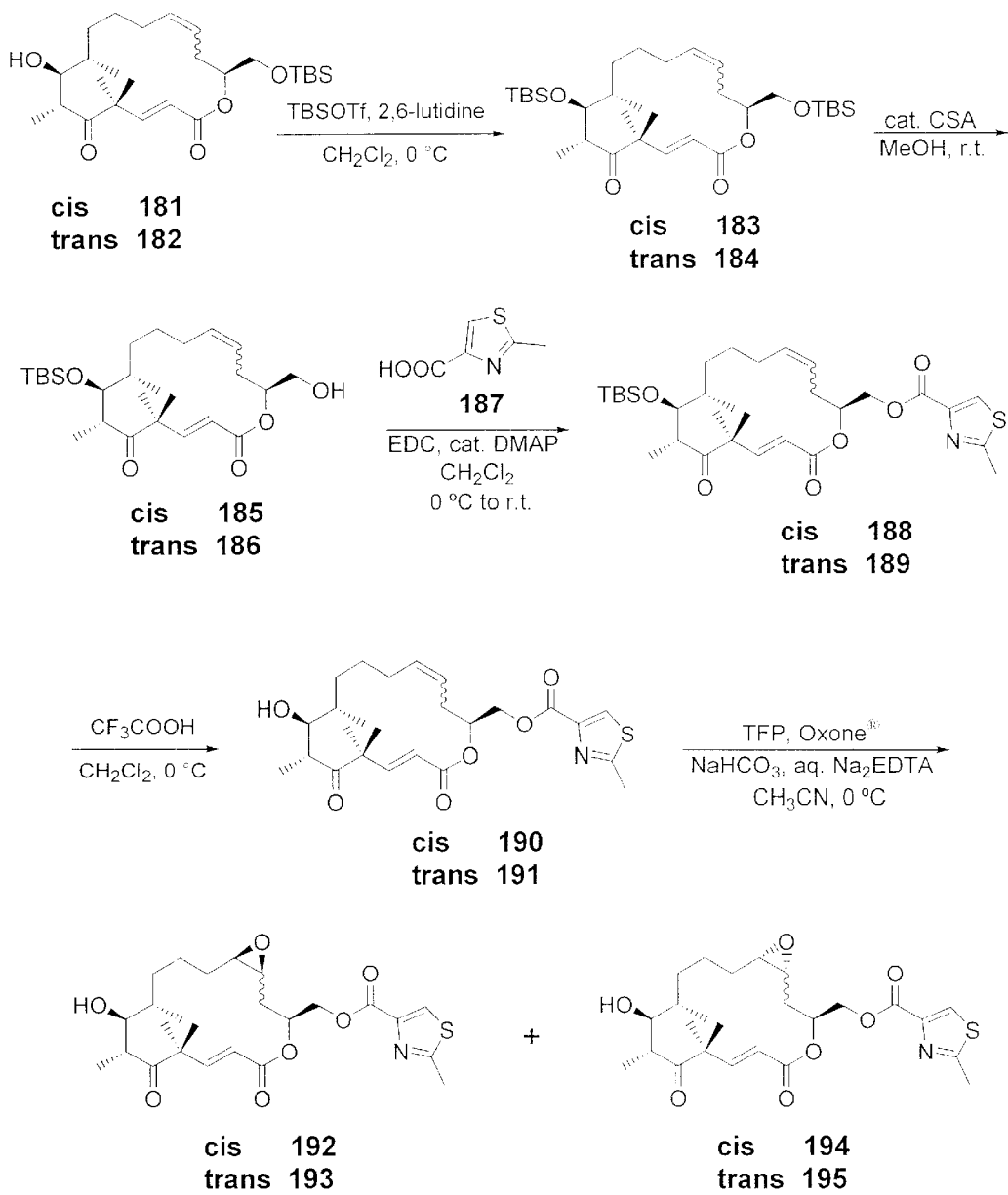

FIG. 29 illustrates the synthesis of epothilone analogs 192, 193, 194 and 195.

Figure 30:
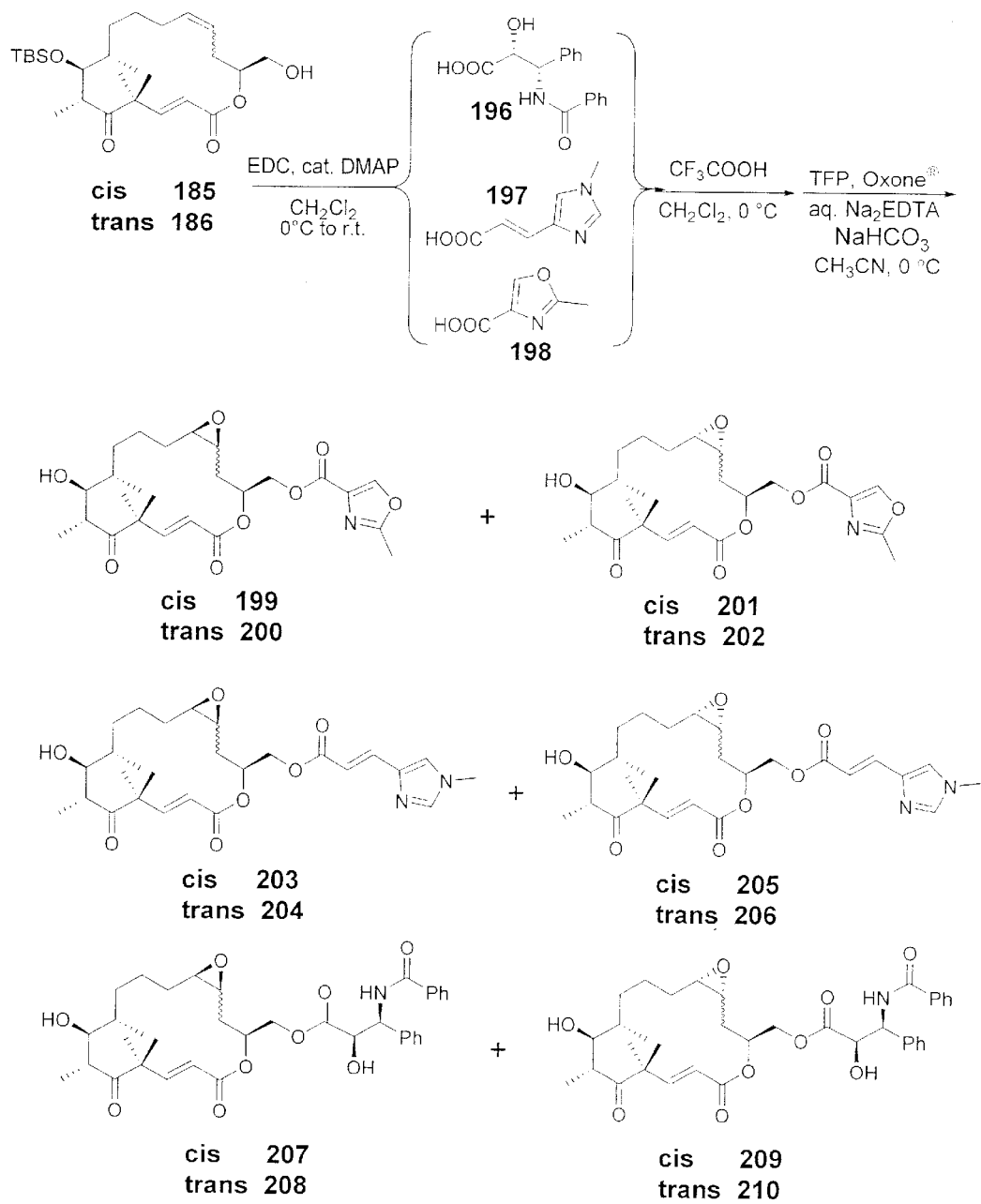

FIG. 30 illustrates the synthesis of epothilone analogs 199, 200, 201, 202, 203, 204, 205, 206, 207, 208, 209, and 210.

Figure 31:
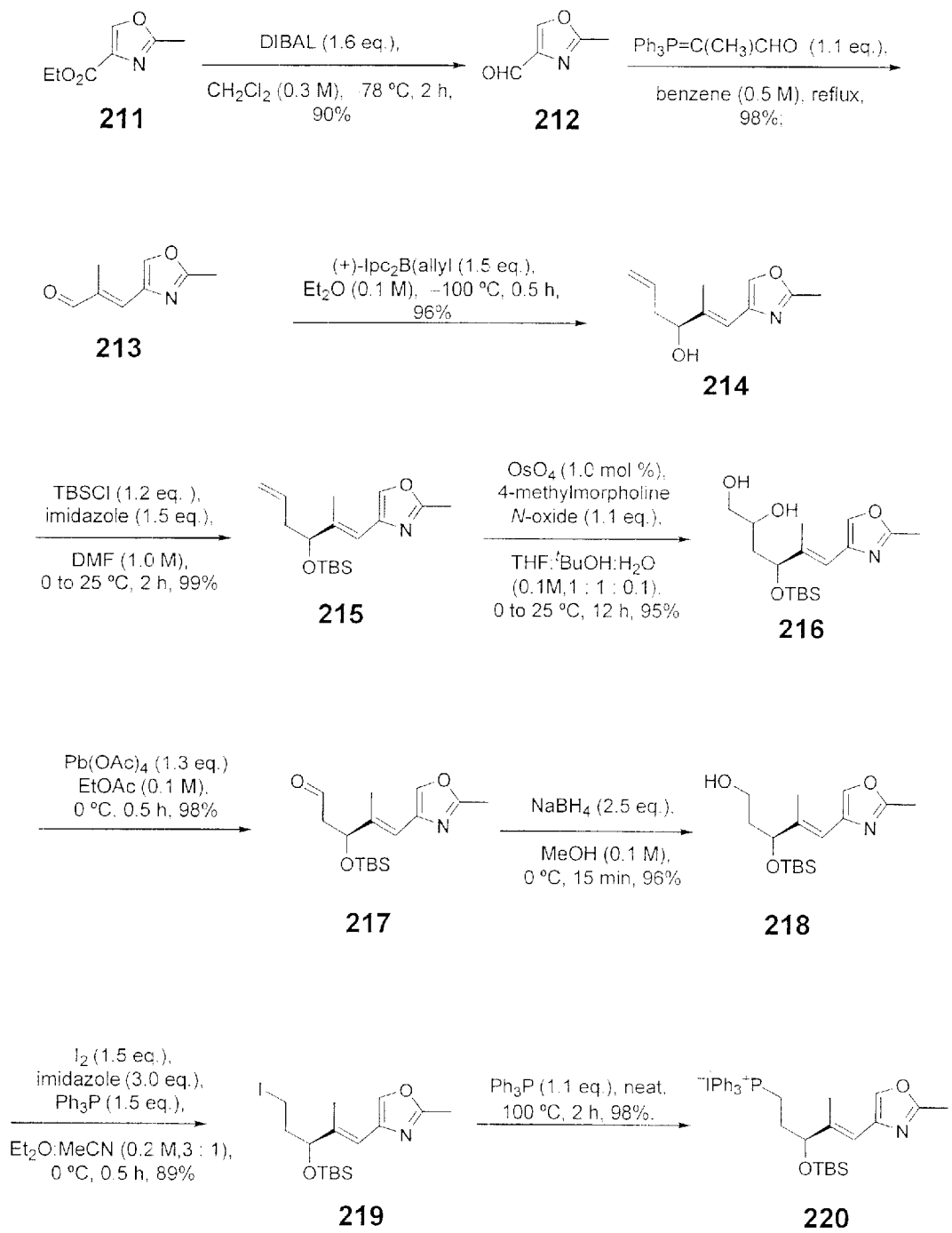

FIG. 31 illustrates the synthesis of phosphonium analog 220.

Figure 32:
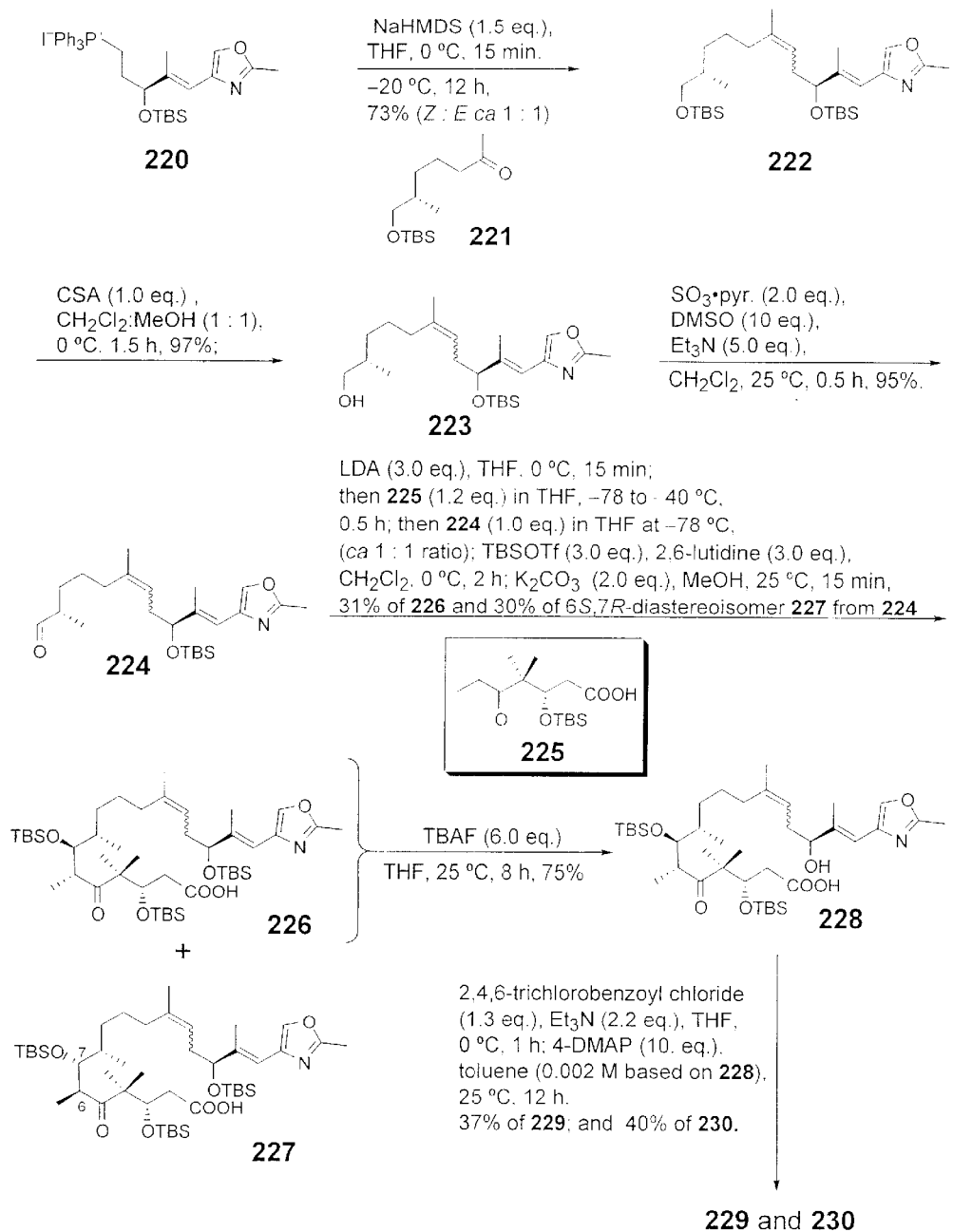

FIG. 32 illustrates the synthesis of epothilone advanced intermediate macrolides 229 and 230.

Figure 33:
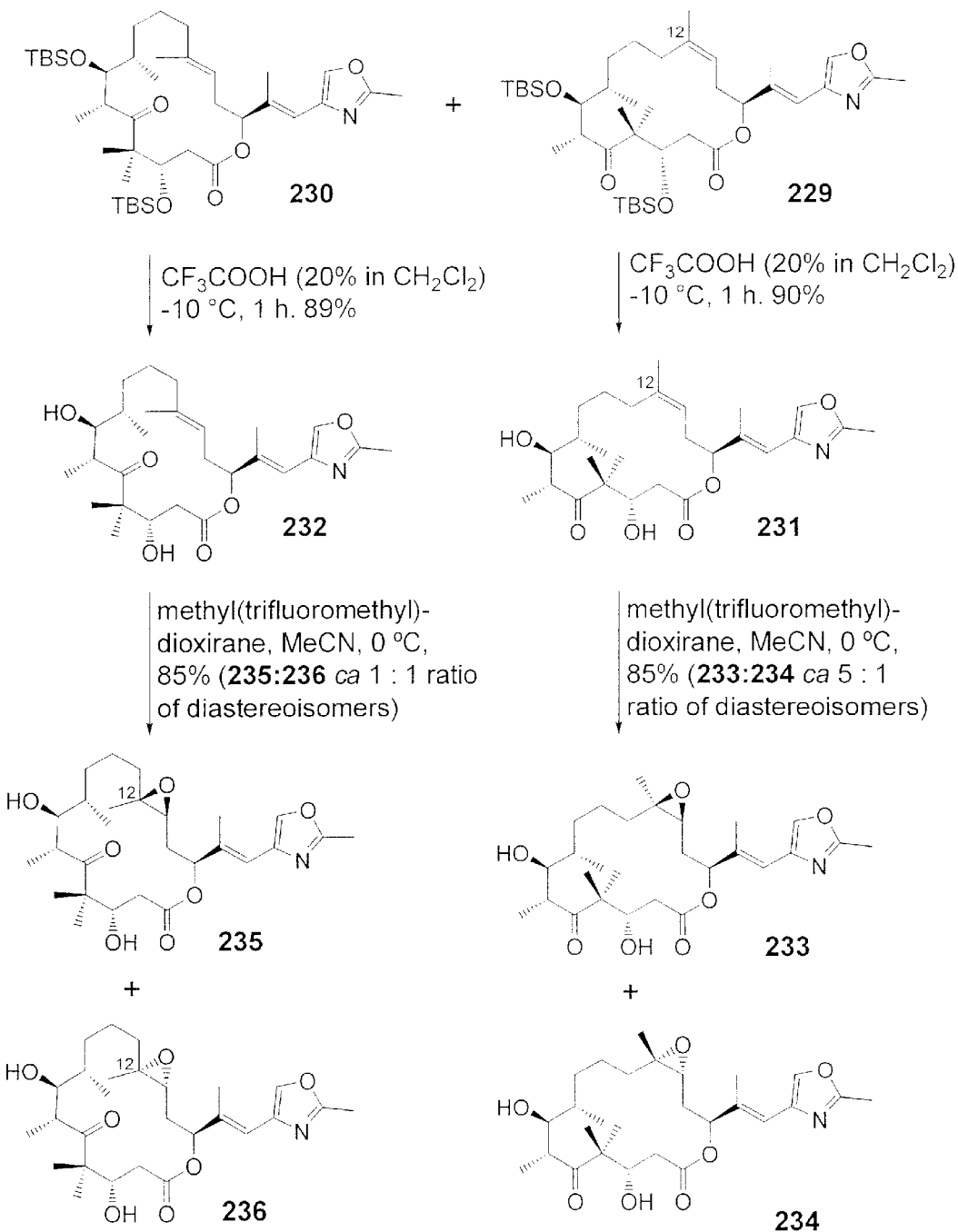

FIG. 33 illustrates the synthesis of epothilone analogs 233, 234, 235, and 236.

Figure 34:
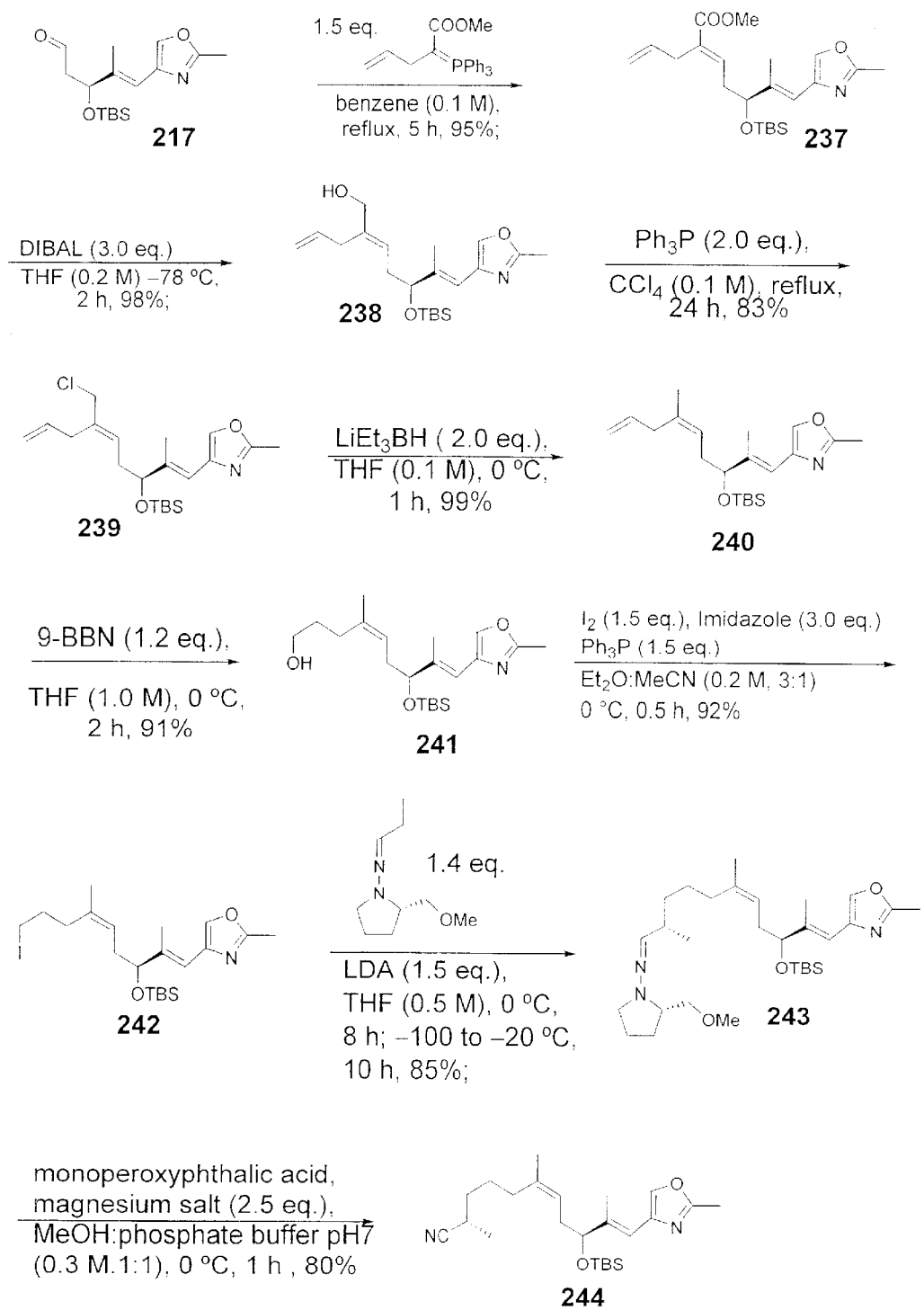

FIG. 34 illustrates the synthesis of advanced intermediate nitrile 244.

Figure 35:
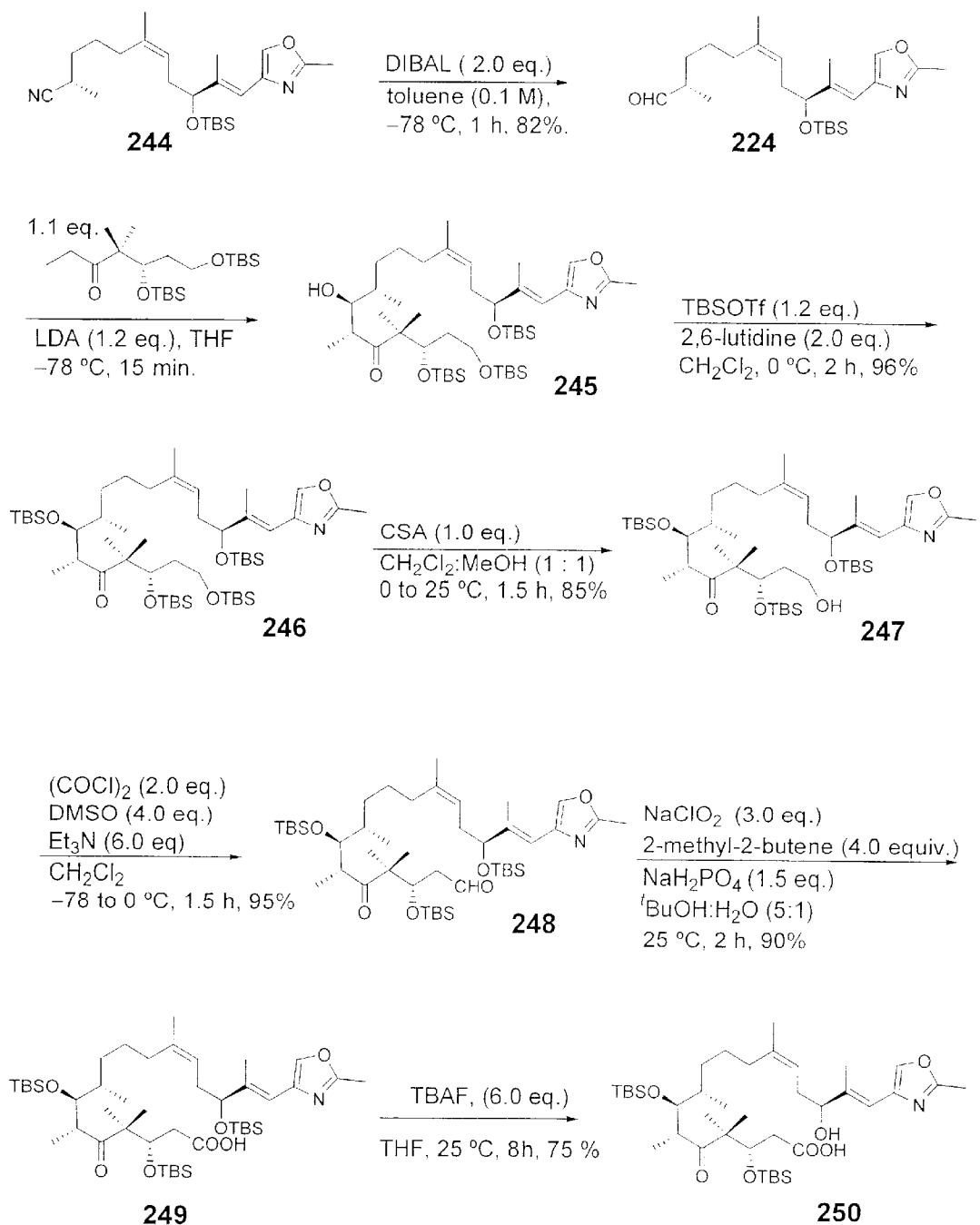

FIG. 35 illustrates the synthesis of epothilone analog 249.

FIG. 36 illustrates the synthesis of epothilone analog 229.

Figure 37:
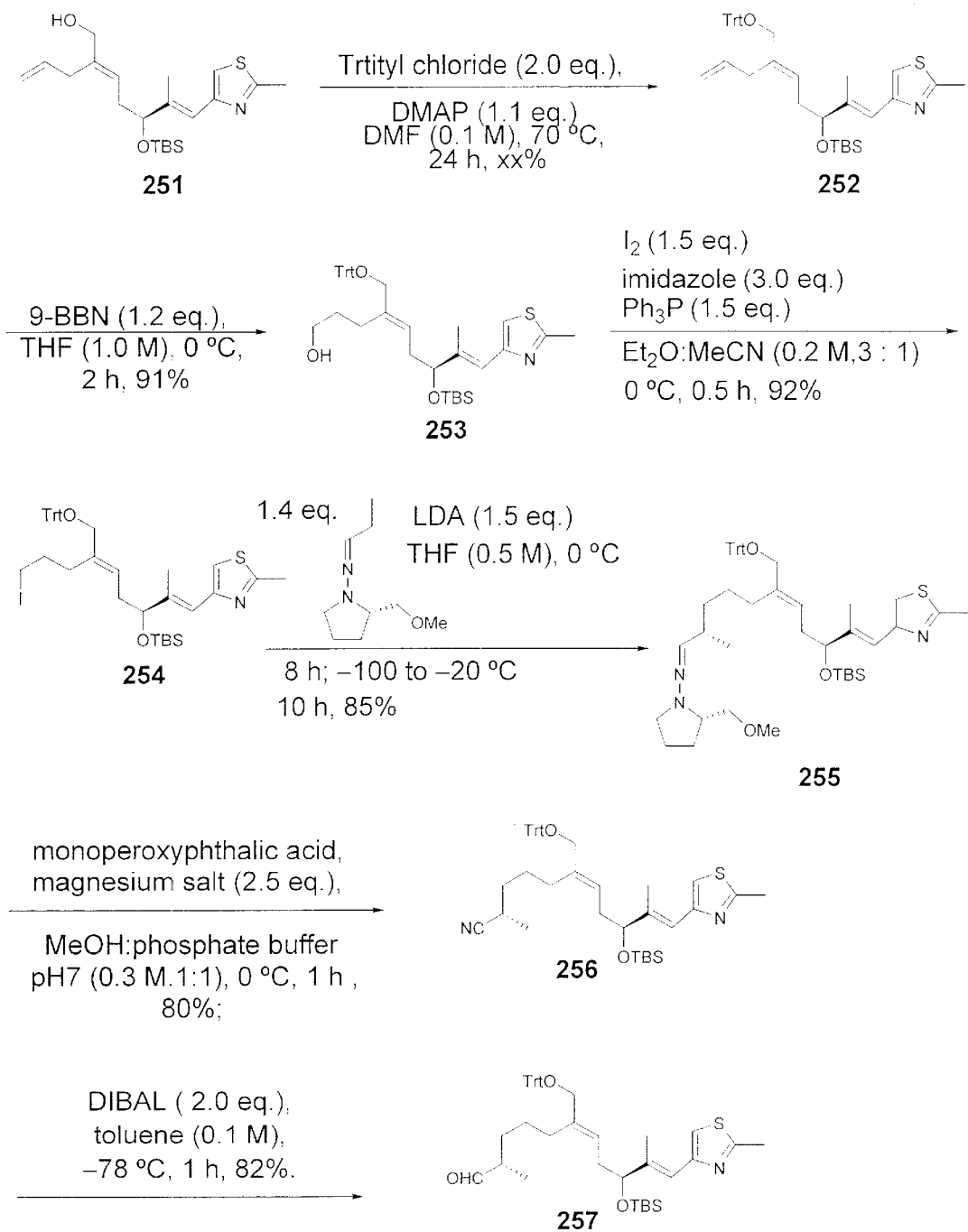

FIG. 37 illustrates the synthesis of advanced intermediate aldehyde 257.

Figure 38:
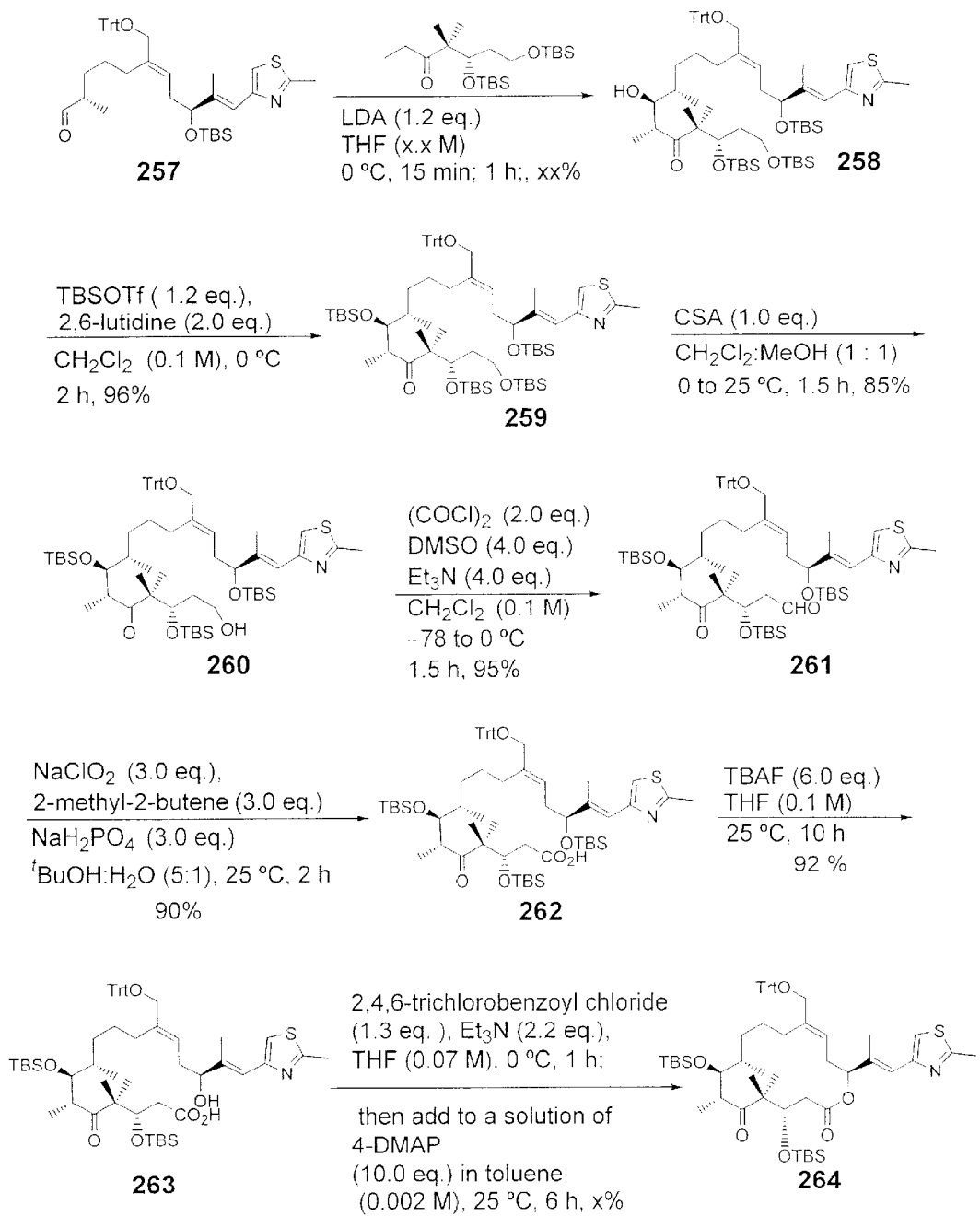

FIG. 38 illustrates the synthesis of epothilone analog 263.

Figure 39:
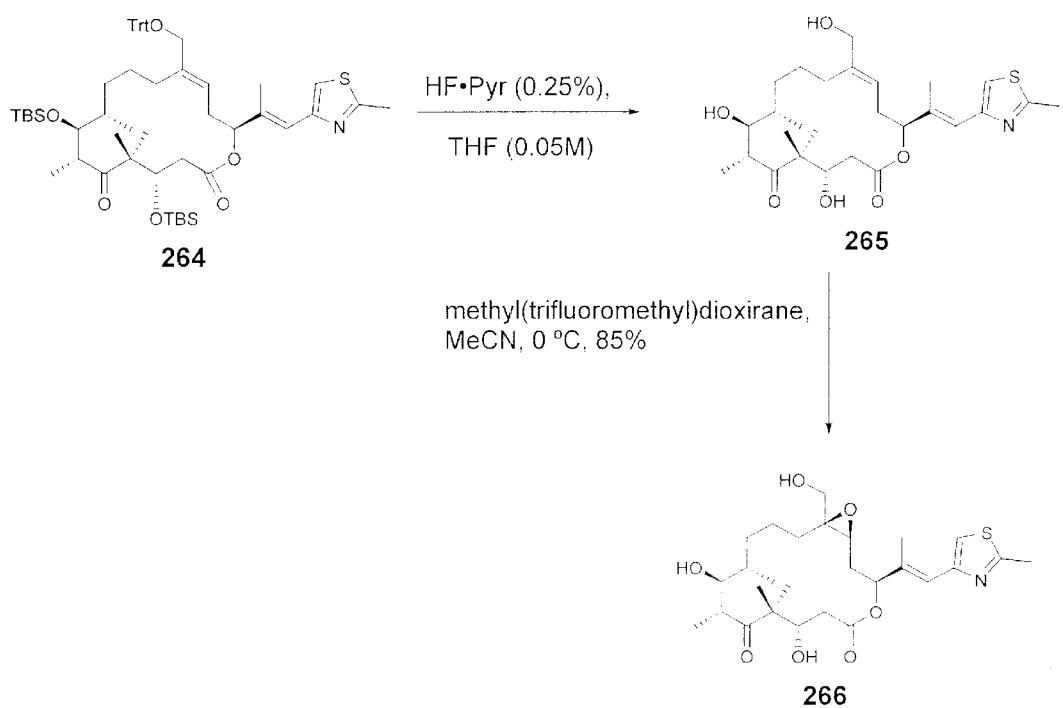

FIG. 39 illustrates the synthesis of epothilone analog 266.

Figure 40:
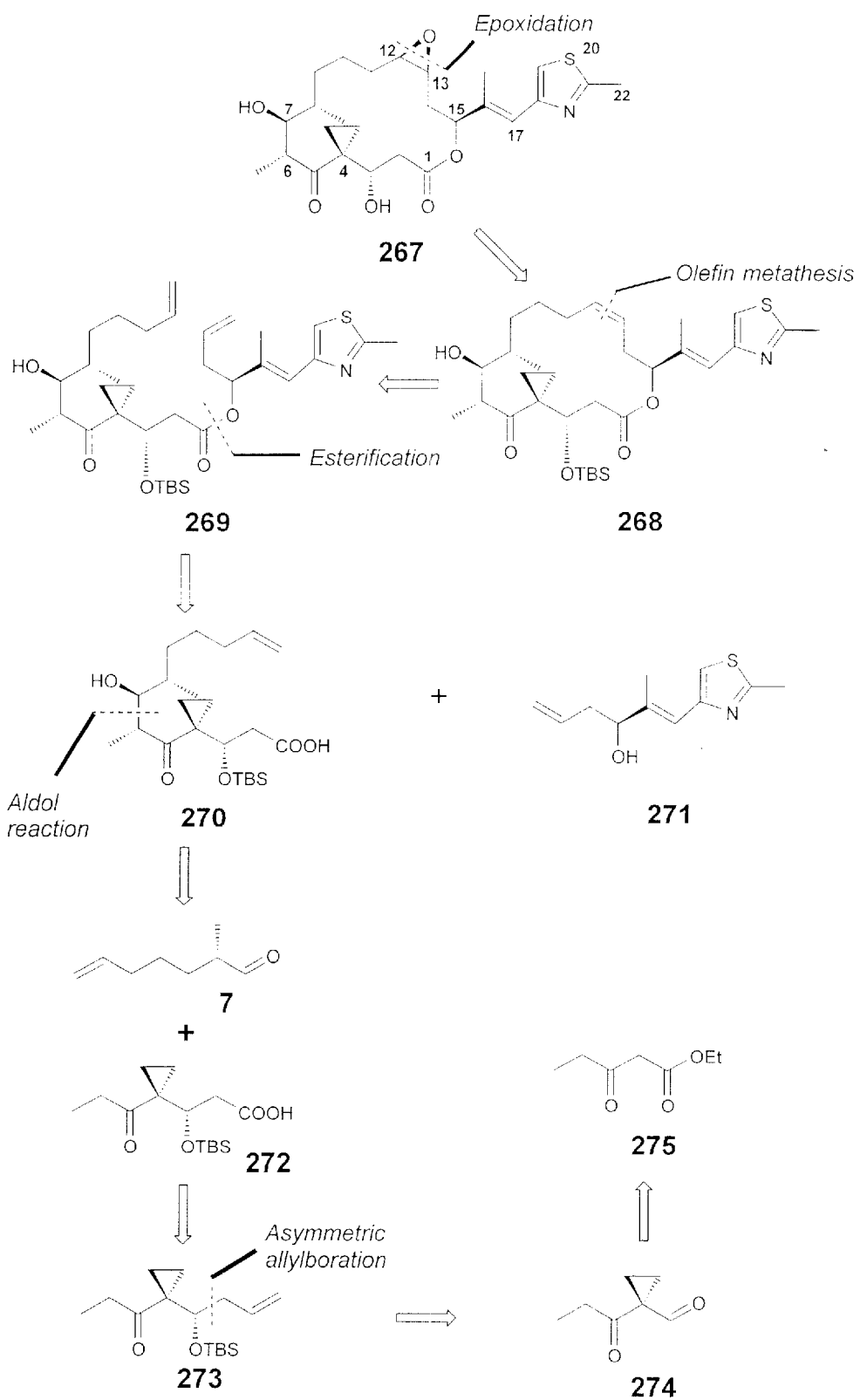

FIG. 40 illustrates the retrosynthetic analysis of 4,4-ethano epothilone A analog 267.

Figure 41:
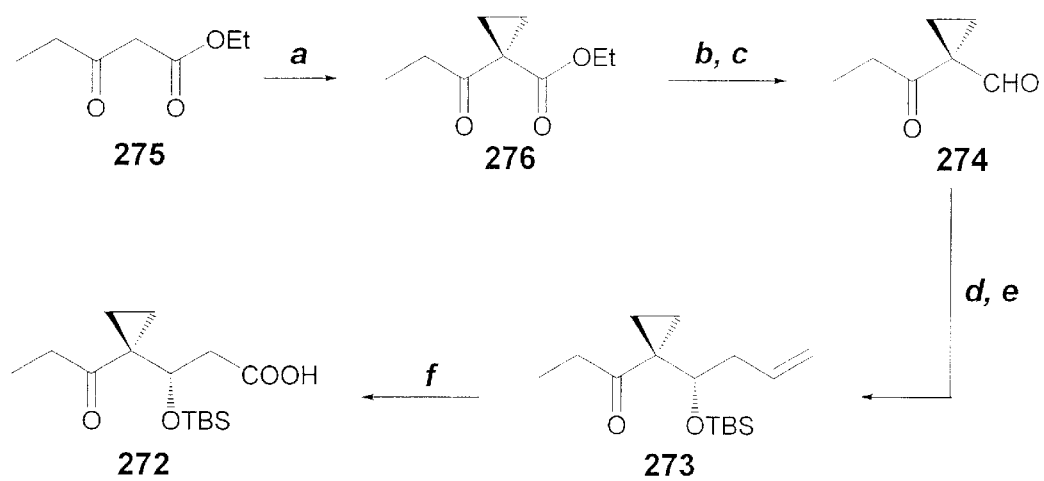

FIG. 41 illustrates the synthesis of ketoacid 272. Reagents and conditions: (a) 1.3 equiv of BrCH2CH2Br, 3.0 equiv of K2CO3, DMF, 25° C., 15 h, 60%; (b) 2.0 equiv of LiAlH4, Et2O, −20 to 0° C., 2.5 h, 93%; (c) 4.0 equiv of DMSO, 3.0 equiv of (COCl)2, 8.0 equiv of Et3N, CH2Cl2, −78 to 0° C., 64%; (d) 1.1 equiv of (+)-Ipc2B(allyl), Et2O, −100° C.; (e) 3.8 equiv of TBSOTf, 4.6 equiv of 2,6-lutidine, CH2Cl2, −78° C.; (f) 4.1 equiv of NaIO4, 0.05 equiv of RuCl3.H2O, MeCN:H2O:CCl4 (2:3:2), 25° C., 43% for 3 steps. DMSO= dimethyl sulfoxide; TBS=tert-butyldimethylsilyl; (+)-Ipc2B (allyl)=diisopinocampheylallyl borane.

Figure 42:
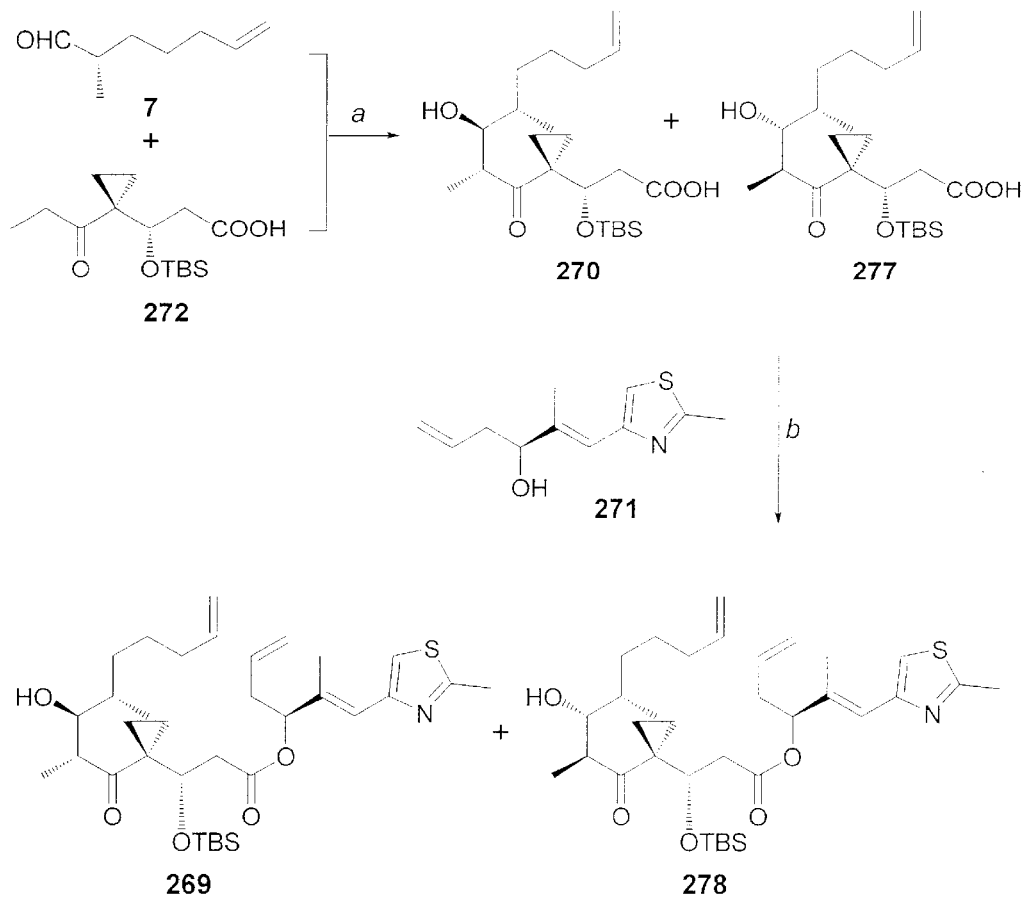

FIG. 42 illustrates the coupling of building blocks and construction of advanced intermediates 269 and 278. Reagents and conditions: (a) 2.4 equiv of LDA, −30° C., THF, 2 h, then 7 in THF, −30° C., 0.5 h, (29:36 ca. 2:3); (c) 2.5 equiv of 30, 1.2 equiv of EDC, 0.1 equiv of 4-DMAP, CH2Cl2, 0æ25° C., 2 h, 15% (269) plus 36% (278) for two steps. TBS=tert-butyldimethylsilyl; LDA=lithium diisopropylamide; EDC=1-Ethyl-(3-dimethylaminopropyl)-3-carbodiimide hydrochloride; 4-DMAP=4-dimethylaminopyridine.

Figure 43:
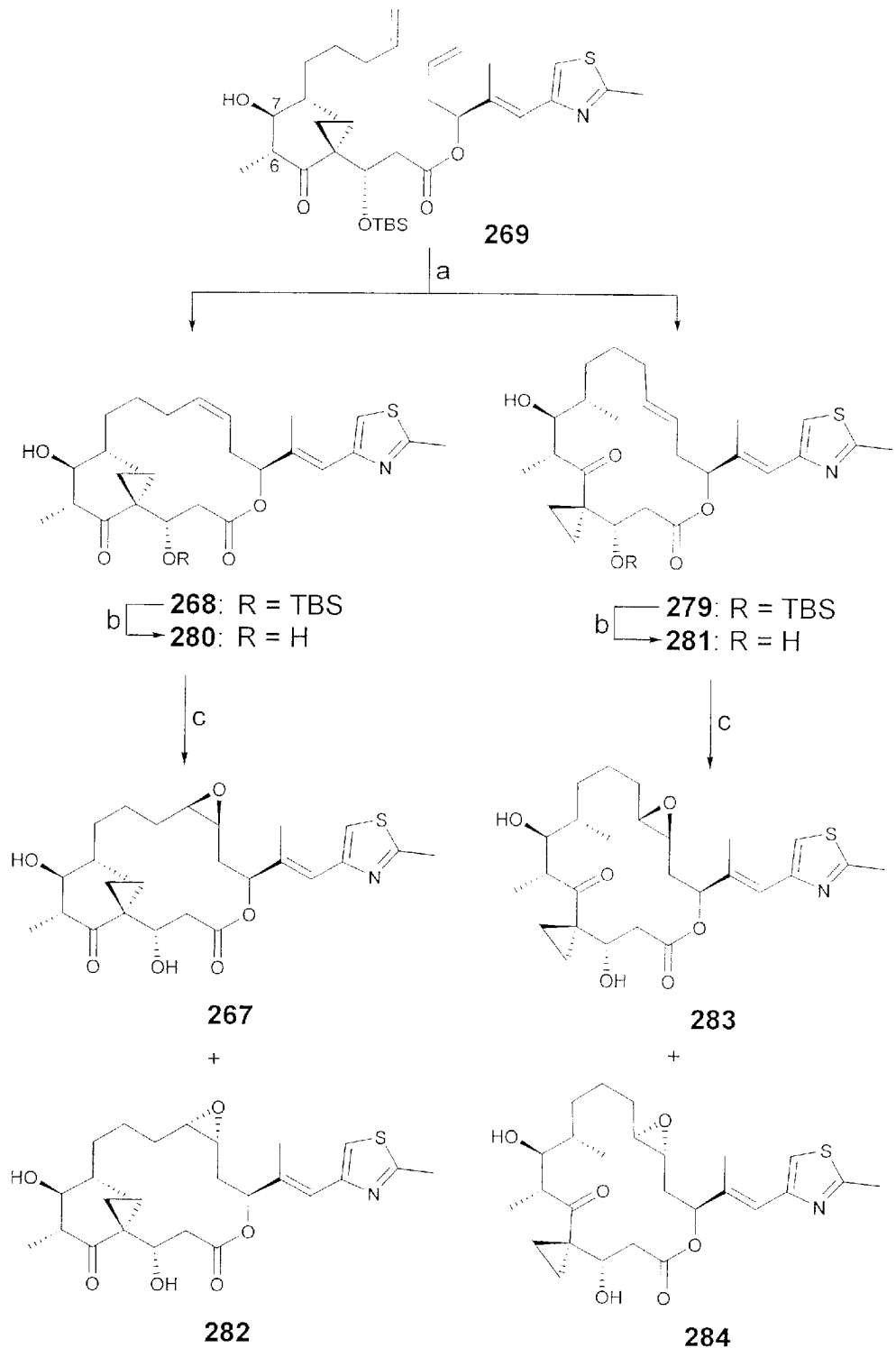

FIG. 43 illustrates an olefin metathesis of diene 269 and synthesis of 4,4-ethano epothilone A analogs and 282–284. Reagents and conditions: (a) 10 mol % of RuCl2(=CHPh) (PCy3)2, CH2Cl2, 25° C., 2 h, 37% (268) plus 35% (279); (b) 25% HF·Py in THF, 0 to 25° C., 28 h, 65% (280), 62% (281); (c) CH2Cl2:CH3CN:Na2EDTA (1:2:1.5), 50 equiv of CF3COCH3, 11 equiv of NaHCO3, 7.0 equiv of Oxone®, 0° C., 50% (267 or 282) plus 29% (282 or 267); 11% (283 or 284) plus 31% (284 or 283).

Figure 44:
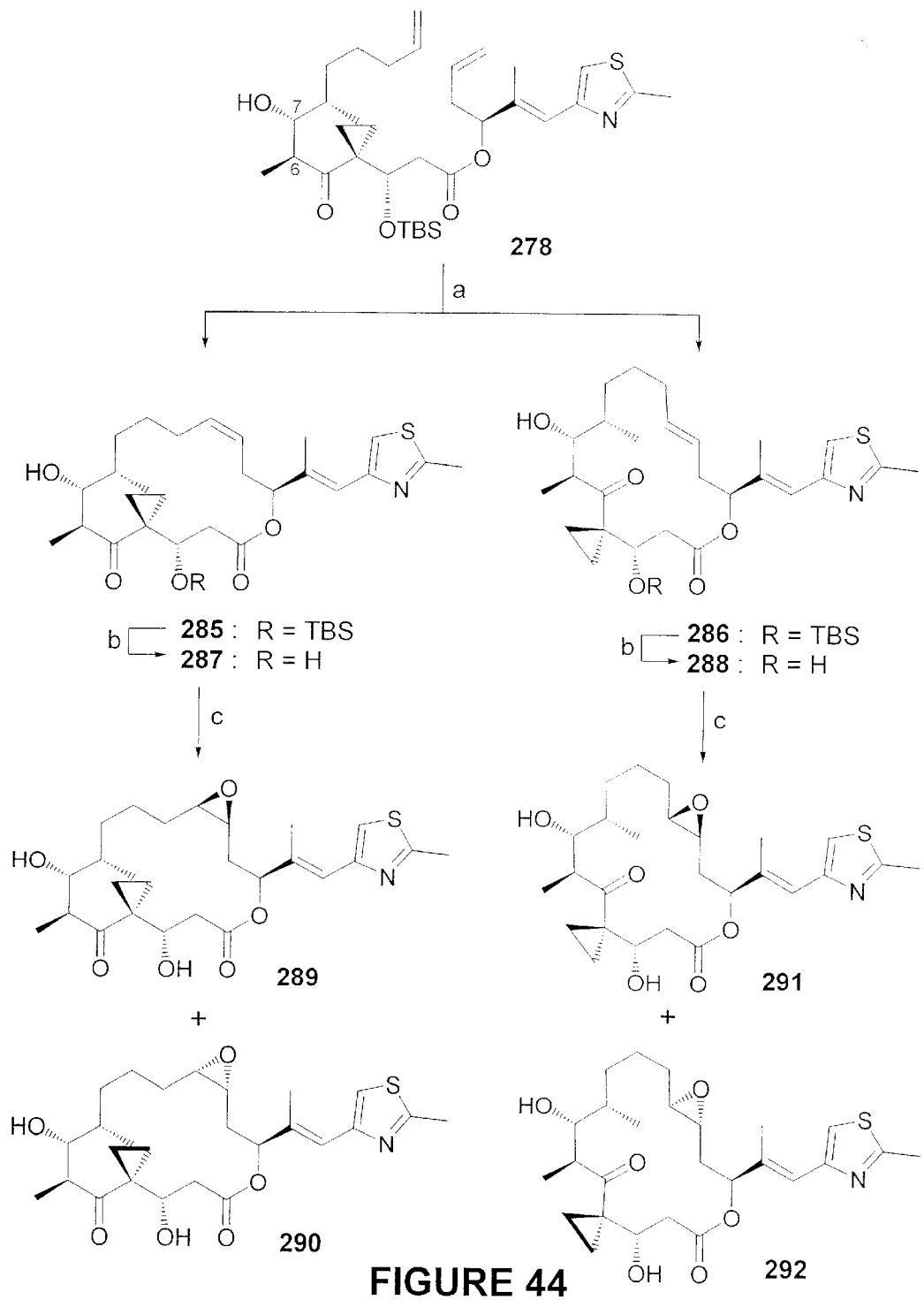

FIG. 44 illustrates the olefin metathesis of C6–C7 diastereomeric diene 278 and synthesis of 4,4-ethano epothilone A analogs 289–292. Reagents and conditions: (a) 9 mol % of RuCl2(=CHPh)(PCy3)2, CH2Cl2, 25° C., 1 h, 18% (285) plus 58% (286); (b) 25% HF·Py in THF, 0 to 25° C., 22 h,. 54% (287), 76% (288); (c) CH2Cl2:CH3CN:Na2EDTA (4:4:1), 50 equiv of CF3COCH3, 16 equiv of NaHCO3, 10 equiv of Oxone®, 0° C., 39% (289 or 290) plus 35% (290 or 289); 22% (291 or 292) plus 27% (292 or 291).

Figure 45:
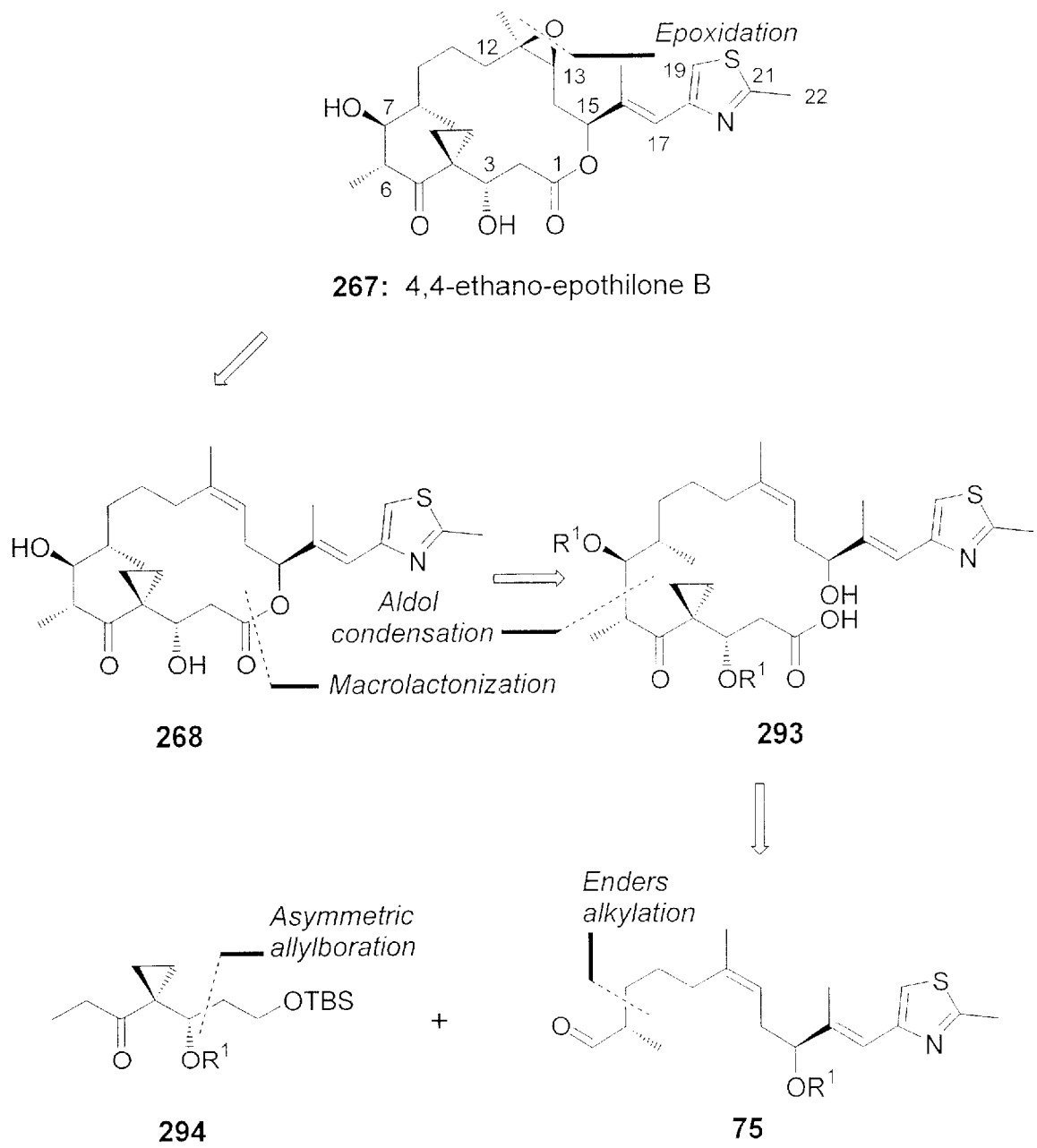

FIG. 45 illustrates themolecular structure and retrosynthetic analysis of the 4,4-ethano analog of epothilone B (267). R1=TBS=SitBuMe$_2$.

Figure 46:
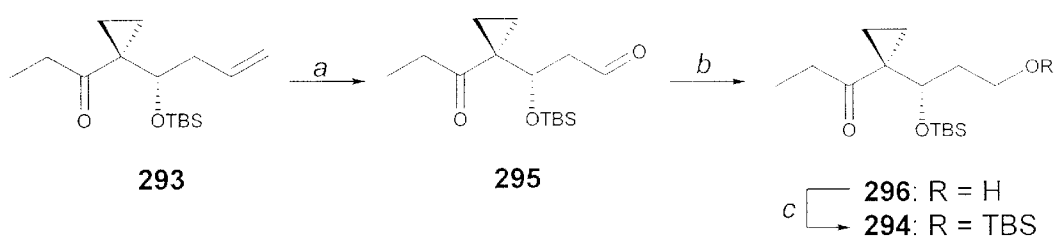

FIG. 46 illustrates the synthesis of ketone 294. Reagents and conditions: (a) O$_3$, CH$_2$Cl$_2$, −78° C., 0.5 h; then 1.2 equiv. Ph3P, −78→25° C., 1 h, 90%; (b) 1.1 equiv. of LiAl(OtBu)3H, THF, −78→0° C., 15 min; (c) 2.0 equiv. of TBSCl, 3.0 equiv. of Et3N, 0.02 equiv. of 4-DMAP, CH2Cl2, 0→25° C., 12 h, 83% for 2 steps.

Figure 47:
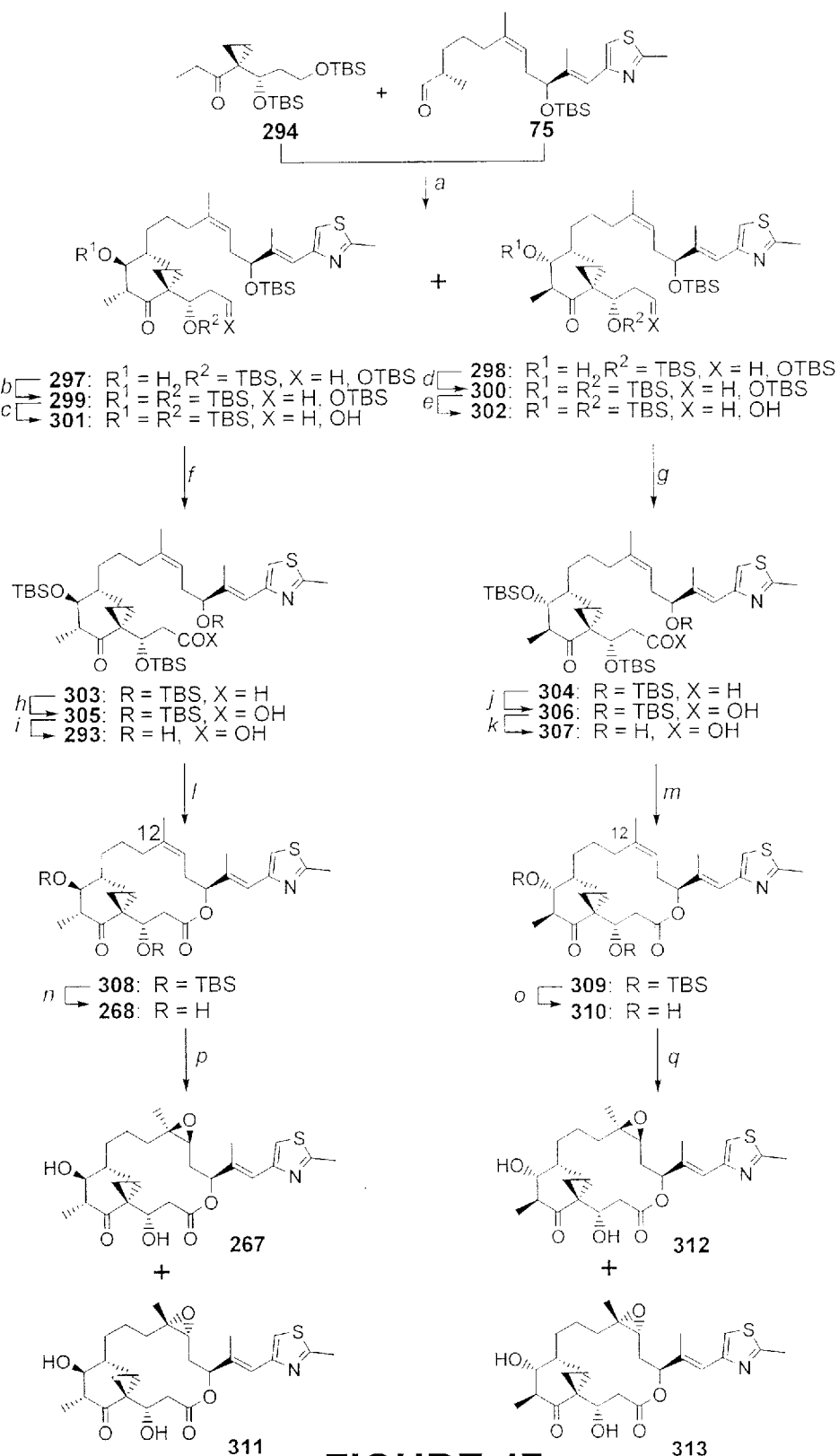

FIG. 47 illustrates the total synthesis of 4,4-ethano analogs of epothilone B. Reagents and conditions: (a) 1.5 equiv. of LDA, THF, 0° C., 15 min; then 1.4 equiv. of 294 in THF, −78→−60° C., 1 h; then 1.0 equiv. of 75 in THF at −78° C., 24% of 297 and 47% of its 6S, 7R-diastereoisomer 298 (ca 1:2 ratio); (b) 1.2 equiv. of TBSOTf, 2.0 equiv. of 2,6-lutidine, CH2Cl2, 0° C., 2 h, 92%; (c) 1.0 equiv. of CSA portionwise, CH2Cl2:MeOH (1:1), 0→25° C., 0.5 h, 74%; (d) same as b, 89%; (e) same as c, 60%; (f) 2.0 equiv. of (COCl)2, 4.0 equiv. of DMSO, 6.0 equiv. of Et3N, CH2Cl2, −78→0° C., 1.0 h, 96%; (g) same as f, 69t; (h) 6.0 equiv. of NaClO2, 10.0 equiv. of 2-methyl-2-butene, 3.0 equiv. of NaH2PO4, tBuOH:H2O (5:1), 25° C., 0.5 h, 91%; (i) 6.0 equiv. of TBAF, THF, 25° C., 8 h, 62%; (j) same as h, 99%; (k) same as i, 50%; (l) 1.1 equiv. of 2,4,6-trichlorobenzoylchloride, 2.2 equiv. of Et3N, THF, 0° C., 1 h; then add to a solution of 2.0 equiv. of 4-DMAP in toluene (0.002 M based on 293), 25° C., 3 h, 70%; (m) same as l, 72%; (n) 20% HF·pyr (by volume) in THF, 0→25° C., 24 h, 92%; (o) same as n, 90%; (p) methyl(trifluoromethyl) dioxirane, MeCN, 0° C., 86% (267:311 ca 8:1 ratio of diastereoisomers); (q) same as p, 89% (312:313 ca 2:1 ratio of diastereoisomers).

Figure 48:
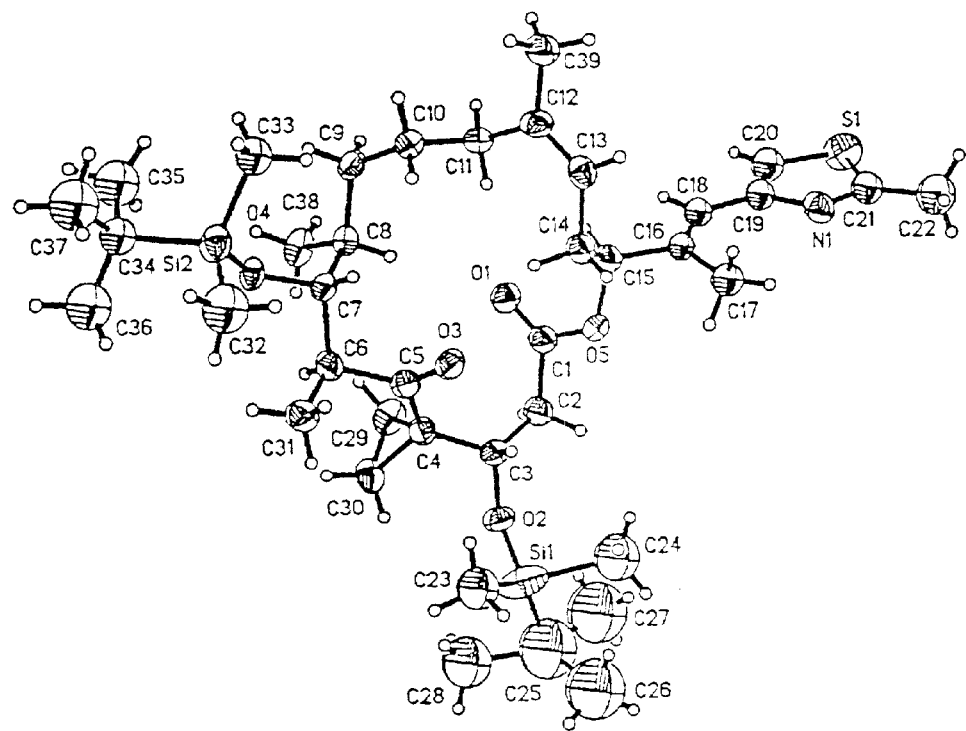

FIG. 48 illustrates ORTEP view of compound 309.

FIG. 49 illustrates the synthesis of key aldehydes 320, 321, 323 and 329.

FIG. 50 illustrates the solid phase strategy for the synthesis of epothilone analogs with key intermediates 330, 331 and 332 and employing the metathesis approach.

Figure 51:
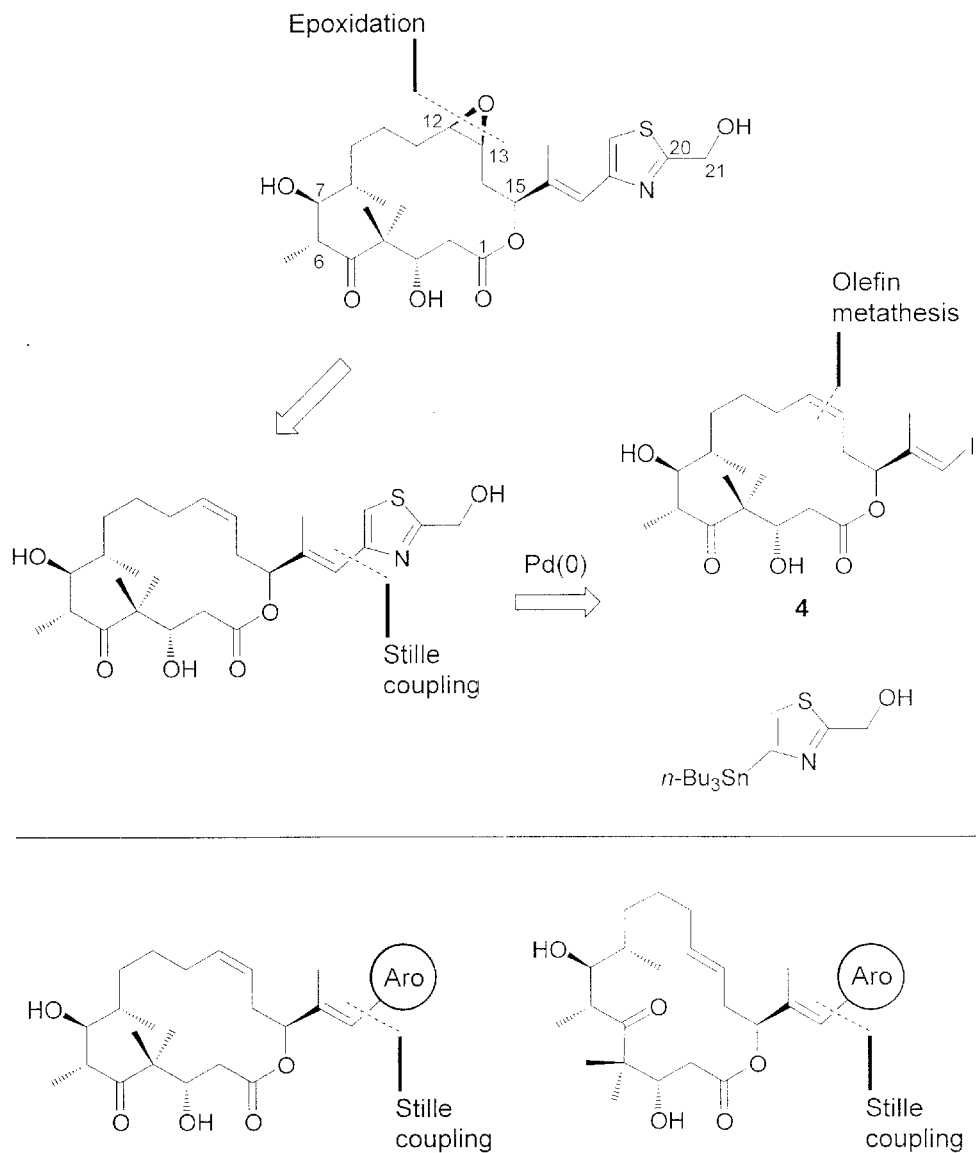

FIG. 51 illustrates the retrosynthetic analysis and strategy for the total synthesis of epothilone E and side chain epothilone analogs. Aro=aromatic moiety.

Figure 52:
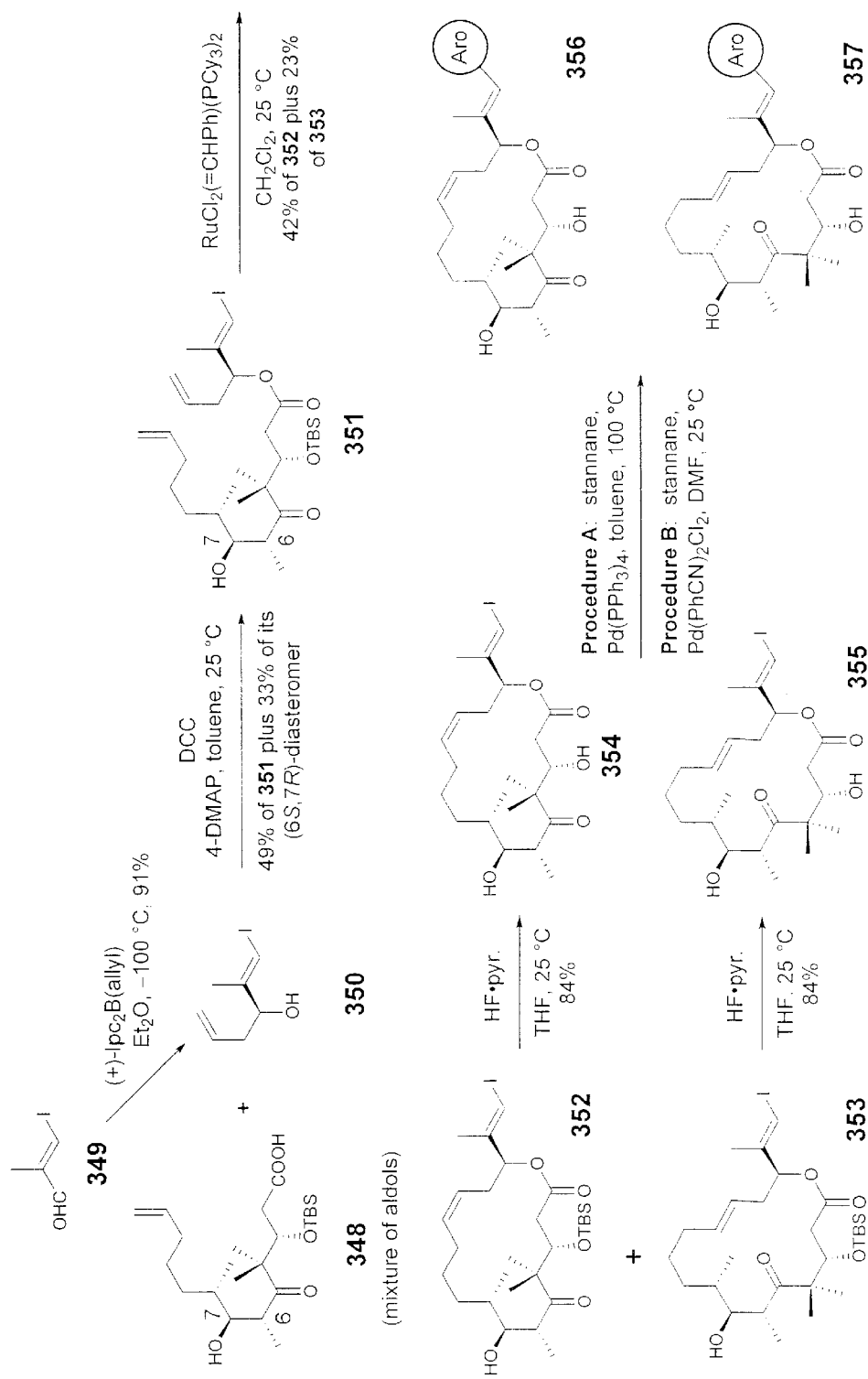

FIG. 52 illustrates the synthesis of epothilone analogs via the Stille coupling reaction.

Figure 53A:
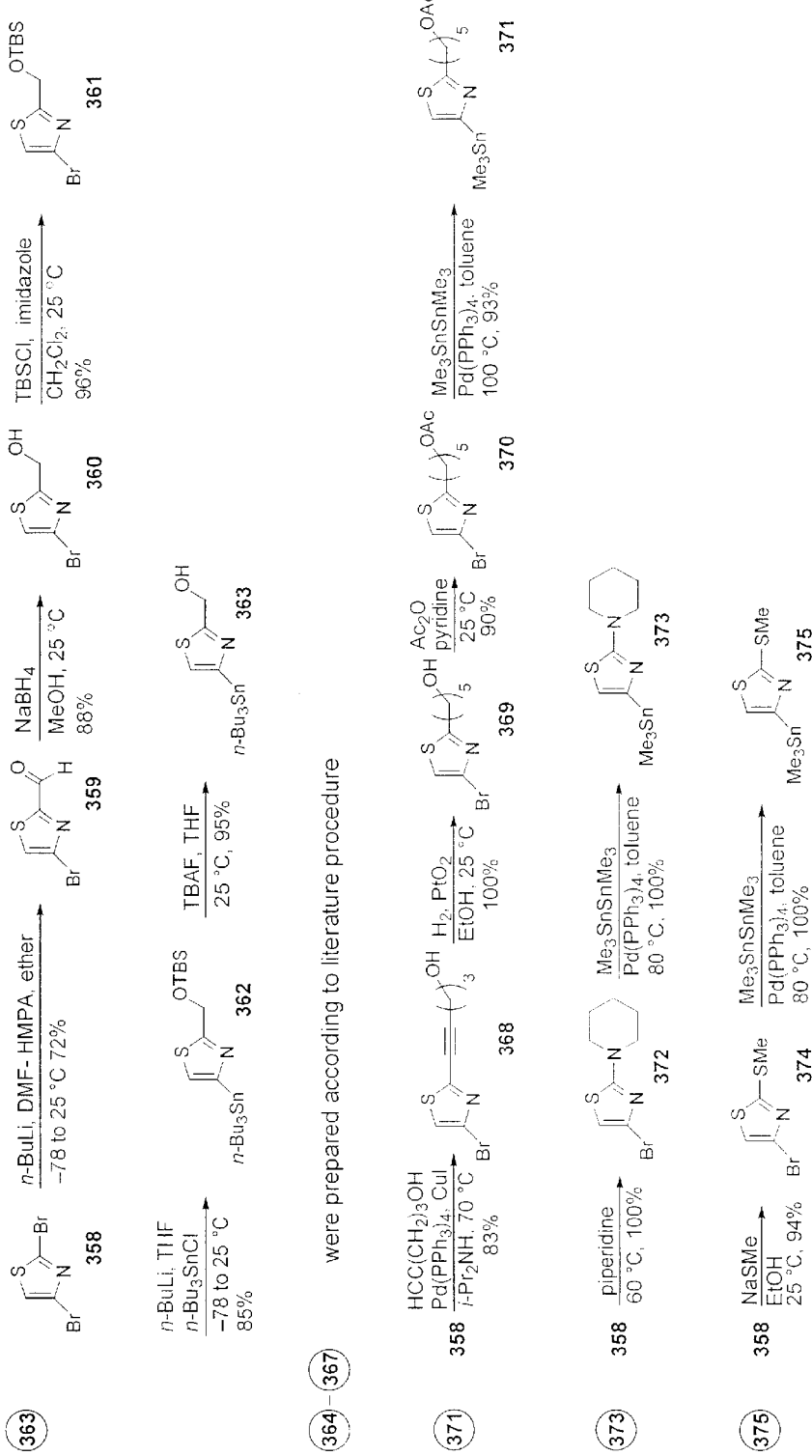
Figure 53B:
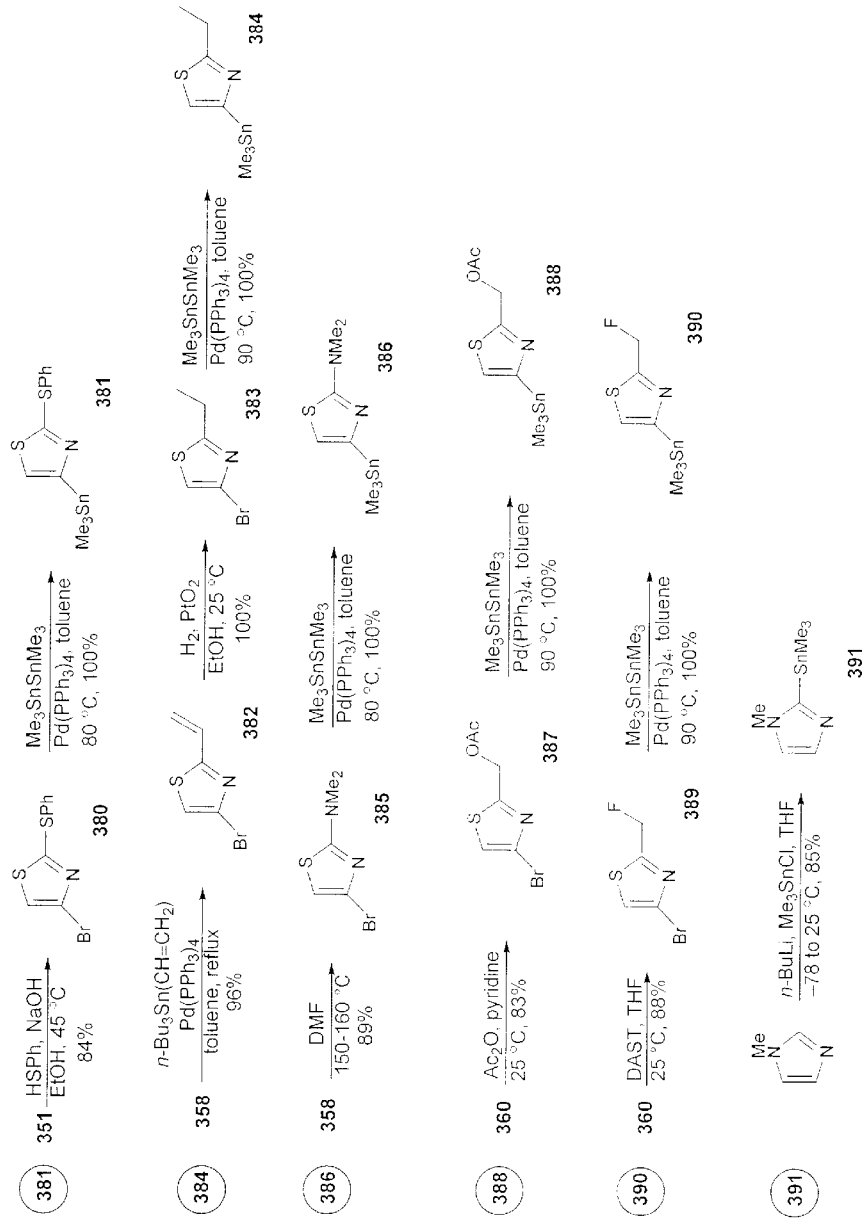

FIGS. 53a and 53b illustrate the synthesis of recommended stannanes for the synthesis of epothilone analogs via the Stille coupling reaction.

Figure 54A:
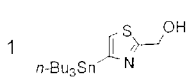

FIGS. 54a and 54b show a table of achieved compounds using the noted stannanes. Compound 356 and 357 are stereoisomers of each other wherein 356 is the cis olefin and 357 represents the trans olefin analog with indicated yield.

FIG. 55 shows a table of achieved compounds using the noted stannanes. Compound 356 and 357 are stereoisomers of each other wherein 356 is the cis olefin and 357 represents the trans olefin analog with indicated yield.

Figure 56:
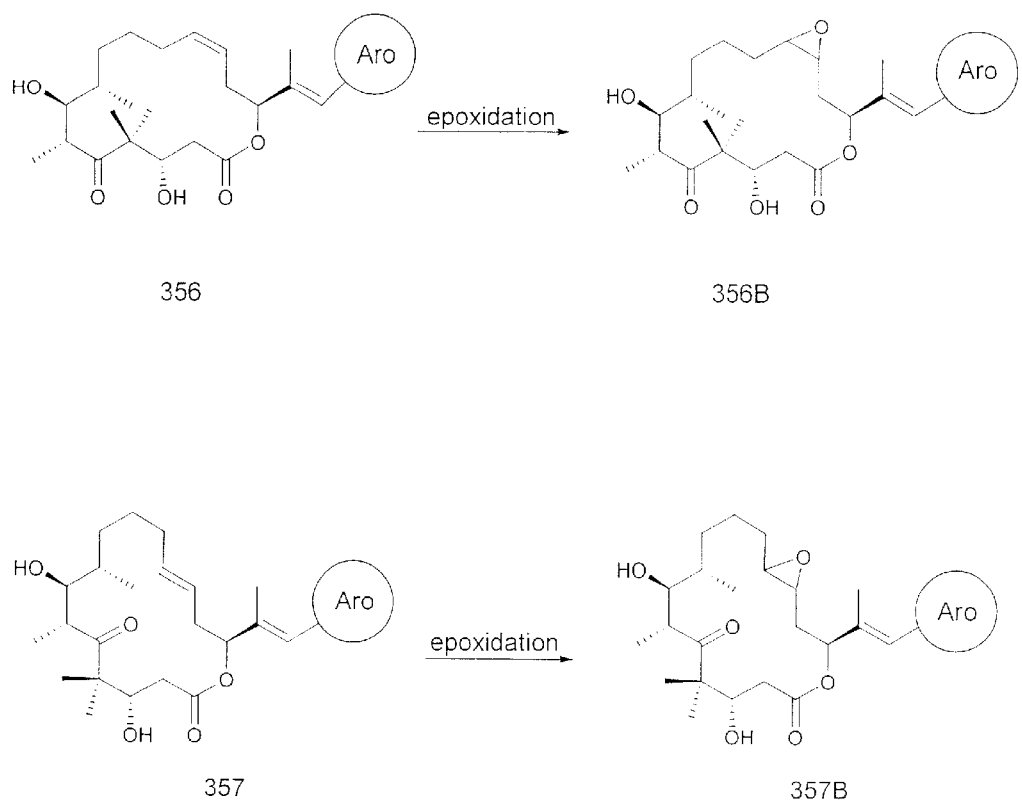

FIG. 56 illustrates the synthesis of epothilone E. Reagents and conditions: (a) 33 equiv of H2O2, 60 equiv of CH3CN, 9.0 equiv of KHCO3, MeOH, 25° C., 4 h, 65% (based on 50% conversion).

Figure 57:
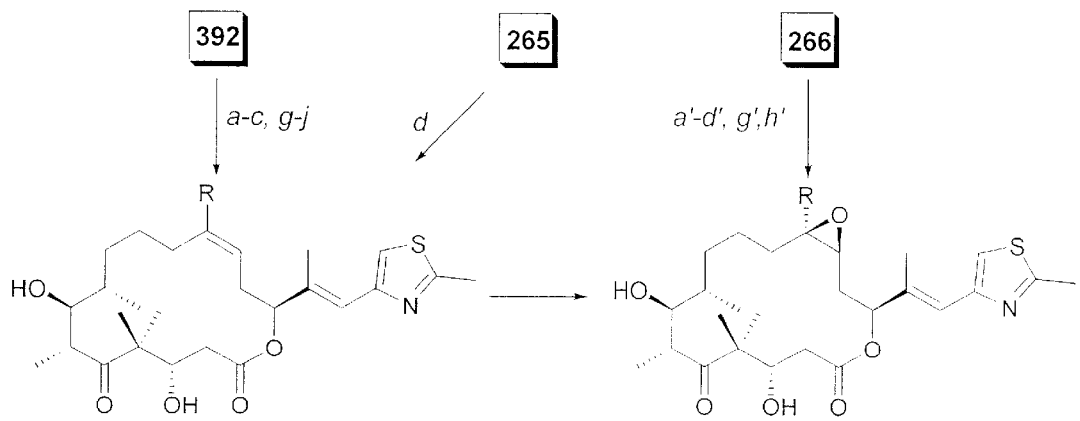

FIG. 57 illustrates the synthesis of 26-hydroxycompounds. Reagents and conditions: (a) 1.3 equiv. of Ac2O, 1.0 equiv. of 4-DMAP, EtOAc, 0° C., 0.5 h, 95%; then 25% HF·pyr. (by volume) in THF, 0→25° C., 24 h, 92%; (b) 3.0 equiv. of pivaloyl chloride, 4.0 equiv. of Et3N, 0.05 equiv. of 4-DMAP, CH2Cl2, 0° C., 0.5 h, 93%; then desilylation as in (a), 90%; (c) 3.0 equiv. of benzoyl chloride, 4.0 equiv. of Et3N, 0.05 equiv. of 4-DMAP, CH2Cl2, 0° C., 0.5 h, 85%; then desilylation as in (a), 90%; (d) 5.0 equiv. of MnO2, Et2O, 25° C., 3 h, 85%; (e) 5.0 equiv. of NaClO2, 70 equiv. of 2-methyl-2-butene, 2.5 equiv. of NaH2PO4, tBuOH:H2O (5:1), 0° C., 0.5 h, 98%; (f) CH2N2, Et2O, 0° C., 80%; (g) 4.0 equiv. of Ph3P, CCl4, 75° C., 24 h, 85%; then desilylation as in (a), 86%; (h) 1.1 equiv. of NaH, 20 equiv. of MeI, DMF, 0° C., 1 h, 65%; then desilylation as in (a), 89%; (i) 1.1 equiv. of NaH, 20 equiv. of BnBr, DMF, 0→25° C., 1 h, 40%; then desilylation as in (a), 87%; (j) 1.1 equiv. of DAST, CH2Cl2, −78→25° C., 1 h, 60%; then desilylation as in (a), 85%; (k) 5.0 equiv. of MnO2, Et2O, 25° C., 3 h, 90%; then 2.0 equiv. of Ph3P+ CH3Br−, 2.0 equiv. of LiHMDS, THF, 0° C. 85%; then desilylation as in (a), 85%; (a') 1.1 equiv. of Ac2O, 1.0 equiv. of 4-DMAP, EtOAc, 0° C., 0.5 h, 90%; (b') 3.0 equiv. of pivaloyl chloride, 4.0 equiv. of Et3N, 0.05 equiv. of 4-DMAP, CH2Cl2, 0° C., 0.5 h, 90%; (c') 1.2 equiv. of benzoyl chloride, 4.0 equiv. of Et3N, 0.05 equiv. of 4-DMAP, CH2Cl2, 0° C., 0.5 h, 75%; (d') 1.5 equiv. of TEMPO (0.008 M solution in CH2Cl2), 1.0 equiv. of NaOCl (0.035 M solution in 5% aqueous NaHCO3), 0.1 equiv of KBr (0.2 M aqueous solution), CH2Cl2, 0° C., 0.5 h, 75%; (e') 5.0 equiv. of NaClO2, 70 equiv. of 2-methyl-2-butene, 2.5 equiv. of NaH$_2$PO$_4$, tBuOH:H2O (5:1), 0° C., 0.5 h, 95%; (f') CH2N2, Et2O:EtOAc (1:2), 0° C., 2 h, 90%; (g') 4.0 equiv. of Ph3P, CH3CN:CCl4 (1:3), 25° C., 1 h, 85%; (h') 1.1 equiv. of NaH, 20 equiv. of MeI, DMF, 50%.

Bn=benzyl; DAST=diethylaminosulfur trifluoride; LIHMDS=lithium bis(trimethylsilyl)amide; TEMPO=2,2,6,6-tetramethyl-1-piperidinyloxy, free radical.

Figure 58:
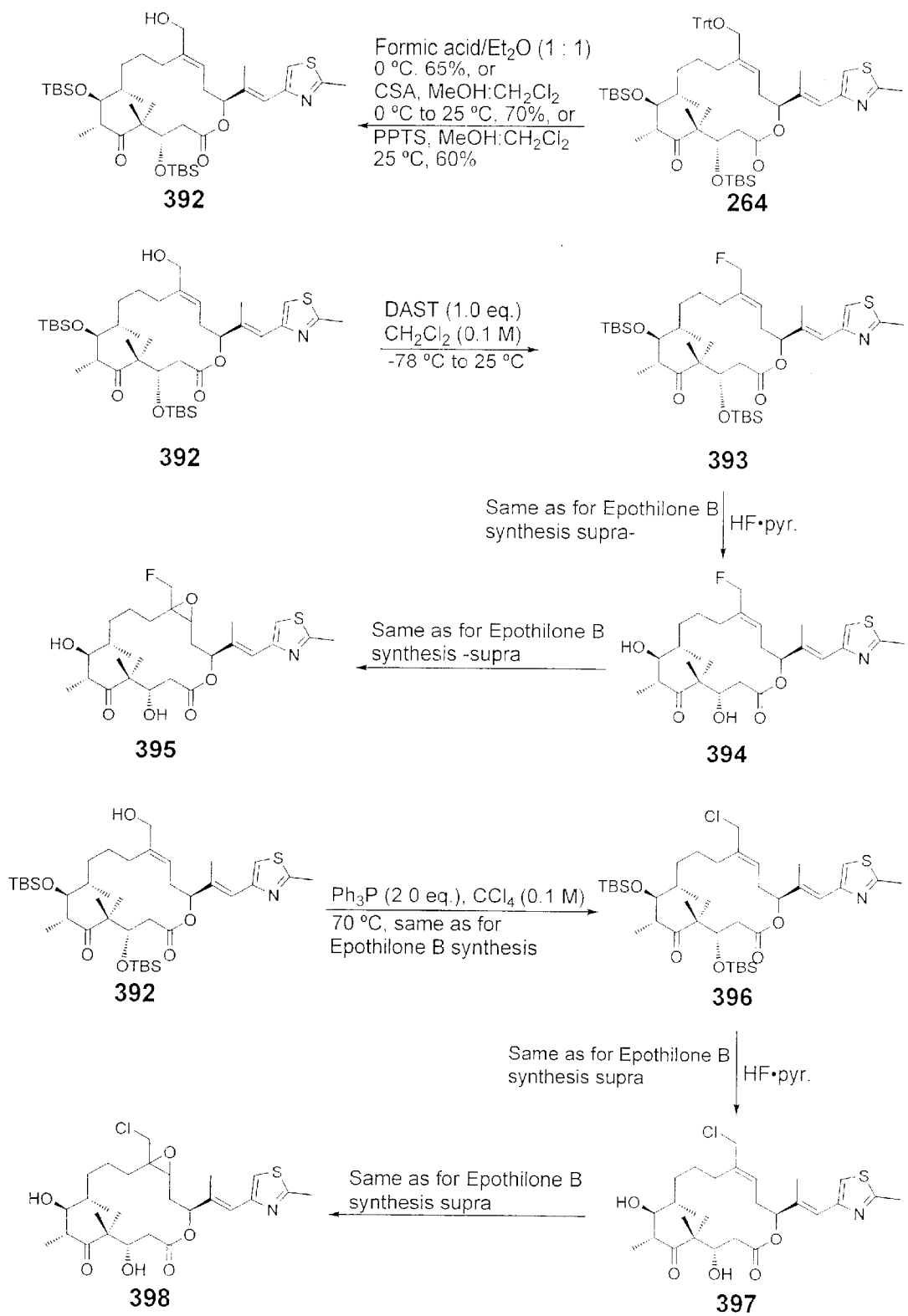

FIG. 58 illustrates synthesis of 26-halogen substituted epothilone analogs.

Figure 59:
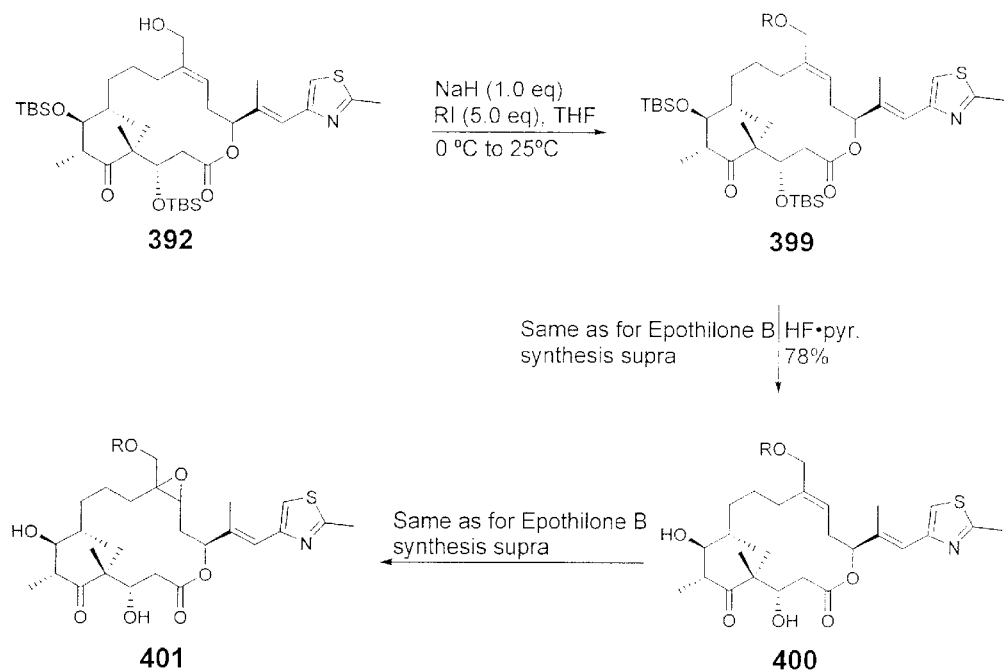

FIG. 59 illustrates synthesis of 26-alkoxy substituted epothilone analogs.

Figure 60:
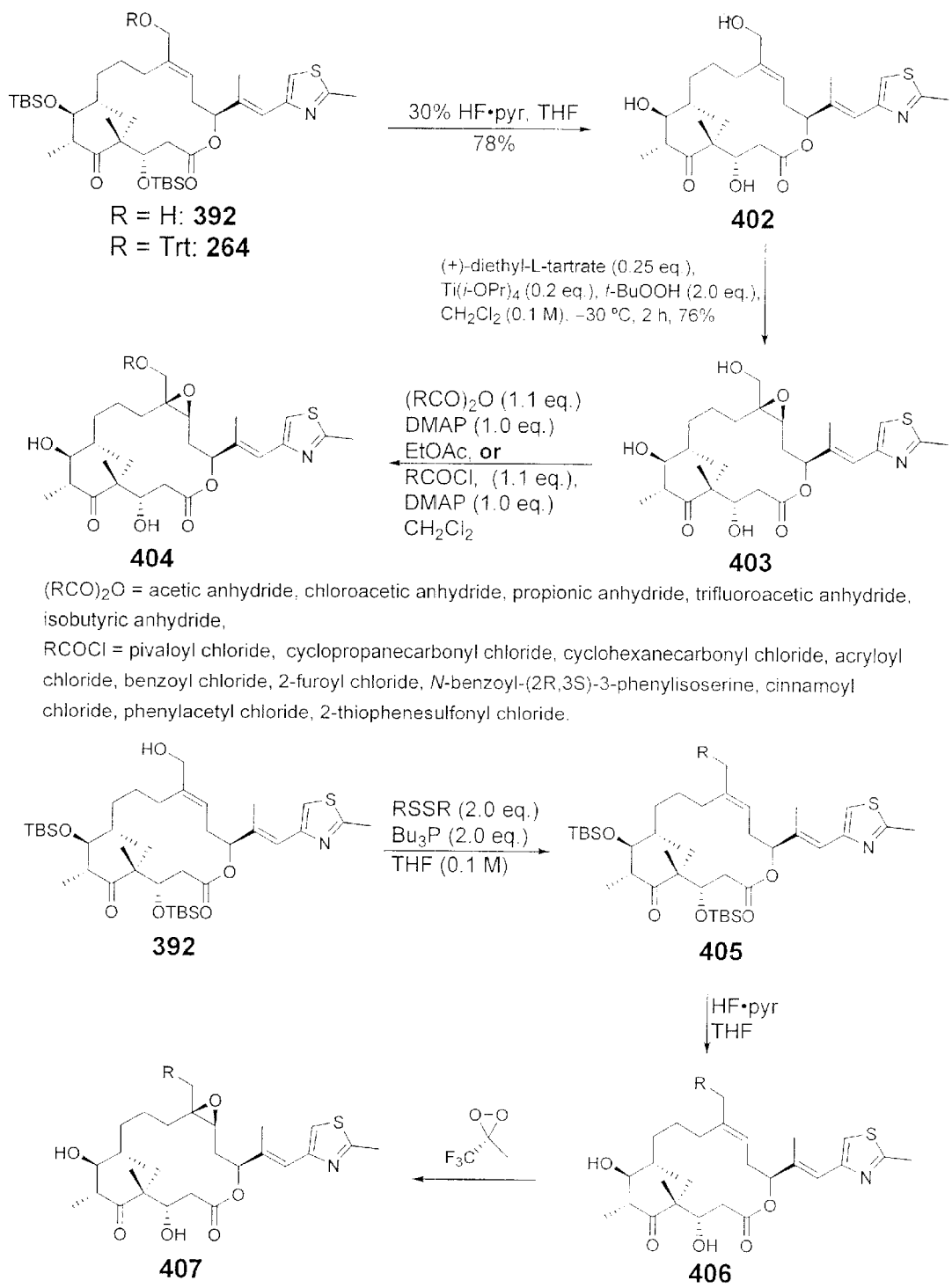

FIG. 60 illustrates synthesis of 26-ester substituted epothilone analogs (top scheme) and 26-thio ether substituted epothilone analogs (bottom scheme).

FIG. 61 illustrates synthesis of 26-amine substituted epothilone analogs.

Figure 62:
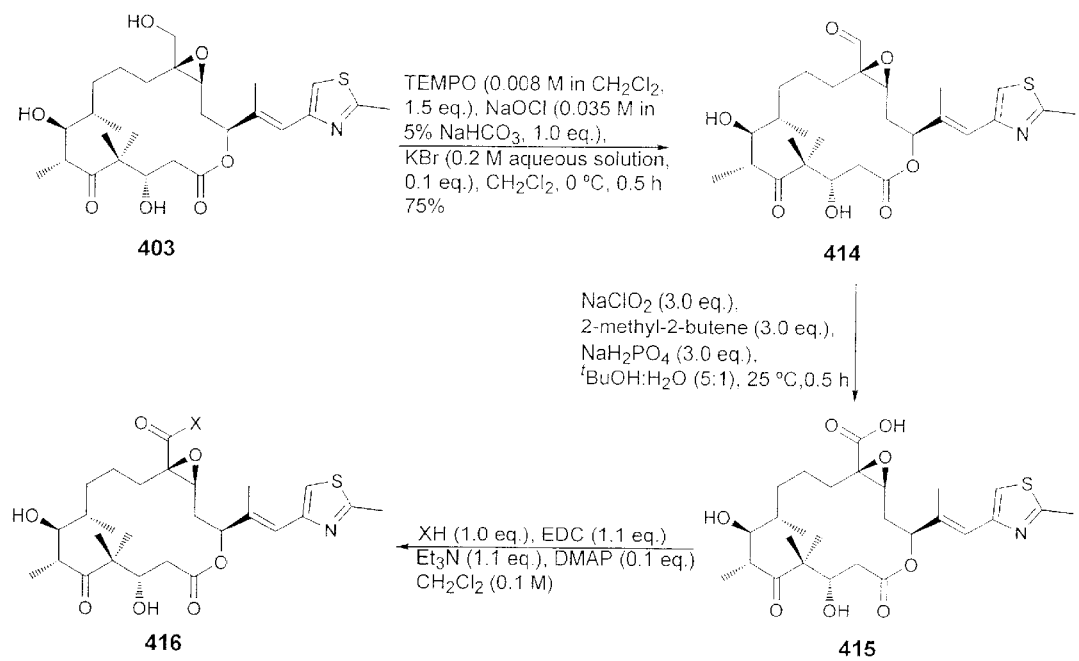

FIG. 62 illustrates synthesis of 26-aldehyde substituted epothilone analog 414 and 26-acid and ester substituted epothilone analogs 415 and 416.

Figure 63:
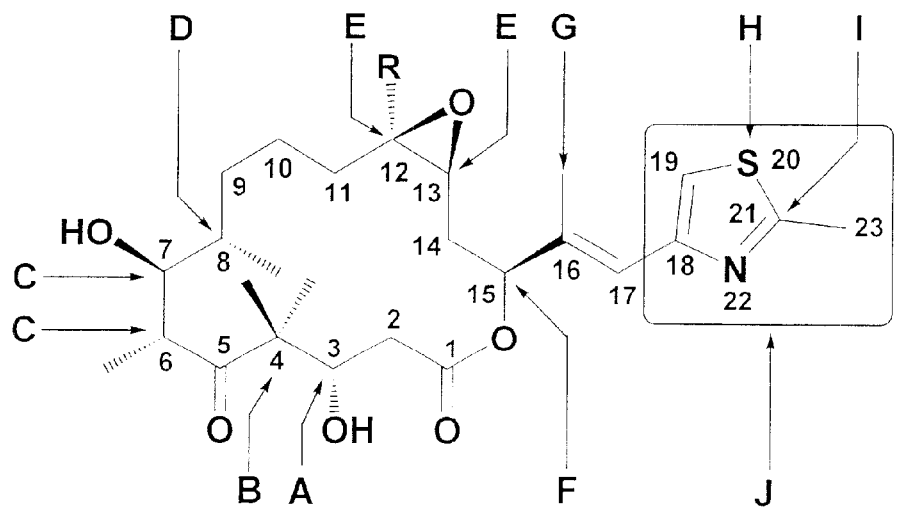

FIG. 63 illustrates epothilone structure activity relationships (tubulin binding assay): A: 3S -stereochemistry important; B: 4,4-ethano group not tolerated; C: 6R,7S-stereochemistry crucial; D: 8S-stereochemistry important, 8,8-dimethyl group not tolerated; E: epoxide not essential for tubulin polymerization activity, but may be important for cytotoxicity; epoxide stereochemistry may be important; R group important; both olefin geometries tolerated; F: 15S-stereochemistry important; G: bulkier group reduces activity; H: oxygen substitution tolerated; I: substitution important; J: heterocycle important.

Figure 64A:
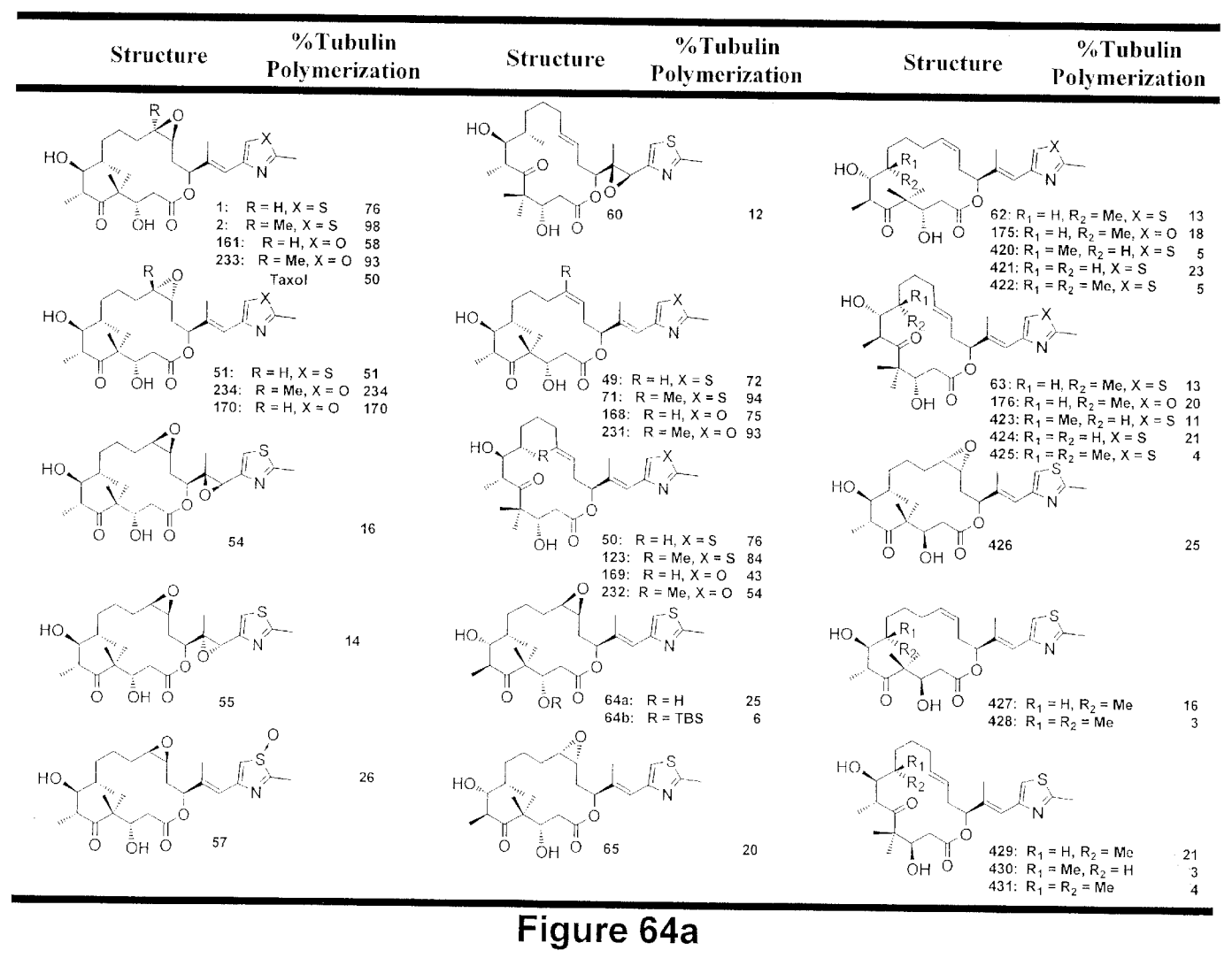
Figure 64B:
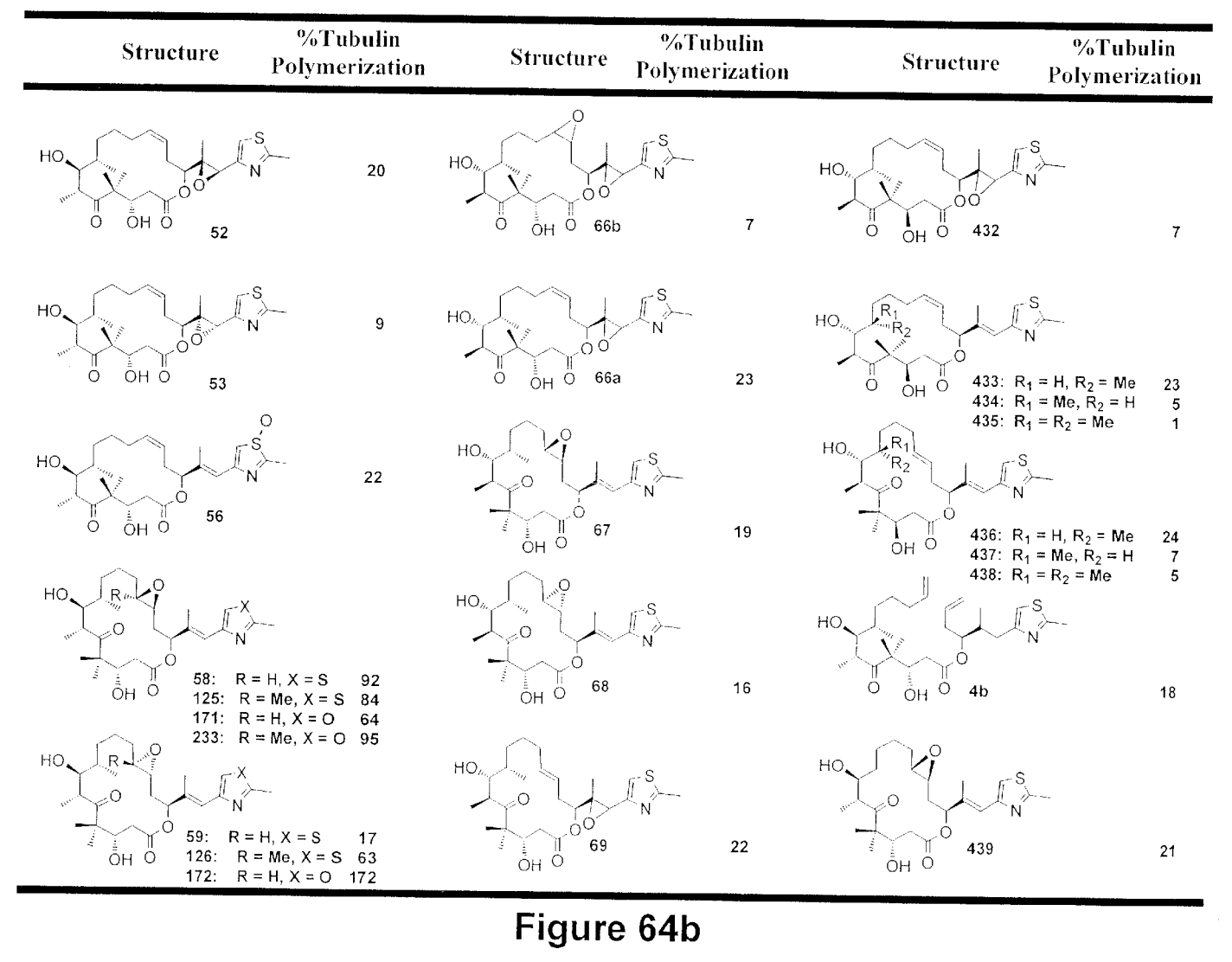

FIGS. 64a and 64b show a table of achieved compounds using both metathesis and esterification procedures with noted % tubulin polymerization accomplished via each analog.

Figure 65A:
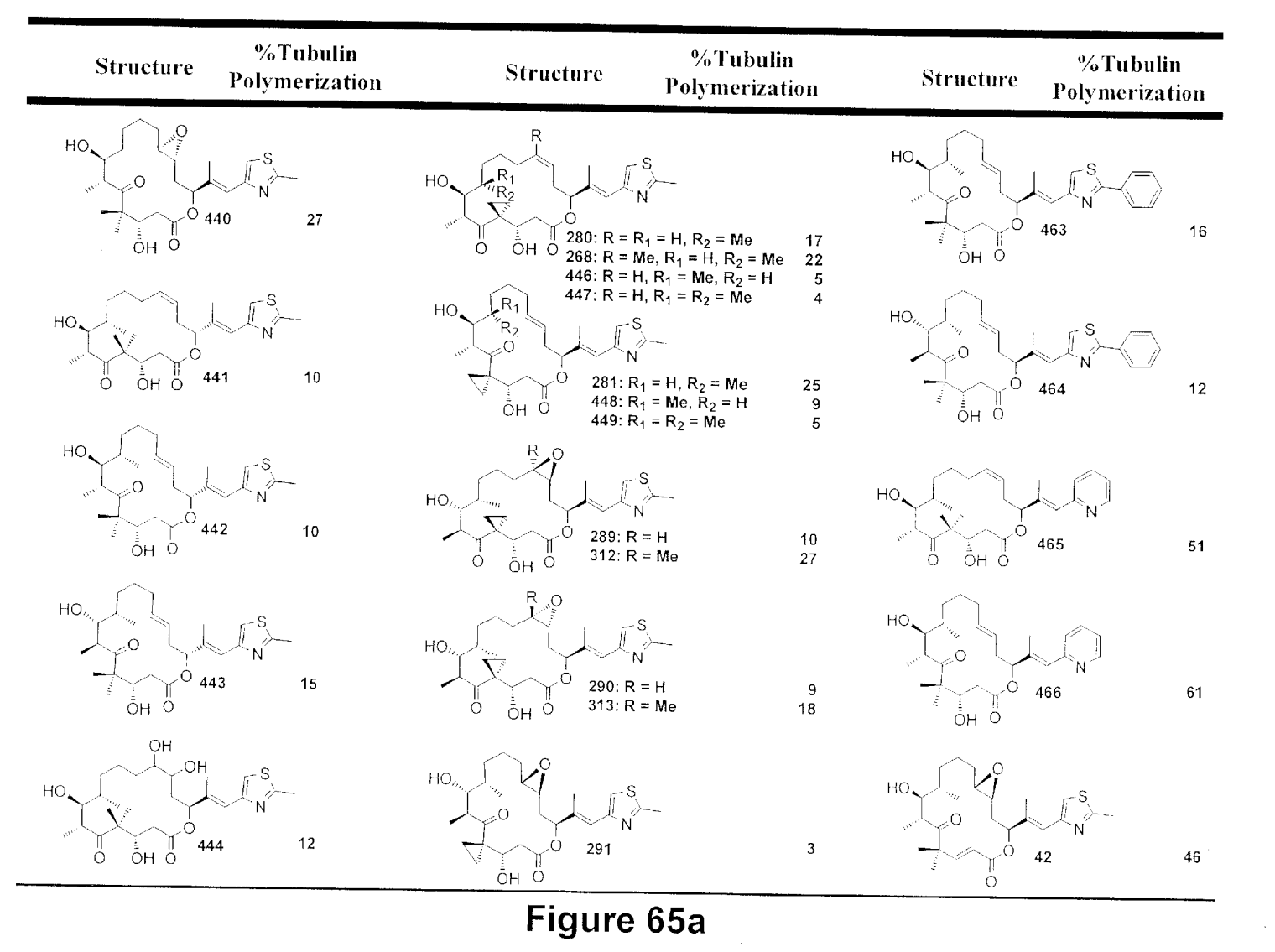
Figure 65B:
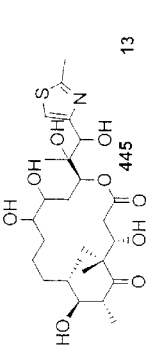

FIGS. 65a and 65b show a table of achieved compounds using both metathesis and esterification procedures with noted % tubulin polymerization accomplished via each analog.

FIG. 66 is as shown and noted as follows: [a] From FIGS. 64–65 [b] Assay performed as described vida supra; reaction mixtures contained 10 mM purified tubulin, 0.7 M monosodium glutamate, 5% DMSO and drug; incubation was for 20 min at room temperature and reaction mixtures were centrifuged at 14,000 rpm; supernatant protein concentration was measured and the $EC_{50}$ value is defined as the drug concentration resulting in a 50% reduction in supernatant protein relative to control values; each EC50 value shown is an average obtained in 2–4 independent assays, with standard deviations within 20% of the average. [c] Cell growth was evaluated by measurement of increase in cellular protein. [d] The parental ovarian cell line, derived as a clone of line A2780, was used to generate Taxol-resistant cell lines by incubating the cells with increasing concentrations of Taxol with verapamil; the cells were grown in the presence of drug for 96 h; values shown in the Figure were single determinations, except for those of Taxol, 1 and 2 (average of 6 determinations each); the values for 1 and 2 are averages of data obtained with both synthetic and natural samples (generously provided to E.H. by Merck Research Laboratories), which did not differ significantly. [e] The MCF7 cells were obtained from the National Cancer Institute drug screening program; cells were grown in the presence of drug for 48 h; each value represents an average of two determinations. [f] Relative resistance is defined as the $IC_{50}$ value obtained for the β-tubulin mutant line divided by that obtained for the parental cell line.

Figure 67:
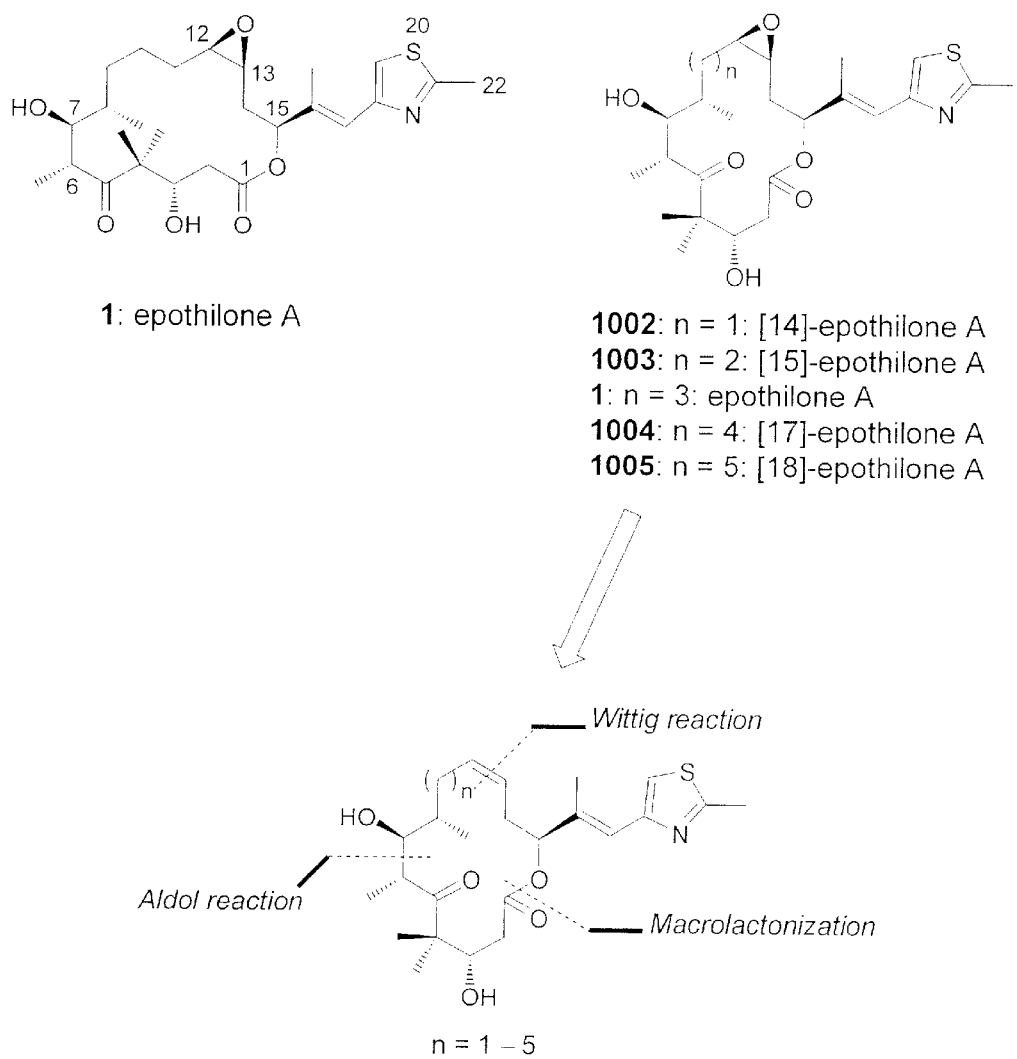

FIG. 67 illustrates the structures and numbering of [n]-epothilones A, where n=1–5.

Figure 68:
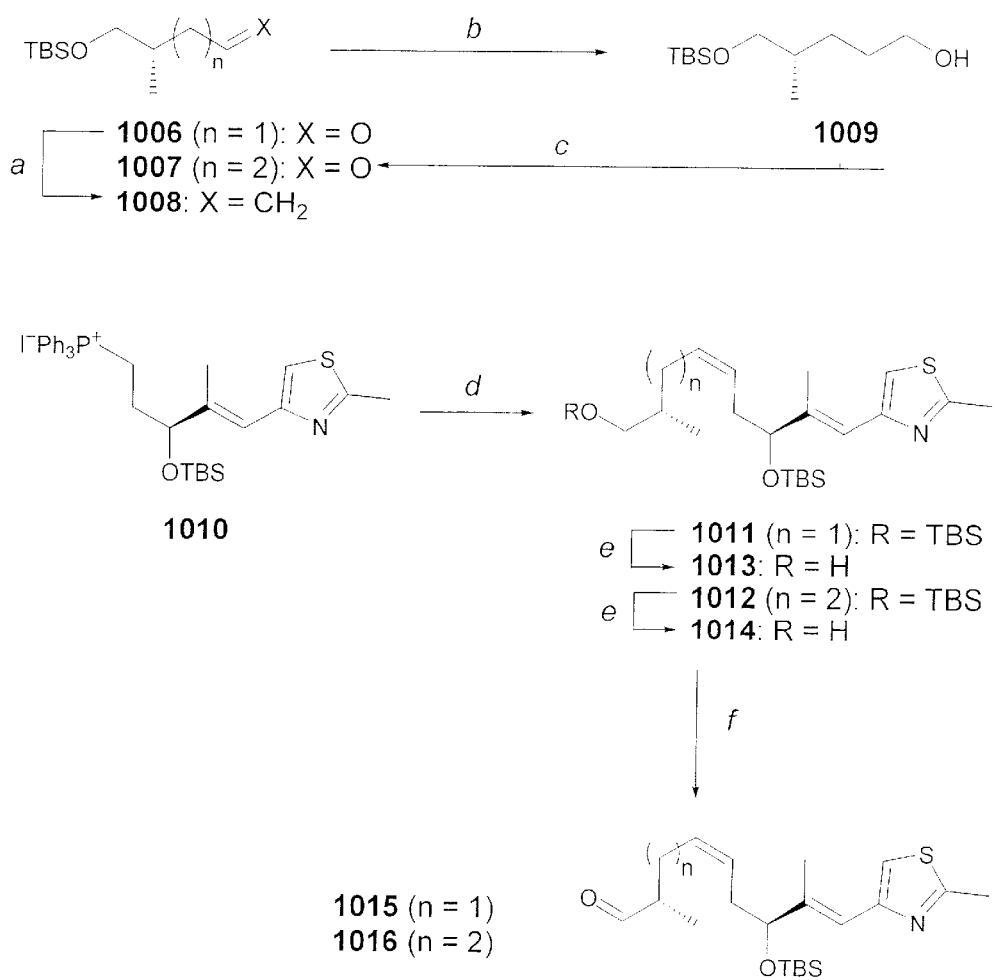

FIG. 68 illustrates the synthesis of aldehydes 1015 and 1016. Reagents and conditions: (a) 2.0 equiv. of $Ph_3P^+CH_3$ Br⁻, 1.98 equiv of NaHMDS, THF, 0° C., 15 min; then 1.0 equiv of 1006 in THF, 0° C., 0.5 h, 95%; (b) 1.5 equiv. of 9-BBN 0.5 M, THF, 25° C., 3 h; then 6 equiv. of 3 N NaOH and 6.0 equiv of 30% $H_2O_2$, 0° C., 1 h, 85%; (c) 2.0 equiv of $(COCl)_2$, 4.0 equiv of DMSO, 6.0 equiv of $Et_3N$, $CH_2Cl_2$, −78 to 0° C., 1.5 h, 98%; (d) 1.2 equiv of 1010, 1.2 equiv of NaHMDS, THF, 0° C., 15 min; then add 1.0 equiv of aldehyde 1006 or 1007, 0° C., 15 min, 77% (Z:E ca. 9:1) for 1011 or 83% (Z:E ca. 9:1) for 1012; (e) 1.0 equiv of CSA added portionwise over 1 h, $CH_2Cl_2$:MeOH (1:1), 0 to 25° C., 0.5 h, 81% for 1013 and 61% for 1014; (f) 2.0 equiv of $SO_3$·pyr., 10.0 equiv of DMSo, 5.0 equiv of $Et_3N$, $CH_2Cl_2$, 25° c, 0.5 h, 81% for 1015 and 84% for 1016. NaHMDS= sodium bis(trimethylsilyl)amide; 9-BBN=9-borabicyclo [3.3.1]nonane; DMSO=dimethylsulfoxide; CSA=10-camphorsulfonic acid; TBS=tert-butyldimethylsilyl.

Figure 69:
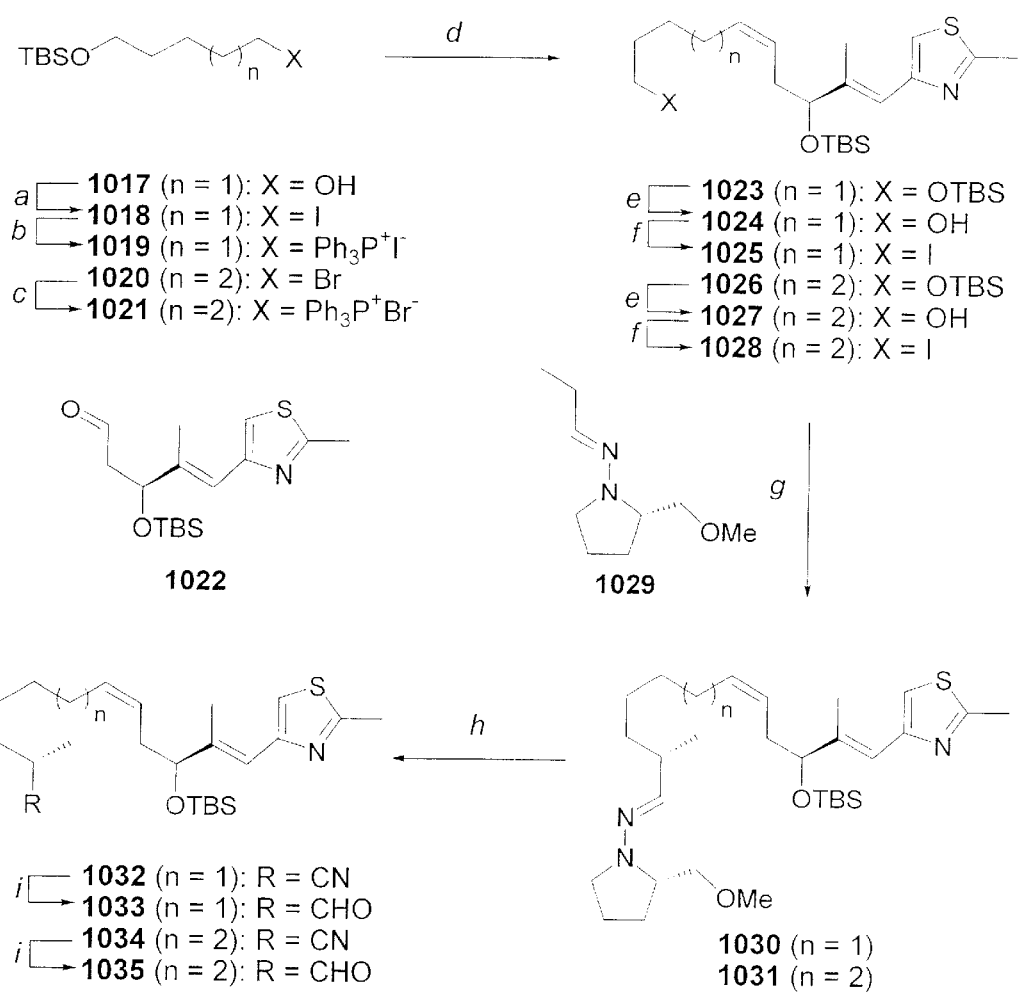

FIG. 69 illustrates the synthesis of aldehydes 1033 and 1035. Reagents and conditions: (a) 1.5 equiv of $I_2$, 3.0 equiv of imidazole, 1.5 equiv of $Ph_3P$, $Et_2O$:MeCN (3:1), 0° C., 0.5 h, 95%; (b) 1.1 equiv of $Ph_3P$, neat, 100° C., 2 h, 97%; (c) 1.5 equiv of $Ph_3P$, neat, 100° C., 7 h, 99%; (d) 1.2 equiv of 1019 or 1021, 1.2 equiv of NaHMDS, THF, 0° C., 15 min; then add 1.0 equiv of aldehyde 1022, 0° C., 15 min, 85% (Z:E ca 9:1) for 1023, 79% (Z:E ca 9:1) for 1026; (e) 1.0 equiv of CSA added portionwise over 1 h, $CH_2Cl_2$:MeOH (1:1), 0 TO 25° C., 3 h, 99% for 1024, 95% for 1027; (f) 1.5 equiv of $I_2$, 3.0 equiv of imidazole, 1.5 equiv of $Ph_3P$, $Et_2O$:MeCN (3:1), 0° C., 0.5 h, 84% for 1025, 98% for 1028; (g)1.5 equiv of 1029, 1.5 equiv of LDA, THF, 0° C., 16 h; then 1.0 equiv of 1025 or 1028 in THF, −100 TO −20° C., 10 h, 60% for 1030, or 82% for 1031; (h) 2.5 equiv of monoperoxyphthalic acid, magnesium salt (MMPP), MeOH:phosphate buffer pH7 (1:1), 0° C., 1 h, 99% for 32, 96% for 1034; (i) 2.0 equiv DIBAL, toluene, −78° C., 1 h, 90% for 1033, 81% for 1035. LDA=lithium diisopropylamide; DIBAL=diisobutylaluminum hydride.

Figure 70:
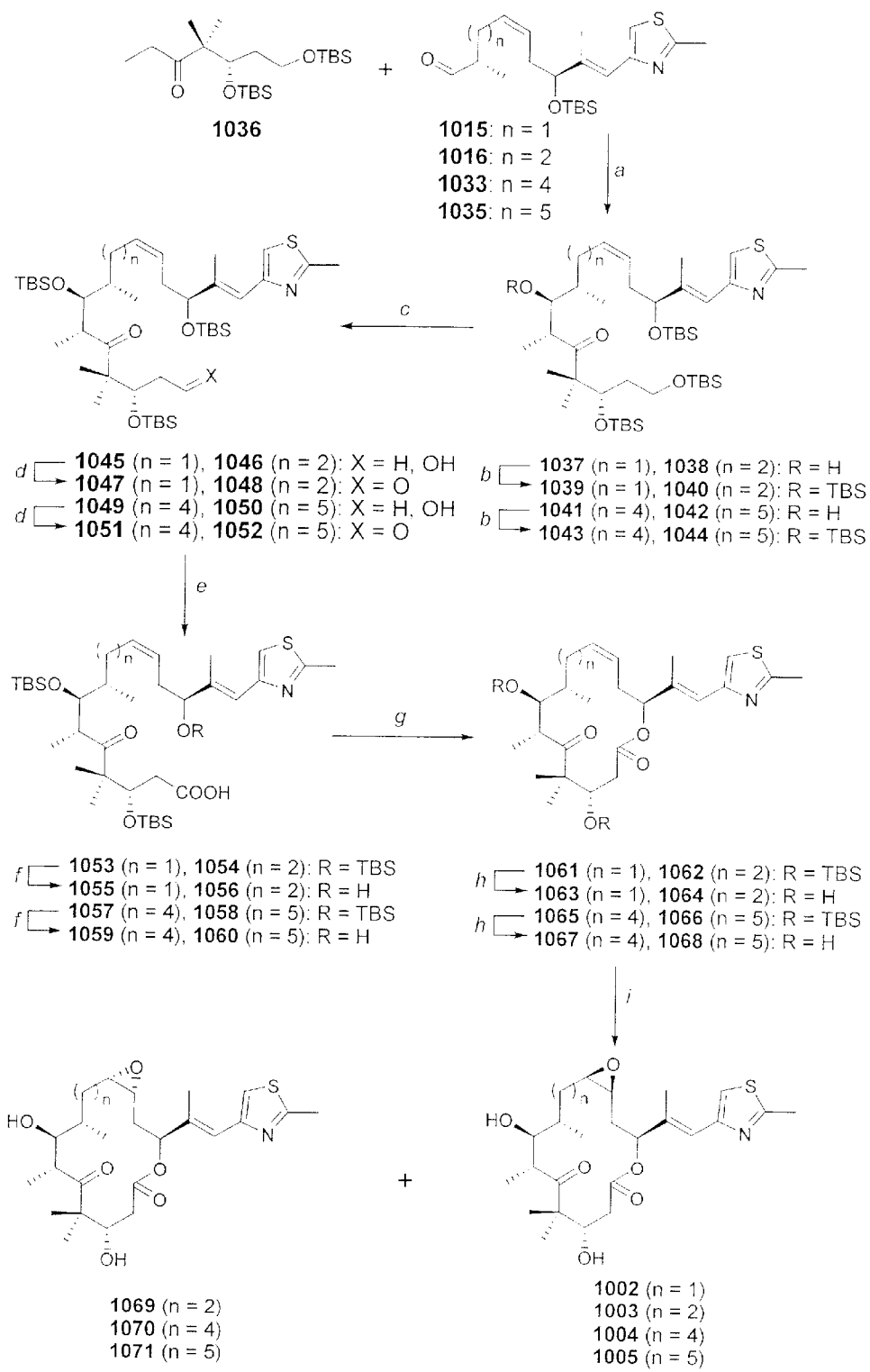

FIG. 70 illustrates the synthesis of epothilone A analogs 1002–1005. Reagents and conditions: (a) 1.2 equiv of LDA, THF, 0° C., 15 min; then 1.2 equiv of 1036 in THF, −78° C., 1 h; then 1.0 equiv of aldehyde (1015, 1016, 1033, 1035) in THF at −78° C., 71% for 1037 (single diastereoisomer), 72% for 1038 and its 6S,7R-diastereoisomer (ca. 4:1 ratio), 77% for 1041 and its 6S,7R-diastereoisomer (ca. 6:1 ratio), 60% for 1042 and its 6S,7R-diastereoisomer (ca. 5:1 ratio); (b) 1.5 equiv of TBSOTf, 2.0 equiv of 2,6-lutidine, methylene chloride, 0° C., 1 h, 94% for 1039, 93% for 1040, 85% for 1043, 95% for 1044; (c) 1.0 equiv of CSA added portionwise over 1 h, methylene chloride:MeOH (1:1), 0° C., 3 h, 77% for 1045, 82% for 1046, 91% for 1049, 83% for 1050; (d) 2.0 equiv of $(COCl)_2$, 4.0 equiv of DMSO, 6.0 equiv of $Et_3N$, CH2Cl2, −78 to 0° C., 1.5 h, 93% for 1047, 85% for 1048, 99% for 1051, 95% for 1052; (e) 5.0 equiv of $NaClO_2$, 10.0 equiv of 2-methyl-2-butene, 2.5 equiv of $NaH_2PO_4$l tBuOH:$H_2O$ (5:1), 0° C., 1 h, 99% for 1053, 95% for 1054, 99% for 1057, 98% for 1058; (f) 6.0 equiv of TBAF, THF, 25° C., 10 h, 92% for 1055, 77% for 1056, 85% for 1059, 85% for 1060; (g) 2.5 equiv of 2,4,6-trichlorobenzoylchloride, 5.0 equiv of $Et_3N$, THF, 0 to 25° C., 1 h; then slow addition (1 mL/h) to a solution of 2.0 equiv of 4-DMAP in toluene (0.005 M based on hydroxy acid), 70° C., 0.5–8 h, 70% for 1061, 82% for 1062, 73% for 1065, 75% for 1066; (h) 20% HF·pyr (by volume) in THF, 25° C., 24 h, 82% for 1063, 91% for 1064, 86% for 1067, 71% for 1068; (i) methyl(trifluoromethyl)dioxirane, MeCN, 0° C., 54% for 1002 (single diastereoisomer), 35% of 1003 and 35% of 1069 (ca. 1:1 ratio of diastereoisomers), 97% for 1004 and 1070 (ca. 6:1 ratio of diastereoisomers), 53% of 1005 and 26% of 1071 (ca. 2:1 ratio of diastereoisomers). Tf=triflate; TBAF=tetra-n-butylammonium fluoride; 4-DMAP=4-dimethylaminopyridine.

DETAILED DESCRIPTION OF THE INVENTION

The invention is directed to epothilone analogs and methods for producing such analogs using solid and solution phase chemistries based on approaches used to synthesize epothilones A and B (Nicolaou et al. Angew. Chem. Int. Ed. Engl. 35, 2399–2401 (1996); Nicolaou et al. Angew. Chem. Int. Ed. Engl. 36, 166–168 (1997); Nicolaou et al. Angew. Chem. Int. Ed. Engl., 36, 525–527 (1997)).

The following examples illustrate methods for the total synthesis of epothilone A (1), epothilone B (2), designed analogs and the generation of epothilone libraries. The examples rely on the olefin metathesis reaction and macrocyclization as a means to form the macrocyclic ring. The disclosed methods promise the discovery of anticancer agents which will be superior to existing ones. The examples represent exemplary conditions which demonstrate the versatility of the methodology and are not meant to be restrictive with the models disclosed.

EXAMPLE 1

Solution Phase Synthesis of Epothilone A and B and Analoas Using an Olefin Metathesis Approach (FIGS. 1–10)

A method using the olefin metathesis approach to synthesize epothilone A (1) and several analogs (39–41, 42–44, 51–57, 58–60, 64–65, and 67–69) is described (FIGS. 1–10). In this example, we describe the details of our olefin metathesis approach to epothilone A (1) and its application to the synthesis of several of its analogs. Key building blocks 6, 7 and 8 were constructed in optically active form and were coupled and elaborated to olefin metathesis precursor 4 via an aldol reaction and an esterification coupling. Olefin metathesis of compound 4, under the catalytic influence of $RuCl_2(=CHPh)(PCy_3)_2$ catalyst, furnished cis- and trans-cyclic olefins 3 and 48. Epoxidation of 49 gave epothilone A (1) and several analogs, whereas epoxidation of 50 resulted in additional epothilones. Similar elaboration of isomeric as well as simpler intermediates resulted in yet another series of epothilone analogs and model systems.

Figure 2:
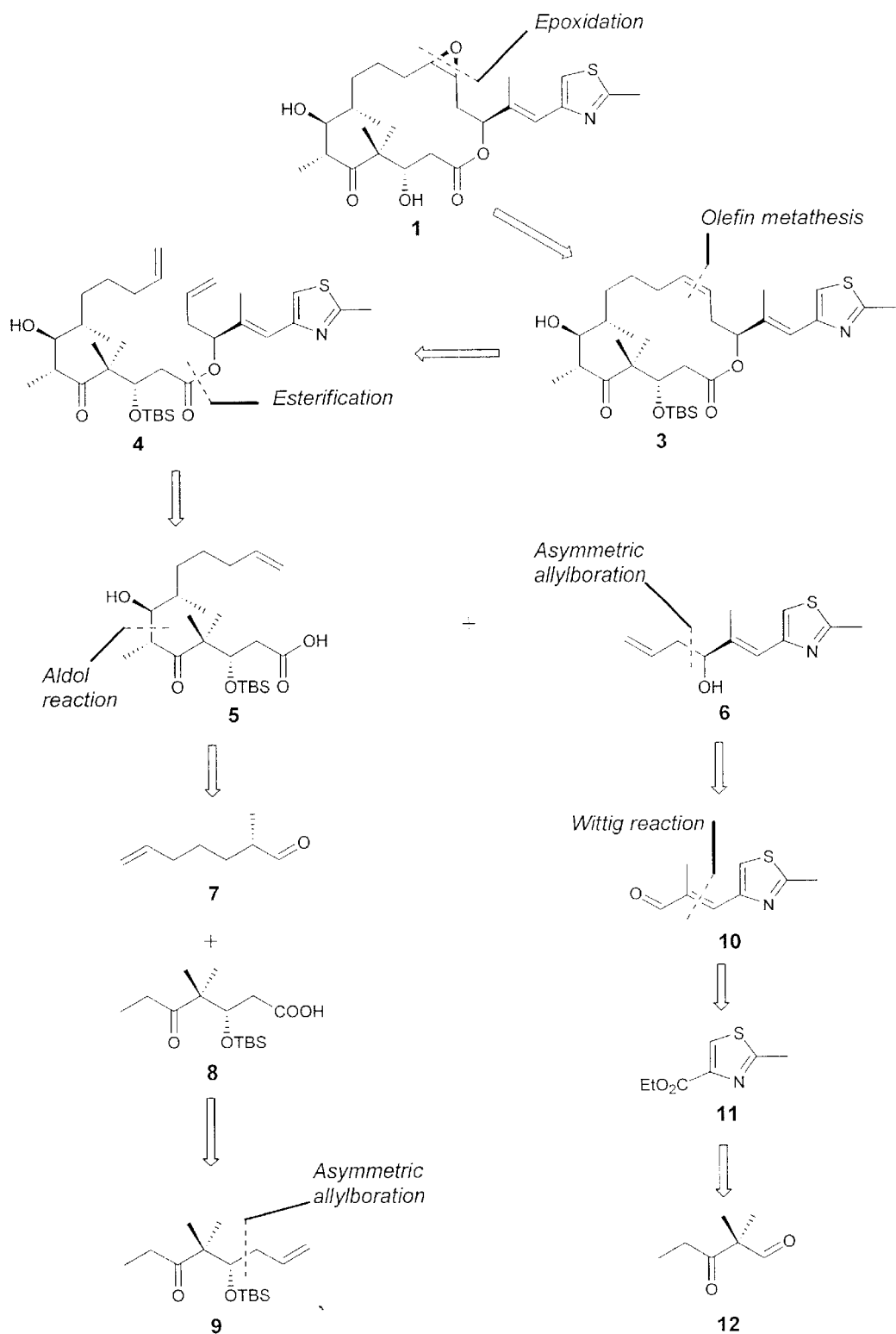
FIG. 2 illustrates the retrosynthetic analysis of the natural product compound epothilone A(1).

A. Retrosynthetic Analysis and Strategy (FIG. 2)

Figure 1:
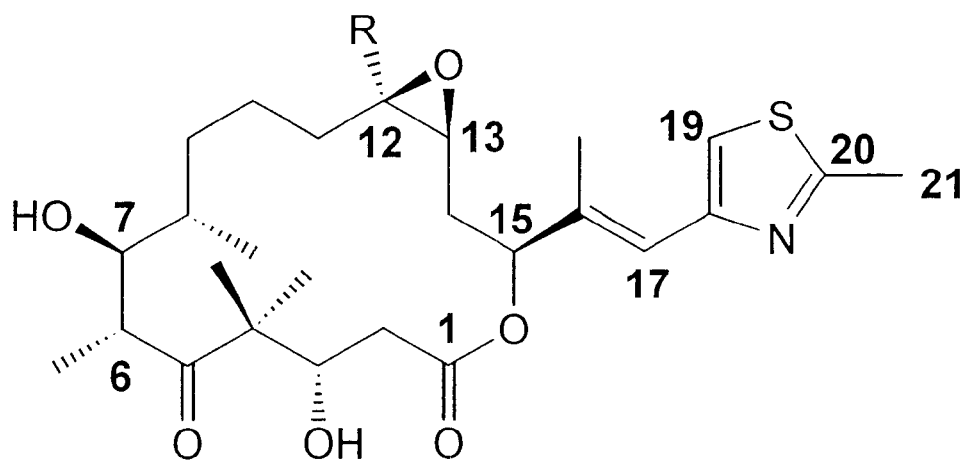
FIG. 1 illustrates the structure and numbering of epothilone A(1) and B(2).

The structure of epothilone A (1) is characterized by a 16-membered macrocyclic lactone carrying a cis-epoxide moiety, two hydroxyl groups, two secondary methyl groups, and a gem dimethyl group, as well as a side-chain consisting of a trisubstituted double bond and a thiazole moiety (FIG. 1). With its seven stereocenters and two geometrical elements, epothilone A (1) presents a considerable challenge as a synthetic target, particularly with regard to stereochemistry and functional group sensitivity. In search for a suitable synthetic strategy, we sought to apply new principles of organic synthesis and, at the same time, retain optimum flexibility for structural diversity and construction of libraries.

In recent years, the olefin metathesis reaction became a powerful tool for organic synthesis (For the development of the olefin metathesis as a ring forming reaction, see: Zuercher et al. J. Am. Chem. Soc. 1996, 118, 6634–6640; Schwab et al. J. Am. Chem. Soc. 1996, 118, 100–110; Grubbs et al. Acc. Chem. Res. 1995, 28, 446–452; Tsuji et al. Tetrahedron Lett. 1980, 21, 2955–2959; Katz et al. Tetrahedron Lett. 1976, 4247–4250; Katz et al. Tetrahedron Lett. 1976, 4241–4254; Katz et al. J. Am. Chem. Soc. 1976, 98, 606–608; Katz et al. Advances in Organomet. Chem. 1977, 16, 283–317).

In particular, a number of publications report application of this chemistry to the construction of macrocycles (For a number of applications of the olefin metathesis reaction in medium and large ring synthesis, see: Borer et al. Tetrahedron Lett. 1994, 35, 3191–3194; Clark et al. J. Am. Chem. Soc. 1995, 117, 12364–12365; Houri et al. J. Am. Chem. Soc. 1995, 117, 2943–2944; Fürstner et al. J. Org. Chem. 1996, 61, 3942–3943; Martin et al. Tetrahedron 1996, 52, 7251–7264; Xu et al. J. Am. Chem. Soc. 1996, 118, 10926–10927).

Inspection of the structure of epothilone A (1; FIG. 2) reveals the intriguing possibility of applying the olefin metathesis reaction to bis(terminal) olefin 4 to yield the cis-olefin containing macrocyclic lactone 3, which could be converted to the natural product by simple epoxidation, as retrosynthetically outlined in FIG. 2. Daring as it was, this strategy has the potential of delivering both the cis- and trans cyclic olefins corresponding to 4 for structural variation. Proceeding with the retrosynthetic analysis, an esterification reaction was identified as a means to allow disconnection of 4 to its components, carboxylic acid 5 and secondary alcohol 6. The aldol moiety in 5 allows the indicated disconnection, defining the aldehyde 7 and keto acid 8 as potential intermediates. Carboxylic acid 8 can then be traced to intermediate 9, whose asymmetric synthesis via allylboration of the known keto aldehyde 12 is straightforward. An asymmetric allylboration can also be envisioned as a means to construct alcohol 6, leading to precursor 10, which can be derived from the known thiazole derivative 11. This retrosynthetic analysis led to a highly convergent and flexible synthetic strategy, the execution of which proved to be highly rewarding in terms of delivering epothilone A (1) and a series of analogs of this naturally occurring substance for biological screening (FIG. 2).

B. Construction of Key Building Blocks and Models as Illustrated in FIGS. 3–6

As a prelude to the total synthesis, a number of building blocks were synthesized and utilized in model studies. Thus, fragments 7, 18a, 18b and 21 (FIG. 3; schemes A–C) were targeted for synthesis. Aldehyde 7 was constructed by two different routes, one of which is summarized in FIG. 3A. Thus, Oppolzer's acylated sultam derivative 13 (Oppolzer et al. Tetrahedron Lett. 1989, 30, 5603–1989; Oppolzer et al. Pure & Appl. Chem. 1990, 62, 1241–1250) was alkylated with 5-iodo-1-pentene in the presence of sodium bis (trimethylsilyl)amide (NaHMDS) to furnish compound 14 as a single diastereoisomer (by $^1H$ NMR). Lithium aluminum hydride reduction of 14 gave alcohol 15 in 60% overall yield from sultam 13. Oxidation of 15 with tetrapropylammonium perruthenate(VII) (TPAP) and 4-methylmorpholine-N-oxide (NMO) yielded the desired aldehyde 7 in 95% yield.

The synthesis of the two antipodal alcohols 18a and 18b is outlined in FIG. 3B. Thus, glycidols 16a and 16b were converted to the corresponding tert-butyldiphenylsilyl ethers (OTPS) 17a (90% yield) and 17b (94% yield), respectively, by a standard procedure (TPSCl, imidazole), and then to 18a (86% yield) and 18b (83% yield) by reaction with the vinyl cuprate reagent derived from copper(I) cyanide and vinyllithium.

FIG. 3C summarizes the synthesis of the third required building block, keto acid 21, starting with the known and readily available keto aldehyde 12 (Inuka et al. J. Org. Chem. 1967, 32, 404–407). Condensation of 12 with the sodium salt of phosphonate 19 produced α,β-unsaturated ester 20 in 99% yield. Cleavage of the tert-butyl ester with $CF_3COOH$ in Methylene chloride resulted in a 99% yield of carboxylic acid 21.

With the requisite fragments in hand, we turned our attention to a feasibility study of the olefin metathesis strategy. FIG. 4 summarizes the results of our work in this area. Thus, coupling of fragments 18a and 21, mediated by the action of EDC and 4-DMAP, led to ester 22a in 86% yield. Aldol condensation of the lithium enolate of keto ester 22a (generated by the action of LDA) and aldehyde 7 resulted in the formation of aldols 23 and 24 in ca. 4:3 ratio. Chromatographic separation allowed the isolation of pure 23 (42% yield) and 24 (33% yield). The stereochemical assignments of compounds 23 and 24 were based on an X-ray crystallographic analysis of a subsequent intermediate as will be described below. In FIG. 4, exposure of 2.3 to the $RuCl_2$(=CHPh) $(PCy_3)_2$ catalyst in Methylene chloride solution under high-dilution conditions at 25° C. for 12 hours resulted in clean formation of a single trans-macrocyclic olefin (25) ($J_{12,13}$=15.5 Hz) in 85% yield. Similar treatment of 24 generated the diastereomeric trans-olefin 26 ($J_{12,13}$=15.2 Hz) as the sole product in 79% yield. Desilylation of 25 and 26 with TBAF and AcOH in THF at 25° C. gave dihydroxy lactones 27 (92% yield) and 28 (95% yield, mp 128–129° C., EtOAc-hexanes), respectively.

X-ray crystallographic analysis of macrocyclic diol 28 revealed the trans nature of the double bond and defined the stereochemistry of all stereogenic centers. Comparison of the $^1$H NMR spectra of 26 and 28 with those of 25 ($J_{12,13}$=15.5 Hz), 27, 31 (J12,13=15.7 Hz) and 32 (vide infra) supported the trans geometry of the double bond generated by the olefin metathesis, and the C6–C7 stereochemistry. Therefore, the original assignment (Nicolaou et al. Angew. Chem. Int. Ed. Engl. 1996, 35, 2399–2401) of the cis geometry for this double bond and the C6–C7 stereochemistry of the aldol products in these model systems should now be revised as shown. Ironically, it was this erroneous, but encouraging assignment that let us to embark on the final plan to synthesize epothilone, A by the olefin metathesis approach. As events unfolded (vide infra), the real system produced both the cis- and the trans-cyclic olefins and the metathesis approach turned out to be fruitful.

For the purposes of analog synthesis, the 15R fragment 18b was utilized in these studies as well, as shown in FIG. 5. Coupling of 18b and 21 with DCC and 4-DMAP led to a 95% yield of ester 22b, the enantiomer of 22a. LDA-mediated aldol condensation of 22b with aldehyde 7 furnished aldols 29 (54% yield) and 30 (24% yield), which are diastereomeric with 23 and 24 of FIG. 4. Olefin metathesis of 29 and 30 with the $RuCl_2$(=CHPh) $(PCy_3)_2$ catalyst led to cyclic systems 31 ($J_{12,13}$=15.7 Hz) (80% yield) and 32 ($J_{12,13}$=15.4 Hz) (81% yield), respectively. Compounds 27, 28, 31 and 32 may serve as suitable precursors for the construction of a series of designed epothilones for biological investigations. At this juncture, however, it was considered more urgent to investigate the compatibility of the thiazole side-chain with the conditions of olefin metathesis and epoxidation.

To this end, the chemistry shown in FIG. 6 was studied. The enolate of keto acid 21 (2.3 equivalents of LDA, THF, −78° C.) reacted with aldehyde 7 to afford hydroxy acids 33 and 34 as a mixture of C6–C7 (ca 2:3 by $^1$H NMR) in good yield. This mixture was coupled with alcohol 6 in the presence of EDC and 4-DMAP, to afford two diastereomeric esters, 35 and 36 (29% and 44% yield, respectively, for two steps). Both products, 35 and 36 were subjected to the olefin metathesis reaction, and we were delighted to observe a smooth ring closure leading to trans-macrocycles 37 ($J_{12,13}$=15.5 Hz) (86%) and 38 ($J_{12,13}$=15.0 Hz) (66%). With cyclized product 37 and 38 in hand, we then proceeded to demonstrate the feasibility of epoxidizing the C12–C13 double bond in the presence of the sulfur and olefin functionalities in the thiazole side chain. Thus, treatment of both 37 and 38 with 0.9–1.2 equivalents of mCPBA in $CHCl_3$ at 0° C. resulted in the formation of epoxides 39 (or 40) (40%), 40 (or 39) (25%, stereochemistry unassigned), and 41 (18%, stereochemistry unassigned), as well as 42 (or 43) (22%), 43 (or 42) (11%) and 44 (7%) along with some unidentified side products. These results paved the way for the final drive towards epothilone A (1). More recently we found that methyl(trifluoromethyl)dioxirane (Yang et al. J. Org. Chem. 1995, 60, 3887–3889) gives superior results in the epoxidation reactions in regard to regioselectivity and yields. Thus, olefins 37 and 38 were converted to epoxides 39 (or 40) (45%) and 40 (or 39) (28%), and epoxides 42 (or 43) (60%) and 43 (or 42) (15%), respectively. No side-chain epoxidation was observed in either case.

C. Total Synthesis of Epothilone A and Analogs

Encouraged by the results of the model studies described above, we proceeded to assemble epothilone A (1). FIG. 7 shows the initial stages of the construction beyond the key building blocks 6–8. Thus, aldol condensation of 8 (2.3 equivalents of LDA) with aldehyde 7 afforded diastereomeric products 45 and 46 (ca 3:2 ratio by $^1$H NMR), which were coupled as a mixture with allylic alcohol 6 in the presence of EDC and 4-DMAP, to afford, after chromatographic purification, pure esters 4 (52% overall from 8) and 43 (31% overall from 8).

The olefin metathesis reaction of 4 (6R, 7S stereochemistry as proven by conversion to epothilone A) proceeded smoothly in the presence of the $RuCl_2$(=CHPh) $(PCy_3)_2$ catalyst, as shown in FIG. 8, to afford cyclic systems 8 ($J_{12,13}$=10.5 Hz) (46%) and 48 ($J_{12,13}$=15.0 Hz) (39%). The silyl ethers from 3 and 48 were removed by exposure to $CF_3COOH$ in Methylene chloride, affording dihydroxy compounds 49 (90% yield) and 50 (92% yield), respectively.

The cis-olefin 49 was converted to epothilone A (1) by the action of mCPBA (0.8–1.2 equivalents) in a reaction that, in addition to 1 (35% yield), produced the isomeric epoxides 51 (13% yield), 52 (or 53) (9% yield, stereochemistry unassigned) and 53 (or 52) (7% yield, stereochemistry unassigned), as well as bis(epoxides) 54 (or 55) and 55 (or 54) (10% total yield, stereochemistry unassigned). Reaction of olefin 49 with excess mCPBA (1.3–2.0 equivalents) gave a different product distribution: 1 (15%), 51 (10%), 52 (or 53) (10%), 53 (or 52) (8%), 54 (or 55) (8%), 55 (or 54) (7%), 56 (5%), and 57 (5%). The action of dimethyldioxirane (Murray et al. J. Org. Chem. 1985, 50, 2847–2853) (Methylene chloride, 0° C.) on 49 gave mainly 1 (50%) and 51 (15%), together with small amounts of 53 (or 54) and 54 (or 53) (10% total yield).

However, we found that the preferred procedure for this epoxidation was the one employing methyl(trifluoromethyl) dioxirane ($CH_3CN$, $Na_2EDTA$, $NaHCO_3$, Oxone®, 0° C.; Yang et al. J. Org. Chem. 1995, 60, 3887–3889), a method that furnished epothilone A (1) in 62% yield, together with smaller amount of its α-epoxide epimer 51 (13% yield). Chromatographically purified synthetic epothilone A (1) exhibited identical properties to those of an authentic sample (TLC, HPLC, $[α]_D$, IR, $^1$H and $^{13}$C NMR, and Mass spec).

Further, epoxidation of pure 1 with mCPBA (0.8–1.1 equivalents) resulted in the formation of bis(epoxides) 54 (or 55) (35%) and 55 (or 54) (32%) along with sulfoxide 57 (6%), confirming the C12–C13 stereochemical assignments shown in FIG. 8. Under similar conditions, α-isomeric epoxide 51 was recovered unreacted.

The trans-olefinic compound 50 gave rise to another series of epothilones A (58–60) as shown in FIG. 9. Thus, epoxidation of 50 with 1.0 equivalent of mCPBA furnished compounds 58 (or 59) (5%, stereochemistry unassigned), 59 (or 58) (5%, stereochemistry unassigned) and 60 (60%, stereochemistry unassigned). Similarly, epoxidation of 50 with 1.0 equivalent of dimethyldioxirane resulted in the formation of 58 (or 59) (10%), 59 (or 58) (10%) and 60 (40%). Interestingly, however, the action of methyl (trifluoro-methyl)dioxirane led only to 58 (or 59) (45%) and 59 (or 58) (35%) in a much cleaner fashion.

In order to expand the epothilone A library, we utilized the 6S,7R-stereoisomer 61 (obtained from 47 by $CF_3COOH$-induced desilylation in 90% yield) in the olefin metathesis reaction, to afford cyclic compounds 62 ($J_{12,13}$=9.8 Hz) (20%) and 63 ($J_{12,13}$=15.0 Hz) (69%) (FIG. 10). Epoxidation of the dihydroxy macrocyclic compound 62 with mCPBA (0.8–1.2 equivalents) in $CHCl_3$ at −20 to 0° C. gave isomeric epoxides 64 (or 65) (25%) and 65 (or 64) (23%). Side-chain epoxide 66 was not isolated in this case. Similarly, diol 63 furnished 67 (or 68) (24%), 68 (or 67) (19%), and 69 (31%) under the same reaction conditions. The stereochemistry of epothilones 64–69 remains unassigned. Again, epoxidation of compounds 62 and 63 using methyl(trifluoromethyl) dioxirane resulted in epoxides 64 (or 65) (58%) and 65 (or 64) (29%), and in epoxides 67 (or 68) (44%) and 68 (or 67) (21%), respectively, in a cleaner fashion (FIG. 10).

In example 1, we illustrate methods culminating in the total synthesis of epothilone A (1) and of analogs by an olefin metathesis approach. Furthermore, besides defining the scope and limitations of this new methodology in total synthesis, the methods provide a series of epothilone A analogs for biological investigations and further chemical explorations. The high convergence and relative simplicity of the chemistry involved in this construction make this strategy amenable to combinatorial synthesis for the generation of large libraries of these structures, as illustrated in a later example.

EXAMPLE 2

Solution Phase Synthesis of Epothilone A and B and Analoas Using a Macrolactonization Approach as Illustrated in FIGS. 11–19

In this example, we illustrate methods for the total synthesis of both epothilones A (1) and B (2) and of a number of analogs using our macrolactonization strategy (Nicolaou Angew. Chem. Int. Ed. Engl. 1997, 36, 525–527). The reported strategy relies on a macrolactonization approach and features selective epoxidation of the macrocycle double bond in precursors 70 and 71 (FIG. 1), respectively, as well as high convergency and flexibility. Building blocks 76–79 and 82 were constructed by asymmetric processes and coupled via Wittig, aldol, and macrolactonization reactions to afford the basic skeleton of epothilones and that of several of their analogs by a relatively short route. The utilization of intermediate 81, obtained via a stereoselective Wittig reaction and its Enders coupling to SAMP hydrazone 80 (FIG. 17), in combination with a stereoselective aldol reaction with the modified substrate 136 (FIG. 19) improved the stereoselectivity and efficiency of the total synthesis of these new and highly potent microtubule binding antitumor agents.

A. Retrosynthetic Analysis

FIG. 11 outlines the macrolactonization-based retrosynthetic analysis of epothilones A (1) and B (2). Thus, retrosynthetic removal of the epoxide oxygen from 1 and 2 reveals the corresponding Z-olefins, 70 and 71, as potential precursors, respectively. The second major retrosynthetic step along this route is the disconnection of the macrocyclic ring at the lactone site, leading to hydroxy acids 72 and 73 as possible key intermediates. Moving further along the retrosynthetic path, an aldol-type disconnection allows the generation of keto acid 76 as a common intermediate, and aldehydes 74 and 75 as reasonable building blocks for 72 and 73, respectively. Keto acid 76 can be envisioned to arise from an asymmetric allylboration of the corresponding aldehyde, followed by appropriate elaboration of the terminal olefin. The larger intermediates, 74 and 75, can be disconnected by two slightly different ways. The first disconnection (route a) involves a retro-Wittig type reaction accompanied by a number of functional group interchanges, leading to compounds 77, 78 and 79. The second disconnection, specifically sought for its potential to address the geometry issue of the trisubstituted double bond of epothilone B (2) (route b), involves: (i) a retro-Enders alkylation, leading to hydrazone 80 and iodide 81; and (ii) a retro-Wittig type disconnection of the latter intermediate (81) to reveal aldehyde 82 and stabilized ylide 83 as potential building segments. An asymmetric allylboration of 82 then points to Brown's chiral allylborane, and an aldehyde carrying the required thiazole moiety as potential starting points.

B. Total Synthesis

1. Construction of Building Blocks (FIGS. 12–13):

The strategy derived from the retrosynthetic analysis discussed above (FIG. 1), required building blocks 76–79, 82, and related compounds. Their construction in optically active form proceeded as follows. FIG. 12 summarizes the synthesis of keto acid 76 starting with the known keto aldehyde 84. Thus, addition of (+)-Ipc$_2$B(allyl) to 84 in ether at −100° C. resulted in the formation of enantiomerically enriched alcohol 85 (74% yield, ee >98% by Mosher ester determination). Silylation of 85 with tert-butyldimethylsilyl triflate (TBSOTf) furnished, in 98% yield, silyl ether 86. The conversion of terminal olefin 86 to carboxylic acid 76 was carried out in two steps: (i) ozonolysis in Methylene chloride at −78° C. followed by exposure to Ph$_3$P to give aldehyde 87 (90% yield); and (ii) oxidation of 87 with NaClO$_2$ in the presence of 2-methyl-2-butene and NaH$_2$PO$_4$ in tBuOH-H$_2$O (5:1) (93% yield).

The synthesis of the thiazole-containing fragments 82 and 79 was accomplished as shown in FIG. 12. Thus, the known thiazole derivative 88 was reduced with DIBAL (1.6 equivalents, Methylene chloride, −78° C.) to aldehyde 89 (90% yield), which reacted with the appropiate stabilized ylide [Ph$_3$P=C(Me)CHO] in benzene at 80° C. to afford the required (E)-α, β-unsaturated-aldehyde 90 in 98% yield. Addition of (+)-Ipc$_2$B(allyl) to 90 in ether/pentane at −100° C. gave allylic alcohol 91 in 96% yield (>97% ee by Mosher ester analysis). Protection of the hydroxyl group in 91 as a TBS ether (TBSCl, imid., DMF, 99% yield), followed by chemoselective dihydroxylation (OsO$_4$ cat., NMO) of the terminal olefin (95% yield) and Pb(OAc)$_4$ cleavage of the resulting diol (98% yield), furnished aldehyde.82 via intermediate 92. Finally, NaBH$_4$ reduction of 82 (96% yield), followed by iodination (I2, imidazole, Ph$_3$P, 89% yield) and phosphonium salt formation (Ph₃P, neat, A, 98% yield) gave the requisite fragment 79 via the intermediacy of alcohol 93 and iodide 94.

The construction of aldehyde 77 and ketone 78 proceeded from SAMP hydrazone 80 as shown in FIG. 13. Thus, reaction of propionaldehyde with SAMP, furnished 80, which upon sequential treatment with LDA (THF, 0° C.) and 4-iodo-1-benzyloxybutane (THF, −100 to 0° C.) led to compound 95 in 92% yield and >98% de ($^1$H NMR). Cleavage of the hydrazone moiety by exposure to ozone (Methylene chloride, −78° C., 77% yield), or by treatment with MeI at 60° C. followed by acidic workup (aq HCl, 86% yield), followed by NaBH₄ reduction of the resulting aldehyde (96), furnished alcohol 97 in 98% yield. The latter compound (97) was then silylated with TBSCl in Methylene chloride in the presence of Et₃N and 4-DMAP to afford silyl ether 98 in 95% yield. Cleavage of the benzyl ether in 98 by hydrogenolysis [H₂, Pd(OH)₂ cat., THF, 50 psi], gave primary alcohol 99 (95% yield), which was smoothly oxidized to the desired aldehyde 77 under Swern conditions [(COCl)₂, DMSO, Et₃N, 98% yield]. Addition of MgMgBr to 77 proceeded in 84% yield, and was followed by TPAP-NMO oxidation of the resulting secondary alcohol (100) to give the other required building block, ketone 78, in 96% yield (FIG. 13).

With the appropriate building blocks at hand the convergent approach to epothilones A (1) and B (2) could now enter its second phase.

2. Total Synthesis of Epothilones A as Illustrated in FIG. 14

The couplings of building blocks 76, 77 and 79 and the total synthesis of epothilone A (1) and its 6S, 7R-diastereoisomers (111 and 112) are shown in FIG. 14. Thus, generation of the ylide from phosphonium salt 79 with sodium bis(trimethylsilyl)amide (NaHMDS), followed by reaction with aldehyde 77 resulted in the formation of the desired Z-olefin 101 ($J_{12,13}$=10.8 Hz, obtained from decoupling experiments) as the predominant product in 77% yield, [Z:E ca 9:1; the minor isomer (E) was removed chromatographically in subsequent steps]. Parenthetically, key intermediate 101 was also prepared by Wittig coupling of phosphonium salt 114 and aldehyde 82 in a reversal of the reacting functionalities of the two fragments as shown in FIG. 15. Thus, alcohol 99 was directly converted to iodide 113 by the action of I₂, imidazole, and Ph₃P (91% yield), and then to phosphonium salt 114 by heating with Ph₃P (91% yield). Generation of the ylide from 114 with equimolar amounts of NaHMDS in THF, followed by reaction with aldehyde 82 yielded Z-olefin 101 in 69% and in ca 9:1 ratio with its E-isomer.

Returning to FIG. 14, selective desilylation of the primary hydroxyl group from 101, was achieved by the action of camphorsulfonic acid (CSA) in MeOH:Methylene chloride (1:1), leading to hydroxy compound 102 in 86% yield. Oxidation of 102 to aldehyde 74 was then carried out using SO₃·pyr., DMSO and Et₃N (94% yield). With the availability of 74, we were then in a position to investigate its aldol condensation with keto acid 76. It was found that the optimum conditions for this coupling reaction required generation of the dilithioderivative of 76 (1.2 equivalents) with 3.0 equivalents of lithium diisopropylamide (LDA) in THF (−78 to −40° C.), followed by addition of aldehyde 74 (1.0 equivalent), resulting in the formation of a mixture of the desired product 103a and its 6S, 7R-diastereoisomer 103b in ca 1:1 ratio and in high yield. Despite the lack of stereoselectivity in this reaction, the result was welcome at least with regard to the prospect it provided for the construction of the 6S, 7R-diastereoisomer of epothilones A and B. This mixture was then carried through to the stage of carboxylic acids 105 and 106 (FIG. 14), where it was chromatographically separated to its components. Thus, exposure of 103a/103b to excess of TBSOTf and 2,6-lutidine furnished a mixture of tetra-silylated products 104a/104b, which was then briefly treated with K₂CO₃ in MeOH₂ to afford, after silica gel flash or preparative layer chromatography, carboxylic acids 105 (31% overall yield from 7) and 106 (30% overall yield from 74) (105: Rf=0.61; 39: Rf=0.70, silica gel, 5% MeOH in Methylene chloride). The indicated stereochemistry at C7 and C6 in compounds 105 and 106 was assigned later and was based on the successful conversion of 105 to epothilone A (1) as described below.

At this stage, it was necessary to selectively remove the TBS group from the allylic hydroxyl group of 105, so as to allow macrolactonization of the seco-acid substrate (72). This goal was achieved by treatment of 38 with tetra-n-butylammonium fluoride (TBAF) in THF at 25° C., generating the desired hydroxy acid 72 in 78% yield. The key macrolactonization reaction of 72 was carried out using the Yamaguchi method (2,4,6-trichlorobenzoyl chloride, Et₃N, 4-DMAP) at 25° C., affording compound 108 in 90% yield. Removal of both TBS groups from 108 (CF₃COOH, Methylene chloride, 0° C.) furnished diol 70 in 92% yield. Finally, treatment of 70 with methyl(trifluoromethyl)dioxirane led cleanly to epothilone A (1) (62% yield) and its α-epoxide epimer (13% yield). Synthetic epothilone A (1) was chromatographically purified (preparative thin layer chromatography, silica gel) and exhibited identical properties to those of an authentic sample (TLC, HPLC, [α]D, IR, $^1$H and $^{13}$C NMR and HRMS).

A similar sequence was followed for the synthesis of the 6S,7R-diastereoisomers 111 and 112 of epothilone A (1) from compound 106 (FIG. 14) via intermediates 107 (82% yield from 106), 109 (85% yield from 107), and 110 (95% yield from 109). Epothilone 111 was obtained as the major product, together with its a-epoxide epimer 112 (87% total yield, ca 2:1 ratio) from olefinic precursor 110 by methyl (trifluoromethyl)dioxirane epoxidation.

3. Total Synthesis of Epothilones B (FIG. 16)

The first approach to epothilone B (2) was designed with the aim of delivering, not only the natural substance, but also its 12S-diastereoisomer 125 (FIG. 16), which in turn required the generation of both 12Z- and 12E-olefins. To this end, the ylide generated from phosphonium salt 79 with equimolar amounts of NaHMDS in THF, was reacted with ketone 78 to afford a mixture of Z- and E-olefins 115 (ca 1:1 ratio) in 73% total yield. This mixture was carried through the sequence to the stage of carboxylic acids 119 and 120 (see FIG. 16 for details), which were chromatographically separable. Carboxylic acid 120 (mixture of geometrical isomers) with the wrong stereochemistry at C6 and C7 (6S, 7R) was abandoned at this stage, whereas the mixture of Z- and E-isomers 119 with the correct stereochemistry at C6 and C7 (6R, 7S) was taken to the macrolactone stage (compounds 121 and 122) via hydroxy acid 6', by: (i) selective desilylation of the C15 hydroxyl group (TBAF, THF, 75% yield); and (ii) Yamaguchi cyclization (37% yield of 121, plus 40% of 122). Deprotection of bis(silylether) 121 by treatment with CF₃COOH in Methylene chloride afforded diol 71 in 91% yield. Finally, epoxidation of 71 with mCPBA in benzene at 3° C. gave epothilone B (2), together with its α-epoxide epimer 124 in 66% total yield and ca 5:1 ratio ($^1$H NMR) while the use of dimethyldioxirane, gave 2 and 124 in 75% total yield in the same ratio (ca 5:1 in favor of 2). Epoxidation of 71 with methyl(trifluoromethyl)dioxirane in $CH_3CN$ at 0° C. improved the yield of epothilone B (2) and its α-epimer 124 to 85%, but did not significantly change the diastereoselectivity of the reaction. Epothilone B (2) was purified by silica gel preparative layer chromatography and exhibited identical properties (TLC, HPLC, [α]D, IR, $^1H$ and $^{13}C$ NMR, and HRMS) with those of an authentic sample.

By the same sequence, and in similar yields, the macrocycle 122 containing the E-endocyclic double bond (FIG. 16), was converted to the 12S-epimeric epothilone B 125 and its α-epoxy epimer 126 via dihydroxy macrocyclic compound 123 (epoxidation with methyl(trifluoromethyl)dioxirane).

In order to improve the efficiency of the route to epothilone B (2), a more stereoselective total synthesis was devised and executed as follows. FIG. 17 addresses the stereoselective construction of intermediate 75 with the 12Z-geometry. Thus, condensation of the stabilized ylide 83 (obtained from 4-bromo-1-butene by: (i) phosphonium salt formation; (ii) anion formation with NaHMDS; and (iii) quenching with MeOC(O)Cl) with aldehyde 82 proceeded smoothly to afford olefinic compound 127 in 95% yield and as a single isomer. Reduction of the methyl ester in 127 with DIBAL resulted in the formation of allylic alcohol 128 (98% yield), which was deoxygenated by first reacting it with $Ph_3P—CCl_4$, and thence with $LiEt_3BH$, to afford the desired trisubstituted 12Z-olefin 130, via chloride 129, in 82% overall yield. The latter compound 130 was regioselectively hydroborated with 9-BBN and converted to the primary alcohol 131 (91%), which was then treated with 2-imidazole-$Ph_3P$ to afford iodide 81 (92% yield). This iodide was then used in an Enders alkylation reaction with SAMP hydrazone 80 to give compound 132 as a single isomer ($^1H$ NMR) and in 70% yield. Treatment of hydrazone 132 with monoperoxyphthalic acid magnesium salt (MMPP) in MeOH:phosphate pH 7 buffer (1:1) resulted in clean conversion to nitrile 133 (80% yield), which formed aldehyde 75 (82% yield) upon exposure to DIBAL at −78° C. in toluene solution.

The homogeneous aldehyde 75 was converted to epothilone B (2) by the sequence depicted in FIG. 18. Thus, condensation of the dianion of 76 with 75 as before (FIG. 16), produced two diastereoisomers, 117a (6R, 7S stereoisomer) and 117b (6S,7R stereoisomer) in high yield, and in ca 1.3:1.0 ratio (117a:117b). This mixture was carried through the indicated sequence to carboxylic acids 119 (32% overall yield from 75) and 119 (28% overall yield from 75), which were separated by silica gel preparative layer or flash column chromatography and taken individually further along the sequence as described for the corresponding stereoisomeric mixtures shown in FIG. 16. Thus, 119 was selectively deprotected with TBAF to afford hydroxy acid 73 (73% yield), which was then cyclized to macrolactone 121 in 77% yield by the Yamaguchi method. The conversion of 121 to epothilone B (2) and its α-epoxide epimer 119 has already been described above (FIG. 16).

In an effort to improve the diastereoselectivity of the aldol condensation between C1–C6 and C7–C15 fragments, the following chemistry was explored (FIG. 19). Thus, ketone 136 (prepared from ketone 87, FIG. 12, by selective reduction, followed by silylation) was converted to its enolate with stoichiometric amounts of LDA and reacted with aldehyde 75 (Z-isomer), affording coupling products 137 and 138 in 85% total yield and ca 3:1 ratio, with the desired compound 137 predominating as proven by its conversion to 119 and epothilone B (2). Thus, chromatographic purification (silica gel, 20% ether in hexanes) led to 137, which was efficiently transformed to the previously synthesized intermediate 119 (FIG. 18) as follows. The newly generated hydroxyl group in 137 was silylated with TBSOTf-2,6-lutidine to furnish 139 (96% yield), which was then selectively desilylated at the primary position by the mild action of camphorsulfonic acid (CSA) in MeOH-Methylene chloride, leading to 140 (85%). Finally, sequential oxidation of the primary alcohol with $(COCl)_2$-DMSO-$Et_3N$ (95% yield) and $NaClO_2$—$NaH_2PO_4$ (90% yield) led to hydroxy acid 119 via aldehyde 141. The conversion of 119 to 2 has already been described above (FIG. 18). This sequence represents a stereoselective and highly efficient synthesis of epothilone B (2) and opens the way for the construction of further analogs within this important family of microtubule binding agents.

The chemistry described in this example defines a concise methodology for the construction of epothilones A (1) and B (2) based on a macrolactonization strategy, and which enjoys convergency and flexibility for structural diversity. The methodology is not limited to epothilones A (1) and B (2), but can be extended to numerous intermediates and structural analogs included herein. In addition, the resultant analogs will play a crucial role in elucidating structure-activity relationships of these new substances and in determining their relevance to cancer chemotherapy. Binding assays, vida infra, have demonstrated that compounds 70, 71, 123 and 125 show binding affinities to microtubules comparable to those of epothilones A (1), B (2), and Taxol™.

EXAMPLE 3

Solid Phase Synthesis of the Epothilones as Illustrated in FIGS. 20–21 and FIGS. 49–50

In this example, we demonstrate the first solid phase synthesis of epothilone A (1) and the total synthesis of epothilone B (2), the generation of a small epothilone library, and the identification of a synthetic epothilone that interacts with tubulin more potently than epothilones A (1) and B (2) and Taxol (FIGS. 20–24 and FIGS. 49–50). The solid phase construction of 1 may herald a new era of natural products synthesis and, together with the solution phase synthesis of 2, paves the way for the generation of large combinatorial libraries of these important molecules for biological screening.

The strategy for the solid phase synthesis of epothilone A (1) was based on the retrosynthetic analysis indicated in FIG. 20 (Nicolaou et al. Angew. Chem. Int. Ed. Engl. 35, 2399–2401 (1996); Yang et al. Angew. Chem. Int. Ed. Engl. 36, 166–168 (1997)). Thus, it was anticipated that the three requisite fragments (143–145), one on a solid support (145), would be coupled together sequentially through an aldol reaction, an esterification reaction, and an olefin metathesis reaction, the latter simultaneously cyclizing and liberating the product from the solid support (144+145+143 leads to 142 which leads to 141; FIG. 20). A simple desilylation and epoxidation reaction would then complete the total synthesis of epothilone A (1) and analogues thereof (141 leads to 1; FIG. 20). The outlook for obtaining two products at each of the aldol, metathesis, and epoxidation steps was considered advantageous for the purposes of library generation.

As illustrated in FIG. 21, Merrifield resin (146) was converted to phosphonium salt 147 in >90% yield by sequential reaction with: (i) 1,4-butanediol-NaH-n-$Bu_4$NI catalyst; (ii) $Ph_3P$-iodine-imidazole; and (iii) $Ph_3P$. Preferred alternative resins, other than the Merrifield resin, employable in this procedure include PEG-polystyrene, hydroxymethyl polystyrene, formyl polystyrene, aminomethyl polystyrene and phenolic polystyrene. Ylide 148 generated from 147 by the action of NaHMDS in THF:DMSO at 25° C., reacted with aldehyde 149 at 0° C. to form olefinic compound 150 in >70% yield. The geometry of the double bond in 150 was tentatively assigned as Z, but its geometry was neither rigorously determined nor did it matter for our purposes. Desilylation of 150 with HF·pyr., followed by Swern oxidation of the resulting primary alcohol furnished aldehyde 145 in high yield (>95%). The aldol condensation of the polymer-bound aldehyde 145 with the dianion derived from keto acid 144 in the presence of $ZnCl_2$ in THF gave a mixture of diastereoisomers (ca 90% yield, ca 1:1 ratio). Finally, introduction of the heterocyclic segment 143 onto the growing substrate was achieved by esterification, leading to the required precursor 152 in ca 80% yield. Exposure of 152 to $RuCl_2$(=CHPh) $(PCy_3)_2$ catalyst (153) in Methylene chloride at 25° C. released from the resin olefinic compounds 154–156 and 141 (52% total yield, 154:155:156:141 ca 3:3:1:3 as determined by HPLC). Compounds 154–156 and 141 could be separated either by HPLC or by preparative layer silica gel chromatography, and the two with the correct C6–C7 stereochemistry (e.g. 155 and 141) were desilylated by exposure to TFA to afford epothilone precursors 157 (92%) and 158 (90%), respectively. Epoxidation of 157 and 158 with trifluoro(methyl)dioxirane then furnished epothilone A (1, 70%) and its diastereoisomer 159 (45%), respectively. The α-epoxy isomers of 1 and 159 were also obtained in these epoxidation reactions. Pure synthetic epothilone A (1) exhibited identical properties (TLC, $[\alpha]_D$, $^1H$ and $^{13}C$ NMR, IR and HRMS) to those of an authentic sample (FIG. 21).

The solid phase synthesis of epothilone A (1) described herein (FIGS. 20–24 and FIGS. 49–50) represents a new concept for the total synthesis of natural products, traces a highly efficient pathway to the naturally occurring epothilones, and opens the way for the generation of large combinatorial epothilone libraries. The biological results demonstrate that more potent microtubule binding analogues than the parent epothilones can be obtained (e.g. compound 71; biological results vida infra) by chemical synthesis. Furthermore, our findings point to lipophilic substituents rather than the epoxide moiety as important elements for binding activity.

The epothilone library (FIGS. 24–25) was designed without a methyl group at C-8 (the necessity of this methyl group for biological activity will be tested first, through the synthesis of 8-nor epothilone A prior to undertaking the construction of this library) for simplicity. The C1–C5 fragment is varied as outlined in FIGS. 24–25, whereas the stereochemistry at C-6, C-7, C-12 and C-15 is deliberately varied to multiply the number of compounds by two for each center. In addition, groups R1, R3 and R4 also vary. The requisite building blocks (boxes, lower part of FIGS. 24–25) are known in the prior art and synthesized by standard methods; solid support is prepared from polystyrene as shown in FIGS. 24–25. The enolates of the corresponding ketoacids are generated by the action of LDA and the aldol products are derivatized with R3 and condensed with 165 to afford 166. Palladium catalyzed coupling of 166 with specific aromatic stannanes, followed by olefin metathesis, form the macroring and simultaneously release the substrate from the solid support. The remaining two steps are carried out in solution. The epoxidation is carried out using a solid phase-bound peracid or dimethyloxirane, (for minimal work-up procedures) and the desilylation step is conveniently achieved by HF·pyr in Methylene chloride. The final products are generally pure enough for characterization and biological assay (or they can, if necessary, be purified by HPLC) and their numbers may vary from hundreds to thousands (see description of figures section for FIG. 25 for a calculation of such a library).

EXAMPLE 4

Total Synthesis of Epoxalones A and Epoxalone Analogs as Illustrated in FIGS. 24–39

In this example, we report the total synthesis of a novel series of designed epothilones with an oxygen instead of a sulfur atom at position 20 (see FIG. 24). The name epoxalones (ep for epoxide, oxa for oxazole, one for ketone; cf epothilone: ep for epoxide, thi for thiazole, one for ketone) is proposed for this new class of compounds.

The synthesis of the epoxalone A series was based on our olefin metathesis strategy toward epothilone A (1). This highly convergent and flexible sequence led to the construction of compounds 161, 168, 169, 170, 171, 172, 175, 176, 177, 178, 179, and 180 in rapid fashion starting with building blocks 7, 8 and 163 (FIG. 25). Thus, asymmetric allylboration of aldehyde 162 (obtained via the procedure by Kende et al. Tetrahedron Lett. 1995, 36, 4741–4744) with Brown's (+)-$Ipc_2B$(allyl) in $Et_2O$-pentane at –100° C. furnished compound 163 in 91% yield and >98% ee. This alcohol was esterified with the mixture of carboxylic acids 45 and 46 (ca. 5:3 ratio) obtained by aldol condensation of fragments 8 and 7 to afford compounds 164 and 165 as a ca. 5:3 mixture (82% total yield). Chromatographic separation (flash column, silica gel, 20% EtOAc in hexanes) of this mixture gave pure diastereoisomers 164 and 165.

Subjection of precursor 164 (possessing the correct C6–C7 stereochemistry) to the olefin metathesis reaction [$RuCl_2$(=CHPh) $(PCy_3)_2$, $CH_2Cl_2$, 25° C.] resulted in the formation of cyclic olefins 166 (40% yield) and 167 (29% yield) which were chromatographically separated (flash column, silica gel, 20% EtOAc in hexanes, 1:1) (FIG. 26). Exposure of 166 to 20% trifluoroacetic acid in $CH_2Cl_2$ at 25° C. furnished diol 168 in 89% yield. Similar treatment of 167 led to 169 (95% yield). Epoxidation of 168 with methyl (trifluoromethyl)dioxirane furnished epoxides 161 (34% yield) and 170 (15% yield) which were separated by preparative layer chromatography (silica gel, 75% EtOAc in hexanes). Similar treatment of 169 led to epoxides 171 (25%) and 172 (20%) (As illustrated in FIG. 26).

A parallel sequence starting with diastereoisomer 165 led to the 6S, 7R series of epoxalones 175–180 as summarized in FIG. 27.

The synthesized compounds (161, 168, 169, 170, 171, 172, 175, 176, 177, 178, 179, and 180) were tested for their tubulin assembly properties using the Filtration-Colorimetric Assay (outlined vida infra) at 20 mM concentrations at 30° C. and with pure tubulin. The most potent ones (161, 168, 169, 171 and 172) were then assayed at 0.1, 1.0, 2.0, 3.0, 4.0 and 5.0 mM concentrations under the same conditions leading to the plots shown in FIG. 28. Thus, both epoxalones 161 and 171 were found to be more potent than Taxol in inducing tubulin polymerization, whereas compounds 168, 169 and 172 showed comparable or slighlty less potencies than Taxol. The high potency of the trans-epoxide epoxalone 171 is perhaps the most striking observation in these studies and holds true for the corresponding trans-epoxides of epothilones A and B.

The implementation of the macrolactonization strategy towards the oxazole series of epothilones B proceeded along a similar path developed for the corresponding thiazole series of epothilones. FIG. 31 shows the stereoselective construction of the requisite aldehyde 217 and phosphonium salt 220 starting with the readily available oxazole derivative 213. Thus, asymmetric addition of (+)-Ipc$_2$B(allyl) to aldehyde 213 (see FIG. 31), as described in the preceding section gave alcohol 214. Silylation of 214 with TBSCl (for abbreviations, see description of figures) and imidazole gave 99% yield of silylether 215. Selective dihydroxylation of the terminal olefin in 215 employing the Upjohn procedure (NMO-OsO4 cat.), followed by NaIO$_4$ cleavage of the resulting diol led to aldehyde 217 in excellent yield (93%). Reduction of the aldehyde group in 217 with NaBH$_4$ (99% yield) followed by exposure to Ph$_3$P-I$_2$-imidazole furnished iodide 219 (87% yield) via primary alcohol 218. Finally, heating of 219 with Ph$_3$P at 100° C. gave phosphonium salt 220 in 90% yield.

In order to obtain both the 12E- and 12Z-isomers of epothilone B analogs, we initially undertook the non-stereoselective synthesis depicted in FIGS. 32 and 33 in which the first step involves a Wittig reaction, yielding a 1:1 mixture of geometrical isomers. Thus, generation of the ylide from phosphonium salt 220 by the action of NaHMDS in THF at −20° C., followed by addition of ketone 221, furnished compound 222 in 68% yield as a 1:1 mixture of E:Z isomers. Preparation of the desired aldehyde 224 from 222 required selective desilylation of the primary hydroxyl group (CSA, CH$_2$Cl$_2$—MeOH, 0 to 25° C., 92% yield) and oxidation of the resulting alcohol (223) with SO$_3$·pyr.-DMSO-Et$_3$N (98% yield).

The condensation of aldehyde 224 (mixture of 12E- and 12Z-geometrical isomers, FIGS. 32 and 33) with the anion derived from ketone (LDA, THF) proceeded smoothly at −78° C. to afford a mixture of diastereomeric aldols 226 and 227 (ca 4:1 ratio) in 73% combined yield. Chromatographic separation (silica, preparative layer) led to pure 2226 and 227, each consisting of E- and Z- geometrical isomers (ca. 1:1). Only the 6R,7S diastereoisomer 226 (less polar mixture of D12,13 geometrical isomers) was taken forward (polarity and comparison with the natural series was used as a guide to choose the desired 6R,7S-diastereoisomer at this stage). The geometrical isomers were separated after the macrolactonization reaction (vide infra).

The next task in the synthesis was to prepare hydroxyacid (FIG. 33). To this end, the hydroxy group in 226 was silylated (TBSOTf-2,6-lutidine, 96%) to afford tris (silylether) and, thence, selectively deprotected at the primary position by exposure to CSA in MeOH:CH2Cl2 at 0 to 25° C. leading to 228 (85% yield). A stepwise protocol was used to oxidize primary alcohol to the desired carboxylic acid: (i) (COCl)$_2$-DMSO-Et$_3$N, −78 to 0° C., yielding aldehyde (94% yield); and (ii) NaClO$_2$-2-methyl-2-butene, NaH2PO4, furnishing acid (99% yield). Selective desilylation at the allylic position with TBAF in THF then gave hydroxyacid in 78% yield.

Yamaguchi macrolactonization of hydroxyacid as in the natural series (2,4,6-trichlorobenzoylchloride-Et3N-4-DMAP, high dilution, 25° C.), followed by preparative thin layer chromatography (silica, 20% ether/hexanes) led to lactones 229 (Rf=0.24, 35%) and 230 (Rf=0.20, 42%). The identity of 229 was proven by comparison with an authentic sample prepared by a stereoselective route. Deprotection of 229 and 230 was carried out with HF·pyr. in THF at 25° C. and furnished diols 231 (62% yield) and 232 (82% yield), respectively. Finally, epoxidation of 231 and 232 with mCPBA in CHCl3 at 0° C. furnished the corresponding α- and β-epoxides (2+30, 40% total yield, ca 5:1 ratio, and 31+32, 45% total yield, ca 6:1 ratio). The stereochemical assignments shown in FIG. 33 for these compounds are tentative and are exclusively based on comparisons with the series related to natural epothilone B.

A stereoselective synthesis of the D12,13-series of the oxazole-containing epothilones (231, 233 and 234) was also developed and is shown in Schemes 33, 34 and 35. Thus, the desired geometry of the D12,13 position was fixed by condensation of the stabilized ylide (FIG. 34) with aldehyde 217 (benzene, D), a reaction that led to 90% yield of compound 237. Subsequent reduction of the ester group of 237 (DIBAL, CH2Cl2, −78° C., 99% yield), chlorination (Ph$_3$P, CCl$_4$, D, 81%), and further reduction (LiEt$_3$BH, THF, 0° C., 97% yield) furnished intermediate 240 via allylic alcohol 238 and chloride 239. Selective hydroboration of 240 at the terminal olefin site was achieved by the use of 9-BBN, and after oxidative work up, primary alcohol 241 was obtained in 92% yield. Conversion of 241 to iodide 242 was subsequently carried out by the standard I$_2$-imidazole-Ph$_3$P procedure (89% yield). The iodide 242 was then used to alkylate the SAMP hydrazone (LDA, THF, −100 to −20° C.), furnishing hydrazone 243 in 70% yield. The latter compound (243) was then transformed sequentially to nitrile 244 (MMPP, MeOH-phosphate buffer pH 7, 0° C., 46% yield), and thence to aldehyde 224 (DIBAL, toluene, −78° C., 84% yield).

The aldol condensation of the lithioderivative of the ketone with stereochemically homogeneous aldehyde 224 (FIG. 35) proceeded in a similar fashion to the case of the E:Z mixture described above, leading to pure compounds 245 and 246. After chromatographic separation, the pure 6R, 7S-diastereoisomer 245 [tentative assignment of stereochemistry based on polarity (less polar) and comparison to the natural series] was taken through the sequence, and on to the final products 233 as detailed in FIG. 35.

EXAMPLE 5

The 4,4-ethano Series of Epothilone A Analogs

A. Olefin Metathesis Approach as Illustrated in FIGS. 40–48

Applying the olefin metathesis approach to epothilones, we have synthesized a series of cyclopropane containing epothilone A analogs. These compounds considerably enrich the known epothilone libraries in terms of molecular diversity and numbers. Biological investigations with these analogs established useful structure-activity relationships within this important class of compounds. Interestingly, while the oxazole series of compounds exhibited comparable tubulin polymerization activity and cytotoxicity to the corresponding thiazole series, the 4,4-ethano-epothilones proved inactive. These results underscore the importance of conformational precision in these compounds for biological action.

Following the same retrosynthetic rationale as the one outlined above for the oxazole analogs, the 4,4-ethano epothilone A was analyzed as shown in FIG. 40. This time, the analysis led to building blocks 271, 7 and 272. The latter compound (272) was easily traced to β-ketoester 275 via intermediates 273 and 274. The forward construction of 267 and its congeners proceeded as follows.

We began with the synthesis of cyclopropyl-ketoacid 31 (FIG. 41). Thus, reaction of 1,2-dibromoethane with ethyl propionylacetate (275) in the presence of K$_2$CO$_3$ at ambient temperature resulted in the formation of cyclopropyl ketoester 276 (60% yield). Reduction of the ester- and keto-groups with LiAlH$_4$ (93% yield) followed by Swern oxidation of the resulting diol [(COCl)$_2$; DMSO; Et$_3$N] furnished ketoaldehyde 274 in 64% yield. Chemo- and stereoselective addition of (+)-Ipc$_2$B(allyl) to aldehyde 274 (>85% ee by Mosher ester analysis), followed by silylation (TBSOTf; 2,6-lutidine) of the generated secondary alcohol, gave silyl ether 273. Finally, cleavage of the terminal olefin in 273 with NaIO$_4$ in the presence of catalytic amounts of RuCl$_3$.H$_2$O in MeCN—H$_2$O—CCl$_4$ (2:3:2) at 25° C. yielded the desired ketoacid 272 in 43% overall yield from cyclopropyl ketoaldehyde 274.

The dianion of ketoacid 272 (LDA in THF at −30° C.) reacted with aldehyde 7 to form aldols 270 and 277 in ca. 2:3 (ratio by $^1$H NMR) (FIG. 42). The coupling of the mixture of 270 and 277 with fragment 271 was facilitated by EDC and 4-DMAP and the resulting hydroxyesters were chromatographically separated to afford pure 269 (15%) and 278 (36%).

Ring closure of advanced intermediate 269 and epoxidation of the desilylated cyclic diols are shown in FIG. 43. Thus, stirring of 269 with RuCl$_2$(=CHPh) (PCy$_3$)$_2$ catalyst in CH$_2$Cl$_2$ at 25° C. followed by chromatographic separation (silica gel, preparative thin layer) furnished cis- and trans-olefins 268 (37% yield) and 279 (35% yield), respectively. The corresponding diols 280 (65% yield) and 281 (62% yield) were obtained by treating the respective silyl ethers with 25% HF·pyr. in THF at ambient temperature. Finally, epoxidation of 280 with methyl (trifluoromethyl)dioxirane gave epoxides 267 (or 282) (50% yield) and 282 (or 267) (29% yield), whereas similar treatment of 281 furnished 283 (or 284) (11% yield) and 284 (or 283) (31% yield). The stereochemistry of epoxides 267, 282-4 remains unassigned.

The other aldol product, compound 278, was processed in a similar way as described above for 269, furnishing the 4,4-ethano-epothilone A analogs 287–292 as shown in FIG. 44. Again, the stereochemical details of these compounds remain unassigned.

B. Macrolactonization Approach

The 4,4-ethano analogs of epothilones B were designed in order to test the tolerance of the receptor site for the substitution of the gem-dimethyl group of the natural substance. As the retrosynthetic analysis of FIG. 45 succinctly shows, the requisite fragments for the synthesis of the designed 4,4-ethanoepothilone B (267) and its relatives, are defined as fragments 75 and 294. The synthesis of building block 294 was described in conjuction with the stereoselective total synthesis of epothilone B, whereas that of building block 294 is shown in FIG. 46. Thus, the ketocyclopropane derivative 273 (FIG. 46), described in the preceding section was subjected to ozonolysis and subsequent reduction with Ph$_3$P to afford aldehyde 295 in 90% yield. Further reduction [LiAl(OtBu)$_3$H, THF, −78° C.], followed by silylation of the resulting primary alcohol 296 (TBSCl, Et$_3$N, 4-DMAP) furnished ketocyclopropane fragment 294 in 83% overall yield.

FIG. 47 details the coupling of fragments 294 and 75 and the assembly of a series of 4,4-ethano-epothilone B analogs. Thus, generation of the lithium enolate of ketone 294 with LDA in THF at −78° C. to −60° C., followed by addition of aldehyde 75 resulted in the formation of aldols 297 and 298 in ca 1:2 ratio and 71% total yield. Stereochemical assignments were based on a X-ray crystallographic analysis of a subsequent intermediate, and will be discussed below. The difference in the ratio of aldol products between fragments 298 (ca 1:2, FIG. 47) and 297 (ca 4:1, see FIG. 36) is rather striking, and it may have its origin in the effect of the cyclopropane ring on the transition state of the reaction. The two diastereomeric aldol products 297 and 298 were chromatographically separated (silica, flash column chromatography) and processed separately in order to obtain both the 6S, 7R and 6R, 7S series of compounds.

Thus, stereoisomer 297 (FIG. 47) was silylated with TBSOTf and 2,6-lutidine affording tris(silylether) 299 in 92% yield, and then exposed to the action of CSA in CH2Cl2:MeOH at 0 to 25° C. to give hydroxy bis(silylether) 301 (74% yield) in which only the primary hydroxyl group was liberated. Stepwise oxidation of 301 with: (i) (COCl)2, DMSO, Et3N, −78 to 0° C., 96% yield, and (ii) NaClO2, 2-methyl-2-butene, NaH2PO4, 91% yield, gave sequentially aldehyde 303 and carboxylic acid 305. Selective desilylation of 305 with TBAF in THF at 25° C. furnished the desired hydroxyacid 293 in 62% yield.

The intended macrolactonization of 293 was accomplished by the Yamaguchi method (2,4,6-trichlorobenzoylchloride, Et3N, 4-DMAP, toluene, 25° C., high dilution), furnishing compound 308 in 70% yield. Exposure of 308 to HF·pyr. in THF at 25° C. resulted in the removal of both silyl groups, leading to diol 268 in 92% yield. Finally, epoxidation of 268 with (trifluoromethyl) methyldioxirane in MeCN resulted in the formation of epothilone B analogs 267 and 311 in ca 8:1 ratio (by 1H NMR) and 86% total yield. Preparative thin layer chromatography (silica, 5% MeOH in CH2Cl2) gave pure epothilone B analogs 267 and 312.

The same chemistry was performed with diastereoisomer 298 (FIG. 47) leading to epothilone B analogs 310, 312 and 313 via intermediates in similar yields to those described for 297. The latter compound (309) crystallized as long needles from MeOH—EtOH (mp. 157° C.) and yielded to X-ray crystallographic analysis which revealed its stereochemical structure (see ORTEP drawing in FIG. 48).

EXAMPLE 6

Solid Phase Synthesis of Desianed Epothilone Analogs Based on Combinatorial Approach, Tubulin Assembly Properties of Compounds and Cytotoxic Actions Against Tumor Cell Lines as Illustrated in FIGS. 49–50 and FIGS. 63–66

In this example, we illustrate (a) the solid phase synthesis of several epothilone A analogs based on a combinatorial approach; (b) the tubulin assembly properties of an extensive library of compounds; and (c) the cytotoxic actions against breast and ovarian carcinoma cells (including a number of Taxol-resistant tumor cell lines) of a selected number of these designed epothilones. The results provide comprehensive information on structure-activity relationships of epothilones and set the foundation for their further development.

The structures of epothilones are amenable to modification by changing the configuration of certain stereocenters, the geometry of the double bonds, the size of the rings, and the nature of their substituents. Our synthetic strategies towards these molecules were, therefore, designed on the premise of modifying these elements so as to reach optimum molecular diversity and obtain a maximum number of library members. FIGS. 64*a* and 64*b* include the structures of an epothilone library obtained by solution and solid phase combinatorial methods as described vida supra. Biological screening of these compounds was expected to lead to the establishment of sufficient structure-activity relationships to allow the next phase of the program, the design, synthesis and identification of potential drug candidates, to proceed along a narrower track.

The strategy for the construction of a library of epothilone A analogs was based on our epothilone A and an established variation of solid phase synthesis using Radiofrequency Encoded Combinatorial (REC™) chemistry (Nicolaou et al. *Angew. Chem.* 1995, 107, 2476–2479; *Angew. Chem. Int. Ed. Engl.* 1995, 34, 2289–2291; Moran et al. *J. Am. Chem. Soc.* 1995, 117, 10787–10788). FIG. 50 summarizes the synthesis of a library of 12,13-desoxyepothilones A from the three key fragments generically denoted as 330, 331 and 332. Thus, SMART Microreactors™ containing Merrifield resin were smoothly converted to Microreactors 148 by chain extension and phosphonium salt formation as outlined in FIG. 50 (The reported combinatorial chemistry was performed using MicroKans™, while a single MicroTube™ was utilized to synthesize a set of four epothilones A (i.e. 422, 425, 455 and 460, FIGS. 64*a* and 65*b*)). Phosphonium salt resin 148 was then sorted according to the radiofrequency tag and treated with NaHMDS to generate the corresponding ylides which were reacted with the aldehydes 330. The SMART Microreactors 333 were pooled for washing and subsequent deprotection and oxidation to obtain the polymer-bound aldehydes 335. Further sorting and treatment with the dianion of the ketoacids 331 provided the polymer bound carboxylic acids 336 as a mixture of diastereoisomers. Resorting and esterification with alcohols 332 afforded dienes 337. The SMART Microreactors were separately treated with RuCl$_2$(=CHPh) (PCy$_3$)$_2$ catalyst to simultaneously effect cyclization via olefin metathesis, and cleavage of the products, leading to products as mixtures of four 12,13-desoxyepothilones A (339, 340, 341, 342). Each mixture was identified and subjected to preparative thin-layer chromatography to provide pure compounds, which were individually deprotected by treatment with TFA in dichloromethane and then epoxidized accordingly.

The epothilone library (FIGS. 64*a* and 64*b*) was screened for induction of tubulin assembly with 5 mM compound at 37° C. Previously tested compounds (in FIGS. 64*a* and 64*b*) were re-evaluated for comparative purposes. Most analogs were subjected to more detailed investigation in cytotoxicity assays with human ovarian and breast cancer cells, including Taxol-resistant lines, and a quantitative tubulin assembly assay that differentiates between potent taxoid compounds (FIGS. 65*a* and 65*b*). It soon became apparent that compounds with assembly values below 40% in the screen yielded high EC$_{50}$ values in the quantitative assay and had little inhibitory effect on cell growth (only positive results shown in FIGS. 65*a* and 65*b*).

A standard glutamate assay tested the hypothesis that taxoids more active than Taxol in tubulin assembly would also be more cytotoxic, and this was validated with over fifty analogs. With the epothilones, however, the quantitative assay was less successful. A low glutamate concentration resulted in a high false negative rate in predicting cytotoxicity, while higher glutamate concentrations (e.g. 0.7 M, FIGS. 65*a* and 65*b*) were comparable to the screening assay in identifying cytotoxic analogs. If "significant" cytotoxicity is defined as an IC$_{50}$ value below 10 nM, we identified nine analogs with activity against the breast and ovarian lines (161, 234, 48, 125, 171, 233, 126, 172, 71, and 231). With the screening assay, there were no false negatives, but there were seven false positives (agents with limited cytotoxicity yielding >40% polymerization) among examined compounds. With the glutamate assay, the same results were obtained. The nine cytotoxic analogs had EC$_{50}$ values of 3.3–13 mM, but an additional nine agents had EC$_{50}$ values of 6.0–17 mM.

Two Taxol-resistant lines were generated from the 1A9 ovarian cells, and resistance resulted from mutations in the M40 gene, which codes for a highly expressed b$_I$ isotype in the parental and resistant cell lines. The altered amino acids were residue 270 in the 1A9PTX10 line (Phe->Val) and 364 in 1A9PTX22 (Al->Thr). This agreed with other observations that the Taxol binding site is on β-tubulin. In preliminary results reported with 1 (vida supra) and several analogs that 1A9PTX22 cells retained nearly complete sensitivity to epothilones, while 1A9PTX10 cells remained partially resistant to the drugs. These findings have been confirmed (FIG. 65). The relative resistance observed with 1A9PTX22 cells was 27-fold with Taxol and 1.0–2.7-fold with the eleven cytotoxic epothilones. With 1A9PTX10 cells, relative resistance was 23-fold with Taxol and 3.5–9.1-fold with the epothilones. The Taxol and epothilone binding sites could overlap, since 1 and 2 are competitive inhibitors of Taxol binding to tubulin polymer. If one assumes that Phe$_{270}$ and Ala$_{364}$ interact directly with Taxol, the results with the resistant cells suggest that Phe$_{270}$ is more important than Ala$_{364}$ in the interaction of epothilones at the Taxol binding site.

The data shown in FIGS. 64*a*, 64*b*, 64*c* and 65*b*; , together with previously reported results, revealed important information regarding structure-activity relationships for in vitro tubulin polymerization and cytotoxicity, and lead to several conclusions. That the macrocycle is important was confirmed by the lack of significant tubulin polymerization activity of the open chain olefin metathesis precursor 4b. Inversion of the 3-OH stereochemistry resulted in reduced tubulin polymerization potency. Interestingly, however, α,β-unsaturated lactones (e.g. 42 and 38) retained significant tubulin assembly properties (FIGS. 65*a* and 65*b*) suggesting a conformational, rather than a direct binding effect, for this hydroxyl group. Neither 42 nor 38, however, exhibited significant cytotoxicity indicating an additional role for the 3-OH group. Substitution of the 4-gem-dimethyl with a 4,4-ethano moiety (e.g. 267a and 267b) resulted in loss of tubulin polymerization activity in all cases, pointing to the crucial importance of a proper conformation of epothilones for biological activity. Apparently the partial sp$^2$ character and the accompanied widening of the C3-C4-C5 angle introduced intolerable conformational changes within the macrocycle for effective interaction with tubulin. Another clear requirement for tubulin polymerization activity was the (6R, 7S) stereochemistry as revealed by the failure of all (6S, 7R) stereoisomers to induce tubulin polymerization at significant concentrations (e.g. 64, 425, 432–438, 443, 289, 312, 290, 313, 287, 319, 450–451, 464, and 37, FIGS. 64*a*, 64*b*, 65*a* and 65*b*). Interesting, also, was the notable decrease in interaction with tubulin upon inversion of the C8 methyl group (e.g. 458 vs 49), introduction of a gem-dimethyl group at C8 (460 49 and 455 vs 50), and removal of the C8 methyl group (e.g. 459 vs 49 and 456 vs 49 and 439 vs 58).

The importance of the natural stereochemistry (12S, 13R) for the epoxide was demonstrated by the general trend of the unnatural 12R, 13S epoxides to exhibit lower activities in inducing tubulin assembly. Most interestingly, both the cis and trans olefins corresponding to epothilones A and B were active in the tubulin assembly assays, and the activities of the cis olefins were comparable to those of the natural substances. However, we found that the cis and, especially, the trans olefins were significantly less cytotoxic than the naturally occurring epoxides (49 and 50 vs 1, 71 and 123 vs 2). Moreover, both the α- and β-epoxides derived from the 12,13 E-olefinic precursors exhibited considerable ability to induce tubulin assembly and inhibit cell growth (58, 171 and 172 vs 1, 125 and 126 vs 2; in fact, compound 125 appears to be the most cytotoxic analog from those shown in FIGS. 64a and 64b).

The C12-methyl group consistently bestowed higher potency to all epothilones studied as compared to the C12-des-methyl counterparts (e.g. 2 vs 1 and 233 vs 161), with the exception of compounds 55 and 57 where comparable results were obtained. Inversion of configuration at C15 led to loss of ability to induce tubulin polymerization (141 vs 49, 346 vs 50). Replacement of the C16-methyl with an ethyl group also reduced activity in the tubulin assay (461 vs 49, 457 vs 50) suggesting that the methyl group may play a role in maintaining the planar conformation of the side-chain. The inactivity of the C16–C17 epoxides further supports this conclusion. The epothilone pharmacophore tolerated some heterocycle modifications. Thus, a number of oxazole derivatives exhibited activity comparable to the corresponding thiazoles. Furthermore, replacement of the thiazole with a 2-pyridyl moiety led only to a slight decrease in activity in the tubulin assays, whereas substitution of the C23-methyl with a phenyl group yielded inactive compounds). FIG. 63 summarizes graphically the structure-activity relationships within the epothilone family of compounds as derived from these and previous studies.

The reported work demonstrates the power of interfacing combinatorial chemistry with chemical biology as facilitated by solid phase synthesis, REC chemistry and modern biological assays. Furthermore, this research should facilitate the process of drug discovery and development in the area of cancer chemotherapy.

EXAMPLE 7

Total Synthesis of Epothilone E and Side-Chain Epothilone Analogs via the Stille Couplina Reaction as Illustrated in FIGS. 51–56

In this example we report the first total synthesis of the naturally occurring epothilone E (FIG. 51) via an olefin metathesis reaction to form the macrocycle and a Stille coupling to construct the side chain. In addition, the developed strategy was applied to the synthesis of a library of analogs containing a variety of aromatic systems in place of the 2-methylthiazole moiety of natural epothilone A (see FIGS. 54a, 54b and 55).

FIG. 51 outlines, in retrosynthetic format, the highly convergent metathesis-Stille strategy towards epothilone E and the analogs shown in FIGS. 54a, 54b and 55. The utilization of a common advanced intermediate gives this Stille strategy a distinct advantage in delivering rapidly a plethora of side-chain modified epothilone analogs for biological screening.

The epothilones shown in FIGS. 54a, 54b and 55 were constructed as summarized in FIG. 52. Thus, alcohol 350, prepared in 91% yield by addition of (+)-allyldiisopinocampheyl borane [Icp$_2$B(allyl)] to aldehyde 349 was coupled with carboxylic acid 348 (mixture of C6–C7 diastereoisomers in ca. 3:2 ratio in favor of 348) with DCC and 4-DMAP to afford ester 351 (49% yield, after chromatographic separation from its C6–C7 diastereoisomer). Exposure of 351 to catalytic amounts of RuCl$_2$ (=CHPh) (PCy$_3$)$_2$ in CH$_2$Cl$_2$ at ambient temperature resulted in a mixture of cis- and trans-cyclic olefins which were chromatographically separated on silica gel followed by desilylation leading to diols 354 (84%) and 355 (85%), respectively.

The required stannanes were either commercially available, synthesized according to literature procedures or by the sequences shown in FIGS. 53a and 53b. For the synthesis of epothilone E, dibromide 358 was selectively metallated with n-BuLi and then reacted, in the presence of HMPA, with dimethylformamide (DMF) to afford after NaBH, reduction alcohol 360 in 63% overall yield. Protection of 360 as a silyl ether (TBSCl, imidazole, 96% yield) followed by a second metallation (n-BuLi) and exposure to n-Bu$_3$SnCl (85% yield) furnished after desilylation (TBAF, 95% yield) stannane 363. The synthesis of stannane 371 required: (i) Sonogashira coupling of dibromide 358 with 4-pentyn-1-ol [(Pd(PPh$_3$)$_4$-CuI, i-Pr$_2$NH, 70 ∞C, 83% yield] (ii) chemoselective hydrogenation of the triple bond (cat. PtO$_2$—H$_3$, 100% yield); and (iii) reaction with Me$_3$SnSnMe$_3$-cat. Pd(PPh$_3$)$_3$ (toluene, 100° C., 93% yield). Stannane 373 was prepared from dibromide 358 by reaction with piperidine (60° C.,100% yield), followed by palladium-catalyzed coupling with Me$_3$SnSnMe$_3$ [Pd(PPh$_3$)$_4$, toluene, 80 ∞C, 100% yield]. Similarly, 375 was obtained from 358 by reaction with NaSMe (EtOH, 25 ∞C, 94% yield) followed by exposure to cat. Pd(PPh$_3$)$_4$ and Me$_3$SnSnMe$_3$ (toluene, 80° C., 100%).

Attachment of the aromatic moieties onto the macrocyclic framework of vinyl iodides 354 and 355 was performed with the aromatic stannanes shown in FIGS. 54a, 54b and 55 under palladium-catalyzed Stille-type conditions A [Pd (PPh$_3$)$_4$, toluene, 100° C.] or B [Pd(CN)$_2$Cl$_2$, DMF, 25° C.]. FIGS. 54a, 54b and 55 include a selection of the synthesized epothilone A analogs, the coupling method, and the obtained yields.

Epothilone E (356b, FIG. 56) was synthesized from its desoxy analog 356a (FIG. 54a) by epoxidation with H$_2$O$_2$—KHCO$_3$—CH,CN in methanol as shown in FIG. 56 (65% yield, based on 50% conversion). Synthetic 356b exhibited identical $^1$H and $^{13}$C NMR spectra to those of the natural substance.

Epothilone E (356b) exhibited 52% tubulin polymerization as compared to 76% for epothilone A, 98% for epothilone B and 50% for Taxol in the filtration-colorimetric tubulin polymerization assay.

EXAMPLE 8

Construction of 26-substituted Epothilones as Illustrated in FIGS. 57–62

In this example, a series of 26-substituted epothilones have been constructed by total synthesis involving a selective Wittig olefination, an aldol reaction, and a macrolactonization as key steps.

The approach to the C26-modified epothilones B, follows the same path as that developed for epothilone B (vida supra), and involved the following steps: (a) a stereoselective Wittig olefination; (b) an aldol condensation; and (c) a macrolactonization (see FIGS. 57–62).

With large quantities of the allylic alcohol 392 (FIG. 37) at our disposal, our immediate task was the selection of a suitable group for the protection of the primary hydroxyl functionality at C26. A triphenylmethyl (trityl) group was judged to be most useful for this purpose, and indeed served admirably throughout the course of the synthesis. Thus, the key C7–C22 aldehyde fragment 257 was synthesized from 251 as shown in FIG. 37. Protection of 251 as a trityl ether (trityl chloride, 4-DMAP, DMF) furnished 252 in 99% yield. Regioselective hydroboration employing 9-BBN, and an ensuing basic hydrogen peroxide work-up led to primary alcohol 253 in 94% yield, which was converted to iodide 254 by the action of $Ph_3P$, iodine and imidazole in the mixed solvent system of MeCN:Et2O (3:1, 90% yield). Stereoselective alkylation of SAMP hydrazone via its lithio derivative (LDA, THF, −78 to 0° C.), with iodide 254 (−100 to −20° C., 94% yield, based on ca. 70% conversion) led to hydrazone 255. The transformation of 255 to nitrile 256 proceeded smoothly under the influence of MMPP (91% yield), and reduction of the latter with DIBAL in toluene at −78° C. provided the key aldehyde 257 in excellent yield (97%).

The coupling of the C1–C6 ketone fragment with aldehyde 257 via a syn-selective aldol reaction (LDA, −78° C.) as shown in FIG. 38, furnished compound 258 along with its (6S, 7R)-diastereoisomer (85% total yield, ca. 3:1 ratio in favor of 13). Chromatographic purification (silica gel, 20% $Et_2O$ in hexanes), followed by silylation (TBSOTf, 2,6-lutidine, methylene chloride, 0° C., 92% yield) gave tetra (silyl) ether 259. The use of buffered pyridinium hydrofluoride in THF (alternatively CSA in methylene chloride/methanol) permitted selective desilylation of the primary TBS group (74% yield), which was sequentially oxidized to aldehyde 261 [$(COCl)_2$, DMSO, $Et_3N$], and thence to carboxylic acid 262 ($NaClO_2$, 99%). Selective desilylation at C15 was achieved by the use of TBAF in THF providing the seco-acid 263 in 89% yield. The latter compound was in turn subjected to the macrolactonization conditions described by Yamaguchi allowing isolation of the lactone 264 in 75% yield. Exposure of 264 to pyridinium hydrofluoride in THF promoted concomitant removal of both the silyl groups and the trityl moiety, leading to triol 265 in 78% yield. Alternatively, treatment of 264 with camphorsulfonic acid in MeOH and methylene chloride resulted in the selective removal of the trityl group, giving 265 in 70% yield. Sharpless asymmetric epoxidation of 265 then gave 26-hydroxyepothilone B (266) in 76% yield and as a single diastereoisomer (as judged by both TLC and 1H NMR analysis).

The ready availability of the above compound 266 and intermediates facilitated rapid access to a number of 26-substituted epothilones. As indicated in FIGS. 57–62, allylic alcohol 392 was converted, in high yield, to the corresponding esters via steps a–c (see FIG. 57 description of figures for explanation of steps) by reaction with the corresponding acid anhydride or chloride under basic conditions followed by desilylation. $MnO_2$ oxidation of 265 proved highly efficient, providing α,β-unsaturated aldehyde (step d in 85% yield. Further oxidation with $NaClO_2$ led to carboxylic acid (step e) (98%) which was converted to methyl ester (step f) by treatment with $CH_2N_2$ (80%). Methylation (NaH-MeI) and benzylation (NaH—$PhCH_2Br$) of 266, followed by desilylation afforded methoxy and benzyloxy compounds, respectively. Halogenation (DAST or $CCl_4$—$Ph_3P$), followed by desilylation led to chloride 397 or 398 (as epoxide) (73% overall yield) or fluoride 395 (51% overall yield). The aldehyde obtained from $MnO_2$ oxidation of 403 (90%) was subjected to Wittig methylenation (85%) furnishing, after desilylation (85%), terminal olefin. Similar chemistry was employed for the preparation of epothilones 395, 398, 401, 404, 407, 413 and 415 as shown in FIGS. 57–62.

EXAMPLE 9

Construction of 14-, 15-, 17- and 18-membered Ring Relatives of Epothilone A as Illustrated in FIGS. 67–70

This example describes the construction of 14-, 15-, 17- and 18-membered ring relatives of epothilone A and their desoxy counterparts have been obtained by total synthesis and biologically evaluated for their tubulin polymerization properties as shown in FIGS. 67–70.

This example reveales considerable structural distortions inherent in the [14]-, [15]- and [17]-membered ring epothilones, whereas the overall shape of [18]-epothilone A remained relatively unchanged as compared to natural epothilone A ([16]-epothilone A), heightening expectations for biological activity of the latter compound, if not for the others.

The charted route projected epoxidation of the C12–C13 double bond of the macrocycle as the final step and a convergent assembly of the epothilone skeleton via a Wittig reaction, an aldol condensation, and a macrolactonization. This strategy required fragments 1006, 1007 and 1010— FIGS. 67–70 (made exactly as similar analogs described vida supra)or the construction of the key intermediates 1015 and 1016 (FIGS. 67–70) needed for the 14- and 15- membered rings. A slightly different strategy for the synthesis of key building blocks 1033 and 1035 needed for the 17- and 18-membered rings was adopted requiring fragments 1019, 1021 and 1022 FIGS. 67–70 (made exactly as similar analogs described vida supra).

Aldehyde 1006 (FIG. 68) was available via a literature procedure (Eguchi et al. J. Chem. Soc. Chem. Commun. 1994, 137–138) and served a precursor for the second required aldehyde, 7. Thus, olefination of 1006, hydroboration of the resulting olefin, and oxidation of the formed primary alcohol 1009 furnished the desired aldehyde 1007 in excellent overall yield (see FIG. 68). Each of these two aldehydes (1006 and 1007) were condensed separately with the ylide derived from phosphonium salt 1010 (NaHMDS, THF) to afford the corresponding Z-olefins [1011 (77%) and 1012 (83%)] as the major geometrical isomer in each case (ca. 9:1 ratio). The silyl group was then selectively removed from the primary hydroxyl group by the action of CSA leading to alcohols 1013 (81%) and 1014. (61%). Finally, oxidation of 1013 and 1014 with $SO_3$·pyr. (DMSO-Et3N) led to the targeted intermediates 1015 and 1016 in 81 and 84% yield, respectively.

The reverse ylide-aldehyde condensation approach shown in FIG. 69 was utilized for the construction of advanced intermediates 1033 and 1035. Thus, alcohol 1017 was converted to iodide 1018 by treatment with $Ph_3P$-$I_2$-imidazole (95%) and thence to phosphonium salt 1019 by heating with $Ph_3P$ (neat, 100° C., 97%). A similar sequence was used to prepare phosphonium salt 1021 from the bromide 1020 as the intermediate. The ylides derived from 1019 and 1021 (NaHMDS, THF) reacted with aldehyde 1022 to produce Z-olefins 1023 and 1026 in 85 and 79% yields, respectively, as the major isomer (ca. 9:1 Z:E ratio).

Each product, 1023 and 1026, was selectively desilylated at the primary position with CSA, furnishing alcohols 1024 (99%) and 1027 (95%), respectively, and then converted to the corresponding iodides 1025 (84%) and 1028 (98%) by exposure to $Ph_3P$—$I_2$-imidazole.

The iodides 1025 and 1028 were used to alkylate SAMP hydrazone 1029 according to the method of Enders, furnishing compounds 1030 and 1031 in 60 and 82% yield, respectively. Each hydrazone (1030 and 1031) was converted to the corresponding nitrile (1032, 99% and 1034, 96%) by reaction with MMPP, and then to the desired aldehydes 1033 (90%) and 1035 (81%) by DIBAL reduction.

FIG. 70 shows the coupling of the C1–C6 segment 1036 with fragments 1015, 1016, 1033 and 1035 and the elaboration of the products to the targeted epothilones. All synthesis described in this example are carried out with identical conditions and amounts as that of epothilone A and B. Thus, the enolate generated from ketone 1036 (LDA, THF, −78° C.) reacted smoothly with aldehydes 1015, 1016, 1033 and 1035, affording compounds 1037 (71%), 1038 (72%), 1041 (77%) and 1042 (60%) as the aldol products together with their 6S, 7R-diastereoisomers (see FIG. 70 for individual yields) which were removed by silica gel chromatography. These compounds were then silylated (TBSOTf-2,6-lutitine) leading to tetra(silyl)ethers 1039, 1040, 1043 and 1044 in 85–95% yield. Selective removal of the silyl group from the primary position with CSA led to alcohols 1045, 1046, 1049 and 1050 which were oxidized to the corresponding aldehydes (1047, 1048, 1051 and 1052) under Swern conditions [$(COCl)_2$-DMSO-$Et_3N$] in 85–99% yield. Further oxidation to the desired carboxylic acids (1053, 1054, 1057 and 1058) was achieved by reaction with $NaClO_2$ (95–98% yield).

The carboxylic acids were then selectively desilylated at C-15 by the action of TBAF producing hydroxyacids 1055, 1056, 1059 and 1060 in 77–92% yield. Ring closure of 1055, 1056, 1059 and 1060 was accomplished by the Yamaguchi method as exactly described for epothilones A and B, furnishing macrocyclic lactones 1061, 1062, 1065 and 1066 in yields ranging from 70–82% (see FIG. 70). The silyl ethers were removed from 1061, 1062, 1065 and 1066 by exposure to HF·pyr. in THF, leading to [14]-, [15]-, [17]- and [18]-desoxyepothilones 1063, 1064, 1067 and 1068 (71–91% yield).

Epoxidation of [14]-desoxyepothilone A (1063) with methyl(trifluoromethyl)dioxirane gave [14]-epothilone A (1002) essentially as a single product (52% yield), whereas epoxidation of the [15]-desoxyepothilone A (1064) under the same conditions led to a mixture of [15]-epothilone A (1003 or 1069) and its diastereomeric epoxide 1069 (or 1003) (70% yield, ca. 1:1 ratio). The [17]-membered ring 1067 furnished a 6:1 ratio of diastereomeric epoxides (97% combined yield) and the [18]-membered ring led to a ca. 2:1 ratio of products (79% total yield). In all cases, the isomeric epoxides were chromatographically separated but their stereochemical identities remain presently unassigned.

Preliminary biological investigations with these compounds revealed significant tubulin polymerization activity for [18]-desoxyepothilone A (1068) (40% as compared to 72% for epothilone A and 53% for Taxol), but relatively weak activity for the two epimeric [18]-epothilones A (1005 and 1071) and for all [14]-, [15]- and [17]-epothilones A (1063, 1064, 1067, 1002–1004, 1069 and 1070) in the filtration-colorimetric tubulin assay. These results provide further support for the limited tolerance of the epothilone pharmacophore and its highly specific binding to the tubulin receptor. Further biological studies with 1068 and related compounds are in progress.

EXAMPLE 10

Bioloaical Evaluation of Synthesized Compounds as Tabulated in FIGS. 23, 28, and 64–66

We have carried out microtubule assays following literature procedures and evaluated synthesized compounds for their ability to form and stabilize microtubules. Cytotoxicty studies have also been carried out in our laboratories and preliminary data is disclosed vida infra.

The synthesized epothilones were tested for their action on tubulin assembly using purified tubulin with an assay developed to amplify differences between compounds more active than Taxol. As demonstrated in FIG. 22, both epothilone B (2) ($EC_{50}$=4.0 ±1 mM) and its progenitor 71 ($EC_{50}$=3.3±0.2 mM) were significantly more active than Taxol ($EC_{50}$=15.0±2 mM) and epothilone A (1) ($EC_{50}$= 14.0±0.4 mM), whereas compounds 125, 158 and 123 were less effective than Taxol (Lin et al. Cancer Chemother. Pharmacol. 38, 136–140 (1996); Rogan et al. Science 244, 994–996 (1984)).

As shown in FIG. 23, cytotoxicity experiments with 1A9, 1A9PTX10 (β-tubulin mutant), 1A9PTX22 (β-tubulin mutant) and A2780AD cell lines revealed a number of interesting results (FIG. 23). Thus, despite its high potency in the tubulin assembly assay, compound 71 did not display the potent cytotoxicity of 2 against 1A9 cells, being similar to 1 and Taxol. These data suggest that while the C12–C13 epoxide is not required for the epothilone-tubulin interaction, it may play an important role in localizing the agent to its target within the cell. Like the naturally occurring epothilones 1 and 2, analogue 71 showed significant activity against the MDR line A2780AD and the altered B-tubulin-expressing cell lines 1A9PTX10 and 1A9PTX22, suggesting, perhaps, different contact points for the epothilones and Taxol with tubulin (i.e. stronger binding of epothilones around residue 364 than around 270 relative to taxoids).

See example 6 (vida supra) for further discussion about analogs which possess strong tubulin binding properties and that which possess potent cytotoxic action against tumor cell lines.

Colorimetric Cytotoxicity Assay for Anticancer-Drug Screening

The colorimetric cytotoxicity assay used was adapted from Skehan et al (*Journal of National Cancer Inst* 82:1107–1112, 19901). The procedure provides a rapid, sensitive, and inexpensive method for measuring the cellular protein content of adherent and suspension cultures in 96-well microtiter plates. The method is suitable for ordinary laboratory purposes and for very large-scale applications, such as the National Cancer Institute's disease-oriented in vitro anticancer-drug discovery screen, which requires the use of several million culture wells per year.

In particular, cultures fixed with trichloroacetic acid were stained for 30 minutes with 0.4% (wt/vol) sulforhodamine B (SRB) dissolved in 1% acetic acid. Unbound dye was removed by four washes with 1% acetic acid, and protein-bound dye was extracted with 10 mM unbuffered Tris base [tris (hydroxymethyl)aminomethane] for determination of optical density in a computer-interfaced, 96-well microtiter plate reader. The SRB assay results were linear with the number of cells and with values for cellular protein measured by both the Lowry and Bradford assays at densities ranging from sparse subconfluence to multilayered supraconfluence. The signal-to-noise ratio at 564 nm was approximately 1.5 with 1,000 cells per well. The sensitivity of the SRB assay compared favorably with sensitivities of several fluorescence assays and was superior to those of both the Lowry and Bradford assays and to those of 20 other visible dyes.

The SRB assay provides a calorimetric end point that is nondestructive, indefinitely stable, and visible to the naked eye. It provides a sensitive measure of drug-induced cytotoxicity, is useful in quantitating clonogenicity, and is well suited to high-volume, automated drug screening. SRB fluoresces strongly with laser excitation at 488 nm and can be measured quantitatively at the single-cell level by static fluorescence cytometry (Skehan et al (*Journal of National Cancer Inst* 82:1107–1112, 19901)).

Filtration Colorimetric Assay

Microtubule protein (0.25 ml of 1 mg/ml) was placed into an assay tube and 2.5 µl of the test compound were added. The sample was mixed and incubated at 37° C. for 30 minutes. Sample (150 µl) was transferred to a well in a 96-well Millipore Multiscreen Durapore hydrophilic 0.22 µm pore size filtration plate which had previously been washed with 200 µl of MEM buffer under vacuum. The well was then washed with 200 µl of MEM buffer.

To stain the trapped protein on the plate, 50 µl amido black solution [0.1% naphthol blue black (Sigma)/45% methanol/ 10% acetic acid] were added to the filter for 2 minutes; then the vacuum was reapplied. Two additions of 200 µl amido black destain solution (90% methanol/2% acetic acid) were added to remove unbound dye. The signal was quantitated by the method of Schaffner and Weissmann et al. *Anal. Biochem.*, 56: 502–514, 1973 as follows:

200 µl of elution solution (25 mM NaOH-0.05 mm EDTA-50% ethanol) were added to the well and the solution was mixed with a pipet after 5 minutes. Following a 10-minutes incubation at room temperature, 150 µl of the elution solution were transferred to the well of a 96-well plate and the absorbance was measured on a Molecular Devices Microplate Reader.

Synthetic Protocals

All reactions were carried out under an argon atmosphere with dry, freshly distilled solvents under anhydrous conditions, unless otherwise noted. Tetrahydrofuran (THF), toluene and ethyl ether (ether) were distilled from sodium-benzophenone, and methylene chloride (Methylene chloride), from calcium hydride. Anhydrous solvents were also obtained by passing them through commercially available alumina column. Yields refer to chromatographically and spectroscopically ($^1$H NMR) homogeneous materials, unless otherwise stated. Reagents were purchased at highest commercial quality and used without further purification unless otherwise stated. Reactions were monitored by thin layer chromatography carried out on 0.25 mm E. Merck silica gel plates (60F-254) using UV light as visualizing agent and 7% ethanolic phosphomolybdic acid or p-anisaldehyde solution and heat as developing agents. E. Merck silica gel (60, particle size 0.040–0.063 mm) was used for flash column chromatography. Preparative thin-layer chromatography (PTLC) separations were carried out on 0.25, 0.50 or 1 mm E. Merck silica gel plates (60F-254). NMR spectra were recorded on Brucker AMX-600 or AMX-500 instruments and calibrated using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. Optical rotations were recorded on a Perkin-Elmer 241 polarimeter. High resolution mass spectra (HRMS) were recorded on a VG ZAB-ZSE mass spectrometer under fast atom bombardment (FAB) conditions with NBA as the matrix. Melting points (mp) are uncorrected and were recorded on a Thomas Hoover Unimelt capillary melting point apparatus.

Synthesis of Sultam 14 Sodium-Mediated Alkylation of N-Acylsultam 13 as Illustrated in FIG. 3

A solution of sodium bis(trimethylsilyl)amide (NaHMDS, 236 mL, 1 M in THF, 1.05 equiv) was added over 30 min at −78° C. to a solution of N-acylsultam 13 (synthesized according to Oppolzer et al. Tetrahedron Lett. 1989, 30, 5603–1989; Oppolzer, W. Pure & Appl. Chem. 1990, 62, 1241–1250) (61.0 g, 0.225 mol) in THF (1.1 L, 0.2 M). After stirring the resulting sodium enolate solution at −78° C. for 1 hour, freshly distilled 5-iodo-1-pentene (58 mL, 0.45 mol, 2.0 equiv) in hexamethylphosphoramide (HMPA, 117 mL, 0.675 mol, 3.0 equiv) was added. The reaction mixture was allowed to slowly warm to 25° C., quenched with water (1.5 L) and extracted with ether (3×500 mL). Drying (MgSO$_4$) and evaporation of the solvents gave crude sultam 14 (76.3 g), which was used without further purification. A pure sample of 14 was obtained by preperative thin layer chromatography (250 mm silica gel plate, 10% EtOAc in hexanes). Rf=0.57 (silica gel, 20% EtOAc in hexanes); [α]$_{22}$D −50.5 (c 2.00, CHCl$_3$); IR (film) nmax 2939, 1694, 1331, 1216, 1131, 540 cm$^{-1}$; $^1$H NMR (500 MHZ, CDCl3) δ 5.79–7.72 (m, 1H, CH2CH═CH2), 5.00–4.90 (m, 2H, CH2CH═CH2), 3.89 (dd, J=7.5, 5.5 Hz, 1H, CH2CHN), 3.50 (d, J=14.0 Hz, 1H, CH2SO2), 3.43 (d, J=14.0 Hz, 1H, CH2SO2), 3.15–3.06 (m, 1H, (C═O)CH(CH3)), 2.10–2.00 (m, 3H), 1.96–1.84 (m, 2H), 1.78–1.68 (m, 1H), 1.50–1.30 (m, 6H), 1.16 (s, 3H, C(CH3)2), 1.15 (d, J=7.5 Hz, 3H, CHCH3), 0.97 (s, 3H, C(CH3)2); 13C NMR (125.7 MHz, CDCl3) d 176.4, 138.2, 114.5, 65.1, 53.0, 48.1, 47.6, 44.5, 39.5, 38.5, 34.7, 33,2, 32.7, 26.3, 26.0, 20.7, 19,8, 16.5; HRMS (FAB), calcd for C18H30NO3S (M+H+) 340.1946, found 340.1942.

Synthesis of Alcohol 15 as Illustrated in FIG. 3A
Reductive Cleavage of Sultam 14

A solution of crude sultam 14 (76.0 g, 0.224 mol) in ether (200 mL) was added to a stirred suspension of lithium aluminum hydride (LAH, 9.84 g, 0.246 mol, 1.1 equiv) in ether (900 mL) at −78 ° C. The reaction mixture was stirred at −78° C. for 15 min, quenched by addition of water (9.8 mL) and warmed to 0° C. Sequential addition of 15% aqueous sodium hydroxide solution (9.8 mL) and water (29.4 mL) was followed by warming the reaction mixture to 25° C. After stirring for 5 h, the aluminum salts were removed by filtration through celite, the filtrate was dried (MgSO4) and the solvent was removed by distillation under atmospheric pressure. Vaccum distillation (bp. 85° C./8 mm Hg) furnished pure alcohol 15 as a colorless oil (17.1 g, 60% from sultam 14). Rf=0.40 (silica gel, 20% EtOAc in hexanes); [α]22D −11.1 (c 1.41, CHCl3); IR (film) nmax 3344, 2956, 2927, 2873, 1641, 1460, 1033, 910, 803 cm−1; 1H NMR (500 MHz, CDCl3) d 5.85–5.77 (m, 1H, CH2CH═CH2), 5.03–4.93 (m, 2H, CH2CH═CH2), 3.53–3.49 (dd, J=10.5, 6.0 Hz, 1 H, CH2OH), 3.44–3.41 (dd, J=10.5, 6.5 Hz, 1H, CH2OH), 2.09–2.01 (m, 2H), 1.67–1.58 (m, 1H, HOCH2CH(CH3)) 1.51–1.34 (m, 3 H), 1.17–1.08 (m, 1H) 0.92 (d, J=6.5 Hz, 3H, CH3); 13C NMR (125.7 MHz, CDCl3) d 138.8, 114.2, 68.0, 35.5, 33.9, 32.5, 26.2, 16.4.

Synthesis of Aldehyde 7 as Illustrated in FIG. 3A
Oxidation of Alcohol 15

To a solution of alcohol 15 (0.768 g, 6.0 mmol) in Methylene chloride (30 mL, 0.2 M) were added powdered 4 Å molecular sieves (1.54 g), 4-methylmorpholine N-oxide (NMO, 1.06 g, 9.0 mmol, 1.5 equiv) and tetrapropylammonium perruthenate (TPAP, 0.105 g, 0.3 mmol, 0.05 equiv) at room temperature. After stirring for 30 min the disappearance of starting material was indicated by TLC. Celite was added (1.54 g) and the suspension was filtered through silica gel and eluted with Methylene chloride. The solvent was carefully distilled off under atmospheric pressure to yield aldehyde 7 (0.721 g, 95%) as a colorless oil. Rf=0.69 (silica gel, 20% EtOAc in hexanes); [α]22D +18.3 (c 2.35, CHCl3); IR (film) nmax 2934, 1707, 1463, 1238, 912 cm–1; 1H NMR (500 MHz, CDCl3) d 9.58 (d, 1H, CHO), 5.80–5.71 (m, 1H, CH2CH=CH2), 5.00–4.90 (m, 2H, CH2CH=CH2), 2.36–2.27 (m, 1H), 2.10–2.00 (m, 2H), 1.73–1.65 (m, 1H), 1.42–1.30 (m, 3H), 1.06 (d, J=7.0 Hz, 3H, CH3); 13C NMR (125.7 MHz, CDCl3) d 204.9, 138.0, 114.7, 46.0, 33.5, 29.7, 26.0, 13.1.

Synthesis of Silyl Ether 17a as Illustrated in FIG. 3B

Silylation of Alcohol 16a.

Alcohol 16a (5.0 g, 0.068 mol; glycidol; Aldrich/Sigma) was dissolved in DMF (70 mL, 1.0 M), the solution was cooled to 0° C. and imidazole (9.2 g, 0.135 mol, 2.0 equiv) was added. After stirring for 10 min, tert-butylchlorodiphenylsilane (TPSCl, 24 mL, 0.088 mol, 1.3 equiv) was added and the reaction mixture was allowed to stir for 30 min at 0° C. and for 1 h at 25° C. Ether (70 mL) was added, followed by saturated aqueous NaHCO3 solution (70 mL). The organic phase was separated and the aqueous layer was extracted with ether (50 mL), washed with water (2×120 mL) and with saturated aqueous NaCl solution (120 mL). The organic extract was dried (MgSO4), filtered through celite, and the solvents were removed under reduced pressure. Flash column chromatography (silica gel, 5% EtOAc in hexanes) provided silyl ether 17a (18.9 g, 90%). Rf=0.28 (5% EtOAc in hexanes); [α]22D –1.8 (c 1.14, CHCl3); IR (film) nmax 2957, 2930, 2857, 1471, 1427, 1111, 824, 703 cm–1; 1H NMR (500 MHz, CDCl3) d 7.72–7.67 (m, 4H, SiC(CH3)3(C6HS)2), 7.47–7.38 (m, 6H, SiC(CH3)3(C6H5)2), 3.86 (dd, J=12.0, 3.0 Hz, 1H, CH2OTPS), 3.72 (dd, J=12.0, 4.5 Hz, 1H, CH2OTPS), 3.16–3.12 (m, 1H, CH2-O(epoxide)CH, 2.76 (dd, J=5.0, 4.0, 1H, CH2-O(epoxide)CH), 2.62 (dd, J=5.0, 3.0, 1H, CH2-O (epoxide)CH), 1.08 (s, 9H, SiC(CH3)3(C6H5)2); 13C NMR (125.7 MHz, CDCl3) d 135.5, 133.2, 129.7, 127.6, 64.2, 52.2, 44.3, 26.7, 19.1.

Synthesis of Silyl Ether 17b as Illustrated in FIG. 3B.

Silylation of alcohol 16b.

Following the procedure described for the synthesis of silyl ether 17a, alcohol 16b (5.0 g, 0.068 mol; Aldrich/Sigma) in DMF (70 mL, 1.0 M) was treated with imidazole (9.2 g, 0.135 mol, 2.0 equiv) and tert-butylchlorodiphenylsilane (24 mL, 0.088 mol, 1.3 equiv) to yield silyl ether 17b (19.8 g, 94%). Rf=0.28 (5% EtOAc in hexanes); [α]22D +2.3 (c 2.00, CHCl3); IR (film nmax 2957, 2930, 2857, 1471, 1427, 1111, 824, 703 cm–1; 1H NMR (500 MHz, CDCl3) d 7.72–7.67 (m, 4H, SiC(CH3)3 (C6H5)2), 7.47–7.38 (m, 6H, SiC(CH3)3(C6H5)2), 3.86 (dd, J=12.0, 3.0 Hz, 1H, CH2OTPS), 3.72 (dd, J=12.0, 4.5 Hz, 1H, CH2OTPS), 3.16–3.12 (m, 1H, CH2-O(epoxide) CH), 2.76 (dd, J=5.0, 4.0, 1H, CH2-O(epoxide)CH), 2.62 (dd, J=5.0, 3.0, 1H, CH2-O(epoxide)CH) 1.08 (s, 9H, SiC (CH3)3(C6H5)2); 13C NMR (125.7 MHz, CDCl3) d 135.5, 133.2, 129.7, 127.6, 64.2, 52.2, 44.3, 26.7, 19.1.

Synthesis of Alcohol 18a as Illustrated in FIG. 3B

Opening of Epoxide 17a with Vinylcuprate.

To a solution of tetravinyltin (3.02 mL, 16.6 mmol, 1.25 equiv) in THF (44 mL) was added n-butyllithium (41.5 mL, 1.6 M in hexanes, 5.0 equiv) at –78° C. and the reaction mixture was stirred for 45 min. The resulting solution of vinyllithium was transferred via cannula to a solution of azeotropically dried (2×5 mL toluene) copper(I) cyanide (2.97 g, 33.2 mmol, 2.5 equiv) in THF (44 mL) at –78° C., and the mixture was allowed to warm to –30° C. Epoxide 17a (4.14 g, 13.3 mmol) in THF (44 mL) was transferred via cannula to this vinyl cuprate solution, and the mixture was stirred at –30° C. for 1 h. The reaction mixture was quenched with saturated aqueous NH4Cl solution (150 mL), filtered through celite, extracted with ether (2×100 mL) and dried (MgSO4). After removal of the solvents under reduced pressure, flash column chromatography (silica gel, 3% EtOAc in hexanes) furnished alcohol 18a (5.01 g, 86%) as a pale yellow oil. Rf=0.33 (silica gel, 10% EtOAc in hexanes); [α]22D –2.0 (c 2.20, CHCl3); IR (film) nmax 3071, 2930, 2858, 1428, 1111, 703 cm–1; 1H NMR (500 MHz, CDCl3) d 7.70–7.65 (m, 4H, SiC(CH3)3(C6H5)2), 7.47–7.38 (m, 6H, SiC(CH3)3(C6H5)2), 5.84–5.75 (m, 1H, CH2CH=CH2), 5.11–5.04 (m, 2H, CH2CH=CH2), 3.82–3.76 (m, 1H, CHOH), 3.67 (dd, J=10.5, 3.5 Hz, 1H, CH2OTPS), 3.56 (dd, J=10.5, 7.0 Hz, 1H, CH2OTPS), 2.27–2.22 (m, 2H, CH2CH=CH2), 2.17 (bs, 1H, OH), 1.08 (s, 9H, SiC(CH3)3(C6H5)2); 13C NMR (125.7 MHz, CDCl3) d 135.6, 135.4, 134.3, 134.3, 133.1, 129.9, 129.7, 127.8, 127.6, 117.4, 71.2, 67.3, 37.5, 26.8, 19.2; HRMS (FAB), calcd for C21H28NaO2Si (M+Na+) 363.1756, found 363.1773.

Synthesis of Alcohol 18b as Illustrated in FIG. 3B

Opening of Epoxide 17b with Vinylcuprate

Following the procedure described for the synthesis of alcohol 18a, epoxide 17b (1.97 g, 6.3 mmol) yielded alcohol 18b (1.78 g, 83%). Rf=0.33 (silica gel, 10% EtOAc in hexanes); [α]22D +2.2 (c 2.00, CHCl3); IR (film) nmax 3071, 2930, 2858, 1428, 1111, 703 cm–1; 1H NMR (500 MHz, CDCl3) d 7.70–7.65 (m, 4H, SiC(CH3)3(C6H5)2), 7.47–7.38 (m, 6H, SiC(CH3)3(C6H5)2), 5.84–5.75 (m, 1H; CH2CH=CH2), 5.11–5.04 (m, 2H, CH2CH=CH2), 3.82–3.76 (m, 1H, CHOH), 3.67 (dd, J=10.5, 3.5 Hz, 1H, CH2OTPS), 3.56 (dd, J=10.5, 7.0 Hz, 1H, CH2OTPS), 2.27–2.22 (m, 2H, CH2CH=CH2), 2.17 (bs, 1H, OH), 1.08 (s, 9H, SiC(CH3)3(C6H5)2); 13C NMR (125.7 MHz, CDCl3) d 135.6, 135.4, 134.3, 134.3, 133.1, 129.9, 129.7, 127.8, 127.6, 117.4, 71.2, 67.3, 37.5, 26.8, 19.2; HRMS (FAB), calcd for C21H28NaO2Si (M+Na+) 363.1756, found 363.1773.

Synthesis of Keto Ester 20 as Illustrated in FIG. 3C

Horner-Wadsworth-Emmons Reaction of Aldehyde 12 with Phosphonate 19.

A solution of phosphonate 19 (23.6 g, 94 mmol, 1.2 equiv; Aldrich) in THF (100 mL) was transferred via cannula to a suspension of sodium hydride (60% dispersion in mineral oil, 5.0 g, 125 mmol, 1.6 equiv) in THF (200 mL) at 25° C. After stirring for 15 min, the reaction mixture was cooled to 0° C., and a solution of aldehyde 12 (10.0 g, 78 mmol; synthesized according to Inuka, T.; Yoshizawa, R. J. Org. Chem. 1967, 32, 404–407) in THF (20 mL) was added via cannula and the ice-bath was removed. After 1 h at 25° C., TLC indicated the disappearance of aldehyde 12. The mixture was then separated between water (320 mL) and hexanes (100 mL). The aqueous layer was extracted with hexanes (100 mL) and the combined organic layers were succesively washed with water (200 mL) and saturated aqueous NaCl solution (200 mL). Drying (MgSO4), concentration under reduced pressure and purification by flash column chromatography (silica gel, 10% EtOAc in hexanes) yielded keto ester 20 (17.4 g, 99%) as a yellow oil. Rf=0.58 (silica gel, 20% EtOAc in hexanes); IR (film) nimax 2977, 1714, 1645, 1318, 1297, 1158 cm–1; 1H NMR (500 MHz, CDCl3) d 6.91 (d, J=15.5 Hz, 1H, CH=CHCOO), 5.77 (d, J=15.5 Hz, 1H, CH=CHCOO), 2.47 (q, J=7.0 Hz, 2H, CH2CH3), 1.47 (s, 9 H, C(CH3)3), 1.25 (s, 6H, C(CH3)2), 0.99 (t, J=7.0 Hz, 3H, CH2CH3); 13C NMR (125.7 MHz, CDCl3) d 211.7, 165.5, 150.3, 122.2, 80.5, 50.2, 31.2, 28.0, 23.5, 7.9; HRMS (FAB), calcd for C13H23O3 (M+H+) 227.1647, found 227.1656.

Synthesis of Keto Acid 21 as Illustrated in FIG. 3C
Hydrolysis of Keto Ester 20.

Keto ester 20 (17.4 g, 77 mmol) in Methylene chloride (39 mL, 2 M) was treated with trifluoroacetic acid (TFA, 39 mL, 2 M) at 25° C. Within 30 minutes TLC indicated disappearance of the ester. The mixture was concentrated under reduced pressure, dissolved in saturated aqueous NaHCO3 solution (20 mL) and washed with ether (2×20 mL). The aqueous phase was then acidified to pH~2 with 4 N HCl, saturated with NaCl, and extracted with EtOAc (6×20 mL). The organic layer was dried (MgSO4) and concentrated under reduced pressure to give pure keto acid 21 (13.0 g, 99%) as a clear oil, which solidified on standing. Rf=0.20 (silica gel, 2% TFA in Methylene chloride); mp 56–57° C. (EtOAc); IR (film) nmax 2979, 1712, 1647, 1300, 1201 cm-1; 1H NMR (500 MHz, CDCl3) d 7.18 (d, J=16.0 Hz, 1H, CH=CHCOOH), 5.89 (d, J=16.0 Hz, 1H, CH=CHCOOH), 2.50 (q, J=7.0 Hz, 2H, CH2CH3), 1.31 (s, 6H, C(CH3)2), 1.03 (t, J=7.0 Hz, 3H, CH2CH3); 13C NMR (125.7 MHz, CDCl3) d 211.8, 171.3, 154.3, 119.6, 50.4, 31.2, 23.2, 7.7; HRMS (FAB), calcd for C9H14NaO3 (M+Na+) 193.0841, found 193.0846.

Synthesis of Keto Ester 22a as Illustrated in FIG. 4
EDC Coupling of Alcohol 18a with Keto Acid 21.

A solution of keto acid 21 (2.43 g, 14.3 mmol, 1.2 equiv), 4-(dimethylamino)pyridine (4-DMAP, 0.145 g, 1.2 mmol, 0.1 equiv) and alcohol 18a (4.048 g, 11.9 mmol, 1.0 equiv) in Methylene chloride (40 mL, 0.3 M) was cooled to 0° C. and then treated with 1-ethyl-(3-dimethylaminopropyl)-3-carbodiimide hydrochloride (EDC, 2.74 g, 14.3 mmol, 1.2 equiv). The reaction mixture was stirred at 0° C. for 2 h and then at 25° C. for 12 h. The solution was concentrated to dryness in vacuo, and the residue was taken up in EtOAc (10 mL) and water (10 mL). The organic layer was separated, washed with saturated NH4Cl solution (10 mL) and water (10 mL) and dried (MgSO4). Evaporation of the solvents followed by flash column chromatography (silica gel, 4% EtOAc in hexanes) resulted in pure keto ester 22a (5.037 g, 86%). Rf=0.41 (silica gel, 10% EtOAc in hexanes); [α]22D -6.1 (c 1.22, CHCl3); IR (film) nmax 3072, 2960, 2933, 2858, 1715, 1645, 1470, 1428, 1295, 1181, 1112, 704 cm-1; 1H NMR (500 MHz, CDCl3) d 7.66–7.64 (m, 4H, SiC(CH3)3(C6H5)2), 7.44–7.36 (m, 6H, SiC(CH3)3(C6H5)2), 7.05 (d, 1H, J=16.0 Hz, CH=CHCOO), 5.86 (d, J=16.0 Hz, 1H, CH=CHCOO), 5.79–5.70 (m, 1H, CH2CH=CH2), 5.15–5.04 (m, 3H, CH2CH=CH2 and CO2CH), 3.76–3.70 (m, 2H, CH2OTPS), 2.53–2.36 (m, 4H), 1.29 (s, 6H, C(CH3)2), 1.04 (s, 9H, SiC(CH3)3(C6H5)2), 1.01 (t, J=7.0 Hz, 3H, CH3CH2C=O); 13C NMR (125.7 MHz, CDCl3) d 211.4, 165.7, 151.7, 135.5, 135.4, 133.2, 129.6, 127.6, 120.6, 117.9, 73.6, 64.3, 50.4, 35.0, 31.3, 26.6, 23.6, 23.5, 19.2, 7.9; HRMS (FAB), calcd for C30H40CsO4Si (M+Cs+) 625.1750, found 625.1765.

Synthesis of Dienes 23 and 24 as Illustrated in FIG. 4
Aldol Condensation of Ester 22a with Aldehyde 7.

A solution of keto ester 22a (1.79 g, 3.63 mmol, 1.0 equiv) in THF (15 mL) was added via cannula to a freshly prepared solution of lithium diisopropylamide [LDA; formed by addition of n-BuLi (2.83 mL, 1.6 M solution in hexanes, 4.58 mmol, 1.25 equiv) to a solution of diisopropylamine (0.61 mL, 4.36 mmol, 1.2 equiv) in THF (30 mL) at -10° C. and stirring for 30 min] at -78° C. After 15 min the reaction mixture was allowed to warm to -40° C. and was stirred for 45 min. The reaction mixture was cooled to -78° C. and a solution of aldehyde 7 (0.740 g, 5.8 mmol, 1.6 equiv) in THF (15 mL) was added dropwise. The resulting mixture was stirred for 15 min, then warmed to -40° C. for 30 min, cooled back to -78° C. and then quenched by slow addition of saturated aqueous NH4Cl solution (10 mL). The reaction mixture was warmed to 25° C., diluted with EtOAc (10 mL) and the aqueous phase was extracted with EtOAc (3×10 mL). The combined organic layers were dried (MgSO4), concentrated under reduced pressure and subjected to flash chromatographic purification (silica gel, 5 E 20% EtOAc in hexanes) to afford a mixture of aldol products 23 (926 mg, 42%) and 24 (724 mg, 33%), along with unreacted starting keto ester 22a (178 mg, 10%). 23: Rf=0.40 (silica gel, 18% EtOAc in hexanes); [α]22D -11.4 (c 1.00, CHCl3); IR (film) nmax 3518, 2962, 2932, 2858, 1722, 1644, 1294, 1182, 1114, 989, 702 cm-1; 1H NMR (600 MHz, CDCl3) d 7.67–7.63 (m, 4H, SiC(CH3)3(C6H5)2), 7.45–7.40 (m, 2H, SiC(CH3)3(C6H5)22), 7.40–7.35 (m, 4H, SiC(CH3)3 (C6H5)2), 7.03 (d, 1H, J=15.8 Hz, CH=CHCOO), 5.92 (d, J=15.8 Hz, 1H, CH=CHCOO), 5.84–5.76 (m, 1H, CH2CH=CH2), 5.76–5.68 (m, 1H, CH2CH=CH2), 5.14–5.09 (m, 1H, CO2CH), 5.08 (d, J=17.2 Hz, 1H, CH2CH=CH2), 5.04 (d, J=10.1 Hz, 1H, CH2CH=CH2), 4.99 (d, J=18.9 Hz, 1H, CH2CH=CH2), 4.92 (d, J=10.2 Hz, 1H, CH2CH=CH2), 3.76–3.69 (m, 2H, CH2OTPS), 3.29 (d, J=8.9 Hz, 1 H, CHOH(CHCH3)), 3.16 (s, 1H, CHOH (CHCH3)), 3.13 (qd, J=7.0, 1.8 Hz, 1H, CH3CH(C=O)), 2.52–2.45 (m, 1H), 2.42–2.35 (m, 1H), 2.09–1.97 (m, 2H), 1.76–1.68 (m, 1H), 1.52–1.43 (m, 2H), 1.30 (s, 3H, C(CH3) 2), 1.30 (s, 3H, C(CH3)2), 1.30–1.25 (m, 1H), 1.12–1.00 (m, 1H), 1.03 (s, 9H, SiC(CH3)3(C6H5)2), 1.01 (d, J=7.1 Hz, 3H, CH3CH(C=O), 0.77 (d, J=6.8 Hz, 3H, CH3CHCH2; 13C NMR (150.9 MHz, CDCl3) d 217.0, 165.2, 150.1, 138.9, 135.4, 135.4, 135.4, 133.1, 133.1, 129.6, 129.6, 127.6, 127.5, 121.5, 117.9, 114.2, 74.9, 73.8, 64.4, 51.6, 41.5, 35.5, 35.2, 34.3, 32.2, 26.8, 26.2, 23.3, 23.3, 19.4, 15.6, 10.4; HRMS (FAB), calcd for C38H54CsO5Si (M+Cs+) 751.2795, found 751.2766. 24: Rf=0.30 (silica gel, 18% EtOAc in hexanes); [α]22D -1.33 (c 0.60, CHCl3); IR (film) nmax 3521, 2962, 2932, 2858, 1722, 1644, 1294, 1182, 1113, 988, 702 cm-1; 1H NMR (600 MHz, CDCl3) d 7.68–7.63 (m, 4H, SiPh2), 7.45–7.40 (m, 2H, SiC(CH3)3 (C6H5)2), 7.40–7.35 (m, 4H, SiC(CH3)3(C6H5)2), 7.03 (d, 1H, J=15.8 Hz, CH=CHCOO), 5.90 (d, J=15.8 Hz, 1H, CH=CHCOO), 5.82–5.68 (m, 2H, 2×CH2CH=CH2), 5.14–5.08 (m, 1H, CO2CH), 5.09 (d,. J=16.9 Hz, 1H, CH2CH=CH2), 5.05 (d, J=10.1 Hz, 1H, CH2CH=CH2), 4.99 (d, J=17.1 Hz, 1H, CH2CH=CH2), 4.95 (d, J=10.1 Hz, 1H, CH2CH=CH2), 3.76–3.69 (m, 2H, CH2OTPS), 3.44 (dd, J=6.6, 3.9 Hz, 1H, CHOH(CHCH3)), 3.13–3.08 (m, 1H, CH3CH(C=O)), 2.69 (bs, 1H, CHOH(CHCH3)), 2.53–2.47 (m, 1H), 2.43–2.37 (m, 1H), 2.07–1.95 (m, 2H), 1.48–1.25 (m, 5H), 1.31 (s, 3H, C(CH3)2), 1.29 (s, 3H C(CH3)2), 1.05 (d, J=7.0 Hz, 3H, CH3CH(C=O)), 1.03 (s, 9H, SiC(CH3) 3(C6HS)2), 0.92 (d, J=6.6 Hz, 3H, CH3CHCH2); 13C NMR (150.9 MHz, CDCl3) d 216.1, 165.2, 150.3, 138.5, 135.5, 135.4, 135.4, 133.1, 133.1, 129.6, 129.6, 127.6, 127.6, 121.4, 117.9, 114.6, 75.1, 73.8, 64.4, 51.5, 42.6, 35.5, 35.1, 33.9, 32.6, 26.8, 26.0, 23.6, 23.3, 19.4, 15.0, 12.3; HRMS (FAB), calcd for C38H54CsO5Si (M+Cs+) 751.2795, found 751.2771.

Synthesis of Hydroxy Lactone 25 as Illustrated in FIG. 4.

Olefin Metathesis of Diene 23.

To a solution of diene 23 (0.186 g, 0.3 mmol) in Methylene chloride (100 mL, 0.003 M) was added bis(tricyclohexylphosphine)benzylidine ruthenium dichloride (RuCl2(=CHPh)(PCy3)2, 25 mg, 0.03 mol, 0.1 equiv; available from Aldrich) and the reaction mixture was allowed to stir at 25° C. for 12 h. After the completion of the reaction was established by TLC, the solvent was removed under reduced pressure and the crude product was purified by flash chromatography (silica gel, 30% EtOAc in hexanes) to give trans-hydroxy lactone 25 (151 mg, 85%). Rf=0.50 (silica gel, 30% EtOAc in hexanes); [α]22D +65.9 (c 0.80, CHCl3); IR (film) nmax 3520, 2960, 2932, 2858, 1711, 1705, 1646, 1292, 1183, 1114, 982, 702, 505 cm−1; 1H NMR (500 MHz, CDCl3) d 7.69–7.64 (m, 4H, SiC(CH3)3(C6H5)2), 7.46–7.36 (m, 6H, SiC(CH3)3(C6H5)2), 6.78 (d, J=15.5 Hz, 1H, CH=CHCOO), 5.98 (d, J=15.5 Hz, 1H, CH=CHCOO), 5.40 (ddd, J=15.5, 8.5, 4.0 Hz, 1H, CH=CHCH2), 5.38 (ddd, J=15.5, 8.5, 4.5 Hz, 1H, CH=CHCH2), 5.22–5.16 (m, 1H, CO2CH), 3.75 (dd, J=10.5, 6.0 Hz, 1H, CH2OTPS), 3.70 (dd, J=10.5, 5.0 Hz, 1H, CH2OTPS), 3.58 (bs, 1H, CHOH(CHCH3)), 3.05 (qd, J=6.5, 5.5 Hz, 1H, CH3CH(C=O)), 2.42 (d, J=14.0 Hz, 1H), 2.24–2.16 (m, 2H), 2.12–2.04 (m, 1H), 2.03–1.94 (m, 1H), 1.55–1.40 (m, 2H), 1.37 (s, 3H, C(CH3)2), 1.28–1.04 (m, 3H), 1.20 (s, 3H, C(CH3)2), 1.15 (d, J=7.0 Hz, 3H, CH3CH(C=O)), 1.05 (s, 9H, SiC(CH3)3(C6H5)2), 0.93 (d, J=7.0 Hz, 3H, CH3CHCH2); 13C NMR (125.7 MHz, CDCl3) d 214.8, 164.9, 149.6, 135.5, 135.4, 133.2, 133.2, 132.7, 129.6, 129.6, 127.6, 127.6, 126.3, 122.5, 75.7, 73.2, 65.6, 52.2, 42.1, 38.2, 34.8, 33.2, 30.3, 27.2, 26.9, 23.4, 23.2, 19.4, 16.3, 14.6; HRMS (FAB), calcd for C36H50O5CsSi (M+Cs+) 723.2482, found 723.2508.

Synthesis of Hydroxy Lactone 26 as Illustrated in FIG. 4

Olefin Metathesis of Diene 24.

Following the procedure described above for the synthesis of hydroxy lactone 25, a solution of diene 24 (0.197 g, 0.32 mmol) in Methylene chloride (100 mL, 0.003 M) was treated with bis(tricyclohexylphosphine)benzylidine ruthenium dichloride ((RuCl2(=CHPh)(PCy3)2, 26 mg, 0.032 mol, 0.1 equiv), to produce, after flash chromatography (silica gel, 18 E 25% EtOAc in hexanes), trans-hydroxy lactone 26 (150 mg, 79%). Rf=0.3 (silica gel, 18% EtOAc in hexanes); [α]22D −3.00 (c=0.40, CHCl3); IR (film) nmax 3522, 2961, 2931, 2857, 1718, 1698, 1646, 1294, 1182, 1113, 702 cm−1; 1H NMR (600 MHz, CDCl3): d 7.67–7.63 (m, 4H, SiC(CH3)3(C6H5)2), 7.45–7.41 (m, 2H, SiC(CH3)3(C6H5)2), 7.40–7.36 (m, 4H, SiC(CH3)3(C6H5)2), 7.07 (d, J=16.0 Hz, 1H, CH=CHCOO), 5.86 (d, J=16.0 Hz, 1H, CH=CHCOO), 5.30 (ddd, J=15.2, 7.4, 4.2 Hz, 1H, CH=CHCH2), 5.28 (ddd, J=15.2, 7.5, 4.2 Hz, 1H, CH=CHCH2), 5.26–5.21 (m, 1H, CO2CH), 3.77 (dd, J=10.7, 6.3 Hz, 1H, CH2OTPS), 3.70 (dd, 1H, J=10.7, 5.2 Hz, CH2OTPS), 3.27 (d, J=9.0, 1H, CHOH(CHCH3)), 3.13 (q, J=6.9 Hz, 1H, CH3CH(C=O)), 2.87 (bs, 1H, CHOH (CHCH3)), 2.52–2.45 (m, 1H), 2.34–2.26 (m, 1H), 2.15–2.08 (m, 1H), 1.97–1.89 (m, 1H), 1.52–1.44 (m, 1H), 1.40–1.31 (m, 1H), 1.31 (s, 3H, C(CH3)2), 1.30–1.20 (m, 1H), 1.24 (s, 3H, C(CH3)2), 1.12–1.00 (m, 1H), 1.04 (s, 9H, SiC(CH3)3(C6H5)2), 1.01 (d, 3H, J=6.9 Hz, CH3CH (C=O)), 0.96 (d, 3H, J=6.6 Hz, CH3CHCH2), 0.93 (m, 1H); 13C NMR (150.9 MHz, CDCl3) d 217.4, 165.3, 151.1, 135.5, 135.4, 133.3, 133.2, 133.1, 129.6, 129.6, 127.6, 127.6, 125.6, 121.5, 75.0, 73.4, 64.9, 51.0, 43.6, 35.6, 34.2, 32.7, 32.0, 26.9, 25.6, 25.2, 24.0, 19.4, 16.0, 7.0; HRMS (FAB), calcd for C36H50O5CsSi (M+Cs+) 723.2482, found 723.2506.

Synthesis of Diol 27 as Illustrated in FIG. 4

Desilylation of TPS Ether 25.

A solution of TPS ether 25 (145 mg, 0.23 mmol) in THF (4.7 mL, 0.05 M) was treated with glacial acetic acid (70 mL, 1.15 mmol, 5.0 equiv) and tetrabutylammonium fluoride (TBAF, 490 mL, 1 M solution in THF, 0.46 mmol, 2.0 equiv) at 25° C. After stirring for 36 h, no starting material was detected by TLC and the reaction mixture was quenched by addition of saturated aqueous NH4Cl (10 mL). Extractions with ether (3×10 mL), drying (MgSO4) and concentration was followed by flash chromatographic purification (silica gel, 50% EtOAc in hexanes) to provide diol 27 (78 mg, 92%). Rf=0.30 (silica gel, ether), [α]22D +144.5 (c 0.51, CHCl3); IR (film) nmax 3440, 2933, 1706, 1646, 1293, 1183, 982 cm−1; 1H NMR (600 MHz, CDCl3) d 6.82 (d, J=16.0 Hz, 1H, CH=CHCOO), 6.08 (d, J=16.0 Hz, 1H, CH=CHCOO), 5.42 (ddd, J=15.5, 8.0, 4.5 Hz, 1H, CH=CHCH2), 5.40 (ddd, J=15.5, 8.5, 4.5 Hz, 1H, CH=CHCH2), 5.20–5.14 (m, 1H, CO2CH), 3.76 (dd, J=12.0, 4.0 Hz, 1H, CH2OH), 3.72 (dd, J=12.0, 6.5 Hz, 1H, CH2OH), 3.58 (dd, J=5.0, 2.5 Hz, 1H, CHOH(CHCH3)), 3.06 (qd, J=7.0, 6.0 Hz, 1H, CH3CH(C=O)), 2.38–2.34 (m, 1H), 2.28–2.20 (m, 1H), 2.12–2.03 (m, 1H), 2.03–1.95 (m, 1H), 1.55–1.42 (m, 2H), 1.40 (s, 3H, C(CH3)2), 1.22–1.08 (m, 2H), 1.22 (s, 3H, C(CH3)2), 1.15 (d, J=7.0 Hz, 3H, CH3CH(C=O)), 1.08–0.86 (m, 1H), 0.94 (d, J=7.0 Hz, 3H, CH3CHCH2); 13C NMR (125.7 MHz, CDCl3) d 214.8, 165.3, 150.4, 133.0, 126.0, 122.1, 75.5, 73.7, 64.9, 52.1, 41.9, 38.0, 34.4, 33.0, 30.1, 26.9, 23.2, 22.7, 16.1, 14.6; HRMS (FAB), calcd for C20H33O5 (M+H+) 353.2328, found 353.2319.

Synthesis of Diol 28 as Illustrated in FIG. 4

Desilylation of TPS Ether 26.

In accordance with the procedure describing the desilylation of TPS ether 25, a solution of TPS ether 26 (31 mg, 0.05 mmol) in THF (1.0 mL, 0.05 M) was treated with glacial acetic acid (15 mL, 0.25 mmol, 5.0 equiv) and tetrabutylammonium fluoride (TBAF, 105 mL, 1 M solution in THF, 0.10 mmol, 2.0 equiv) to yield diol 28 (17 mg, 95%) as a crystalline solid. Rf=0.15 (silica gel, 50% EtOAc in hexanes); mp 128–129° C. (EtOAc-hexanes); [α]22D +45.6 (c 0.80, CHCl3); IR (film) nmax 3442, 2932, 1702, 1647, 1296, 1184, 974 cm−1; 1H NMR (600 MHz, CDCl3) d 7.14 (d, J=16.0 Hz, 1H, CH=CHCOO), 5.94 (d, J=16.0 Hz, 1H, CH=CHCOO), 5.34 (ddd, J=15.4, 7.6, 4.2 Hz, 1H, CH=CHCH2), 5.32 (ddd, J=15.4, 7.6, 4.2 Hz, 1H, CH=CHCH2), 5.20–5.16 (m, 1H, CO2CH), 3.75–3.73 (m, 2H, CH2OH), 3.28 (dd, J=9.0, 1.2 Hz, 1H, CHOH (CHCH3)), 3.13 (qd, J=7.0, 1.2 Hz, 1H, CH3CH(C=O)), 2.81 (bs, 1H, CHOH(CHCH3)), 2.46–2.42 (m, 1H), 2.36–2.30 (m, 1H), 2.17–2.13 (m, 1H), 1.97–1.92 (m, 1H), 1.86 (bs, 1H, CH2OH), 1.51–1.46 (m, 1H), 1.40–1.22 (m, 2H), 1.33 (s, 3H, C(CH3)2), 1.27 (s, 3H, C(CH3)2), 1.12–0.89 (m, 2H) 1.01 (d, J=7.0 Hz, 3H, CH3CH(C=O)), 0.96 (d, J=6.6 Hz, 3H, CH3CHCH2); 13C NMR (125.7 MHz, CDCl3) d 217.4, 165.8, 151.9, 133.6, 125.3, 121.2, 75.0, 74.4, 64.7, 51.0, 43.8, 35.6, 34.3, 32.7, 32.0, 25.5, 25.3, 24.0, 16.0, 9.9; HRMS (FAB), calcd for C20H33O5 (M+H+) 353.2328, found 353.2323.

Synthesis of Ester 22b as Illustrated in FIG. 5

DCC Coupling of Alcohol 18b with Keto Acid 21.

To a solution of alcohol 18b (1.000 g, 2.94 mmol, 1.0 equiv), 1,3-dicyclohexylcarbodiimide (DCC, 0.836 g, 4.06 mmol, 1.4 equiv) and 4-dimethylaminopyridine (4-DMAP, 0.496 g, 4.06 mmol, 1.4 equiv) in toluene (30 mL, 0.1 M) was added keto acid 21 (0.638 g, 3.75 mmol, 1.2 equiv) at 25° C. After 12 h the reaction was complete, as indicated by TLC. The reaction mixture was then passed through a short plug of silica gel, eluted with toluene and concentrated under reduced pressure. The crude material was submitted to flash column chromatography (silica gel, 5% EtOAc in hexanes) to yield pure 22b (1.38 g, 95%). Rf=0.50 (silica gel, 17% EtOAc in hexanes); [α]22D +7.2 (c 2.00, CHCl3); IR (film) nmax 3072, 2960, 2933, 2858, 1715, 1645, 1470, 1428, 1295, 1181, 1112, 704 cm−1; 1H NMR (500 MHz, CDCl3) d 7.66–7.64 (m, 4H, SiC(CH3)3(C6H5)2), 7.44–7.36 (m, 6 H, SiC(CH3)3(C6H5)2), 7.05 (d, 1H, J=16.0 Hz, CH═CHCOO), 5.86 (d, J=16.0 Hz, 1H, CH═CHCOO), 5.79–5.70 (m, 1H, CH2CH═CH2), 5.15–5.04 (m, 3H, CH2CH═CH2 and CO2CH), 3.76–3.70 (m, 2H, CH2OTPS), 2.53–2.36 (m, 4H), 1.29 (s, 6H, C(CH3)2), 1.04 (s, 9H, SiC(CH3)3(C6H5)2), 1.01 (t, J=7.0 Hz, 3H, CH3CH (C═O)); 13C NMR (125.7 MHz, CDCl3) d 211.4, 165.7, 151.7, 135.5, 135.4, 133.2, 129.6, 127.6, 120.6, 117.9, 73.6, 64.3, 50.4, 35.0, 31.3, 26.6, 23.6, 23.5, 19.2, 7.9; HRMS (FAB), calcd for C30H40CsO4Si (M+Cs+) 625.1750, found 625.1775.

Synthesis of Dienes 29 and 30 as Illustrated in FIG. 5

Aldol Condensation of Ester 22b with Aldehyde 7.

In accordance with the procedure described for the preparation of dienes 23 and 24, keto ester 22b (0.702 g, 1.43 mmol, 1.0 equiv) in THF (8.0 mL) was treated with lithium diisopropylamide [LDA; freshly prepared from n-butyllithium (1.12 mL, 1.6 M solution in hexanes, 1.79 mmol, 1.25 equiv) and diisopropylamine (241 mL, 1.72 mmol, 1.2 equiv) in THF(16 mL)] and aldehyde 7 (289 mg, 2.29 mmol, 1.6 equiv) in THF (3.0 mL) to afford a mixture of aldol products 29 (0.478 g, 54%) and 30 (0.210 g, 24%) and along with unreacted starting material 22b (79 mg, 11%). 29: Rf=0.39 (silica gel, 17% EtOAc in hexanes); [α]22D −6.0 (c 0.30, CHCl3); IR (film) nmax 2962, 2931, 2858, 1722, 1698, 1294, 1182, 1114, 990, 702 cm−1; 1H NMR (600 MHz, CDCl3) d 7.66–7.62 (m, 4H, SiPh2), 7.45–7.40 (m, 2H, SiC(CH3)3(C6H5)2), 7.40–7.35 (m, 4H, SiC(CH3)3(C6H5)2), 7.03 (d, 1H, J=16.0 Hz, CH═CHCOO), 5.90 (d, J=16.0 Hz, 1H, CH═CHCOO), 5.84–5.76 (m, 1H, CH2CH═CH2), 5.76–5.68 (m, 1H, CH2CH═CH2), 5.14–5.08 (m, 1H, CO2CH), 5.09 (d, J=17.9 Hz, 1H, CH2CH═CH2), 5.06 (d, J=10.3 Hz, 1H, CH2CH═CH2), 4.99 (d, J=17.1 Hz, 1H, CH2CH═CH2), 4.93 (d, J=10.2 Hz, 1H, CH2CH═CH2), 3.76–3.69 (m, 2H, CH2OTPS), 3.30 (d, J=8.8 Hz, 1H, CHOH(CHCH3)), 3.17 (s, 1H, CHOH(CHCH3)), 3.12 (q, J=7.0 Hz, 1H, CH3CH (C═O)), 2.52–2.46 (m, 1H), 2.42–2.36 (m, 1H), 2.09–1.98 (m, 2H), 1.76–1.68 (m, 1H), 1.52–1.43 (m, 2H), 1.31 (s, 3H, C(CH3)2), 1.29 (s, 3H, C(CH3)2), 1.30–1.25 (m, 1H), 1.12–1.05 (m, 1H), 1.03 (s, 9H, SiC(CH3)3(C6H5)2), 1.00 (d, J=7.0 Hz, 3H, CH3CH(C═O)), 0.77 (d, J=6.7 Hz, 3H, CH3CHCH2); 13C NMR (150.9 MHz, CDCl3) d 217.0, 165.2, 150.1, 138.9, 135.4, 135.4, 135.4, 133.1, 133.1, 129.6, 129.6, 127.6, 127.6, 121.5, 117.9, 114.2, 75.0, 73.9, 64.4, 51.5, 41.6, 35.5, 35.1, 34.3, 32.2, 26.8, 26.2, 23.5, 23.2, 19.4, 15.6, 10.4; HRMS (FAB), calcd for C38H54CsO5Si (M+Cs+) 751.2795, found 751.2761. 30: Rf=0.28 (silica gel, 17% EtOAc in hexanes); [α]22D +6.2 (c 1.00, CHCl3); IR (film) nmax 2962, 2932, 2858, 1722, 1644, 1294, 1182, 1114, 988, 702 cm−1; 1H NMR (500 MHz, CDCl3) d 7.68–7.63 (m, 4H, SiC(CH3)3(C6H5)2), 7.45–7.40 (m, 2H, SiC(CH3)3(C6H5)2), 7.40–7.35 (m, 4H, SiC(CH3)3(C6H5) 2), 7.03 (d, 1H, J=16.0 Hz, CH═CHCOO), 5.92 (d, J=16.0 Hz, 1H, CH═CHCOO), 5.83–5.68 (m, 2H, 2×CH2CH═CH2), 5.14–5.09 (m, 1H, CO2CH), 5.09 (d, J=18.5 Hz, 1H, CH2CH═CH2), 5.04 (d, J=10.5 Hz, 1H, CH2CH═CH2), 4.99 (d, J=17.5 Hz, 1H, CH2CH═CH2), 4.94 (d, J=10.0 Hz, 1H, CH2CH═CH2), 3.77–3.69 (m, 2H, CH2OTPS), 3.43 (dd, J=6.5, 4.0 Hz, 1H, CHOH(CHCH3)), 3.14–3.07 (m, 1H, CH3CH(C═O)), 2.70 (bs, 1H, CHOH (CHCH3)), 2.53–2.46 (m, 1H), 2.43–2.36 (m, 1H), 2.07–1.95 (m, 2H), 1.48–1.00 (m, 5H), 1.30 (s, 3H, C(CH3) 2), 1.30 (s, 3H, C(CH3)2), 1.05 (d, J=7.0 Hz, 3H, CH3CH (C═O)), 1.04 (s, 9H, SiC(CH3)3(C6H5)2), 0.91 (d, J=7.0 Hz, 3H, CH3CHCH2); 13C NMR (125.7 MHz, CDCl3) d 216.4, 165.4, 150.4, 138.7, 135.6, 135.5, 135.5, 133.3, 133.2, 129.7, 129.7, 127.7, 127.7, 121.4, 118.0, 114.6, 75.0, 73.8, 64.3, 51.5, 42.4, 35.4, 35.1, 33.8, 32.5, 26.7, 25.9, 23.3, 19.2, 14.8, 12.2; HRMS (FAB), calcd for C38H54CsO5Si (M+Cs+) 751.2795, found 751.2770.

Synthesis of Hydroxy Lactone 31 as Illustrated in FIG. 5

Olefin Metathesis of Diene 29.

A solution of diene 29 (104 mg, 0.17 mmol) in Methylene chloride (25 mL, 0.007 M) was treated with bis (tricyclohexylphosphine)benzylidine ruthenium dichloride ((RuCl2(═CHPh)(PCy3)2, 14 mg, 0.017 mmol, 0.1 equiv; Aldrich), in accordance with the procedure described for the preparation of hydroxy lactone 25, to furnish, after flash column chromatography (silica gel, 5æ 17% EtOAc in hexanes), hydroxy lactone 31 (79 mg, 80%). Rf=0.18 (silica, 20% EtOAc in hexanes); [α]22D +37.5 (c=0.50, CHCl3); IR (film) nmax 3519, 2961, 2931, 2857, 1719, 1698, 1644, 1292, 1185, 1113 cm−1; 1H NMR (600 MHz, CDCl3): d 7.67–7.62 (m, 4H, SiC(CH3)3(C6H5)2), 7.45–7.41 (m, 2H, SiC(CH3)3(C6H5)2), 7.41–7.36 (m, 4H, SiC(CH3)3(C6H5) 2), 7.02 (d, J=16.0 Hz, 1H, CH═CHCOO), 5.83 (d, J=16.0 Hz, 1H, CH═CHCOO), 5.34 (ddd, J=15.7, 7.4, 4.7 Hz, 1H, CH═CHCH2), 5.32 (ddd, J=15.7, 8.0, 3.8 Hz, 1H, CH═CHCH2), 5.26–5.21 (m, 1H, CO2CH), 3.74 (dd, J=10.8, 6.1 Hz, 1H, CH2OTPS), 3.68 (dd, 1H, J=10.8, 4.8 Hz, CH2OTPS), 3.58 (bs, 1H, CHOH(CHCH3)), 3.04 (qd, J=6.8, 2.7 Hz, 1H, CH3CH(C═O)), 2.49–2.41 (m, 2H), 2.30–2.22 (m, 1H), 2.17–2.10 (m, 1H), 1.92–1.83 (m, 1H), 1.65–1.50 (m, 2H), 1.35 (s, 3H, C(CH3)2), 1.21 (s, 3H, C(CH3)2), 1.30–1.00 (m, 3H), 1.11 (d, 3H, J=6.7 Hz, CH3CH(C═O)), 1.03 (s, 9H, SiC(CH3)3(C6H5)2), 0.92 (d, 3H, J=7.0 Hz, CH3CHCH2); 13C NMR (150.9 MHz, CDCl3) d 216.4, 165.3, 150.7, 135.4, 135.4, 133.6, 133.2, 133.1, 129.6, 129.6, 127.6, 127.6, 125.7, 122.0, 74.3, 73.5, 65.3, 51.1, 43.0, 38.3, 34.4, 31.9, 31.4, 26.8, 26.8, 25.0, 23.6, 19.4, 15.3, 12.9; HRMS (FAB), calcd for C36H50O5CsSi (M+Cs+) 723.2482, found 723.2506.

Synthesis of Hydroxy Lactone 32 as Illustrated in FIG. 5.

Olefin Metathesis of Diene 30.

A solution of diene 30 (20 mg, 0.03 mmol) in Methylene chloride (10 mL, 0.003 M) was treated with bis (tricyclohexylphosphine)benzylidine ruthenium dichloride ((RuCl2(═CHPh)(PCy3)2, 2.5 mg, 0.003 mmol, 0.1 equiv; Aldrich), in accordance with the procedure described for the preparation of hydroxy lactone 25, to produce after preparative thin layer chromatography (250 mm silica gel plate, 10% EtOAc in hexanes) hydroxy lactone 32 (15 mg, 81%). Rf=0.34 (silica gel, 17% EtOAc in hexanes); [α]22D −90.0 (c 0.60, CHCl3); IR (film) nmax 3524, 2960, 2931, 2856, 1722, 1698, 1294, 1185, 1113, 988, 702, 505 cm−1; 1H NMR (600 MHz, CDCl3) d 7.67–7.64 (m, 4H, SiC(CH3)3

(C6H5)2), 7.45–7.41 (m, 2H, SiC(CH3)3(C6H5)2), 7.40–7.36 (m, 4H, SiC(CH3)3(C6H5)2), 6.91 (d, J=15.8 Hz, 1H, CH=CHCOO), 5.98 (d, J=15.8 Hz, 1H, CH=CHCOO), 5.36 (ddd, J=15.4, 7.3, 4.6 Hz, 1H, CH=CHCH2), 5.35 (ddd, J=15.4, 7.7, 4.1 Hz, 1H, CH=CHCH2), 5.22–5.16 (m, 1H, CO2CH), 3.73 (dd, J=10.7, 5.7 Hz, 1H, CH2OTPS), 3.69 (dd, J=10.7, 4.9 Hz, 1H, CH2OTPS), 3.14 (q, J=6.9 Hz, 1H, CH3CH(C=O)), 3.11 (d, J=9.7 Hz, 1H, CHOH(CHCH3), 2.95 (bs, 1H, CHOH(CHCH3)), 2.44–2.39 (m, 1H), 2.30–2.23 (m, 1H), 2.16–2.11 (m, 1H), 1.99–1.92 (m, 1H), 1.44–1.38 (m, 2H), 1.33 (s, 3H, C(CH3)2), 1.23–1.05 (m, 3H), 1.22 (s, 3H, C(CH3)2), 1.04 (s, 9H, SiC(CH3)3(C6H5)2), 1.02 (d, J=6.9 Hz, 3H, CH3CH(C=O)), 0.96 (d, J=6.5 Hz, 3H, CH3CHCH2); 13C NMR (125.7 MHz, CDCl3) d 216.6, 164.8, 150.0, 135.5, 135.4, 133.2, 133.2, 132.9, 129.6, 129.6, 127.6, 127.6, 126.3, 122.5, 73.8, 73.3, 65.6, 52.0, 41.1, 36.0, 34.6, 33.6, 32.4, 26.9, 25.7, 22.8, 22.8, 19.4, 16.2, 10.5; HRMS (FAB), calcd for C36H50O5CsSi (M+Cs+) 723.2482, found 723.2508.

Synthesis of Hydroxy Acids 33 and 34 as Illustrated in FIG. 6

Aldol Condensation of Acid 21 with Aldehyde 7.

A solution of keto acid 21 (752 mg, 4.42 mmol, 1.0 equiv) in THF (22 mL) was added dropwise at −78° C. to a freshly prepared solution of LDA [formed by addition of n-BuLi (6.49 mL, 1.6 M solution in hexanes, 10.4 mmol, 2.35 equiv) to a solution of diisopropylamine (1.43 mL, 10.2 mmol, 2.3 equiv) in THF (44 mL) at −10° C. and stirring for 30 min]. After stirring for 15 min the reaction mixture was allowed to warm to −30° C. and stirred at that temperature for 1.5 h. The reaction mixture was cooled back to −78° C. and a solution of aldehyde 7 (0.891 g, 7.07 mmol, 1.6 equiv) in THF (22 mL) was added via cannula. The resulting mixture was stirred for 15 min at −78° C., then warmed to −40° C. and stirred for 1 h, cooled to −78° C. and quenched by slow addition of saturated aqueous NH4Cl (10 mL) solution. The reaction mixture was warmed to 0° C., and acetic acid (1.26 mL, 22.1 mmol, 5.0 equiv) was added, followed by warming to 25° C. Extractions with EtOAc (6×15 mL), filtration throught a short plug of silica gel and concentration afforded, in high yield, a mixture of aldol products 33 and 34 along with unreacted starting acid 21 in a 35:50:15 ratio (1H NMR). This crude material was used without further purification. 1H NMR (500 MHz, CDCl3; only signals for 33 and 34 are reported) d 7.16 (d, J=16.0 Hz, 1H, CH=CHCOOH), 5.95 (d, J=16.0 Hz, 1H, CH=CHCOOH), 5.86–5.73 (m, 1H, CH2CH=CH2), 5.02–4.91 (m, 2H, CH2CH=CH2), 3.46–3.32 (m, 1H, CHOH(CHCH3)), 3.17–3.11 (m, 1H, CH3CH(C=O)), 2.09–1.98 (m, 2H, CH2CH=CH2), 1.72–1.24 (m, 9H), 1.14–1.02 (m, 5H), 0.95–0.81 (m, 3H); HRMS (FAB), calcd for C17H29O4 (M+H+) 297.2066, found 297.2074.

Synthesis of Esters 35 and 36 as Illustrated in FIG. 6

EDC Coupling of Alcohol 6 with Keto Acids 33 and 34.

By analogy to the procedure described above for the synthesis of ester 22a, a solution of keto acids 33 and 34 (1.034 g crude), 4-dimethylaminopyridine (4-DMAP, 43 mg, 0.35 mmol), and alcohol 6 (1.1 g, 5.24 mmol; synthesized vida infra as compound 91; eg. alcohol 6 as shown in FIG. 6 is the same compound as compound 91 as shown in FIG. 12) in Methylene chloride (4 mL) was treated with 1-ethyl-(3-dimethylaminopropyl)-3-carbodiimide hydrochloride (EDC, 1.00 g, 5.24 mmol) to provide, after column chromatography (silica gel, 20% EtOAc in hexanes), ester 35 (0.567 g, 29% from keto acid 21) and ester 36 (0.863 g, 44% from keto acid 21). 35: Rf=0.27 (silica gel, 20% EtOAc in hexanes); [α]22D −7.3 (c 2.90, CHCl3); IR (film) nmax 3510, 2973, 2932, 1719, 1703, 1641, 1459, 1293, 1179, 985 cm−1; 1H NMR (500 MHz, CDCl3) d 7.03 (d, J=16.0 Hz, 1H, CH=CHCOO), 6.95 (s, 1H, ArH), 6.53 (s, 1H, ArCH=CCH3), 5.95 (d, J=16.0 Hz, 1H, CH=CHCOO), 5.80–5.69 (m, 2H, 2×CH2CH=CH2), 5.39 (t, J=6.5 Hz, 1H, CO2CH), 5.10 (d, J=17.5 Hz, 1H, CH2CH=CH2), 5.05 (d, J=10.5 Hz, 1H, CH2CH=CH2), 4.97 (d, J=17.0 Hz, 1H, CH2CH=CH2), 4.93 (d, J=10.0 Hz, 1H, CH2CH=CH2), 3.43 (dd, J=6.5, 4.0 Hz, 1H, CHOH(CHCH3)), 3.11 (qd, J=7.0, 4.0 Hz, 1H, CH3CH(C=O)), 2.76 (bs, 1H, CHOH (CHCH3)), 2.69 (s, 3H, CH3Ar), 2.57–2.47 (m, 2H, CH2CH=CH2), 2.08 (d, J=1.0 Hz, 3H, ArCH=CCH3), 2.07–1.93 (m, 2H, CH2CH=CH2), 1.47–1.28 (m, 4H), 1.30 (s, 3H, C(CH3)2), 1.28 (s, 3H, C(CH3)2), 1.05 (d, J=7.0 Hz, 3H, CH3CH(C=O)), 1.05–0.98 (m, 1H), 0.91 (d, J=6.5 Hz, 3H, CH3CHCH2); 13C NMR (125.7 MHz, CDCl3) d 216.3, 165.0, 164.7, 152.2, 150.5, 138.6, 136.9, 133.2, 121.4, 120.8, 117.8, 116.4, 114.6, 78.4, 75.0, 51.5, 42.6, 37.5, 35.3, 33.7, 32.5, 25.9, 23.2, 23.2, 19.1, 14.8, 12.2; HRMS (FAB), calcd for C28H42NO4S (M+H+) 488.2835, found 488.2843. 36: Rf=0.34 (silica gel, 20% EtOAc in hexanes); [α]22D −9.2 (c 1.00, CHCl3); IR (film) nmax 3519, 2930, 1716, 1641, 1457, 1293, 1179, 986 cm−1; 1H NMR (500 MHz, CDCl3) d 7.04 (d, J=16.0 Hz, 1H, CH=CHCOO), 6.95 (s, 1H, ArH), 6.54 (s, 1H, ArCH=CCH3), 5.96 (d, J=15.5 Hz, 1H, CH=CHCOO), 5.84–5.69 (m, 2H, 2×CH2CH=CH2), 5.40 (t, J=6.5 Hz, 1H, CO2CH), 5.10 (d, J=17.0 Hz, 1H, CH2CH=CH2), 5.05 (d, J=10.5 Hz, 1H, CH2CH=CH2), 4.98 (d, J=17.5 Hz, 1H, CH2CH=CH2), 4.92 (d, J=9.0 Hz, 1H, CH2CH=CH2), 3.30 (dd, J=8.5, 1.5 Hz, 1H, CHOH(CHCH3)), 3.13 (qd, J=7.0, 2.0 Hz, 1H, CH3CH(C=O)), 2.70 (s, 3H, CH3Ar), 2.57–2.49 (m, 2H, CH2CH=CH2), 2.09 (s, 3H, ArCH=CCH3), 2.09–1.96 (m, 2H, CH2CH=CH2), 1.74–1.68 (m, 1H), 1.52–1.43 (m, 2H), 1.32 (s, 3H, C(CH3)2), 1.30 (s, 3H, C(CH3)2), 1.30–1.01 (m, 2H), 1.02 (d, J=7.0 Hz, 3H, CH3CH(C=O)), 0.79 (d, J=6.5 Hz, 3H, CH3CHCH2); 13C NMR (125.7 MHz, CDCl3) d 217.3, 165.1, 164.7, 152.4, 150.4, 139.0, 136.8, 133.2, 121.6, 121.0, 117.8, 116.4, 114.3, 78.5, 74.9, 51.5, 41.5, 37.5, 35.4, 34.1, 32.1, 26.0, 23.2, 23.0, 19.2, 15.5, 14.7, 10.2; HRMS (FAB), calcd for C28H44CsNO4S (M+Cs+) 620.1811, found 620.1838.

Synthesis of Hydroxy Lactone 37 as Illustrated in FIG. 6

Olefin Metathesis of Diene 35.

A solution of diene 35 (58 mg, 0.12 mmol) in Methylene chloride (129 mL, 0.001 M) was treated with bis (tricyclohexylphosphine)benzylidine ruthenium dichloride ((RuCl2(=CHPh)(PCy3)2, 10 mg, 0.0012 mmol, 0.1 equiv; Aldrich), in accordance with the procedure described for the synthesis of hydroxy lactone 25, to furnish, after column chromatography (silica gel, 15% EtOAc in hexanes) hydroxy lactone 37 (48 mg, 86%). Rf=0.63 (silica gel, 33% EtOAc in hexanes); [α]22D −14.8 (c 1.90, CHCl3); IR (film) nmax 3510, 2931, 1709, 1646, 1458, 1295, 1178, 976, 732 cm−1; 1H NMR (500 MHz, CDCl3) d 7.15 (d, J=16.0 Hz, 1H, CH=CHCOO), 6.96 (s, 1H, ArH), 6.58 (s, 1H, ArCH= CCH3), 5.95 (d, J=16.0 Hz, 1H, CH=CHCOO), 5.56 (dd, J=9.5, 3.0 Hz, 1H, CO2CH), 5.36 (ddd, J=15.5, 7.3, 3.5 Hz, 1H, CH=CHCH2), 5.35 (ddd, J=15.5, 7.3, 3.5 Hz, 1H, CH=CHCH2), 3.33 (d, J=9.0 Hz, 1H, CHOH(CHCH3)), 3.16 (q, J=7.0 Hz, 1H, CH3CH(C=O)), 2.88 (bs, 1H, CHOH(CHCH3)), 2.71 (s, 3H, CH3Ar), 2.56–2.42 (m, 2H, CH=CHCH2), 2.18–2.06 (m, 1H, CH=CHCH2), 2.10 (s, 3H, ArCH=CCH3), 1.99–1.90 (m, 1H, CH=CHCH2), 1.52–1.20 (m, 3H), 1.31 (s, 3H, C(CH3)2), 1.28 (s, 3H, C(CH3)2), 1.17–0.90 (m, 2H), 1.02 (d, J=7.0 Hz, 3H, CH3CH(C=O)), 0.97 (d, J=6.5 Hz, 3H, CH3CHCH2); 13C NMR (125.7 MHz, CDCl3) d 217.8, 165.1, 164.8, 152.1, 151.5, 138.3, 133.4, 125.8, 121.5, 119.3, 116.0, 76.8, 74.9, 50.8, 43.7, 36.7, 35.5, 32.5, 31.8, 25.4, 25.2, 23.9, 19.0, 15.8, 15.5, 9.7; HRMS (FAB), calcd for C26H37CsNO4S (M+Cs+) 592.1498, found 592.1516.

Synthesis of Hydroxy Lactone 38 as Illustrated in FIG. 6

Olefin Metathesis of Diene 36.

A solution of diene 36 (167 mg, 0.34 mmol) in Methylene chloride (340 mL, 0.001 M) was treated with bis (tricyclohexylphosphine)benzylidine ruthenium dichloride ((RuCl2(=CHPh)(PCy3)2, 28 mg, 0.034 mmol, 0.1 equiv; Aldrich), in accordance with the procedure described for the synthesis of hydroxy lactone 25, to furnish, after column chromatography (silica gel, 20% EtOAc in hexanes) hydroxy lactone 38 (103 mg, 66%). Rf=0.38 (silica gel, 30% EtOAc in hexanes); [α]22D +70.4 (c 1.60, CHCl3); IR (film) nmax 2933, 1703, 1640, 1292, 1179, 982 cm−1; 1H NMR (500 MHz, CDCl3) d 6.99 (d, J=16.0 Hz, 1H, CH=CHCOO), 6.97 (s, 1H, ArH), 6.55 (s, 1H, ArCH=CCH3), 6.02 (d, J=16.0 Hz, 1H, CH=CHCOO), 5.51 (dd, J=8.0, 2.5 Hz, 1H, CO2CH), 5.47 (ddd, J=15.0, 7.5, 7.5 Hz, 1H, CH=CHCH2), 5.38 (ddd, J=15.0, 7.5, 7.5 Hz, 1H, CH=CHCH2), 3.60 (d, J=6.8 Hz, 1H, CHOH(CHCH3)), 3.14 (dq, J=7.0, 7.0 Hz, 1H, CH3CH(C=O)), 2.70 (s, 3H, CH3Ar), 2.48–2.37 (m, 2H, CH=CHCH2), 2.21–2.12 (m, 1H, CH=CHCH2), 2.08 (s, 3H, ArCH=CCH3), 1.98–1.90 (m, 1H, CH=CHCH2), 1.62–1.52 (m, 1H), 1.41–1.32 (m, 2H), 1.36 (s, 3H, C(CH3)2), 1.21 (s, 3H, C(CH3)2), 1.17–1.07 (m, 1H), 1.14 (d, J=7.0 Hz, 3H, CH3CH(C=O)), 0.98–0.87 (m, 1H), 0.97 (d, J=7.0 Hz, 3H, CH3CHCH2); 13C NMR (125.7 MHz, CDCl3) d 215.5, 165.0, 164.6, 152.2, 150.9, 137.4, 133.6, 126.0, 121.9, 119.4, 115.6, 76.6, 76.2, 51.6, 44.1, 37.9, 36.2, 33.3, 29.6, 27.1, 24.0, 23.0, 18.9, 17.0, 15.9, 15.4; HRMS (FAB), calcd for C26H38NO4S (M+H+) 460.2522, found 460.2534.

Synthesis of Epothilones 39, 40 and 41 as Illustrated in FIG. 6

Epoxidation of trans-Hydroxy Lactone 37.

Procedure A: A solution of trans-hydroxy lactone 37 (20 mg, 0.06 mmol) in CHCl3 (1 mL, 0.06 M) was treated with metα-chloroperbenzoic acid (mCPBA, 57–86%, 15 mg, 0.05–0.07 mol, 0.9–1.2 equiv) at −20° C., and the reaction mixture was allowed to warm up to 0° C. After 12 h, disappearance of starting material was detected by TLC, and the reaction mixture was then washed with saturated aqueous NaHCO3 solution (2 mL) and the aqueous phase was extracted with EtOAc (3×2 mL). The combined organic layer was dried (MgSO4), filtered and concentrated. Purification by preparative thin layer chromatography (250 mm silica gel plate, 30% EtOAc in hexanes) furnished epothilones 39 (or 40) (12 mg, 40%), 40 (or 39) (7.5 mg, 25%) and 41 (5.4 mg, 18%). Procedure B: To a solution of trans-hydroxy lactone 37 (32 mg, 0.07 mmol) in acetonitrile (1.0 mL) was added a 0.0004 M aqueous solution of disodium salt of ethylenediaminetetraacetic acid (Na2EDTA, 0.5 mL) and the reaction mixture was cooled to 0° C. Excess of 1,1,1-trifluoroacetone (0.2 mL) was added, followed by a portionwise addition of Oxone® (200 mg, 0.35 mmol, 5.0 equiv) and NaHCO3 (50 mg, 0.56 mmol, 8.0 equiv) with stirring, until the disappearance of starting material was detected by TLC. The reaction mixture was then treated with excess dimethyl sulfide (150 mL) and water (1.0 mL) and then extracted with EtOAc (4×2 mL). The combined organic layer was dried (MgSO4), filtered, and concentrated. Purification by preparative thin layer chromatography (250 mm silica gel plate, 70% EtOAc in hexanes) provided a mixture of diastereomeric epoxides, epoxide 39 (or 40) (15 mg, 45%) and α-isomeric epoxide 40 (or 39) (9.2 mg, 28%). 39 (or 40): Rf=0.23 (silica gel, 33% EtOAc in hexanes); [α]22D −23.7 (c 0.30, CHCl3); IR (film) nmax 3500, 2970, 2930, 2859, 1714, 1696, 1651, 1643, 1634, 1293, 1176, 991 cm−1; 1H NMR (600 MHz, CDCl3) d 7.18 (d, J=16.0 Hz, 1H, CH=CHCOO), 6.97 (s, 1H, ArH), 6.56 (s, 1H, ArCH=CCH3), 5.94 (d, J=16.0 Hz, 1H, CH=CHCOO), 5.71 (d, J=11.1 Hz, 1H, CO2CH), 3.52 (d, J=6.0 Hz, 1H, CHOH(CHCH3)), 3.07 (q, J=6.9 Hz, 1H, CH3CH(C=O)), 2.76 (d, J=8.0 Hz, 1H), 2.70 (s, 3H, CH3Ar), 2.61 (bs, 2H), 2.29 (d, J=14.5 Hz, 1H), 2.09 (s, 3H, ArCH=CCH3), 1.82–1.76 (m, 1H), 1.75–1.68 (m, 1H), 1.60–0.98 (m, 6H), 1.35 (s, 3H, C(CH3)2), 1.29 (s, 3H, C(CH3)2), 1.11 (d, J=6.9 Hz, 3H, CH3CH(C=O)), 1.01 (d, J=6.7 Hz, 3H, CH3CHCH2); 13C NMR (125.7 MHz, CDCl3) d 216.4, 165.1, 164.7, 152.0, 151.9, 136.7, 121.3, 120.5, 116.6, 76.3, 72.3, 59.3, 56.6, 51.1, 45.2, 36.7, 36.7, 33.3, 32.2, 25.3, 23.5, 22.4, 19.4, 15.5, 15.1, 10.9; HRMS (FAB), calcd for C26H37NO5S (M+H+) 608.1447, found 608.1469; 40 (or 39): Rf=0.26 (silica gel, 33% EtOAc in hexanes); [α]22D −20.0 (c 0.25, CHCl3); IR (film) nmax 3517, 2927, 2856, 1715, 1698, 1644, 1293, 1176, 989 cm−1; 1H NMR (500 MHz, CDCl3) d 7.26 (d, J=16.0 Hz, 1H, CH=CHCOO), 6.97 (s, 1H, ArH), 6.56 (s, 1H, ArCH=CCH3), 5.98 (d, J=16.0 Hz, 1H, CH=CHCOO), 5.50 (d, J=6.5 Hz, 1H, CO2CH), 3.47 (d, J=8.0 Hz, 1H, CHOH (CHCH3)), 3.19 (q, J=7.0 Hz, 1H, CH3CH(C=O)), 2.78 (t, J=6.5 Hz, 2H), 2.71 (s, 3H, CH3Ar), 2.32–2.26 (m, 1H), 2.11 (s, 3H, ArCH=CCH3), 1.91–1.86 (m, 1H), 1.76–1.17 (m, 7H), 1.36 (s, 3H, C(CH3)2), 1.30 (s, 3H, (C(CH3)2), 1.08 (d, J=7.0 Hz, 3H, CH3CH(C=O)), 0.98 (d, J=6.5 Hz, 3H, CH3CHCH2); 13C NMR (125.7 MHz, CDCl3) d 216.9, 165.0, 164.6, 152.0, 151.4, 136.6, 121.7, 119.6, 116.3, 76.1, 73.6, 57.3, 54.1, 51.2, 44.1, 35.3, 35.0, 32.8, 30.8, 24.3, 23.6, 21.9, 19.3, 16.1, 15.5, 10.7; HRMS (FAB), calcd for C26H38CsNO5S (M+Cs+) 608.1447, found 608.1469. 41: Rf=0.43 (silica gel, 33% EtOAc in hexanes); [α]22D −14.0 (c 0.10, CHCl3); IR (film) nmax 3482, 2925, 1722, 1642, 1176 cm−1; 1H NMR (500 MHz, CDCl3) d 7.14 (d, J=16.0 Hz, 1H, CH=CHCOO), 6.97 (s, 1H, ArH), 5.92 (d, J=16.0 Hz, 1H, CH=CHCOO), 5.35–5.33 (m, 2H, CH=CHCH2), 5.13 (dd, J=10.5, 3.0 Hz, 1H, CO2CH), 4.20 (s, 1H, ArCH—O(epoxide)CCH3), 3.30 (d, J=9.0 Hz, 1H, CHOH (CHCH3)), 3.13 (q, J=7.5 Hz, 1H, CH3CH(C=O)), 2.76 (d, J=2.0 Hz, 1H), 2.72 (s, 3H, CH3Ar), 2.58 (dd, J=14.1, 2.4 Hz, 1H), 2.46–2.40 (m, 1H), 2.22–2.16 (m, 1H), 2.02–1.87 (m, 2H) 1.68–0.82 (m, 3H), 1.31 (s, 3H, C(CH3)2), 1.28 (s, 3H, C(CH3)2), 1.25 (s, 3H, ArCH—O(epoxide)CCH3), 1.01 (d, J=7.0 Hz, 3H, CH3CH(C=O)), 0.97 (d, J=6.5 Hz, 3H, CH3CHCH2); 13C NMR (125.7 MHz, CDCl3) d 217.5, 166.3, 165.1, 152.1, 150.9, 133.8, 125.4, 121.0, 115.5, 75.1, 74.2, 59.5, 51.0, 44.0, 35.7, 34.1, 32.7, 32.0, 29.8, 25.6, 25.5, 24.1, 19.3, 16.0, 13.0, 9.8; HRMS (FAB), calcd for C26H37CsNO5S (M+Cs+) 608.1447, found 608.1423.

Synthesis of Epothilones 42, 43 and 44 as Illustrated in FIG. 6

Epoxidation of trans-Hydroxy Lactone 38.

Procedure A: A solution of trans-hydroxy lactone 38 (32 mg, 0.07 mmol) in CHCl3 (1.4 mL) was reacted with metα-chloroperbenzoic acid (mCPBA, 57–86%, 17.8 mg, 0.06–0.09 mmol, 0.9–1.3 equiv), according to procedure A described for the epoxidation of 37, resulting in the isolation of epoxides 42 (or 43) (7.3 mg, 22%), 43 (or 42) (3.7 mg, 11%), and 44 (2.2 mg, 7%) (stereochemistry unassigned for all compounds), along with unreacted starting material (3.5 mg, 11%), after two consecutive preparative thin layer chromatographic purifications (250 mm silica gel plate, ether). Procedure B: As described in procedure B for the epoxidation of trans-hydroxy lactone 37, cis-hydroxy lactone 38 (24 mg, 0.05 mmol) in MeCN (800 mL) was treated with a 0.0004 M aqueous solution of disodium salt of ethylenediaminetetraacetic acid (Na2EDTA, 380 mL), 1,1,1-trifluoroacetone (150 mL), Oxone® (144 mg, 0.25 mmol, 5.0 equiv) and NaHCO3 (36 mg, 0.40 mmol, 8.0 equiv), to yield, after purification by preparative thin layer chromatography (250 mm silica gel plate, ether), epoxides 42 (or 43) (15 mg, 60%), 43 (or 42) (3.8 mg, 15%). 42 (or 43): Rf=0.60 (silica gel, ether); [α]22D +78.5 (c 0.94, CHCl3); IR (film) nmax 3500, 2929, 1714, 1644, 1462, 1293, 1179, 982 cm−1; 1H NMR (500 MHz, CDCl3) d 6.98 (s, 1H, ArH), 6.89 (d, J=16.0 Hz, 1H, CH=CHCOO), 6.58 (s, 1H, ArCH=CCH3), 6.06 (d, J=16.0 Hz, 1H, CH=CHCOO), 5.69 (d, J=11.0 Hz, 1H, CO2CH), 3.80–3.73 (m, 1H, CHOH(CHCH3)), 3.11 (dq, J=7.0, 7.0 Hz, 1H, CH3CH(C=O)), 2.82–2.74 (m, 2H), 2.71 (s, 3H, CH3Ar), 2.43 (d, J=14.5 Hz, 1H), 2.11 (s, 3H, ArCH=CCH3), 1.93–1.85 (m, 1H), 1.60–0.98 (m, 7H), 1.46 (s, 3H, C(CH3)2), 1.24 (s, 3H, C(CH3)2), 1.14 (d, J=7.0 Hz, 3H, CH3CH(C=O)), 1.01 (d, J=7.0 Hz, 3H, CH3CHCH2); 13C NMR (150.9 MHz, CDCl3) d 212.7, 165.0, 164.7, 152.0, 151.7, 137.0, 121.1, 120.6, 116.7, 76.2, 75.7, 58.7, 57.7, 52.2, 44.4, 37.3, 36.1, 33.5, 30.0, 24.2, 23.0, 22.1, 19.3, 18.1, 14.9, 14.5; HRMS (FAB), calcd for C26H37NO5S (M+H+) 476.2471, found 476.2485. 43 (or 42): Rf=0.64 (silica gel, ether); [α]22D +38.0 (c 0.20, CHCl3); IR (film) nmax 3479, 2926, 2855, 1721, 1702, 1643, 1455, 1174 cm−1; 1H NMR (500 MHz, CDCl3) d 7.08 (d, J=16.0 Hz, 1H, CH=CHCOO), 7.01 (s, 1H, ArH), 6.63 (s, 1H, ArCH=CCH3), 6.05 (d, J=16.0 Hz, 1H, CH=CHCOO), 5.47 (dd, J=7.6, 2.6 Hz, 1H, CO2CH), 3.65 (dd, J=6.5, 3.5 Hz, 1H, CHOH(CHCH3)), 3.19 (dq, J=6.8, 6.8 Hz, 1H, CH3CH(C=O)), 2.85–2.80 (m, 1H), 2.78–2.72 (m, 1H), 2.73 (s, 3H, CH3Ar), 2.52 (ddd, J=15.0, 8.5, 4.0 Hz, 1H), 2.10 (s, 3H, ArCH=CCH3), 1.73 (ddd, J=15.0, 7.5, 3.5 Hz, 1H), 1.65–0.80 (m, 7H), 1.43 (s, 3H, C(CH3)2), 1.26 (s, 3H, C(CH3)2), 1.15 (d, J=6.8 Hz, 3H, CH3CH(C=O)), 0.99 (d, J=7.0 Hz, 3H, CH3CHCH2); 13C NMR (150.9 MHz, CDCl3) d 215.1, 165.5, 164.7, 152.1, 152.0, 130.9, 128.8, 120.9, 115.9, 75.7, 75.2, 57.6, 55.6, 51.7, 44.3, 37.5, 34.4, 32.3, 31.1, 23.9, 23.3, 22.8, 18.8, 17.2, 15.8, 14.6; HRMS (FAB), calcd for C26H37NO5S (M+H+) 476.2471, found 476.2489. 44: Rf=0.60 (silica gel, ether); [α]22D +23.3 (c 0.06, CHCl3); IR (film) nmax 3443, 2924, 1731, 1462, 1260 cm−1; 1H NMR (500 MHz, CDCl3) d 6.97 (s, 1H, ArH), 6.84 (d, J=16.0 Hz, 1H, CH=CHCOO), 6.04 (d, J=16.0 Hz, 1H, CH=CHCOO), 5.51–5.43 (m, 1H, CH=CHCH2), 5.42–5.35 (m, 1H, CH=CHCH2), 5.05 (dd, J=10.0, 2.5 Hz, 1H, CO2CH), 4.18 (s, 1H, ArCH—O (epoxide)CCH3), 3.60–3.57 (m, 1H, CHOH(CHCH3)), 3.06 (dq, J=7.0, 7.0 Hz, 1H, CH3CH(C=O)), 2.72 (s, 3H, CH3Ar), 2.56–2.50 (m, 1H), 2.40–2.32 (m, 1H), 2.30–2.22 (m, 1H), 2.14–1.96 (m, 2H), 1.60–0.98 (m, 4H), 1.38 (s, 3H, ArCH—O(epoxide)CCH3), 1.30 (s, 3H, C(CH3)2), 1.22 (s, 3H, C(CH3)2), 1.14 (d, J=7.0 Hz, 3H, CH3CH(C=O)), 0.95 (d, J=7.0 Hz, 3H, CH3CHCH2); HRMS (FAB), calcd for C26H38NO5S (M+H+) 476.2471, found 476.2492.

Synthesis of Hydroxy Keto Acids 45 and 46 as Illustrated in FIG. 7

Aldol Condensation of Keto Acid 8 and Aldehyde 7.

In accordance with the procedure described for the synthesis of keto acids 33 and 34, keto acid 8 (0.896 g, 2.97 mmol, 1.0 equiv) in THF (10 mL) was treated with lithium diisopropylamide [LDA; freshly prepared from n-BuLi (4.36 mL, 1.6 M solution in hexanes, 7.41 mmol, 2.5 equiv) and diisopropylamine (960 mL, 6.83 mmol, 2.3 equiv) in THF (30 mL)] and aldehyde 7 (0.68 g, 5.3 mmol, 1.8 equiv) in THF (30 mL) to afford a mixture of aldol products 45 and 46 in high yield and in a ca 3:2 ratio (1H NMR), along with unreacted keto acid 8 (5%). Rf=0.20 (silica gel, 50% EtOAc in hexanes); 1H NMR (500 MHz, CDCl3; only signals for 45 and 46 are reported) d 5.88–5.73 (m, 1H, CH2CH=CH2), 5.04–4.92 (m, 2H, CH2CH=CH2), 4.51–4.47 (m, 0.4H, CHOTBS), 4.44–4.40 (m, 0.6H, (CH3)2CCH(OTBS)), 3.42 (d, J=8.0 Hz, 0.4H, CHOH(CHCH3)), 3.32 (d, J=9.0 Hz, 0.6H, CHOH(CHCH3)), 3.30–3.20 (m, 1H, CH3CH(C=O)), 2.51–2.45 (m, 1H, CH2COOH), 2.38 (dd, J=16.5, 6.5 Hz, 0.4H, CH2COOH), 2.35 (dd, J=16.5, 6.5 Hz, 0.6H, CH2COOH), 2.11–1.98 (m, 2H), 1.80–1.21 (m, 5H), 1.20 (s, 1.8H, C(CH3)2), 1.19 (s, 1.2H, C(CH3)2), 1.16 (s, 1.8H, C(CH3)2), 1.14 (s, 1.2H, C(CH3)2), 1.06 (d, J=6.5 Hz, 1.2H), 1.05 (d, J=6.5 Hz, 1.8H), 1.00 (d, J=6.5 Hz, 1.2H), 0.89 (s, 5.4H, SiC(CH3)3(CH3)2), 0.87 (s, 3.6H, SiC(CH3)3(CH3)2), 0.85 (d, J=7.0 Hz, 1.8H), 0.11 (s, 1.8H, SiC(CH3)3(CH3)2), 0.09 (s, 1.2H, , SiC(CH3)3(CH3)2), 0.08 (s, 1.2H, , SiC(CH3)3(CH3)2), 0.07 (s, 1.8H, SiC(CH3)3(CH3)2); HRMS (FAB), calcd for C23H44NaO5Si (M+Na+) 451.2856, found 451.2867.

Synthesis of Hydroxy Esters 4 and 47 as Illustrated in FIG. 7

EDC Coupling of Carboxylic Acids 45 and 46 and Alcohol 6.

The crude mixture of keto acids 45 and 46 (1.30 g), 4-(dimethylamino)pyridine (4-DMAP, 0.037 g, 0.3 mmol), and alcohol 6 (1.90 g, 9.0 mmol;synthesized vida infra as compound 91; eg. alcohol 6 as shown in FIG. 6 is the same compound as compound 91 as shown in FIG. 12) in Methylene chloride (5 mL) was treated with 1-ethyl-(3-dimethylaminopropyl)-3-carbodiimide hydrochloride (EDC, 0.7 g, 3.6 mmol), according to the procedure described for the synthesis of keto ester 22a, producing pure hydroxy esters 4 (0.940 g, 52% from keto acid 8) and 47 (0.569 g, 31% from keto acid 8) after flash column chromatography (silica gel, 18% EtOAc in hexanes). 4: Rf=0.30 (silica gel, 18% EtOAc in hexanes); [α]22D −53.4 (c 1.00, MeOH); IR (film) nmax 3508, 2932, 1737, 1690, 1650, 1178, 1088, 835 cm−1; 1H-NMR (500 MHz, CDCl3): d 6.93 (s, 1H, ArH), 6.47 (s, 1H, ArCH=CCH3), 5.81–5.73 (m, 1H, CH2CH=CH2), 5.73–5.65 (m, 1H, CH2CH=CH2), 5.27 (dd, J=7.0, 6.5 Hz, 1H, CO2CH), 5.09 (d, J=17.5 Hz, 1H, CH2CH=CH2), 5.03 (d, J=10.0 Hz, 1H, CH2CH=CH2), 4.96 (d, J=17.0 Hz, 1H, CH2CH=CH2), 4.89 (d, J=10.5 Hz, 1H, CH2CH=CH2), 4.39 (dd, J=6.0, 4.0 Hz, 1H, (CH3)2CCH(OTBS)), 3.42 (bs, 1H, CHOH(CHCH3)), 3.28 (q, J=7.0 Hz, 1H, CH3CH(C=O)), 3.24 (d, J=9.5 Hz, 1H, CHOH(CHCH3)), 2.67 (s, 3H, CH3Ar), 2.54–2.43 (m, 2H), 2.43 (dd, J=10.0, 4.0 Hz, 1H, CH2COO), 2.31 (dd, J=10.0, 6.0 Hz, 1H, CH2COO), 2.04 (s, 3H, ArCH=CCH3), 2.03–1.90 (m, 2H, CH2CH=CH2), 1.75–1.65 (m, 1H), 1.48–1.43 (m, 1H), 1.43–1.36 (m, 1H), 1.22–1.10 (m, 2H), 1,17 (s, 3H, C(CH3)2), 1,09 (s, 3H, C(CH3)2), 1.01 (d, J=6.5 Hz, 3H, CH3CH(C=O)), 0.86 (s, 9H, SiC(CH3)3 (CH3)2), 0.81 (d, J=7.0 Hz, 3H CH3CHCH2), 0.09 (s, 3H, SiC(CH3)3(CH3)2), 0.04 (s, 3H, SiC(CH3)3(CH3)2); 13C NMR (125.7 MHz, CDCl3) d 221.8, 170.9, 164.6, 152.4, 139.0, 136.6, 133.2, 121.0, 117.8, 116.4, 114.1, 78.8, 74.5, 73.4, 53.9, 41.2, 40.1, 37.4, 35.4, 34.1, 32.3, 26.0, 25.9, 21.9, 19.9, 19.2, 18.1, 15.2, 14.6, 9.7, −4.3, −4.9; HRMS (FAB), calcd for C34H57CsNO5SSi (M+Cs+) 752.2781, found 752.2760. 47: Rf=0.20 (silica gel, 18% EtOAc in hexanes); [α]22D −27.3 (c 1.00, CHCl3); IR (film) nmax 3509, 2932, 2857, 1737, 1691, 1465, 1381, 1292, 1253, 1177, 1088, 984, 835 cm−1; 1H NMR (500 MHz, CDCl3) d 6.95 (s, 1H, ArH), 6.49 (s, 1H, ArCH=CCH3), 5.83–5.69 (m, 2H, 2×CH2CH=CH2), 5.29 (dd, J=6.5, 6.5 Hz, 1H, CO2CH), 5.11 (d, J=17.0 Hz, 1H, CH2CH=CH2), 5.05 (d, J=10.0 Hz, 1H, CH2CH=CH2), 5.01 (d, J=17.0 Hz, 1H, CH2CH=CH2), 4.95 01 (d, J=10.5 Hz, 1H, CH2CH=CH2), 4.50 (dd, J=6.5, 4.0 Hz, 1H, (CH3)2CCH (OTBS)), 3.42 (dd, J=8.0, 1.5 Hz, 1H, CHOH(CHCH3)), 3.21 (qd, J=7.0, 2.0 Hz, 1H, CH3CH(C=O)), 2.70 (s, 3H, CH3Ar.), 2.54–2.33 (m, 4H), 2.11–1.98 (m, 2H), 2.07 (s, 3H, ArCH=CCH3), 1.53–0.98 (m, 5H), 1.15 (s, 3H, C(CH3)2), 1.11 (s, 3H, C(CH3)2), 1.01 (d, J=7 Hz, 3H, CH3CH (C=O)), 0.99 (d, J=6.5 Hz, 3H, CH3CHCH2), 0.86 (s, 9H, SiC(CH3)3(CH3)2), 0.08 (s, 3H, SiC(CH3)3(CH3)2), 0.07 08 (s, 3H, SiC(CH3)3(CH3)2); 13C NMR (125.7 MHz, CDCl3) d 220.8, 170.9, 164.4, 152.2, 138.6, 136.6, 133.1, 120.9, 117.8, 116.3, 114.5, 78.8, 74.8, 72.5, 53.9, 41.3, 40.1, 37.4, 35.2, 33.7, 32.0, 25.9, 25.8, 21.7, 19.6, 19.1, 18.1, 15.4, 14.5, 10.5, −4.4, −4.8; HRMS (FAB), calcd for C34H58NO5SSi (M+H+) 620.3805, found 620.3813.

Synthesis of Hydroxy Lactones 3 and 48 as Illustrated in Figure 8

Cyclization of Diene 42 via Olefin Metathesis.

A solution of diene 4 (0.186 g, 0.3 mmol) in Methylene chloride (200 mL, 0.0015 M) was treated with bis (tricyclohexyl-phosphine)-benzylidine ruthenium dichloride (RuCl2(=CHPh)(PCy3)2, 25 mg, 0.03 mol, 0.1 equiv; Aldrich), for 20 h, in accordance with the procedure described for the synthesis of hydroxy lactone 25, producing hydroxy lactones 3 (83 mg, 46%) and 48 (70 mg, 39%) after flash chromatography (7 to 25% EtOAc in hexanes). 3: Rf=0.18 (silica, 20% EtOAc in hexanes); [α]22D −79.5 (c=1.00, CHCl3); IR (film) nmax 3422, 2930, 1739, 1688, 1255, 1180, 1090, 598 cm−1; 1H NMR (500 MHz, CDCl3) d 6.96 (s, 1H, ArH), 6.55 (s, 1H, ArCH=CCH3), 5.45 (ddd, J=10.5, 10.5, 3.0 Hz, 1H, CH=CHCH2), 5.35 (ddd, J=10.5, 10.5, 5.5 Hz, 1H, CH=CHCH2), 5.03 (d, J=10.0 Hz, 1H, CO2CH), 4.06 (t, J=6.0 Hz, 1H, (CH3)2CCH(OTBS)), 3.94 (bs, 1H, CHOH(CHCH3)), 3.05 (qd, J=6.5, 3.5 Hz, 1H, CH3CH(C=O)), 3.00 (bs, 1H, CHOH(CHCH3)), 2.80 (d, J=6.0 Hz, 2H, CH2COO), 2.78–2.69 (m, 1H), 2.70 (s, 3H, CH3Ar), 2.40–2.30 (m, 1H), 2.10 (s, 3H, ArCH=CCH3), 2.12–2.03 (m, 1H), 2.00–1.93 (m, 1H), 1.80–1.74 (m, 1H), 1.70–1.58 (m, 1H), 1.50–1.43 (m, 1H), 1.30–1.15 (m, 2H), 1.17 (s, 6H, C(CH3)2), 1.14 (d, 3H, J=5.0 Hz, CH3CH (C=O)), 1.02 (d, 3H, J=5.0 Hz, CH3CHCH2), 0.82 (s, 9H, SiC(CH3)3(CH3)2), 0.12 (s, 3H, SiC(CH3)3(CH3)2), −0.05 (s, 3H, SiC(CH3)3(CH3)2); 13C NMR (150.9 MHz, CDCl3) d 217.7, 170.7, 164.4, 152.2, 138.1, 134.5, 124.0, 119.5, 116.0, 79.0, 76.3, 73.2, 53.6, 43.1, 39.1, 38.9, 33.7, 32.0, 28.5, 28.0, 26.3, 24.9, 23.0, 19.3, 18.7, 16.6, 15.4, 14.3, −3.4, −5.3; HRMS (FAB), calcd for C32H53CsNO5SSi (M+Cs+) 724.2468, found 724.2466. 48: Rf=0.40 (silica, 20% EtOAc in hexanes); [α]22D −71.5 (c=0.80, CHCl3); IR (film) nmax 3381, 2958, 2928, 1727, 1273, 1122, 1072 cm−1; 1H NMR (600 MHz, CDCl3) d 7.00 (s, 1H, ArH), 6.62 (s, 1H, ArCH=CCH3), 5.36 (ddd, J=15.0, 7.3, 7.3 Hz, 1H, CH=CHCH2), 5.27 (ddd, J=15.0, 7.3, 7.3 Hz, 1H, CH=CHCH2), 5.19 (dd, J=6.5, 3.6 Hz, 1H, CO2CH), 4.43 (dd, J=8.6, 2.7 Hz, 1H, (CH3)2CCH(OTBS)), 3.87–3.83 (m, 1H, CHOH(CHCH3)), 3.33–3.25 (bs, 1H, CHOH (CHCH3)), 3.19 (qd, J=6.9, 5.4 Hz, 1H, CH3CH(C=O)), 2.71 (s, 3H, CH3Ar), 2.72–2.67 (m, 1H), 2.65 (dd, J=15.4, 8.6 Hz, 1H, CH2COO), 2.59 (dd, J=15.4, 2.7 Hz, 1H, CH2COO), 2.45–2.37 (m, 1H), 2.20–2.12 (m, 1H), 2.08 (s, 3H, CH3C=CH), 2.00–1.93 (m, 1H), 1.65–1.44 (m, 4H), 1.22 (d, 3H, J=6.9 Hz, CH3CH(C=O)), 1.2–1.12 (m, 1H), 1.15 (s, 3H, C(CH3)2), 1.09 (s, 3H, C(CH3)2), 1.03 (d, 3H, J=6.9 Hz, CH3CHCH2), 0.86 (s, 9H, SiC(CH3)3(CH3)2), 0.08 (s, 3H, SiC(CH3)3(CH3)2), 0.00 (s, 3H, SiC(CH3)3 (CH3)2); 13C NMR (150.9 MHz, CDCl3) d 217.9, 169.9, 164.7, 152.1, 136.3, 134.5, 124.9, 119.4, 115.4, 77.4, 75.1, 74.1, 54.1, 43.9, 41.0, 38.5, 35.3, 33.0, 30.9, 27.0, 26.2, 23.8, 21.7, 19.1, 18.5, 17.0, 16.1, 14.8, −3.8, −4.2; HRMS (FAB), calcd for C32H53CsNO5SSi (M+Cs+) 724.2468, found 724.2479.

Synthesis of cis-Dihydroxy Lactone 49 as Illustrated in FIG. 8

Desilylation of Compound 3.

Silyl ether 3 (30 mg, 0.05 mmol) was treated with a freshly prepared solution of 20% (v/v) trifluoroacetic acid-Methylene chloride (0.3 mL, 0.17 M) at 0° C. The reaction mixture was stirred at 0° C. for 3 h (completion of the reaction by TLC), and the solvents were evaporated under reduced pressure. The crude reaction mixture was purified by preparative thin layer chromatography (0.5 mm silica gel plate, 50% EtOAc in hexanes) to obtain cis-dihydroxy lactone 49 (22 mg, 90%). Rf=0.30 (silica gel, 50% EtOAc in hexanes); [a]22D −80.2 (c 1.36, CHCl3); IR (thin film) nmax 3453, 2929, 1733, 1686, 1506, 1464, 1250, 978 cm−1; 1H NMR (400 MHz, CDCl3) d 6.95 (s, 1H, ArH), 6.59 (s, 1H, ArCH=C(CH3)), 5.44 (ddd, J=10.5, 10.5, 4.5 Hz, 1H, CH=CHCH2), 5.36 (ddd, J=10.5, 10.5, 5.0 Hz, 1H, CH=CHCH2), 5.28 (d, J=9.4 Hz, 1H, CO2CH), 4.23 (d, J=11.1 Hz, 1H, (CH3)2CCH(OH)), 3.72 (m, 1H, CHOH (CHCH3)), 3.43–3.37 (m, 1H, OH), 3.14 (q, J=6.7 Hz, 1H, CH3CH(C=O)), 3.05 (bs, 1 H, OH), 2.72–2.63 (m, 1H), 2.69 (s, 3H, CH3Ar), 2.48 (dd, J=14.8, 11.3 Hz, 1H, CH2COO), 2.33 (dd, J=14.8, 2.0 Hz, 1H, CH2COO), 2.30–2.13 (m, 2H) 2.07 (s, 3H, ArCH=CCH3), 2.07–1.98 (m, 1H), 1.80–1.60 (m, 2H), 1.32 (s, 3H, C(CH3)2), 1.36–1.13 (m, 3H), 1.17 (d, J=6.8 Hz, 3H, CH3CH(C=O)), 1.06 (s, 3H, C(CH3)2), 0.99 (d, J=7.0 Hz, 3H, CH3CHCH2); 13C NMR (150.9 MHz, CDCl3) d 220.6, 170.4, 165.0 151.9, 138.7, 133.4, 125.0, 119.4, 115.8, 78.4, 74.1, 72.3, 53.3, 41.7, 39.2, 38.5, 32.4, 31.7, 27.6, 27.4, 22.7, 19.0, 18.6, 15.9, 15.5, 13.5; HRMS (FAB), calcd for C26H39CsNO5S (M+Cs+) 610.1603, found 610.1580.

Synthesis of trans-Dihydroxy Lactone 50 as Illustrated in FIG. 8

Desilylation of Compound 48.

Silyl ether 48 (32 mg, 0.05 mmol) was treated with a freshly prepared solution of 20% (v/v) trifluoroacetic acid (TFA)-Methylene chloride (0.3 mL, 0.17 M), according to the procedure described for cis-dihydroxy lactone 49, to yield, after preparative thin layer chromatography (0.5 mm silica gel plate, 50% EtOAc in hexanes), trans-dihydroxy ester 50 (24 mg, 92%). Rf=0.15 (silica gel, 50% EtOAc in hexanes); [α]22D −62.7 (c 1.65, CHCl3); IR (film) nmax 3428, 2932, 1730, 1692, 1468, 1253, 976 cm−1; 1H NMR (500 MHz, CDCl3) d 6.97 (s, 1H, ArH), 6.56 (s, 1H, ArCH=CCH3), 5.49 (ddd, J=15.0, 4.7, 4.7 Hz, 1H, CH=CHCH2), 5.38 (dd, J=5.7, 5.7 Hz, 1H, CO2CH), 5.37 (ddd, J=15.0, 6.5, 6.5 Hz, 1H, CH=CHCH2), 4.18 (d, J=10.5 Hz, 1H, (CH3)2CCH(OH)), 3.73 (m, 1H, CHOH (CHCH3)), 3.27–3.20 (m, 2H, CH3CH(C=O) and OH), 2.82 (bs, 1H, OH), 2.70 (s, 3H, CH3Ar), 2.55 (dd, J=15.5, 10.5 Hz, 1H, CH2COO), 2.48–2.43 (m, 3H), 2.18–2.12 (m, 1H), 2.07 (s, 3H, ArCH=CCH3), 1.98–1.91 (m, 1H), 1.63–1.55 (m, 2H), 1.46 (dddd, J=12.5, 12.5, 4.0, 4.0 Hz, 1H), 1.27 (s, 3H, C(CH3)2), 1.19 (m, 2H), 1.17 (d, J=6.5 Hz, 3H, CH3CH(C=O)), 1.06 (s, 3H, C(CH3)2), 0.97 (d, J=6.5 Hz, 3H, CH3CHCH2); 13C NMR (125.7 MHz, CDCl3) d 219.8, 170.4, 164.9, 151.9, 137.1, 134.2, 125.6, 119.6, 115.9, 77.5, 75.7, 72.2, 52.5, 43.5, 38.8, 37.6, 36.1, 32.3, 31.2, 26.9, 21.3, 21.1, 19.1, 17.0, 15.7, 14.3; HRMS (FAB), calcd for C26H40NO5S (M+H+) 478.2627, found 478.2612.

Synthesis of Epothilones A (1) and 51–57 as Illustrated in FIG. 8

Epoxidation of cis-Dihydroxy Lactone 49.

Procedure A:

A solution of cis-dihydroxy lactone 49 (24 mg, 0.05 mmol) in CHCl3 (4.0 mL) was reacted with meta-chloroperbenzoic acid (mCPBA, 57–86%, 13.0 mg, 0.04–0.06 mmol, 0.8–1.2 equiv), at −20 to 0° C., according to the procedure described for the epoxidation of 37, resulting in the isolation of epothilone A (1) (8.6 mg, 35%), its isomeric a-epoxide 51 (2.8 mg, 13%), and compounds 52 (or 53) (1.6 mg, 9%), 53 (or 52) (1.5 mg, 7%), 54 (or 55) (1.0 mg, 5%), and 55 (or 54) (1.0 mg, 5%) (stereochemistry unassigned for 52 and 53 and for 54 and 55), after two consecutive preparative thin layer chromatographic purifications (250 mm silica gel plate, 5% MeOH in Methylene chloride and 70% EtOAc in hexanes). Procedure B: To a solution of cis-dihydroxy lactone 49 (15 mg, 0.03 mmol) in Methylene chloride (1.0 mL) at 0° C. was added dropwise a solution of dimethyldioxirane in acetone (ca 0.1 M, 0.3 mL, ca 1.0 equiv) until no starting lactone was detectable by TLC. The solution was then concentrated in vacuo and the crude product was subjected to two consecutive preparative thin layer chromatographic purifications (250 mm silica gel plate, 5% MeOH in Methylene chloride and 70% EtOAc in hexanes), to obtain pure epothilone A (1) (7.4 mg, 50%), its isomeric α-epoxide 51 (2.3 mg, 15%), and epothilones 52 (or 53) (0.8 mg, 5%) and 53 (or 52) (0.8 mg, 5%) (stereochemistry unassigned for 52 and 53. Procedure C: As described in procedure B for the epoxidation of trans-hydroxy lactone 37, cis-dihydroxy lactone 49 (10.0 mg, 0.02 mmol) in MeCN (200 mL) was treated with a 0.0004 M aqueous solution of disodium salt of ethylenediaminetetraacetic acid (Na2EDTA, 120 mL), excess 1,1,1-trifluoroacetone (100 mL), Oxone® (61 mg, 0.10 mmol, 5.0 equiv) and NaHCO3 (14 mg, 0.16 mmol, 8.0 equiv), to yield, after purification by preparative thin layer chromatography (250 mm silica gel plate, ether), a mixture of diastereomeric epoxides, epothilones A (1) (6.4 mg, 62%) and a-isomeric epoxide 51 (1.3 mg, 13%). Procedure D: A solution of cis-dihydroxy lactone 49 (18 mg, 0.037 mmol) in CHCl3 (1.0 mL) was treated with meta-chloroperbenzoic acid (mCPBA, 57–86%, 15 mg, 0.049–0.074 mmol, 1.3–2.0 equiv), according to the procedure described for the epoxidation of 37, furnishing compounds 1 (2.7 mg, 15%), 51 (1.8 mg, 10%), 52 (or 53) (1.8 mg, 10%), 53 (or 52) (1.4 mg, 8%), 54 (or 55) (1.4 mg, 8%), 55 (or 54) (1.26 mg, 7%), 56 (0.9 mg, 5%), and 57 (0.9 mg, 5%) (stereochemistry unassigned for 52–57), after two consecutive preparative thin layer chromatographic purifications (250 mm silica gel plate, 5% MeOH in Methylene chloride and 70% EtOAc in hexanes). Epothilone A (1): Rf=0.23 (silica gel, 33% MeOH-Methylene chloride); HPLC (Watman EOC, C-18, 4 m, 108×4.6 mm column, solvent gradient: 0≈20 min, 30 E 80% MeOH in H2O) Rt=14.8 min; [a]D=−45.0 (c 0.02, MeOH); IR (film) nmax 3476, 2974, 1738, 1692 cm−1; 1H-NMR (600 MHz, C6D6) d=6.71 (s, 1H, ArH), 6.45 (s, 1H, ArCH=CCH3), 5.45 (dd, 1H, J=8.2, 2.3 Hz, CO2CH), 4.15 (dd, 1 H, J=10.8, 2.9 Hz, (CH3)2CCH(OH)), 3.81–3.78 (m, 1H, CHOH(CHCH3)), 3.65 (bs, 1H, OH), 3.03 (qd, J=6.9, 6.5 Hz, 1H, CH3CH(C=O)), 2.77 (ddd, J=7.9, 4.0, 4.0 Hz, 1H, CH2CH—O(epoxide)CH), 2.62–2.58 (m, 1H, CH2CH—O(epoxide)CH), 2.40 (dd, J=14.4, 10.8 Hz, 1H, CH2COO), 2.26 (bs, 1H, OH), 2.21 (s, 3 H, CH3Ar), 2.19 (dd, J=14.4, 2.9 Hz, 1H, CH2COO), 2.05 (s, 3 H, ArCH=CCH3), 1.86 (ddd, J=15.2, 2.5, 2.5 Hz, 1H, CH2CH—O(epoxide)CH), 1.81–1.74 (m, 1H, CH2CH—O(epoxide)CH), 1.68 (ddd, J=15.2, 7.6, 7.6 Hz, 1H, CH2CH—O(epoxide)CH), 1.53–1.49 (m, 1 H, CH2CH—O(epoxide)CH), 1.40–1.15 (m, 5H), 1.06 (d, 3H, J=7.0 Hz, CH3CH(C=O)), 1.03 (s, 3H, C(CH3)2), 0.97 (s, 3H, C(CH3)2), 0.95 (d, J=6.9 Hz, 3H, CH3CHCH2); 13C NMR (150.9 MHz, C6D6) d 219.0, 170.2, 164.7, 153.0, 137.5, 119.9, 116.6, 76.6, 75.2, 73.5, 57.2, 54.2, 52.9, 43.8, 39.1, 36.3, 31.7, 30.3, 27.3, 23.9, 21.1, 20.6, 18.7, 17.4, 15.7, 14.6; HRMS (FAB), calcd for C26H39CsNO6S (M+Cs+) 626.1552, found 626.1531. 51: Rf=0.35 (silica gel, 70% EtOAc in hexanes); [a]22D −23.0 (c 0.10, CHCl3); IR (film) nmax 3416, 2925, 2855, 1732, 1688, 1457 1258, 1150 cm−1; 1H NMR (500 MHz, C6D6) d 6.79 (s, 1H, ArH), 6.57 (s, 1H, ArCH=CCH3), 5.82 (d, J=8.0 Hz, 1H, CO2CH), 4.31 (dd, J=10.5, 2.5 Hz, 1H, (CH3)2CCH(OH)), 4.19–4.15 (m, 1H, CHOH(CHCH3)), 3.78 (bs, 1H), 3.31 (qd, J=7.0, 3.0 Hz, 1H, CH3CH(C=O)), 2.82 (ddd, J=10.0, 4.2, 4.2 Hz, 1H, CH2CH—O(epoxide)CH), 2.76 (bs, 1H), 2.55 (ddd, J=9.0, 9.0, 4.5 Hz, 1H, CH2CH—O(epoxide)CH), 2.40 (dd, J=13.0, 10.5, 1H, CH2COO), 2.33 (dd, J=13.0, 2.5 Hz, 1H, CH2COO), 2.31 (s, 3H, CH3Ar), 2.20 (s, 3H, ArCH=CCH3), 1.97–1.92 (m, 1H), 1.72 (ddd, J=15.0, 8.5, 8.5 Hz, 1H), 1.56 (ddd, J=15.0, 4.5, 2.0 Hz, 1H), 1.54–1.28 (m, 6H), 1.17 (d, J=7.0 Hz, 3H, CH3CH(C=O)), 1.13 (s, 3H, C(CH3)2), 1.06 (d, J=7.0 Hz, 3H, CH3CHCH2), 0.97 (s, 3H, C(CH3)2); 13C NMR (150.9 MHz, C6D6) d 221.7, 171.0, 165.5, 154.2, 138.3, 120.7, 117.6, 77.0, 74.8, 73.2, 57.7, 56.8, 52.4, 43.5, 39.5, 38.5, 33.0, 31.4, 28.3, 24.6, 21.6, 19.5, 19.2, 17.0, 15.7, 13.9; HRMS (FAB), calcd for C26H40NO6S (M+H+) 494.2576, found 494.2558. 52 (or 53): Rf=0.3 (silica gel, 30% EtOAc in hexanes); [a]22D −21.2 (c 0.17, CHCl3); IR (film) nmax 3477, 2926, 1740, 1686, 1465, 1259, 1060 cm−1; 1H NMR (500 MHz, C6D6) d 6.58 (s, 1H, ArH), 5.44 (ddd, J=10.5, 10.5, 5.0 Hz, 1H, CH=CHCH2), 5.35 (ddd, J=10.5, 10.5, 5.5 Hz, 1H, CH=CHCH2), 5.23 (dd, J=11.0, 2.0 Hz, 1 H, CO2CH), 5.05–4.98 (m, 1H), 4.44 (s, 1H, ArCH—O(epoxide)CCH3), 4.35 (dd, J=11.5, 2.0 Hz, 1H, (CH3)2CCH(OH)), 3.66–3.62 (m, 1H, CHOH(CHCH3)), 3.46 (s, 1H, OH), 2.93 (q, J=7.0 Hz, 1H, CH3CH(C=O)), 2.69 (ddd, J=14.5, 11.0, 11.0 Hz, 1 H), 2.58 (dd, J=14.0, 11.5 Hz, 1H, CH2COO), 2.17 (s, 3H, CH3Ar), 2.17–2.07 (m, 2H), 2.06 (dd, J=14.0, 2.0 Hz, 1H, CH2COO), 1.90–1.78 (m, 2H), 1.55–1.28 (m, 4H), 1.23 (s, 3H, C(CH3)2), 1.20 (s, 3H, C(CH3)2), 1.15 (d, J=7.0 Hz, 3H, CH3CH(C=O)), 1.05 (s, 3H, ArCH—O(epoxide)CCH3), 1.01 (d, J=7.0 Hz, 3H, CH3CHCH2); 13C NMR (125.7 MHz, C6D6) d 220.5, 169.7, 167.2, 151.0, 133.9, 124.2, 115.4, 74.5, 73.7, 71.9, 63.7, 59.2, 54.3, 40.9, 40.7, 38.2, 32.0, 29.1, 28.1, 26.9, 24.0, 18.3, 16.0, 15.6, 13.0 (two peaks overlapping); HRMS (FAB), calcd for C26H40N06S (M+H+) 494.2576, found 494.2561. 53 (or 52): Rf=0.25 (silica gel, 30% EtOAc in hexanes); [a]22D +3.2 (c 0.25, CHCl3); IR (film) nmax 3333, 2928, 2855, 1737, 1686, 1463, 1381, 1248 cm−1; 1H NMR (500 MHz, C6D6) d 6.62

(s, 1H, ArH), 5.67 (d, J=6.5 Hz, 1H, (CH3)2CCH(OH)), 5.47 (dd, J=11.5, 2.5 Hz, 1H, CO2CH), 5.45–5.37 (m, 1H, CH=CHCH2), 5.37–5.28 (m, 1H, CH=CHCH2), 4.44 (ddd, J=12.0, 6.5, 2.5 Hz, 1H, (CH3)2CCH(OH)), 4.22 (s, 1H, ArCH—O(epoxide)CCH3), 3.64 (d, J=4.5 Hz, 1H, CHOH(CHCH3)), 3.47 (s, 1H, CHOH(CHCH3)), 2.96 (q, J=7.0 Hz, 1 H, CH3CH(C=O)), 2.60 (dd, J=14.5, 12.0 Hz, 1H, CH2COO), 2.55 (ddd, J=15.5, 11.0, 11.0 Hz, 1H), 2.20–2.02 (m, 2H), 2.11 (s, 3H, CH3Ar), 1.99 (dd, J=14.5, 2.5 Hz, 1H, CH2COO), 1.90–1.78 (m, 2H), 1.58–1.49 (m, 1H), 1.31 (s, 3H, C(CH3)2), 1.28–0.85 (m, 3H), 1.25 (s, 3H, ArCH—O(epoxide)CCH3), 1.25 (s, 3H, C(CH3)2), 1.21 (d, J=7.0 Hz, 3H, CH3CH(C=O)), 1.03 (d, J=7.5 Hz, 3H, CH3CHCH2); 13C NMR (125.7 MHz, C6D6) d 219.8, 169.2, 167.1, 151.0, 133.2, 124.7, 114.8, 74.8, 73.6, 70.8, 64.7, 57.5, 54.1, 40.2, 39.6, 38.2, 31.8, 27.5, 27.2, 26.8, 24.1, 16.3, 15.9, 15.2, 15.0, 7.1; HRMS (FAB), calcd for C26H40NO6S (M+H+) 494.2576, found 494.2594. 54 (or 55): Rf=0.20 (silica gel, 70% EtOAc in hexanes); [a]22D −12.1 (c 0.14, CHCl3); IR (film) nmax 3410, 2925, 2854, 1735, 1686, 1642, 1464 cm−1; 1H NMR (600 MHz, C6D6) d 6.52 (s, 1H, ArH), 5.72 (d, J=6.1 Hz, 1H, OH), 5.42 (dd, J=11.8, 2.0 Hz, 1H, CO2CH), 4.32–4.28 (m, 1H, (CH3) 2CCH(OH)), 4.05 (s, 1H, ArCH(—O)(epoxide)CCH3), 3.64 (bs, 1 H, CHOH(CHCH3)), 2.92–2.86 (m, 1H), 2.78–2.75 (m, 1H), 2.66–2.63 (m, 1H), 2.58 (dd, J=14.0, 11.8 Hz, 1H, CH2COO), 2.11 (d, J=15.4 Hz, 1H), 2.03 (s, 3H, CH3Ar), 1.99 (dd, J=14.0, 2.8 Hz, 1H, CH2COO), 1.74–1.62 (m, 2H), 1.61–1.52 (m, 2H), 1.50–1.05 (m, 5H), 1.20 (s, 3H, C(CH3) 2), 1.19 (s, 3H, C(CH3)2), 1.18 (s, 3H, ArCH—O(epoxide) CCH3), 1.10 (d, J=7.2 Hz, 3H, CH3CH(C=O)), 0.84 (d, J=7.2 Hz, 3H, CH3CHCH2); 13C NMR (125.7 MHz, C6D6) d 218.9, 170.3, 129.2, 115.9, 103.8, 74.7, 71.5, 65.6, 58.7, 57.9, 55.4, 55.2, 44.1, 40.7, 37.7, 32.2, 31.7, 29.1, 28.3, 24.5, 23.5, 18.9, 17.9, 17.5, 17.1, 7.2; HRMS (FAB), calcd for C26H40NO7S (M+H+) 510.2526, found 510.2511. 55 (or 54): Rf=0.15 (silica gel, 70% EtOAc in hexanes); [a]22D −10.0 (c 0.15, CHCl3); IR (film) nmax 3459, 2926, 2861, 1738, 1689, 1456 cm−1; 1H NMR (500 MHz, C6D6) d 6.56 (d, J 1.0 Hz, 1H, ArH), 5.55 (d, J=4.0 Hz, 1H, OH), 5.22 (dd, J=11.5, 2.0 Hz, 1H, CO2CH), 4.35 (s, 1H, ArCH—O (epoxide)CCH3), 4.34–4.27 (m, 1 H, (CH3)2CCH(OH)), 3.71–3.68 (m, 1H, CHOH(CHCH3)), 3.04–2.98 (m, 1H), 2.95 (qd, J=7.0, 3.5 Hz, CH3CH(C=O)), 2.88–2.83 (m, 1H), 2.68–2.64 (m, 1H), 2.61 (dd, J=14.0, 11.5 Hz, 1H, CH2COO), 2.21–2.16 (m, 1H), 2.14 (s, 3H, CH3Ar), 2.09 (dd, J=14.0, 2.0 Hz, 1H, CH2COO), 1.81–1.65 (m, 3H), 1.49–1.31 (m, 6H), 1.25 (s, 3H, C(CH3)2), 1.20 (s, 3H, C(CH3)2), 1.12 (d, J=6.5 Hz, 3 H, CH3CH(C=O)), 0.96 (s, 3H, ArCH—O(epoxide)CCH3), 0.88 (d, J=6.5 Hz, 3H, CH3CHCH2); 13C NMR (125.7 MHz, C6D6) d 219.7, 169.5, 150.9, 124.2, 115.0, 74.9, 73.6, 71.2, 63.2, 58.9, 56.7, 53.7, 40.0, 35.1, 31.2, 29.7, 30.7, 28.6, 28.0, 24.1, 22.7, 17.2, 16.3, 16.0, 12.3, 11.9; HRMS (FAB), calcd for C26H39CsNO7S (M+Cs+) 642.1502, found 642.1521. 56: Rf=0.10 (silica gel, 5% MeOH in Methylene chloride); [a]22D −110.0 (c 0.20, CHCl3); IR (film) nmax 3222, 2928, 2855, 1737, 1683, 1462 cm−1; 1H NMR (500 MHz, CDCl3) d 7.16 (s, 1H, ArH), 5.84 (s, 1H, ArCH=CCH3), 5.43 (ddd, J=10.0, 10.0, 5.0 Hz, 1H, CH=CHCH2), 5.42–5.35 (m, 1H, CH=CHCH2), 5.40 (d, J=10.0 Hz, 1H, CO2CH), 4.90 (d, 1H, J=12.0 Hz, (CH3)2CCH(OH)), 3.76 (bs, 1H), 3.75 (d, J=5.0 Hz, 1 H, CHOH(CHCH3)), 3.15 (q, J=7.0 Hz, 1H, CH3CH(C=O)), 2.70 (dd, J=12.5, 12.5 Hz, 1H, CH2COO), 2.50 (ddd, J=15.0, 10.0, 10.0 Hz, 1H, CH=CHCH2), 2.21–2.12 (m, 2H), 2.07 (dd, J=13.0, 2.5 Hz, 1H, CH2COO), 1.97 (s, 3H, CH3Ar), 1.97–1.90 (m, 3H), 1.63 (s, 3H, ArCH=CCH3), 1.62–1.54 (m, 2H), 1.46 (s, 3H, C(CH3)2), 1.34 (s, 3H, C(CH3)2), 1.26–1.16 (m, 3H), 1.20 (d, J=7.0 Hz, 3H, CH3CH(C=O)), 1.06 (d, J=6.5 Hz, 3H, CH3CHCH2); 13C NMR (125.7 MHz, C6D6) d 221.0, 169.5, 144.0, 143.2, 142.7, 133.2, 125.0, 111.0, 109.0, 75.8, 73.8, 71.5, 55.0, 40.1, 38.5, 32.6, 31.6, 29.5, 27.6, 26.9, 23.9, 17.2, 15.3, 14.9, 13.2, 12.8; HRMS (FAB), calcd for C26H39CsNO6S 626.1552 (M+Cs+) 626.1552, found 626.1584. 57: Rf=0.05 (silica gel, 5% MeOH in Methylene chloride); [a]22D −58.0 (c 0.10, CHCl3); IR (film) nmax 3340, 2921, 2851, 1736, 1686, 1459, 1248 cm−1; 1H NMR (500 MHz, CDCl3) d 7.13 (s, 1H, ArH), 6.84 (s, 1H, ArCH=CCH3), 5.34 (d, J=11.0 Hz, 1H, CO2CH), 4.55 (dd, 1H, J=10.0, 1.0 Hz, (CH3)2CCH(OH)), 3.74 (dd, J=5.5, 2.0 Hz, 1H, CHOH(CHCH3)), 3.25 (qd, J=6.5, 1.5 Hz, 1H, CH3CH(C=O)), 3.10–2.94 (m, 1H), 2.70–2.64 (m, 2H), 2.50 (dd, J=12.5, 12.5 Hz, 1H), 2.25 (d, J=14.0 Hz, 1H, CH2COO), 2.15 (dd, J=14.0, 2.5 Hz, 1H), 2.10 (s, 3H, CH3Ar), 1.93–1.15 (m, 7H), 1.46 (s, 3H, ArCH=CCH3), 1.25 (s, 3H, C(CH3)2), 1.20 (d, J=7.0 Hz, 3H, CH3CH (C=O)), 1.04 (s, 3H, C(CH3)2), 1.01 (d, J=7.0 Hz, 3H, CH3CHCH2); HRMS (FAB), calcd for C26H39CsNO7S (M+Cs+) 642.1502, found 642.1522.

Synthesis of Compounds 54, 55, and 57 as Illustrated in FIG. 8

Oxidation of Epothilone A (1) with mCPBA.

A solution of epothilone A (1) (3.0 mg, 0.006 mmol) in CHCl3 (120 mL, 0.05 M) was reacted with meta-chloroperbenzoic acid (mCPBA, 57–86%, 1.1 mg, 0.0023–0.0032 mmol, 0.8–1.1 equiv; Aldrich), at −20 to 0° C., according to the procedure described for the epoxidation of 37, resulting in the formation of bis(epoxides) 54 (or 55) (1.1 mg, 35%) and 55 (or 54) (1.0 mg, 32%) along with sulfoxide 57 (0.2 mg, 6%).

Synthesis of Epothilones 58–60 as Illustrated in FIG. 9

Epoxidation of trans-Dihydroxy Lactone 50.

Procedure A: A solution of trans-dihydroxy lactone 50 (20 mg, 0.042 mmol) in CHCl3 (4.0 mL) was treated with meta-chloroperbenzoic acid (mCPBA, 57–86%, 11.0 mg, 0.036–0.054 mmol, 0.9–1.3 equiv) at −20 to 0° C., according to the procedure described for the epoxidation of compound 37, to give a epothilones 58 (or 59) (1.0 mg, 5%), 59 (or 58) (1.0 mg, 5%), and 60 (12 mg, 60%) (stereochemistry unassigned for all three), after preparative thin layer chromatography (250 mm silica gel plate, 70% EtOAc in hexanes). Procedure B: According to procedure B for the epoxidation of cis-dihydroxy lactone 49, a solution of trans-dihydroxy lactone 50 (10.0 mg, 0.02 mmol) in Methylene chloride (1.0 mL) was reacted with a solution of dimethyldioxirane (ca 0.1 M, 0.2 mL, ca 1.0 equiv) in acetone at 0° C., and after preparative thin layer chromatography (250 mm silica gel plate, 70% EtOAc in hexanes), epothilones 58 (or 59) (1.0 mg, 10%), 59 (or 58) (1.0 mg, 10%), and 60 (4.0 mg, 40%) were obtained. Procedure C. As described in procedure B for the epoxidation of trans-hydroxy lactone 37, trans-dihydroxy lactone 50 (5.1 mg, 0.01 mol) in MeCN (100 mL) was treated with a 0.0004 M aqueous solution of disodium salt of ethylenediaminetetraacetic acid (Na2EDTA, 60 mL), excess 1,1,1-trifluoroacetone (100 mL), Oxone® (32 mg, 0.05 mmol, 5.0 equiv) and NaHCO3 (7.0 mg, 0.08 mmol, 8.0 equiv), to yield, after purification by preparative thin layer chromatography (250 mm silica gel plate, ether), epothilones 58 (or 59) (2.3 mg, 45%) and 59 (or 58) (1.8 mg, 35%). 58 (or 59): Rf=0.15 (silica gel, ether); [a]22D −23.3 (c 0.40, CHCl3); IR (film) nmax 3454, 2926, 2856, 1731, 1690, 1464, 1376, 1259, 1151, 980 cm−1; 1H NMR (500 MHz, C6D6) d 6.73 (s, 1H, ArH), 6.53 (s, 1H, ArCH═C(CH3)), 5.54 (dd, J=8.0, 2.0 Hz, 1H, CO2CH), 4.18 (d, J=10.0 Hz, 1H, (CH3)2CCH(OH)), 3.87 (dd, J=4.5, 2.0 Hz, 1H, CHOH(CHCH3)), 3.43 (bs, 1H), 3.13 (dq, J=7.0, 7.0 Hz, 1H, CH3CH(C═O)), 2.74–2.72 (m, 1H), 2.63–2.60 (m, 1H), 2.45 (dd, J=15.0, 10.5 Hz, 1H, CH2COO), 2.33 (dd, J=15.0, 3.0 Hz, 1H, CH2COO), 2.32–2.24 (m, 1H), 2.28 (s, 3H, CH3Ar), 2.12 (s, 3H, ArCH═CCH3), 2.00 (ddd, J=15.0, 3.0, 2.5 Hz, 1H), 1.75–1.65 (m, 3H), 1.60–0.98 (m, 4H), 1.18 (d, J=7.0 Hz, 3H, CH3CH(C═O)), 1.10 (5, 3H, C(CH3)2), 1.05 (s, 3H, C(CH3)2), 0.97 (d, J=7.0 Hz., 3H, CH3CHCH2); 13C NMR (125.7 MHz, C6D6) d 217.2, 170.3, 164.6, 153.2, 137.0, 120.4, 116.9, 76.7, 75.6, 72.8, 58.0, 56.0, 53.0, 44.7, 38.8, 36.5, 35.8, 32.0, 30.3, 30.1, 22.6, 21.0, 20.9, 17.1, 15.3, 14.9; HRMS (FAB), calcd for C26H39CsNO6S (M+Cs+) 626.1552, found 626.1538. 59 (or 58): Rf=0.2 (silica gel, ether); [a]22D −25.3 (c 0.30, CHCl3); IR (film) nmax 3419, 2923, 1732, 1691, 1464, 1259 cm−1; 1H NMR (500 MHz, C6D6) d 6.82 (s, 1 H, ArH), 6.56 (s, 1H, ArCH═C(CH3)), 5.53 (dd, J=7.5, 3.5 Hz, 1 H, CO2CH), 4.47 (d, J=8.5 Hz, 1H, (CH3)2CCH(OH)), 3.94 (bs, 1 H, CHOH(CHCH3)), 3.65–3.58 (m, 1H), 3.35 (dq, J=6.5, 6.5 Hz, 1 H, CH3CH(C═O)), 2.73–2.65 (m, 1H), 2.65–2.61 (m, 1H), 2.52–2.46 (m, 1H), 2.41 (dd, J=14.0, 9.5 Hz, 1H, CH2COO), 2.33 (dd, J=14.0, 4.0 Hz, 1H, CH2COO), 2.31 (s, 3H, CH3Ar), 2.03 (s, 3H, ArCH═CCH3), 1.91–1.81 (m, 2H), 1.78–1.53 (m, 4H), 1.41–1.32 (m, 2H), 1.22 (d, J=7.0 Hz, 3H, CH3CH(C═O)), 1.21 (s, 3H, C(CH3)2), 1.08 (d, J=7.0 Hz, 3H, CH3CHCH2), 1.05 (s, 3H, C(CH3)2); 13C NMR (150.9 MHz, C6D6) d 215.7, 167.6, 161.7, 149.8, 133.8, 116.6, 113.4, 73.8, 73.2, 70.1, 55.2, 52.4, 49.9, 41.7, 36.4, 34.0, 32.3, 28.0, 27.8, 27.4, 19.9, 17.8, 15.8, 14.6, 13.0, 12.3; HRMS (FAB), calcd for C26H39CsNO6S (M+Cs+) 626.1552, found 626.1531. 60: Rf=0.6 (silica gel, 70% EtOAc in hexanes); [a]22D −28.3 (c 0.30, CHCl3); IR (film) nmax 3472, 2928, 1735, 1691, 1466 cm−1; 1H NMR (500 MHz, C6D6) d 6.67 (s, 1 H, ArH), 5.48–5.41 (m, 1H, CH═CHCH2), 5.36–5.23 (m, 2H, CH═CHCH2 and CO2CH), 4.36–4.30 (m, 1H, (CH3)2CCH(OH)), 3.79–3.73 (m, 1H), 3.63–3.58 (m, 1H), 3.17–3.10 (m, 1H, CH3CH(C═O)), 2.81 (bs, 1H), 2.53 (dd, J=15.0, 10.5 Hz, 1H, CH2COO), 2.40–2.29 (m, 2H), 2.26–2.19 (m, 2H), 2.25 (s, 3H, CH3Ar), 2.20–1.95 (m, 1H), 1.80–1.72 (m, 1H), 1.62–1.53 (m, 1H), 1.46–1.33 (m, 2H), 1.20 (d, J=6.5 Hz, 3H, CH3CH(C═O)), 1.13 (s, 3H, C(CH3)2), 1.10 (s, 3H, C(CH3)2), 1.08 (d, J=7.0 Hz, 3H, CH3CHCH2), 1.06 (s, 3H, ArCH—O(epoxide)CCH3); 13C NMR (125.7 MHz, C6D6) d 219.7, 169.6, 166.9, 151.3, 135.4, 124.6, 115.8, 78.3, 72.8, 72.6, 64.2, 59.1, 53.3, 43.4, 40.2, 38.8, 34.3, 33.1, 31.4, 27.5, 21.8, 19.8, 18.9, 16.5, 15.3, 14.0; HRMS (FAB), calcd for C26H40NO6S (M+H+) 494.2576, found 494.2587.

Synthesis of Dihydroxy Ester 61 as Illustrated in FIG. 10

Desilylation of Compound 47.

Silyl ether 47 (48 mg, 0.079 mmol) was treated with a freshly prepared solution of 20% (v/v) trifluoroacetic acid (TFA)-Methylene chloride (1.6 mL, 0.05 M), according to the procedure described for the desilylation of compound 3, to yield, after flash column chromatography (silica gel, 5%æ50% EtOAc in hexanes), dihydroxy ester 61 (35 mg, 90%). Rf=0.68 (silica gel, 50% EtOAc in hexanes); [a]22D −18.0 (c 0.40, CHCl3); IR (film) nmax 3420, 2931, 1732, 1383, 1177, 979 cm−1; 1H NMR (500 MHz, CDCl3) d 6.97 (s, 1H, ArH), 6.54 (s, 1 H, ArCH═CCH3), 5.82–5.70 (m, 2H, 2×CH2CH═CH2), 5.37 (dd, J=7.0, 7.0 Hz, 1H, CO2CH), 5.10 (d, J=17.0 Hz, 1H, CH2CH═CH2), 5.07 (d, J=10.0 Hz, 1H, CH2CH═CH2), 5.00 (d, J=17.0 Hz, 1H, CH2CH═CH2), 4.95 (d, J=10.0 Hz, 1H, CH2CH═CH2), 4.24 (dd, J=10.0, 2.0 Hz, 1H, (CH3)2CCHOH), 3.50 (dd, J=8.0, 3.0 Hz, 1H, CHOH(CHCH3)), 3.26 (qd, J=6.5, 2.5 Hz, 1H, CH3CH(C═O)), 2.70 (s, 3H, CH3Ar), 2.52–2.46 (m, 2H), 2.41 (dd, J=16.5, 10.5 Hz, 1H, CH2COO), 2.08 (s, 3H, ArCH═CCH3), 2.08–1.99 (m, 2H, CH2CH═CH2), 1.60–1.06 (m, 6H), 1.17 (s, 6H, C(CH3)2), 1.07 (d, J=7.0 Hz, 3H, CH3CH(C═O)), 0.97 (d, J=6.5 Hz, 3H, CH3CHCH2); 13C NMR (125.7 MHz, CDCl3) d 221.5, 171.9, 164.7, 152.1, 138.7, 136.7, 133.1, 120.9, 117.9, 116.4, 114.5, 78.7, 74.8, 72.3, 52.1, 41.4, 37.5, 36.8, 35.0, 33.8, 32.3, 25.7, 21.5, 19.1, 19.0, 15.2, 14.7, 11.5; HRMS (FAB), calcd for C28H43CsNO5S (M+Cs+) 638.1916, found 638.1902.

Synthesis of Dihydroxy Lactones 62 and 63 as Illustrated in FIG. 10

Olefin Metathesis of Dihydroxy Ester 61.

A solution of compound 61 (48 mg, 0.095 mmol) in Methylene chloride (20 mL, 0.005 M) was treated with bis(tricyclohexylphosphine)benzylidine ruthenium dichloride (RuCl2(═CHPh)(PCy3)2, 16 mg, 0.019 mmol, 0.2 equiv; FIG. 10), according to the procedure described for the cyclization of 25, producing dihydroxy lactones 62 (9.1 mg, 20%) and 63 (32 mg, 69%), after preparative thin layer chromatography (0.5 mm silica gel plate, 33% EtOAc in hexanes). 62: Rf=0.30 (silica gel, 6% MeOH in Methylene chloride); [a]22D −93.1 (c 0.10, CHCl3); IR (thin film) nmax 3450, 2929, 1735, 1685, 1464, 1380, 1250, 1182, 1045, 978, 732 cm−1; 1H NMR (600 MHz, CDCl3) d 6.96 (s, 1H, ArH), 6.51 (s, 1H, ArCH═CCH3), 5.58 (dd, J=9.5, 2.0 Hz, 1H, CO2CH), 5.56 (ddd, J=9.8, 9.8, 6.5 Hz, 1H, CH═CHCH2), 5.37 (ddd, J=9.8, 9.8, 4.5 Hz, 1H, CH═CHCH2), 4.25 (d, J=10.0 Hz, 1H, (CH3)2CCH(OH)), 3.55 (d, J=9.6 Hz, 1H, CHOH(CHCH3)), 3.39 (bs, 1H, OH), 3.31 (q, J=6.9 Hz, 1H, CH3CH(C═O)), 2.99 (bs, 1H, OH), 2.71 (s, 3H, CH3Ar), 2.69–2.61 (m, 1H, CH═CHCH2), 2.59 (dd, J=16.3, 1.5 Hz, 1H, CH2COO), 2.41 (dd, J=16.3, 10.0 Hz, 1H, CH2COO), 2.45–2.35 (m, 1H, CH═CHCH2), 2.20–2.10 (m, 1H, CH═CHCH2), 2.08 (s, 3H, ArCH═CCH3), 1.98–1.90 (m, 1H, CH═CHCH2), 1.59–1.50 (m, 1H), 1.49–1.30 (m, 4H), 1.17 (s, 3H, C(CH3)2), 1.11 (d, J=6.9 Hz, 3H, CH3CH(C═O)), 1.03 (s, 3H, C(CH3)2), 1.01 (d, J=7.0 Hz, 3 H, CH3CHCH2); 13C NMR (150.9 MHz, CDCl3) d 222.2, 171.1, 165.2, 153.5, 139.5, 133.2, 125.1, 120.0, 116.7, 78.4, 74.1, 72.9, 52.5, 40.7, 39.5, 37.9, 34.5, 32.7, 31.3, 27.6, 24.7, 22.2, 18.9, 17.5, 15.5, 15.3; HRMS (FAB), calcd for C26H39NO5S (M+H+) 478.2627, found 478.2610. 63: Rf=0.69 (silica gel, 50% EtOAc in hexanes); [a]22D −68.3 (c 1.30, CHCl3); IR (film) nmax 3498, 2932, 1730, 1694, 1383, 1260, 1154, 1076, 1043, 974, 756 cm−1; 1H NMR (500 MHz, CDCl3) d 6.95 (s, 1H, ArH), 6.49 (s, 1H, ArCH═CCH3), 5.50 (t, J=6.5 Hz, 1H, CO2CH), 5.48 (ddd, J=15.0, 7.0, 6.0 Hz, 1H, CH═CHCH2), 5.36 (ddd, J=15.0, 6.5, 6.5 Hz, 1H, CH═CHCH2), 4.24 (dd, J=10.5, 1.0 Hz, 1H, (CH3)2CCHOH), 3.55 (d, J=9.5 Hz, 1H, CHOH(CHCH3)), 3.37 (q, J=7.0 Hz, 1H, CH3CH(C═O)), 2.69 (s, 3H, CH3Ar), 2.58 (dd, J=15.5, 1.5 Hz, 1H, CH2COO), 2.50–2.48 (m, 2H, CH═CHCH2), 2.39 (dd, J=15. 5, 10.5 Hz, 1H, CH2COO), 2. 16–2.0:8 (m, 1H, CH═CHCH2), 2.08 (s, 3H, ArCH═CCH3), 1.97–1.91 (m, 1H, CH═CHCH2), 1.62–1.56 (m, 1H), 1.41–1.11 (m, 4H), 1.20 (s, 3H, C(CH3)2), 1.12 (d, J=7.0 Hz, 3H, CH3CH(C═O)), 1.03 (s, 3H, C(CH3)2), 0.98 (d, J=6.5 Hz, 3H, CH3CHCH2); 13C NMR (125.7 MHz, CDCl3) d 221.8, 171.1, 164.8, 152.1, 136.7, 134.2, 124.9, 119.8, 116.4, 78.1, 74.6, 73.2, 52.8, 40.9, 38.3, 36.1, 34.6, 32.9, 32.9, 24.9, 22.9, 19.2, 17.7, 16.0, 15.5, 11.5; HRMS (FAB), calcd for C26H39CsNO5S (M+Cs+) 610.1603, found 610.1587.

Synthesis of Epothilones 64–65 as Illustrated in FIG. 10

Epoxidation of cis-Dihydroxy Lactone 62.

Procedure A: A solution of cis-dihydroxy lactone 62 (10.0 mg, 0.021 mmol) in CHCl3 (210 mL) was treated with meta-chloroperbenzoic acid (mCPBA, 57–86%, 5.0 mg, 0.0165–0.0252 mmol, 0.8–1.2 equiv) at −20æ0° C., according to the procedure described for the epoxidation of compound 37, to produce, after preparative thin layer chromatography (250 mm silica gel plate, 70% EtOAc in hexanes), epothilones 64 (or 65) (2.6 mg, 25%) and 65 (or 64) (2.4 mg, 23%) (stereochemistry unassigned for all three). Procedure B. As described in procedure B for the epoxidation of trans-hydroxy lactone 37, cis-dihydroxy lactone 62 (10.0 mg, 0.021 mmol) in MeCN (400 mL) was treated with a 0.0004 M aqueous solution of disodium salt of ethylenediaminetetraacetic acid (Na2EDTA, 200 mL), excess 1,1,1-trifluoroacetone (150 mL), Oxone® (65 mg, 0.105 mmol, 5.0 equiv) and NaHCO3 (14 mg, 0.168 mmol, 8.0 equiv), to yield, after purification by preparative thin layer chromatography (250 mm silica gel plate, ether), epothilones 64 (or 65) (6.0 mg, 58%) and 65 (or 64) (3.0 mg, 29%). 64 (or 65): Rf=0.23 (silica gel, 6% MeOH in Methylene chloride); [a]22D −20.0 (c 0.20, CHCl3); IR (thin film) nmax 3448, 2919, 1725, 1684, 1455, 1378, 1284, 1149, 1061, 1020, 973, 750 cm−1; 1H NMR (500 MHz, CDCl3) d 6.99 (s, 1H, ArH), 6.68 (s, 1H, ArCH=CCH3), 5.64–5.61 (m, 1H, CO2CH), 4.43 (d, J=2.1 Hz, 1H, (CH3)2CCH(OH)), 4.29 (ddd, J=7.6, 2.5, 2.5 Hz, 1H, (CH3)2CCH(OH)), 3.82 (d, J=8.2 Hz, 1H, CHOH(CHCH3)), 3.35 (bs, 1H, CHOH (CHCH3), 3.22 (q, J=7.0 Hz, 1H, CH3CH(C=O)), 3.14 (ddd, J=10.3, 4.1, 3.2 Hz, 1H, CH2CH—O(epoxide)CH), 2.90 (ddd, J=10.3, 4.3, 2.3 Hz, 1H, CH2CH—O(epoxide) CH), 2.71 (s, 3H, CH3Ar), 2.54 (dd, J=13.7, 7.6 Hz, 1H, CH2COO), 2.51 (dd, J=13.7, 2.5 Hz, 1H, CH2COO), 2.21–2.19 (m, 1H), 2.18 (s, 3H, ArCH=CCH3), 1.94 (ddd, J=15.3, 10.3, 3.7 Hz, 1H), 1.77–1.69 (m, 2H), 1.60–1.00 (m, 5H), 1.15 (s, 3H, C(CH3)2), 1.14 (d, J=6.9 Hz, 3H, CH3CH (C=O)), 1.06 (s, 3H, C(CH3)2), 1.02 (d, J=7.0 Hz, 3H, CH3CHCH2); 13C NMR (150.9 MHz, CHCl3) d 221.8, 172.1, 165.1, 152.6, 134.7, 119.8, 116.8, 76.0, 74.4, 72.8, 56.4, 53.8, 53.0, 40.2, 39.1, 34.1, 32.7, 29.4, 27.8, 22.7, 20.9, 19.0, 16.1, 15.9, 15.0, 11.8; HRMS (FAB), calcd for C26H40NO6S (M+H+) 494.2576, found 494.2587. 65 (or 64): Rf=0.22 (silica gel, 6% MeOH in Methylene chloride); [a]22D −42.5 (c 0.20, CHCl3); IR (thin film) nmax 3384, 2890, 1738, 1685, 1451, 1375, 1155, 1061, 1064 cm−1; 1H NMR (600 MHz, CDCl3) d 6.99 (s, 1H, ArH), 6.58 (s, 1H, ArCH=CCH3), 5.88 (d, J=10.4 Hz, 1H, CO2CH), 4.74 (d, J=9.8 Hz, 1H, (CH3)2CCH(OH)), 3.70–3.65 (m, 2H, CHOH (CHCH3) and OH), 3.45–3.40 (m, 2H, CH3CH(C=O) and OH), 3.19 (ddd, J=9.7, 3.8, 2.1 Hz, 1H, CH2CH—O (epoxide)CH), 3.08 (ddd, J=9.0, 4.5, 4.5 Hz, 1H, CH2CH—O(epoxide)CH), 2.71 (s, 3H, CH3Ar), 2.51 (d, J=13.8, 1H, CH2COO), 2.45 (dd, J=13.7, 9.8 Hz, 1H, CH2COO), 2.18–2.02 (m, 2H), 2.11 (s, 3H, ArCH=CCH3), 1.80–0.96 (m, 7H), 1.16 (s, 3H, C(CH3)2), 1.13 (d, J=7.0 Hz, 3H, CH3CH(C=O)), 1.05 (s, 3H, C(CH3)2), 1.03 (d, J=6.8 Hz, 3H, CH3CHCH2); 13C NMR (150.9 MHz, CHCl3) d 222.2, 171.1, 164.8, 151.8, 136.6, 120.3, 116.7, 76.9, 73.7, 72.9, 56.6, 54.8, 52.8, 40.2, 38.8, 34.1, 33.0, 31.7, 25.0, 23.3, 20.4, 19.4, 16.7, 15.8, 15.6, 11.9; HRMS (FAB), calcd for C26H39CsNO6S (M+Cs+) 626.1552, found 626.1573.

Synthesis of Epothilones 67–69 as Illustrated in FIG. 10

Epoxidation of trans-Dihydroxy Lactone 63.

Procedure A. A solution of trans-dihydroxy lactone 63 (17.0 mg, 0.033 mmol) in CHCl3 (2.0 mL) was treated with meta-chloroperbenzoic acid (mCPBA, 57–86%, 8.9 mg, 0.029–0.044 mmol, 0.9–1.3 equiv) at −20 to 0° C., according to the procedure described for the synthesis of epoxide 37, to produce, after preparative thin layer chromatography (250 mm silica gel plate, 70% EtOAc in hexanes), epothilones 67 (or 68) (4.2 mg, 24%), 68 (or 67) (3.3 mg, 19%) and 69 (5.4 mg, 31%) (stereochemistry unassigned for all three). Procedure B. As described in procedure C for the epoxidation of cis-lactone 49, trans-dihydroxy lactone 63 (6.0 mg, 0.0126 mmol) in MeCN (240 mL) was treated with a 0.0004 M aqueous solution of disodium salt of ethylenediaminetetraacetic acid (Na2EDTA, 90 mL), 1,1,1-trifluoroacetone (90 mL), Oxone® (40 mg, 0.063 mmol, 5.0 equiv) and NaHCO3 (8.4 mg, 0.100 mmol, 8.0 equiv), to yield, after purification by preparative thin layer chromatography (250 mm silica gel plate, ether), epothilones 67 (or 68) (2.7 mg, 44%) and 68 (or 67) (1.3 mg, 21%). 67 (or 68): Rf=0.47 (silica gel, 50% EtOAc in hexanes); [a]22D −27.3 (c 0.30, CHCl3); IR (film) nmax 3459, 2932, 1732, 1152, 978 cm−1; 1H NMR (600 MHz, CDCl3) d 6.97 (s, 1H, ArH), 6.57 (s, 1H, ArCH=CCH3), 5.72 (d, J=10.4 Hz, 1H, CO2CH), 4.41 (d, J=9.8 Hz, 1H, (CH3)2CCH(OH)), 4.27 (bs, 1H, OH), 3.76 (d, J=6.1 Hz, 1H, CHOH(CHCH3)), 3.27 (q, J=7.0 Hz, 1H, CH3CH(C=O), 2.94–2.88 (m, 1H), 2.75–2.71 (m, 1H), 2.70 (s, 3H, CH3Ar), 2.49 (d, J=12.9 Hz, 1H, CH2COO), 2.41 (dd, J=12.9, 9.8 Hz, 1H, CH2COO), 2.18–2.11 (m, 1H), 2.09 (s, 3H, ArCH=CCH3), 1.95–1.87 (m, 1H), 1.80–1.00 (m, 5H), 1.16 (s, 3H, C(CH3)2), 1.14 (d, 3H, J=6.9 Hz, CH3CH(C=O)), 1.04 (s, 3H, C(CH3)2), 0.92 (d, 3H, J=6.9 Hz, CH3CHCH2); 13C NMR (125.7 MHz, CDCl3) d 220.4, 171.9, 164.7, 151.9, 136.5, 120.2, 116.6, 76.9, 74.5, 73.6, 58.1, 56.0, 53.1, 42.2, 39.2, 36.2, 34.7, 33.1, 29.4, 22.4, 21.9, 19.3, 16.2, 15.2, 13.7, 12.4; HRMS (FAB), calcd for C26H40NO6S (M+H+) 494.2576, found 494.2561. 68 (or 67): Rf=0.46 (silica gel, 50% EtOAc in hexanes); [a]22D −55.2 (c 0.25, CHCl3); IR (film) nmax 3442, 2931, 1731, 1687, 1153, 982, 732 cm−1; 1H NMR (600 MHz, CDCl3) d 6.97 (s, 1H, ArH), 6.57 (s, 1H, ArCH=CCH3), 5.56 (dd, J=8.6, 3.1 Hz, 1H, CO2CH), 4.23 (d, J=9.3 Hz, 1H, (CH3) 2CCH(OH)), 3.73 (dd, J=7.4, 1.1 Hz, 1H, CHOH(CHCH3)), 3.57 (bs, 1H), 3.34 (dq, J=7.0, 1.3 Hz, CH3CH(C=O)), 3.12 (bs, 1H), 2.76 (dt, J=5.5, 2.2 Hz, 2H), 2.72–2.68 (m, 1H), 2.71 (s, 3H, CH3Ar), 2.61 (dd, J=15.4, 1.6 Hz, 1H, CH2COO), 2.41 (dd, J=15.4, 10.6 Hz, 1H, CH2COO), 2.15 (ddd, J=15.0, 5.1, 3.5 Hz, 1H), 2.07 (s, 3H, ArCH=CCH3), 1.91–1.86 (m, 1H), 1.76–1.17 (m, 5H), 1.29 (s, 3H, C(CH3) 2), 1.30 (s, 3H, C(CH3)2), 1.12 (d, J=7.0 Hz, 3H, CH3CH (C=O)), 0.95 (d, J=6.7 Hz, 3H, CH3CHCH2); 13C NMR (150.9 MHz, CDCl3) d 221.2, 171.2, 164.9, 151.8, 135.9, 120.1, 116.6, 77.1, 74.0, 72.8, 58.7, 55.8, 52.7, 42.3, 38.4, 35.3, 35.1, 33.0, 32.0, 22.6, 22.0, 19.3, 18.5, 15.5, 15.2, 12.2; HRMS (FAB), calcd for C26H40NO6S (M+H+) 494.2562, found 494.2576. 69: Rf=0.67 (silica gel, 50% EtOAc in hexanes); [a]22D −30.5 (c=0.40, CHCl3); IR (film) nmax 3500, 2932, 1732, 1693, 1184, 975 cm−1; 1H NMR (600 MHz, CDCl3) d 6.95 (s, 1H, ArH), 5.51 (ddd, J=14.3, 7.0, 7.0 Hz, 1H, CH=CHCH2), 5.37 (ddd, J=14.3, 7.1, 7.1 Hz, 1H, CH=CHCH2), 5.16 (dd, J=9.2, 3.4 Hz, 1H, CO2CH), 4.20 (d, J=10.7 Hz, 1H, (CH3)2CCH(OH)), 4.16 (s, 1H, OH), 3.48 (d, J=9.2 Hz, 1H, CHOH(CHCH3)), 3.37 (q, J=6.9 Hz, 1H, CH3CH(C=O), 2.70 (s, 3H, CH3Ar), 2.62 (d, J=15.7 Hz, 1H, CH2COO), 2.60–2.54 (m, 1H), 2.50–2.43 (m, 1H), 2.38 (dd, J=15.7, 10.7 Hz, 1H, CH2COO), 2.23–2.15 (m, 1H, CH=CHCH2), 2.00–1.92 (m, 1H, CH=CHCH2), 1.80–1.00 (m, 5H), 1.24 (s, 3H, C(CH3)2), 1.20 (s, 3H, C(CH3)2), 1.10 (d, 3H, J=6.9 Hz, CH3CH(C=O), 1.02 (s, 3H, ArCH—O(epoxide)CCH3), 0.98 (d, 3H, J=6.7 Hz, CH3CHCH2); 13C NMR (125.7 MHz, CDCl3) d 221.4, 170.9, 166.3, 150.6, 135.4, 124.3, 115.4, 74.8, 74.1, 73.1, 63.0, 58.8, 52.7, 41.1, 38.1, 34.8, 33.5, 33.2, 32.9, 25.2, 22.9, 19.3, 18.1, 16.1, 13.4, 11.7; HRMS (FAB), calcd for C26H40NO6S (M+H+) 494.2576, found 494.2587.

Synthesis of Alcohol 85 as Illustrated in FIG. 12
Allylboration of Keto Aldehyde 84.

Aldehyde 84 (16.0 g, 0.125 mol; Inuka, T.; Yoshizawa, R. J. Org. Chem. 1967, 32, 404–407) was dissolved in ether (400 mL) and cooled to –100° C. To this solution was added (+)-diisopinocampheylallylborane (800 mL, 0.15 M in pentane, 0.125 mol, 1.0 equiv) by cannulation during 45 min. [(+)-Diisopinocampheylallylborane in pentane is prepared by the adaptation of the standard methods reported by Brown]. Allylmagnesium bromide (66.0 mL, 1 M solution in ether, 0.066 mol) was added dropwise to a well stirred solution of (–)-B-methoxydiisopinocampheyl borane (20.9 g, 0.066 mol) in ether (400 mL) at 0° C. After the completion of the addition, the reaction mixture was stirred at room temperature for 1 h and the solvent was removed under reduced pressure. The residue was extracted with pentane (3×400 mL) under argon and stirring was discontinued to allow precipitation of the magnesium salts. The clear pentane solution was cannulated into another flask using a double ended needle through a Kramer filter and used without further purification. After the addition was complete, the mixture was stirred at the same temperature for 30 min. Methanol (20 mL) was added at –100° C., and the reaction mixture was allowed to reach room temperature. To this solution was added saturated aqueous NaHCO3 solution (200 mL), followed by H2O2 (80 mL of 50% solution in H2O) and the reaction mixture was allowed to stir at room temperature for 12 h. The reaction mixture was extracted with EtOAc (3×200 mL), and the organic extracts were combined, washed with saturated aqueous NH4Cl solution (100 mL) and dried (Na2SO4). Evaporation of the solvents followed by flash column chromatography (silica gel, 3% acetone in Methylene chloride) resulted in pure alcohol 85 (14.6 g, 74%). 85: colorless oil; Rf=0.20 (silica gel, 3% acetone in Methylene chloride); [a]22D –4.0 (c 1.5, CHCl3); IR (thin film) nmax 3492, 2976, 2939, 1699, 1641, 1469, 1379, 1087, 1020, 990, 973, 914 cm–1; 1H NMR (600 MHz, CDCl3) d 5.85–5.80 (m, 1H, CH=CH2), 5.11–5.07 (m, 2H, CH=CH2), 3.73 (dd, J 10.5, 2.0 Hz, 1H, CHOH), 2.54–2.40 (m, 3H), 2.25–2.18 (m, 1H), 2.03–1.96 (m, 1H), 1.14 (s, 3H, C(CH3)2), 1.10 (s, 3H, C(CH3)2), 0.99 (t, J=7.0 Hz, 3 H, CH3CH2); 13C NMR (150.9 MHz, CDCl3) d 217.2, 135.6, 117.7, 75.5, 51.2, 36.4, 31.3, 21.8, 19.5, 7.8; FAB HRMS (NBA/NaI) m/e 193.1200, M+Na+ calcd for C1OH18O2 193.1204.

Synthesis of Ketone 86 as Illustrated in FIG. 12.
Silylation of Alcohol 85.

Alcohol 85 (11.0 g, 0.0647 mol) was dissolved in Methylene chloride (200 mL), the solution was cooled at –78° C., and 2,6-lutidine (10.5 mL, 0.0906 mol, 1.4 equiv) was added. After stirring for 5 min at that temperature, tert-butyldimethylsilyl triflate (19.3 mL, 0.0841 mol, 1.3 equiv) was added dropwise and the reaction mixture was allowed to stir at –78° C. for 45 min, after which time no starting material was detected by TLC. Saturated aqueous NH4Cl solution (30 mL) was added, and the reaction mixture was allowed to warm up to room temperature. The organic phase was separated, and the aqueous layer was extracted with ether (3×20 mL). The combined organic extracts were dried (MgSO4), filtered through celite and the solvents were removed under reduced pressure. Purification by flash column chromatography (silica gel, 2 to 10% ether in hexanes) gave pure 86 (18.0 g, 98%): Rf=0.75 (silica gel, 20% ether in hexanes); [a]22D +2.6 (c 0.8, CHCl3); IR (thin film) nmax 2935, 1705, 1467, 1362, 1254, 1089, 911, 836, 775 cm–1; 1H NMR (600 MHz, CDCl3) d 5.78–5.71 (m, 1H, CH=CH2), 5.01–4.94 (m, 2H, CH=CH2), 3.97 (dd, J=6.2, 5.2 Hz, 1H, CHOSi), 2.54 (dq, J=14.3, 7.2 Hz, 1H, CH2CH3), 2.44 (dq, J=14.2, 7.1 Hz, 1H, CH2CH3), 2.21–2.16 (m, 1H, CH2CH=CH2), 2.14–2.08 (m, 1H, CH2CH=CH2), 1.10 (s, 3H, C(CH3)2), 1.07 (s, 3H, C(CH3)2), 0.98 (t, J=7.1 Hz, 3H, CH3CH2), 0.87 (s, 9H, SiC(CH3)3), 0.05 (s, 3H, Si(CH3)2), 0.01 (s, 3H, Si(CH3)2); 13C NMR (150.9 MHz, CDCl3) d 215.9, 136.2, 116.5, 76.7, 52.9, 39.0, 31.9, 26.0, 22.4, 20.1, 18.2, 7.7, –3.6, –4.4.

Synthesis of Keto Aldehyde 87 as Illustrated in
FIG. 12
Ozonolysis of Ketone 86.

Alkene 86 (2.84 g, 10 mmol) was dissolved in Methylene chloride (25 mL) and the solution was cooled to –78° C. Oxygen was bubbled through for 2 min after which time ozone was passed through until the reaction mixture adopted a blue color (ca 30 min). The solution was then purged with oxygen for 2 min at –78° C. (disappearance of blue color) and Ph3P (3.16 g, 12.0 mmol, 1.2 equiv) was added. The cooling bath was removed and the reaction mixture was allowed to reach room temperature and stirred for an additional 1 h. The solvent was removed, under reduced pressure and the mixture was purified by flash column chromatography (silica gel, 25% ether in hexanes) to provide pure keto aldehyde 87 (2.57 g, 90%): Rf=0.45 (silica gel, 20% ether in hexanes); [α]22D –1.9 (c 4.0, CHCl3); IR (thin film) nmax 2935, 2858, 1707, 1467, 1388, 1255, 1093, 1004, 837, 777 cm–1; 1H NMR (500 MHz, CDCl3) d 9.78 (dd, J=2.1, 2.0 Hz, CHO), 4.55 (dd, J=6.0, 4.5 Hz, 1H, CHOSi), 2.59–2.44 (m, 4H, CH2CH3, CH2CH=O), 1.13 (s, 3H, C(CH3)2), 1.09 (s, 3H, C(CH3)2), 1.00 (t, J=7.0 Hz, 3H, CH3CH2), 0.85 (s, 9H, (CH3)3C), 0.06 (s, 3H, Si(CH3)2), 0.03 (s, 3H, Si(CH3)2); 13C NMR (125.7 MHz, CDCl3) d 215.3, 200.9, 71.3, 52.3, 48.5, 31.9, 25.8, 21.3, 20.4, 18.0, 7.5, –4.4, –4.9; FAB HRMS (NBA/NaI) m/e 309.1854, M+Na+ calcd for C15H30O3Si 309.1862.

Synthesis of Keto Acid 76 as Illustrated in FIG. 12
Oxidation of Keto Aldehyde 87.

Aldehyde 87 (2.86 g, 10 mmol), tBuOH (50 mL), isobutylene (20 mL, 2 M solution in THF, 40 mmol, 4.0 equiv), H2O (10 mL), NaClO2 (2.71 g, 30.0 mmol, 3.0 equiv) and NaH2PO4 (1.80 g, 15.0 mmol, 1.5 equiv) were combined and stirred at room temperature for 4 h. The reaction mixture was concentrated under reduced pressure and the residue was subjected to flash column chromatography (silica gel, 50% ether in hexanes) to produce pure keto acid 76 (2.81 g, 93%). Rf=0.12 (silica gel, 20% ether in hexanes); [α]22D +16.1 (c 1.0, CHCl3); IR (thin film) nmax 2934, 2858, 1710, 1467, 1254, 1093, 834 cm–1; 1H NMR (600 MHz, CDCl3) d 4.46 (dd, J=7.0, 3.6 Hz, 1H, CHOSi), 2.64–2.34 (m, 3H, CH2CH3, CH2COOH), 2.32 (q, J=7.0 Hz, 1H, CH2CH3), 1.13 (s, 3H, C(CH3)2), 1.11 (s, 3H, C(CH3)2), 0.99 (t, J=7.0 Hz, 3H, CH3CH2), 0.83 (s, 9H, (CH3)3C), 0.04 (s, 3H, Si(CH3)2), 0.03 (s, 3H, Si(CH3)2); 13C NMR (125.7 MHz, CDCl3) d 215.1, 178.2, 73.4, 52.4, 39.2, 31.6, 25.8, 20.8, 20.5, 18.0, 7.6, −4.5, −5.0; FAB HRMS (NBA) m/e 303.1996, M+H+ calcd for C15H30O3Si 303.1992.

Synthesis of Aldehyde 89 as Illustrated in FIG. 12
Reduction of Ester 88.

Ethyl ester 88 (52.5 g, 0.306 mol; Aldrich) was dissolved in Methylene chloride (1 L) and cooled to −78° C. DIBAL (490.0 mL, 1 M solution in Methylene chloride, 0.4896 mol, 1.6 equiv) was added dropwise via a cannula while the temperature of the reaction mixture was maintained at −78° C. After the addition was complete, the reaction mixture was stirred at the same temperature until its completion was verified by TLC (ca 1 h). Methanol (100 mL) was added at −78° C. and was followed by addition of EtOAc (1 L) and saturated aqueous NH4Cl solution (300 mL). The quenched reaction mixture was allowed to warm up to room temperature and stirred for 12 h. The organic layer was separated, and the aqueous phase was extracted with EtOAc (3×200 mL). The combined organic phase was dried over MgSO4, filtered, and concentrated under reduced pressure. Flash column chromatography (silica gel, 10 to 90% ether in hexanes) furnished the desired aldehyde 89 (33.6 g, 90%): Rf=0.68 (silica gel, ether); IR (thin film) nmax 3095, 2828, 1695, 1485, 1437, 1378, 1334, 1178, 1129, 1011 cm−1; 1H NMR (500 MHz, CDCl3) d 9.96 (s, 1H, CHO), 8.0 (s, 1H, SCH=C), 2.77 (s, 3H, N=C(S)CH3); 13C NMR (125.7 MHz, CDCl3) d 184.2, 167.5, 154.8, 128.0, 19.1; FAB HRMS (NBA/NaI) m/e 149.9992, M+Na+ calcd for C5H5NOS 149.9990.

Synthesis of Aldehyde 90 as Illustrated in FIG. 12

Aromatic aldehyde 89 (31.1 g, 0.245 mol) was dissolved in benzene (500 mL) and 2-(triphenylphosphoranilidene)-propionaldehyde (90.0 g, 0.282 mol, 1.15 equiv) was added. The reaction mixture was heated at reflux until the reaction was complete as judged by TLC (ca 2 h). Evaporation of the solvent under reduced pressure, followed by flash column chromatography (10 to 90% ether in hexanes) produced the desired aldehyde 90 (40.08 g, 98%): Rf=0.78 (silica gel, ether); IR (thin film) nmax 3089, 1675, 1624, 1190, 1141, 1029, 947.6, 881 cm−1; 1H NMR (500 MHz, CDCl3) d 9.57 (s, 1H, CHO), 7.46 (s, 1H), 7.26 (s, 1H), 2.77 (s, 3H, N=C(S)CH3), 2.20 (s, 3H, CH=C(CHO)CH3); 13C NMR (125.7 MHz, CDCl3) d 195.3, 165.7, 151.9, 140.9, 138.2, 122.6, 19.2, 10.9; FAB HRMS (NBA) m/e 168.0481, M+H+ calcd for C8H9NOS 168.0483.

Synthesis of Alcohol 91 as Illustrated in FIG. 12
Allylboration of Aldehyde 90.

Aldehyde 90(20.0 g, 0.120 mol) was dissolved in anhydrous ether(400 mL) and the solution was cooled to −100° C. (+)-Diisopinocampheylallyl borane (1.5 equiv in pentane, prepared from 60.0 g of (−)-Ipc2BOMe and 1.0 equiv of allyl magnesium bromide according to the method described for the synthesis of alcohol 85), was added dropwise under vigorous stirring, and the reaction mixture was allowed to stir for 1 h at the same temperature. Methanol (40 mL) was added at −100° C., and the reaction mixture was allowed to warm up to room temperature. Amino ethanol (72.43 mL, 1.2 mol, 10.0 equiv) was added and stirring was continued for 15 h. The work-up procedure was completed by the addition of saturated aqueous NH4Cl solution (200 mL), extraction with EtOAc (4×100 mL) and drying of the combined organic layers with MgSO4. Filtration, followed by evaporation of the solvents under reduced pressure and flash column chromatography (silica gel, 35% ether in hexanes for several fractions until all the boron complexes were removed; then 70% ether in hexanes) provided alcohol 91 (24.09 g, 96%): Rf=0.37 (60% ether in hexanes); [a]22D −20.2 (c 1.0, CHCl3); IR (thin film) nmax 3357, 2923, 1642, 1505, 1437, 1322, 1186, 1018, 914, 878 cm−1; 1H NMR (600 MHz, CDCl3) d 6.81 (s, 1H, SCH=C), 6.46 (s, 1H, CH=CCH3), 5.87–5.79 (m, 1H, CH=CH2), 5.02 (d, J=17.1 Hz, 1H, CH=CH2), 4.97 (d, J=10.3 Hz, 1H, CH=CH2), 4.12 (dd, J=7.8, 5.0 Hz, 1H, CHOH), 3.8 (bs, 1H, OH), 2.59 (s, 3H, N=C(S)CH3), 2.31 (dd, J=7.0, 6.5 Hz, 2H, CH2=CHCH2), 1.91 (s, 3H, CH=CCH3); 13C NMR (150.9 MHz, CDCl3) d 164.5, 152.5, 141.8, 134.8, 118.7, 117.1, 115.1, 76.3, 39.8, 18.8, 14.1; FAB HRMS (NBA) m/e 210.0956, M+H+ calcd for C11H15NOS 210.0953.

Synthesis of Compound 92 as Illustrated in FIG. 12
Silylation of Alcohol 91.

Alcohol 91 (7.0 g, 0.033 mol) was dissolved in DMF (35 mL, 1.0 M), the solution was cooled to 0° C. and imidazole (3.5 g, 0.050 mol, 1.5 equiv) was added. After stirring for 5 min, tert-butyldimethylsilyl chloride (6.02 g, 0.040 mol, 1.2 equiv) was added portionwise and the reaction mixture was allowed to stir at 0° C. for 45 min, and then at 25° C. for 2.5 h, after which time no starting alcohol was detected by TLC. Methanol (2 mL) was added at 0° C. and the solvent was removed under reduced pressure. Ether (100 mL) was added, followed by saturated aqueous NH4Cl solution (20 mL), the organic phase was separated and the aqueous phase was extracted with ether (2×20 mL). The combined organic solution was dried (MgSO4), filtered over celite and the solvents were removed under reduced pressure. Flash column chromatography (silica gel, 10 to 20% ether in hexanes) provided pure 92 (10.8 g, 99%): Rf=0.70 (40% ether in hexanes); [a]22D +1.39 (c 3.0, CHCl3); IR (thin film) nmax 2931, 2060, 1496, 1460, 1249, 1173, 1073, 908, 837, 779 cm−1; 1H NMR (600 MHz, CDCl3) d 6.91 (s, 1H, SCH=C), 6.45 (s, 1H, CH=CCH3), 5.80–5.75 (m, 1H, CH=CH2), 5.03 (ddd, J=17.1, 3.5, 1.5 Hz, 1H, CH=CH2), 4.99 (ddd, J=10.2, 2.1, 0.9 Hz, 1H, CH=CH2), 4.14 (dd, J=6.6, 6.1 Hz, 1H, CHOH), 2.69 (s, 3H, N=C(S)CH3), 2.37–2.32 (m, 1H, CH2=CHCH2), 2.31–2.25 (m, 1H, CH2=CHCH2), 1.99 (s, 3H, CH=CCH3), 0.88 (s, 9H, SiC(CH3)3), 0.05 (s, 3H, Si(CH3)2), 0.00 (s, 3H, Si(CH3)2); 13C NMR (150.9 MHz, CDCl3) d 165.2, 153.9, 142.9, 136.2, 119.7, 117.4, 115.9, 79.3, 42.1, 26.7, 20.1, 19.0, 14.8, −3.8, −4.1; FAB HRMS (NBA) m/e 324.1804, M+H+ calcd for C17H29NOSSi 324.1817.

Synthesis of Aldehyde 82 as Illustrated in FIG. 12
Dihydroxylation of Olefin 92 and 1,2 Glycol Cleavage.

Olefin 92 (16.7 g, 51.6 mmol) was dissolved in THF/tBuOH (1 : 1, 500 mL) and H2O (50 mL). 4-Methylmorpholine N-oxide (NMO) (7.3 g, 61.9 mmol, 1.2 equiv) was added at 0° C., followed by OsO4 (5.2 mL, solution in tBuOH 1.0 mol%, 2.5% by weight). The mixture was vigorously stirred for 2.5 h at 0° C. and then for 12 h at 25° C. After completion of the reaction, Na2SO3 (5.0 g) was added at 0° C., followed by H2O (100 mL). Stirring was continued for another 30 min and then ether (1 L) was added, followed by saturated aqueous NaCl solution (2×100 mL). The organic phase was separated and the aqueous phase was extracted with ether (2×100 mL). The combined organic extracts were dried (MgSO4), filtered, and the solvents were removed under reduced pressure. Flash column chromatography (silica gel, ether to EtOAc) provided 17.54 g (95%) of the expected 1,2-diol as a 1:1 mixture of diastereoisomers: Rf=0.55 (silica gel, EtOAc); IR (thin film) nmax 3380, 2931, 2856, 1656, 1505, 1465, 1460, 1254, 1187, 1073, 908, 837, 777 cm−1; 1H NMR (500 MHz, CDCl3) d 6.90 and 6.88 (singlets, 1 H total, SCH═C), 6.52 and 6.47 (singlets, 1 H total, CH═CCH3), 4.44–4.39 (m, 1H), 3.95–3.84 (m, 1H), 3.81–3.72 and 3.63–3.34 (m, 4 H total), 2.66 and 2.65 (singlets, 3 H total, N═C(S)CH3), 1.96 and 1.95 (singlets, 3 H total), 1.82–1.75 and 1.69–1.56 (m, 2 H total), 0.87 and 0.86 (singlets, 9 H total, SiC(CH3)3), 0.08 and −0.01 (singlets, 3 H total, Si(CH3)2), 0.07 and 0.10 (singlets, 3 H total, Si(CH3)2); 13C NMR (125.7 MHz, CDCl3) d 164.6, 164.5, 152.8, 152.4, 141.6, 141.5, 119.4, 118.4, 115.3, 115.2, 78.0, 75.4, 70.4, 68.8, 66.8, 66.5, 38.9, 38.7, 25.7, 19.0, 18.9, 18.0, 17.9, 14.6, 13.5, −4.6, −4.8, −5.2, −5.4; FAB HRMS (NBA/NaI) m/e 380.1699, M+Na+ calcd for C17H31NO3SSi 380.1692.

The diol obtained from 92 as described above (5.2 g, 14.5 mmol) was dissolved in EtOAc (150 mL) and cooled to 0° C. Pb(OAc)4 (8.1 g, 95% purity, 18.3 mmol, 1.2 equiv) was then added portionwise over 10 min, and the mixture was vigorously stirred for 15 min at 0° C. After completion of the reaction, the mixture was filtered through silica gel and washed with 60% ether in hexanes. The solvents were then removed under reduced pressure providing pure aldehyde 82 (4.7 g, 98%): Rf=0.76 (silica gel, 60% ether in hexanes); [a]22D −20.3 (c 1.4, CHCl3); IR (thin film) nmax 2931, 2856, 1726, 1504, 1466, 1389, 1254, 1182, 1087, 999, 839, 784 cm−1; 1H NMR (500 MHz, CDCl3) d 9.69 (dd, J=2.7, 2.2 Hz, 1H, CHO), 6.86 (s, 1H, SCH═C), 6.48 (s, 1 H, CH═CCH3), 4.60 (dd, J=8.2, 3.9 Hz, 1H, CHOSi), 2.64 (ddd, J=15.5, 8.3, 2.9 Hz, 1H, CHOCH2), 2.59 (s, 3H, N═C(S)CH3), 2.41 (ddd, J=15.5, 4.0, 2.0 Hz, 1H, CHOCH2), 1.95 (s, 3H, CH═CCH3), 0.79 (s, 9H, SiC(CH3)3), 0.00 (s, 3H, Si(CH3)2), −0.06 (s, 3H, Si(CH3)2); 13C NMR (125.7 MHz, CDC, 3) d 201.0, 164.5, 152.4, 140.3, 119.0, 115.8, 73.7, 49.9, 25.6, 18.9, 17.9, 13.9, −4.8, −5.4; FAB HRMS (NBA) m/e 326.1615, M+H+ calcd for C16H27NO2SSi 326.1610.

Synthesis of Alcohol 93 as Illustrated in FIG. 12
Reduction of Aldehyde 82.

A solution of aldehyde 82 (440 mg, 1.35 mmol) in MeOH (13 mL) was treated with NaBH4 (74 mg, 2.0 mmol, 1.5 equiv) at 0° C. for 15 min. The solution was diluted with ether (100 mL) and then saturated aqueous NH4Cl solution (5 mL) was carefully added. The organic phase was washed with brine (10 mL), dried (MgSO4) and concentrated. Flash column chromatography (silica gel, 60% ether in hexanes) gave alcohol 93 (425 mg, 96%) as a colorless oil. 26: Rf=0.52 (silica gel, 60% ether in hexanes); [a]22D −29.4 (c 0.8, CHCl3); IR (thin film) nmax 3362, 2950, 2856, 1656, 1505, 1466, 1362, 1254, 1186, 1075, 839, 777 cm−1; 1H NMR (500 MHz, CDCl3) d 6.86 (s, 1 H., SCH═C), 6.40 (s, 1H, CH═CCH3), 4.30 (dd, J=7.6, 5.3 Hz, 1H, CHOSi), 3.69–3.59 (m, 2 H, CH2OH), 3.15 (s, 1H, OH), 2.61 (s, 3H, N═C(S)CH3), 1.92 (s, 3H, CH═CCH3), 1.82–1.76 (m, 1H, CH2CH2OH), 1.73–1.67 (m, 1H, CH2CH2OH), 0.82 (s, 9H, SiC(CH3)3), 0.02 (s, 3H, Si(CH3)2), −0.05 (s, 3H, Si(CH3)2); 13C NMR (150.9 MHz, CDCl3) d 164.3, 152.7, 141.6, 118.5, 115.1, 76.6, 59.6, 38.3, 25.8, 18.9, 18.0, 14.0, −4.8, −5.4; FAB HRMS (NBA/CsI) m/e 460.0727, M+Cs+ calcd for C16H29NO2SSi 460.0743.

Synthesis of Iodide 94 as Illustrated in FIG. 12
Iodination of Alcohol 93.

A solution of alcohol 93 (14.0 g, 42.7 mmol) in ether:MeCN (3:1, 250 mL) was cooled to 0° C. Imidazole (8.7 g, 128.1 mmol, 3.0 equiv), Ph3P (16.8 g, 64.1 mmol, 1.5 equiv), and iodine (16.3 g, 64.1 mmol, 1.5 equiv) were sequentially added and the mixture was stirred for 0.5 h at 0° C. A saturated aqueous solution of Na2S2O3 (50 mL) was added, followed by the addition of ether (600 mL). The organic phase was washed with brine (50 mL), dried (MgSO4), and the solvents were removed under vacuum. Flash column chromatography (silica gel, 15% ether in hexanes) gave pure iodide 94 (16.6 g, 89%) as a colorless oil: Rf=0.40 (silica gel, 10% ether in hexanes); [a]22D +11.0 (c 1.0, CHCl3); IR (thin film) nmax 2951, 2856, 1503, 1466, 1253, 1179, 1081, 936, 884, 836, 777 cm−1; 1H NMR (600 MHz, CDCl3) d 6.90 (s, 1H, SCH═C), 6.53 (s, 1H, CH═CCH3), 4.19 (dd, J=7.7, 4.5 Hz, 1H, CHOSi), 3.18 (t, J=7.3 Hz, 2H, CH2I), 2.67 (s, 3H, N═C(S)CH3), 2.10–2.05 (m, 1H, CH2CH2I), 2.01–1.95 (m, 1H, CH2CH2I), 1.99 (s, 3H, CH═CCH3), 0.87 (s, 9H, SiC(CH3)3), 0.09 (s, 3H, Si(CH3)2), 0.00 (s, 3H, Si(CH3)2); 13C NMR (150.9 MHz, CDCl3) d 164.4, 152.7, 140.9, 119.3, 115.4, 78.0, 40.2, 25.8, 19.2, 18.1, 13.9, 3.1, −4.6, −5.0; FAB HRMS (NBA) m/e 438.0768, M+H+ calcd for C16H28INOSSi 438.0784.

Synthesis of Phosphonium Salt 79 as Illustrated in FIG. 12

A mixture of iodide 94 (16.5g, 37.7 mmol) and Ph3P (10.9 g, 41.5 mmol, 1.1 equiv) was heated neat at 100° C. for 2 h. Purification by flash column chromatography (silica gel, Methylene chloride; then 7% MeOH in Methylene chloride) provided phosphonium salt 79 (25.9 g, 98%) as a white solid: Rf=0.50 (silica gel, 7% MeOH in Methylene chloride); [a]22D +3.7 (c 0.7, CHCl3); IR (thin film) nmax 2951, 2856, 1503, 1466, 1253, 1179, 1081, 936, 884, 836, 777 cm−1; 1H NMR (600 MHz, CDCl3) d 7.78–7.28 (m, 15H, aromatic), 6.97 (s, 1H, SCH═C), 6.57 (s, 1H, CH═CCH3), 4.48 (dd, J=6.3, 4.8 Hz, 1H, CHOSi), 3.72–3.65 (m, 1H, CH2P), 3.31–3.25 (m, 1H, CH2P), 2.61 (s, 3H, N═C(S)CH3), 1.91 (s, 3H, CH═CCH3), 1.95–1.86 (m, 1H, CH2CH2P), 1.82–1.74 (m, 1H, CH2CH2 P), 0.83 (s, 9 H, SiC(CH3)3), 0.07 (s, 3H, Si(CH3)2), −0.02 (s, 3H, Si(CH3)2); 13C NMR (150.9 MHz, CDCl3) d 164.4, 152.3, 139.4, 135.1, 133.3, 133.2, 130.5, 130.4, 128.1, 119.8, 117.9, 117.3, 116.5, 76.0, 28.9, 25.7, 19.1, 18.4, 17.9, 14.5, −4.8.

Synthesis of Hydrazone 95 as Illustrated in FIG. 13
Alkylation of Hydrazone 80.

Hydrazone 80 (20.0 g, 117.0 mmol, 1.0 equiv), dissolved in THF (80 mL), was added to a freshly prepared solution of LDA [19.75 mL of diisopropylamine (141.0 mmol, 1.2 equiv) was added to a solution of 88.1 mL of 1.6 M solution of n-BuLi in hexanes (141 mmol, 1.2 equiv) in 160 mL of THF at 0° C.] at 0° C. After stirring at this temperature for 8 h, the resulting yellow solution was cooled to −100° C., and a solution of 4-iodo-1-benzyloxybutane (36.0 g, 124.0 mmol, 1.2 equiv) in THF (40 mL) was added dropwise over a period of 30 min. The mixture was allowed to warm to room temperature over 8 h, and was then poured into saturated aqueous NH4Cl solution (40 mL) and extracted with ether (3×200 mL). The combined organic extracts were dried (MgSO4), filtered and evaporated. Purification by flash column chromatography on silica gel (20% ether in hexanes) provided hydrazone 95 as a yellow oil (35.8 g, 92%, de>98% by 1H NMR): Rf=0.45 (silica gel, 50% ether in hexanes); [a]22D −55.0 (c 1.2, CHCl3); IR (thin film) nmax 2929, 2862, 1603, 1455, 1362, 1198, 1108, 737, 698 cm−1; 1H NMR (500 MHz, CDCl3) d 7.33 (s, 5H, Ph), 6.48 (d, J=6.5 Hz, 1H, CH═NN), 4.46 (s, 2H, CH2Ph), 3.54 (dd, J=9.0, 3.8 Hz, 1H, CH2OCH3), 3.44 (t, J=6.5 Hz, 2H, CH2OBn), 3.40 (dd, J=9.0, 6.8 Hz, 1H, CH2OCH3), 3.33 (s, 3H, OCH3), 2.65 (m, 1H, CHCH2OCH3), 2.29 (m, 1H, CH(CH3)C=N), 1.94–1.76 (m, 4H), 1.61 (m, 2H), 1.45–1.36 (m, 6H), 1.01 (d, J=6.8 Hz, 3H, CHCH3); 13C NMR (125.7 MHz, CDCl3) d 144.6, 138.6, 128.2, 127.5, 127.3, 74.7, 72.7, 70.2, 63.4, 59.1, 50.4, 37.0, 35.2, 29.7, 26.4, 23.7, 22.0, 18.9; FAB HRMS (NBA) m/e 333.2552, M+H+ calcd for C20H32N2O2 333.2542.

Synthesis of Aldehyde 96 as Illustrated in FIG. 13
Cleavage of Hydrazone 95.

Procedure A: A solution of hydrazone 95 (13.0 g, 39.1 mmol) in Methylene chloride (50 mL) was treated with ozone at −78° C. until the solution turned blue-green. The solution was purged with oxygen for 2 min at −78° C., allowed to warm to room temperature, and then concentrated. The crude mixture so obtained was purified by flash column chromatography (silica gel, 10% ether in hexanes) to give aldehyde 96 (6.6 g, 77%) as a colorless oil. Procedure B: A solution of hydrazone 95 (30 g, 90.3 mmol) in MeI (100 mL) was heated at 60° C. After 5 h, the reaction was complete (TLC), and the mixture was concentrated. The resulting crude product was suspended in n-pentane (360 mL) and was treated with 3 N aqueous HCl (360 mL). The two-phase system was vigorously stirred for 1 h, and the aqueous phase was extracted with n-pentane (3×200 mL). The combined organic solution was dried (MgSO4), concentrated and purified by flash column chromatography (silica gel, 10% ether in hexanes) to give 96 (17.1 g, 86%): Rf=0.49 (silica gel, 50% ether in hexanes); [a]22D +11.6 (c 1.7, CHCl3); IR (thin film) nmax 2932, 2856, 1715, 1450, 1361, 1272, 1202, 1102, 920, 732, 697 cm−1; 1 H NMR (500 MHz, CDCl3) d 9.60 (d, J=2.0 Hz, 1H, CHO), 7.34 (s, 5H, Ph), 4.50 (s, 2H, CH2Ph), 3.47 (t, J=6.5 Hz, 2H, CH2OBn), 2.33 (m, 1H, CH(CH3)CO), 1.75–1.69 (m, 1H), 1.65–1.61 (m, 2H), 1.49–1.34 (m, 3H), 1.08 (d, J=7.0 Hz, 3H, CHCH3); 13C NMR (125.7 MHz, CDCl3) d 205.0, 138.4, 128.2, 127.5, 127.4, 72.8, 69.9, 46.1, 30.1, 29.6, 23.6, 13.2; FAB HRMS (NBA) m/e 221.1538, M+H+ calcd for C14H20O2 221.1542.

Synthesis of Alcohol 97 as Illustrated in FIG. 13
Reduction of Aldehyde 96.

A solution of aldehyde 96 (17.0 g, 77.0 mmol) in MeOH (200 mL) was treated with NaBH4 (8.6 g, 228 mmol, 3.0 equiv) at 0° C. for 15 min. The solution was then diluted with ether (400 mL) and saturated aqueous NH4Cl solution (50 mL) was carefully added. The organic phase was washed with brine (50 mL), dried (MgSO4), and concentrated. The crude product was purified by flash column chromatography (silica gel, 40% ether in hexanes) to give alcohol 97 (16.8 g, 98%) as a colorless oil: Rf=0.23 (silica gel, 50% ether in hexanes); [a]22D −5.1 (c 1.9, CHCl3); IR (thin film) nmax 3401, 2931, 2860, 1455, 1361, 1267, 1202, 1102, 1037, 937, 732, 697 cm−1; 1H NMR (500 MHz, CDCl3) d 7.35 (s, 5H, Ph), 4.51 (s, 2H, CH2Ph), 3.50 (dd, J=11.0, 6.0 Hz, 1H, CH2OH), 3.48 (t, J=6.5 Hz, 2H, CH2OBn), 3.42 (dd, J=11.0, 6.5 Hz, 1H, CH2OH), 1.65–1.59 (m, 2H), 1.47–1.34 (m, 4 H), 1.15–1.12 (m, 1H), 0.91 (d, J=6.7 Hz, 3H, CHCH3); 13C NMR (125.7 MHz, CDCl3) d 138.6, 128.2, 127.6, 127.3, 72.9, 70.3, 68.1, 35.7, 32.9, 30.1, 23.6, 14.1; FAB HRMS (NBA) m/e 223.1705, M+H+ calcd for C14H22O2 223.1698.

Synthesis of Silyl Ether 98 as Illustrated in FIG. 13
Silylation of Alcohol 97.

Alcohol 97 (17.0 g, 76.0 mmol) was dissolved in Methylene chloride (350 mL), the solution was cooled to 0° C. and Et3N (21.2 mL, 152.0 mmol, 2.0 equiv) and 4-DMAP (185 mg, 1.52 mmol, 0.05 equiv) were added. After stirring for 5 min, tert-butyldimethylsilyl chloride (17.3 g, 115 mmol, 1.5 equiv) was added portionwise, and the reaction mixture was allowed to stir at 0° C. for 2 h, and then at 25° C. for 10 h. Methanol (20 mL) was added at 0° C. and the solvents were removed under reduced pressure. Ether (200 mL) and saturated aqueous NH4Cl solution (30 mL) were sequentially added, and the organic phase was separated. The aqueous phase was extracted with ether (2×100 mL) and the combined organic layer was dried (MgSO4), filtered and concentrated under reduced pressure. Purification by flash column chromatography (silica gel, 5% ether in hexanes) provided pure silyl ether 98 (24.4 g, 95%): Rf=0.54 (silica gel, 10% ether in hexanes); [a]22D −2.3 (c 1.1, CHCl3); IR (thin film) nmax 2931, 2860, 1461, 1361, 1249, 1091, 839, 773, 738 cm−1; 1H NMR (500 MHz, CDCl3) d 7.35 (s, 5H, Ph), 4.51 (s, 2H, CH2Ph), 3.48 (t, J=6.5 Hz, 2H, CH2OBn), 3.43 (dd, J=10.5, 6.0 Hz, 1 H, CH2OSi), 3.36 (dd, J=10.5, 6.5 Hz, 1H, CH2OSi), 1.64–1.60 (m, 3H), 1.47–1.29 (m, 3H), 1.15–1.05 (m, 1H), 0.90 (s, 9H, SiC(CH3)3), 0.87 (d, J=6.8 Hz, 3H, CHCH3), 0.043 (s, 3H, Si(CH3)2), 0.041 (s, 3H, Si(CH3)2); 13C NMR (125.7 MHz, CDCl3) d 138.6, 128.2, 127.5, 127.3, 72.7, 70.3, 68.3, 35.6, 32.9, 30.0, 25.8, 23.5, 18.1, 16.6, −5.5; FAB HRMS (NBA) m/e 337.2553, M+H+ calcd for C20H36O2Si 337.2563.

Synthesis of Alcohol 99 as Illustrated in FIG. 13
Hydrogenolysis of Benzyl Ether 98

To a solution of benzyl ether 98 (21.0 g, 62.5 mmol) in THF (200 mL) was added 10% Pd(OH)2/C (1.0 g). The reaction was allowed to proceed under an atmosphere of H2 at a pressure of 50 psi and at 25° C. (Parr hydrogenetor apparatus). After 15 min, no starting benzyl ether was detected by TLC, and the mixture was filtered through celite. The clear solution was concentrated under reduced pressure and the resulting crude product was purified by flash column chromatography (silica gel, 40% ether in hexanes) to give alcohol 99 (14.7 g, 95%) as a colorless oil: Rf=0.32 (silica gel, 50% ether in hexanes); [a]22D −3.6 (c 3.6, CHCl3); IR (thin film) nmax 3342, 2931, 2860, 1467, 1384, 1249, 1085, 838, 773, 667 cm−1; 1H NMR (500 MHz, CDCl3) d 3.63 (t, J=7.0 Hz, 2H, CH2OH), 3.42 (dd, J=11.0, 6.0 Hz, 1H, CH2OSi), 3.35 (dd, J=11.0, 7.0 Hz, 1H, CH2OSi), 1.57–1.53 (m, 3H), 1.42–1.39 (m, 3H), 1.16–1.06 (m, 1H), 0.88 (s, 9H, SiC(CH3)3), 0.85 (d, J=6.5 Hz, 3 H, CHCH3), 0.03 (s, 3H, Si(CH3)2), 0.02 (s, 3H, Si(CH3)2); 13C NMR (125.7 MHz, CDCl3) d 68.2, 62.7, 35.6, 32.9, 32.8, 25.7, 23.0, 18.2, 16.5, −5.5; FAB HRMS (NBA) m/e 247.2097, M+H+ calcd for C13H30O2Si 247.2093.

Synthesis of Aldehyde 77 as Illustrated in FIG. 13
Oxidation of Alcohol 99.

To a solution of oxalyl chloride (5.6 mL, 65.0 mmol, 2.0 equiv) in Methylene chloride (250 mL) was added dropwise DMSO (9.2 mL, 130 mmol, 4.0 equiv) at −78° C. After stirring for 15 min, a solution of alcohol 99 (8.0 g, 32.0 mmol, 1.0 equiv) in Methylene chloride (50 mL) was added dropwise at −78° C. over a 15 min period. The solution was stirred for further 30 min at −78° C., and Et3N (27.1 mL, 194 mmol, 6.0 equiv) was added at the same temperature. The reaction mixture was allowed to warm to 0° C. over 30 min and then ether (400 mL) was added, followed by saturated aqueous NH4Cl solution (100 mL). The organic phase was separated, and the aqueous phase was extracted with ether (2×300 mL). The combined organic solution was dried (MgSO4), filtered and concentrated under reduced pressure. Purification by flash column chromatography (silica gel, 20% ether in hexanes) provided aldehyde 77 (7.9 g, 98%) as a colorless oil: Rf=0.64 (silica gel, 50% ether in hexanes); [a]22D −5.1 (c 0.7, CHCl3); IR (thin film) nmax 2952, 2858, 1728, 1466, 1389, 1254, 1095, 841, 776 cm−1; 1H NMR (500 MHz, CDCl3) d 9.74 (t, J=1.5 Hz, 1H, CHO), 3.39 (dd, J=9.8, 6.1 Hz, 1H, CH2OSi), 3.36 (dd, J=9.8, 6.3 Hz, 1H, CH2OSi), 2.39 (m, 2H, CH2CHO), 171–1.64 (m, 1H), 1.61–1.53 (m, 2H), 1.44–1.38 (m, 1 H), 1.11–1.05 (m, 1H), 0.87 (s, 9H, SiC(CH3)3), 0.85 (d, J=6.5 Hz, 3H, CHCH3), 0.019 (s, 3H, Si(CH3)2), 0.004 (s, 3H, Si(CH3)2); 13C NMR (125.7 MHz, CDCl3) d 202.7, 68.9, 44.1, 35.5, 32.6, 25.8, 23.0, 18.2, 16.5, −5.5; FAB HRMS (NBA) m/e 245.1932, M+H+ calcd for C13H28O2Si 245.1937.

Synthesis of Alcohol 100 as Illustrated in FIG. 13

To a cold (0° C.) solution of aldehyde 77 (7.8 g, 32.0 mmol) in THF (300 mL) was slowly added MeMgBr (1.0 M solution in THF, 48.0 mL, 48.0 mmol, 1.5 equiv). The reaction mixture was stirred for 15 min at 0° C. and then it was diluted with ether (500 mL) and quenched by carefull addition of saturated aqueous NH4Cl solution (100 mL). The organic phase was washed with brine (100 mL), dried (MgSO4), and concentrated. The crude product so obtained was purified by flash column chromatography (silica gel, 30% ether in hexanes) to give alcohol 100 (7.0 g, 84%) as a colorless oil: Rf=0.38 (silica gel, 50% ether in hexanes); IR (thin film) nmax 3352, 2931, 2858, 1465, 1384, 1253, 1096, 839, 775 cm−1; 1H NMR (500 MHz, CDCl3) d 3.79 (m, 1H, CH(CH3)OH), 3.43 (dd, J=9.8, 6.0 Hz, 1H, CH2OSi), 3.36 (dd, J=9.8, 6.8 Hz, 1H, CH2OSi), 1.61–1.57 (m, 1H), 1.47–1.35 (m, 4H), 1.30–1.26 (m, 1H), 1.19 (d, J=6.1 Hz, 3H, CH(OH)CH3), 1.09–1.05 (m, 1H), 0.89 (s, 9H, SiC (CH3)3), 0.86 (d, J=6.7 Hz, 3H, CHCH3), 0.04 (s, 6H, Si(CH3)2); 13C NMR (125.7 MHz, CDCl3) d 68.2, 67.9, 39.5, 35.6, 33.0, 25.9, 23.4, 23.1, 18.2, 16.6, −5.4; FAB HRMS (NBA) m/e 261.2256, M+H+ calcd for C14H32O2Si 261.2250.

Synthesis of Ketone 78 as Illustrated in FIG. 13
Oxidation of Alcohol 100.

To a solution of alcohol 100 (7.0 g, 27.0 mmol) in Methylene chloride (250 mL) was added molecular sieves (4 Å, 6.0 g) 4-methylmorpholine-N-oxide (NMO) (4.73 g, 40.0 mmol, 1.5 equiv) and tetrapropylammonium perruthenate (TPAP) (189 mg, 0.54 mmol, 0.02 equiv) at room temperature. After stirring for 45 min (depletion of starting material, TLC), the reaction mixture was filtered through celite, and the solvent was removed under reduced pressure. The crude product was purified by flash column chromatography (silica gel, 20% ether in hexanes) to give ketone 78 (6.6 g, 96%) as a colorless oil: Rf=0.67 (silica gel, 50% ether in hexanes); [a]22D −4.5 (c 1.1, CHCl3); IR (thin film) nmax 2931, 2849, 1713, 1461, 1355, 1249, 1161, 1091, 838, 773, 667 cm−1; 1H NMR (500 MHz, CDCl3) d 3.41 (dd, J=9.8, 6.0 Hz, 1H, CH2OSi), 3.36 (dd, J=9.8, 6.3 Hz, 1H, CH2OSi), 2.41 (m, 2 H, CH2COCH3), 2.13 (s, 3H, COCH3), 168–1.48 (m, 3H), 1.42–1.35 (m, 1H), 1.09–1.00 (m, 1H), 0.88 (s, 9H, SiC (CH3)3), 0.86 (d, J=6.7 Hz, 3H, CHCH3), 0.03 (s, 6H, Si(CH3)2); 13C NMR (125.7 MHz, CDCl3) d 209.8, 68.0, 43.9, 35.5, 32.6, 29.7, 25.8, 21.2, 18.2, 16.4, −5.5; FAB HRMS (NBA) m/e 259.2097, M+H+ calcd for C14H30O2Si 259.2093.

Synthesis of Iodide 113 as Illustrated in FIG. 15
Iodination of Alcohol 99.

A solution of alcohol 99 (3.8 g, 15.0 mmol) in ether-:MeCN 3:1 (150 mL) was cooled to 0° C. Imidazole (3.1 g, 45.0 mmol, 3.0 equiv), Ph3P (5.9 g, 22.5 mmol, 1.5 equiv) and iodine (5.7 g, 22.5 mmol, 1.5 equiv) were sequentially added and the reaction mixture was stirred at 0° C. for 0.5 h. A saturated aqueous solution of Na2S2O3 (200 mL) was added followed with ether (200 mL). The organic phase was washed with brine (200 mL), dried (MgSO4) and the solvents were removed under vacuum. The crude product was purified by flash column chromatography (silica gel, 10% ether in hexanes) to give pure iodide 113 (4.9 g, 91%) as a colorless oil: Rf=0.68 (silica gel, 10% ether in hexanes); [a]22D −4.3 (c 1.2, CHCl3); IR (thin film) nmax 2929, 2860, 1461, 1386, 1248, 1090, 836, 774, 664 cm−1; 1H NMR (500 MHz, CDCl3) d 3.42 (dd, J=10.0, 6.5 Hz, 1H, CH2OSi), 3.38 (dd, J=10.0, 6.0 Hz, 1H, CH2OSi), 3.19 (t, J=7.0 Hz, 2H, CH2I), 1.85–1.78 (m, 2H), 1.61–1.55 (m, 1H), 1.47–1.33 (m, 3H), 1.10–1.02 (m, 1H, CH2), 0.89 (s, 9H, SiC(CH3)3), 0.87 (d, J=6.7 Hz, 3H, CHCH3), 0.04 (s, 6H, Si(CH3)2); 13C NMR (125.7 MHz, CDCl3) d 68.1, 35.4, 33.7, 31.8, 27.8, 25.8, 18.2, 16.5, 7.1, −5.5; FAB HRMS (NBA) m/e 229.1983, M−I− calcd for C13H39IOSi 229.1988.

Synthesis of Phosphonium Salt 114 as Illustrated in FIG. 15

A mixture of iodide 113 (4.7 g, 13.1 mmol) and Ph3P (3.8 g, 14.4 mmol, 1.1 equiv) was heated neat at 100° C. for 2 h. Purification by flash column chromatography (silica gel, Methylene chloride to 7% MeOH in Methylene chloride) provided phosphonium salt 114 (7.4 g, 91%) as a white solid: Rf=0.42 (silica gel, 5% MeOH in Methylene chloride); [a]22D −7.3 (c 1.5, CHCl3); IR (thin film) nmax 2931, 2849, 1578, 1461, 1431, 1243, 1184, 1102, 997, 914, 838, 720, 685, 532, 503 cm−1; 1H NMR (500 MHz, CDCl3) d 7.82–7.77 (m, 9H, Ph), 7.74–7.68 (m, 6H, Ph), 3.62 (dt, J=12.5, 8.0 Hz, 2H, CH2P), 3.34 (dd, J=9.5, 6.5 Hz, 1H, CH2OSi), 3.30 (dd, J=9.5, 6.5 Hz, 1H, CH2OSi), 1.69–1.55 (m, 4H), 1.50–1.46 (m, 1H), 1.39–1.32 (m, 1H), 1.10–1.01 (m, 1H), 0.83 (s, 9H, SiC(CH3)3), 0.79 (d, J=6.6 Hz, 3H, CHCH3), −0.04 (s, 6H, Si(CH3)2); 13C NMR (125.7 MHz, CDCl3) d 135.0, 133.6, 133.5, 133.2, 130.5, 130.4, 68.0, 35.2, 32.4, 27.8, 25.8, 23.2, 22.7, 18.2, 16.4, −5.5.

Synthesis of Olefin 101 as Illustrated in FIG. 15
Method A.

From Phosphonium Salt 79 and Aldehyde 77. Phosphonium salt 79 (13.60 g, 19.4 mmol, 1.2 equiv) was dissolved in THF (80 mL, 0.2 M) and the solution was cooled to 0° C. Sodium hexamethyldisilylamide (NaHMDS, 19.4 mL, 19.4 mmol, 1.0 M solution in THF, 1.2 equiv) was slowly added and the resulting mixture was stirred for 15 min before aldehyde 77 (3.96 g, 16.2 mmol, 1.0 equiv, in 10 mL of THF) was added at the same temperature. Stirring was continued for another 15 min at 0° C. and then, the reaction mixture was quenched with saturated aqueous NH4Cl solution (25 mL). Ether (250 mL) was added and the organic phase was separated and washed with brine (2×40 mL), dried (MgSO4) and concentrated under vacuo. The crude product was purified by flash column chromatography (silica gel, 10% ether in hexane) to afford olefin 34 (6.70 g, 77%) as a mixture of Z- and E-isomers (ca 9 : 1 by 1H NMR). Method B. From Phosphonium Salt 114 and Aldehyde 82. Phosphonium salt 114 (7.40 g, 11.96 mmol, 1.2 equiv) was dissolved in THF (120 mL, 0.1 M) and the solution was cooled to 0° C. Sodium hexamethyldisilylamide (NaHMDS, 11.96 mL, 11.96 mmol, 1.0 M solution in THF, 1.2 equiv) was slowly added at the same temperature and the resulting mixture was stirred for 15 min, before aldehyde 82 (3.20 g, 9.83 mmol, 1.0 equiv, in 20 mL of THF; vida supra) was slowly added. Stirring was continued for another 15 min at 0° C. and then the mixture was quenched with saturated aqueous NH4Cl solution (150 mL). Ether (200 mL) was added and the organic phase was separated and washed with brine (2×150 mL), dried (MgSO4) and concentrated under reduced pressure to afford the crude product. Flash column chromatography (silica gel, 10% ether in hexane) furnished olefin 101 (3.65 g, 69% yield) as a mixture of Z- and E-isomers (ca 9:1 by 1H NMR): Rf=0.75 (silica gel, 50% ether in hexane); [a]22D +4.0 (c 0.5, CHCl3); IR (thin film) nmax 2930, 2856, 1465, 1388, 1253, 1089, 939, 838 cm−1; 1H NMR (500 MHz, CDCl3) (signals for the Z-isomer (34) only reported) d 6.92 (s, 1H, SCH═C), 6.46 (s, 1H, CH═CCH3), 5.49–5.31 (m, 2H, CH═CH), 4.12 (dd, J=6.5, 6.4 Hz, 1H, CHOSi), 3.44 (dd, J=9.8, 5.8 Hz, 1H, CH2OSi), 3.34 (dd, J=9.8, 6.8 Hz, 1H, CH2OSi), 2.71 (s, 3H, N═C(S)CH3), 2.39–2.24 (m, 2H, CH2CHOSi), 2.00 (s, 3H, CH═CCH3), 2.05–1.96 (m, 2H), 1.59–1.51 (m, 1H), 1.42–1.23 (m, 3H), 1.10–0.98 (m, 1H), 0.89 (s, 18H, SiC(CH3)3), 0.85 (d, J=6.8 Hz, 3 H, CH3CH), 0.06 (s, 3H, Si(CH3)2), 0.04 (s, 6H, Si(CH3)2), 0.01 (s, 3H, Si(CH3)2); 13C NMR (150.9 MHz, CDCl3) d 164.3, 153.1, 142.2, 131.4, 125.7, 118.8, 114.9, 78.7, 68.3, 35.7, 34.6, 32.9, 27.8, 27.1, 25.9, 25.8, 19.2, 18.3, 18.2, 16.7, 13.9, −4.7, −4.9, −5.4; FAB HRMS (NBA) m, e 538.3582, M+H+ calcd for C29H55NO2SSi2 538.3570.

Synthesis of alcohol 102 as Illustrated in FIG. 14

Compound 101 (1.77 g, 3.29 mmol) was dissolved in Methylene chloride MeOH (1:1, 66 mL) and the solution was cooled to 0° C. and CSA (764 mg, 3.29 mmol, 1.0 equiv) was added over a 5 min period. The mixture was stirred for 30 min at 0° C., and then for 1 h at 25° C. Et3N (2.0 mL) was added, and the solvents were removed under reduced pressure. Flash column chromatography (silica gel, 50% ether in hexanes) furnished the desired alcohol 35 (1.2 g, 86%): Rf=0.72 (silica gel, 80% ether in hexanes); [a]22D +1.1 (c 1.0, CHCl3); IR (thin film) nmax 3370, 2923, 2857, 1464, 1384, 1253, 1185, 1074, 836, 776 cm−1; 1H NMR (500 MHz, CDCl3) d 6.91 (s, 1H, SCH═C), 6.44 (s, 1H, CH═CCH3), 5.45–5.32 (m, 2H, CH═CH), 4.12 (dd, J=6.5, 6.4 Hz, 1H, CHOSi), 3.46 (dd, J=10.5, 5.9 Hz, 1H, CH2OH), 3.37 (dd, J=10.5, 6.5 Hz, 1H, CH2OH), 2.68 (s, 3H, N═C(S)CH3), 2.39–2.21 (m, 2H, CH2CHOSi), 2.21 (s, 1H, OH), 1.98 (s, 3H, CH═CCH3), 2.05–1.95 (m, 2H), 1.59–1.51 (m, 1H), 1.42–1.23 (m, 3H), 1.10–0.98 (m, 1H), 0.88 (d, J=6.5 Hz, 3H, CH3CH), 0.87 (s, 9H, SiC(CH3)3), 0.05 (s, 3 H, Si(CH3)2), −0.01 (s, 3H, Si(CH3)2); 13C NMR (125.7 MHz, CDCl3) d 164.4, 152.9, 142.2, 131.2, 125.8, 118.7, 114.8, 78.6, 67.9, 35.5, 34.6, 32.7, 27.5, 26.9, 25.8, 25.7, 18.9, 16.5, 13.7, −4.8, −5.1; FAB HRMS (NBA/NaI) m/e 446.2534, M+Na+ calcd for C23H41NO2SSi 446.2525.

Synthesis of Aldehyde 74 as Illustrated in FIG. 14
Oxidation of Alcohol 102.

Alcohol 102 (1.9 g, 4.5 mmol) was dissolved in Methylene chloride (45 mL, 0.1 M). DMSO (13.5 mL), Et3N (3.0 mL, 22.4 mmol, 5.0 equiv) and SO3·pyr (1.43 g, 8.98 mmol, 2.0 equiv) were added at 25° C. and the resulting mixture was stirred for 30 min. Saturated aqueous NH4Cl solution (100 mL) and ether (200 mL) were added sequentially. The organic phase was washed with brine (2×30 mL), dried (MgSO4) and the solvents were removed under reduced pressure. Flash column chromatography (silica gel, 30% ether in hexanes) furnished aldehyde 74 (1.79 g, 94%): Rf=0.55 (silica gel, 40% ether in hexanes); [a]22D +13.3 (c 0.7, CHCl3); IR (thin film) nmax 2930, 2856, 1725, 1504, 1462, 1385, 1253, 1182, 1076, 938, 836, 776 cm−1; 1H NMR (600 MHz, CDCl3) d 9.57, (d, J=1.8 Hz, 1H, CHO), 6.91 (s, 1H, SCH═C), 6.44 (s, 1 H, CH═CCH3), 5.45–5.35 (m, 2H, CH═CH), 4.11 (dd, J=6.6, 6.3 Hz, 1 H, CHOSi), 2.69 (s, 3H, N═C(S)CH3), 2.34–2.24 (m, 3H), 2.05–2.01 (m, 2H), 1.98 (s, 3H, CH═CCH3), 1.71–1.64 (m, 1H), 1.41–1.29 (m, 3H), 1.05 (d, J=7.0 Hz, 3H, CH3CH), 0.87 (s, 9 H, SiC(CH3)3), 0.04 (s, 3H, Si(CH3)2), −0.01 (s, 3H, Si(CH3)2); 13C NMR (150.9 MHz, CDCl3) d 205.2, 164.4, 153.0, 142.0, 130.6, 126.4, 118.8, 115.0, 78.7, 46.2, 34.7, 30.0, 27.3, 26.9, 25.8, 19.2, 18.2, 13.9, 13.2, −4.7, −5.0; FAB HRMS (NBA) m/e 422.2559, M+H+ calcd for C23H39NO2SSi 422.2549.

Synthesis of Compounds 105 and 106 as Illustrated in FIG. 14
Aldol Reaction of Keto Acid 76 with Aldehyde 74.

A solution of keto acid 76 (1.52 g, 5.10 mmol, 1.2 equiv; synthesized vida supra) in THF (10 mL) was added dropwise to a freshly prepared solution of LDA [diisopropylamine (1.78 mL, 12.78 mmol) was added to n-BuLi (7.95 mL, 1.6 M solution in hexanes, 12.78 mmol) in 20 mL of THF at 0° C.] at −78° C. After stirring for 15 min, the solution was allowed to warm to −40° C., and after 0.5 h at that temperature it was recooled to −78° C. A solution of aldehyde 74 (1.79 g, 4.24 mmol, 1.0 equiv) was added dropwise and the resulting mixture was stirred for 15 min, and then quenched at −78° C. by slow addition of saturated aqueous NH4Cl solution (20 mL). The reaction mixture was warmed to 0° C., and AcOH (2.03 mL, 26.84 mmol, 6.3 equiv) was added, followed by addition of EtOAc (50 mL). The organic layer was separated and the aqueous phase was extracted with EtOAc (3×25 mL). The combined organic solution was dried over MgSO4 and concentrated under vacuum to afford a mixture of aldol products 103a:103b in a ca 1:1 ratio (1H NMR) and unreacted keto acid 76. The mixture was dissolved in Methylene chloride (50 mL) and treated, at 0° C., with 2,6-lutidine (3.2 mL, 27.36 mmol) and tert-butyldimethylsilyl trifluoromethanesulfonate (4.2 mL, 18.24 mmol). After stirring for 2 h (complete reaction by TLC), aqueous HCl (20 mL, 10% solution) was added and the resulting biphasic mixture was separated. The aqueous phase was extracted with Methylene chloride (3×20 mL) and the combined organic solution was washed with brine (50 mL), dried (MgSO4) and concentrated under reduced pressure to give a mixture of the tetra-tert-butyldimethylsilyl ethers 104a and 104b. The crude product was dissolved in MeOH (50 mL) and K2CO3 (1.40 g, 10.20 mmol) was added at 25° C. The reaction mixture was vigorously stirred for 15 min, and then filtered. The residue was washed with MeOH (20 mL) and the solution was acidified with ion exchange resin (DOWEX 50WX8-200) to pH 4–5, and filtered again. The solvent was removed under reduced pressure and the resulting residue was dissolved in EtOAc (50 mL) and washed with saturated aqueous NH4Cl solution (50 mL). The aqueous phase was extracted with EtOAc (4×25 mL) and the combined organic solution was dried (MgSO4), filtered and concentrated to furnish a mixture of carboxylic acids 105, 106 and 76. Purification by preparative thin layer chromatography (silica gel, 5% MeOH in Methylene chloride), gave pure acids 105 (1.1 g, 31% from 7) and 106 (1.0 g, 30% from 7) as colorless oils. 38: Rf=0.61 (silica gel, 5% MeOH in Methylene chloride); [a]22D −8.8 (c 0.8, CHCl3); IR (thin film) nmax 2931, 2856, 1712, 1466, 1254, 1083, 836 cm−1; 1H NMR (600 MHz, CDCl3) d 6.94 (s, 1H, SCH═C), 6.61 (s, 1H, CH═CCH3), 5.44–5.41 (m, 2H, CH═CH), 4.40 (dd, J=6.5, 3.2 Hz, 1H, (CH3)2CCHOSi), 4.11 (dd, J=6.5, 5.9 Hz, 1H, CH2CHOSi), 3.75 (dd, J=6.5, 3.0 Hz, 1H, CH(CH3)CHOSi), 3.12 (dq, J=7.0, 6.5 Hz, 1H, C(O)CH(CH3)), 2.69 (s, 3 H., N═C(CH3)S), 2.48 (dd, J=16.0, 3.2 Hz, 1H, CH2COOH), 2.35 (dd, J=16.0, 6.7 Hz, 1H, CH2COOH), 2.39–2.28 (m, 2H, CH2CH=CH), 2.10–1.92 (m, 2H, CH=CHCH2), 1.95 (s, 3H, CH=C(CH3)), 1.42–1.30 (m, 5H, CH(CH3), 2×CH2), 1.18 (s, 3H, C(CH3)2), 1.10 (s, 3H, C(CH3)2), 1.06 (d, J=7.0 Hz, 3H, CH(CH3)), 0.90–0.85 (m, 30H, CH(CH3), 3×SiC(CH3)3), 0.12 (s, 3 H, Si(CH3)2), 0.09 (s, 3H, Si(CH3)2), 0.07 (s, 3H, Si(CH3)2), 0.05 (s, 3H, Si(CH3)2), 0.04 (s, 3H, Si(CH3)2), 0.03 (s, 3H, Si(CH3)2); 13C NMR (150.9 MHz, CDCl3) d 218.1, 176.7, 164.8, 152.8, 142.6, 131.3, 125.9, 118.6, 114.7, 78.6, 77.4, 73.4, 53.5, 44.9, 40.1, 38.8, 34.6, 30.7, 28.0, 27.8, 26.2, 26.0, 25.8, 23.6, 19.1, 18.8, 18.5, 18.2, 17.4, 15.7, 13.8, −3.7, −3.8, −4.2, −4.6, −4.7, −4.9; FAB HRMS (NBA/CsI) m/e 970.4318, M+Cs+ calcd for C44H83NO6SSi3 970.4303. 39: Rf=0.70 (silica gel, 5% MeOH in Methylene chloride); [a]22D +2.2 (c 3.5, CHCl3); IR (thin film) nmax 2929, 2856, 1713, 1470, 1386, 1254, 1082, 988, 836, 776 cm−1; 1H NMR (600 MHz, CDCl3) d 6.91 (s, 1H, SCH=C), 6.45 (s, 1H, CH=CCH3), 5.44–5.38 (m, 1H, CH=CH), 5.37–5.32 (m, 1H, CH=CH), 4.55 (dd, J=6.7, 3.7 Hz, 1H, (CH3)2CCHOSi), 4.11 (dd, J=6.7, 6.2 Hz, 1H, CH2CHOSi), 3.83 (d, J=8.4, 1H, CH(CH3)CHOSi), 3.09 (dq, J=7.0, 6.9 Hz, 1H, C(O)CH(CH3)), 2.73 (s, 3H, N=C(CH3)S), 2.40 (dd, J=16.3, 3.8 Hz, 1H, CH2COOH), 2.35–2.22 (m, 3H, CH2COOH, CH2CH=CH), 1.98–1.94 (m, 2 H, CH=CHCH2), 1.92 (s, 3H, CH=C(CH3)), 1.34–1.21 (m, 5H, CH(CH3), 2×CH2), 1.18 (s, 3H, C(CH3)2), 1.07 (s, 3H, C(CH3)2), 1.05 (d, J=7.0 Hz, 3H, CH(CH3)), 0.89 (s, 9H, SiC(CH3)3), 0.88 (s, 9H, SiC(CH3)3), 0.85 (s, 9H, SiC(CH3)3), 0.82 (d, J=6.9 Hz, 3H, CH(CH3)), 0.07 (s, 6H, 2×Si(CH3)2), 0.06 (s, 3H, Si(CH3)2), 0.05 (s, 3H, Si(CH3)2), 0.04 (s, 3H, Si(CH3)2), 0.01 (s, 3H, Si(CH3)2); 13C NMR (150.9 MHz, CDCl3) d 217.7, 175.3, 165.4, 152.4, 143.1, 131.3, 125.9, 118.3, 114.6, 78.6, 76.7, 72.3, 53.8, 45.7, 40.1, 37.9, 34.9, 34.6, 27.7, 27.3, 26.3, 26.2, 26.0, 25.8, 22.4, 19.0, 18.6, 18.2, 18.1, 16.8, 13.9, 13.5, −3.4, −3.6, −4.3, −4.6, −4.7, −4.9; FAB HRMS (NBA/CsI) m/e 970.4331, M+Cs+ calcd for C44H83NO6SSi3 970.4303.

Synthesis of Hydroxy Acid 72 as Illustrated in FIG. 14

Selective Desilylation of tris(Silyl) Ether 105.

A solution of tris(silyl) ether 105 (300 mg, 0.36 mmol) in THF (7.0 mL) at 25° C. was treated with TBAF (2.2 mL, 1 M solution in THF, 2.2 mmol, 6.0 equiv). After stirring for 8 h, the reaction mixture was diluted with EtOAc (10 mL) and washed with aqueous HCl (10 mL, 1 N solution). The aqueous solution was extracted with EtOAc (4×10 mL) and the combined organic phase was washed with brine (10 mL), dried (MgSO4) and concentrated. The crude mixture was purified by flash column chromatography (silica gel, 5% MeOH in Methylene chloride) to provide hydroxy acid 72 (203 mg, 78%) as a yellow oil: Rf=0.40 (silica gel, 5% MeOH in Methylene chloride); [a]22D −19.2 (c 0.1, CHCl3); IR (thin film) nmax 3358, 2932, 2857, 1701, 1466, 1254, 1088, 988, 835 cm−1; 1H NMR (600 MHz, CDCl3) d 6.95 (s, 1 H SCH=C), 6.67 (s, 1H, CH=CCH3), 5.58–5.54 (m, 1H, CH=CH), 5.43–5.39 (m, 1H, CH=CH), 4.39 (dd, J=6.7, 3.9 Hz, 1H, (CH3)2CCHOSi), 4.18 (dd, J=7.5, 5.0 Hz, 1H, CH2CHOH), 3.78 (dd, J=6.9, 1.0 Hz, 1H, CH(CH3)CHOSi), 3.11 (dq, J=6.9, 6.7 Hz, 1H, C(O)CHCH3), 2.70 (s, 3H, N=C(CH3)S), 2.43 (dd, J=16.2, 3.9 Hz, 1H, CH2COOH), 2.40–2.35 (m, 2H, CH2CH=CH), 2.35 (dd, J=16.2, 6.7 Hz, 1H, CH2COOH), 2.15–2.10 (m, 1H, CH=CHCH2), 2.00 (s, 3H, CH=C(CH3)), 1.99–1.95 (m, 1H, CH=CHCH2), 1.48–130 (m, 5H, CH(CH3), 2×CH2), 1.18 (s, 3H, C(CH3)2), 1.08 (s, 3H, C(CH3)2), 1.05 (d, J=6.7 Hz, 3H, CH(CH3)), 0.89–0.84 (m, 21H, CH(CH3), SiC(CH3)3), 0.09 (s, 3H, Si(CH3)2), 0.05 (s, 3H, Si(CH3)2), 0.04 (s, 3H, Si(CH3)2), 0.03 (s, 3H, Si(CH3)2); 13C NMR (150.9 MHz, CDCl3) d 218.9, 175.4, 166.3, 152.8, 143.5, 134.4, 125.7, 119.5, 115.9, 74.4, 54.7, 45.5, 40.9, 40.0, 34.3, 31.9, 30.6, 28.9, 28.8, 27.0, 26.8, 26.7, 24.4, 20.0, 19.6, 19.3, 19.1, 17.9, 17.1, 15.5, −2.9, −3.1, −3.3, −3.8; FAB HRMS (NBA/CsI) m/e 856.3459, M+Cs+ calcd for C38H69NO6SSi2 856.3439.

Synthesis of Hydroxy Acid 107 as Illustrated in FIG. 14

Selective Desilylation of tris(Silyl) Ether 106.

Carboxylic acid 106 (150 mg, 0.18 mmol) was converted to hydroxy acid 107 (107 mg, 82%) according to the procedure described above for 72. 107: Yellow oil; Rf=0.45 (silica gel, 5% MeOH in Methylene chloride); [a]22D −8.0 (c 0.2, CHCl3); IR (thin film) nmax 3225, 2943, 2860, 1719, 1690, 1461, 1384, 1296, 1250, 1190, 1085, 985, 832, 761, 667 cm−1; 1H NMR (600 MHz, CDCl3) d 6.93 (s, 1H SCH=C), 6.60 (s, 1H, CH=CCH3), 5.54–5.50 (m, 1H, CH=CH), 5.40–5.34 (m, 1H, CH=CH), 4.54 (dd, J=6.4, 3.7 Hz, 1H, (CH3)2CCHOSi), 4.15 (dd, J=6.5, 6.3 Hz, 1H, CH2CHOH), 3.82 (d, J=7.6 Hz, 1H, CH(CH3)CHOSi), 3.09 (dq, J=6.9, 6.5 Hz, 1H, C(O)CHCH3), 2.71 (s, 3H, N=C(CH3)S), 2.37–2.32 (m, 3H, CH2CH=CH, CH2COOH), 2.30 (dd, J=16.3, 6.4 Hz, 1H, CH2COOH), 2.15–2.10 (m, 2H, CH=CHCH2), 1.97 (s, 3H, CH=C(CH3)), 1.36–1.18 (m, 5H, CH(CH3), 2×CH2), 1.17 (s, 3H, C(CH3)2), 1.07 (s, 3H, C(CH3)2), 1.05 (d, J=6.8 Hz, 3H, CH(CH3)), 0.88 (s, 9H, SiC(CH3)3), 0.85–0.82 (m, 12H, CH(CH3), SiC(CH3)3), 0.07 (s, 3H, Si(CH3)2), 0.06 (s, 3H, Si(CH3)2), 0.05 (s, 6H, Si(CH3)2); 13C NMR (150.9 MHz, CDCl3) d 218.2, 175.4, 165.4, 152.2, 142.0, 133.1, 124.9, 118.6, 115.1, 74.4, 53.8, 45.8, 40.2, 38.9, 37.7, 34.8, 33.2, 27.9, 27.5, 27.1, 26.2, 26.1, 26.0, 22.6, 21.4, 18.8, 18.6, 16.9, 14.5, 13.3, −3.4, −3.6, −4.3, −4.6; FAB HRMS (NBA/CsI) m/e 856.3402, M+Cs+ calcd for C38H69NO6SSi2 856.3439.

Synthesis of Lactone 108 as Illustrated in FIG. 14

Macrolactonization of Hydroxy Acid 72.

A solution of hydroxy acid 72 (200 mg, 0.28 mmol) in THF (4 mL) was treated at 0° C. with Et3N (0.23 mL, 1.68 mmol, 6.0 equiv) and 2,4,6-trichlorobenzoyl chloride (0.22 mL, 1.40 mmol, 5.0 equiv). The reaction mixture was stirred at 0° C. for 15 min, and then added to a solution of 4-DMAP (342 mg, 2.80 mmol, 10.0 equiv) in toluene (140 mL) at 25° C. and stirred at that temperature for 0.5 h. The reaction mixture was concentrated under reduced pressure to a small volume and filtered through silica gel. The residue was washed with 40% ether in hexanes, and the resulting solution was concentrated. Purification by flash column chromatography (silica gel, 2% MeOH in Methylene chloride) furnished lactone 108 (178 mg, 90%) as a colorless oil: Rf=0.37 (silica gel, 30% ether in hexanes); [a]22D −22.9 (c 0.3, CHCl3); IR (thin film) nmax 2925, 2854, 1734, 1693, 1464, 1381, 1252, 1187, 1158, 1099, 988, 829, 758 cm−1; 1H NMR (600 MHz, CDCl3) d 6.98 (s, 1H, SCH=C), 6.58 (s, 1H, CH=CCH3), 5.53 (m, 1H, CH=CH ), 5.43–5.34 (m, 1H, CH=CH), 5.00 (d, J=10.2 Hz, 1H, O=COCH), 4.03 (d, J=10.5 Hz, 1H, CHOSi), 3.89 (d, J=9.0 Hz, 1H, CHOSi), 2.98 (dq, J=6.9, 6.7 Hz, 1H, C(O)CHCH3), 2.85 (d, J=16.7 Hz, 1 H, CH2COO), 2.72 (s, 3H, N=C(CH3)S), 2.66 (dd, J=16.7, 10.7 Hz, 1H, CH2COO), 2.40–2.30 (m, 1H, CH=CHCH2), 2.11 (s, 3H, CH=C(CH3)), 2.10–2.04 (m, 2H, CH2CH=CH), 1.92–1.83 (m, 1H, CH=CHCH2), 1.66–1.38 (m, 5H, CH(CH3), 2×CH2), 1.17 (s, 3H, C(CH3)2), 1.13 (s, 3H, C(CH3)2), 1.06 (d, J=7.0 Hz, 3H, CH(CH3)), 0.94 (d, J=7.0 Hz, 3H, CH(CH3)), 0.92 (s, 9H, SiC(CH3)3), 0.83 (s, 9H, SiC(CH3)3), 0.09 (s, 3H, Si(CH3)2), 0.07 (s, 3H, Si(CH3)2), 0.05 (s, 3H, Si(CH3)2), −0.12 (s, 3H, Si(CH3)2); 13C NMR (150.9 MHz, CDCl3) d 215.0, 171.3, 165.4, 135.7, 135.1, 125.8, 122.7, 119.9, 115.9, 79.5, 76.4, 53.3, 48.0, 38.8, 31.7, 31.3, 29.7, 29.2, 28.4, 26.4, 26.2, 26.1, 25.9, 24.2, 19.1, 18.7, 18.6, 17.7, 15.3, −3.1, −3.2, −3.7, −5.8; FAB HRMS (NBA) m/e 706.4382, M+H+ calcd for C38H67NO5SSi2 706.4357.

Synthesis of Lactone 109 as Illustrated in FIG. 14
Macrolactonization of Hydroxy Acid 107.

The cyclization of hydroxy acid 107 (100 mg, 0.14 mmol) was carried out exactly as described for 108 above and yielded lactone 109 (84 mg, 85%) as a colorless oil: Rf=0.40 (silica gel, 30% ether in hexanes); [a]22D −40.5 (c 0.2, CHCl3); IR (thin film) nmax 2929, 2855, 1739, 1690, 1469, 1384, 1253, 1180, 1089, 1053, 985, 835, 775 cm−1; 1H NMR (600 MHz, CDCl3) d 6.94 (s, 1H, SCH═C), 6.53 (s, 1H, CH═CCH3), 5.55–5.46 (m, 1H, CH═CH ), 5.39–5.30 (m, 1H, CH═CH), 5.32 (dd, J=7.0, 3.0 Hz, 1H, O═COCH), 4.43 (dd, J=7.5, 2.9 Hz, 1H, CHOSi), 3.99 (d, J=7.1 Hz, 1H, CHOSi), 3.20 (dq, J=7.3, 7.1 Hz, 1H, C(O)CHCH3), 2.71 (s, 3H, N═C(CH3)S), 2.59 (m, 1H, CH═CHCH2), 2.21 (dd, J=14.6, 3.2 Hz, 1H, CH2COO), 2.20 (dd, J=14.6, 7.6 Hz, 1H, CH2COO), 2.16 (s, 3H, CH═C(CH3)), 2.15–1.95 (m, 3H, CH═CHCH2, CH2CH═CH), 1.60–1.50 (m, 3H, CH(CH3), 2×CH2), 1.47–1.35 (m, 2H, CH(CH3), 2×CH2), 1.24 (s, 3H, C(CH3)2), 1.11 (d, J=7.2 Hz, 3H, CH(CH3)), 1.09 (s, 3H, C(CH3)2), 0.90 (s, 9H, SiC(CH3)3), 0.86 (s, 9H, SiC(CH3)3), 0.83 (d, J=6.7 Hz, 3H, CH(CH3)), 0.09 (s, 6H, 2×Si(CH3)2), 0.01 (s, 3H, Si(CH3)2), −0.05 (s, 3H, Si(CH3)2); 13C NMR (150.9 MHz, CDCl3) d 221.2, 171.6, 165.8, 134.9, 134.1, 125.7, 125.2, 120.7, 117.1, 78.8, 75.2, 74.5, 54.3, 48.1, 42.5, 37.9, 33.7, 32.4, 26.8, 26.7, 26.5, 26.2, 25.8, 19.7, 19.2, 19.0, 18.8, 17.7, 15.9, 14.1, −3.0, −3.3, −3.7, −4.3; FAB HRMS (NBA) m/e 706.4333, M+H+ calcd for C38H67NO5SSi2 706.4357.

Synthesis of Dihydroxy Lactone 70 as Illustrated in FIG. 14

To lactone 108 (50 mg, 0.071 mmol), cooled to −20° C., was added a freshly prepared 20% (v/v) CF3COOH solution in Methylene chloride (400 mL). The reaction mixture was allowed to reach 0° C. and was stirred for 1 h at that temperature. The solvents were evaporated under reduced pressure and the crude product was purified by preparative thin layer chromatography (silica gel, 6% MeOH in Methylene chloride) to afford pure dihydroxy lactone 70 (31 mg, 92%): Rf=0.38 (silica gel, 5% MeOH in Methylene chloride); [a]22D −80.2 (c 1.7, CHCl3); IR (thin film) nmax 3470, 2929, 1733, 1686, 1464, 1380, 1250, 1182, 1045, 978, 732 cm−1; 1H NMR (500 MHz, C6D6) d 6.83 (s, 1H, SCH═C), 6.56 (s, 1H, CH═CCH3), 5.48 (dd, J=7.0, 3.0 Hz, 1H, O═COCH ), 5.43–5.41 (m, 2H, CH═CH), 4.21 (d, J=11.5 Hz, 1H, CHOH), 3.77 (bs, 1H, CHOH), 3.13 (bs, 1H, OH), 3.01 (bs, 1H, OH), 2.95 (m, 1H, C(O)CHCH3), 2.70–2.62 (m, 1H, CH2COO), 2.47 (ddd, J=14.6, 11.5 Hz, 1H, CH2COO), 2.27 (s, 3H, N═C(CH3)S), 2.18–2.12 (m, 2H, CH═CHCH2), 2.15 (s, 3H, CH═C(CH3)), 1.97–1.83 (m, 2H, CH2CH═CH), 1.56–1.50 (m, 1H, CH(CH3)), 1.41–1.22 (m, 4H, 2×CH2), 1.15 (d, J=7.0 Hz, 3H, CH(CH3)), 1.07 (d, J=6.0 Hz, 3H, CH(CH3)), 1.07 (s, 3H, C(CH3)2), 1.06 (s, 3H, C(CH3)2); 13C NMR (150.9 MHz, C6D6) d 220.2, 170.6, 165.4, 153.8, 139.2, 134.1, 126.1, 120.4, 116.9, 79.2, 74.9, 73.2, 54.2, 42.5, 40.3, 39.5, 32.9, 32.6, 28.6, 28.4, 23.3, 19.3, 19.1, 16.4, 16.3, 14.4; FAB HRMS (NBA/CsI) m/e 610.1580, M+Cs+ calcd for C26H39NO5S 610.1603.

Synthesis of Dihydroxy Lactone 110 as Illustrated in FIG. 14

Lactone 109 (38.0 mg, 0.054 mmol) was treated with CF3COOH in exactly the same way as described above for 70, yielding dihydroxy lactone 110 (24.5 mg, 95%): Rf=0.30 (silica gel, 6% MeOH in Methylene chloride); [a]22D −93.1 (c 0.1, CHCl3); IR (thin film) nmax 3450, 2929, 1735, 1685, 1464, 1380, 1250, 1182, 1045, 978, 732 cm−1; 1H NMR (600 MHz, CDCl3) d 6.96 (s, 1H, SCH═C), 6.51 (s, 1H, CH═CCH3), 5.60–5.50 (m, 2H, CH═CH), 5.40–5.32 (m, 1H, O═COCH ), 4.25 (d, J=9.5 Hz, 1H, CHOH), 3.55 (d, J=9.6 Hz, 1H, CHOH), 3.39 (bs, 1H, OH), 3.31 (dq, J=6.9, 6.7 Hz, 1H, C(O)CHCH3), 2.99 (bs, 1H, OH), 2.71 (s, 3H, N═C(CH3)S), 2.69–2.61 (m, 1H, CH═CHCH2), 2.59 (d, J=16.3 Hz, 1H, CH2COO), 2.45–2.35 (m, 2H, CH2COO, CH═CHCH2), 2.20–2.10 (m, 1H, CH2CH═CH), 2.08 (s, 3H, CH═C(CH3)), 1.98–1.90 (m, 1H, CH2CH═CH), 1.59–1.50 (m, 1H, CH(CH3)), 1.49–1.30 (m, 4H, 2×CH2), 1.17 (s, 3H, C(CH3)2), 1.11 (d, J=6.9 Hz, 3H, CH(CH3)), 1.03 (s, 3H,. C(CH3)2), 1.01 (d, J=7.0 Hz, 3H, CH(CH3)); 13C NMR (150.9 MHz, CDCl3) d 222.2, 171.1, 165.2, 153.5, 139.5, 133.2, 125.1, 120.0, 116.7, 78.4, 74.1, 72.9, 52.5, 40.7, 39.5, 37.9, 34.5, 32.7, 31.3, 27.6, 24.7, 22.2, 18.9, 17.5, 15.5, 15.3; FAB HRMS (NBA) m/e 478.2610, M+H+ calcd for C26H39NO5S 478.2627.

Synthesis of Epothilone A (1) as Illustrated in FIG. 14
Epoxidation of Lactone 70 with Methyl(trifluoromethyl)dioxirane.

To a solution of 70 (10 mg, 21.0 mmol) in MeCN (200 mL) was added 4.10–4.00 M aqueous solution of disodium ethylenediaminetetraacetate (Na2EDTA, 120 mL; Aldrich) and the reaction mixture was cooled to 0° C. 1,1,1-Trifluoroacetone (200 mL) was added followed by a mixture of Oxone® (61 mg, 0.10 mmol, 5.0 equiv) and NaHCO3 (14.0 mg, 0.17 mmol, 8.0 equiv) with stirring until completion of the reaction was revealed by TLC. The reaction mixture was treated with excess Me2S (100 mL) and water (500 mL) and was then extracted with EtOAc (4×2 mL). The combined organic phase was dried (MgSO4), filtered, and concentrated. Purification by preparative thin layer chromatography (silica gel, 5% MeOH in Methylene chloride) gave a mixture of epothilones A (1) and its α-epoxide epimer (8.6 mg, 78% total yield). A second preparative thin layer chromatography (silica gel, 70% EtOAc in hexanes) furnished pure epothilone A (1) (6.4 mg, 65%) as a white solid. 1: Rf=0.23 (silica gel, 5% MeOH in Methylene chloride); [a]22D −45.0 (c 0.02, MeOH); IR (thin film) nmax 3476, 2974, 1738, 1692 cm−1; 1H NMR (600 MHz, C6D6) d 6.71 (s, 1H, SCH═C), 6.45 (s, 1H, CH═CCH3), 5.45 (dd, J=8.2, 2.3 Hz, 1H, O═COCH ), 4.15 (dd, J=10.8, 2.9 Hz, 1H, CHOH), 3.81–3.78 (m, 1H, CHOH), 3.65 (bs, 1H, OH), 3.03 (dq, J=6.9, 6.5 Hz, 1H, C(O)CHCH3), 2.77 (ddd, J=7.9, 4.0, 4.0 Hz, 1H, CH2CHO), 2.62–2.58 (m, 1H, CH2CHO), 2.40 (dd, J=14.4, 10.8 Hz, 1H, CH2COO), 2.26 (bs, 1H, OH), 2.21 (s, 3H, N═C(CH3)S), 2.19 (dd, J=14.4, 2.9 Hz, 1H, CH2COO), 2.05 (s, 3H, CH═C(CH3)), 1.86 (ddd, J=15.2, 2.5, 2.5 Hz, 1H, CH2CHO), 1.81–1.74 (m, 1H, CH2CHO), 1.68 (ddd, J=15.2, 7.6, 7.6 Hz, 1H, CH2CHO), 1.53–1.49 (m, 1H, CH2CHO), 1.40–1.15 (m, 5H, CH(CH3), 2×CH2), 1.06 (d, J=7.0 Hz, 3H, CH(CH3)), 1.03 (s, 3H, C(CH3)2), 0.97 (s, 3H, C(CH3)2), 0.95 (d, J=6.9 Hz, 3H, CH(CH3)); 13C NMR (150.9 MHz, C6D6) d 219.0, 170.2, 164.7, 153.0, 137.5, 119.9, 116.6, 76.6, 75.2, 73.5, 57.2, 54.2, 52.9, 43.8, 39.1, 36.3, 31.7, 30.3, 27.3, 23.9, 21.1, 20.6, 18.7, 17.4, 15.7, 14.6; HRMS (FAB), calcd for C26H39CsNO6S (M+Cs+) 626.1552, found 626.1531.

Synthesis of 6S,7R-Epothilones 111 and 112 as Illustrated in FIG. 14

Epoxidation of Lactone 110.

To a solution of lactone 110 (9.0 mg, 18.8 mmol) in MeCN (0.5 mL) was added disodium ethylenediaminetetraacetate (Na2EDTA, 4.10–4 M aqueous solution, 200 mL) and 1,1,1-trifluoroacetone (200 mL) at 0° C. The resulting solution was stirred at 0° C. while a mixture of solid Oxone® (58 mg, 94.0 mmol, 5.0 equiv) and NaHCO3 (14.0 mg, 0.17 mmol, 8.8 equiv) was added portionwise until completion of the reaction was established by TLC). The reaction mixture was treated with excess Me2S (100 mL) and water (500 mL) and was extracted with EtOAc (4×2 mL). The combined organic phase was dried (MgSO4), filtered, and concentrated. Purification by preparative thin layer chromatography (silica gel, 5% MeOH in Methylene chloride) gave a mixture of epothilones 111 and 112 (8.1 mg, 87% total yield, ca 2:1 ratio by 1H NMR). The major diastereoisomer (111, stereochemistry unassigned) was isolated by preparative thin layer chromatography (silica gel, 70% EtOAc in hexanes) (5.4 mg, 58%) and exhibited the following properties: Rf=0.23 (silica gel, 6% MeOH in Methylene chloride); [α]22D −20.0 (c 0.2, CHCl3); IR (thin film) nmax 3448, 2919, 1725, 1684, 1455, 1378, 1284, 1149, 1061, 1020, 973, 750 cm−1; 1H NMR (500 MHz, CHCl3) d 6.99 (s, 1H, SCH═C), 6.68 (s, 1H, CH═CCH3), 5.64–5.61 (m, 1H, O═COCH ), 4.43 (d, J=2.1 Hz, 1H, OH), 4.29 (ddd, J=7.6, 2.5, 2.5 Hz, 1H, CHOH), 3.82 (d, J=8.2 Hz, 1 H, CHOH), 3.35 (bs, 1H, OH), 3.22 (q, J=7.0 Hz, 1H, C(O)CHCH3), 3.14 (ddd, J=10.3, 4.1, 3.2 Hz, 1H, CH2CHO), 2.90 (ddd, J=10.3, 4.3, 2.3 Hz, 1H, CH2CHO), 2.71 (s, 3H, N═C(CH3)S), 2.54 (dd, J=13.7, 7.6 Hz, 1H, CH2COO), 2.51 (dd, J=13.7, 2.5 Hz, 1H, CH2COO), 2.21–2.19 (m, 1H, CH2CHO), 2.18 (s, 3H, CH═C(CH3)), 1.94 (ddd, J=15.3, 10.3, 3.7 Hz, 1H, CH2CHO), 1.77–1.69 (m, 2H, CH2CHO), 1.60–1.00 (m, 5H, CH(CH3), 2×CH2), 1.15 (s, 3H, C(CH3)2), 1.14 (d, J=6.9 Hz, 3H, CH(CH3)), 1.06 (s, 3H, C(CH3)2), 1.02 (d, J=7.0 Hz, 3H, CH(CH3)); 13C NMR (150.9 MHz, CHCl3) d 221.8, 172.1, 165.1, 152.6, 134.7, 119.8, 116.8, 76.0, 74.4, 72.8, 56.4, 53.8, 53.0, 40.2, 39.1, 34.1, 32.7, 29.4, 27.8, 22.7, 20.9, 19.0, 16.1, 15.9, 15.0, 11.8; FAB HRMS (NBA) m/e 494.2587, M+H+ calcd for C26H39NO6S 494.2576.

Synthesis of Olefinic Compound 115 as Illustrated in FIG. 16

Phosphonium salt 79 (9.0 g, 12.93 mmol, 1.5 equiv; vida supra) was dissolved in THF (90 mL) and the solution was cooled to 0° C. Sodium bis(trimethylsilyl)amide (NaHMDS, 1.0 M solution in THF, 12.84 mL, 12.84 mmol, 1.48 equiv) was slowly added and the resulting mixture was stirred at 0° C. for 15 min. The reaction mixture was then cooled to −20° C. before ketone 78 (2.23 g, 8.62 mmol, 1.0 equiv) in THF (10 mL) was added and the reaction mixture was stirred at the same temperature for 12 h. Saturated aqueous NH4Cl solution (50 mL) was added and the mixture was extracted with ether (200 mL). The organic phase was washed with brine (2×100 mL), dried (MgSO4) and concentrated to afford, after flash column chromatography (silica gel, 2% ether in hexanes) olefins 115 (3.8g, 73%, Z:E ca. 1:1 by 1H NMR): Rf=0.56 (silica gel, 20% ether in hexanes); IR (thin film) nmax 2931, 2857, 1465, 1386, 1253, 1089, 942, 838, 776 cm−1; 1H NMR (600 MHz, CDCl3) d 6.90, 6.89 (singlets, 1H total, SCH═C), 6.44 (s, 1H, CH═CCH3), 5.15–5.10 (m, 1H, C(CH3)═CH), 4.08 (m, 1H, CHOSi), 3.42 (m, 1H, CH2OSi), 3.33 (dd, J=13.3, 6.8 Hz, 0.5H, CH2OSi), 3.32 (dd, J=13.3, 6.7 Hz, 0.5H, CH2OSi), 2.69 (s, 3H, N═C(S)CH3), 2.31–2.19 (m, 2H, CH2CHOSi), 1.99 (s, 3H, CH═CCH3), 1.99–1.96 (m, 1H, CH2C(CH3)═CH), 1.95–1.91 (m, 1H, CH2C(CH3)═CH), 1.65 (s, 1.5H, C(CH3)═CH), 1.58 (s, 1.5H, C(CH3)═CH), 1.56–1.52 (m, 1H), 1.43–1.28 (m, 3H), 1.05–0.97 (m, 1H), 0.88 (s, 18H, 2×SiC(CH3)3), 0.86 (d, J=6.8 Hz, 1.5H, CH3CH), 0.83 (d, J=6.7 Hz, 1.5H, CH3CH), 0.04 (s, 3H, Si(CH3)2), 0.02 (s, 3H, Si(CH3)2), 0.01 (s, 3H, Si(CH3)2), −0.01 (s, 3H, Si(CH3)2); 13C NMR (150.9 MHz, CDCl3) d 164.2, 153.3, 142.7, 142.6, 136.9, 136.8, 121.4, 120.6, 118.6, 118.5, 114.9, 114.8, 79.0, 78.8, 68.3, 40.1, 35.8, 35.7, 35.5, 35.4, 33.2, 32.9, 32.3, 25.9, 25.8, 25.4, 25.3, 23.5, 19.2, 18.3, 18.2, 16.7, 16.2, 13.9, −4.6, −4.9, −5.3; FAB HRMS (NBA) m/e 552.3710, M+H+ calcd for C30H57NO2SSi2 552.3727.

Synthesis of Hydroxy Olefins 116 as Illustrated in FIG. 16

Desilylation of Silylether 115.

Silylether 115 (3.80 g, 6.88 mmol) was dissolved in Methylene chloride:MeOH (1:1, 70 mL) and the solution was cooled to 0° C. prior to addition of CSA (1.68 g, 7.23 mmol, 1.05 equiv) during a 5 min period. The resulting mixture was stirred for 30 min at 0° C., and then for 1 h at 25° C. Et3N (1.57 mL, 7.23 mmol, 1.05 equiv) was added, and the solvents were removed under reduced pressure. Flash column chromatography (silica gel, 50% ether in hexanes) furnished pure hydroxy compound 116 (2.9 g, 97%): Rf=0.33 (silica gel, 50% ether in hexanes); IR (thin film)nmax 3370, 2929, 2857, 1463, 1382, 1252, 1185, 1072, 836, 776 cm−1; 1H NMR (600 MHz, CDCl3) (mixture of Z:E olefins, ca 1:1) d 6.91, 6.90 (singlets, 1H total, SCH═C), 6.43, 6.41 (singlets, 1H total, CH═CCH3), 5.14 (t, J=6.9 Hz, 0.5H, C(CH3)═CH), 5.06 (t, J=6.8 Hz, 0.5H, C(CH3)═CH), 4.08 (m, 1H, CHOSi), 3.47 (dd, J=10.4, 5.9 Hz, 0.5H, CH2OH), 3.41 (dd, J=10.6, 6.1 Hz, 0.5H, CH2OH), 3.40–3.36 (m, 1H, CH2OH), 2.68 (s, 3H, N═C (S)CH3), 2.31–2.18 (m, 2H, CH2CHOSi), 2.05–1.99 (m, 1H, CH2C(CH3)═CH), 1.96, 1.95 (singlets, 3H total, CH═CCH3), 1.95–1.93 (m, 1H, CH2C(CH3)═CH), 1.65 (s, 1.5H, C(CH3)═CH), 1.56 (s, 1.5H, C(CH3)═CH), 1.60–1.51 (m, 1H), 1.52–1.27 (m, 3H), 1.10–0.96 (m, 1H), 0.89 (d, J=6.9 Hz, 1.5H, CH3CH), 0.87 (s, 9H, SiC(CH3)3), 0.85 (d, J=6.8 Hz, 1.5H, CH3CH), 0.04, 0.03 (singlets, 3H total, Si(CH3)2), −0.01, −0.02 (singlets, 3H total, Si(CH3) 2); 13C NMR (150.9 MHz, CDCl3) d 164.5, 164.4, 153.0, 152.9, 142.7, 142.3, 136.7, 136.5, 121.5, 120.5, 118.8, 118.6, 114.9, 114.8, 114.7, 79.1, 78.8, 68.2, 68.1, 39.7, 35.7, 35.6, 35.4, 35.2, 33.0, 32.4,. 32.1, 25.9, 25.2, 24.8, 23.4, 19.1, 18.9, 18.2, 18.1, 16.6, 16.3, 15.9, 13.9, 13.7, −4.7, −4.9; FAB HRMS (NBA) m/e 438.2875, M+H+ calcd for C24H43NO2SSi 438.28.

Synthesis of Aldehyde 75' as Illustrated in FIG. 16

Oxidation of Alcohol 116.

Alcohol 116 (mixtures of Z and E geometrical isomers, 4.60 g, 10.64 mmol) was dissolved in Methylene chloride (105 mL, 0.1 M). DMSO (35 mL), Et3N (7.4 mL, 53.20 mmol, 5.0 equiv) and SO3·pyr (3.4 g, 21.28 mmol, 2.0 equiv) were added at 25° C. and the resulting mixture was stirred for 30 min. Saturated aqueous NH4Cl solution (50 mL) and ether (300 mL) were added, and the organic phase was separated and washed with brine (2×30 mL), dried (MgSO4), and concentrated under reduced pressure. Flash column chromatography (silica gel, 20% ether in hexanes) furnished aldehyde 75' (4.40 g, mixture of Z:E isomers, ca 1:1, 95%): Rf=0.48 (silica gel, 50% ether in hexanes); IR (thin film) nmax 2931, 2860, 1725, 1495, 1455, 1378, 1249, 1173, 1073, 938, 832, 773 cm−1; 1H NMR (500 MHz, CDCl3) d 9.60, (d, J=1.9 Hz, 0.5H, CHO), 9.55 (d, J=1.9 Hz, 0.5H, CHO), 6.92, 6.91 (singlets, 1H total, SCH═C), 6.45, 6.44 (singlets, 1H total, CH═CCH3), 5.18–5.13 (m, 1H, CH2CH═CCH3), 4.12–4.07 (m, 1H, CHOSi), 2.71, 2.70 (singlets, 3H total, N═C(S)CH3), 2.36–2.20 (m, 3H), 2.07–1.90 (m, 1H), 1.99 (s, 3H, CH═CCH3), 1.71–1.60 (m, 1H), 1.66 (d, J=1.0 Hz, 1.5H, CH2CH═CCH3), 1.58 (d, J=1.0 Hz, 1.5H, CH2CH═CCH3), 1.43–1.25 (m, 4H), 1.08 (d, J=7.0 Hz, 1.5H, CH3CH), 1.04 (d, J=7.0 Hz, 1.5H, CH3CH), 0.88 (s, 9H, SiC(CH3)3), 0.05, 0.04 (singlets, 3H total, Si(CH3)2), −0.01 (s, 3H, Si(CH3)2); 13C NMR (125.7 MHz, CDCl3) d 205.2, 205.0, 164.4, 153.1, 142.3, 136.0, 135.9, 122.0, 121.2, 118.7, 118.6, 115.0, 114.9, 78.8, 78.7, 46.2, 46.1, 35.4, 35.3, 31.7, 31.6, 30.2, 30.0, 25.7, 25.1, 25.0, 23.3, 22.6, 19.1, 18.2, 16.1, 14.0, 13.9, 13.8, 13.3, 13.2, −4.8, −5.1; FAB HRMS (NBA) m/e 436.2715, M+H+ calcd for C24H41NO2SSi 436.2706.

Synthesis of tris(Silylethers) 119' and 120' as Illustrated in FIG. 16

Aldol Reaction of Keto Acid 76 with Aldehyde 75'.

A solution of keto acid 76 (773 mg, 2.56 mmol, 1.2 equiv; vida supra) in THF (7.0 mL) was reacted with aldehyde 75' (930 mg, mixture of Z:E olefins, ca 1:1, 2.13 mmol, 1.0 equiv) according to the same procedure as described above for the condensation of 76 and 74 (FIG. 14), to afford, after similar processing, pure carboxylic acids 119' (564 mg, mixture of Z and E isomers, ca 1:1, 31% from 8') and 120' (545 mg, mixture of Z and E isomers, ca 1:1, 30% from 8') as colorless oils and recovered keto acid 76 (125 mg). 119': Rf=0.56 (silica gel, 5% MeOH in Methylene chloride); IR (thin film) nmax 2942, 2856, 1706, 1464, 1388, 1361, 1248, 1183, 1087, 989, 833, 774, 731 cm−1; 1H NMR (600 MHz, CDCl3) d 6.89 (s, 1H, SCH═C), 6.50, 6.49 (singlets, 1H total, CH═CCH3), 5.15 (m, 1H, (CH3)C═CHCH2), 4.39 (m, 1H, (CH3)2CCHOSi), 4.10–4.03 (m, 1H, CH2CHOSi), 3.78–3.70 (m, 1H, CH(CH3)CHOSi), 3.13 (dq, J=7.2, 6.7 Hz, 1H, C(O)CH(CH3)), 2.68 (s, 3H, N═C(CH3)S), 2.49 (dd, J=16.4, 2.6 Hz, 0.5H, CH2COOH), 2.44 (dd, J=16.4, 3.1 Hz, 0.5H, CH2COOH), 2.31–2.15 (m, 3H, CH2COOH, CH2C(CH3)═CHCH2), 2.05–1.85 (m, 2H, CH2C(CH3) ═CH), 1.95 (s, 1.5H, CH═C(CH3)), 1.94 (s, 1.5H, CH═C (CH3)), 1.64 (s, 1.5H, CH2C(CH3)═CH), 1.55 (s, 1.5H, CH2C(CH3)═CH), 1.45–1.25 (m, 4H), 1.19 (s, 3H, C(CH3)2), 1.10 (s, 3H, C(CH3)2), 1.21–1.09 (m, 1H), 1.06 (d, J=6.8 Hz, 1.5H, CH(CH3)), 1.05 (d, J=6.8 Hz, 1.5H, CH(CH3)), 0.90–0.85 (m, 30H, CH(CH3), 3×SiC(CH3)3), 0.10 (s, 1.5H, Si(CH3)2), 0.08 (s, 1.5H, Si(CH3)2), 0.07 (s, 1.5H, Si(CH3)2), 0.05 (s, 1.5H, Si(CH3)2), 0.04 (s, 3H, Si(CH3)2), 0.03 (s, 3H, Si(CH3)2), 0.02 (s, 3H, Si(CH3)2), −0.02 (s, 3H, Si(CH3)2); 13C NMR (150.9 MHz, CDCl3) d 218.1, 217.9, 176.7, 176.6, 164.8, 152.8, 142.9, 142.8, 136.7, 121.5, 120.5, 118.4, 118.3, 114.6, 78.9, 78.8, 77.7, 77.3, 73.5, 73.4, 53.5, 53.4, 45.3, 44.8, 40.4, 40.1, 38.9, 38.6, 35.4, 35.3, 32.5, 31.0, 30.4, 26.2, 26.0, 25.8, 25.7, 25.6, 23.5, 23.4, 19.1, 18.8, 18.7, 18.5, 18.4, 17.8, 17.6, 17.3, 16.2, 15.8, 15.6, 13.9, 13.8, −3.6, −3.7, −3.9, −4.2, −4.3, −4.6, −4.7, −5.0; FAB HRMS (NBA/CsI) m/e 984.4422, M+Cs+ calcd for C45H85NO6SSi3 984.4460. 53': Rf=0.65 (silica gel, 5% MeOH in Methylene chloride); IR (thin film) nmax 2954, 2856, 1713, 1470, 1386, 1253, 1080, 988, 836, 776 cm−1; 1H NMR (600 MHz, CDCl3) d 6.91 (s, 1H, SCH═C), 6.45 (s, 1H, CH═CCH3), 5.13 (dd, J=7.0, 6.9 Hz, 0.5H, (CH3)C═CHCH2), 5.09 (dd, J=7.1, 6.9 Hz, 0.5H, (CH3)C═CHCH2), 4.58 (dd, J=6.1, 3.5 Hz, 0.5H, (CH3) 2CCHOSi), 4.56 (dd, J=6.0, 3.5 Hz, 0.5H, (CH3)2CCHOSi), 4.16 (dd, J=6.7, 6.6 Hz, 0.5H, CH2CHOSi), 4.06 (dd, J=6.7, 6.0 Hz, 0.5H, CH2CHOSi), 3.85–3.80 (m, 1H, CH(CH3) CHOSi), 3.11 (dq, J=7.1, 7.0 Hz, 1H, C(O)CH(CH3)), 2.74 (s, 3H, N═C(CH3)S), 2.43–2.10 (m, 4H), 1.96–1.80 (m, 2H), 1.92 (s, 1.5H, CH═C(CH3)), 1.91 (s, 1.5H, CH═C (CH3)), 1.66 (s, 1.5H, CH2C(CH3)═CH), 1.56 (s, 1.5H, CH2C(CH3)═CH), 1.35–1.02 (m, 14H, CH(CH3), 2×CH2, C(CH3)2, C(CH3)2, CH(CH3)), 0.92–0.80 (m, 30 H., 3×SiC (CH3)3, CH(CH3)), 0.10–0.03 (m, 18H, 3×Si(CH3)2); 13C NMR (150.9 MHz, CDCl3) d 218.1, 217.9, 174.8, 174.7, 165.6, 165.5, 152.4, 143.6, 137.0, 136.8, 121.4, 121.0, 118.4, 117.9, 114.4, 78.9, 78.6, 76.4, 72.4, 72.3, 53.9, 53.8, 45.8, 45.7, 40.3, 40.2, 39.4, 38.4, 37.5, 35.6, 35.3, 35.0, 34.7, 32.2, 26.6, 26.3, 26.0, 25.8, 25.6, 23.8, 23.1, 22.7, 19.1, 18.7, 18.6, 18.5, 18.4, 18.2, 17.1, 16.9, 14.0, 13.8, 13.6, 13.4, −3.4, −3.6, −4.3, −4.6, −4.7, −4.9; FAB HRMS (NBA/CsI) m/e 984.4489, M+Cs+ calcd for C45H85NO6SSi3 984.4460.

Synthesis of Hydroxy Acid 73' as Illustrated in FIG. 16

Selective Desilylation of 119'.

Carboxylic acid 119' (300 mg, mixture of Z and E isomers, ca 1:1, 0.35 mmol) was converted to hydroxy acid 73' (194 mg, mixture of Z and E isomers, ca 1:1, 75%) according to the same procedure described above for hydroxy acid 72 (FIG. 14). Compound 73': Yellow oil; Rf=0.41 (silica gel, 5% MeOH in Methylene chloride); IR (thin film) nmax 3260, 2923, 2852, 1707, 1463, 1381, 1249, 1187, 1085, 984, 831, 775 cm−1; 1H NMR (500 MHz, CDCl3) d 6.95, 6.94 (singlets, 1H total, SCH═C), 6.62, 6.57 (singlets, 1H total, CH═CCH3), 5.20–5.14 (m, 1H, CH3C═CHCH2), 4.41 (dd, J=6.0, 3.5 Hz, 0.5H, (CH3) 2CCHOSi), 4.37 (dd, J=7.0, 3.0 Hz, 0.5H, (CH3)2CCHOSi), 4.16 (dd, J=6.6, 6.5 Hz, 1H, CH2CHOH), 3.77 (d, J=6.9 Hz, 1H, CH(CH3)CHOSi), 3.17–3.09 (m, 1H, C(O)CHCH3), 2.72, 2.71 (singlets, 3H total, N═C(CH3)S), 2.50 (dd, J=16.0, 6.0 Hz, 0.5H, CH2COOH), 2.47 (dd, J=16.0, 2.7 Hz, 0.5H, CH2COOH), 2.40–2.28 (m, 3H), 2.17–2.10 (m, 1H), 2.00 (s, 1.5H, CH═C(CH3)), 1.98 (s, 1.5H, CH═C(CH3)), 1.99–1.90 (m, 1H), 1.70 (s, 1.5H, CH2C(CH3)═CH), 1.62 (s, 1.5H, CH2C(CH3)═CH), 1.53–1.30 (m, 5H), 1.19 (s, 3H, C(CH3)2), 1.11 (s, 1.5H, C(CH3)2), 1.10 (s, 1.5H, C(CH3)2), 1.06 (d, J=6.7 Hz, 1.5H, CH(CH3)), 1.04 (d, J=6.7 Hz, 1.5H, CH(CH3)), 0.89 (s, 18H, SiC(CH3)3), 0.86 (d, J=7.0 Hz, 3H, CH(CH3)), 0.09 (s, 3H, Si(CH3)2), 0.06 (s, 6H, Si(CH3)2), 0.05 (s, 3H, Si(CH3)2); 13C NMR (150.9 MHz, CDCl3) d 218.0, 217.9, 176.4, 176.1, 165.0, 164.9, 152.6, 152.5, 142.1, 141.8, 139.2, 138.9, 120.3, 119.5, 118.8, 118.7, 115.2, 115.1, 77.5, 77.4, 73.4, 73.3, 53.7, 53.5, 45.1, 44.8, 40.3, 40.1, 38.9, 38.7, 34.1, 34.0, 32.5, 31.1, 30.5, 26.3, 26.2, 26.0, 23.6, 23.4, 19.2, 19.1, 18.9, 18.8, 18.5, 18.4, 18.2, 17.6, 17.2, 16.3, 15.9, 15.8, 14.5, 14.4, −3.6, −3.7, −3.8, −3.9, −4.2, −4.6; FAB HRMS (NBA/CsI) m/e 870.3564, M+Cs+ calcd for C39H71NO6SSi2 870.3595.

Synthesis of Lactones 121 and 122 as Illustrated in FIG. 16

Macrolactonization of Hydroxy Acid 73'. A solution of hydroxy acid 73' (140 mg, mixture of Z and E isomers, ca 1:1, 0.189 mmol) in THF (2.6 mL) was treated at 0° C. with Et3N (58 mL, 0.416 mmol, 2.2 equiv) and 2,4,6-trichlorobenzoyl chloride (29.4 mL, 0.246 mmol, 1.3 equiv). The reaction mixture was stirred at 0° C. for 1 h, and then added to a solution of 4-DMAP (233 mg, 1.896 mmol, 10.0 equiv) in toluene (90 mL, 0.002 M) at 25° C. and stirred at that temperature for 10 h. The solvents were removed in vacuo, and the crude product obtained was suspended in 40% ether in hexanes and filtered through silica gel. Concentration, followed by preparative thin layer chromatography (silica gel, 5% MeOH in Methylene chloride), gave pure lactones 121 (50 mg, 37%) and 122 (54 mg, 40%) as colorless oils. 121: Rf=0.40 (silica gel, 1% MeOH in Methylene chloride); [a]22D −11.8 (c 0.8, CHCl3); IR (thin film) nmax 2931, 2848, 1737, 1690, 1461, 1378, 1249, 1184, 1158, 1097, 1020, 984, 835, 775 cm−1; 1H NMR (600 MHz, CDCl3) d 6.95 (s, 1H, SCH=C), 6.56 (s, 1H, CH=CCH3), 5.16 (dd, J=8.4, 7.5 Hz, 1H, CH3C=CHCH2), 4.96 (d, J=10.1 Hz, 1H, CH2COOCH), 4.02 (d, J=9.9 Hz, 1H, CHOSi), 3.88 (d, J=8.9 Hz, 1H, CHOSi), 3.02 (dq, J=6.9, 6.7 Hz, 1H, C(O)CHCH3), 2.79 (d, J=25 15.6 Hz, 1H, CH2COOCH), 2.70 (s, 3H, N=C(CH3)S), 2.70–2.65 (m, 2H), 2.48–2.40 (m, 1H), 2.10 (s, 3H, CH=C(CH3)), 2.10–2.04 (m, 2H), 1.75–1.69 (m, 2H), 1.67 (s, 3H, CH2C(CH3)=CH), 1.66–1.45 (m, 3H), 1.18 (s, 3H, C(CH3)2), 1.13 (s, 3H, C(CH3)2), 1.09 (d, J=6.8 Hz, 3H, CH(CH3)), 0.97 (d, J=6.8 Hz, 3H, CH(CH3)), 0.94 (s, 9H, SiC(CH3)3), 0.84 (s, 9H, SiC(CH3)3), 0.10 (s, 3H, Si(CH3)2), 0.09 (s, 3H, Si(CH3)2), 0.07 (s, 3H, Si(CH3)2), −0.12 (s, 3H, Si(CH3)2); 13C NMR (150.9 MHz, CDCl3) d 215.1, 171.2, 164.6, 152.5, 140.6, 138.8, 119.3, 119.1, 115.9, 79.9, 76.3, 53.4, 39.1, 32.4, 31.9, 31.4, 29.7, 27.4, 26.4, 26.1, 26.0, 24.5, 24.3, 23.1, 19.2, 18.7, 18.6, 17.8, 15.3, −3.3, −3.7, −5.7; FAB HRMS (NBA) m/e 720.4534, M+H+ calcd for C39H69NO5SSi2 720.4513. 122: Rf=0.50 (silica gel, 1% MeOH in Methylene chloride); [a]22D −22.7 (c 0.6, CHCl3); IR (thin film) nmax 2931, 2860, 1731, 1696, 1461, 1378, 1249, 1179, 1079, 985, 832, 773 cm−1; 1H NMR (600 MHz, CDCl3) d 6.92 (s, 1H, SCH=C), 6.53 (s, 1H, CH=CCH3), 5.27 (dd, J=8.0, 2.7 Hz, 1H, CH2COOCH), 5.16 (dd, J=6.9, 6.6 Hz, 1H, CH3C=CHCH2), 4.47 (t, J=5.1 Hz, 1H, CHOSi), 3.89 (dd, J=4.5, 1.0 Hz, 1H, CHOSi), 3.05 (dq, J=6.7, 6.2 Hz, 1H, C(O)CHCH3), 2.70 (s, 3H, N=C(CH3)S), 2.60 (dd, J=15.8, 5.8 Hz, 1H, CH2COOCH), 2.55 (m, 1H, CH3C=CHCH2), 2.51–2.47 (m, 2H, CH2COOCH, CH3C=CHCH2), 2.13 (s, 3H, CH=C(CH3)), 2.10–2.05 (m, 1H, CH2C(CH3)=CH), 1.91 (m, 1 H, CH2C(CH3)=CH), 1.68–1.45 (m, 4H), 1.57 (s, 3H, CH2C(CH3)=CH), 1.27–1.23 (m, 1H), 1.17 (s, 3H, C(CH3)2), 1.04 (d, J=6.8 Hz, 3H, CH(CH3)), 1.07 (s, 3H, C(CH3)2), 0.93 (d, J=6.9 Hz, 3H, CH(CH3)), 0.88 (s, 9H, SiC(CH3)3), 0.86 (s, 9H, SiC(CH3)3), 0.07 (s, 6H, Si(CH3)2), 0.06 (s, 3H, Si(CH3)2), 0.05 (s, 3H, Si(CH3)2); 13C NMR (150.9 MHz, CDCl3) d 217.2, 171.3, 165.5, 153.6, 139.0, 138.3, 120.9, 120.2, 117.0, 80.1, 77.2, 73.9, 54.8, 44.9, 42.7, 41.1, 40.2, 32.8, 26.9, 26.8, 25.6, 23.5, 21.1, 20.1, 19.2, 19.1, 17.7, 16.8, 16.6, 16.3, −2.7, −3.1, −3.4, −3.6; FAB HRMS (NBA) m/e 720.4533, M+H+ calcd for C39H69NO5SSi2 720.4513.

Synthesis of Dihydroxy lactone 71 as Illustrated in FIG. 16

Dihydroxy lactone 71 was prepared from bis(silylether) lactone 121 (13.3 mg, 0.018 mmol) by treatment with CF3COOH according to the same procedure described above for the preparation of 70 (FIG. 14), to obtain pure lactone 71 (8.4 mg, 91%) as a colorless oil. 71: Rf=0.21 (silica gel, 4% MeOH in Methylene chloride); [a]22D −91.5 (c 0.3, CHCl3); IR (thin film) nmax 3460, 2954, 2919, 1725, 1684, 1455, 1379, 1290, 1249, 1184, 1143, 1043, 1008, 973, 750 cm−1; 1H NMR (600 MHz, CDCl3) d 6.94 (s, 1H, SCH=C), 6.57 (s, 1H, CH=CCH3), 5.20 (d, J=9.7 Hz, 1H, CH2COOCH), 5.13 (dd, J=9.6, 4.6 Hz, 1H, CH3C=CHCH2), 4.28 (d, J=9.7 Hz, 1H, (CH3)2CCHOH), 3.71 (s, 1H, CHOH), 3.47 (bs, 1H, OH), 3.15 (q, J=6.8 Hz, 1H, C(O)CHCH3), 3.04 (bs, 1H, OH), 2.68 (s, 3H, N=C(CH3)S), 2.62 (ddd, J=15.0, 10.2, 10.1 Hz, 1H, CH2CH=CCH3), 2.45 (dd, J=14.7, 11.1 Hz, 1H, CH2COOCH), 2.38–2.24 (m, 1H), 2.28 (dd, J=14.8, 2.2 Hz, CH2COOCH), 2.22 (d, J=14.9 Hz, 1H, CH2C(CH3)=CHCH2), 2.06 (s, 3H, CH=CCH3), 1.90–1.84 (m, 1H), 1.76–1.69 (m, 1H), 1.65 (s, 3H, CH2C(CH3)=CH), 1.33 (s, 3H, C(CH3)2), 1.32–1.22 (m, 4H), 1.19 (d, J=6.8 Hz, 3H, CH(CH3)), 1.06 (s, 3H, C(CH3)2), 1.00 (d, J=7.0 Hz, 3H, CH(CH3)); 13C NMR (150.9 MHz, CDCl3) d 220.4, 170.2, 164.9, 151.8, 139.1, 138.3, 120.8, 119.1, 115.5, 78.9, 74.1, 72.3, 53.6, 41.7, 39.7, 32.6, 31.8, 31.7, 25.4, 23.0, 19.1, 18.1, 16.0, 15.8, 13.5; FAB HRMS (NBA) m/e 492.2795, M+H+ calcd for C27H41NO5S 492.2784.

Synthesis of Dihydroxy Lactone 123 as Illustrated in FIG. 16

Dihydroxy lactone 123 was prepared from bis(silylether) lactone 122 (40.0 mg, 0.055 mmol) by treatment with CF3COOH according to the same procedure described above for the preparation of 70 (FIG. 14). Obtained pure 123 (24.3 mg, 89%): Rf=0.19 (silica gel, 4% MeOH in Methylene chloride); [a]22D −61.0 (c 0.2, CHCl3); IR (thin film) nmax 3418, 2932, 1731, 1691, 1466, 1381, 1252, 1159, 1067, 1044, 1012, 978, 755 cm−1; 1H NMR (600 MHz, CDCl3) d 6.99 (s, 1H, SCH=C), 6.54 (s, 1H, CH=CCH3), 5.38 (dd, J=6.7, 3.8 Hz, 1H, CH2COOCH), 5.08 (t, J=6.9 Hz, 1H, CH3C=CHCH2), 4.32 (dd, J=10.0, 2.4 Hz, 1H, (CH3)2CCHOH), 3.65 (t, J=3.4 Hz, 1H, CHOH), 3.25 (dq, J=6.7, 3.9 Hz, 1H, C(O)CHCH3), 2.68 (s, 3H, N=C(CH3)S), 2.55–2.43 (m, 3H, CH2COOCH, C(CH3)=CHCH2), 2.40 (dd, J=15.3, 2.5 Hz, 1H, CH2COOCH), 2.17–2.10 (m, 1H, CH2C(CH3)=CH), 2.05 (s, 3H, CH=CCH3), 1.95 (ddd, J=13.4, 10.0, 3.3 Hz, 1H, CH2C(CH3)=CH), 1.70–1.57 (m, 3H), 1.57 (s, 3H, CH2C(CH3)=CH), 1.50–1.35 (m, 2H), 1.33 (s, 3H, C(CH3)2), 1.15 (d, J=6.8 Hz, 3H, CH(CH3)), 1.03 (s, 3H, C(CH3)2), 0.97 (d, J=7.0 Hz, 3H, CH(CH3)); 13C NMR (150.9 MHz, CDCl3) d 220.7, 170.7, 165.3, 152.3, 138.5, 137.4, 119.6, 119.4, 115.7, 77.7, 76.2, 71.6, 52.7, 42.7, 39.4, 39.0, 37.3, 30.7, 24.5, 20.5, 19.7, 18.7, 15.9, 15.8, 15.5, 14.3; FAB HRMS (NBA) m/e 492.2772, M+H+ calcd for C27H41NO5S 492.2784.

Synthesis of Epothilone B (2) and its α-epoxide epimer 126 as illustrated in FIG. 16

Epoxidation of Lactone 71.

Procedure A: To a solution of lactone 71 (3.0 mg, 6.1 mmol) in benzene (0.2 mL) at −10° C. was added meta-chloroperbenzoic acid (2.9 mg, 50–60% purity, 8.4–10.1 mmol, 1.4–1.6 equiv) and the reaction mixture was stirred at that temperature for 2 h at which time TLC indicated completion of the reaction. The reaction mixture was diluted with EtOAc (5 mL), washed with saturated aqueous NaHCO3 solution (2 mL), and the aqueous phase was extracted with EtOAc (3×2 mL). The combined organic layer was dried (MgSO4), filtered and concentrated. Purification by preparative thin layer chromatography (silica gel, 5% MeOH in Methylene chloride) provided a mixture of epothilone B (2) and its α-epoxy diastereoisomer 124 (2.0 mg, 66%, ca 5:1 ratio by 1H NMR), which was separated to its components by a second preparative thin layer chromatography (silica gel, 70% EtOAc in hexanes) furnishing pure epothilone B (2) (1.6 mg, 52%) as a white solid. Procedure B: To a solution of lactone 71 (5.0 mg, 10.2 mmol) in Methylene chloride (0.5 mL) at −50° C. was added dropwise a solution of dimethyldioxirane in acetone untill the starting material disappeared (TLC). The resulting solution was concentrated, and the crude product was subjected to preparative thin layer chromatography (silica gel, 5% MeOH in Methylene chloride) to give epothilone B (2) and its a-epoxy diastereoisomer 124 in ca 5:1 ratio (3.9 mg, 75%). Pure epothilone B (2) was obtained (3.1 mg, 60%) by preparative thin layer chromatography as described above. Procedure C: Lactone 71 (3.0 mg, 6.1 mmol) was epoxidised with methyl (trifluoromethyl)dioxirane according to the procedure described above for the epoxidation of 70 (FIG. 14), to yield a mixture of 2 and its α-epoxy diastereoisomer 124 in ca 5:1 ratio by 1H NMR (2.6 mg, 85% yield). The major diastereoisomer, epothilone B (2) was isolated as described above (2.1 mg, 69%). 2: Colorless crystals; mp 93° C. (crystallized in Methylene chloride/petroleum ether); Rf=0.24 (silica gel, 4% MeOH in Methylene chloride); [a]22D −34.3 (c 0.2, MeOH); IR (thin film) nmax 3436, 2954, 2931, 1731, 1684, 1455, 1373, 1290, 1249, 1184, 1143, 1043, 1049, 973, 750 cm−1; 1H NMR (600 MHz, CDCl3) d 6.97 (s, 1H, SCH═C), 6.59 (s, 1H, CH═CCH3), 5.41 (dd, J=7.8, 2.8 Hz, 1H, CH2COOCH), 4.22 (bs, 2H, (CH3)2CCHOH, OH), 3.77 (dd, J=4.3, 4.2 Hz, 1H, CHOH), 3.30 (dq, J=6.8, 4.1 Hz, 1H, C(O)CHCH3), 2.80 (dd, J=7.6, 4.7 Hz, 1H, CHOCCH3), 2.70 (s, 3H, N═C(CH3)S), 2.64 (bs, 1H, OH), 2.54 (dd, J=14.0, 10.2 Hz, 1H, CH2COOCH), 2.36 (d, J=14.0, 2.9 Hz, 1H, CH2COOCH), 2.12 (dd, J=4.7, 2.8 Hz, 1H, (CH3)COCHCH2CHO), 2.08 (s, 3H, CH═CCH3), 1.91 (ddd, J=15.4, 7.8, 7.6 Hz, 1H, (CH3)COCHCH2CHO), 1.77–1.68 (m, 3H), 1.53–1.46 (m, 2H), 1.43–1.37 (m, 2H), 1.36 (s, 3H, C(CH3)OCHCH2), 1.27 (s, 3H, C(CH3)2), 1.16 (d, J=6.9 Hz, 3H, CH(CH3)), 1.08 (s, 3H, C(CH3)2), 1.00 (d, J=7.0 Hz, 3H, CH(CH3)); 1H NMR (600 MHz, DMSO-d6) d 7.34 (s, 1H, SCH═C), 6.49 (s, 1H, CH═CCH3), 5.27 (dd, J=9.0, 2.0 Hz, 1H, CH2COOCH), 5.07 (d, J=6.9 Hz, 1H, OH), 4.45 (bs, 1H, OH), 4.08 (m, 1H, (CH3)2CCHOH), 3.47 (d, J=7.4 Hz, 1H, CHOH), 3.10 (dq, J=6.8, 6.5 Hz, 1H, C(O)CHCH3), 2.81 (dd, J=9.5, 3.3 Hz, 1H, CHOCCH3), 2.64 (s, 3H, N═C(CH3)S), 2.40–2.30 (m, 2H, CH2COOCH), 2.08 (s, 3H, CH═CCH3), 2.05 (ddd, J=15.0, 2.6, 1.0 Hz, 1H, (CH3)COCHCH2CHO), 1.83 (ddd, J=15.0, 9.3, 9.1 Hz, 1H, (CH3)COCHCH2CHO), 1.61 (m, 1H), 1.45–1.35 (m, 3H), 1.35–1.25 (m, 3H), 1.17 (s, 6H, C(CH3)OCHCH2, C(CH3)2), 1.05 (d, J=6.6 Hz, 3H, CH(CH3)), 0.87 (d, J=7.0 Hz, 3H, CH(CH3)), 0.86 (s, 3H, C(CH3)2); 13C NMR (150.9 MHz, DMSO-d6) d 218.1, 170.7, 164.8, 152.5, 137.6, 119.5, 118.0, 76.7, 75.7, 70.7, 61.6, 61.1, 53.3, 44.9, 35.6, 33.0, 32.1, 29.6, 23.0, 22.4, 22.0, 19.7, 18.8, 18.4, 16.4, 14.1; FAB HRMS (NBA/CsI) m/e 640.1725, M+Cs+ calcd for C27H41NO6S 640.1709. A natural sample of epothilone B (2) exhibited identical properties to those reported above.

Synthesis of Epothilone 125 and 126 as Illustrated in FIG. 16

Epoxidation of Lactone 123.

Procedure A: Compound 123 (5.0 mg, 10.2 mmol) was epoxidised with mCPBA according to procedure A described above for 2 to yield a mixture of 12S-epi-epothilone B (125) and its α-epoxy-diastereoisomer 126 (3.7 mg, 73% total yield, ca 4:1 by 1H NMR). Purification by preparative thin layer chromatography (silica gel, 5% MeOH in Methylene chloride) gave pure 12S-epothilone 126 (2.5 mg, 49%) as a white solid. Procedure B: The epoxidation of 123 (3.0 mg, 6.1 mmol) according to the procedure described above for 1 led to epothilones 126 and its α-epoxy diastereoisomer 126 (2.6 mg, 86% total yield, ca 1:1 ratio by 1H NMR). Preparative thin layer chromatography (silica gel, 5% MeOH in Methylene chloride) furnished pure epothilone 125 (1.3 mg, 43%) and its α-epoxy diastereoisomer 126 (1.3 mg, 43%). 125: Rf=0.55 (silica gel, 5% MeOH in Methylene chloride); [α]22D −34.5 (c 0.1, CHCl3); IR (thin film) nmax 3440, 2929, 1731, 1693, 1467, 1384, 1294, 1257, 1151, 1050, 977, 755 cm−1; 1H NMR (600 MHz, CDCl3) d 6.97 (s, 1H, SCH═C), 6.60 (s, 1H, CH═CCH3), 5.50 (dd, J=8.0, 4.0 Hz, 1H, CH2COOCH), 4.25 (dd, J=10.1, 3.2 Hz, 1H, (CH3)2CCHOH), 3.80 (bs, 1H, OH), 3.75 (dd, J=5.5, 3.6 Hz, 1H, CHOH), 3.31 (dq, J=6.7, 6.3 Hz, 1H, C(O)CHCH3), 2.88 (dd, J=6.3, 4.5 Hz, 1H, CHOCCH3), 2.69 (s, 3H, N═C(CH3)S), 2.59 (bs, 1H, OH), 2.55 (dd, J=13.5, 10.4 Hz, 1H, CH2COOCH), 2.45 (dd, J=13.5, 3.7 Hz, 1H, CH2COOCH), 2.08 (s, 3H, CH═CCH3), 2.05–1.97 (m, 3H), 1.95–1.90 (m, 1H, (CH3)COCHCH2CHO), 1.75–1.70 (m, 2H), 1.51–1.45 (m, 3H), 1.37 (s, 3H, C(CH3)OCHCH2), 1.27 (s, 3H, C(CH3)2), 1.14 (d, J=6.9 Hz, 3H, CH(CH3)), 1.04 (s, 3H, C(CH3)2), 0.95 (d, J=6.9 Hz, 3H, CH(CH3)); 13C NMR (150.9 MHz, CDCl3) d 219.6, 170.7, 164.9, 152.1, 136.6, 119.8, 116.4, 77.6, 75.9, 73.3, 61.3, 59.9, 52.9, 44.2, 38.8, 37.2, 36.4, 32.9, 31.3, 21.9, 21.3, 19.8, 19.4, 17.9, 17.4, 14.8; FAB HRMS (NBA/CsI) m/e 640.1686, M+Cs+ calcd for C27H41NO6S 640.1709.

Synthesis of α,β-Unsaturated Ester 127 as Illustrated in FIG. 17

A mixture of aldehyde 82 (5.17 g, 15.9 mmol) and stabilized ylide 83 (8.92 g, 24.0 mmol, 1.5 equiv, prepared from 4-bromo-1-butene by: (i) phosphonium salt formation; (ii) anion formation with NaHMDS; and (iii) quenching with MeOC(O)Cl as described in Murray, R. W.; Jeyaraman, R. J. Org. Chem. 1985, 50, 2847–2853) in benzene (300 mL, 0.05 M) was heated at reflux for 3 h. After cooling to 25° C., the solvent was removed under reduced pressure and the residue was subjected to flash column chromatography (silica gel, 30% ether in hexanes) to afford α,β-unsaturated ester 127 (7.15 g, 95%): Rf=0.65 (silica gel, 40% ether in hexanes); [α]22D +10.4 (c 1.4, CHCl3); IR (thin film) nmax 2939, 2856, 1715, 1644, 1504, 1464, 1437, 1365, 1284, 1252, 1209, 1076, 955, 836, 776 cm−1; 1H NMR (500 MHz, CDCl3) d 6.91 (s, 1H, SCH═C), 6.87 (d, J=7.4 Hz, 1H, CH═CCOOCH3), 6.47 (s, 1H, CH═CCH3), 5.83–5.71 (m, 1H, CH═CH2), 5.01–4.92 (m, 2H, CH═CH2), 4.19 (dd, J=7.7, 4.9 Hz, 1H, CHOSi), 3.69 (s, 3H, COOCH3), 3.05 (d, J=6.0 Hz, 2H, CH2CH═CH2), 2.67 (s, 3H, N═C(S)CH3), 2.46 (ddd, J=15.1, 7.7, 7.4 Hz, 1H, CH2CHOSi), 2.39 (ddd, J=15.0, 7.5, 5.0 Hz, 1H, CH2CHOSi), 1.99 (s, 3H, CH═CCH3), 0.86 (s, 9H, SiC(CH3)3), 0.03 (s, 3H, Si(CH3)2), −0.02 (s, 3H, Si(CH3)2); 13C NMR (125.7 MHz, CDCl3) d 167.8, 164.4, 152.8, 141.5, 140.6, 135.3, 130.7, 119.1, 115.5, 115.1, 77.6, 51.7, 36.1, 30.9, 25.7, 19.2, 18.1, 13.9, −4.7, −5.1; FAB HRMS (NBA/CsI) m/e 554.1168, M+Cs+ calcd for C22H35NO3SSi 554.1161.

Synthesis of Allylic Alcohol 128 as Illustrated in FIG. 17

Methyl ester 127 (6.1 g, 14.4 mmol) was dissolved in THF (80 mL) and cooled to −78° C. DIBAL (44.0 mL, 1 M solution in Methylene chloride, 44.0 mmol, 3.0 equiv) was added dropwise at −78° C., and the reaction mixture was stirred for 3 h. The reaction mixture was quenched with MeOH (1.0 mL) at −78° C., and then ether (100 mL) was added, followed by saturated aqueous sodium-potassium tartrate solution (10 mL). The resulting mixture was allowed to warm up to room temperature, where it was stirred for 3 h. The organic layer was separated and the aqueous phase was extracted with ether (2×50 mL). The combined organic phase was dried (MgSO4), filtered and concentrated under reduced pressure. Flash column chromatography (silica gel, 40 to 80% ether in hexanes) furnished alcohol 128 (5.58 g, 98%): Rf=0.18 (silica gel, 40% ether in hexanes); [a]22D +6.6 (c 1.1, CHCl3); IR (thin film) nmax 3380, 2928, 2855, 1637, 1505, 1464, 1386, 1253, 1185, 1074, 836, 776 cm−1; 1H NMR (600 MHz, CDCl3) d 6.88 (s, 1H, SCH═C), 6.41 (s, 1H, CH═CCH3), 5.77–5.69 (m, 1H, CH═CH2), 5.48 (dd, J=7.3, 7.2 Hz, 1H, CH═CCH2OH), 5.00 (dd, J=15.5, 3.3 Hz, 1H, CH═CH2), 4.93 (dd, J=10.0, 3.3 Hz, 1H, CH═CH2), 4.12 (dd, J=6.5, 6.4 Hz, 1H, CHOSi), 3.97 (s, 2H, CH2OH), 2.86–2.76 (m, 2 H, CH2CH═CH2), 2.65 (s, 3H, N═C(S)CH3), 2.53 (bs, 1H, OH), 2.36–2.24 (m, 2 H, CH2CHOSi), 1.94 (s, 3H, CH═CCH3), 0.86 (s, 9H, SiC(CH3)3), 0.02 (s, 3H, Si(CH3)2), −0.02 (s, 3H, Si(CH3)2); 13C NMR (150.9 MHz, CDCl3) d 164.5, 152.8, 142.0, 138.1, 123.7, 118.7, 115.2, 114.9, 78.3, 66.6, 34.7, 32.4, 25.7, 19.0, 18.1, 13.7, −4.8, −5.0; FAB HRMS (NBA) m/e 394.2232, M+H+ calcd for C21H35NO2SSi 394.2236.

Synthesis of Compound 129 as Illustrated in FIG. 17

Chlorination of Alcohol 128.

Alcohol 128 (3.00 g, 7.60 mmol) was dissolved in CCl4 (75 mL, 0.1 M) and Ph3P (4.00 g, 15.2 mmol, 2.0 equiv) was added. The reaction mixture was stirred at 100° C. for 24 h, cooled to room temperature and the solvent was removed under reduced pressure. Flash column chromatography (silica gel, 10% ether in hexanes) furnished pure 129 (2.6 g, 83%): Rf=0.50 (silica gel, 15% ether in hexanes); [a]22D +13.7 (c 1.0, CHCl3); IR (thin film) nmax 2953, 2928, 2855, 1637, 1504, 1470, 1439, 1387, 1254, 1182, 1075, 953, 917, 836, 776 cm−, ; 1H NMR (600 MHz, CDCl3) d 6.93 (s, 1H, SCH═C), 6.47 (s, 1H, CH═CCH3), 5.77–5.69 (m, 1H, CH═CH2), 5.66 (dd, J=7.5, 7.2 Hz, 1H, CH2CH═CCH2Cl), 5.07 (dd, J=17.1, 1.6 Hz, 1H, CH═CH2), 5.02 (dd, J=10.1, 1.4 Hz, 1H, CH═CH2), 4.14 (dd, J=7.2, 5.5 Hz, 1H, CHOSi), 4.02 (s, 2H, CH2Cl), 2.99–2.89 (m, 2H, CH2CH═CH2), 2.71 (s, 3H, N═C(S)CH3), 2.52–2.27 (m, 2H, CH2CHOSi), 1.99 (s, 3H, CH═CCH3), 0.88 (s, 9H, SiC(CH3)3), 0.05 (s, 3H, Si(CH3)2), 0.00 (s, 3H, Si(CH3)2); 13C NMR (150.9 MHz, CDCl3) d 164.3, 152.9, 141.8, 134.9, 134.7, 128.9, 119.0, 116.2, 115.2, 78.1, 49.9, 35.3, 32.3, 25.8, 19.2, 18.2, 13.9, −4.7, −5.0; FAB HRMS (NBA) m/e 412.1884, M+H+ calcd for C21H34ClNOSSi 412.1897.

Synthesis of Compound 130 as Illustrated in FIG. 17

Reduction of 129.

Compound 129 (2.60 g, 6.30 mmol) was dissolved in THF (60 mL, 0.1 M) and cooled to 0° C. LiEt3BH (12.6 ml, 1.0 M solution in THF, 12.6 mmol, 2.0 equiv) was added dropwise and the reaction mixture was stirred at 0° C. for 1 h. Aqueous NaOH (1.0 mL, 3.0 N) solution was added followed by addition of Et2O (150 mL). The organic phase was washed with brine (2×20 mL), dried (MgSO4) and concentrated. Flash column chromatography (silica gel, 20% ether in hexanes) furnished pure 130 (2.38 g, 99%): Rf=0.60 (silica gel, 15% ether in hexanes); [α]22D +17.1 (c 0.7, CHCl3); IR (thin film) nmax 2928, 2856, 1637, 1505, 1464, 1253, 1181, 1075, 946, 836, 776 cm−1; 1H NMR (600 MHz, CDCl3) d 6.91 (s, 1H, SCH═C), 6.45 (s, 1H, CH═CCH3), 5.77–5.68 (m, 1H, H═CH2), 5.22 (dd, J=7.3, 7.0 Hz, 1H, CH2CH═CCH3), 5.01 (dd, J=17.1, 3.2 Hz, 1H, CH═CH2), 4.96 (dd, J=10.1, 3.3 Hz, 1H, CH═CH2), 4.09 (dd, J=7.2, 5.9 Hz, 1H, CHOSi), 2.80 (dd, J=14.5, 6.5 Hz, 1H, CH2CH═CH2), 2.73–2.68 (m, 1H, CH2CH═CH2), 2.70 (s, 3H, N═C(S)CH3), 2.32–2.19 (m, 2H, CH2CHOSi), 1.99 (s, 3H, CH═CCH3), 1.66 (s, 3H, CH2CH═CCH3), 0.88 (s, 9H, SiC(CH3)3), 0.04 (s, 3H, Si(CH3)2), −0.01 (s, 3H, Si(CH3)2); 13C NMR (150.9 MHz, CDCl3) d 164.3, 153.2, 142.5, 136.0, 134.4, 122.5, 118.7, 115.1, 114.9, 78.9, 36.6, 35.3, 25.8, 23.5, 19.2, 18.2, 13.9, −4.8, −5.0; FAB HRMS (NBA) m/e 378.2279, M+H+ calcd for C21H35NOSSi 378.2287.

Synthesis of Primary Alcohol 131 as Illustrated in FIG. 17

Selective Hydroboration of Olefinic Compound 130.

Compound 130 (1.1 g, 2.91 mmol) was dissolved in THF (3.0 mL, 1.0 M) and the solution was cooled to 0° C. 9-BBN (7.0 mL, 0.5 M solution in THF, 3.5 mmol, 1.2 equiv) was added, and the reaction mixture was stirred for 2 h at 0° C. Aqueous NaOH (7.0 mL, 3 N solution, 21.0 mmol, 7.2 equiv) was added with stirring, followed by H2O2 (2.4 mL, 30%, aqueous solution). Stirring was continued for 0.5 h at 0° C., after which time the reaction mixture was diluted with ether (30 mL). The organic solution was separated and the aqueous phase was extracted with ether (2×15 mL). The combined organic layer was washed with brine (2×5 mL), dried (Na2SO4) and concentrated in vacuo. Flash column chromatography (silica gel, 50 to 80% ether in hexanes) furnished primary alcohol 131 (1.0 g, 91%): Rf=0.17 (silica gel, 50% ether in hexanes); [α]22D +3.6 (c 0.2, CHCl3); IR (thin film) nmax 3381, 2953, 2929, 2856, 1723, 1660, 1469, 1444, 1376, 1253, 1185, 1073, 941, 837, 776 cm−1; 1H NMR (600 MHz, CDCl3) d 6.91 (s, 1H, SCH═C), 6.44 (s, 1H, CH═CCH3), 5.17 (dd, J=7.0, 6.9 Hz, 1H, CH2CH═CCH3), 4.11 (dd, J=7.1, 5.7 Hz, 1H, CHOSi), 3.59 (dd, J=6.5, 6.4 Hz, 2H, CH2OH), 2.70 (s, 3H, N═C(S)CH3), 2.35–2.28 (m, 1H, CH2CHOSi), 2.27–2.20 (m, 1H, CH2CHOSi), 2.10 (dd, J=7.6, 7.5 Hz, 2H CH2CH2CH2OH), 1.98 (s, 3H, CH═CCH3), 1.67 (s, 3H, CH2CH═CCH3), 1.67–1.58 (m, 2H, CH2CH2OH), 0.88 (s, 9H, SiC(CH3)3), 0.04 (s, 3H, Si(CH3)2), −0.01 (s, 3H, Si(CH3)2); 13C NMR (150.9 MHz, CDCl3) d 164.5, 153.0, 142.7, 136.2, 122.2, 118.5, 115.0, 78.9, 62.4, 35.4, 30.7, 28.0, 25.8, 23.3, 19.2, 18.3, 14.0, −4.7, −5.0; FAB HRMS (NBA) m/e 396.2382, M+H+ calcd for C21H37NO2SSi 396.2393.

Synthesis of Iodide 81 as Illustrated in FIG. 17

Iodide 81 (1.18 g, 92%) was prepared from alcohol 131 (1.0 g, 2.53 mmol) according to the procedure described above for 94 (FIG. 12). 81: Colorless oil; Rf=0.65 (silica gel, 20% ether in hexanes); [α]22D +7.5 (c 0.8, CHCl3); IR (thin film) nmax 2955, 2930, 2855, 1504, 1462, 1444, 1376, 1360, 1253, 1183, 1074, 942, 837, 776 cm−1; 1H NMR (500 MHz, CDCl3) d 6.91 (s, 1H, SCH═C), 6.46 (s, 1H, CH═CCH3), 5.20 (dd, J=7.3, 7.1 Hz, 1H, CH2CH═CCH3), 4.09 (dd, J=7.4, 5.5 Hz, 1H, CHOSi), 3.14 (dd, J=7.1, 7.0 Hz, 2H, CH2I), 2.69 (s, 3H, N═C(S)CH3), 2.34–2.27 (m, 1H, CH2CHOSi), 2.26–2.19 (m, 1H, CH2CHOSi), 2.17–2.03 (m, 2H), 2.00 (s, 3H, CH═CCH3), 1.93–1.86 (m, 2H), 1.67 (s, 3H, CH2CH═CCH3) 0.88 (s, 9H, SiC(CH3)3), 0.04 (s, 3H, Si(CH3)2), −0.01 (s, 3H, Si(CH3)2); 13C NMR (125.7 MHz, CDCl3) d 164.2, 153.1, 142.3,–134.6, 123.1, 118.6, 115.0, 78.8, 35.4, 32.6, 31.9, 25.8, 23.4, 19.2, 18.2, 14.0, 6.5, −4.7, −5.0; FAB HRMS (NBA) m/e 506.1422, M+H+ calcd for C21H36INOSSi 506.1410.

Synthesis of Hydrazone 132 as Illustrated in FIG. 17

Alkylation of SAMP Hydrazone 80 with Iodide 81.

SAMP hydrazone 80 (337 mg, 0.2 mmol, 2.0 equiv; Aldrich) in THF (2.5 mL), was added to a freshly prepared solution of LDA at 0° C. (diisopropylamine (277 mL, 0.20 mmol, 2.0 equiv) was added to n-BuLi (1.39 mL, 1.42 M solution in hexanes, 0.20 mmol. 2.0 equiv) in 2.5 mL of THF at 0° C.] at 0° C. After stirring at that temperature for 8 h, the resulting yellow solution was cooled to −100° C., and a solution of iodide 81 (0.5 g, 0.99 mmol, 1.0 equiv) in THF (3 mL) was added dropwise over a period of 5 min. The mixture was allowed to warm to −20° C. over 10 h, and then poured into saturated aqueous NH4Cl solution (5 mL) and extracted with ether (3×25 mL). The combined organic extracts were dried (MgSO4), filtered and evaporated. Purification by flash column chromatography on silica gel (20 to 40% ether in hexanes) provided hydrazone 132 (380 mg, 70%, de >98% by 1H NMR) as a yellow oil: Rf=0.17 (silica gel, 20% ether in hexanes); [a]22D −27.8 (c 2.6, CHCl3); IR (thin film) nmax 2931, 2861, 1724, 1653, 1599, 1499, 1451, 1374, 1249, 1178, 1077, 940, 834, 774, 727, 673 cm−1; 1H NMR (500 MHz, CDCl3) d 6.91 (s, 1H, SCH=C), 6.48 (d, J=6.6 Hz, 1H, CNH), 6.44 (s, 1H, CH=CCH3), 5.12 (dd, J=7.1, 6.9 Hz, 1H, CH2CH=CCH3), 4.07 (dd, J=6.8, 6.2 Hz, 1H, CHOSi), 3.55 (dd, J=9.1, 3.7 Hz, 1H, CH2OCH3), 3.41 (dd, J=9.1, 6.9 Hz, 1 H, CH2OCH3), 3.36 (s, 3H, CH2OCH3), 3.35–3.32 (m, 2H, CH2N), 2.70 (s, 3 H, N=C(S)CH3), 2.69–2.62 (m, 1H), 2.31–2.17 (m, 3H), 2.04–1.84 (m, 5H), 1.99 (s, 3H, CH=CCH3), 1.79–1.72 (m, 1H), 1.64 (s, 3H, CH2CH=CCH3) 1.41–1.22 (m, 4H), 1.01 (d, J=6.9 Hz, CHCH3), 0.88 (s, 9H, SiC(CH3)3), 0.04 (s, 3H, Si(CH3)2), −0.01 (s, 3H, Si(CH3)2); 13C NMR (125.7 MHz, CDCl3) d 164.2, 153.1, 144.3, 142.4, 136.6, 121.5, 118.5, 114.8, 78.9, 74.7, 63.4, 59.1, 50.4, 37.0, 35.3, 35.2, 31.8, 26.4, 25.7, 25.4, 23.3, 22.0, 19.1, 18.9, 18.1, 13.8, −4.8, −5.0; FAB HRMS (NBA) m/e 548.3728, M+H+ calcd for C30H53N3O2SSi 548.3706.

Synthesis of Nitrile 66 as Illustrated in FIG. 17

Monoperoxyphthalic acid magnesium salt (MMPP·6H2O, 233 mg, 0.38 mmol, 2.5 equiv; Aldrich) was suspended in a rapidly stirred mixture of MeOH and pH 7 phosphate buffer (1:1, 3.0 mL) at 0° C. Hydrazone 132 (83 mg, 0.15 mmol, 1.0 equiv) in MeOH (1.0 mL) was added dropwise, and the mixture was stirred at 0° C. until the reaction was complete by TLC (ca 1 h). The resulting suspension was placed in a separating funnel along with ether (15 mL) and saturated aqueous NaHCO3 solution (5 mL). The organic layer was separated and the aqueous phase was extracted with ether (10 mL). The combined organic solution was washed with water (5 mL) and brine (5 mL), dried (MgSO4) and concentrated. Flash column chromatography (silica gel, 50% ether in hexanes) afforded nitrile 133 (53 mg, 80%) as a colorless oil: Rf=0.44 (silica gel, 50% ether in hexanes); [a]22D +10.3 (c 3.2, CHCl3); IR (thin film) nmax 2926, 2855, 1503, 1457, 1381, 1250, 1179, 1072, 935, 833, 773, cm−1; 1H NMR (500 MHz, CDCl3) d 6.92 (s, 1H, SCH=C), 6.45 (s, 1H, CH=CCH3), 5.18 (dd, J=7.0, 6.5 Hz, 1H, CH2CH=CCH3), 4.08 (dd, J=6.5, 6.0 Hz, 1H, CHOSi), 2.70 (s, 3H, N=C(S)CH3), 2.60–2.53 (m, 1H), 2.30–2.18 (m, 2H), 2.11–1.97 (m, 2H), 1.99 (s, 3H, CH=CCH3), 1.67 (s, 3H, CH2CH=CCH3) 1.67–1.45 (m, 4H), 1.29 (d, J=6.9 Hz, CHCH3), 0.88 (s, 9H, SiC(CH3)3), 0.04 (s, 3H, Si(CH3)2), −0.01 (s, 3H, Si(CH3)2); 13C NMR (125.7 MHz, CDCl3) d 164.3, 153.0, 142.3, 135.5, 122.8, 122.4, 118.6, 114.9, 78.4, 35.3, 33.6, 31.1, 25.7, 25.4, 25.1, 23.2, 19.1, 18.1, 17.9, 13.9, −4.8, −5.1; FAB HRMS (NBA) m/e 433.2720, M+H+ calcd for C24H40N2OSSi 433.2709.

Synthesis of Aidehyde 75 as Illustrated in FIG. 17

Nitrile 133 (53 mg, 0.12 mmol) was dissolved in toluene (2.0 mL) and cooled to −78° C. DIBAL (245 mL, 1 M solution in toluene, 0.22 mmol, 2.0 equiv) was added dropwise at −78° C. and the reaction mixture was stirred at that temperature until its completion was verified by TLC (ca 1 h). Methanol (150 mL) and aqueous HCl (150 mL, 1 N solution) were sequentially added and the resulting mixture was brought up to 0° C. and stirred at that temperature for 30 min. Ether (5 mL) and water (2 mL) were added, and the organic layer was separated. The aqueous phase was extracted with ether (2×5 mL) and the combined organic solution was washed with brine (5 mL), dried (MgSO4), filtered and concentrated under reduced pressure. Flash column chromatography (silica gel, 15% ether in hexanes) furnished pure aldehyde 75 (44 mg, 82%): Rf=0.48 (silica gel, 50% ether in hexanes); [α]22D +14.7 (c 1.7, CHCl3); IR (thin film) nmax 2915, 2859, 1721, 1500, 1455, 1381, 1251, 1183, 1070, 940, 832, 770 cm−1; 1H NMR (500 MHz, CDCl3) d 9.60 (d, J=1.9 Hz, 1H, CHO), 6.92 (s, 1H, SCH=C), 6.45 (s, 1H, CH=CCH3), 5.16 (dd, J=7.1, 7.0 Hz, 1H, CH2CH=CCH3), 4.08 (dd, J=7.0, 5.5 Hz, 1H, CHOSi), 2.70 (s, 3H, N=C(S)CH3), 2.36–2.18 (m, 3H), 2.07–2.01 (m, 2H), 1.99 (s, 3H, CH=CCH3) 1.71–1.64 (m, 1H), 1.66 (d, J=1.0 Hz, 3H, CH2CH=CCH3), 1.43–1.29 (m, 3H), 1.08 (d, J=7.0 Hz, 3H, CH3CH), 0.88 (s, 9H, SiC(CH3)3), 0.04 (s, 3H, Si(CH3)2), −0.01 (s, 3H, Si(CH3)2); 13C NMR (125.7 MHz, CDCl3) d 205.0, 164.4, 153.1, 142.3, 135.9, 122.0, 118.6, 114.9, 78.8, 46.1, 35.3, 31.7, 30.2, 25.7, 25.1, 23.3, 19.1, 18.2, 13.8, 13.2, −4.8, −5.1; FAB HRMS (NBA) m/e 436.2717, M+H+ calcd for C24H41NO2SSi 436.2706.

Synthesis of 12Z-Carboxylic Acids 119a and 119b as Illustrated in FIG. 18

Aldol Reaction of Keto Acid 76 with 12Z-aldehyde 75.

A solution of keto acid 76 (365 mg, 1.21 mmol, 1.6 equiv) in THF (5.0 mL) was reacted with 12Z-aldehyde 75. (330 mg, 0.76 mmol, 1.0 equiv) according to the same procedure as described above for the condensation of 76 and 75 to afford, after similar processing, geometrically pure 12Z-carboxylic acids 119a (207 mg, 32%) and 119b (181 mg, 28%) and recovered 76. 12Z-carboxylic acid 119a: Rf=0.56 (silica gel, 5% MeOH in Methylene chloride); [a]22D −2.9 (c 0.8, CHCl3); IR (thin film) nmax 2933, 2854, 1708, 1464, 1385, 1249, 1187, 1079, 983, 830, 773 cm−1; 1H NMR (500 MHz, CDCl3) d 6.92 (s, 1H, SCH=C), 6.58 (s, 1H, CH=CCH3), 5.15 (dd, J=7.4, 7.1 Hz, 1H, (CH3)C=CHCH2), 4.39 (dd, J=6.7, 3.0 Hz, 1H, (CH3)2CCHOSi), 4.11 (dd, J=7.3, 5.7 Hz, 1H, CH2CHOSi), 3.74 (dd, J=6.1, 1.8 Hz, 1H, CH(CH3)CHOSi), 3.13 (dq, J=7.0, 6.5 Hz, 1H, C(O)CH(CH3)), 2.70 (s, 3H, N=C(CH3)S), 2.44 (dd, J=16.4, 3.1 Hz, 1H, CH2COOH), 2.31 (dd, J=16.4, 6.8 Hz, 1H, CH2COOH), 2.28–2.04 (m, 3H, CH2C(CH3)=CH, CH2C(CH3)=CHCH2), 1.94 (s, 3H, CH=C(CH3)), 1.96–1.86 (m, 1H), 1.66 (s, 3H, CH2C(CH3)=CH), 1.47–1.31 (m, 4H), 1.17 (s, 3H, C(CH3)2), 1.12 (s, 3H, C(CH3)2), 1.21–1.09 (m, 1H), 1.08 (d, J=6.8 Hz, 3H, CH(CH3)), 0.90–0.85 (m, 30H, CH(CH3), 3×SiC(CH3)3), 0.10 (s, 3H, Si(CH3)2), 0.06 (s, 3H, Si(CH3)2), 0.05 (s, 3H, Si(CH3)2), 0.03 (s, 3H, Si(CH3)2), 0.02 (s, 3H, Si(CH3)2), −0.02 (s, 3H, Si(CH3)2); 13C NMR (125.7 MHz, CDCl3) d 218.2, 175.5, 165.0, 152.8, 143.4, 137.0, 121.6, 118.2, 114.5, 79.1, 73.1, 53.8, 44.4, 40.0, 39.2, 35.3, 32.4, 31.4, 26.2, 26.0, 25.8, 25.7, 23.5, 23.4, 18.8, 18.7, 18.4, 18.2, 16.8, 15.8, 13.9, −3.9, −4.0, −4.1, −4.6, −4.7, −5.0; FAB HRMS (NBA/CsI) m/e 984.4427, M+Cs+ calcd for C45H85NO6SSi3 984.4460. 12Z-carboxylic acid 119b: Rf=0.65 (silica gel, 5% MeOH in Methylene chloride); [a]22D +6.2 (c 0.6, CHCl3); IR (thin film) nmax 2933, 2854, 1708, 1459, 1386, 1249, 1074, 988, 830, 773 cm−1; 1H NMR (500 MHz, CDCl3) d 6.91 (s, 1H, SCH=C), 6.45 (s, 1H, CH=CCH3), 5.12 (dd, J=7.4, 6.9 Hz, 1 H, (CH3)C=CHCH2), 4.56 (dd, J=6.1, 5.6 Hz, 1H, (CH3)2CCHOSi), 4.07 (dd, J=7.6, 5.6 Hz, 1H, CH2CHOSi), 3.85 (d, J=8.4 Hz, 1H, CH(CH3)CHOSi), 3.10 (dq, J=7.1, 7.0 Hz, 1H, C(O)CH(CH3)), 2.75 (s, 3H, N=C(CH3)S), 2.43–2.10 (m, 4H), 1.96–1.88 (m, 2H), 1.91 (s, 3H, CH=C(CH3)), 1.66 (s, 3H, CH2C(CH3)=CH), 1.35–1.02 (m, 14H, CH(CH3), 2×CH2, C(CH3)2, C(CH3)2, CH(CH3)), 0.92–0.80 (m, 30H, 3×SiC(CH3)3, CH(CH3)), 0.09–0.01 (m, 18H, 3×Si(CH3)2); 13C NMR (125.7 MHz, CDCl3) d 218.1, 174.2, 165.4, 152.3, 143.7, 137.1, 121.6, 117.9, 114.4, 78.9, 72.4, 53.8, 45.8, 40.4, 38.3, 35.6, 35.3, 32.3, 26.7, 26.3, 26.2, 26.0, 25.8, 25.7, 23.9, 23.3, 18.6, 18.5, 18.4, 17.1, 13.9, 13.4, −3.4, −3.6, −4.3, −4.6, −4.7, −4.9; FAB HRMS (NBA/CsI) m/e 984.4430, M+Cs+ calcd for C45H85NO6SSi3 984.4460.

Synthesis of 12Z-Hydroxy Acid 73 as Illustrated in FIG. 18

12Z-carboxylic acid 119a (400 mg, 0.47 mmol) was converted to 12Z-hydroxy acid 73 (253 mg, 73% yield) according to the same procedure described above for 72 (FIG. 14). 73: Yellow oil; Rf=0.41 (silica gel, 5% MeOH in Methylene chloride); [a]22D −10.4 (c 0.4, CHCl3); IR (thin film) nmax 3227, 2933, 2852, 1711, 1696, 1468, 1387, 1245, 1189, 1087, 986, 834, 773 cm−1; 1H NMR (500 MHz, CDCl3) d 6.95 (s, 1H, SCH=C), 6.67 (s, 1H, CH=CCH3), 5.19 (dd, 1H, J=7.5, 7.0 Hz, CH3C=CHCH2), 4.41 (dd, J=6.0, 3.5 Hz, 1H, (CH3)2CCHOSi), 4.16 (dd, J=6.6, 6.5 Hz, 1H, CH2CHOH), 3.78 (d, J=6.9 Hz, 1H, CH(CH3)CHOSi), 3.13 (dq, J=6.9, 6.6 Hz, 1H, C(O)CHCH3), 2.72 (s, 3H, N=C(CH3)S), 2.47 (dd, J=16.2, 3.9 Hz, 1H, CH2COOH), 2.40–2.35 (m, 3H, CH2C(CH3)=CH, CH2COOH), 2.17–2.10 (m, 1H, C(CH3)=CHCH2), 2.00 (s, 3H, CH=C(CH3)), 1.99–1.93 (m, 1H, C(CH3)=CHCH2), 1.72 (s, 3H, CH2C(CH3)=CH), 1.53–1.35 (m, 5H), 1.19 (s, 3H, C(CH3)2), 1.14 (s, 3H, C(CH3)2), 1.07 (d, J=6.7 Hz, 3H, CH(CH3)), 0.94–0.84 (m, 21H, CH(CH3), SiC(CH3)3), 0.11 (s, 3H, Si(CH3)2), 0.07 (s, 6H, Si(CH3)2), 0.05 (s, 3H, Si(CH3)2); 13C NMR (125.7 MHz, CDCl3) d 217.9, 174.8, 165.1, 152.3, 142.1, 139.4, 120.2, 118.5, 115.0, 73.2, 53.8, 44.5, 40.0, 39.1, 34.1, 32.4, 31.2, 26.2, 26.1, 25.9, 23.5, 23.3, 18.9, 18.6, 18.3, 18.1, 16.8, 16.0, 14.6, −3.9, −4.1, −4.2, −4.7; FAB HRMS (NBA/CsI) m/e 870.3632, M+Cs+ calcd for C39H71NO6SSI2 870.3595.

Synthesis of Hydroxy Acid 134 as Illustrated in FIG. 18

12Z-carboxylic acid 119b (200 mg, 0.24 mmol) was converted to 12Z-hydroxy acid 134 (123 mg, 71% yield) according to the procedure described above for 72 (FIG. 14). 134: yellow oil; Rf=0.45 (silica gel, 5% MeOH in Methylene chloride); [a]22D −8.1 (c 0.3, CHCl3); IR (thin film) nmax 3227, 2933, 2862, 1711, 1691, 1463, 1382, 1250, 1189, 1082, 986, 834, 773cm−1; 1H NMR (500 MHz, CDCl3) d 6.96 (s, 1H, SCH=C), 6.61 (s, 1H, CH=CCH3), 5.15 (dd, 1H, J=7.5, 7.0 Hz, CH3C=CHCH2), 4.55 (dd, J=6.1, 3.5 Hz, 1H, (CH3)2CCHOSi), 4.12 (dd, J=8.0, 4.5 Hz, 1H, CH2CHOH), 3.86 (d, J=8.2 Hz, 1H, CH(CH3)CHOSi), 3.12 (dq, J=7.2, 7.0 Hz, 1H, C(O)CHCH3), 2.75 (s, 3H, N=C(CH3)S), 2.37–2.30 (m, 5H, CH2C(CH3)=CH, CH2COOH, C(CH3)=CHCH2), 1.98 (s, 3H, CH=C(CH3)), 1.94–1.89 (m, 1H), 1.72 (s, 3H, CH2C(CH3)=CH), 1.39–1.04 (m, 14 H, CH(CH3), CH(CH3), 2×CH2, C(CH3)2), 0.95–0.84 (m, 21H, SiC(CH3)3, CH(CH3)), 0.09 (s, 3H, Si(CH3)2), 0.08 (s, 3H, Si(CH3)2), 0.07 (s, 6H, Si(CH3)2); 13C NMR (125.7 MHz, CDCl3) d 218.6, 174.0, 165.6, 152.0, 142.4, 139.4, 120.1, 118.0, 114.7, 72.4, 53.8, 45.8, 40.4, 38.4, 35.5, 34.0, 32.1, 26.4, 26.2, 26.0, 25.9, 23.8, 23.6, 18.5, 18.4, 18.2, 17.2, 14.9, 13.2, −3.5, −3.7, −4.4, −4.8; FAB HRMS (NBA/CsI) m/e 870.3574, M+Cs+ calcd for C39H71NO6SSi2 870.3595.

Synthesis of Lactone 121 as Illustrated in FIG. 18
Macrolactonization of 12Z-hydroxy Acid 73.

12Z-hydroxy acid 73 (8.1 mg, 0.011 mmol) was cyclized according to the procedure described above for 73' (FIG. 16) to afford lactone 121 (6.1 mg, 77%).

Synthesis of Lactone 135 as Illustrated in FIG. 18
Macrolactonization of 12Z-Hydroxy Acid 134.

The macrolactonization of 12Z-hydroxy acid 134 (5.0 mg, 0.007 mmol) to lactone 135 (3.7 mg, 76%) was carried out according to the procedure described above for 73' (FIG. 16). 135: Colorless oil; Rf=0.83 (silica gel, 2% MeOH in Methylene chloride); [α]22D −31.8 (c 0.1, CHCl3); IR (thin film) nmax 2931, 2860, 1736, 1690, 1461, 1384, 1360, 1296, 1249, 1084, 985, 832, 773 cm−1; 1H NMR (600 MHz, CDCl3) d 6.98 (s, 1H, SCH=C), 6.45 (s, 1H, CH=CCH3), 5.07–5.21 (m, 2H, CH3C=CHCH2, CH2COOCH), 4.32 (dd, J=6.8, 5.0 Hz, 1H, CHOSi), 4.05 (d, J=5.7 Hz, 1H, CHOSi), 3.17 (dq, J=7.0, 6.8 Hz, 1H, C(O)CHCH3), 2.70 (s, 3H, N=C(CH3)S), 2.57–2.52 (m, 1H), 2.29 (dd, J=14.4, 4.6 Hz, 1H, CH2COOCH), 2.27–2.13 (m, 1H), 2.25 (dd, J=14.5, 7.0 Hz, 1H, CH2COO), 2.20–2.15 (m, 1H), 2.14 (s, 3H, CH=C(CH3)), 1.88–1.82 (m, 1H), 1.57–1.52 (m, 2H), 1.47–1.38 (m, 3H), 1.30 (s, 3H, C(CH3)2), 1.11 (d, J=7.2 Hz, 3H, CH(CH3)), 1.08 (s, 3H, C(CH3)2), 0.91 (s, 9H, SiC(CH3)3), 0.89–0.82 (bs, 12H, SiC(CH3)3, CH(CH3)), 0.11 (s, 3H, Si(CH3)2), 0.09 (s, 3H, Si(CH3)2), 0.06 (s, 3H, Si(CH3)2), −0.03 (s, 3H, Si(CH3)2); 13C NMR (150.9 MHz, CDCl3) d 220.2, 170.9, 164.8, 153.1, 140.0, 137.6, 120.2, 118.9, 116.3, 79.3, 74.0, 53.3, 48.0, 41.2, 39.7, 34.9, 31.4, 31.3, 26.6, 26.1, 25.9, 25.3, 23.9,. 19.0, 18.5, 18.4, 18.1, 16.2, 14.9, 13.8, −3.9, −4.4, −4.6, −4.9; FAB HRMS (NBA/CsI) m/e 852.3451, M+Cs+ calcd for C39H69NO5SSi2 852.3489.

Synthesis of Ketone 69 as Illustrated in FIG. 19

To a solution of aldehyde 87 (1.3 g, 4.53 mol) in THF (20 mL) at −78° C. was added dropwise lithium tri-tert-butoxyaluminohydride (4.98 mL, 1.0 M solution in THF, 4.98 mmol, 1.1 equiv). After 5 min, the reaction mixture was brought up to 0° C. and stirred at that temperature for 15 min, before quenching with saturated aqueous solution of sodium-potassium tartrate (25 mL). The aqueous phase was extracted with ether (3×20 mL) and the combined organic layer was dried (MgSO4), filtered and concentrated. The crude primary alcohol so obtained was dissolved in Methylene chloride (25 mL) and cooled to 0° C. Et3N (2.5 mL, 15.85 mmol, 3.5 equiv), 4-DMAP (60 mg, 0.09 mmol, 0.02 equiv) and tert-butyldimethylsilyl chloride (2.0 g, 13.59 mmol, 3.0 equiv) were added. The reaction mixture was allowed to stir at 0° C. for 2 h, then at 25° C. for 10 h. MeOH (5 mL) was added and the solvents were removed under reduced pressure. Ether (100 mL) was added followed by saturated aqueous NH4Cl solution (25 mL) and the organic phase was separated. The aqueous phase was extracted with ether (2×50 mL) and the combined organic solution was dried (MgSO4), filtered and concentrated under reduced pressure. Purification by flash column chromatography (silica gel, 5% ether in hexanes) provided pure bis (silylether) 136 (1.26 g, 70% yield from 20): Rf=0.67 (silica gel, 20% ether in hexanes); [a]22D −7.3 (c 1.8, CHCl3); IR (thin film) nmax 2941, 2856, 1701, 1466, 1388, 1252, 1095, 1024, 946, 832, 775 cm−1; 1H NMR (500 MHz, CDCl3) d 4.06 (dd, J=8.0, 3.0 Hz, 1H, CHOSi), 3.65–3.56 (m, 2H, CH2OSi), 2.56 (dq, J=18.5, 7.0 Hz, 1H, CH2CH3), 2.46 (dq, J=18.5, 7.0 Hz, 1H, CH2CH3), 1.56–1.43 (m, 2H, CH2CH2OSi), 1.11 (s, 3H, C(CH3)2), 1.04 (s, 3H, C(CH3)2), 0.98 (t, J=7.0 Hz, 3H, CH3CH2), 0.88 (s, 9H, SiC(CH3)3), 0.87 (s, 9H, SiC(CH3)3), 0.09 (s, 3H, Si(CH3)2), 0.04 (s, 3H, Si(CH3)2), 0.03 (s, 3H, Si(CH3)2), 0.02 (s, 3H, Si(CH3)2); 13C NMR (125.7 MHz, CDCl3) d 215.5, 73.2, 59.9, 52.9, 37.1, 31.4, 25.9, 25.7, 22.0, 19.8, 18.2, 18.1, 7.6, −4.1, −4.2, −5.4, −5.5; FAB HRMS (NBA) m/e 403.3075, M+H+ calcd for C21H46O3Si2 403.3064.

Synthesis of tris(Silylethers) 137 and 138 as Illustrated in FIG. 19

Aldol Reaction of Ketone 136 with Aldehyde 75.

A solution of ketone 136 (270 mg, 0.67 mmol, 1.2 equiv) in THF (1.5 mL) was added dropwise to a freshly prepared solution of LDA [diisopropylamine (94 mL, 0.67 mmol) was added to n-BuLi (0.43 mL, 1.6 M solution in hexanes, 0.67 mmol) in 2.5 mL of THF at 0° C.] in THF (2.5 mL) at −78° C. After stirring for 15 min at −78° C., the solution was allowed to warm to −40° C. over a period of 1 h. The reaction mixture was cooled to −78° C., and a solution of aldehyde 8 (244 mg, 0.56 mmol, 1.0 equiv) in THF (1.0 mL) was added dropwise. The resulting mixture was stirred for 15 min at −78° C., and then quenched by dropwise addition of saturated aqueous NH4Cl solution (2 mL). The aqueous phase was extracted with ether (3×5 mL) and the combined organic layer was dried (MgSO4) and concentrated. Purification by flash column chromatography (silica gel, 20% ether in hexanes) provided a mixture of aldol products 137:138 (354 mg (85%) of ca 3:1 by 1H NMR). Separation of these diastereoisomers was carried out by preparative thin layer chromatography (silica gel, 20% ether in hexanes) leading to pure 137 (270 mg, 64%) and 138 (84 mg, 20%). 137: Colorless oil; Rf=0.40 (silica gel, 20% ether in hexanes); [a]22D −17.5 (c 0.5, CHCl3); IR (thin film) nmax 3490, 2932, 2873, 1683, 1463, 1385, 1249, 1089, 840, 775cm−1; 1H NMR (500 MHz, CDCl3) d 6.89 (s, 1H, SCH=C), 6.44 (s, 1H, CH=CCH3), 5.12 (dd, J 7.1, 7.0 Hz , 1H, C(CH3)=CHCH2), 4.08 (dd, J=6.8, 6.5 Hz, 1H, (CH3)2CCHOSi), 3.89 (dd, J=7.6, 2.7 Hz, 1H, CH2CHOSi), 3.69–3.65 (m, 1H, CH(CH3)CHOH), 3.59 (t, J=7.5 Hz, 2H, CH2OSi), 3.32–3.27 (m, 1H, C(O)CH(CH3)), 2.68 (s, 3H, N=C(CH3)S), 2.30–2.19 (m, 2H, C(CH3)=CHCH2), 2.10–1.90 (m, 2H, CH2C(CH3)=CH), 1.98 (s, 3H, CH=C(CH3)), 1.65 (s, 3H, C(CH3)=CHCH2), 1.80–1.46 (m, 5H), 1.34–1.25 (m, 2H), 1.19 (s, 3H, C(CH3)2), 1.07 (s, 3H, C(CH3)2), 1.01 (d, J=6.8 Hz, 3H, CH(CH3)), 0.89 (s, 18H, 2×SiC(CH3)3), 0.87 (s, 9H, SiC(CH3)3), 0.81 (d, J=6.8 Hz, 3H, CH(CH3)), 0.10 (s, 3H, Si(CH3)2), 0.08 (s, 3H, Si(CH3)2), 0.03 (s, 3H, Si(CH3)2), 0.02 (s, 6H, Si(CH3)2), −0.01 (s, 3H, Si(CH3)2); 13C NMR (125.7 MHz, CDCl3) d 222.0, 164.1, 153.1, 142.4, 136.7, 121.3, 118.5, 114.7, 78.9, 74.7, 74.0, 60.3, 53.8, 41.2, 37.7, 35.9, 32.8, 32.5, 32.2, 26.0, 25.9, 25.8, 25.0, 24.9, 23.5, 22.8, 20.4, 19.0, 18.2, 18.1, 18.0, 15.2, 13.8, 9.5, −3.8, −4.2, −4.8, −5.1, −5.4; FAB HRMS (NBA/CsI) m/e 970.4620, M+Cs+ calcd for C45H87NO5SSi3 970.4667. 138: Colorless oil; Rf=0.33 (silica gel, 20% ether in hexanes); IR (thin film) nmax 3490, 2932, 2873, 1683, 1463, 1385, 1249, 1089, 840, 775 cm−1; 1H NMR (500 MHz, CDCl3) d 6.90 (s, 1H, SCH=C), 6.44 (s, 1H, CH=CCH3), 5.16–5.12 (m, 1H, C(CH3)=CHCH2), 4.09–4.05 (m, 1H, (CH3)2CCHOSi), 3.65–3.58 (m, 3H, CH2CHOSi, CH2OSi), 3.42–3.38 (m, 1H, CH(CH3)CHOH), 3.24–3.19 (m, 1H, C(O)CH(CH3)), 2.69 (s, 3H, N=C(CH3)S), 2.31–2.18 (m, 2H, C(CH3)=CHCH2), 1.98 (s, 3H, CH=C(CH3)), 1.99–1.88 (m, 2H, CH2C(CH3)=CH), 1.67 (s, 3H, C(CH3)=CHCH2), 1.55–1.40 (m, 5H), 1.35–1.25 (m, 2H), 1.20 (s, 3H, C(CH3)2), 1.13 (s, 3H, C(CH3)2), 1.09 (d, J=7.0 Hz, 3H, CH(CH3)), 0.95 (d, J=7.0 Hz, 3H, CH(CH3)), 0.88 (s, 18H, 2×SiC(CH3)3), 0.87 (s, 9H, SiC(CH3)3), 0.10 (s, 3H, Si(CH3)2), 0.05 (s, 3H, Si(CH3)2), 0.04 (s, 3H, Si(CH3)2), 0.03 (s, 6H, Si(CH3)2), −0.01 (s, 3H, Si(CH3)2); FAB HRMS (NBA) m/e 838.5653, M+Cs+ calcd for C45H87NO5SSi3 838.5691.

Synthesis of tetra(Silylether) 139 as Illustrated in FIG. 19

Compound 137 (275 mg, 0.33 mmol) was dissolved in Methylene chloride (5.0 mL), cooled to 0° C. and treated with 2,6-lutidine (76 mL, 0.66 mmol, 2.0 equiv) and tert-butyldimethylsilyl trifluoromethanesulfonate (88 mL, 0.39 mmol, 1.2 equiv). After stirring for 2 h at 0° C., the reaction mixture was quenched with aqueous HCl (5 mL, 1.0 N solution) and the aqueous phase was extracted with Methylene chloride (3×5 mL). The combined organic solution was washed with brine (5 mL), dried (MgSO4) and concentrated under reduced pressure. Purification by flash column chromatography (silica gel, 3% ether in hexanes) provided tetra(silylether) 139 (300 mg, 96%) as a colorless oil. 139: Rf=0.56 (silica gel, 10% ether in hexanes); [a]22D −10.8 (c 0.5, CHCl3); IR (thin film) nmax 2919, 2872, 1690, 1461, 1384, 1361, 1249, 1085, 985, 838, 773, 732, 667 cm−1; 1H NMR (500 MHz, CDCl3) d 6.88 (s, 1H, SCH=C), 6.43 (s, 1H, CH=CCH3), 5.13 (dd, J=7.1, 7.0 Hz, 1H, C(CH3)=CHCH2), 4.08 (dd, J=6.8, 6.7 Hz, 1H, (CH3)2CCHOSi), 3.89 (dd, J=7.6, 2.7 Hz, 1H, CH2CHOSi), 3.77 (dd, J=6.7, 1.0 Hz, 1H, CH(CH3)CHOSi), 3.67–3.62 (m, 1H, CH2OSi), 3.58–3.53 (m, 1H, CH2OSi), 3.14 (dd, J=6.8, 6.7 Hz, 1H, C(O)CH(CH3)), 2.68 (s, 3H, N=C(CH3)S), 2.29–2.17 (m, 2H, C(CH3)=CHCH2), 1.98 (s, 3H, CH=C(CH3)), 1.97–1.89 (m, 2H, CH2C(CH3)=CH), 1.64 (s, 3H, C(CH3)=CHCH2) 1.50–1.45 (m, 5H), 1.34–1.23 (m, 2H), 1.20 (s, 3H, C(CH3)2), 1.02 (d, J=6.8 Hz, 3H, CH(CH3)), 1.00 (s, 3H, C(CH3)2), 0.88–0.86 (m, 39H, CH(CH3), 4×SiC(CH3)3), 0.08 (s, 3H, Si(CH3)2), 0.07 (s, 3H, Si(CH3)2), 0.04 (s, 3H, Si(CH3)2), 0.03 (s, 3H, Si(CH3)2), 0.02 (s, 6H, Si(CH3)2), 0.01 (s, 3H, Si(CH3)2), −0.02 (s, 3H, Si(CH3)2); 13C NMR (125.7 MHz, CDCl3) d 218.2, 164.2, 153.2, 142.4, 136.6, 121.5, 118.5, 114.9, 78.8, 77.3, 73.9, 60.9, 53.6, 44.9, 38.8, 37.9, 35.2, 32.4, 30.9, 26.2, 26.1, 25.9, 24.4, 23.4, 19.2, 19.1, 18.5, 18.3, 18.2, 18.1, 17.5, 13.9, −3.7, −3.8, −4.0, −4.7, −4.9, −5.2, −5.3; FAB HRMS (NBA) m/e 952.6515, M+H+ calcd for C51H101NO5SSi4 952.6556.

Synthesis of Alcohol 140 as Illustrated in FIG. 19

Alcohol 140 (200 mg, 85%) was obtained from compound 139 (264 mg, 0.28 mmol) according to the procedure described above for 102. 140: Colorless oil; Rf=0.25 (silica gel, 20% ether in hexanes); [a]22D −9.3 (c 0.2, CHCl3); IR (thin film) nmax 3392, 2939, 2865, 1689, 1463, 1378, 1357, 1252, 1083, 988, 867, 835, 772, 730 cm−1; 1H NMR (500 MHz, CDCl3) d 6.90 (s, 1H, SCH=C), 6.44 (s, 1H, CH=CCH3), 5.14 (dd, J=7.0, 6.9 Hz, 1H, C(CH3)=CHCH2), 4.10–4.05 (m, 2H, (CH3)2CCHOSi, CH2CHOSi), 3.78 (dd, J=7.0, 1.0 Hz, 1H, CH(CH3)CHOSi), 3.63 (t, J=7.0 Hz, 2H, CH2OH), 3.11 (dd, J=7.0, 6.8 Hz, 1H, C(O)CH(CH3)), 2.70 (s, 3H, N=C(CH3)S), 2.27–2.19 (m, 2H, C(CH3)=CHCH2), 1.99 (d, J=1.0 Hz, 3H, CH=C(CH3)), 2.10–1.90 (m, 2H, CH2C(CH3)=CH), 1.65 (s, 3H, C(CH3)=CHCH2), 1.50–1.39 (m, 2H), 1.36–1.29 (m, 3H), 1.21 (s, 3H, C(CH3)2), 1.20–1.10 (m, 2H), 1.05 (s, 3H, C(CH3)2), 1.04 (d, J=6.8 Hz, 3H, CH(CH3)), 0.91–0.87 (m, 30H, CH(CH3), 3×SiC(CH3)3), 0.11 (s, 3H, Si(CH3)2), 0.07 (d, 3H, Si(CH3)2), 0.06 (s, 6H, Si(CH3)2), 0.04 (s, 3H, Si(CH3)2), −0.01 (s, 3H, , Si(CH3)2); 13C NMR (125.7 MHz, CDCl3) d 219.5, 164.2, 153.1, 142.4, 136.6, 121.5, 118.5, 114.8, 78.8, 77.4, 72.9, 60.1, 53.6, 45.8, 44.9, 38.6, 38.2, 35.2, 32.4, 30.6, 26.1, 25.9, 24.7, 23.4, 19.1, 18.4, 18.1, 18.0, 17.6, 15.5, 13.8, −3.7, −3.8, −4.0, −4.7, −5.1; FAB HRMS (NBA/CsI) m/e 970.4694, M+Cs+ calcd for C45H87NO5SSi3 970.4667.

Synthesis of Aldehyde 141 as Illustrated in FIG. 19

Oxidation of Alcohol 140.

To a solution of oxalyl chloride (54 mL, 0.61 mmol, 2.0 equiv) in Methylene chloride (5.0 mL) was added dropwise DMSO (86 mL, 1.21 mmol, 4.0 equiv) at −78° C. After stirring for 15 min at −78° C., a solution of alcohol 73 (255 mg, 0.305 mmol, 1.0 equiv) in Methylene chloride (2.0 mL) was added dropwise at −78° C. over a period of 5 min. The solution was stirred at −78° C. for 30 min, and then Et3N (250 mL, 1.82 mmol, 6.0 equiv) was added. The reaction mixture was allowed to warm to 0° C. over a period of 30 min and then ether (20 mL) was added, followed by saturated aqueous NH4Cl solution (10 mL). The organic phase was separated and the aqueous phase was extracted with ether (2×10 mL). The combined organic solution was dried (MgSO4), filtered and concentrated under reduced pressure. Purification by flash column chromatography (silica gel, 20% ether in hexanes) provided aldehyde 141 (241 mg, 95%) as a colorless oil. 141: Rf=0.47 (silica gel, 20% ether in hexanes); [a]22D −12.0 (c 0.1, CHCl3); IR (thin film) nmax 2943, 2849, 1725, 1690, 1461, 1384, 1249, 1079, 985, 832, 773 cm−1; 1H NMR (500 MHz, CDCl3) d 9.74 (m, 1H, CHO), 6.89 (s, 1H, SCH=C), 6.43 (s, 1H, CH=CCH3), 5.14 (dd, J=7.1, 7.0 Hz, 1H, C(CH3)=CHCH2), 4.48–4.44 (m, 1H, (CH3)2CCHOSi), 4.07 (dd, J=6.1, 5.3 Hz, 1H, CH2CHOSi), 3.75 (dd, J=7.4, 1.0 Hz, 1H, CH(CH3)CHOSi), 3.11 (dd, J=7.0, 6.7 Hz, 1H, C(O)CH(CH3)), 2.69 (s, 3H, N=C(CH3)S), 2.50 (ddd, J=16.6, 4.5, 1.0 Hz, 1H, CH2CHO), 2.37 (ddd, J=16.6, 3.2, 1.0 Hz, 1H, CH2CHO), 2.28–2.16 (m, 2H, C(CH3)=CHCH2), 1.97 (s, 3H, CH=C(CH3)), 1.97–1.89 (m, 2H, CH2C(CH3)=CH), 1.64 (s, 3H, C(CH3)=CHCH2), 1.50–1.25 (m, 5H), 1.22 (s, 3H, C(CH3)2), 1.05 (s, 3H, C(CH3)2), 1.01 (d, J=6.9 Hz, 3H, CH(CH3)), 0.89–0.84 (m, 30H, CH(CH3), 3×SiC(CH3)3), 0.08 (s, 3H, Si(CH3)2), 0.04 (s, 6H, Si(CH3)2), 0.03 (s, 3H, Si(CH3)2), 0.02 (s, 3H, Si(CH3)2), −0.02 (s, 3H, Si(CH3)2); 13C NMR (125.7 MHz, CDCl3) d 218.5, 201.0, 164.3, 153.2, 142.7, 136.7, 121.5, 118.5, 114.8, 78.9, 77.7, 71.3, 53.4, 45.1, 38.7, 35.3, 32.5, 30.7, 26.2, 25.9, 25.8, 24.1, 23.5, 19.1, 18.7, 18.6, 18.5, 17.7, 15.6, 13.9, −3.6, −3.7, −4.1, −4.5, −4.7, 5.0; FAB HRMS (NBA) m/e 836.5500, M+H+ calcd for C45H85NO5SSi3 836.5535.

Synthesis of Carboxylic Acid 119 as Illustrated in FIG. 19

Oxidation of Aldehyde 141.

Aldehyde 141 (224 mg, 0.29 mmol), tBuOH (5.0 mL), isobutylene (5.0 mL, 2 M solution in THF, 10.0 mmol), H2O (1.0 mL), NaClO2 (90 mg, 0.86 mmol, 3.0 equiv) and NaH2PO4 (60 mg, 0.43 mmol, 1.5 equiv) were combined and stirred at room temperature for 1 h. The reaction mixture was concentrated under reduced pressure and the residue was subjected to flash column chromatography (silica gel, 6% MeOH in Methylene chloride) to afford carboxylic acid 52 (220 mg, 90%) whose spectroscopic data were identical to those exhibited by 119 obtained above.

Selected physical data for compound 158: 1H NMR (400 MHz, CDCl3) d 6.95 (s, 1H, ArH), 6.59 (s, 1H, ArCH=C(CH3)), 5.44 (ddd, J=10.5, 10.5, 4.5 Hz, 1H, CH=CHCH2), 5.36 (ddd, J=10.5, 10.5, 5.0 Hz, 1H, CH=CHCH2), 5.28 (d, J=9.4 Hz, 1H, CO2CH), 4.23 (d, J=11.1 Hz, 1H, (CH3)2CCH(OH)), 3.72 (m, 1H, CHOH(CHCH3)), 3.43–3.37 (m, 1H, OH), 3.14 (q, J=6.7 Hz, 1H, CH3CH(C=O)), 3.05 (bs, 1H, OH), 2.72–2.63 (m, 1H), 2.69 (s, 3H, CH3Ar), 2.48 (dd, J=14.8, 11.3 Hz, 1H, CH2COO), 2.33 (dd, J=14.8, 2.0 Hz, 1H, CH2COO), 2.30–2.13 (m, 2 H) 2.07 (s, 3H, ArCH=CCH3), 2.07–1.98 (m, 1H), 1.80–1.60 (m, 2H), 1.32 (s, 3H, C(CH3)2), 1.36–1.13 (m, 3H), 1.17 (d, J=6.8 Hz, 3H, CH3CH(C=O)), 1.06 (s, 3H, C(CH3)2), 0.99 (d, J=7.0 Hz, 3H, CH3CHCH2); 13C NMR (150.9 MHz, CDCl3) d 220.6, 170.4, 165.0 151.9, 138.7, 133.4, 125.0, 119.4, 115.8, 78.4, 74.1, 72.3, 53.3, 41.7, 39.2, 38.5, 32.4, 31.7, 27.6, 27.4, 22.7, 19.0, 18.6, 15.9, 15.5, 13.5; IR (thin film) nmax 3453, 2929, 1733, 1686, 1506, 1464, 1250, 978 cm−1; [a]22D −80.2 (c 1.36, CHCl3); HRMS (FAB), calcd for C26H39CsNO5S (M+Cs+) 610.1603, found 610.1580.

Synthesis of aldehyde 149 as illustrated in FIG. 21

Step 1) A solution of (R)-3-bromo-2-methyl-1-propanol (Aldrich) (6.50 g, 42.4 mmol, 1.0 equiv.) in DMF (30 mL) at 0° C. was treated with t-butylchlorodimethylsilane (8.23 g, 54.6 mmol, 1.3 equiv.) and imidazole (4.32 g, 63.6 mmol, 1.5 equiv.). After stirring for 90 min at 0° C., the reaction mixture was diluted with Et2O (250 mL) and poured in a 1 M HClaq. solution (150 mL). The organic phase was separated, washed with a 1 M HClaq. solution (2×150 mL), brine (150 mL), dried over MgSO4 and concentrated in vacuo. Flash chromatography (silica gel, 4% Et2O in hexane) afforded 11.2 g (99% yield) of pure compound as a colorless oil.

Step 2) A solution of above compound (11.2 g, 42.0 mmol, 1.0 equiv.) in acetone (200 mL) was treated with sodium iodide (18.9 g, 126 mmol, 3.0 equiv.) and refluxed for 15 h. The reaction mixture was then diluted with a 1:1 (v/v) solution of Et2O/hexane (400 mL) and poured in a H2O (250 mL). The organic phase was separated, washed with brine (2×250 mL), dried over MgSO4 and concentrated in vacuo. Flash chromatography (silica gel, 4% Et2O in hexane) afforded 12.7 g (96% yield) of pure product as a colorless oil.

Step 3) A 0.01 M Li2CuCl4 solution in THF was prepared by mixing LiCl (85 mg, 2.0 mmol, 2.0 equiv.) and CuCl2 (136 mg, 1.0 mmol, 1.0 equiv.) in THF (100 mL). Above compound made in step 2 (12.7 g, 40.44 mmol, 1.0 equiv.) was dissolved in THF (25 mL), cooled to 0° C. and treated with a solution of 3-butenylmagnesium bromide (0.5 M in THF, 100 mL, 50.0 mmol, 1.25 eqiv.), followed by the Li2CuCl4 solution (40.0 mL, 0.40 mmol, 0.01 equiv.). The reaction mixture was stirred at 0° C. for 1 h then diluted with Et2O (500 mL) and poured in a 1 M HClaq. (250 mL). The organic phase was separated, washed with brine (2×250 mL), dried over MgSO4 and concentrated in vacuo. Flash chromatography (silica gel, 4% Et2O in hexane) afforded 9.3 g (93% yield) of olefin 1003 as a colorless oil.

Step 4) Olefin made in step 3 (4.0 g, 16.4 mmol) was cooled to −78° C. A gentle stream of ozone was passed through this solution until it turned deep blue. The reaction mixture was then allowed to warm up to room temperature and excess ozone was discharged by sparging argon through the solution. The reaction mixture was then treated with Me2S (20 mL), Et3N (10 mL) and MeOH (20 mL). This mixture was stirred at 23° C. for 1 h then diluted with Et2O (300 mL) and poured in a 1M HClaq. (250 mL). The organic phase was separated, washed with 1 M HClaq. (2×250 mL), dried over MgSO4 and concentrated in vacuo. Flash chromatography (silica gel, 8% Et2O in hexane) afforded 3.9 g (96% yield) of a pure colorless oil of compound 149.

Synthesis of Phosphonium Resin 147 as Illustrated in FIG. 21

Step 1) Alkylation of Merrifield Resin: A solution of 1,4-butanediol (7.18 g, 80.0 mmol, 5.0 equiv.) in DMF (600 mL) was cooled to 0° C. and sodium hydride (60%, 3.20 g, 80.0 mmol, 5.0 equiv.) was added. The reaction mixture was stirred at 0° C. for 2 h and Merrifield resin (40.0 g, 16.0 mmol, 1.0 equiv.) followed by n-Bu4NI (0.58 g, 1.60 mmol, 0.1 equiv.) were added. The reaction mixture was stirred at 23° C. for 20 h, then poured into a frit and the polymer was-washed with MeOH (2×500 mL), DMF (500 ml), H2O at 80° C. (500 mL), DMF (500 ml), MeOH (500 mL), CH2Cl2 (500 mL), Et2O (2×300 mL). The resin was dried under high vacuum to a constant weight of 40.8 g.

Step 2) Conversion of alcohol resin. A suspension of resin from above step 1 (40.8 g, 16.0 mmol, 1.0 equiv.) in $CH_2Cl_2$ (700 mL) at 23° C. was treated with Ph3P (20.9 g, 80.0 mmol, 5.0 equiv.), imidazole (6.46 g, 80.0 mmol, 5.0 equiv.) and iodine (16.0 g, 64.0 mmol, 4.0 equiv.). The reaction mixture was stirred at 23° C. for 3 h then poured into a frit and the polymer was washed with CH2Cl2 (500 mL), MeOH (500 mL), CH2Cl2 (500 mL), MeOH (500 mL), CH2Cl2 (500 mL), Et2O (2×300 mL). The resin was dried under high vacuum to a constant weight of 42.6 g.

Step 3) Reaction of iodo resin formed in step 2 with $Ph_3P$. A suspension of iodo resin (42.6 g, 16.0 mmol, 1.0 equiv.) in DMF (200 mL) at 23° C. was treated with Ph3P (41.9 g, 160 mmol, 10 equiv.). The reaction mixture was stirred at 90° C. for 12 h then poured into a frit and the polymer was washed with DMF at 80° C. (3×500 mL), CH2Cl2 (500 mL), DMF (500 mL), Et2O (3×500 mL). The resin was dried under high vacuum to a constant weight of 46.61 g.

Synthesis of Ylide Resin 148 as Illustrated in FIG. 21

Deprotonation of Phosphonim Resin 147:

A suspension of resin 147 (15.0 g, 5.11 mmol, 1.0 equiv.) in a mixture of DMSO (50 mL) THF (35 mL) at 23° C. was treated with a 1 M solution of NaHMDS in THF (15.3 mL, 15.3 mmol, 3.0 equiv.). The reaction mixture was stirred at 23° C. for 12 h then canulated into a Schlenk frit and the polymer was washed under argon with THF (3×100 mL).

Synthesis of Resin 150 as Illustrated in FIG. 21
Wittig Reaction of Ylide Resin 148 with Aldehyde 149 (vida supra).

A solution of aldehyde 149 (2.50 g, 10.22 mmol, 2.0 equiv.) in THF (25 mL) was cooled at −78° C. and added to the freshly prepared resin 148 (5.11 mmol, 1.0 equiv.) via canula. The resulting suspension was shaken at 23° C. for 3h and the supernatant was filtered off. The polymer was washed with THF (100 ml), MeOH (100 mL), CH2Cl2 (100 mL), MeOH (100 mL), CH2Cl2 (100 mL), Et2O (2×100 mL). The resin was dried under high vacuum to a constant weight of 14.12 g.

Synthesis of Resin 145 as Illustrated in FIG. 21

Step 1) Desilylation of resin 150 with HF.Pyridine complex. Resin 150 (14.0 g, 5.05 mmol, 1.0 equiv.) was suspended in THF (135 mL) and treated at 0° C. with HF.Pyridine complex (15 mL). The mixture was allowed to warm to 23° C. and shaken for 12 h. The suspension was poured into a frit and the polymer was filtered, washed with THF (100 mL), CH2Cl2 (100 mL), MeOH (100 mL), CH2Cl2 (100 mL), Et2O (2×100 mL) and dried under high vacuum to give 13.42 g of deprotected resin.

Step 2) Swern oxidation of deprotected resin. To an Oxalyl Chloride (2.56 g, 1.76 mL, 20.0 mmol, 4.0 equiv.) solution in CH2Cl2 (50 mL) at −78° C., was added dropwise DMSO (3.12 g, 2.84 mL, 40.0 mmol, 8.0 equiv.). The solution was stirred at −78° C. for 1 h and canulated into a suspension of resin (13.26 g, 5.0 mmol, 1.0 equiv.) in CH2Cl2 , previously cooled to −78° C. The resulting mixture was stirred for an additional hour and treated with Et3N (6.25 g, 8.0 mL, 62.5 mmol, 12.5 equiv.), allowed to warm to 23° C. and stirred for 1 h. The mixture was filtered and the polymer washed successively with CH2Cl2 (250 mL), MeOH (250 mL), CH2Cl2 (250 mL), Et2O (2×300 mL), dried under high vacuum to afford 13.25 g of resin 145.

Synthesis of Resin 151 as Illustrated in FIG. 21

Step 1) Enolate formation. To a precooled solution of LDA (6.60 mmol, 4.4 equiv.) obtained by treating Duisopropyl amine (0.92 ml, 6.60 mmol, 4.4 equiv.) in THF (25 mL) at 0° C. with n-butyllithium (1.6 M solution in THF, 4.12 mL, 6.60 mmol, 4.4 equiv.) was added a solution of ketoacid 144 (vida supra) (0.93 g, 3.0 mmol, 2.0 equiv.) in THF (25 mL) at −78° C. via canula. The solution was allowed to warm to −40° C. and stirred for 1 h.

Step 2) Aldol reaction. A suspension of resin 145(4.0 g, 1.50 mmol, 1.0 equiv.), ZnCl2 (1.0 M solution in Et2O, 3.0 mL, 3.0 mmol, 2.0 equiv.) in THF (25 mL), was treated at −78° C. with the enolate solution described above. The suspension was allowed to warm to −40° C., stirred for 2 h, quenched with saturated NH4Claq (8 mL) and neutralised at 23° C. with AcOH (0.76 mL, 13.2 mmol, 8.8 equiv). The mixture was poured into a frit, the polymer was washed with THF (100 mL), Et2O (100 mL), CH2Cl2 (100 mL), H2O (100 mL), MeOH (100 mL), CH2Cl2 (100 mL), 1% TFA v/v in CH2Cl2 (3×75 mL), CH2Cl2 (2×100 mL), Et2O (2×100 mL) and dried under vacuum to afford 1.96 of resin 151.

Synthesis of Resin 152 as Illustrated in FIG. 21
Esterification of Resin 151 with Alcohol 143.

A mixture of resin 151 (1.40 g, 0.46 mmol, 1.0 equiv.), alcohol 143 (vida supra) 0.49 g, 2.31 mmol, 5.0 equiv.), 4-DMAP (0.32 g, 2.31 mmol, 5.0 equiv.) and DCC (0.46 g, 2.31 mmol, 5.0 equiv.) in CH2Cl2 (10 mL) was shaken al 23° C. for 15 h. The polymer was filtered, washed with CH2Cl2 (2×50 mL), MEOH (2×50 mL), CH2Cl2 (2×50 mL), Et2O (2×50 mL) and dried under vacuum to afford 1.48 g of resin 152.

Synthesis of 154 as Illustrated in FIG. 21
Metathesis of Resin 152.

A suspension of resin 152 (500 mg) in CH2Cl2 (40 mL) was treated with bis(tricyclohexylphosphine)benzylidine ruthenium dichloride (RuCl2(=CHPh)(PCy3)2) (20 mg) and stirred at 23° C. for 48 h. The polymer was filtered and the filtrate was evaporated and purified by preparative thin layer chromatography (silicagel, 20% ethyl acetate in hexanes) to give compounds 154, 155, 156, 157=ca:3:3:1:3. 52% yield from the calculated loading of heterocycle in resin 152.

Synthesis of 157 and 158 as Illustrated in FIG. 21
trans-Dihydroxy Lactone 157 and 158.

Desilylation of Compound 141 and 155. Silyl ether 141 or 155 (44 mg, 0.074 mmol) was treated with a freshly prepared solution of 20% (v/v) trifluoroacetic acid (TFA)-CH2Cl2 (7.4 mL, 0.01 M) to yield, after flash column chromatography (silica gel, 50% EtOAc in hexanes), trans-dihydroxy ester 157 or 158 (33 mg, 93%)

Synthesis of Eposterones 159 and 1 as Illustrated in FIG. 21
Epoxidation of cis-Hydroxy Lactone 157 and 158.

To a solution of cis-hydroxy lactone 157 and 158 (19 mg, 0.039 mmol) in acetonitrile (390 mL, 0.1 M) is added a 0.0004 M aqueous solution of disodium salt of ethylenediaminetetraacetic acid (Na2EDTA, 200 mL, 0.2 M) and the reaction mixture is cooled to 0° C. Excess of 1,1,1-trifluoroacetone (80 mL, 0.5 M) is added, followed by a portionwise addition of Oxone® (120 mg, 0.20 mmol, 5.0 equiv) and NaHCO3 (26 mg, 0.31 mmol, 8.0 equiv) with stirring, until the disappearance of starting material is detected by TLC. The reaction mixture is then directly passed through silica gel and eluted with 50% EtOAc in hexanes. Purification by preparative thin layer chromatography (250 mm silica gel plate, 70% EtOAc in hexanes) provides the diastereomeric eposterones 159 or 1 (epothilone A).

Synthesis of Alcohol 163. Allylboration of Aldehyde 162 as Illuststrated in FIG. 25

Aldehyde 162 (1.0 equiv) was dissolved in anhydrous ether (0.3 M) and the solution was cooled to −100° C. (+)-Diisopinocampheylallyl borane (1.2 equiv in pentane, prepared from (−)-$Ipc_2$BOMe and 1.0 equiv of allyl magnesium bromide) was added dropwise under vigorous stirring, and the reaction mixture was allowed to stir for 1 h at the same temperature. Methanol was added at −100° C., and the reaction mixture was allowed to warm up to room temperature. Amino ethanol (10.0 equiv) was added and stirring was continued for 15 h. The work-up procedure was completed by the addition of saturated aqueous $NH_4Cl$ solution, extraction with EtOAc and drying of the combined organic layers with $MgSO_4$. Filtration, followed by evaporation of the solvents under reduced pressure and flash column chromatography (silica gel, 35% ether in hexanes for several fractions until all the boron complexes were removed; then 70% ether in hexanes) provided alcohol 163 (91%).

Synthesis of Hydroxy Esters 164 and 165. EDC Coupling of Carboxylic Acids 45 and 46 and Alcohol 163 as Illustrated in FIG. 25

The crude mixture of keto acids 45 and 46 (1.0 equiv; vida supra), 4-(dimethylamino)pyridine (4-DMAP, 1.5 equiv), and alcohol 163 (2.0 equiv) in $CH_2Cl_2$ (2.0 M) was cooled to 0° C. and then treated with 1-ethyl-(3-dimethylaminopropyl)-3-carbodiimide hydrochloride (EDC, 1.5 equiv). The reaction mixture was stirred at 0° C. for 2 h and then at 25° C. for 12 h. The work-up procedure was completed by the addition of saturated aqueous $NHCO_3$ solution, extraction with ether and drying of the combined organic layers with $MgSO_4$. Evaporation of the solvents followed by flash column chromatography (silica gel, 15% EtOAc in hexanes) resulted in pure hydroxy esters 164 (49% from keto acid 8) and 165 (33% from keto acid 8).

Synthesis of Hydroxy Lactones 166 and 167 as Illustrated in FIG. 26
Cyclization of Diene 164 via Olefin Metathesis.

To a solution of diene 164 (1.0 equiv) in $CH_2Cl_2$ (0.0015 M) was added bis(tricyclohexylphosphine)benzylidine ruthenium dichloride ($RuCl_2$(=CHPh) $(PCy_3)_2$, 0.2 equiv) and the reaction mixture was allowed to stir at 25° C. for 20 h. After the completion of the reaction was established by TLC, the solvent was removed under reduced pressure and the crude product was purified by flash chromatography (silica gel, 20% EtOAc in hexanes) to give hydroxy lactones 166 (40%) and 167 (29%).

Synthesis of cis-Dihydroxy Lactone 168 as Illustrated in FIG. 26
Desilylation of Compound 166.

Silyl ether 166 (1.0 equiv) was treated with a freshly prepared solution of 20% (v/v) trifluoroacetic acid-$CH_2Cl_2$ (0.01 M) at 0° C. The reaction mixture was stirred at 0° C. for 30 min (completion of the reaction by TLC). The work-up procedure was completed by the addition of saturated aqueous $NHCO_3$ solution, extraction with EtOAc and drying of the combined organic layers with $MgSO_4$. Evaporation of the solvents followed by flash column chromatography (silica gel, ether) resulted in pure cis-dihydroxy lactone 168 (89%). Rf=0.21 (silica gel, 50% EtOAc in hexanes); $[\alpha]^{22}_D$ −46.5 (c 0.71, $CHCl_3$); IR (thin film) nmax 3406, 2930, 1733, 1686, 1584, 1251, 733 cm−1; 1H NMR (500 MHz, CDCl3) δ 7.47 (s, 1H, ArH), 6.31 (s, 1H, ArCH=C(CH3)), 5.43 (ddd, J=10.5, 10.5, 4.0 Hz, 1H, CH=CHCH2), 5.36 (ddd, J=10.5, 10.5, 4.5 Hz, 1H, CH=CHCH2), 5.28 (d, J=9.5 Hz, 1H, CO2CH), 4.15 (d, J=11.0 Hz, 1H, (CH3)2CCH(OH)), 3.72 (m, 1H, CHOH (CHCH3)), 3.11 (qd, J=7.0, 2.5 Hz, 1H, CH3CH(C=O)), 3.02 (bs, 2H, OH), 2.70–2.62 (m, 1H), 2.50 (dd, J=15.5, 11.0 Hz, 1H, CH2COO), 2.43 (s, 3H, CH3Ar), 2.38 (dd, J=15.5, 2.5 Hz, 1H, CH2COO), 2.26–2.13 (m, 2H), 2.07–1.98 (m, 1H), 1.98 (s, 3H, ArCH=CCH3), 1.80–1.60 (m, 2H), 1.31 (s, 3H, C(CH3)2), 1.37–1.13 (m, 3H), 1.17 (d, J=7.0 Hz, 3H, CH3CH(C=O)), 1.07 (s, 3H, C(CH3)2), 0.98 (d, J=7.0 Hz, 3H, CH3CHCH2); 13C NMR (150.9 MHz, CDCl3) d 220.3, 170.3, 160.9, 137.8, 137.4, 135.6, 133.5, 124.8, 115.9, 78.3, 74.2, 72.6, 53.0, 42.0, 39.0, 38.5, 32.4, 31.6, 27.6, 27.5, 22.5, 19.3, 15.9, 15.6, 13.8, 13.7; HRMS (FAB), calcd for C26H40NO6 (M+H+) 462.2856, found 462.2844.

Synthesis of trans-Dihydroxy Lactone 169.
Desilylation of Compound 167 as Illustrated in FIG. 26

Silyl ether 167 (1.0 equiv) was treated with a freshly prepared solution of 20% (v/v) trifluoroacetic acid-CH2Cl2 (0.01 M) at 0° C. The reaction mixture was stirred at 0° C. for 60 min (completion of the reaction by TLC). The work-up procedure was completed by the addition of saturated aqueous NHCO3 solution, extraction with EtOAc and drying of the combined organic layers with MgSO4. Evaporation of the solvents followed by flash column chromatography (silica gel, ether) resulted in pure trans-dihydroxy ester 169 (95%). Rf=0.22 (silica gel, 50% EtOAc in hexanes); $[\alpha]22D$ −37.9 (c 0.70, CHCl3); IR (film) nmax 3400, 2933, 1733, 1688, 1583, 1466, 1251, 756 cm−1; 1H NMR (500 MHz, CDCl3) d 7.49 (s, 1H, ArH), 6.29 (s, 1H, ArCH=CCH3), 5.50 (ddd, J=15.0, 7.5, 7.5 Hz, 1H, CH=CHCH2), 5.37 (dd, J=5.5, 5.5 Hz, 1H, CO2CH), 5.34 (ddd, J=15.0, 7.5, 7.5 Hz, 1H, CH=CHCH2), 4.19 (d, J=10.0, 3.0 Hz, 1H, (CH3)2CCH(OH)), 3.73 (dd, J=5.5, 2.5 Hz, 1H, CHOH(CHCH3)), 3.26 (qd, J=7.0, 6.5 Hz, 1H, CH3CH(C=O)), 3.01 (bs, 1H, OH), 2.86 (bs, 1H, OH), 2.55 (dd, J=15.5, 10.0 Hz, 1H, CH2COO), 2.49 (dd, J=15.5, 3.0 Hz, 1H, CH2COO), 2.45 (s, 3H, CH3Ar), 2.46–2.40 (m, 2H), 2.23–2.14 (m, 1H), 2.00–1.92 (m, 1H), 1.96 (s, 3H, ArCH=CCH3), 1.64–1.56 (m, 2H), 1.47 (dddd, J=12.5, 12.5, 4.0, 4.0 Hz, 1H), 1.40–1.00 (m, 2H), 1.26 (s, 3H, C(CH3)2), 1.18 (d, J=7.0 Hz, 3H, CH3CH(C=O)), 1.06 (s, 3H, C(CH3)2), 0.98 (d, J=6.5 Hz, 3H, CH3CHCH2); 13C NMR (125.7 MHz, CDCl3) d 219.9, 170.5, 161.0, 137.4, 136.8, 135.6, 134.5, 125.6, 116.1, 77.2, 76.1, 72.5, 52.3, 43.8, 38.8, 37.6, 36.1, 32.6, 30.3, 27.2, 21.5, 20.4, 16.6, 16.0, 15.1, 13.7; HRMS (FAB), calcd for C26H40NO6 (M+H+) 462.2856, found 462.2866.

Synthesis of Hydroxy Lactones 173 and 174 as Illustrated in FIG. 27
Cyclization of Diene 165 via Olefin Metathesis.
To a solution of diene 165 (1.0 equiv) in CH2Cl2 (0.0015 M) was added bis(tricyclohexylphosphine)benzylidine ruthenium dichloride (RuCl$_2$ (=CHPh) (PCy$_3$)$_2$, 0.2 equiv) and the reaction mixture was allowed to stir at 25° C. for 20 h. After the completion of the reaction was established by TLC, the solvent was removed under reduced pressure and the crude product was purified by flash chromatography (silica gel, 20% EtOAc in hexanes) to give hydroxy lactones 173 (25%) and 174 (63%).

Synthesis of cis-Dihydroxy Lactone 175 as Illustrated in FIG. 27.
Desilylation of Compound 173
Silyl ether 173 (1.0 equiv) was treated with a freshly prepared solution of 20% (v/v) trifluoroacetic acid-CH2Cl2 (0.01 M) at 0° C. The reaction mixture was stirred at 0° C. for 3 h (completion of the reaction by TLC). The work-up procedure was completed by the addition of saturated aqueous NHCO3 solution, extraction with EtOAc and drying of the combined organic layers with MgSO4. Evaporation of the solvents followed by flash column chromatography (silica gel, ether) resulted in pure cis-dihydroxy lactone 175 (75%).

Synthesis of trans-Dihydroxy Lactone 176 as Illustrated in FIG. 27;
Desilylation of Compound 174
Silyl ether 174 (1.0 equiv) was treated with a freshly prepared solution of 20% (v/v) trifluoroacetic acid-CH2Cl2 (0.01 M) at 0° C. The reaction mixture was stirred at 0° C. for 8 h (completion of the reaction by TLC). The work-up procedure was completed by the addition of saturated aqueous NHCO3 solution, extraction with EtOAc and drying of the combined organic layers with MgSO4. Evaporation of the solvents followed by flash column chromatography (silica gel, ether) resulted in pure trans-dihydroxy ester 9 (72%).

Synthesis of Epoxalones 161 and 170 as Illustrated in FIG. 26;
Epoxidation of cis-Hydroxy Lactone 168
To a solution of 168 (1.0 equiv) in acetonitrile (0.05 M) was added a 0.0004 M aqueous solution of disodium salt of ethylenediaminetetraacetic acid (Na2EDTA, 1.0 equiv) and the reaction mixture was cooled to 0° C. 1,1,1-Trifluoroacetone (1.0 equiv) was added, followed by a portionwise addition of Oxone® (10.0 equiv) and NaHCO3 (16.0 equiv) with stirring, until the disappearance of starting material was detected by TLC. The reaction mixture was then treated with excess dimethyl sulfide and immediately purified by flash column chromatography (silica gel, ether). Further purification by preparative thin layer chromatography (250 mm silica gel plate, ether) provided epoxide 161 (34%) and a-isomeric epoxide 5 (15%). 161 : Rf=0.23 (silica gel, Ether); [α]D=−25.2 (c 0.31, CHCl3); IR (film) nmax 3417, 2927, 2866, 1731, 1692, 1584, 1260, 756 cm-1; 1H-NMR (500 MHz, CDCl3) d=7.50 (s, 1H, ArH), 6.35 (s, 1H, ArCH=CCH3), 5.44 (dd, 1H, J=25 8.0, 2.5 Hz, CO2CH), 4.12 (dd, 1H, J=10.0, 3.0 Hz, (CH3)2CCH(OH), 3.81 (dd, J=5.0, 4.0 Hz, 1H, CHOH(CHCH3)), 3.66 (bs, 1H, OH), 3.23 (qd, J=7.0, 5.5 Hz, 1H, CH3CH(C=O)), 3.02 (ddd, J=7.0, 4.5, 4.5 Hz, 1H, CH2CH—O(epoxide)CH), 2.90 (ddd, J=7.5, 4.0, 4.0 Hz, 1H, CH2CH—O(epoxide)CH), 2.54 (dd, J=14.5, 10.0 Hz, 1H, CH2COO), 2.46 (s, 3H, CH3Ar), 2.45 (dd, J=14.5, 3.0 Hz, 1H, CH2COO), 2.08 (ddd, J=15.0, 5.0, 3.0 Hz, 1H, CH2CH—O(epoxide)CH), 2.01 (s, 3H, ArCH=CCH3), 1.88 (ddd, J=15.5, 7.5, 7.5 Hz, 1H, CH2CH—O(epoxide)CH), 1.78–1.72 (m, 1H), 1.72–1.65 (m, 1H), 1.40–1.15 (m, 5H), 1.36 (s, 3H, C(CH3) 2), 1.17 (d, 3H, J=7.0 Hz, CH3CH(C=O)), 1.11 (s, 3H, C(CH3)2), 1.00 (d, J=6.9 Hz, 3H, CH3CHCH2); 13C NMR (125.7 MHz, CDCl3) d 220.1, 170.5, 161.0, 137.2, 136.7, 135.9, 116.3, 76.3, 74.9, 73.8, 57.4, 54.3, 52.6, 43.8, 38.7, 36.1, 31.3, 30.4, 26.9, 23.8, 21.4, 21.1, 17.2, 15.8, 14.4, 13.8; HRMS (FAB), calcd for C26H40NO7 (M+H+) 478.2805, found 478.2790.

Synthesis of Epoxalones 171 and 172 as Illustrated in FIG. 26;
Epoxidation of trans-Hydroxy Lactone 169
To a solution of 169 (1.0 equiv) in acetonitrile (0.05 M) was added a 0.0004 M aqueous solution of disodium salt of ethylenediaminetetraacetic acid (Na2EDTA, 1.0 equiv) and the reaction mixture was cooled to 0° C. 1,1,1-Trifluoroacetone (1.0 equiv) was added, followed by a portionwise addition of Oxone® (10.0 equiv) and NaHCO3 (16.0 equiv) with stirring, until the disappearance of starting material was detected by TLC. The reaction mixture was then treated with excess dimethyl sulfide and immediately purified by flash column chromatography (silica gel, ether). Further purification by preparative thin layer chromatography (250 mm silica gel plate, ether) provided epoxide 171 (25%) and α-isomeric epoxide 172 (20%).

Synthesis of Epoxalones 177 and 178 as Illustrated in FIG. 27;
Epoxidation of cis-Hydroxy Lactone 175
To a solution of 175 (1.0 equiv) in acetonitrile (0.05 M) was added a 0.0004 M aqueous solution of disodium salt of ethylenediaminetetraacetic acid (Na2EDTA, 1.0 equiv) and the reaction mixture was cooled to 0° C. 1,1,1-Trifluoroacetone (1.0 equiv) was added, followed by a portionwise addition of Oxone® (10.0 equiv) and NaHCO3 (16.0 equiv) with stirring, until the disappearance of starting material was detected by TLC. The reaction mixture was then treated with excess dimethyl sulfide and immediately purified by flash column chromatography (silica gel, ether). Further purification by preparative thin layer chromatography (250 mm silica gel plate, ether) provided epoxide 177 (38%) and a-isomeric epoxide 178 (17%).

Synthesis of Epoxalones 179 and 180 as Illustrated in FIG. 27;

Epoxidation of trans-Hydroxy Lactone 176

To a solution of 176 (1.0 equiv) in acetonitrile (0.05 M) was added a 0.0004 M aqueous solution of disodium salt of ethylenediaminetetraacetic acid (Na2EDTA, 1.0 equiv) and the reaction mixture was cooled to 0° C. 1,1,1-Trifluoroacetone (1.0 equiv) was added, followed by a portionwise addition of Oxone® (10.0 equiv) and NaHCO3 (16.0 equiv) with stirring, until the disappearance of starting material was detected by TLC. The reaction mixture was then treated with excess dimethyl sulfide and immediately purified by flash column chromatography (silica gel, ether). Further purification by preparative thin layer chromatography (250 mm silica gel plate, ether) provided epoxide 179 (22%) and α-isomeric epoxide 180 (13%).

Synthesis of cis-Bis(TBS) Ether 183 as Illustrated in FIG. 29

A solution of alcohol 181 (148 mg, 0.32 mmol) and 2,6-lutidine (560 ml, 4.8 mmol, 15 equiv) in $CH_2Cl_2$ (3.2 mL, 0.1 M), at 0° C., is treated with tert-butyldimethylsilyl trifluoromethanesulfonate (TBSOTf, 735 mL, 3.2 mmol, 10 equiv) and stirred at this temperature for 30 minutes, whereupon no starting material is detected by TLC. The reaction mixture is quenched by pouring it into saturated aqueous $NH_4Cl$ (10 mL). Extractions with ether (2×10 mL), drying ($MgSO_4$) and concentration is followed by flash chromatographic purification (silica gel, 7% EtOAc in hexanes) to provide bis(TBS)ether 183 (182 mg, 99%).

Synthesis of trans-Bis(TBS) Ether 184 as Illustrated in FIG. 29

Silylation of Alcohol 182.

In accordance with the procedure describing the silylation of alcohol 181, a solution of alcohol 182 (77 mg, 0.17 mmol) and 2,6-lutidine (300 ml, 2.6 mmol, 15 equiv) in CH2Cl2 (1.7 mL, 0.1 M), at 0° C., is treated with tert-butyldimethylsilyl trifluoromethanesulfonate (TBSOTf, 390 mL, 1.7 mmol, 10 equiv) to provide bis(TBS)ether 183 (92 mg, 97%).

Synthesis of cis-Alcohol 185 as Illustrated in FIG. 29

A solution of TBS ether 183 (182 mg, 0.31 mmol) in MeOH (3.1 mL, 0.1 M) is treated with 10-camphorsulfonic acid (CSA, 72 mg, 0.31 mmol, 1.0 equiv) at room temperature for 12 h, until TLC indicates the disappearance of starting material. The mixture is then poured into into saturated aqueous NaHCO3 (10 mL), extracted with ether (3×10 mL) and dried (MgSO4). Flash column chromatography (silica gel, 20% EtOAc in hexanes) yields pure 185 (98 mg, 67%).

Synthesis of trans-Alcohol 186 as Illustrated in FIG. 29

In accordance with the procedure describing the desilylation of TPS ether 183, a solution of TPS ether 184 (31 mg, 0.05 mmol) in methanol (1.6 mL, 0.1 M) was treated with 10-camphorsulfonic acid (CSA, 37 mg, 0.16 mmol, 1.0 equiv) to yield diol 186 (51 mg, 69%) as a crystalline solid.

Synthesis of Carboxylic acid 187 as Illustrated in FIG. 29

Ethyl bromopyruvate (1.66 mL, 13.2 mmol, 1 equiv) and thioacetamide (1.05 g, 13.9 mmol, 1.05 equiv) are dissolved in 95% aqueous ethanol (14 mL, 1 M) and heated at reflux for 5 minutes. Completion of the reaction is indicated by TLC. The reaction mixture is then cooled to room temperature, concentrated in vacuo, suspended in CHCl3 (20 mL) and washed with saturated aqueous NaHCO3 (2×20 mL) and with H2O (20 mL). Drying (MgSO4) and concentration is followed by flash chromatographic purification (silica gel, EtOAc) to yield the corresponding ethyl ester of acid 7 (2.26 g, 100%). This ester is dissolved in THF-H2O (1:1; 14 mL, 1 M) and submitted to the action of lithium hydroxide (1.66 g, 39.6 mmol, 3.0 equiv). After stirring at room temperature for 45 min TLC indicates the disappearance of starting material. The mixture is poured into H2O (20 mL) and extracted with ether (2×20 mL). Acidification to pH~2 to 3 with aqueous 4 N HCl is followed by extractions with EtOAc (6×20 mL). Drying (MgSO4) and concentration gives pure carboxylic acid 187 (1.36 g, 72%).

Synthesis of cis-Keto Ester 188 as Illustrated in FIG. 29

EDC Coupling of Alcohol 185 with Thiazole Acid 187.

A suspension of thiazole acid 187 (54 mg, 0.38 mmol, 2.0 equiv), 4-(dimethylamino)pyridine (4-DMAP, 2.3 mg, 0.019 mmol, 0.1 equiv) and alcohol 185 (88 mg, 0.19 mmol, 1.0 equiv) in CH2Cl2 (3.8 mL, 0.05 M) is cooled to 0° C. and then treated with 1-ethyl-(3-dimethylaminopropyl)-3-carbodiimide hydrochloride (EDC, 109 mg, 0.57 mmol, 3.0 equiv). The reaction mixture is stirred at 0° C. for 2 h and then at 25° C. for 12 h, until TLC indicates completion of the reaction. The solution is separated between EtOAc (10 mL) and water (10 mL). The aqueous layer is extracted with EtOAc (2×10 mL) and dried (MgSO4). Evaporation of the solvents is followed by flash column chromatography (silica gel, 30% EtOAc in hexanes) results in pure keto ester 188 (102 mg, 92%).

Synthesis of trans-Keto Ester 189 as Illustrated in FIG. 29

By analogy to the procedure described above for the synthesis of keto ester 188, a solution of thiazole acid 187 (28 mg, 0.198 mmol, 2.0 equiv), 4-dimethylaminopyridine (4-DMAP, 1.2 mg, 0.0099 mmol, 0.1 equiv), and alcohol 186 (46 mg, 0.099 mmol, 1.0 equiv) in CH2Cl2 (2.0 mL) is treated with 1-ethyl-(3-dimethylaminopropyl)-3-carbodiimide hydrochloride (EDC, 57 mg, 0.297 mmol, 3.0 equiv) to provide, after flash column chromatography (silica gel, 20% EtOAc in hexanes), keto ester 189 (49 mg, 84%).

Synthesis of cis-Hydroxy Lactone 190 as Illustrated in FIG. 29

Silyl ether 188 (95 mg, 0.16 mmol) was treated with a freshly prepared solution of 20% (v/v) trifluoroacetic acid-CH2Cl2 (16 mL, 0.01 M) at 0° C. The reaction mixture was stirred at 0° C. for 45 min (completion of the reaction by TLC), and then poured into sturated aqueous NaHCO3 (50 mL), extracted with EtOAc (3×20 mL), dried over MgSO4 and evaporated under reduced pressure. The crude reaction mixture was purified by flash column chromatography (silica gel, 50% EtOAc in hexanes) to obtain cis-hydroxy lactone 190 (74 mg, 96%).

Synthesis of trans-Dihydroxy Lactone 191 as Illustrated in FIG. 29

Silyl ether 189 (44 mg, 0.074 mnmol) was treated with a freshly prepared solution of 20% (v/v) trifluoroacetic acid (TFA)-CH2Cl2 (7.4 mL, 0.01 M), according to the procedure described for cis-dihydroxy lactone 8, to yield, after flash column chromatography (silica gel, 50% EtOAc in hexanes), trans-dihydroxy ester 191 (33 mg, 93%)

Synthesis of Eposterones 192 and 194 as Illustrated in FIG. 29

To a solution of cis-hydroxy lactone 190 (19 mg, 0.039 mmol) in acetonitrile (390 mL, 0.1 M) is added a 0.0004 M aqueous solution of disodium salt of ethylenediaminetetraacetic acid (Na2EDTA, 200 mL, 0.2 M) and the reaction mixture is cooled to 0° C. Excess of 1,1,1-trifluoroacetone (80 mL, 0.5 M) is added, followed by a portionwise addition of Oxone® (120 mg, 0.20 mmol, 5.0 equiv) and NaHCO3 (26 mg, 0.31 mmol, 8.0 equiv) with stirring, until the disappearance of starting material is detected by TLC. The reaction mixture is then directly passed through silica gel and eluted with 50% EtOAc in hexanes. Purification by preparative thin layer chromatography (250 mm silica gel plate, 70% EtOAc in hexanes) provides the diastereomeric eposterones 192 (9.5 mg, 48%) and 194 (3.4 mg, 17%).

Synthesis of Eposterones 193 and 195 as Illustrated in FIG. 29

As described for the epoxidation of cis-hydroxy lactone 190, trans-hydroxy lactone 191 (22 mg, 0.046 mmol) in MeCN (460 mL, 0.1 M) was treated with a 0.0004 M aqueous solution of disodium salt of ethylenediaminetetraacetic acid (Na2EDTA, 230 mL, 0.2 M), 1,1,1-trifluoroacetone (92 mL, 0.5 M), Oxone® (141 mg, 0.23 mmol, 5.0 equiv) and NaHCO3 (31 mg, 0.37 mmol, 8.0 equiv), to yield, after purification by preparative thin layer chromatography (250 mm silica gel plate, ether), eposterones 193 (7.3 mg, 32%) and 195 (5.2 mg, 23%).

Synthesis of Eposterones 199, 200, 201, 202, 203, 204, 205, 206, 207, 208, 209 and 210 as Illustrated in FIG. 30

By simple modification of the esterification step, i.e. replacing the thiazole carboxylic acid 187 in FIG. 29 with the known carboxylic acids found in epoxalone (198), eleutherobin (197) and taxol (196), other members of the eposterone family can be created including the various isomers: 199, 200, 201, 202, 203, 204, 205, 206, 207, 208, 209 and 210.

Aldehyde 212. Reduction of Ester 211 as Illustrated in FIG. 31

Ethyl ester 211 (52.5 g, 0.306 mol) was dissolved in $CH_2Cl_2$. (1 L, 0.3 M) and cooled to −78° C. DIBAL (490.0 mL, 1 M solution in $CH_2Cl_2$, 0.4896 mol, 1.6 equiv) was added dropwise via a cannula while the temperature of the reaction mixture was maintained at −78° C. After the addition was complete, the reaction mixture was stirred at the same temperature until its completion was verified by TLC (ca 1 h). Methanol (100 mL) was added at −78° C. and was followed by addition of EtOAc (1 L) and saturated aqueous $NH_4Cl$ solution (300 mL). The quenched reaction mixture was allowed to warm up to room temperature and stirred for 12 h. The organic layer was separated, and the aqueous phase was extracted with EtOAc (3×200 mL). The combined organic phase was dried over $MgSO_4$, filtered, and concentrated under reduced pressure. Flash column chromatography (silica gel, 10 æ 90% ether in hexanes) furnished the desired aldehyde 212 (33.6 g, 90%):

Synthesis of Aldehyde 213 as Illustrated in FIG. 31

Aromatic aldehyde 212 (31.1 g, 0.245 mol) was dissolved in benzene (500 mL) and 2-(triphenylphosphoranilidene)-propionaldehyde (90.0 g, 0.282 mol, 1.15 equiv) was added. The reaction mixture was heated at reflux until the reaction was complete as judged by TLC (ca 2 h). Evaporation of the solvent under reduced pressure, followed by flash column chromatography (10 æ 90% ether in hexanes) produced the desired aldehyde 213 (40.08 g, 98%):

Synthesis of Alcohol 214. Allylboration of Aldehyde 213 as Illustrated in FIG. 31

Aldehyde 213 (20.0 g, 0.120 mol) was dissolved in anhydrous ether(400 mL) and the solution was cooled to −100° C. (+)-Diisopinocampheylallyl borane (1.5 equiv in pentane, prepared from 60.0 g of (−)-Ipc2BOMe and 1.0 equiv of allyl magnesium bromide according to the method described for the synthesis the corresponding thiazole), was added dropwise under vigorous stirring, and the reaction mixture was allowed to stir for 1 h at the same temperature. Methanol (40 mL) was added at −100° C., and the reaction mixture was allowed to warm up to room temperature. Amino ethanol (72.43 mL, 1.2 mol, 10.0 equiv) was added and stirring was continued for 15 h. The work-up procedure was completed by the addition of saturated aqueous NH4Cl solution (200 mL), extraction with EtOAc (4×100 mL) and drying of the combined organic layers with MgSO4. Filtration, followed by evaporation of the solvents under reduced pressure and flash column chromatography (silica gel, 35% ether in hexanes for several fractions until all the boron complexes were removed; then 70% ether in hexanes) provided alcohol 214 (24.09 g, 96%):

Synthesis of Compound 5. Silylation of Alcohol 214 as Illustrated in FIG. 31

Alcohol 214 (7.0 g, 0.033 mol) was dissolved in DMF (35 mL, 1.0 M), the solution was cooled to 0° C. and imidazole (3.5 g, 0.050 mol, 1.5 equiv) was added. After stirring for 5 min, tert-butyldimethylsilyl chloride (6.02 g, 0.040 mol, 1.2 equiv) was added portionwise and the reaction mixture was allowed to stir at 0° C. for 45 min, and then at 25° C. for 2.5 h, after which time no starting alcohol was detected by TLC. Methanol (2 mL) was added at 0° C. and the solvent was removed under reduced pressure. Ether (100 mL) was added, followed by saturated aqueous NH4Cl solution (20 mL), the organic phase was separated and the aqueous phase was extracted with ether (2×20 mL). The combined organic solution was dried (MgSO4), filtered over celite and the solvents were removed under reduced pressure. Flash column chromatography (silica gel, 10 æ 20% ether in hexanes) provided pure 215 (10.8 g, 99%).

Synthesis of Aldehyde 217 as Illustrated in FIG. 31 Dihydroxylation of Olefin 215 and 1,2 Glycol Cleavage of diol 216.

Olefin 215 (16.7 g, 51.6 mmol) was dissolved in THF/tBuOH (1:1, 500 mL) and H2O (50 mL). 4-Methylmorpholine N-oxide (NMO) (7.3 g, 61.9 mmol, 1.2 equiv) was added at 0° C., followed by OsO4 (5.2 mL, solution in tBuOH 1.0 mol %, 2.5% by weight). The mixture was vigorously stirred for 2.5 h at 0° C. and then for 12 h at 25° C. After completion of the reaction, Na2SO3 (5.0 g) was added at 0° C., followed by H2O (100 mL). Stirring was continued for another 30 min and then ether (1 L) was added, followed by saturated aqueous NaCl solution (2×100 mL). The organic phase was separated and the aqueous phase was extracted with ether (2×100 mL). The combined organic extracts were dried (MgSO4), filtered, and the solvents were removed under reduced pressure. Flash column chromatography (silica gel, ether æ EtOAc) provided 17.54 g (95%) of the expected 1,2-diol 216 as a 1:1 mixture of diastereoisomers:

The diol obtained from 215 as described above (5.2 g, 14.5 mmol) was dissolved in EtOAc (150 mL) and cooled to 0° C. Pb(OAc)4 (8.1 g, 95% purity, 18.3 mmol, 1.2 equiv) was then added portionwise over 10 min, and the mixture was vigorously stirred for 15 min at 0° C. After completion of the reaction, the mixture was filtered through silica gel and washed with 60% ether in hexanes. The solvents were then removed under reduced pressure providing pure aldehyde 217 (4.7 g, 98%):

Synthesis of Alcohol 218 as Illustrated in FIG. 31

Reduction of Aldehyde 217.

A solution of aldehyde 215 (440 mg, 1.35 mmol) in MeOH (13 mL) was treated with NaBH4 (74 mg, 2.0 mmol, 1.5 equiv) at 0° C. for 15 min. The solution was diluted with ether (100 mL) and then saturated aqueous NH4Cl solution (5 mL) was carefully added. The organic phase was washed with brine (10 mL), dried (MgSO4) and concentrated. Flash column chromatography (silica gel, 60% ether in hexanes) gave alcohol 218 (425 mg, 96%) as a colorless oil.

Synthesis of Iodide 219 as Illustrated in FIG. 31

Iodination of Alcohol 218.

A solution of alcohol 218 (14.0 g, 42.7 mmol) in ether:MeCN (3:1, 250 mL) was cooled to 0° C. Imidazole (8.7 g, 128.1 mmol, 3.0 equiv), Ph3P (16.8 g, 64.1 mmol, 1.5 equiv), and iodine (16.3 g, 64.1 mmol, 1.5 equiv) were sequentially added and the mixture was stirred for 0.5 h at 0° C. A saturated aqueous solution of Na2S2O3 (50 mL) was added, followed by the addition of ether (600 mL). The organic phase was washed with brine (50 mL), dried (MgSO4), and the solvents were removed under vacuum. Flash column chromatography (silica gel, 15% ether in hexanes) gave pure iodide 219 (16.6 g, 89%) as a colorless oil:

Synthesis of Phosphonium Salt 220 as Illustrated in FIG. 31

A mixture of iodide 219 (16.5 g, 37.7 mmol) and Ph3P (10.9 g, 41.5 mmol, 1.1 equiv) was heated neat at 100° C. for 2 h. Purification by flash column chromatography (silica gel, CH2Cl2; then 7% MeOH in CH2Cl2) provided phosphonium salt 220 (25.9 g, 98%) as a white solid.

Synthesis of Olefinic Compound 222 as Illustrated in FIG. 32

Phosphonium salt 220 (9.0 g, 12.93 mmol, 1.5 equiv) was dissolved in THF (90 mL) and the solution was cooled to 0° C. Sodium bis(trimethylsilyl)amide (NaHMDS, 1.0 M solution in THF, 12.84 mL, 12.84 mmol, 1.48 equiv) was slowly added and the resulting mixture was stirred at 0° C. for 15 min. The reaction mixture was then cooled to −20° C. before ketone 221 (2.23 g, 8.62 mmol, 1.0 equiv) in THF (10 mL) was added and the reaction mixture was stirred at the same temperature for 12 h. Saturated aqueous NH4Cl solution (50 mL) was added and the mixture was extracted with ether (200 mL). The organic phase was washed with brine (2×100 mL), dried (MgSO4) and concentrated to afford, after flash column chromatography (silica gel, 2% ether in hexanes) olefins 222 (3.8 g, 73%, Z:E ca. 1:1 by 1H NMR).

Synthesis of Hydroxy Olefins 223 as Illustrated in FIG. 32

Desilylation of Silylether 222.

Silylether 222 (3.80 g, 6.88 mmol) was dissolved in CH2Cl2 MeOH (1:1, 70 mL) and the solution was cooled to 0° C. prior to addition of CSA (1.68 g, 7.23 mmol, 1.05 equiv) during a 5 min period. The resulting mixture was stirred for 30 min at 0° C., and then for 1 h at 25° C. Et3N (1.57 mL, 7.23 mmol, 1.05 equiv) was added, and the solvents were removed under reduced pressure. Flash column chromatography (silica gel, 50% ether in hexanes) furnished pure hydroxy compound 223 (2.9 g, 97%).

Synthesis of Aldehyde 224 as Illustrated in FIG. 32

Oxidation of Alcohol 223.

Alcohol 223 (mixtures of Z and E geometrical isomers, 4.60 g, 10.64 mmol) was dissolved in CH2Cl2 (105 mL, 0.1 M). DMSO (35 mL), Et3N (7.4 mL, 53.20 mmol, 5.0 equiv) and SO3·pyr (3.4 g, 21.28 mmol, 2.0 equiv) were added at 25° C. and the resulting mixture was stirred for 30 min. Saturated aqueous NH4Cl solution (50 mL) and ether (300 mL) were added, and the organic phase was separated and washed with brine (2×30 mL), dried (MgSO4), and concentrated under reduced pressure. Flash column chromatography (silica gel, 20% ether in hexanes) furnished aldehyde 224 (4.40 g, mixture of Z:E isomers, ca 1:1, 95%).

Synthesis of tris(Silylethers) 226 and 227 as Illustrated in FIG. 32

Aldol Reaction of Keto Acid 225 with Aldehyde 224.

A solution of keto acid 225 (1.52 g, 5.10 mmol, 1.2 equiv) in THF (10 mL) was added dropwise to a freshly prepared solution of LDA [diisopropylamine (1.78 mL, 12.78 mmol) was added to n-BuLi 7.95 mL, 1.6 M solution in hexanes, 12.78 mmol) in 20 mL of THF at 0° C.] at −78° C. After stirring for 15 min, the solution was allowed to warm to −40° C., and after 0.5 h at that temperature it was recooled to −78° C. A solution of aldehyde 224 (1.79 g, 4.24 mmol, 1.0 equiv) was added dropwise and the resulting mixture was stirred for 15 min, and then quenched at −78° C. by slow addition of saturated aqueous NH4Cl solution (20 mL). The reaction mixture was warmed to 0° C., and AcOH (2.03 mL, 26.84 mmol, 6.3 equiv) was added, followed by addition of EtOAc (50 mL). The organic layer was separated and the aqueous phase was extracted with EtOAc (3×25 mL). The. combined organic solution was dried over MgSO4 and concentrated under vacuum to afford a mixture of aldol products in a ca 1:1 ratio (1H NMR) and unreacted keto acid 225. The mixture was dissolved in CH2Cl2 (50 mL) and treated, at 0° C., with 2,6-lutidine (3.2 mL, 27.36 mmol) and tert-butyldimethylsilyl trifluoromethanesulfonate (4.2 mL, 18.24 mmol). After stirring for 2 h (complete reaction by TLC), aqueous HCl (20 mL, 10% solution) was added and the resulting biphasic mixture was separated. The aqueous phase was extracted with CH2Cl2 (3×20 mL) and the combined organic solution was washed with brine (50 mL), dried (MgSO4) and concentrated under reduced pressure to give a mixture of the tetra-tert-butyldimethylsilyl ethers. The crude product was dissolved in MeOH (50 mL) and K2CO3 (1.40 g, 10.20 mmol) was added at 25° C. The reaction mixture was vigorously stirred for 15 min, and then filtered. The residue was washed with MeOH (20 mL) and the solution was acidified with ion exchange resin (DOWEX 50WX8-200) to pH 4–5, and filtered again. The solvent was removed under reduced pressure and the resulting residue was dissolved in EtOAc (50 mL) and washed with saturated aqueous NH4Cl solution (50 mL). The aqueous phase was extracted with EtOAc (4×25 mL) and the combined organic solution was dried (MgSO4), filtered and concentrated to furnish a mixture of carboxylic acids 226, 227 and 225 Purification by preparative thin layer chromatography (silica gel, 5% MeOH in CH2Cl2), gave pure acids226 (1.1 g, 31% from 224) and 227 (1.0 g, 30% from 224) as colorless oils.

Synthesis of Hydroxy Acid 228 as Illustrated in FIG. 32

Selective Desilylation of 226.

A solution of tris(silyl) ether 226 (300 mg, 0.36 mmol) in THF (7.0 mL) at 25° C. was treated with TBAF (2.2 mL, 1 M solution in THF, 2.2 mmol, 6.0 equiv). After stirring for 8 h, the reaction mixture was diluted with EtOAc (10 mL) and washed with aqueous HCl (10 mL, 1 N solution) The aqueous solution was extracted with EtOAc (4×10 mL) and the combined organic phase was washed with brine (10 mL), dried (MgSO4) and concentrated. The crude mixture was purified by flash column chromatography (silica gel, 5% MeOH in CH2Cl2) to provide hydroxy acid 228 (203 mg, 78%) as a yellow oil.

Synthesis of Lactones 230 and 229 as Illustrated in FIG. 33

A solution of hydroxy acid 228 (140 mg, mixture of Z and E isomers, ca 1:1, 0.189 mmol) in THF (2.6 mL) was treated at 0° C. with Et3N (58 mL, 0.416 mmol, 2.2 equiv) and 2,4,6-trichlorobenzoyl chloride (29.4 mL, 0.246 mmol, 1.3 equiv). The reaction mixture was stirred at 0° C. for 1 h, and then added to a solution of 4-DMAP (233 mg, 1.896 mmol, 10.0 equiv) in toluene (90 mL, 0.002 M) at 25° C. and stirred at that temperature for 10 h. The solvents were removed in vacuo, and the crude product obtained was suspended in 40% ether in hexanes and filtered through silica gel. Concentration, followed by preparative thin layer chromatography (silica gel, 5% MeOH in CH2Cl2), gave pure lactones 230 (50 mg, 37%) and 229 (54 mg, 40%) as colorless oils.

Synthesis of Dihydroxy Lactone 232 as Illustrated in FIG. 33

To lactone 230 (50 mg, 0.071 mmol), cooled to −20° C., was added a freshly prepared 20% (v/v) CF3COOH solution in CH2Cl2 (400 mL). The reaction mixture was allowed to reach 0° C. and was stirred for 1 h at that temperature. The solvents were evaporated under reduced pressure and the crude product was purified by preparative thin layer chromatography (silica gel, 6% MeOH in CH2Cl2) to afford pure dihydroxy lactone 232 (31 mg, 92%).

Synthesis of Dihydroxy Lactone 231 as Illustrated in FIG. 33

Dihydroxy lactone 231 was prepared from bis(silylether) lactone 229 (40.0 mg, 0.055 mmol) by treatment with CF3COOH according to the same procedure described above for the preparation of 232. Obtained pure 231 (24.3 mg, 89%).

Synthesis of Compound 235 and its a-epoxide Epimer 236 as Illustrated in FIG. 33

Procedure A:

To a solution of lactone 232 (3.0 mg, 6.1 mmol) in benzene (0.2 mL) at −10° C. was added meta-chloroperbenzoic acid (2.9 mg, 50–60% purity, 8.4–10.1 mmol, 1.4–1.6 equiv) and the reaction mixture was stirred at that temperature for 2 h at which time TLC indicated completion of the reaction. The reaction mixture was diluted with EtOAc (5 mL), washed with saturated aqueous NaHCO3 solution (2 mL), and the aqueous phase was extracted with EtOAc (3×2 mL). The combined organic layer was dried (MgSO4), filtered and concentrated. Purification by preparative thin layer chromatography (silica gel, 5% MeOH in CH2Cl2) provided a mixture of 235 and its a-epoxy diastereoisomer 236 (2.0 mg, 66%, ca 5:1 ratio by 1H NMR), which was separated to its components by a second preparative thin layer chromatography (silica gel, 70% EtOAc in hexanes) furnishing pure 235 (1.6 mg, 52%) as a white solid.

Procedure B:

To a solution of lactone 232 (5.0 mg, 10.2 mmol) in CH2Cl2 (0.5 mL) at −50° C. was added dropwise a solution of dimethyldioxirane in acetone untill the starting material disappeared (TLC). The resulting solution was concentrated, and the crude product was subjected to preparative thin layer chromatography (silica gel, 5% MeOH in CH2Cl2) to give 235 and its a-epoxy diastereoisomer 236 in ca 5:1 ratio (3.9 mg, 75%). Pure 235 was obtained (3.1 mg, 60%) by preparative thin layer chromatography as described above.

Procedure C:

To a solution of 232 (10 mg, 21.0 mmol) in MeCN (200 mL) was added 4.10–4 M aqueous solution of disodium ethylenediaminetetraacetate (Na2EDTA, 120 mL) and the reaction mixture was cooled to 0° C. 1,1,1-Trifluoroacetone (200 mL) was added followed by a mixture of Oxone® (61 mg, 0.10 mmol, 5.0 equiv) and NaHCO3 (14.0 mg, 0.17 mmol, 8.0 equiv) with stirring until completion of the reaction was revealed by TLC. The reaction mixture was treated with excess Me2S (100 mL) and water (500 mL) and was then extracted with EtOAc (4×2 mL). The combined organic phase was dried (MgSO4), filtered, and concentrated. Purification by preparative thin layer chromatography (silica gel, 5% MeOH in CH2Cl2) gave a mixture of 235 and its a-epoxide epimer 236 (8.6 mg, 78% total yield). A second preparative thin layer chromatography (silica gel, 70% EtOAc in hexanes) furnished pure 235 (6.4 mg, 65%) as a white solid.

Synthesis of Epothilone 23 and 24 as Illustrated in FIG. 33

Procedure A:

Compound 231 (5.0 mg, 10.2 mmol) was epoxidised with mCPBA according to procedure A described above for 232 to yield a mixture of 234 and its a-epoxy-diastereoisomer 233 (3.7 mg, 73% total yield, ca 4:1 by 1H NMR).

Procedure B:

The epoxidation of 231 (3.0 mg, 6.1 mmol) according, to the procedure described above for 232 led to epothilones 233 and its a-epoxy diastereoisomer 234 (2.6 mg, 86% total yield, ca 1:1 ratio by 1H NMR).

Synthesis of α,β-Unsaturated Ester 237 as Illustrated in FIG. 34

A mixture of aldehyde 217 (5.17 g, 15.9 mmol) and stabilized ylide (8.92 g, 24.0 mmol, 1.5 equiv, prepared from 4-bromo-1-butene by: (i) phosphonium salt formation; (ii) anion formation with NaHMDS; and (iii) quenching with MeOC(O)Cl)29) in benzene (300 mnL, 0.05 M) was heated at reflux for 3 h. After cooling to 25° C., the solvent was removed under reduced pressure and the residue was subjected to flash column chromatography (silica gel, 30% ether in hexanes) to afford a,b-unsaturated ester 237 (7.15 g, 95%).

Synthesis of Allylic Alcohol 238 as Illustrated in FIG. 34

Methyl ester 237 (6.1 g, 14.4 mmol) was dissolved in THF (80 mL) and cooled to −78° C. DIBAL (44.0 mL, 1 M solution in CH2Cl2, 44.0 mmol, 3.0 equiv) was added dropwise at −78° C., and the reaction mixture was stirred for 3 h. The reaction mixture was quenched with MeOH (1.0 mL) at −78° C., and then ether (100 mL) was added, followed by saturated aqueous sodium-potasium tartrate solution (10 mL). The resulting mixture was allowed to warm up to room temperature, where it was stirred for 3 h. The organic layer was separated and the aqueous phase was extracted with ether (2×50 mL). The combined organic phase was dried (MgSO4), filtered and concentrated under reduced pressure. Flash column chromatography (silica gel, 40 to 80% ether in hexanes) furnished alcohol 238 (5.58 g, 98%).

Synthesis of Compound 239 as Illustrated in FIG. 34

Chlorination of Alcohol 238.

Alcohol 238 (3.00 g, 7.60 mmol) was dissolved in CCl4 (75 mL, 0.1 M) and Ph3P (4.00 g, 15.2 mmol, 2.0 equiv) was added. The reaction mixture was stirred at 100° C. for 24 h, cooled to room temperature and the solvent was removed under reduced pressure. Flash column chromatography (silica gel, 10% ether in hexanes) furnished pure 239 (2.6 g, 83%).

Synthesis of Compound 240 as Illustrated in FIG. 34

Reduction of 239.

Compound 239 (2.60 g, 6.30 mmol) was dissolved in THF (60 mL, 0.1 M) and cooled to 0° C. LiEt3BH (12.6 ml, 1.0 M solution in THF, 12.6 mmol, 2.0 equiv) was added dropwise and the reaction mixture was stirred at 0° C. for 1 h. Aqueous NaOH (1.0 mL, 3.0 N) solution was added followed by addition of Et2O (150 mL). The organic phase was washed with brine (2×20 mL), dried (MgSO4) and concentrated. Flash column chromatography (silica gel, 20% ether in hexanes) furnished pure 240 (2.38 g, 99%).

Synthesis of Primary Alcohol 241 as Illustrated in FIG. 34

Selective Hydroboration of Olefinic Compound 240.

Compound 240 (1.1 g, 2.91 mmol) was dissolved in THF (3.0 mL, 1.0 M) and the solution was cooled to 0° C. 9-BBN (7.0 mL, 0.5 M solution in THF, 3.5 mmol, 1.2 equiv) was added, and the reaction mixture was stirred for 2 h at 0° C. Aqueous NaOH (7.0 mL, 3 N solution, 21.0 mmol, 7.2 equiv) was added with stirring, followed by H2O2 (2.4 mL, 30%, aqueous solution). Stirring was continued for 0.5 h at 0° C., after which time the reaction mixture was diluted with ether (30 mL). The organic solution was separated and the aqueous phase was extracted with ether (2×15 mL). The combined organic layer was washed with brine (2×5 mL), dried (Na2SO4) and concentrated in vacuo. Flash column chromatography (silica gel, 50 æ 80% ether in hexanes) furnished primary alcohol 241 (1.0 g, 91%).

Synthesis of Iodide 242 as Illustrated in FIG. 34

Iodide 242 (1.18 g, 92%) was prepared from alcohol 241 (1.0 g, 2.53 mmol) according to the procedure described above for 219.

Synthesis of Hydrazone 243 as Illustrated in FIG. 34

Alkylation of SAMP Hydrazone with Iodide 242.

SAMP hydrazone (337 mg, 0.2 mmol, 2.0 equiv) in THF (2.5 mL), was added to a freshly prepared solution of LDA at 0° C. [diisopropylamine (277 mL, 0.20 mmol, 2.0 equiv) was added to n-BuLi (1.39 mL, 1.42 M solution in hexanes, 0.20 mmol. 2.0 equiv) in 2.5 mL of THF at 0° C.] at 0° C. After stirring at that temperature for 8 h, the resulting yellow solution was cooled to −100° C., and a solution of iodide 242 (0.5 g, 0.99 mmol, 1.0 equiv) in THF (3 mL) was added dropwise over a period of 5 min. The mixture was allowed to warm to −20° C. over 10 h, and then poured into saturated aqueous NH4Cl solution (5 mL) and extracted with ether (3×25 mL). The combined organic extracts were dried (MgSO4), filtered and evaporated. Purification by flash column chromatography on silica gel (20 æ 40% ether in hexanes) provided hydrazone 243 (380 mg, 70%, de>98% by 1H NMR) as a yellow oil.

Synthesis of Nitrile 244 as Illustrated in FIG. 35

Monoperoxyphthalic acid magnesium salt (MMPP·6H2O, 233 mg, 0.38 mmol, 2.5 equiv) was suspended in a rapidly stirred mixture of MeOH and pH 7 phosphate buffer (1:1, 3.0 mL) at 0° C. Hydrazone 243 (83 mg, 0.15 mmol, 1.0 equiv) in MEOH (1.0 mL) was added dropwise, and the mixture was stirred at 0° C. until the reaction was complete by TLC (ca 1 h). The resulting suspension was placed in a separating funnel along with ether (15 mL) and saturated aqueous NaHCO3 solution (5 mL). The organic layer was separated and the aqueous phase was extracted with ether (10 mL). The combined organic solution was washed with water (5 mL) and brine (5 mL), dried (MgSO4) and concentrated. Flash column chromatography (silica gel, 50% ether in hexanes) afforded nitrile 244 (53 mg, 80%) as a colorless oil.

Synthesis of Aldehyde 224 as Illustrated in FIG. 35

Nitrile 244 (53 mg, 0.12 mmol) was dissolved in toluene (2.0 mL) and cooled to −78° C. DIBAL (245 mL, 1 M solution in toluene, 0.22 mmol, 2.0 equiv) was added dropwise at −78° C. and the reaction mixture was stirred at that temperature until its completion was verified by TLC (ca 1 h). Methanol (150 mL) and aqueous HCl (150 mL, 1 N solution) were sequentially added and the resulting mixture was brought up to 0° C. and stirred at that temperature for 30 min. Ether (5 mL) and water (2 mL) were added, and the organic layer was separated. The aqueous phase was extracted with ether (2×5 mL) and the combined organic solution was washed with brine (5 mL), dried (MgSO4), filtered and concentrated under reduced pressure. Flash column chromatography (silica gel,. 15% ether in hexanes) furnished pure aldehyde 224 (44 mg, 82%):

Synthesis of tris(Silylether) 245 as Illustrated in FIG. 35

Aldol Reaction of Ketone with Aldehyde 224.

A solution of ketone (270 mg, 0.67 mmol, 1.2 equiv) in THF (1.5 mL) was added dropwise to a freshly prepared solution of LDA [diisopropylamine (94 mL, 0.67 mmol) was added to n-BuLi (0.43 mL, 1.6 M solution in hexanes, 0.67 mmol) in 2.5 mL of THF at 0° C.] in THF (2.5 mL) at −78° C. After stirring for 15 min at −78° C., the solution was allowed to warm to −40° C. over a period of 1 h. The reaction mixture was cooled to −78° C., and a solution of aldehyde 224 (244 mg, 0.56 mmol, 1.0 equiv) in THF (1.0 mL) was added dropwise. The resulting mixture was stirred for 15 min at −78° C., and then quenched by dropwise addition of saturated aqueous NH4Cl solution (2 mL). The aqueous phase was extracted with ether (3×5 mL) and the combined organic layer was dried (MgSO4) and concentrated. Purification by flash column chromatography (silica gel, 20% ether in hexanes) provided a mixture of aldol products (354 mg (85%) of ca 3:1 by 1H NMR). Separation of these diastereoisomers was carried out by preparative thin layer chromatography (silica gel, 20% ether in hexanes) leading to pure 245 (270 mg, 64%).

Synthesis of tetra(Silylether) 246 as Illustrated in FIG. 35

Compound 245 (275 mg, 0.33 mmol) was dissolved in CH2Cl2 (5.0 mL), cooled to 0° C. and treated with 2,6-lutidine (76 mL, 0.66 mmol, 2.0 equiv) and tert-butyldimethylsilyl trifluoromethanesulfonate (88 mL, 0.39 mmol, 1.2 equiv). After stirring for 2 h at 0° C., the reaction mixture was quenched with aqueous HCl (5 mL, 1.0 N solution) and the aqueous phase was extracted with CH2Cl2 (3×5 mL). The combined organic solution was washed with brine (5 mL), dried (MgSO4) and concentrated under reduced pressure. Purification by flash column chromatography (silica gel, 3% ether in hexanes) provided tetra (silylether) 246 (300 mg, 96%) as a colorless oil.

Synthesis of Alcohol 247 as Illustrated in FIG. 35

Alcohol 247 (200 mg, 85%) was obtained from compound 246 (264 mg, 0.28 mmol) according to the procedure described above for 223.

Synthesis of Aldehyde 248 as Illustrated in FIG. 35
Oxidation of Alcohol 247.

To a solution of oxalyl chloride (54 mL, 0.61 mmol, 2.0 equiv) in CH2Cl2 (5.0 mL) was added dropwise DMSO (86 mL, 1.21 mmol, 4.0 equiv) at –78° C. After stirring for 15 min at –78° C., a solution of alcohol 247 (255 mg, 0.305 mmol, 1.0 equiv) in CH2Cl2 (2.0 mL) was added dropwise at –78° C. over a period of 5 min. The solution was stirred at –78° C. for 30 min, and then Et3N (250 mL, 1.82 mmol, 6.0 equiv) was added. The reaction mixture was allowed to warm to 0° C. over a period of 30 min and then ether (20 mL) was added, followed by saturated aqueous NH4Cl solution (10 mL). The organic phase was separated and the aqueous phase was extracted with ether (2×10 mL). The combined organic solution was dried (MgSO4), filtered and concentrated under reduced pressure. Purification by flash column chromatography (silica gel, 20% ether in hexanes) provided aldehyde 248 (241 mg, 95%) as a colorless oil.

Synthesis of Carboxylic Acid 249 as Illustrated in FIG. 35

Aldehyde 248 (224 mg, 0.29 mmol), tBuOH (5.0 mL), isobutylene (5.0 mL, 2 M solution in THF, 10.0 mmol), H2O (1.0 mL), NaClO2 (90 mg, 0.86 mmol, 3.0 equiv) and NaH2PO4 (60 mg, 0.43 mmol, 1.5 equiv) were combined and stirred at room temperature for 1 h. The reaction mixture was concentrated under reduced pressure and the residue was subjected to flash column chromatography (silica gel, 6% MeOH in CH2Cl2) to afford carboxylic acid 249 (220 mg, 90%).

Synthesis of Hydroxy Acid 250 as Illustrated in FIG. 35

A solution of tris(silyl) ether 249 (300 mg, 0.36 mmol) in THF (7.0 mL) at 25° C. was treated with TBAF (2.2 mL, 1 M solution in THF, 2.2 mmol, 6.0 equiv). After stirring for 8 h, the reaction mixture was diluted with EtOAc (10 mL) and washed with aqueous HCl (10 mL, 1 N solution). The aqueous solution was extracted with EtOAc (4×10 mL) and the combined organic phase was washed with brine (10 mL), dried (MgSO4) and concentrated. The crude mixture was purified by flash column chromatography (silica gel, 5% MeOH in CH2Cl2) to provide hydroxy acid 250 (203 mg, 78%) as a yellow oil:

Synthesis of Lactone 229 as Illustrated in FIG. 36
Macrolactonization of Hydroxy Acid 250.

A solution of hydroxy acid 250 (140 mg, mixture of Z and E isomers, ca 1:1, 0.189 mmol) in THF (2.6 mL) was treated at 0° C. with Et3N (58 mL, 0.416 mmol, 2.2 equiv) and 2,4,6-trichlorobenzoyl chloride (29.4 mL, 0.246 mmol, 1.3 equiv). The reaction mixture was stirred at 0° C. for 1 h, and then added to a solution of 4-DMAP (233 mg, 1.896 mmol, 10.0 equiv) in toluene (90 mL, 0.002 M) at 25° C. and stirred at that temperature for 10 h. The solvents were removed in vacuo, and the crude product obtained was suspended in 40% ether in hexanes and filtered through silica gel. Concentration, followed by preparative thin layer chromatography (silica gel, 5% MeOH in CH2Cl2), gave pure lactone 229 (104 mg, 77%).

Synthesis of Compound 252 as Illustrated in FIG. 37

Compound 251, trityl chloride (2.0 eq.) and DMAP (1.1 eq.) were dissolved in DMF (0.1 M) and the reaction mixture heated at 60° C. for 12 h. The solvent was removed under reduced pressure and flash column chromatography (silica gel, ether in hexanes) furnished pure 252.

Synthesis of Primary Alcohol 253 as Illustrated in FIG. 37
Selective Hydroboration of Olefinic Compound 252.

Compound 252 was cooled to 0° C. 9-BBN (7.0 mL, 0.5 M solution in THF, 3.5 mmol, 1.2 equiv) was added, and the reaction mixture was stirred for 2 h at 0° C. Aqueous NaOH (7.0 mL, 3 N solution, 21.0 mmol, 7.2 equiv) was added with stirring, followed by H2O2 (2.4 mL, 30%, aqueous solution). Stirring was continued for 0.5 h at 0° C., after which time the reaction mixture was diluted with ether (30 mL). The organic solution was separated and the aqueous phase was extracted with ether (2×15 mL). The combined organic layer was washed with brine (2×5 mL), dried (Na2SO4) and concentrated in vacuo. Flash column chromatography (silica gel, 50 to 80% ether in hexanes) furnished primary alcohol 254 (1.0 g, 91%).

Synthesis of Iodide 254 as Illustrated in FIG. 37

Iodide 254 (1.18 g, 92%) was prepared from alcohol 253 (1.0 g, 2.53 mmol) according to the procedure described above for 219.

Synthesis of Hydrazone 255 as Illustrated in FIG. 37
Alkylation of SAMP Hydrazone with Iodide 254.

SAMP hydrazone (337 mg, 0.2 mmol, 2.0 equiv) in THF (2.5 mL), was added to a freshly prepared solution of LDA at 0° C. [diisopropylamine (277 mL, 0.20 mmol, 2.0 equiv) was added to n-BuLi (1.39 mL, 1.42 M solution in hexanes, 0.20 mmol. 2.0 equiv) in 2.5 mL of THF at 0° C.] at 0° C. After stirring at that temperature for 8 h, the resulting yellow solution was cooled to –100° C., and a solution of iodide 254 (0.5 g, 0.99 mmol, 1.0 equiv) in THF (3 mL) was added dropwise over a period of 5 min. The mixture was allowed to warm to –20° C. over 10 h, and then poured into saturated aqueous NH4Cl solution (5 mL) and extracted with ether (3×25 mL). The combined organic extracts were dried (MgSO4), filtered and evaporated. Purification by flash column chromatography on silica gel (20 to 40% ether in hexanes) provided hydrazone 255 (380 mg, 70%, de >98% by 1H NMR) as a yellow oil.

Synthesis of Nitrile 256 as Illustrated in FIG. 37

Monoperoxyphthalic acid magnesium salt (MMPP·6H2O, 233 mg, 0.38 mmol, 2.5 equiv) was suspended in a rapidly stirred mixture of MeOH and pH 7 phosphate buffer (1:1, 3.0 mL) at 0° C. Hydrazone 255 (83 mg, 0.15 mmol, 1.0 equiv) in MeOH (1.0 mL) was added dropwise, and the mixture was stirred at 0° C. until the reaction was complete by TLC (ca 1 h). The resulting suspension was placed in a separating funnel along with ether (15 mL) and saturated aqueous NaHCO3 solution (5 mL). The organic layer was separated and the aqueous phase was extracted with ether (10 mL). The combined organic solution was washed with water (5 mL) and brine (5 mL), dried (MgSO4) and concentrated. Flash column chromatography (silica gel, 50% ether in hexanes) afforded nitrile 256 (53 mg, 80%) as a colorless oil.

Synthesis of Aldehyde 257 as Illustrated in FIG. 37

Nitrile 256 (53 mg, 0.12 mmol) was dissolved in toluene (2.0 mL) and cooled to −78° C. DIBAL (245 mL, 1 M solution in toluene, 0.22 mmol, 2.0 equiv) was added dropwise at −78° C. and the reaction mixture was stirred at that temperature until its completion was verified by TLC (ca 1 h). Methanol (150 mL) and aqueous HCl (150 mL, 1 N solution) were sequentially added and the resulting mixture was brought up to 0° C. and stirred at that temperature for 30 min. Ether (5 mL) and water (2 mL) were added, and the organic layer was separated. The aqueous phase was extracted with ether (2×5 mL) and the combined organic solution was washed with brine (5 mL), dried (MgSO4), filtered and concentrated under reduced pressure. Flash column chromatography (silica gel, 15% ether in hexanes) furnished pure aldehyde 257 (44 mg, 82%).

Synthesis of tris(Silylether) 258 as Illustrated in FIG. 38

Aldol Reaction of Ketone with Aldehyde 257.

A solution of ketone (270 mg, 0.67 mmol, 1.2 equiv) in THF (1.5 mL) was added dropwise to a freshly prepared solution of LDA [diisopropylamine (94 mL, 0.67 mmol) was added to n-BuLi (0.43 mL, 1.6 M solution in hexanes, 0.67 mmol) in 2.5 mL of THF at 0° C.] in THF (2.5 mL) at −78° C. After stirring for 15 min at −78° C., the solution was allowed to warm to −40° C. over a period of 1 h. The reaction mixture was cooled to −78° C., and a solution of aldehyde 257 (244 mg, 0.56 mmol, 1.0 equiv) in THF (1.0 mL) was added dropwise. The resulting mixture was stirred for 15 min at −78° C., and then quenched by dropwise addition of saturated aqueous NH4Cl solution (2 mL). The aqueous phase was extracted with ether (3×5 mL) and the combined organic layer was dried (MgSO4) and concentrated. Purification by flash column chromatography (silica gel, 20% ether in hexanes) provided a mixture of aldol products (354 mg (85%) of ca 3:1 by 1H NMR). Separation of these diastereoisomers was carried out by preparative thin layer chromatography (silica gel, 20% ether in hexanes) leading to pure 258 (270 mg, 64%).

Synthesis of tetra(Silylether) 259 as Illustrated in FIG. 38

Compound 258 (275 mg, 0.33 mmol) was dissolved in CH2Cl2 (5.0 mL), cooled to 0° C. and treated with 2,6-lutidine (76 mL, 0.66 mmol, 2.0 equiv) and tert-butyldimethylsilyl trifluoromethanesulfonate (88 mL, 0.39 mmol, 1.2 equiv). After stirring for 2 h at 0° C., the reaction mixture was quenched with aqueous HCl (5 mL, 1.0 N solution) and the aqueous phase was extracted with CH2Cl2 (3×5 mL). The combined organic solution was washed with brine (5 mL), dried (MgSO4) and concentrated under reduced pressure. Purification by flash column chromatography (silica gel, 3% ether in hexanes) provided tetra (silylether) 259 (300 mg, 96%) as a colorless oil.

Synthesis of Alcohol 260 as Illustrated in FIG. 38

Alcohol 260 (200 mg, 85%) was obtained from compound 259 (264 mg, 0.28 mmol) according to the procedure described above for 223.

Synthesis of Aldehyde 261 as Illustrated in FIG. 38

Oxidation of Alcohol 260.

To a solution of oxalyl chloride (54 mL, 0.61 mmol, 2.0 equiv) in CH2Cl2 (5.0 mL) was added dropwise DMSO (86 mL, 1.21 mmol, 4.0 equiv) at −78° C. After stirring for 15 min at −78° C., a solution of alcohol 260 (255 mg, 0.305 mmol, 1.0 equiv) in CH2Cl2 (2.0 mL) was added dropwise at −78° C. over a period of 5 min. The solution was stirred at −78° C. for 30 min, and then Et3N (250 mL, 1.82 mmol, 6.0 equiv) was added. The reaction mixture was allowed to warm to 0° C. over a period of 30 min and then ether (20 mL) was added, followed by saturated aqueous NH4Cl solution (10 mL). The organic phase was separated and the aqueous phase was extracted with ether (2×10 mL). The combined organic solution was dried (MgSO4), filtered and concentrated under reduced pressure. Purification by flash column chromatography (silica gel, 20% ether in hexanes) provided aldehyde 261 (241 mg, 95%) as a colorless oil.

Synthesis of Carboxylic Acid 262 as Illustrated in FIG. 38

Oxidation of Aldehyde 261.

Aldehyde 261 (224 mg, 0.29 mmol), tBuOH (5.0 mL), isobutylene (5.0 mL, 2 M solution in THF, 10.0 mmol), H2O (1.0 mL), NaClO2 (90 mg, 0.86 mmol, 3.0 equiv) and NaH2PO4 (60 mg, 0.43 mmol, 1.5 equiv) were combined and stirred at room temperature for 1 h. The reaction mixture was concentrated under reduced pressure and the residue was subjected to flash column chromatography (silica gel, 6% MeOH in CH2Cl2) to afford carboxylic acid 262 (220 mg, 90%).

Synthesis of Hydroxy Acid 263 as Illustrated in FIG. 38

Selective Desilylation of 262.

A solution of tris(silyl) ether 262 (300 mg, 0.36 mmol) in THF (7.0 mL) at 25° C. was treated with TBAF (2.2 mL, 1 M solution in THF, 2.2 mmol, 6.0 equiv). After stirring for 8 h, the reaction mixture was diluted with EtOAc (10 mL) and washed with aqueous HCl (10 mL, 1 N solution). The aqueous solution was extracted with EtOAc (4×10 mL) and the combined organic phase was washed with brine (10 mL), dried (MgSO4) and concentrated. The crude mixture was purified by flash column chromatography (silica gel, 5% MeOH in CH2Cl2) to provide hydroxy acid 263 (203 mg, 78%) as a yellow oil.

Synthesis of Lactone 264 as Illustrated in FIG. 38

Macrolactonization of Hydroxy Acid 263.

A solution of hydroxy acid 263 (1.0 eq) in THF (0.07 M) was treated at 0° C. with Et3N (2.2 equiv) and 2,4,6-trichlorobenzoyl chloride (1.3 equiv). The reaction mixture was stirred at 0° C. for 1 h, and then added to a solution of 4-DMAP (2.0 equiv) in toluene (0.002 M) at 25° C. and stirred at that temperature for 6 h. The solvents were removed in vacuo, and the crude product obtained was suspended in 40% ether in hexanes and filtered through silica gel. Concentration, followed by preparative thin layer chromatography (silica gel, 5% MeOH in CH2Cl2), gave pure lactone 264 (77%).

Synthesis of Triol 265 as Illustrated in FIG. 39

HF.pyr (0.25%) was carefully added to a solution of 264 (1.0 eq.) in THF (0.05 M) and the reaction mixture stirred for 24 hours at 25° C. Aqueous saturated NaHCO3 solution was added followed by extraction with ethyl acetate. The organic phase was dried (MgSO4) and concentrated. The crude mixture was purified by flash column chromatography (silica gel, 5% MeOH in CH2Cl2) to provide triol 265 (78%).

Synthesis of Epoxyde 266 as Illustrated in FIG. 39

The epoxidation of 265 according to the procedure described above for 232 led to epothilone 266.

Synthesis of Spirocyclopropane Ketoester 276 as Illustrated in FIG. 41

Cyclopropanation of Ethyl Propionylacetate 275.

Ethyl propionylacetate 275 (75.0 mL, 0.526 mol; Aldrich) was added to a solution of dry K2CO3 (218.0 g, 1.579 mol, 3.0 equiv) in DMF (526 mL, 1 M) at ambient temperature. This mixture was treated with 1,2-dibromoethane (60.0 mL, 0.684 mol, 1.3 equiv) over a period of 15 min and then rapidly stirred for 15 h, after which time completion of the reaction was indicated by NMR. Following filtration through celite and washing with ether, the solvents were removed in vacuo. Vacuum distillation (bp 64° C./6 mm Hg) of the crude product resulted in pure spirocyclopropane ketoester 276 (53.9 g, 60%) as a colorless oil. Rf=0.45 (silica gel, 17% EtOAc in hexanes); IR (film) nmax 2981, 2940, 1726, 1703, 1372, 1314, 1183, 1098 cm−1; 1H NMR (250 MHz, CDCl3) d 4.20 (q, J=7.1 Hz, 2H, CH3CH2O), 2.86 (q, J=7.3 Hz, 2H, CH3CH2), 1.43 (s, 4H, C(CH2)2), 1.29 (t, J=7.1 Hz, 3H, CH3CH2O), 1.08 (t, J=7.3 Hz, 3H, CH3CH2); 13C NMR (62.9 MHz, CDCl3) d 206.0, 171.1, 61.2, 35.1, 34.6, 18.5, 14.0, 8.3.

Synthesis of Spirocyclopropane Ketoaldehyde 274 as Illustrated in FIG. 41

LiAlH4 Reduction/Swern Oxidation of Spirocyclopropane Ketoester 276.

To a solution of spirocyclopropane ketoester 276 (53.9 g, 0.316 mnol) in ether (1.5 L, 0.2 M) was added a solution of lithium aluminum hydride (LAH; 1 M solution in THF, 632 mL, 0.632 mol, 2.0 equiv) at −20° C. over a period of 2 h and the reaction mixture stirred at −20° C. for 2 h. The reaction mixture was then diluted with ether (250 mL) and quenched by the sequential dropwise addition of water (24 mL), 15% aqueous sodium hydroxide solution (24 mL) and additional water (72 mL). The resulting slurry was allowed to warm to 25° C. over 10 h and the aluminum salts were removed by filtration through celite. The filtrate was dried (MgSO4), and the solvent removed in vacuo to yield the crude diol (38.5 g, 93%), which was used in the oxidation step without further purification. An analytical sample was prepared by flash column chromatography (silica gel, 33 æ 50% EtOAc in hexanes); Rf=0.17 (silica gel, 50% EtOAc in hexanes); IR (film) nmax 3355, 2964, 2934, 2877, 1462, 1433, 1101, 1029, 969 cm−1; 1H NMR (400 MHz, CDCl3) d 4.11 (ddd, J=11.3, 3.9, 1.3 Hz, 1H, CH3CH2CHOH), 3.03 (dd, J=11.3, 5.9 Hz, 1H, CH2OH), 2.97–2.85 (m, 3H, CH2OH, CH2OH and CHOH), 1.75–1.59 (m, 2H, CH3CH2), 0.97 (t, J=7.5 Hz, 3H, CH3CH2), 0.61–0.53 (m, 2H, C(CH2)2), 10 0.43–0.36 (m, 2H, C(CH2)2); 13C NMR (62.9 MHz, CDCl3) d 80.1, 67.2, 27.3, 25.4, 10.7, 9.9, 7.9; HRMS (FAB), calcd for C7H14NaO2 (M+Na+) 153.0892, found 153.0894.

To a solution of oxalyl chloride (35.5 mL, 0.407 mol, 3.0 equiv) in CH2Cl2 (360 mL) was added dropwise DMSO (38.5 mL, 0.543 mol, 4.0 equiv) in CH2Cl2 (100 mL) at −78° C. over 1 h. After stirring for 35 min, a solution of crude diol (17.7 g, 0.136 mol) in CH2Cl2 (200 mL) was added dropwise at −78° C. over a period of 1.5 h. The solution was stirred for a further 1 h at −78° C., before Et3N (151 mL, 1.085 mol, 8.0 equiv) was added over 40 min. After a further 15 min at −78° C. the resulting slurry was allowed to warm to 0° C. over 1 h. Ether (700 mL) and saturated aqueous NH4Cl solution (500 mL) were then added and the organic phase separated. The aqueous phase was re-extracted with ether (500 mL) and the combined organic solution washed with saturated aqueous NH4Cl solution (1.0 L), dried (Na2SO4), filtered and concentrated under reduced pressure. Purification by flash column chromatography (silica gel, 25% ether in hexanes) afforded spirocyclopropane ketoaldehyde 274 (10.9 g, 64%). Rf=0.57 (silica gel, 50% EtOAc in hexanes); (bp 45° C./1.5 mm Hg); IR (film)nmax 2974, 2939, 1723, 1699, 1318, 1176, 1099 cm−1; 1H NMR (400 MHz, CDCl3) d 9.83 (s, 1H, CHO), 2.70 (q, J=7.2 Hz, 2H, CH3CH2), 1.70–1.68 (m, 2H, C(CH2)2), 1.57–1.54 (m, 2H, C(CH2)2), 1.09 (t, J=7.2 Hz, 3H, CH3CH2); 13C NMR (62.9 MHz, CDCl3) d 205.9, 197.8, 40.9, 33.7, 21.2, 7.7; HRMS (FAB), calcd for C7H11O2 (M+H+) 127.0759, found 127.0765.

Synthesis of Silylether 273 as Illustrated in FIG. 41

Allylboration of Spirocyclopropane Ketoaldehyde 33 and Silylation.

Allyllmagnesium bromide (1 M solution in ether, 80 mL, 80.0 mmol, 1.0 equiv) was added dropwise to a well stirred solution of (−)-β-methoxydiisopinocampheyl borane (27.2 g, 86.0 mmol, 1.1 equiv) in ether (500 mL) at 0° C. After the completion of the addition, the gray slurry was stirred at room temperature for 1 h and the solvent was removed under reduced pressure. Pentane (400 mL) was added to the residual solids and the mixture stirred for 10 minutes. The stirring was discontinued to allow precipitation of the magnesium salts and the clear supernatant pentane solution was transferred via cannula carefully avoiding the transfer of any solid materials. This process was repeated four times. The combined pentane fractions were concentrated to a volume of ca. 500 mL and then added dropwise, without further purification, to a solution of ketoaldehyde 274 (10.1 g, 79.7 mmol, 1.0 equiv) in ether (250 mL) at −100° C. After the addition was complete, the mixture was stirred at the same temperature for 30 min. Methanol (10 mL) was added at −100° C., and the reaction mixture was allowed to warm to −40° C. over 40 min. Saturated aqueous NaHCO3 solution (125 mL), followed by H2O2 (50 wt. % solution in H2O, 50 mL) were added and the reaction mixture was allowed to stir at room temperature for 12 h. The organic phase was separated and the aqueous phase extracted with EtOAc (3×250 mL). The combined organic extracts were washed with saturated aqueous NH4Cl solution (500 mL), dried (Na2SO4) and the. solvents removed in vacuo to yield the crude allylic alcohol which was used without further purification. An analytical sample was prepared by flash column chromatography (silica gel, 3% acetone in CH2Cl2); Rf=0.14 (silica gel, 17% EtOAc in hexanes); [α]22D −93.6 (c 0.92, CHCl3), IR (film) nmax 3472, 2978, 2938, 1678, 1641, 1376, 1068, 994, 972, 914 cm−1; 1H NMR (500 MHz, CDCl3) d 5.84 (dddd, J=17.0, 10.0, 7.0, 7.0 Hz, 1H, CH2CH=CH2), 5.10–5.03 (m, 2H, CH2CH=CH2), 3.30 (dd, J=6.5, 6.5 Hz, 1H, CHOH), 3.18 (bs, 1H, CHOH), 2.42–2.37 (m, 2H, CH2CH=CH2), 2.12 (q, J=7.5 Hz, 2H, CH3CH2), 1.26 (ddd, J=9.5, 7.0, 5.0 Hz, 1H, C(CH2)2), 1.16 (ddd, J=9.5, 7.0, 5.0 Hz, 1H, C(CH2)2), 1.07 (ddd, J=9.0, 7.0, 5.0 Hz, 1H, C(CH2)2), 1.00 (t, J=7.5 Hz, 3H, CH3CH2), 0.94 (ddd, J=9.0, 7.0, 5.0 Hz, 1H, C(CH2)2); 13C NMR (62.9 MHz, CDCl3) d 212.5, 135.4, 117.0, 74.9, 39.7, 35.4, 29.4, 14.0, 12.6, 8.0; HRMS (FAB), calcd for C10H16NaO2 (M+Na+) 191.1048, found 191.1042.

This crude alcohol was dissolved in CH2Cl2 (750 mL, 0.3 M) and the solution was cooled to −78° C. The solution was treated with 2,6-lutidine (40 mL, 0.368 mol, 4.6 equiv), and after stirring for 5 min, tert-butyldimethylsilyl triflate (70 mL, 0.305 mmol, 3.8 equiv) was added dropwise. The reaction mixture was allowed to stir at −78° C. for 35 min, after which time no starting material was detected by TLC. Saturated aqueous NH4Cl solution (500 mL) was added, and the reaction mixture was allowed to warm to room temperature. The organic phase was separated, and the aqueous layer was extracted with ether (3×300 mL). The combined organic extracts were dried (MgSO4), filtered through celite and the solvents were removed in vacuo to yield the crude silyl ether 32 which was used without further purification. An analytical sample was prepared by flash column chromatography (silica gel, 2 to 17% ether in hexanes); Rf=0.50 (silica gel, 17% EtOAc in hexanes); [α]22D +20.3 (c 0.94, CHCl3), IR (film) nmax 2955, 2932, 2890, 2857, 1687, 1256, 1086, 838, 776 cm−1; 1H NMR (400 MHz, CDCl3) d 5.79 (dddd, J=17.0, 10.0, 7.0, 7.0 Hz, 1H, CH2CH=CH2), 5.01–4.94 (m, 2H, CH2CH=CH2), 4.16 (dd, J=5.5, 5.5 Hz, 1H, CHOTBS), 2.38–2.21 (m, 2H, CH2CH=CH2), 2.30 (q, J=7.5 Hz, 2H, CH3CH2), 1.13–1.09 (m, 1H, C(CH2)2), 1.00 (t, J=7.5 Hz, 3H, CH3CH2), 0.98–0.90 (m, 3H, C(CH2)2), 0.86 (s, 9H, SiC(CH3)3(CH3)2), 0.04 (s, 3H, SiC(CH3)3 (CH3)2), 0.01 (s, 3H, SiC(CH3)3(CH3)2); 13C NMR (100.6 MHz, CDCl3) d 210.5, 135.5, 116.8, 70.2, 41.6, 36.3, 31.0, 25.8, 18.0, 12.6, 11.3, 8.3, −4.3, −4.6; HRMS (FAB), calcd for C16H31O2Si (M+H+) 283.2093, found 283.2087.

Synthesis of Spirocyclopropane Ketoacid 31 as Illustrated in FIG. 41

Oxidation of Olefin 273.

The crude alkene 273 was dissolved in MeCN (143 mL), CCl4 (143 mL) and H2O (214 mL) and the mixture cooled to 0° C. Sodium periodate (70 g, 327 mmol, 4.1 equiv) and ruthenium(III) chloride hydrate (898 mg, 3.98 mmol, 0.05 equiv) were added and the mixture was stirred at 0° C. for 10 min. The dark mixture was allowed to warm to ambient temperature and stirred for 3 h, after. which time the disappearance of starting material was indicated by TLC. CH2Cl2 (1.5 L) and saturated aqueous NaCl solution (1.5 L) were added and the layers were separated. Extractions of the aqueous phase with CH2Cl2 (3×750 mL), filtration through celite, concentration and flash column chromatography (2 to 80% EtOAc in hexanes) yielded pure spirocyclopropane ketoacid 31 (10.2 g, 43% for three steps); Rf=0.39 (silica gel, 50% EtOAc in hexanes); [a]22D −0.8 (c 1.19, CHCl3); IR (film) nmax 2955, 2930, 2857, 1712, 1687, 1255, 1090, 838, 778 cm−1; 1H NMR (500 MHz, CDCl3) d 4.45 (dd, J=5.5, 5.5 Hz, 1H, CHOTBS), 2.62 (dd, J=15.5, 5.5 Hz, 1H, CH2CHOTBS), 2.61 (dd, J=15.5, 5.5 Hz, 1H, CH2CHOTBS), 2.39 (dq,. J=17.5, 7.0 Hz, 1H, CH3CH2), 2.28 (dq, J=17.5, 7.0 Hz, 1H, CH3CH2), 1.01 (t, J=7.0 Hz, 3H, CH3CH2), 0.84 (s, 9H, SiC(CH3)3(CH3)2), 0.06 (s, 3H, SiC(CH3)3(CH3)2), 0.04 (s, 3H, SiC(CH3)3(CH3)2); 13C NMR (150.9 MHz, CDCl3) d 210.2, 177.4, 68.7, 42.2, 36.4, 30.9, 25.7, 18.0, 13.0, 12.6, 8.2, −4.6, −4.9; HRMS (FAB), calcd for C15H28NaO4Si (M+Na+) 323.1655, found 323.1650.

Synthesis of Hydroxy Acids 270 and 277 as Illustrated in FIG. 42

Aldol Condensation of Ketoacid 272 with Aldehyde 7.

In accordance with the procedure described for the preparation of aldols with epothilones vida supra; ketoacid 272 (1.581 g, 5.26 mmol) in THF (18 mL) was treated with lithium diisopropylamide [LDA; freshly prepared from n-BuLi (7.73 mL, 1.6 M solution in hexanes, 12.37 mmol, 2.35 equiv) and diisopropylamine (1.70 mL, 12.10 mmol, 2.3 equiv) in THF (53 mL)] and aldehyde 8 (1.13 g, 8.94 mmol, 1.7 equiv) in THF (53 mL) to afford a mixture of aldol products 270 and 277 in a ratio of ca. 2:3 (1H NMR). This crude material was used without further purification.

Synthesis of Esters 28 and 37 as Illustrated in FIG. 42

EDC Coupling of Alcohol 271 with the Mixture of Ketoacids 29 and 36.

By analogy to the procedure described above for the synthesis of esters with epothilones vida supra, a solution of the mixture of ketoacids 269 and 277 (2.289 g crude), 4-dimethylaminopyridine (4-DMAP, 66 mg, 0.540 mmol), and alcohol 271 (2.81 g, 13.43 mmol) in CH2Cl2 (8.0 mL) was treated with 1-ethyl-(3-dimethylaminopropyl)-3-carbodiimide hydrochloride (EDC, 1.23 g, 6.42 mmol) to provide, after column chromatography (silica gel, 33 to 50% ether in hexanes), ester 269 (488 mg, 15% from ketoacid 31) and ester 37 (1.171 g, 36% from ketoacid 31). 269: Rf=0.38 (silica gel, 50% ether in hexanes); IR (film) nmax 3508, 3078, 2926, 2855, 1737, 1675, 1378, 1255, 1170, 1095, 987, 836 cm−1; 1H NMR (400 MHz, CDCl3) d 6.96 (s, 1H, ArH), 6.50 (s, 1H, ArCH=CCH3), 5.87–5.65 (m, 2H, 2×CH2CH=CH2), 5.28 (dd, J=6.8, 6.8 Hz, 1H, CO2CH), 5.10 (d, J=17.0 Hz, 1H, CH2CH=CH2), 5.04 (d, J=10.0 Hz, 1H,. CH2CH=CH2), 5.00 (d, J=17.0 Hz, 1H, CH2CH=CH2), 4.93 (d, J=10.0 Hz, 1H, CH2CH=CH2), 4.30 (dd, J=6.2, 5.0 Hz, 1H, (CH2)2CCH(OTBS)), 3.48 (bs, 1H, CHOH(CHCH3)), 3.42 (d, J=9.2 Hz, 1H, CHOH (CHCH3), 2.98 (q, J=6.5 Hz, 1H, CH3CH(C=O)), 2.70 (s, 3H, CH3Ar), 2.66 (dd, J=15.0, 6.8 Hz, 1H, CH2COO), 2.56 (dd, J=15.0, 5.0 Hz, 1H, CH2COO), 2.51–2.45 (m, 2H, CH2CH=CH2), 2.09–2.02 (m, 2H, CH2CH=CH2), 2.06 (d, J=1.0 Hz, 3H, ArCH=CCH3), 1.78–1.74 (m, 1H), 1.73–1.63 (m, 1H), 1.63–1.48 (m, 2H), 1.34–0.96 (m, 5H), 1.01 (d, J=7.0 Hz, 3H, CH3CH(C=O)), 0.87 (s, 9H, SiC(CH3)3(CH3)2), 0.84 (d, J=7.0 Hz, 3H, CH3CHCH2), 0.08 (s, 3H, SiC(CH3)3(CH3)2), 0.07 (s, 3H, SiC(CH3)3(CH3) 2); 13C NMR (100.6 MHz, CDCl3) d 216.0, 170.2, 164.5, 152.3, 138.9, 136.6, 133.2, 121.1, 117.7, 116.3, 114.0, 78.6, 74.3, 69.2, 42.6, 40.5, 37.4, 35.9, 35.4, 34.1, 32.3, 26.0, 25.6, 19.1, 17.9, 15.3, 14.6, 14.0, 12.5, 10.0, −4.5, −5.0; HRMS (FAB), calcd for C34H55CsNO5SSi (M+Cs+) 750.2625, found 750.2649. 37: Rf=0.30 (silica gel, 50% ether in hexanes); [a]22D −12.7 (c 1.38, CHCl3); IR (film) nmax 3499, 3077, 2931, 2857, 1738, 1674, 1375, 1254, 1169, 1096, 982, 836 cm−1; 1H NMR (400 MHz, CDCl3) d 6.96 (s, 1H, ArH), 6.50 (s, 1H, ArCH=CCH3), 5.83–5.69 (m, 2H, 2×CH2CH=CH2), 5.29 (dd, J=6.8, 6.8 Hz, 1H, CO2CH), 5.10 (d, J=17.0 Hz, 1H, CH2CH=CH2), 5.04 (d, J=10.5 Hz, 1H, CH2CH=CH2), 5.00 (d, J=17.0 Hz, 1H, CH2CH=CH2), 4.95 (d, J=10.0 Hz, 1H, CH2CH=CH2), 4.32 (dd, J=6.5, 4.8 Hz, 1H, (CH2)2CCH(OTBS)), 3.50–3.46 (m, 1H, CHOH(CHCH3)), 3.24 (bd, J=2.0 Hz, 1H, CHOH(CHCH3), 2.94 (qd, J=7.0, 2.5 Hz, 1H, CH3CH (C=O)), 2.70 (s, 3H, CH3Ar), 2.65 (dd, J=15.1, 6.5 Hz, 1H, CH2COO), 2.56 (dd, J=15.1, 4.8 Hz, 1H, CH2COO), 2.51–2.45 (m, 2H, CH2CH=CH2), 2.06 (d, J=1.0 Hz, 3H, ArCH=CCH3), 2.06–1.96 (m, 2H,. CH2CH=CH2), 1.66–1.01 (m, 9H), 1.04 (d, J=7.0 Hz, 3H, CH3CH(C=O)), 0.99 (d, J=6.5 Hz, 3H, CH3CHCH2), 0.87 (s, 9H, SiC(CH3) 3(CH3)2), 0.08 (s, 3H, SiC(CH3)3(CH3)2), 0.07 (s, 3H, SiC(CH3)3(CH3)2); 13C NMR (100.6 MHz, CDCl3) d 215.5, 170.3, 164.6, 152.4, 138.7, 136.7, 133.3, 121.2, 117.8, 116.3, 114.6, 78.7, 74.7, 69.2, 42.7, 41.1, 37.4, 36.1, 35.3, 33.9, 32.3, 26.0, 25.8, 19.2, 18.0, 15.4, 14.7, 13.8, 12.5, 11.4, −4.5, −4.8 ; HRMS (FAB), calcd for C34H55CsNO5SSi (M+Cs+) 750.2625, found 750.2649.

Synthesis of Hydroxy Lactones 268 and 279 as Illustrated in FIG. 43

Cyclization of Diene 269 via Olefin Metathesis.

As described for the cyclization of diene vida supra, a solution of diene 269 (79 mg, 0.128 mmol, 1.0 equiv) in CH2Cl2 (128 mL, 0.001 M) was treated with bis (tricyclohexylphosphine)benzylidine ruthenium dichloride ((RuCl2(=CHPh) (PCy3)2 (10.5 mg, 0.013 mmol, 0.1 equiv) for 2 h, to furnish, after preparative thin layer chromatography (250 mm silica gel plate, 17% EtOAc in hexanes) cis-hydroxy lactone 268 (28 mg, 37%) and trans-hydroxy lactone 279 (27 mg, 35%). 268: Rf=0.61 (silica, 50% EtOAc in hexanes); [a]22D −121.3 (c 0.67, CHCl3); IR (film) nmax 2928, 2855, 1738, 1678, 1461, 1381, 1254, 1165, 1104, 1064, 835 cm−1; 1H NMR (500 MHz, CDCl3) d 6.93 (s, 1H, ArH), 6.44 (s, 1H, ArCH=C(CH3)), 5.52–5.45 (m, 1H, CH=CHCH2) 5.30 (ddd, J=10.5, 10.5, 6.5 Hz, 1H, CH=CHCH2), 5.20 (d, J=8.5 Hz, 1H, CO2CH), 4.07–4.00 (m, 1H), 3.86 (bs, 1H, CHOH(CHCH3)), 3.56–3.53 (m, 1H), 2.83 (dd, J=16.0, 11.5 Hz, 1H, CH2COO), 2.87–2.77 (m, 1H), 2.70 (s, 3H, CH3Ar), 2.67–2.56 (m, 1H), 2.55 (dd, J=16.0, 2.0 Hz, 1H, CH2COO), 2.31–2.19 (m, 2H), 2.15–2.09 (m, 1 H), 2.06 (s, 3H, ArCH=CCH3), 1.77–1.73 (m, 1H), 1.67–1.52 (m, 2H), 1.43–1.23 (m, 2H), 1.15 (di J=7.0 Hz, 3H, CH3CH(C=O)), 1.05–0.85 (m, 3H), 1.00 (d, J=7.0 Hz, 3H, CH3CHCH2), 0.92 (s, 9H, SiC(CH3)3(CH3)2), 0.50–0.44 (m, 1H, C(CH2) 2), 0.15 (s, 3H, SiC(CH3)3(CH3)2), 0.15 (s, 3H, SiC(CH3) 3(CH3)2); 13C NMR (125.7 MHz, CDCl3) d; 217.5, 169.5, 164.4, 152.3, 138.3, 133.5, 124.5, 119.0, 115.8, 77.4, 74.1, 73.9, 44.5, 41.1, 39.1, 35.0, 32.8, 31.3, 29.6, 27.7, 25.8, 21.2, 19.1, 18.0, 15.5, 15.3, 14.7, 11.8, −3.0, −5.9; HRMS (FAB), calcd for C32H52NO5SSi (M+H+) 590.3335, found 590.3347. 279: Rf=0.63 (silica gel, 50% EtOAc in hexanes); [a]22D −71.6 (c 0.57, CHCl3); IR (thin film) nmax 2929, 2855, 1738, 1668, 1380, 1254, 1167, 1105, 1066, 1105, 837cm−1; 1H NMR (500 MHz, CDCl3) d 6.93 (s, 1H, ArH), 6.49 (s, 1H, ArCH=C(CH3)), 5.38 (ddd, J=15.0, 11.5, 4.0 Hz, 1H, CH=CHCH2), 5.26 (ddd, J=15.0, 7.5, 7.0 Hz, 1H, CH=CHCH2), 5.11 (dd, J=7.5, 7.0 Hz, 1H, CO2CH), 4.15–4.07 (m, 1H), 3.87 (d, J=4.5 Hz, 1H), 3.60–3.50 (m, 2H), 2.81 (dd, J=16.5, 11.5 Hz, 1H, CH2COO), 2.70 (s, 3H, CH3Ar), 2.57 (dd, J=16.5, 2.0 Hz, 1H, CH2COO), 2.42–2.36 (m, 3H), 2.04 (s, 3H, ArCH=CCH3), 1.93–1.82 (m, 2H), 1.79–1.72 (m, 1H), 1.63–1.53 (m, 2H), 1.28–1.21 (m, 1H), 1.12 (d, J=7.0 Hz, 3H, CH3CH(C=O)), 1.03–0.84 (m, 3H), 1.01 (d, J=7.0 Hz, 3H, CH3CHCH2), 0.93 (s, 9H, SiC(CH3)3(CH3)2), 0.49–0.42 (m, 1H, C(CH2)2), 0.16 (s, 6H, SiC(CH3)3(CH3)2); 13C NMR (125.7 MHz, CDCl3) d 218.8, 169.5, 164.4, 152.3, 137.8, 134.2, 126.2, 119.4, 115.9, 77.8, 73.8, 73.1, 43.0, 41.1, 39.0, 37.6, 35.1, 33.3, 32.6, 29.6, 26.9, 25.9, 19.1, 18.1, 14.8, 14.2, 13.6, 11.5, −3.4, −5.7; HRMS (FAB), calcd for C32H52NO5SSi (M+H+) 590.3335, found 590.3351.

Synthesis of cis-Dihydroxy Lactone 280 as Illustrated in FIG. 43

Desilylation of Compound 268.

Silyl ether 268 (62 mg, 0.105 mmol), in THF (3.0 mL, 0.035 M) was treated with hydrogen fluorideopyridine (1.2 mL, 0.1 M) at 0° C. for 30 min. The mixture was allowed to warm to room temperature over 28 h, after which time TLC indicated the disappearance of starting material. The resulting solution was added dropwise to a mixture of saturated aqueous NaHCO3 (20 mL) and EtOAc (20 mL) and the mixture stirred until effervesence ceased. The two layers were then separated and the aqueous re-extracted with EtOAc (2×20 mL). The combined organic phases were washed with NaHCO3 (30 mL) and brine (30 mL) and dried (MgSO4). Concentration followed by flash column chromatography (silica gel, 17 to 50% EtOAc in hexanes) furnished cis-dihydroxy lactone 280 (32 mg, 65%). Rf=0.28 (silica gel, 50% EtOAc in hexanes); [a]22D −105.5 (c 0.55, CHCl3); IR (thin film) nmax 3465, 2929, 1732, 1675, 1372, 1171, 983, 733 cm−1; 1H NMR (500 MHz, CDCl3) d 6.97 (s, 1H, ArH), 6.53 (s, 1H, ArCH=C(CH3)), 5.61 (ddd, J=10.0, 8.5, 7.5 Hz, 1H, CH=CHCH2), 5.54 (dd, J=9.0, 2.5 Hz, 1H, CO2CH), 5.37 (ddd, J=10.5, 10.5, 5.5 Hz, 1H, CH=CHCH2), 3.87–3.82 (m, 1H), 3.67 (ddd, J=9.5, 3.5, 3.5 Hz, 1H), 3.62–3.56 (m, 2H), 2.78 (dd, J=17.5, 10.0 Hz, 1H, CH2COO), 2.71 (s, 3H, CH3Ar), 2.67 (dd, J=17.5, 3.0 Hz, 1H, CH2COO), 2.63 (ddd, J=15.0, 9.5, 9.5 Hz, 1H, CH=CHCH2), 2.38–2.31 (m, 1H, CH=CHCH2), 2.29–2.20 (m, 1H, CH=CHCH2), 2.07 (s, 3H, ArCH=CCH3), 2.01–1.94 (m, 1H, CH=CHCH2), 1.70–1.50 (m, 2H), 1.48–1.40 (m, 2H), 1.48–1.40 (m, 2H), 1.21 (d, J=7.0 Hz, 3H CH3CH(C=O)), 1.11 (ddd, J=9.5, 7.0, 4.0 Hz, 1H, C(CH2)2), 1.03 (d, J=7.0 Hz, 3H, CH3CHCH2), 0.99 (ddd, J=9.5, 6.5, 4.5 Hz, 1H, C(CH2)2), 0.65 (ddd, J=10.0, 7.0, 4.5 Hz, 1H, C(CH2)2); 13C NMR (125.7 MHz, CDCl3) d; 215.4, 171.9, 164.7, 152.1, 136.8, 133.2, 124.7, 119.7, 116.2, 77.3, 75.5, 70.7, 45.6, 38.5, 37.5, 34.0, 31.5, 30.4, 27.7, 27.0, 19.1, 18.2, 16.6, 15.9, 15.4, 11.2; HRMS (FAB), calcd for C26H38NO5S (M+H+) 476.2471, found 476.2482.

Synthesis of trans-Dihydroxy Lactone 281 as Illustrated in FIG. 43

Desilylation of Compound 279.

Silyl ether 279 (62 mg, 0.105 mmol), in THF (3.0 mL, 0.035 M) was treated with hydrogen fluoride-pyridine (1.2 mL, 0.1 M) at room temperature for 25 h, according to the procedure described for cis-dihydroxy lactone 280, to yield, after flash column chromatography (silica gel, 17 to 50% EtOAc in hexanes), trans-dihydroxy lactone 281 (31 mg, 62%). Rf=0.38 (silica gel, 50% EtOAc in hexanes); [α]22D −72.5 (c 0.24, CHCl3); IR (thin film) nmax 3502, 2922, 2852, 1730, 1672, 1456, 1373, 1179, 976 cm−1; 1H NMR (500 MHz, CDCl3) d 6.96 (s, 1H, ArH), 6.53 (s, 1H, ArCH=C(CH3)), 5.49–5.44 (m, 2H, CH=CHCH2 and CO2CH), 5.35 (ddd, J=15.0, 7.5, 7.5 Hz, 1H, CH=CHCH2), 3.81 (m, 1H), 3.77 (d, J=3.0, 1H), 3.72 (qd, J=7.0, 2.5 Hz, 1H, CH3CH(C=O)), 3.67 (m, 1H), 3.03 (bs, OH), 2.77 (dd, J=17.5, 10.5 Hz, 1H, CH2COO), 2.70 (s, 3H, CH3Ar), 2.64 (dd, J=17.5, 2.5 Hz, 1H, CH2COO), 2.46–2.43 (m, 2H), 2.34–2.27 (m, 1H), 2.10–2.05 (m, 1H), 2.07 (d, J=1.5 Hz, 3H, ArCH=CCH3), 1.96–1.88 (m, 1H), 1.79–1.63 (m, 1H), 1.60–1.00 (m, 3H), 1.47 (ddd, J=9.5, 7.0, 4.0 Hz, 1H, C(CH2)2), 1.17 (d, J=7.0 Hz, 3H, CH3CH (C=O)), 1.11 (ddd, J=9.5, 7.0, 4.0 Hz, 1H, C(CH2)2), 1.01 (d, J=7.0 Hz, 3H, CH3CHCH2), 0.97 (ddd, J=9.5, 7.0, 4.5 Hz, 1H, C(CH2)2), 0.61 (ddd, J=9.5, 6.5, 4.0 Hz, 1H, C(CH2)2); 13C NMR (125.7 MHz, CDCl3) d; 217.2, 171.8, 164.7, 152.1, 136.9, 134.4, 125.5, 120.0, 116.3, 77.8, 73.9, 70.9, 44.0, 38.6, 38.1, 37.0, 32.6, 32.3, 29.6, 26.7, 19.1, 18.7, 15.0, 14.9, 13.9, 11.4; HRMS (FAB), calcd for C26H37CsNO5S (M+Cs+) 608.1447, found 608.1471.

Synthesis of 4,4-Ethano-epothilone A Analogs 267 and 282 as Illustrated in FIG. 43
Epoxidation of cis-Dihydroxy Lactone 280.

To a solution of cis-dihydroxy lactone 280 (8.2 mg, 0.017 mmol) in acetonitrile (200 mL) and CH2Cl2 (100 mL) was added a 0.0004 M aqueous solution of disodium salt of ethylenediaminetetraacetic acid (Na2EDTA, 150 mL) and the reaction mixture was cooled to 0° C. Excess of 1,1,1-trifluoroacetone (100 mL) was added, followed by a portionwise addition of Oxone® (18.0 mg, 0.029 mmol, 1.7 equiv) and NaHCO3 (4.0 mg, 0.048 mmol, 2.8 equiv) with stirring, until the disappearance of most of the starting material was indicated by TLC. The reaction mixture was then immediately passed through a short pad of silica gel with 80% EtOAc in hexanes and concentrated. Purification by preparative thin layer chromatography (250 mm silica gel plate, 75% EtOAc in hexanes) provided a mixture of diastereomeric epoxides, epoxide 267 (or 282) (4.2 mg, 50%) and α-isomeric epoxide 282 (or 267) (2.5 mg, 29%). 267 (or 282): Rf=0.13 (silica gel, 67% EtOAc in hexanes); [a]22D −89.4 (c 0.18, CHCl3); IR (thin film) nmax 3472, 2927, 2871, 1739, 1675, 1453, 1377, 1158, 1091, 985 cm−1; 1H NMR (500 MHz, CDCl3) d 6.98 (s, 1H, ArH), 6.50 (s, 1H, ArCH═C(CH3)), 5.69–5.66 (m, 1H, CO2CH), 3.87 (d, J=8.5 Hz, 1H), 3.86–3.81 (m, 1H), 3.56 (dq, J=7.0, 7.0 Hz, 1H, CH3CH(C═O)), 3.44 (d, J=3.0 Hz, 1H), 3.03 (ddd, J=8.5, 4.5, 4.5 Hz, 1H, CH2CH—O(epoxide)CH), 2.93 (ddd, J=8.0, 4.0, 4.0 Hz, 1H, CH2CH—O(epoxide)CH), 2.83 (dd, J=17.5, 9.5 Hz, 1H, CH2COO), 2.72 (dd, J=17.5, 3.0 Hz, 1H, CH2COO), 2.71 (s, 3H, CH3Ar), 2.27 (ddd, J=15.0, 5.0, 5.0 Hz, 1H, CH2CH—O(epoxide)CH), 2.12 (s, 3H, ArCH═CCH3), 1.79 (ddd, J=15.0, 8.5, 3.5 Hz, 1H, CH2CH—O(epoxide)CH), 1.75–1.15 (m, 8H), 1.22 (d, 3H, J=6.5 Hz, CH3CH(C═O)), 1.12 (ddd, J=9.5, 7.0, 4.5 Hz, 1H, C(CH2)2), 1.06 (d, J=7.0 Hz, 3H, CH3CHCH2), 1.00 (ddd, J=10.0, 7.0, 4.5 Hz, 1H, C(CH2)2), 0.72–0.69 (m, 1H, C(CH2)2); 13C NMR (150.9 MHz, CDCl3) d 214.5, 171.4, 164.9, 151.9, 135.7, 118.9, 116.3, 76.2, 74.8, 70.5, 57.2, 53.4, 46.4, 38.7, 36.6, 34.5, 30.3, 30.0, 29.7, 27.2, 24.2, 19.2, 17.7, 16.6, 16.3, 10.9; HRMS (FAB), calcd for C26H37CsNO6S (M+Cs+) 624.1396, found 624.1374. 41 (or 3): Rf=.0.06 (silica gel, 67% EtOAc in hexanes); [a]22D −43.4 (c 0.13, CHCl3); IR (thin film) nmax 3472, 2924, 2855, 1734, 1677, 1457, 1376, 1159, 1091, 1042, 983 cm−1; 1H NMR (400 MHz, CDCl3) d 6.98 (s, 1H, ArH), 6.55 (s, 1H, ArCH═C(CH3)), 5.61 (dd, J=9.5, 2.5 Hz, 1H, CO2CH), 3.88–3.84 (m, 1H), 3.84–3.81 (m, 1H), 3.51 (d, J=2.5 Hz, 1H), 3.38 (dq, J=7.0, 7.0 Hz, 1H, CH3CH(C═O)), 3.10–3.01 (m, 2H, CH2CH—O(epoxide)CH), 2.80 (dd, J=17.0, 8.0 Hz, 1H, CH2COO)—, 2.70 (s, 3H, CH3Ar), 2.68 (dd, J=17.0, 3.5 Hz, 1H, CH2COO), 2.18–2.12 (ddd, 1H, J=14.7, 3.0, 3.0 Hz, 1H, CH2CH—O (epoxide)CH), 2.08 (s, 3H, ArCH═CCH3), 2.05–1.95 (m, 1H, CH2CH—O(epoxide)CH), 1.86–1.75 (m, 1H, CH2CH—O(epoxide)CH), 1.85 (ddd, J=14.8, 9.4, 9.4 Hz, 1H, CH2CH—O(epoxide)CH), 1.70–1.15 (m, 6H), 1.19 (d, J=6.5 Hz, 3H, CH3CH(C═O)), 1.12 (ddd, J=9.5, 7.0, 4.5 Hz, 1H, C(CH2)2), 1.03 (d, J=7.0 Hz, 3H, CH3CHCH2), 1.01–0.97 (m, 1H, C(CH2)2), 0.85–0.75 (m, 1H, C(CH2)2); 13C NMR (100.6 MHz, CDCl3) d 214.1, 171.9, 166.2, 152.0, 136.2, 120.7, 116.9, 77.3, 75.8, 69.6, 56.1, 55.0, 45.6, 38.4, 36.3, 34.6, 31.0, 29.7, 29.3, 27.7, 22.5, 17.4, 16.3, 16.1, 15.0, 10.6; HRMS (FAB), calcd for C26H37CsNO6S (M+Cs+) 624.1396, found 624.1376.

Synthesis of 4,4-Ethano-epothilone A Analogs 283 and 284 as Illustrated in FIG. 43
Epoxidation of trans-Dihydroxy Lactone 281.

As described in the procedure for the epoxidation of cis-dihydroxy lactone 280, trans-hydroxy lactone 281 (19.0 mg, 0.040 mmol) in MeCN (200 mL) and CH2Cl2 (150 mL) was treated with a 0.0004 M aqueous solution of disodium salt of ethylenediaminetetraacetic acid (Na2EDTA, 120 mL), 1,1,1-trifluoroacetone (200 mL), Oxone® (172 mg, 0.280 mmol, 7.0 equiv) and NaHCO3 (38 mg, 0.452 mmol, 11 equiv), to yield, after purification by preparative thin layer chromatography (250 mm silica gel plate, 6% MeOH in CHCl3), epoxides 283 (or 284) (2.1 mg, 11%) and 284 (or 283) (6.0 mg, 31%). 283 (or 284): Rf=0.06 (silica gel, 50% EtOAc in hexanes); [a]22D −47.1 (c 0.05, CHCl3); IR (thin film) nmax 3472, 2919, 2850, 1730, 1672, 1460, 1164 1053, 732 cm−1; 1H NMR (500 MHz, CDCl3) d 6.98 (s, 1H, ArH), 6.55 (s, 1H, ArCH═C(CH3)), 5.54 (dd, J=10.5, 2.5 Hz, 1H, CO2CH), 4.07–4.02 (m, 1H), 3.87–3.84 (m, 1H), 3.75 (d, J=5.0 Hz, 1H), 3.25 (dq, J=6.5, 6.5 Hz, 1H, CH3CH(C═O)), 2.86 (dd, J=17.5, 7.5 Hz, 1H, CH2COO), 2.77–2.75 (m, 1H, CH2CH—O(epoxide)CH), 2.73–2.69 (m, 1H, CH2CH—O(epoxide)CH), 2.71 (s, 3H, CH3Ar), 2.70 (dd, J=17.5, 3.5 Hz, 1H, CH2COO), 2.37–2.34 (m, 1H), 2.07 (s, 3H, ArCH═CCH3), 2.07–1.98 (m, 1H), 1.95–1.87 (m, 1H), 1.87–1.78 (m, 1H), 1.73–0.80 (m, 9H), 1.16 (d, 3H, J=6.5 Hz, CH3CH(C═O)), 0.98 (d, J=7.0 Hz, 3H, CH3CHCH2); HRMS (FAB), calcd for C26H37CsNO6S (M+Cs+) 624.1396, found 624.1377. 43 (or 42): Rf=0.04 (silica gel, 50% EtOAc in hexanes); [a]22D −87.2 (c 0.11, CHCl3); IR (thin film) nmax 3493, 2921, 2851, 1736, 1674, 1451, 1374, 1162, 982, 731 cm−1; 1H NMR (500 MHz, CDCl3) d 6.98 (s, 1H, ArH), 6.54 (s, 1H, ArCH═C(CH3)), 5.49–5.46 (m, 1H, CO2CH), 4.06–4.00 (m, 1H), 3.88–3.84 (m, 1H), 3.70–3.65 (m, 1H), 3.30 (dq, 1H, J=7.0, 7.0 Hz, 1H, CH3CH(C═O)), 2.86 (dd, J=17.5, 7.5 Hz, 1H, CH2COO), 2.82–2.73 (m, 3H, CH2CH—O(epoxide)CH and CH2COO), 2.71 (s, 3H, CH3Ar), 2.29 (ddd, J=15.0, 6.5, 4.0 Hz, 1H, CH2CH—O(epoxide)CH), 2.10–2.02 (m, 1H, CH2CH—O(epoxide)CH), 2.09 (s, 3H, ArCH═CCH3), 1.84–1.73 (m, 2H), 1.66–0.82 (m, 9H), 1.19 (d, 3H, J=7.0 Hz, CH3CH(C═O)), 1.01 (d, J=6.5 Hz, 3H, CH3CHCH2); 13C NMR (125.7 MHz, CDCl3) d 214.0, 172.0, 164.9, 152.0, 136.0, 119.5, 116.5, 75.7, 75.0, 69.3, 57.8, 55.0, 44.6, 38.1, 36.2, 34.4, 31.4, 30.0, 29.7, 29.3, 22.2, 19.2, 16.9, 15.7, 15.2, 10.6; HRMS (FAB), calcd for C26H37CsNO6S (M+Cs+) 624.1396, found 624.1417.

Synthesis of Hydroxy Lactones 285 and 286 as Illustrated in FIG. 44
Cyclization of Diene 278 via Olefin Metathesis.

As described for the cyclization of diene vida supra, a solution of diene 278 (525 mg, 0.85 mmol) in CH2Cl2 (850 mL, 0.001 M) was treated with bis(tricyclohexylphosphine) benzylidine ruthenium dichloride (RuCl2(═CHPh) (PCy3)2 (64 mg, 0.085 mmol, 0.1 equiv), to furnish, after flash column chromatography (silica gel, 33% ether in hexanes), cis-hydroxy lactone 285 (88 mg, 18%) and trans-hydroxy lactone 286 (284 mg, 58%). 285: Rf=0.70 (silica gel, 50% EtOAc in hexanes); [a]22D −95.7 (c 0.44, CHCl3); IR (film) nmax 2917, 2849, 1737, 1662, 1164, 1100, 834, 777 cm−1; 1H NMR (500 MHz, CDCl3) d 6.94 (s, 1H, ArH), 6.44 (s, 1H, ArCH═C(CH3)), 5.47–5.40 (m, 1H, CH═CHCH2)., 5.37–5.31 (m, 1H, CH═CHCH2), 5.25–5.24 (m, 1H, CO2CH), 4.15–4.08 (m, 1H), 3.8 (bs, 1H, CHOH(CHCH3)), 3.61–3.54 (m, 1H), 3.47 (d, J=10.5 Hz, 1H, CHOH(CHCH3)), 2.99 (dd, J=15.5, 12.5 Hz, 1H, CH2COO), 2.70 (s, 3H, CH3Ar), 2.56 (dd, J=15.5, 2.5 Hz, 1H, CH2COO), 2.40–2.30 (m, 1H), 2.18–2.13 (m, 3H), 2.07 (s, 3H, ArCH=CCH3), 1.70–0.85 (m, 8H), 1.08 (d, J=6.5 Hz, 3H, CH3CH(C=O)), 1.06 (d, J=7.0 Hz, 3H, CH3CHCH2), 0.92 (s, 9H, SiC(CH3)3(CH3)2), 0.65–0.56 (m, 1H, C(CH2)2), 0.14 (s, 3H, SiC(CH3)3(CH3)2), 0.13 (s, 3H, SiC(CH3)3(CH3)2); 13C NMR (125.7 MHz, CDCl3) d 219.4, 169.4, 164.4, 152.3, 137.2, 133.2, 124.6, 118.8, 115.7, 77.1, 76.8, 74.1, 43.0, 41.2, 37.4, 35.1, 35.0, 32.6, 30.9, 29.6, 27.8, 25.8, 23.1, 19.1, 17.9, 15.8, 15.3, 10.5, −2.9, −6.1; HRMS (FAB), calcd for C32H52NO5SSi (M+H+) 590.3335, found 590.3355. 286: Rf=0.71 (silica gel, 50% EtOAc in hexanes); [a]22D −86.0 (c 1.75, CHCl3); IR (film) nmax 2928, 2855, 1738, 1664, 1382, 1165, 1103, 1061, 970, 836, 777 cm−1; 1H NMR (500 MHz, CDCl3) d 6.93 (s, 1H, ArH), 6.51 (s, 1H, ArCH=C(CH3)), 5.31 (ddd, J=15.0, 8.0, 2.0 Hz, 1H, CH=CHCH2), 5.29 (ddd, J=15.0, 7.5, 2.0 Hz, 1H, CH=CHCH2), 5.12 (dd, J=10.5, 4.0 Hz, 1H, CO2CH), 4.17 (q, J=6.0 Hz, 1H, CH3CH(C=O)), 3.81 (m, 1H, OH), 3.56 (d, J=11.5 Hz, 1H, (CH2)2CCH(OTBS)), 3.39 (d, J=9.5 Hz, 1H, CHOH(CHCH3)), 2.92 (dd, J=16.0, 11.5 Hz, 1H, CH2COO), 2.69 (s, 3H, CH3Ar), 2.57 (dd, J=16.0, 2.0 Hz, 1H, CH2COO), 2.48–2.33 (m, 3H, 3 x CH=CHCH2), 2.05 (s, 3H, ArCH=CCH3), 1.97–1.89 (m, 1H, CH=CHCH2), 1.65–0.90 (m, 8H), 1.05 (d, J=6.0 Hz, 3H, CH3CH(C=O)), 1.04 (d, J=7.0 Hz, 3H, CH3CHCH2), 0.92 (s, 9H, SiC(CH3)3(CH3)2), 0.63–0.57 (m, 1H, C(CH2)2), 0.17 (s, 3H, SiC(CH3)3(CH3)2), 0.14 (s, 3H, SiC(CH3)3(CH3)2); 13C NMR (125.7 MHz, CDCl3) d 219.5, 169.4, 164.4, 152.3, 137.8, 133.9, 126.1, 119.3, 115.9, 77.8, 75.1, 74.1, 42.5, 40.9, 37.5, 35.4, 35.1, 32.6, 31.6, 29.6, 25.9, 25.7, 19.1, 18.0, 15.6, 15.0, 14.9, 10.2, −2.9, −6.0; HRMS (FAB), calcd for C32H52NO5SSi (M+H+) 590.3335, found 590.3353.

Synthesis of cis-Dihydroxy Lactone 286 as Illustrated in FIG. 44

Desilylation of Compound 285.

Silyl ether 285 (24 mg, 0.041 mmol), in THF (1.4 mL, 0.03 M), was treated with hydrogen fluoride-pyridine (0.35 mL, 0.1 M) at room temperature for 15 h, according to the procedure described for cis-dihydroxy lactone vida supra, to yield, after flash column chromatography (silica gel, 50% EtOAc in hexanes), trans-dihydroxy lactone 286 (10.5 mg, 54%). Rf=0.41 (silica gel, 50% EtOAc in hexanes); [a]22D −147.4 (c 0.62, CHCl3); IR (thin film) nmax 3510, 2925, 2855, 1735, 1672, 1452, 1375, 1244, 1165, 1087, 980, 732 cm−1; 1H NMR (500 MHz, CDCl3) d 6.97 (s, 1H, ArH), 6.55 (s, 1H, ArCH=C(CH3)), 5.55 (dd, J=8.5, 2.0 Hz, 1H, CO2CH), 5.50 (ddd, J=10.0, 10.0, 6.0 Hz, 1H, CH=CHCH2), 5.37 (ddd, J=10.0, 10.0, 5.5 Hz, 1H, CH=CHCH2), 3.82 (q, J=7.0 Hz, 1H, CH3CH(C=O)), 3.68 (dd, J=11.5, 3.0 Hz, 1H, (CH2)2CCHOH), 3.62 (1H, bs, CHOH(CHCH3)), 3.50 (d, J=10.0 Hz, 1H, CHOH (CHCH3)), 3.19 (d, J=3.0 Hz, 1H, (CH2)2CCHOH), 2.82 (dd, J=17.0, 11.5 Hz, 1H, CH2COO), 2.71 (s, 3H, CH3Ar), 2.70–2.58 (m, 1H, CH=CHCH2), 2.66 (dd, J=17.0, 3.0 Hz, 1H, CH2COO), 2.42–2.35 (m, 1H, CH=CHCH2), 2.21–2.13 (m, 1H, CH=CHCH2), 2.12–2.01 (m, 1H, CH=CHCH2), 2.09 (s, 3H, ArCH=CCH3), 1.64–1.59 (m, 1H), 1.54–1.44 (m, 3H), 1.41–1.35 (m, 1H), 1.15–1.00 (m, 3H), 1.11 (d, J=7.0 Hz, 3H, CH3CH(C=O)), 1.07 (d, J=6.5 Hz, 3H, CH3CHCH2), 0.65–0.61 (m, 1H, C(CH2)2); 13C NMR (125.7 MHz, CDCl3) d 218.4, 171.0, 164.7, 152.1, 136.8, 133.1, 124.5, 119.5, 116.0, 77.3, 74.2, 71.4, 43.8, 39.7, 34.7, 33.8, 32.2, 31.5, 27.6, 25.3, 19.7, 19.1, 15.8, 15.7, 13.3, 10.6; HRMS (FAB), calcd for C26H38NO5S (M+H+) 476.2471, found 476.2485.

Synthesis of trans-Dihydroxy Lactone 288 as Illustrated in FIG. 44

Desilylation of Compound 286.

Silyl ether 286 (9.0 mg, 0.015 mmol, 1.0 equiv), in THF (0.45 mL, 0.03 M), was treated with hydrogen fluoride·pyridine (0.15 mL, 0.1 M) at room temperature for 22 h, according to the procedure described for cis-dihydroxy lactone 39, to yield, after flash column chromatography (silica gel, 50% EtOAc in hexanes), cis-dihydroxy lactone 288 (5.5 mg, 76%). Rf=0.43 (silica gel, 50% EtOAc in hexanes);. [a]22D −89.1 (c 1.09, CHCl3); IR (thin film) nmax 3485, 2930, 2856, 1732, 1665, 1374, 1173, 1092, 1014, 974, 732 cm−1; 1H NMR (500 MHz, CDCl3) d 6.96 (s, 1H, ArH), 6.54 (s, 1H, ArCH=C(CH3)), 5.54 (dd, J=10.0, 4.0 Hz, 1H, CO2CH), 5.39 (ddd, J=15.5, 9.0, 3.5 Hz, 1H, CH=CHCH2), 5.30 (ddd, 1H, J=15.5, 7.5, 4.5 Hz, 1H, CH=CHCH2), 3.88 (q, J=7.0 Hz, 1H, CH3CH(C=O)), 3.72 (bs, 1H, OH), 3.63 (bs, 1H, OH), 3.58 (d, J=11.5 Hz, 1H, (CH2)2CCHOH), 3.42 (d, J=10.0 Hz, 1H, CHOH (CHCH3)), 2.82 (dd, J=17.5, 11.5 Hz, 1H, CH2COO), 2.70 (s, 3H, CH3Ar), 2.64 (dd, J=17.5, 2.5 Hz, 1H, CH2COO), 2.50–2.41 (m, 2H, CH=CHCH2), 2.30–2.22 (m, 1H, CH=CHCH2), 2.08 (s, 3H, ArCH=CCH3), 1.98 dddd, J=14.0, 9.5, 9.5, 4.5 Hz, 1H, CH=CHCH2), 1.63–1.59 (m, 1H), 1.52–1.43 (m, 2H), 1.41–1.32 (m, 1H), 1.30–1.00 (m, 4H), 1.11 (d, J=6.5 Hz, 3H, CH3CH(C=O)), 1.02 (d, J=6.5 Hz, 3H, CH3CHCH2), 0.60 (ddd, J=9.0, 7.0, 4.0 Hz, 1H, C(CH2)2); 13C NMR (125.7 MHz, CDCl3) d 218.7, 171.6, 164.7, 152.1, 137.0, 134.1, 125.4, 120.0, 116.3, 77.6, 75.0, 71.7, 43.6, 39.0, 37.0, 35.0, 33.7, 33.0, 32.0, 25.4, 20.5, 19.1, 15.9, 15.1, 13.4, 10.4; HRMS (FAB), calcd for C26H37CsNO5S (M+Cs+) 608.1447, found 603.1423.

Synthesis of 4,4-Ethano-epothilone A Analogs 289 and 290 as Illustrated in FIG. 44

Epoxidation of cis-Dihydroxy Lactone 287.

As described in the procedure for the epoxidation of cis-dihydroxy lactone vida supra, cis-hydroxy lactone 287 (11.0 mg, 0.023 mmol) in MeCN (200 mL) and CH2Cl2 (300 mL) was treated with a 0.0004 M aqueous solution of disodium salt of ethylenediaminetetraacetic acid (Na2EDTA, 120 mL), 1,1,1-trifluoroacetone (200 mL), Oxone® (114 mg, 0.185 mmol, 8.0 equiv) and NaHCO3 (25 mg, 0.296 mmol, 12.8 equiv), to yield, after purification by preparative thin layer chromatography (250 mm silica gel plate, 17% acetone in CH2Cl2), epoxides 289 (or 290) (4.0 mg, 39%) and 290 (or 289) (4.5 mg, 35%). 289 (or 290): Rf=0.30 (silica gel, 50% EtOAc in hexanes); [a]22D −92.1 (c 0.14, CHCl3); IR (thin film) nmax 3468, 2922, 2854, 1735, 1668, 1456, 1378, 1257, 1161, 1093, 980, 733 cm−1; 1H NMR (400 MHz, CDCl3) d 6.97 (s, 1H, ArH), 6.54 (s, 1H, ArCH=C(CH3)), 5.78 (dd, J=5.0, 4.5 Hz, 1H, CO2CH), 4.12.(bd, J=11.0 Hz, 1H, (CH2)2CCHOH), 3.73 (q, J=7.0 Hz, 1H, CH3CH(C=O)), 3.62 (d, J=10.0 Hz, 1H, CHOH(CHCH3)), 3.59 (bs, 1H, OH), 3.51–3.47 (m, 1H, OH), 3.12 (ddd, J=6.5, 6.5, 4.0 Hz, 1H, CH2CH—O (epoxide)CH), 3.00 (ddd, J=6.5, 6.5, 4.0 Hz, 1H, CH2CH—O(epoxide)CH), 2.72 (dd, J=16.0, 11.0 Hz, 1H, CH2COO), 2.70 (s, 3H, CH3Ar), 2.55 (dd, J=16.0, 2.5 Hz, 1H, CH2COO), 2.11 (d, J=1.0 Hz, 3H, ArCH=CCH3), 2.00–1.93 (m, 2H), 1.75–1.06 (m, 8H), 1.13 (d, J=7.0 Hz, 3H, CH3CH(C=O)), 1.06 (d, J=6.5 Hz, 3H, CH3CHCH2), 1.06–0.95 (m, 2H, C(CH2)2), 0.71–0.68 (m, 1H, C(CH2)2); 13C NMR (150.9 MHz, CDCl3) d 218.4, 171.1, 160.5, 152.0, 136.2, 119.7, 116.5, 75.7, 73.7, 70.1, 56.6, 54.8, 43.3, 39.5, 34.2, 32.4, 31.9, 31.0, 29.7, 26.5, 21.4, 19.2, 15.8, 15.7, 11.3, 11.2; HRMS (FAB), calcd for C26H38NO6S (M+H+) 492.2420, found 492.2434. 290 (or 289): Rf=0.30 (silica gel, 50% EtOAc in hexanes); [a]22D −98.0 (c 0.21, CHCl3); IR (thin film) nmax 3460, 2923, 2855, 1736, 1669, 1454, 1378, 1240, 1159, 1040, 977, 733 cm−1; 1H NMR (400 MHz, CDCl3) d 6.97 (s, 1H, ArH), 6.59 (s, 1H, ArCH=C(CH3)), 5.62 (dd, J=6.0, 3.5 Hz, 1H CO2CH), 4.26 (d, J=10.5 Hz, 1H, (CH2)2CCHOH), 3.87 (bs, 1H, OH), 3.71 (d, J=9.2 Hz, 1H, CHOH(CHCH3)), 3.64–3.56 (m, 2H, CH3CH(C=O) and OH), 3.09 (ddd, J=6.0, 6.0, 4.0 Hz, 1H, CH2CH—O(epoxide)CH), 2.97 (ddd, J=6.0, 6.0, 4.5, 1H, CH2CH—O(epoxide)CH), 2.70 (s, 3H, CH3Ar), 2.62 (dd, J=15.5, 10.5 Hz, 1H, CH2COO), 2.41 (dd, J=15.5, 2.5 Hz, 1H, CH2COO), 2.13 (s, 3H, ArCH=CCH3), 2.08–1.97 (m, 2H), 1.75–1.03 (m, 8H), 1.09 (d, J=7.0 Hz, 3H, CH3CH(C=O)), 1.07 (d, J=6.5 Hz, 3H, CH3CHCH2), 1.00–0.90 (m, 2H, C(CH2)2), 0.74 (ddd, J=9.5, 7.0, 4.5 Hz, 1H, C(CH2)2); 13C NMR (150.9 MHz, CDCl3) d 217.7, 170.8, 164.9, 152.1, 135.6, 119.9, 116.7, 76.4, 73.6, 69.8, 56.6, 54.8, 42.6, 39.7, 34.6, 32.7, 30.9, 30.5, 29.7, 28.2, 21.2, 19.2, 17.1, 16.1, 15.8, 11.2; HRMS (FAB), calcd for C26H38NO6S (M+H+) 492.2420, found 492.2431.

Synthesis of 4,4-Ethano-epothilone A Analogs 291 and 292 as Illustrated in FIG. 44

Epoxidation of trans-Dihydroxy Lactone 286.

As described in the procedure for the epoxidation of cis-dihydroxy lactone 280, trans-hydroxy lactone 288 (20 mg, 0.042 mmol) in MeCN (400 mL) and CH2Cl2 (600 mL) was treated with a 0.0004 M aqueous solution of disodium salt of ethylenediaminetetraacetic acid (Na2EDTA, 400 mL), 1,1,1-trifluoroacetone (250 mL), Oxone® (207 mg, 0.334 mmol, 8.0 equiv) and NaHCO3 (45 mg, 0.538 mmol, 12.8 equiv), to yield, after purification by preparative thin layer chromatography (250 mm silica gel plate, 50% EtOAc in hexanes), epoxides 291 (or 292) (4.5 mg, 22%) and 292 (or 291) (5.6 mg, 27%). 291 (or 292): Rf=0.20 (silica gel, 50% EtOAc in hexanes); [a]22D −49.5 (c 0.33, CHCl3); IR (thin film) nmax 3472, 2923, 2855, 1734, 1666, 1457, 1374, 1263, 1163, 1089, 981, 910, 731 cm−1; 1H NMR (500 MHz, CDCl3) d 6.99 (s, 1H, ArH), 6.56 (s, 1H, ArCH=C(CH3)), 5.49 (dd, J=9.0, 2.5 Hz, 1H, CO2CH), 4.28–4.25 (m, 1H, (CH2)2CCHOH), 3.87 (d, J=3.5 Hz, 1H, OH), 3.69 (qd, J=7.0, 2.0 Hz, 1H, CH3CH(C=O)), 3.63 (d, J=8.5 Hz, 1H, CHOH(CHCH3)), 3.59 (bs, 1H, OH), 2.89 (ddd, J=5.5, 5.5, 2.0 Hz, 1H, CH2CH—O(epoxide)CH), 2.78 (ddd, J=5.5, 5.5, 2.0 Hz 1H, CH2CH—O(epoxide)CH), 2.71 (s, 3H, CH3Ar), 2.63 (dd, J=15.5, 10.5 Hz, 1H, CH2COO), 2.51 (dd, J=15.5, 2.5 Hz, 1H, CH2COO), 2.15 (ddd, J=15.0, 9.0, 6.0 Hz, 1H, CH2CH—O(epoxide)CH), 2.09 (d, J=1 Hz, 3H, ArCH=CCH3), 1.95 (ddd, J=15.0, 5.0, 2.5 Hz, 1H, CH2CH—O(epoxide)CH), 1.66–1.20 (m, 8H), 1.16 (d, J=7.0 Hz, 3H, CH3CH(C=O)), 1.03 (d, J=6.5 Hz, 3H, CH3CHCH2), 1.02–0.96 (m, 2H, C(CH2)2), 0.65–0.61 (m, 1H, C(CH2)2); 13C NMR (150.9 MHz, CDCl3) d 217.5, 171.4, 165.0, 152.0, 136.3, 119.9, 116.6, 76.4, 74.5, 69.5, 57.7, 55.5, 44.0, 39.7, 34.9, 34.6, 34.9, 32.7, 30.6, 29.7, 22.5, 19.2, 16.2, 15.3, 11.6, 10.6; HRMS (FAB), calcd for C26H37CsNO6S (M+Cs+) 624.1396, found 624.1421. 292 (or 291): Rf=0.15 (silica gel, 50% EtOAc in hexanes); [a]22D −73.5 (c 0.14, CHCl3); IR (thin film) nmax 3463, 2917, 2852, 1735, 1668, 1456, 1377, 1259, 1160, 1095, 910, 734 cm−1; 1H NMR (500 MHz, CDCl3) d 6.97 (s, 1H, ArH), 6.55 (s, 1H, ArCH=C(CH3)), 5.63 (dd, J=11.5, 2.5 Hz, 1H, CO2CH), 3.81 (bs, 1H, OH), 3.73 (q, J=7.0 Hz, 1H, CH3CH(C=O)), 3.69 (d, J=11.0 Hz, 1H, (CH2)2CCHOH), 3.66 (d, J=9.0 Hz, 1H, CHOH(CHCH3)), 3.38 (bs, 1H, OH), 2.79 (dd, J=17.0, 11.0 Hz, 1H, CH2COO), 2.73–2.69 (m, 1H, CH2CH—O(epoxide)CH), 2.70 (s, 3H, CH3Ar), 2.68–2.64 (m, 2H, CH2CH—O(epoxide)CH and CH2COO), 2.24 (ddd, J=14.5, 2.5, 2.5 Hz, 1H, CH2CH—O(epoxide)CH), 2.08 (d, J=1 Hz, 3H, ArCH=CCH3), 2.06–1.99 (m, 1H), 1.93–1.85 (m, 1H), 1.77 (ddd, J=14.5, 11.5, 8.0 Hz, 1H, CH2CH—O(epoxide)CH), 1.72–1.68 (m, 1H), 1.67–1.08 (m, 5H), 1.53 (ddd, J=9.5, 7.0, 4.5 Hz, 1H, C(CH2)2), 1.15 (d, J=7.0 Hz, 3H, CH3CH(C=O)), 1.09 (d, J=7.0 Hz, 3H, CH3CHCH2), 0.94 (ddd, J=9.5, 7.0, 4.5 Hz, 1H, C(CH2)2), 0.59 (ddd, J=9.5, 6.5, 4.5 Hz, 1H, C(CH2)2); 13C NMR (125.7 MHz, CDCl3) d 217.9, 171.3, 164.9, 151.9, 136.2, 120.6, 116.8, 76.7, 73.2, 71.4, 60.0, 57.2, 44.3, 39.3, 35.9, 34.7, 34.2, 32.5, 32.3, 29.6, 21.5, 19.1, 18.8, 16.1, 14.7, 11.1; HRMS (FAB), calcd for C26H37CsNO6S (M+Cs+) 624.1396, found 624.1431.

Synthesis of Keto Aldehyde 295 as Illustrated in FIG. 46

Ozonolysis of Ketone 273.

Alkene 273 (3.6 g, 12.7 mmol; synthesized exactly to procedures) was dissolved in CH2Cl2 (50.0 mL, 0.25 M) and the solution was cooled to −78 ° C. Oxygen was bubbled through for 2 min, after which time ozone was passed through until the reaction mixture adopted a blue color (ca 30 min). The solution was then purged with oxygen for 2 min at −78° C. (disappearance of blue color) and Ph3P (6.75 g, 25.4 mmol, 1.2 equiv) was added. The cooling bath was removed and the reaction mixture was allowed to reach room temperature and stirred for an additional 1 hour. The solvent was removed under reduced pressure and the mixture was purified by flash column chromatography (silica gel, 30% ether in hexanes) to provide pure keto aldehyde 295 (3.26 g, 90%). 295: Rf=0.40 (silica gel, 40% ether in hexanes); [a]22D +15.7 (c 5.4, CHCl3); IR (thin film) nmax 2933, 2858, 1726, 1686, 1465, 1379, 1256, 1089, 1040, 1005, 972, 837, 778 cm−1; 1H NMR (400 MHz, CDCl3) d 9.78 (dd, J=2.8, 2.4 Hz, CHO), 4.66 (dd, J=5.8, 4.8 Hz, 1H, CHOSi), 2.68–2.57 (m, 2H, CH2CH=O), 2.29–2.09 (m, 2H, CH2CH3), 1.23–0.97 (m, 7H, C(CH2)2, CH3CH2), 0.83 (s, 9H, (CH3)3C), 0.05 (s, 3H, Si(CH3)2), 0.03 (s, 3H, Si(CH3)2); 13C NMR (125.7 MHz, CDCl3) d 210.1, 201.3, 66.0, 51.0, 36.5, 29.8, 25.6, 17.9, 12.5, 11.1, 8.1, −4.7, −4.8; FAB HRMS (NBA/NaI) m/e 307.1705, M+Na+ calcd for C15H28O3Si 307.1716.

Synthesis of Ketone 294 as Illustrated in FIG. 46

To a solution of aldehyde 295 (2.9 g, 10.2 mol) in THF (50 mL, 0.2 M) at −78° C. was added dropwise lithium tri-tert-butoxyaluminohydride (11.2 mL, 1.0 M solution in THF, 11.2 mmol, 1.1 equiv). After 5 min, the reaction mixture was brought up to 0° C. and stirred at that temperature for 15 min, before quenching with saturated aqueous solution of sodium-potasium tartrate (25 mL). The aqueous phase was extracted with ether (3×75 mL) and the combined organic layer was dried (MgSO4), filtered and concentrated. The crude primary alcohol so obtained was dissolved in CH2Cl2 (50 mL, 0.2 M) and cooled to 0° C. Et3N (68.1 mL, 30.6 mmol, 3.0 equiv), 4-DMAP (120 mg, 0.18 mmol, 0.02 equiv) and tert-butyldimethylsilyl chloride (3.0 g, 20.4 mmol, 2.0 equiv) were added. The reaction mixture was allowed to stir at 0° C. for 2 h, then at 25° C. for 10 h. MeOH (5 mL) was added and the solvents were removed under reduced pressure. Ether (100 mL) was added followed by saturated aqueous NH4Cl solution (25 mL) and the organic phase was separated. The aqueous phase was extracted with ether (2×50 mL) and the combined organic solution was dried (MgSO4), filtered and concentrated under reduced pressure. Purification by flash column chromatography (silica gel, 5% ether in hexanes) provided pure bis (silylether) 294 (1.26 g, 83% yield from 45). 294: Rf=0.45 (silica gel, 5% ether in hexanes); [a]22D −7.1 (c 0.6, CHCl3); IR (thin film) nmax 2941, 2856, 1690, 1467, 1387, 1255, 1095, 1034, 837, 776 cm-1; 1H NMR (500 MHz, CDCl3) d 3.98 (dd, J=7.6, 4.1 Hz, 1H, CHOSi), 3.67–3.59 (m, 2H, CH2OSi), 2.76 (dq, J=17.6, 7.3 Hz, 1H, CH2CH3), 2.44 (dq, J=17.6, 7.3 Hz, 1H, CH2CH3), 1.83–1.73 (m, 2H, CH2CH2OSi), 1.14 (ddd, J=9.6, 6.1, 3.4 Hz, 1H, C(CH2)2), 1.00 (t, J=7.3 Hz, 3H, CH3CH2), 1.03–0.98 (m, 1H, C(CH2)2), 0.87 (s, 18H, SiC(CH3)3), 0.89–0.83 (m, 1H, C(CH2)2), 0.81(ddd, J=9.5, 6.7, 3.6 Hz, 1H, C(CH2)2), 0.06 (s, 3H, Si(CH3)2), 0.03 (s, 3H, Si(CH3)2), 0.02 (s, 6H, Si(CH3)2); 13C NMR (125.7 MHz, CDCl3) d 210.6, 69.3, 59.6, 40.2, 36.4, 32.5, 25.9, 25.8, 18.2, 18.0, 13.7, 13.5, 8.2, −4.3, −4.8, −5.4, −5.5; FAB HRMS (NBA) m/e 401.2923, M+H+ calcd for C21H44O3Si2 401.2907.

Synthesis of tris(Silylethers) 297 and 298 as Illustrated in FIG. 47

Aldol Reaction of Ketone 294 with Aldehyde 75.

The aldol reaction of ketone 294 (682 mg, 1.7 mmol, 1.4 equiv) with aldehyde 75 (530 mg, 1.2 mmol, 1.0 equiv; vida supra) was carried out exactly as described for ketone and aldehyde for epothilone synthesis vida supra, and yielded pure 297 (270 mg, 24%) and 298 (480 mg, 47%). 297: Colorless oil; Rf=0.40 (silica gel, 20% ether in hexanes); [a]22D +1.5 (c 0.8, CHCl3); IR (thin film) nmax 3493, 2942, 2872, 1671, 1505, 1462, 1386, 1254, 1091, 836, 776 cm-1; 1H NMR (600 MHz, CDCl3) d 6.87 (s, 1H, SCH═C), 6.41 (s, 1H, CH═CCH3), 5.10 (dd, J=7.2, 7.1 Hz, 1H, C(CH3)═CHCH2), 4.04 (dd, J=6.7, 5.8 Hz, 1H, (CH2)2CCHOSi), 3.77 (b, 1H, CH2CHOSi), 3.65–3.51 (m, 1H, CH(CH3)CHOH), 3.61 (dd, J=7.3, 7.3 Hz, 2H, CH2OSi), 3.32–3.23 (m, 1H, C(O)CH(CH3)), 2.65 (s, 3H, N═C(CH3)S), 2.30–2.19 (m, 2H), 2.10–1.90 (m, 2H), 1.96 (s, 3H, CH═C(CH3)), 1.76–1.68 (m, 2H), 1.63 (s, 3H, C(CH3)═CHCH2), 1.50–1.40 (m, 2H), 1.26–1.15 (m, 2H), 1.01–0.75 (m, 35H, CH(CH3), SiC(CH3)3), Si(CH2)2), 0.04 (s, 3H, Si(CH3)2), 0.03 (s, 3H, Si(CH3)2), 0.00 (s, 3H, Si(CH3)2), −0.01 (s, 6H, Si(CH3)2), −0.04 (s, 3H, Si(CH3)2); 13C NMR (150.9 MHz, CDCl3) d 216.0, 164.1, 153.1, 142.4, 136.7, 121.3, 118.5, 114.8, 78.9, 74.7, 59.3, 40.4, 35.4, 35.1, 32.8, 32.3, 25.8, 25.2, 23.5, 19.0, 18.1, 17.9, 17.0, 16.5, 15.3, 13.8, 12.6, 10.4, −4.1, −4.8, −4.9, −5.0, −5.4; FAB HRMS (NBA/CsI) m/e 968.4473, M+Cs+ calcd for C45H85NO5SSi3 968.4511. 48: Colorless oil; Rf=0.33 (silica gel, 20% ether in hexanes); IR (thin film) nmax 3492, 2954, 2872, 1672, 1462, 1386, 1255, 1092, 836, 776 cm-1; 1H NMR (600 MHz, CDCl3) d 6.88 (s, 1H, SCH═C), 6.44 (s, 1H, CH═CCH3), 5.11 (dd, J=7.1, 7.0 Hz, 1H, C(CH3)═CHCH2), 4.06 (dd, J=5.8, 5.8 Hz, 1H, (CH3)2CCHOSi), 3.85 (b, 1H), 3.61 (dd, J=6.5, 6.4 Hz, 2H, CH2OSi), 3.42–3.38 (m, 1H, CH(CH3)CHOH), 3.24–3.19 (m, 1H, C(O)CH(CH3)), 2.66 (s, 3H, N═C(CH3)S), 2.31–2.18 (m, 2H, C(CH3)═CHCH2), 1.96 (s, 3H, CH═C(CH3)), 1.97–1.89 (m, 2H, CH2C(CH3)═CH), 1.78–1.69 (m, 2H), 1.64 (s, 3H, C(CH3)═CHCH2), 1.51–1.10 (m, 6H), 1.04 (d, J=6.9 Hz, 3H, CH(CH3)), 0.95 (d, J=6.5 Hz, 3H, CH(CH3)), 1.05–0.6 (m, 8H), 0.86 (s, 9H, SiC(CH3)3), 0.85 (s, 18H, 2×SiC(CH3)3), 0.04 (s, 3H, Si(CH3)2), 0.02 (s, 3H, Si(CH3)2), 0.01 (s, 3H, Si(CH3)2), 0.00 (s, 3H, Si(CH3)2), −0.01 (s, 3H, Si(CH3)2), −0.03 (s, 3H, Si(CH3)2); 13C NMR (150.9 MHz, CDCl3) d 216.8, 164.2, 153.1, 142.4, 136.5, 121.6, 118.6, 114.8, 78.9, 59.4, 42.0, 40.4, 35.9, 35.4, 35.3, 33.0, 32.1, 25.8, 25.7, 25.3, 23.5, 19.1, 18.1, 18.0, 15.3, 13.9, 12.4, 11.8, −4.2, −4.8, −4.9, −5.0, −5.4; FAB HRMS (NBA/CsI) m/e 968.4546, M+Cs+ calcd for C45H85NO5SSi3 968.4511.

Synthesis of tetra(Silylether) 299 as Illustrated in FIG. 47

Compound 299 (271 mg, 92%) was obtained from compound 297 (260 mg, 0.31 mmol) according to the procedure described above. 299: Rf=0.75 (silica gel, 6% ether in hexanes); [a]22D +7.3 (c 0.5, CHCl3); IR (thin film) nmax 2942, 2856, 1679, 1506, 1462, 1386, 1361, 1254, 1090, 1031, 1007, 985, 939, 836, 775, 727, 669 cm-1; 1H NMR (500 MHz, CDCl3) d 6.90 (s, 1H, SCH═C), 6.45 (s, 1H, CH═CCH3), 5.12 (dd, J=7.1, 7.0 Hz, 1H, C(CH3)═CHCH2), 4.19 (b, 1H), 4.07 (dd, J=6.5, 6.2 Hz, 1H, (CH2)2CCHOSi), 3.82 (d, J=8.1 Hz, 1H, CH2CHOSi), 3.64 (dd, J=6.8, 6.8 Hz, 2H, CH2OSi), 2.88–2.68 (m, 1H, C(O)CH(CH3)), 2.69 (s, 3H, N═C(CH3)S), 2.30–2.17 (m, 2H, C(CH3)═CHCH2), 1.99 (s, 3H, CH═C(CH3)), 1.98–1.90 (m, 2H, CH2C(CH3)═CH), 1.78–1.72 (m, 1H), 1.66 (s, 3H, C(CH3)═CHCH2), 1.68–1.61 (m, 1H), 1.45–1.00 (m, 7H), 1.03 (d, J=6.7 Hz, 3H, CH(CH3)), 0.92–0.83 (m, 41H, CH(CH3), (CH2)2CCHOSi, 4×SiC(CH3)3), 0.06 (s, 3H, Si(CH3)2), 0.05 (s, 3H, Si(CH3)2), 0.04 (s, 3H, Si(CH3)2), 0.03 (s, 3H, Si(CH3)2), 0.02 (s, 6H, Si(CH3)2), 0.01 (s, 3H, Si(CH3)2), −0.01 (s, 3H, Si(CH3)2); 13C NMR (125.7 MHz, CDCl3) d 212.9, 164.2, 153.2, 142.4, 136.7, 121.4, 118.7, 114.9, 78.9, 77.8, 67.2, 59.9, 43.4, 40.3, 38.9, 37.9, 35.3, 32.5, 30.9, 26.4, 26.1, 25.9, 25.8, 23.6, 19.2, 18.4, 18.2, 18.1, 18.0, 17.4, 17.3, 13.9, 13.8, 12.4, −3.9, −4.2, −4.7, −4.8, −5.0, −5.3.

Synthesis of tetra(Silylether) 50 as Illustrated in FIG. 47

Compound 300 (567 mg, 89%) was obtained from compound 48 (560 mg, 0.67 mmol) according to the procedure described above vida supra for epothilones. 300: Rf=0.75 (silica gel, 6% ether in hexanes); [a]22D +5.7 (c 0.8, CHCl3); IR (thin film) nmax 2955, 2930, 2857, 1678, 1505, 1462, 1386, 1361, 1254, 1090, 1031, 1007, 985, 939, 836, 775, cm-1; 1H NMR (500 MHz, CDCl3) d 6.91 (s, 1H, SCH═C), 6.45 (s, 1H, CH═CCH3), 5.12 (dd, J=7.0, 6.9 Hz, 1H, C(CH3)═CHCH2), 4.21 (b, 1H), 4.07 (dd, J=6.6, 6.2 Hz, 1H, (CH2)2CCHOSi), 3.82 (d, J=8.8 Hz, 1H, CH2CHOSi), 3.64 (dd, J=7.2, 7.1 Hz, 2H, CH2OSi), 2.88–2.73 (m, 1H, C(O)CH(CH3)), 2.70 (s, 3H, N═C(CH3)S), 2.29–2.18 (m, 2H, C(CH3)═CHCH2), 1.99 (s, 3H, CH═C(CH3)), 1.98–1.90 (m, 1H), 1.78–1.72 (m, 1H), 1.65 (s, 3H, C(CH3)═CHCH2), 1.67–1.61 (m, 1H), 1.45–1.00 (m, 8H), 1.04 (d, J=6.7 Hz, 3H, CH(CH3)), 0.92–0.83 (m, 39H, CH(CH3), 4×SiC(CH3)3), 0.07 (s, 3H, Si(CH3)2), 0.05 (s, 3H, Si(CH3)2), 0.04 (s, 3H, Si(CH3)2), 0.03 (s, 6H, Si(CH3)2), 0.02 (s, 6H, Si(CH3)2), −0.01 (s, 3H, Si(CH3)2); 13C NMR (125.7 MHz, CDCl3) d 215.3, 164.2, 153.2, 142.5, 136.7, 121.5, 118.7, 114.9, 79.0, 76.9, 67.2, 59.8, 44.5, 40.3, 38.4, 37.5, 35.3, 34.7, 32.2, 26.2, 26.1, 25.9, 25.8, 23.5, 19.2, 18.5, 18.3, 18.2, 18.0, 17.6, 14.2, 13.9, 13.0, 3.6, −3.8, −4.2, −4.6, −4.7, −5.0, −5.3; FAB HRMS (NBA/CsI) m/e 1082.5330, M+Cs+ calcd for C51H99NO5SSi4 1082.5375.

Synthesis of Alcohol 301 as Illustrated in FIG. 47

Compound 299 (272 mg, 0.29 mmol) was dissolved in CH2Cl2:MeOH (1:1, 2.9 mL, 0.1 M), the solution was cooled to 0° C. and CSA (67 mg, 0.29 mmol, 1.0 equiv) was added. The mixture was stirred for 30 min at 0° C., and then for 1 h at 10° C. Et3N (0.3 mL) was added, and the solvents were removed under reduced pressure. Flash column chromatography (silica gel, 40% ether in hexanes) furnished the desired alcohol 301 (180 mg, 74%). 301: Colorless oil; Rf=0.60 (silica gel, 40% ether in hexanes); [a]22D +7.8 (c 0.3, CHCl3); 1H NMR (600 MHz, CDCl3) d 6.90 (s, 1H, SCH═C), 6.44 (s, 1H, CH═CCH3), 5.13 (dd, J=7.0, 6.9 Hz, 1H, C(CH3)═CHCH2), 4.43 (b, 1H), 4.07 (dd, J=6.9, 5.8 Hz, 1H, (CH2)2CCHOSi), 3.80 (d, J=8.1 Hz, 1H, CH2CHOSi), 3.71–3.59 (m, 2H, CH2OSi), 2.69 (s, 3H, N=C(CH3)S), 2.52 (q, J=7.2 Hz, 1H, C(O)CH(CH3)), 2.30–2.17 (m, 2H, C(CH3)=CHCH2), 2.05–1.90 (m, 2H, CH2C(CH3)=CH), 1.98 (s, 3H, CH=C(CH3)), 1.78–1.70 (m, 2H), 1.66 (s, 3H, C(CH3)=CHCH2), 1.40–1.00 (m, 7H), 1.02 (d, J=6.7 Hz, 3H, CH(CH3)), 0.92–0.83 (m, 32H, CH(CH3), (CH2)2CCHOSi, 3×SiC(CH3)3), 0.07 (s, 3H, Si(CH3)2), 0.05 (s, 3H, Si(CH3)2), 0.04 (s, 3H, Si(CH3)2), 0.03 (s, 3H, Si(CH3)2), 0.02 (s, 3H, Si(CH3)2), −0.01 (s, 3H, Si(CH3)2); 13C NMR (150.9 MHz, CDCl3) d 213.8, 164.3, 153.0, 142.5, 136.5, 121.5, 118.5, 114.8, 78.8, 76.9, 67.2, 59.4, 42.4, 39.4, 38.8, 36.4, 35.2, 32.3, 31.1, 26.3, 26.0, 25.8, 25.7, 25.6, 23.4, 19.0, 18.3, 18.1, 17.9, 17.6, 17.1, 17.0, 13.8, 11.9, 11.1, −3.9, −4.0, −4.6, −4.8, −4.9, −5.1; FAB HRMS (NBA/CsI) m/e 968.4552, M+Cs+ calcd for C45H85NO5SSi3 968.4511.

Synthesis of Alcohol 302 as Illustrated in FIG. 47

Alcohol 302 (300 mg, 60%) was obtained from compound 300 (567 mg, 0.60 mmol) according to the procedure described above for 299. 302: Colorless oil; Rf=0.60 (silica gel, 40% ether in hexanes); [a]22D +12.3 (c 0.3, CHCl3); IR (thin film) nmax 3441, 2955, 2930, 2856, 1679, 1462, 1366, 1361, 1254, 1072, 836, 775, cm−1; 1H NMR (600 MHz, CDCl3) d 6.89 (s, 1H, SCH=C), 6.42 (s, 1H, CH=CCH3), 5.10 (dd, J=6.9, 6.8 Hz, 1H,. C(CH3)=CHCH2), 4.45 (b, 1H), 4.05 (dd, J=6.7, 6.0 Hz, 1H, (CH2)2CCHOSi), 3.79 (d, J=9.0 Hz, 1H, CH2CHOSi), 3.71–3.59 (m, 2H, CH2OSi), 2.66 (s, 3H, N=C(CH3)S), 2.49 (q, J=7.5 Hz, 1H, C(O)CH (CH3)), 2.30–2.17 (m, 2H, C(CH3)=CHCH2), 1.99–1.83 (m, 2H, CH2C(CH3)=CH), 1.96 (s, 3H, CH=C(CH3)), 1.78–1.70 (m, 2H), 1.62 (s, 3H, C(CH3)=CHCH2), 1.25–0.98 (m, 7H), 1.00 (d, J=6.7 Hz, 3H, CH(CH3)), 0.92–0.83 (m, 32H, CH(CH3), (CH2)2CCHOSi, 3×SiC (CH3)3), 0.06 (s, 3H, Si(CH3)2), 0.03 (s, 3H, Si(CH3)2), 0.02 (s, 3H, Si(CH3)2), 0.01 (s, 3H, Si(CH3)2), 0.00 (s, 3H, Si(CH3)2), −0.03 (s, 3H, Si(CH3)2); 13C NMR (150.9 MHz, CDCl3) d 213.9, 164.2, 153.1, 142.5, 136.5, 121.3, 118.5, 114.8, 78.9, 76.9, 66.7, 59.5, 43.1, 39.4, 38.3, 36.6, 35.2, 34.5, 31.9, 26.3, 26.0, 25.8, 25.7, 23.4, 19.0, 18.4, 18.1, 17.9, 17.6, 14.0, 13.8, 11.9, 10.8, −3.7, −3.8, −4.6, −4.7, −4.8, −5.0.

Synthesis of Aldehyde 303 as Illustrated in FIG. 47
Oxidation of Alcohol 301.

Aldehyde 303 (172 mg, 96%) was obtained from alcohol 301 (182 mg, 0.218 mmol, 1.0 equiv) according to the procedure described above for epothilones. 303: Rf=0.45 (silica gel, 20% ether in hexanes); [a]22D +15.9 (c 0.7, CHCl3); IR (thin film) nmax 2943, 2859, 1728, 1675, 1462, 1255, 1074, 837, 776 cm−1; 1H NMR (600 MHz, CDCl3) d 9.74 (dd, J=3.3, 2.1 Hz, 1H, CHO), 6.90 (s, 1H, SCH=C), 6. 44 (s, 1H, CH=CCH3), 5. 12 (dd, J=6.6, 5.0 Hz, 1H, C(CH3)=CHCH2), 4.77 (dd, J=6.0, 4.4 Hz, 1H, (CH2) 2CCHOSi), 4.07 (dd, J=6.8, 6.2 Hz, 1H, CH2CHOSi), 3.75 (dd, J=8.5, 1.3 Hz, 1H, CH(CH3)CHOSi), 2.69 (s, 3H, N=C(CH3).S), 2.61 (ddd, J=15.5, 4.2, 2.1 Hz, 1H, CH2CHO), 2.51 (ddd, J=15.4, 6.1, 3.5 Hz, 1H, CH2CHO), 2.41–2.16 (m, 3H, C(O)CH(CH3), C(CH3)=CHCH2), 1.97 (s, 3H, CH=C(CH3)), 1.99–1.90 (m, 2H), 1.65 (s, 3H, C(CH3)=CHCH2), 1.50–1.25 (m, 7H), 1.08–0.98 (m, 4H), 1.02 (d, J=6.7 Hz, 3H, CH(CH3)), 0.89–0.84 (m, 32H, (CH2)2CHOSi, CH(CH3), 3×SiC(CH3)3), 0.05 (s, 9H, Si(CH3)2), 0.03 (s, 6H, Si(CH3)2), 0.02 (s, 6H, Si(CH3)2), −0.01 (s, 3H, Si(CH3)2); 13C NMR (150.9 MHz, CDCl3) d 214.0, 202.0, 165.2, 154.1, 143.3, 137.5, 122.4, 119.6, 115.8, 79.8, 79.0, 65.7, 52.3, 42.6, 39.8, 37.6, 36.1, 33.3, 32.1, 27.2, 27.0, 26.7, 26.6, 24.4, 20.1, 19.3, 19.1, 18.8, 18.6, 18.1, 14.7, 12.6, 11.2, −2.9, −3.0, −3.6, −3.8, −4.1; FAB HRMS (NBA/CsI) m/e 966.4392, M+Cs+ calcd for C45H83NO5SSi3 966.4354.

Synthesis of Aldehyde 304 as Illustrated in FIG. 47
Oxidation of Alcohol 302.

Aldehyde 304 (200 mg, 69%) was obtained from alcohol 302 (290 mg, 0.35 mmol) according to the procedure described above vida supra. 304: Colorless oil; Rf=0.80 (silica gel, 20% ether in hexanes); [a]22D +26.7 (c 0.1, CHCl3); IR (thin film) nmax 2943, 2873, 1728, 1674, 1505, 1462, 1383, 1255, 1075, 1032, 989, 940, 837, 776 cm−1; 1H NMR (600 MHz, CDCl3) d 9.78 (dd, J=3.4, 2.2 Hz, 1H, CHO), 6.89 (s, 1H, SCH=C), 6.43 (s, 1H, CH=CCH3), 5.10 (dd, J=6.8, 6.6 Hz, 1H, C(CH3)=CHCH2), 4.73 (dd, J=5.6, 4.6 Hz, 1H, (CH2)2CCHOSi), 4.05 (dd, J=6.7, 6.2 Hz, 1H, CH2CHOSi), 3.78 (d, J=9.0 Hz, 1H, CH(CH3) CHOSi), 2.67 (s, 3H, N=C(CH3)S), 2.60 (ddd, J=15.4, 4.4, 2.1 Hz, 1H, CH2CHO), 2.53 (ddd, J=15.4, 5.9, 3.4 Hz, 1H, CH2CHO), 2.36 (dq, J=9.0, 6.8 Hz, C(O)CH(CH3)), 2.22 (ddd, J=14.5, 7.2, 7.0 Hz, 1H, C(CH3)=CHCH2), 2.19 (ddd, J=14.5, 6.8, 6.6 Hz, 1H, C(CH3)=CHCH2), 1.97 (s, 3H, CH=C(CH3)), 1.99–1.88 (m, 2H, CH2C(CH3)=CH), 1.63 (s, 3H, C(CH3)=CHCH2), 1.35–1.00 (m, 11H), 1.00 (d, J=6.9 Hz, 3H, CH(CH3)), 0.86 (s, 18H, 2×SiC(CH3)3), 0.89–0.85 (m, 2H, (CH2)2CCHOSi), 0.86 (d, J=6.8 Hz, 3H, CH(CH3)), 0.82 (s, 9H, SiC(CH3)3), 0.04 (s, 3H, Si(CH3) 2), 0.03 (s, 3H, Si(CH3)2), 0.02 (s, 6H, Si(CH3)2), −0.03 (s, 3H, Si(CH3)2); 13C NMR (150.9 MHz, CDCl3) d 213.1, 201.0, 164.2, 153.1, 142.4, 136.6, 121.5, 119.6, 118.6, 114.9, 78.9, 76.9, 65.0, 51.3, 42.5, 38.3, 36.7, 35.2, 34.3, 32.1, 26.1, 26.0, 25.8, 25.7, 23.4, 19.1, 18.4, 18.2, 17.9, 17.8, 14.2, 13.8, 11.6, 10.3, −3.7, −3.8, −4.6, −4.7, −5.0.

Synthesis of Carboxylic Acid 305 as Illustrated in FIG. 47
Oxidation of Aldehyde 303.

Carboxylic acid 305 (160 mg, 91%) was obtained from aldehyde 303 (172 mg, 0.206 mmol) according to the procedure described above vida supra. 303: Rf=0.15 (silica gel, 20% ether in hexanes); 1H NMR (500 MHz, CDCl3) d 6.90 (s, 1H, SCH=C), 6.50 (s, 1H, CH=CCH3), 5.12 (dd, J=7.8, 6.6 Hz, 1H, C(CH3)=CHCH2), 4.54 (b, 1H, (CH2) 2CCHOSi), 4.09 (dd, J=6.4, 6.2 Hz, 1H, CH2CHOSi), 3.90 (d, J=5.8 Hz, 1H, CH(CH3)CHOSi), 2.73 (s, 3H, N=C(CH3) S), 2.60 (m, 1H, CH2COOH), 2.50 (m, 1H, CH2COOH), 2.41–2.16 (m, 3H, C(O)CH(CH3), C(CH3)=CHCH2), 1.99–1.90 (m, 2H), 1.90 (s, 3H, CH=C(CH3)), 1.69 (s, 3H, C(CH3)=CHCH2), 1.50–1.25 (m, 7H), 1.08–0.98 (m, 4H), 1.05 (d, J=6.8 Hz, 3H, CH(CH3)), 0.92–0.83 (m, 32H, (CH2)2CHOSi, CH(CH3), 3×SiC(CH3)3), 0.07 (s, 3H, Si(CH3)2), 0.06 (s, 3H, Si(CH3)2), 0.05 (s, 3H, Si(CH3)2), 0.04 (s, 3H, Si(CH3)2), 0.03 (s, 3H, Si(CH3)2), −0.01 (s, 3H, Si(CH3)2); 13C NMR (125.7 MHz, CDCl3) d 212.8, 175.1, 165.2, 152.5, 143.3, 136.7, 121.5, 117.9, 114.5, 78.7, 77.5, 67.9, 42.4, 39.1, 36.3, 35.2, 32.2, 31.6, 31.0, 26.3, 26.0, 25.7, 23.4, 18.6, 18.2, 18.1, 17.9, 17.6, 16.5, 13.9, 12.0, −4.0, −4.1, −4.5, −4.8, −5.7; FAB HRMS (NBA/CsI) m/e 982.4264, M+Cs+ calcd for C45H83NO6SSi3 982.4303.

Synthesis of Carboxylic Acid 306 as Illustrated in FIG. 47
Oxidation of Aldehyde 304.

Acid 306 (204 mg, 99%) was obtained from aldehyde 304 (200 mg, 0.24 mmol) according to the procedure described above. 306: Colorless oil; Rf=0.15 (silica gel, 20% ether in hexanes); [a]22D +20.0 (c 0.3, CHCl3); IR (thin film) nmax 2955, 2888, 2856, 1713, 1680, 1509, 1462, 1384, 1254, 1183, 1077, 1031, 987, 941, 837, 776 cm−1; 1H NMR (600 MHz, CDCl3) d 6.90 (s, 1H, SCH=C), 6.46 (s, 1H, CH=CCH3), 5.12 (dd, J=7.0, 6.8 Hz, 1H, C(CH3)=CHCH2), 4.58 (b, 1H, (CH2)2CCHOSi), 4.06 (dd, J 7.7, 5.4 Hz, 1H, CH2CHOSi), 3.84 (d, J 9.3 Hz, 1H, CH(CH3)CHOSi), 2.71 (s, 3H, N=C(CH3)S), 2.60 (dd, J=15.1, 4.0, Hz, 1H, CH2COOH), 2.60–2.52 (m, 1H, C(O)CH(CH3)), 2.53 (dd, J=15.0, 6.9 Hz, 1H, CH2COOH), 2.30–2.15 (m, 2H, C(CH3)=CHCH2), 1.95–1.88 (m, 2H, CH2C(CH3)=CH), 1.92 (s, 3H, CH=C(CH3)), 1.65 (s, 3H, C(CH3)=CHCH2), 1.35–1.00 (m, 11H), 1.02 (d, J=6.8 Hz, 3H, CH(CH3)), 0.87 (s, 18H, 2×SiC(CH3)3), 0.89–0.85 (m, 2H, (CH2)2CHOSi), 0.84 (s, 9H, SiC(CH3)3), 0.82 (d, J=6.7 Hz, 3H, CH(CH3)), 0.07 (s, 3H, Si(CH3)2), 0.04 (s, 9H, Si(CH3)2), 0.03 (s, 3H, Si(CH3)2), −0.01 (s, 3H, Si(CH3)2); 13C NMR (150.9 MHz, CDCl3) d 213.0, 175.2, 165.1, 152.6, 143.4, 136.9, 121.4, 118.1, 114.5, 78.9, 67.3, 53.4, 43.5, 42.3, 38.2, 36.5, 35.3, 34.9, 32.2, 26.4, 26.2, 25.8, 25.7, 23.7, 18.7, 18.5, 18.2, 18.0, 17.7, 14.1, 13.9, 11.6, 11.3, −3.6, −3.7, −4.6, −4.7, −4.8, −5.0; FAB HRMS (NBA, CsI) m/e 982.4278, M+Cs+ calcd for C45H83NO6SSi3 982.4303.

Synthesis of Lactone 308 as Illustrated in FIG. 47

Selective Desilylation of tris(Silylether) 305 and Macrolactonization of Hydroxy Acid 293. A solution of tris (silylether) 305 (75 mg, 0.088 mmol) in THF (1.8 mL, 0.05 M) at 25° C. was treated with TBAF (0.53 mL, 1.0 M solution in THF, 0.53 mmol, 6.0 equiv). After stirring for 8 h, the reaction mixture was diluted with EtOAc (10 mL) and washed with saturated aqueous NH4Cl (5 mL). The aqueous solution was extracted with EtOAc (2×10 mL) and the combined organic phase was washed with brine (10 mL), dried (MgSO4) and concentrated. The crude mixture was purified by flash column chromatography (silica gel, 5% MeOH in CH2Cl2) to provide hydroxy acid 293 (40 mg, 62%) as a yellow oil [Rf=0.40 (silica gel, 5% MeOH in CH2Cl2)]. A solution of hydroxy acid 293 (40 mg, 0.054 mmol) in THF (0.8 mL, 0.07 M) was treated at 0° C. with Et3N (17 mL, 0.12 mmol, 2.2 equiv) and 2,4,6-trichlorobenzoyl chloride (14.5 mL, 0.06 mmol, 1.1 equiv). The reaction mixture was stirred at 0° C. for 1 h, and then added to a solution of 4-DMAP (1.4 mg, 0.11 mmol, 2.0 equiv) in toluene (28 mL, 0.002 M) at 25° C. and stirred at that temperature for 3 h. The reaction mixture was concentrated under reduced pressure to a small volume and filtered through silica gel. The residue was washed with 40% ether in hexanes, and the resulting solution was concentrated. Purification by flash column chromatography (silica gel, 2% MeOH in CH2Cl2) furnished lactone 308 (27 mg, 70%) as a white solid. 308: Rf=0.35 (silica gel, 30% ether in hexanes); mp 81° C. (from CH2Cl2/hexanes); [a]22D −134.3 (c 0.9, CHCl3); IR (thin film) nmax 2931, 2856, 1740, 1683, 1462, 1380, 1252, 1164, 1102, 1060, 1011, 834, 774 cm−1; 1H NMR (600 MHz, CDCl3) d 6.90 (s, 1H, SCH=C), 6.36 (bs, 1H, CH=CCH3), 5.16 (b, 1H), 5.04 (b, 1H), 3.95 (d, J=7.3 Hz, 1H, CHOSi), 3.55 (b, 1H, C(CH2)2CHOSi), 2.80–2.78 (m, 1H, C(O)CHCH3), 2.68 (s, 3H, N=C(CH3)S), 2.55–2.38 (m, 4H, CH2COOCH, CH3C=CHCH2), 2.03 (s, 3H, CH=C(CH3)), 1.70 (s, 3H, C(CH3)=CHCH2), 1.78–1.03 (m, 7H), 1.11 (d, J=6.6 Hz, 3H, CH(CH3)), 1.01 (d, J=6.6 Hz, 3H, CH(CH3)), 0.89 (s, 9H, SiC(CH3)3), 0.88 (s, 9H, SiC(CH3)3), 0.94–0.83 (m, 3H, C(CH2)2CHOSi), 0.40–0.33 (m, 1H, C(CH2)2CHOSi), 0.14 (s, 3H, Si(CH3)2), 0.13 (s, 3H, Si(CH3)2), 0.08 (s, 3H, Si(CH3)2), 0.04 (s, 3H, Si(CH3)2); 13C NMR (150.9 MHz, CDCl3) d 214.6, 170.0, 164.7, 152.8, 139.0, 137.9, 121.3, 118.8, 116.2, 74.5, 53.3, 48.7, 41.0, 39.4, 35.2, 31.9, 31.8, 31.1, 26.6, 25.9, 25.6, 23.5, 19.7, 19.0, 18.2, 18.1, 17.8, 15.5, 10.0, −3.1, −3.8, −4.2, −6.2; FAB HRMS (NBA) m/e 718.4357, M+H+ calcd for C39H67NO5SSi2 718.4357.

Synthesis of Hydroxy Acid 307 as Illustrated in FIG. 47

Selective Desilylation of tris(Silylether) 306.

Carboxylic acid 306 (200 mg, 0.235 mmol) was converted to hydroxy acid 307 (85 mg, 50%) according to the procedure described above vida supra. 307: Yellow oil; Rf=0.45 (silica gel, 5% MeOH in CH2Cl2); [a]22D +10.0 (c 0.3, CHCl3); IR (thin film) nmax 3440, 2955, 2930, 2871, 1713, 1679, 1462, 1383, 1254, 1185, 1097, 986, 836, 775, 734 cm−1; 1H NMR (500 MHz, CDCl3) d 6.95 (s, 1H, SCH=C), 6.60 (s, 1H, CH=CCH3), 5.15 (dd, J=6.9, 6.7 Hz, 1H, C(CH3)=CH), 4.66 (dd, J=6.4, 3.7 Hz, 1H, (CH2)2CCHOSi), 4.13 (dd, J=6.8, 6.1 Hz, 1H, CH2CHOH), 3.84 (d, J=9.2 Hz, 1H, CH(CH3)CHOSi), 2.73 (s, 3H, N=C(CH3)S), 2.58–2.53 (m, 2H, CH2COOH, C(O)CHCH3), 2.45 (dd, J=15.0, 6.6 Hz, 1H, CH2COOH), 2.34–2.29 (m, 2H, C(CH3)=CHCH2), 2.30 (dd, J=16.3, 6.4 Hz, 1H, CH2COOH), 2.05–1.91 (m, 2H, CH2C(CH3)=CH), 1.98 (s, 3H, CH=C(CH3)), 1.71 (s, 3H, C(CH3)=CHCH2), 1.38–1.17 (m, 7H), 1.05 (d, J=6.8 Hz, 3H, CH(CH3)), 0.89 (s, 9H, SiC(CH3)3), 0.85–0.82 (m, 23H, (CH2)2CHOSi, CH(CH3), SiC(CH3)3), 0.09 (s, 3H, Si(CH3)2), 0.06 (s, 6H, Si(CH3)2), 0.05 (s, 3H, Si(CH3)2); 13C NMR (125.7 MHz, CDCl3) d 213.4, 174.0, 165.3, 152.2, 142.4, 139.5, 120.1, 118.2, 114.9, 77.1, 66.9, 43.5, 42.7, 38.0, 36.9, 35.1, 34.1, 32.2, 26.4, 26.2, 25.8, 23.9, 18.6, 18.5, 18.0, 17.7, 14.8, 13.9, 11.6, 11.0, −3.6, −3.7, −4.6, −4.7; FAB HRMS (NBA/CsI) m/e 856.3402, M+Cs+ calcd for C38H69NO6SSi2 856.3439.

Synthesis of Lactone 309 as Illustrated in FIG. 47

Macrolactonization of Hydroxy Acid 307.

The cyclization of hydroxy acid 307 (80 mg, 0.11 mmol) was carried out exactly as described above and yielded lactone 309 (56 mg, 72%) as a crystalline solid: Rf=0.65 (silica gel, 20% ether in hexanes); mp 157° C. (from MeOH/EtOH); [a]22D −40.5 (c 0.2, CHCl3); 1H NMR (600 MHz, CDCl3) d 6.97 (s, 1H, SCH=C), 6.46 (s, 1H, CH=CCH3), 5.02 (m, 2H, CH3C=CHCH2, CH2COOCH), 3.87 (d, J=8.8 Hz, 1H, CHOSi), 3.,88 (d, J=8.9 Hz, 1H, CHOSi), 2.69 (s, 3H, N=C(CH3)S), 2.62 (dd, J=12.7, 4.4 Hz, 1H, CH2COOCH), 2.58–2.50 (m, 2H), 2.44–2.36 (m, 1H), 2.31–2.24 (m, 1H), 2.17–2.10 (m, 1H), 2.14 (s, 3H, CH=C(CH3)), 1.74–1.68 (m, 1H), 1.64 (s, 3H, CH2C(CH3)=CH), 1.48–1.23 (m, 7H), 1.14–1.07 (m, 1H), 1.02 (d, J=6.8 Hz, 3H, CH(CH3)), 0.97 (d, J=6.8 Hz, 3H, CH(CH3)), 0.88 (s, 9H, SiC(CH3)3), 0.85 (s, 9H, SiC(CH3)3), 0.91–0.82 (m, 2H), 0.06 (s, 3H, Si(CH3)2), 0.05 (s, 3H, Si(CH3)2), 0.04 (s, 3H, Si(CH3)2), 0.03 (s, 3H, Si(CH3)2); 13C NMR (150.9 MHz, CDCl3) d 212.5, 169.2, 164.5, 152.6, 139.3, 136.8, 121.6, 118.8, 116.2, 80.4, 75.9, 42.9, 42.6, 36.5, 35.1, 33.4, 30.7, 30.5, 26.3, 25.8, 24.2, 23.2, 19.2, 18.6, 18.1, 17.8, 14.5, 14.2, 12.4, −3.2, −3.6, −4.8, −5.3; FAB HRMS (NBA) m/e 718.4330, M+H+ calcd for C39H67NO5SSi2 718.4357.

Synthesis of Dihydroxy Lactone 268 as Illustrated in FIG. 47

Dihydroxy lactone 268 (11.0 mg, 92%) was prepared from bis(silylether) 308 (17.6 mg, 0.024 mmol) by treatment with HF·pyr. according to the same procedure described above for the preparation of epothilones. 268: Rf=0.20 (silica gel, 4% MeOH in CH2Cl2); mp 67 OC (from CH2Cl2/hexanes); [a]22D −108.7 (c 0.1, CHCl3); IR (thin film) nmax 3458, 2931, 1730, 1674, 1451, 1375, 1169, 1040, 980, 911, 732 cm−1; 1H NMR (600 MHz, CDCl3) d, 6.95 (s, 1H, SCH=C), 6.47 (s, 1H, CH=CCH3), 5.46 (dd, J=6.8, 3.3 Hz, 1H, CH2COOCH), 5.10 (dd, J=8.0, 7.0 Hz, 1H, CH3C=CHCH2), 3. 82 (dd, J 6. 3, 2. 2 Hz, 1H, CHCH), 3.75 (b, 1H), 3.55–3.48 (m, 2H), 2.78 (dd, J=17.2, 9.2 Hz, 1H, CH2COOCH), 2.69 (s, 3H, N=C (CH3) S), 2. 67 (dd, J=17.3, 3.4 Hz, 1H, CH2COOCH), 2.54–2.45 (m, 1H), 2.44–2.35 (m, 1H), 2.19–2.13 (m, 1H), 2.06 (s, 3H, CH=CCH3), 2.11–2.01 (m, 1H), 1.95–1.86 (m, 1H), 1.73–1.62 (m, 4H), 1.71 (s, 3H. CH2C(CH3)=CH), 1.62–1.52 (m, 2H), 1.49–1.35 (m, 2H), 1.29–1.23 (m, 2H), 1.25 (d, J=6.7 Hz, 3H, CH(CH3)), 1.30–1.20 (m, 1H), 1.19–1.10 (s, 1H, C(CH2)2), 1.00 (d, J=6.9 Hz, 3H, CH(CH3)), 1.00–0.96 (m, 1H, C(CH2)2), 0.75–0.69 (m, 1H, C(CH2)2); 13C NMR (150.9 MHz, CDCl3) d 216.6, 173.0, 165.8, 153.4, 140.1, 137.9, 120.6, 117.0, 77.9, 75.7, 70.3, 45.3, 38.5, 37.3, 34.1, 31.7, 31.6, 30.7, 26.0, 23.9, 19.0, 17.1, 16.5, 15.6, 15.4, 10.9; FAB HRMS (NBA) m/e 490.2639, M+H+ calcd for C27H39NO5S 490.2627.

Synthesis of Dihydroxy Lactone 310 as Illustrated in FIG. 47

Dihydroxy lactone 310 (19.0 mg, 90%) was prepared from bis(silylether) lactone 309 (31 mg, 0.043 mmol) by treatment with HF·pyr. according to the same procedure described above for the preparation of epothilone intermediates (vida supra). 310: Rf=0.45 (silica gel, 5% MeOH in CH2Cl2); [a]22D −122.9 (c 0.1, CHCl3); IR (thin film) nmax 3457, 2934, 2360, 1731, 1667, 1449, 1377, 1242, 1165, 1070, 1039, 978, 911, 732 cm−1; 1H NMR (600 MHz, CDCl3) d 6.95 (s, 1H, SCH=C), 6.53 (s, 1H, CH=CCH3), 5.51 (d, J=6.8 Hz, 1H, CH2COOCH), 5.15 (dd, J=8.1, 7.6 Hz, 1H, CH3C=CHCH2), 3.84 (dd, J=13.4, 6.7 Hz, 1H, CHOH), 3.77 (d, J=11.3 Hz, 1H, CHOH), 3.47 (d, J=6.9 Hz, 1H), 3.46 (s, 1H), 3.00 (s, 1H), 2.78 (dd, J=16.7, 11.5 Hz, 1H, CH2COOCH), 2.70 (s, 3H, N=C(CH3)S), 2.65 (dd, J=16.7, 3.0 Hz, 1H, CH2COOCH), 2.60–2.55 (m, 1H), 2.44–2.35 (m, 1H), 2.35–2.26 (m, 1H), 2.25–2.17 (m, 1H), 2.07 (s, 3H, CH=CCH3), 2.05–1.98 (m, 1H), 1.66 (s, 3H, CH2C(CH3)=CH),1.67–1.55 (m, 3H), 1.48–1.41 (m, 3H), 1.10–0.99 (m, 8H, 2×CH(CH3), C(CH2)2), 0.96–0.88 (m, 1H, C(CH2)2), 0.70–0.64 (m, 1H, C(CH2)2); 13C NMR (150.9 MHz, CDCl3) d 218.7, 171.3, 165.1, 152.5, 137.7, 137.6, 121.4, 119.5, 116.1, 77.9, 74.6, 70.9, 43.5, 40.1, 35.4, 33.9, 32.0, 31.3, 30.8, 26.0, 23.4, 22.1, 18.9, 18.5, 15.8, 15.6, 13.6, 10.1; FAB HRMS (NBA/CsI) m/e 622.1580, M+Cs+ calcd for C27H39NO5S 622.1603.

Synthesis of Epothilones 267 and 311 as Illustrated in FIG. 47

Epoxidation of Lactone 268 with Methyl(trifluoromethyl) dioxirane.

To a solution of 268 (10 mg, 21.0 mmol) in MeCN (200 mL) was added 4.10–4 M aqueous solution of disodium ethylenediaminetetraacetate (Na2EDTA, 120 mL) and the reaction mixture was cooled to 0° C. 1,1,1-Trifluoroacetone (200 mL) was added, followed by a mixture of Oxone® (61 mg, 0.10 mmol, 5.0 equiv) and NaHCO3 (14.0 mg, 0.17 mmol, 8.0 equiv) with stirring until completion of the reaction was revealed by TLC. The reaction mixture was treated with excess Me2S (100 mL) and water (500 mL) and was then extracted with EtOAc (4×2 mL). The combined organic phase was dried (MgSO4), filtered, and concentrated. Purification by preparative thin layer chromatography (silica gel, 80% EtOAc in hexanes) furnished pure (6S, 7R)-4,4-cyclopropyl epothilone B (267) (7.7 mg, 76%) and its a-epoxide epimer 311 (1.0 mg, 10%). 267: Rf=0.45 (silica gel, 80% EtOAc in hexanes); mp 82° C. (from CH2Cl2/hexanes); [a]22D −45.0 (c 0.02, MeOH); IR (thin film) nmax 3443, 2929, 1739, 1674, 1379, 1158, 1093, 754 cm−1; 1H NMR (600 MHz, CDCl3) d 6.94 (s, 1H, SCH=C), 6.49 (s, 1H, CH=CCH3), 5.64 (dd, J=4.1, 3.1 Hz, 1H, O=COCH ), 3.88 (b, 1H), 3.82 (d, J=7.9 Hz, 1H), 3.52–3.44 (m, 2H), 2.97 (s, 2H), 2.85 (dd, J=17.1, 9.1 Hz, 1H, CH2COO), 2.85 (dd, J=7.7, 5.9 Hz, 1H), 2.70 (s, 3H, N=C(CH3)S), 2.71–2.67 (m, 1H), 2.20–2.13 (m, 1H), 2.11 (s, 3H, CH=C(CH3)), 1.85 (ddd, J=11.7, 8.0, 3.7 Hz, 1H, CH2CHO), 1.82–1.74 (m, 1H), 1.63–1.55 (m, 1H), 1.53–1.49 (m, 3H), 1.52–1.37 (m, 6H), 1.33–1.25 (m, 2H), 1.29 (s, 3H, C(CH3)), 1.04 (d, J=6.8 Hz, 3H, CH(CH3)), 1.12 (ddd, J=6.7, 4.4, 2.3 Hz, 3H, C(CH2)2), 1.03 (d, J=6.8 Hz, 3H, CH(CH3)), 1.03–0.98 (m, 1H, C(CH2)2), 0.78–0.72 (m, 1H, C(CH2)2); 13C NMR (150.9 MHz, CDCl3) d 215.1, 171.9, 165.2, 152.4, 136.0, 119.4, 116.5, 76.0, 75.2, 70.0, 61.0, 60.7, 45.8, 42.5, 38.5, 36.3, 34.3, 31.7, 31.4, 29.8, 22.9, 22.5, 19.0, 17.4, 17.0, 15.9, 15.7, 10.6; FAB HRMS (NBA) m/e 506.2561, M+H+ calcd for C27H39NO6S 506.2576. 61: Rf=0.50 (silica gel, 80% EtOAc in hexanes); [a]22D −31.1 (c 0.05, MeOH); IR (thin film) nmax 3463, 2926, 1735, 1378, 1158 cm−1; 1H NMR (600 MHz, CDCl3) d 7.00 (s, 1H, SCH=C), 6.60 (s, 1H, CH=CCH3), 5.45 (dd, J=6.3, 5.0 Hz, 1H, O=COCH ), 4.45 (b, 1H), 3.74–3.68 (m, 2H), 3.01–2.95 (m, 1H), 2.83 (dd, J=16.3, 5.6 Hz, 1H, CH2COO), 2.79 (dd, J=6.3, 6.0 Hz, 1H), 2.70 (s, 3H, N=C(CH3)S), 2.62 (dd, J=16.3, 4.5 Hz, 1H, CH2COO), 2.39 (b, 1H), 2.10 (s, 3H, CH=C(CH3)), 2.10–1.94 (m, 2H), 1.60–1.21 (m, 10H), 1.10–1.05 (m, 2H), 1.07 (d, J=6.8 Hz, 3H, CH(CH3)), 0.94 (d, J=7.0 Hz, 3H, CH(CH3)), 0.88–0.81 (m, 2H, C(CH2)2); FAB HRMS (NBA) m/e 506.2576, M+H+ calcd for C27H39NO6S 506.2593.

Synthesis of Epothilones 312 and 313 as Illustrated in FIG. 47

Epoxidation of Lactone 310.

Compound 310 (10.0 mg, 21.0 mmol) was epoxidized according to the procedure described above for 268 to yield a mixture of (6R, 7S)-4,4-cyclopropyl epothilone B (312) (6.2 mg, 60%) and its a-epoxy-diastereoisomer 313 (2.8 mg, 29%). 312: Rf=0.40 (silica gel, 60% EtOAc in hexanes); mp 143–145° C. (from CH2Cl2/hexanes); [a]22D −60.0 (c 0.1, MeOH); IR (thin film) nmax 3450, 2929, 1736, 1671, 1451, 1379, 1240, 1155, 977, 732 cm−1; 1H NMR (600 MHz, CDCl3) d 6.97 (s, 1H, SCH=C), 6.58 (s, 1H, CH=CCH3), 5.60 (dd, J=4.1, 3.1 Hz, 1H, O=COCH), 4.53 (d, J=9.7 Hz, 1H), 4.45 (b, 1H), 3.73 (d, J=9.1 Hz, 1H), 3.59 (dd, J=14.6, 7.5 Hz, 1H), 3.54, (s, 1H, OH), 2.90 (dd, J=8.3, 4.5 Hz, 1H), 2.70 (s, 3H, N=C(CH3)S), 2.50 (dd, J=14.9, 10.2 Hz, 1H, CH2COO), 2.85 (dd, J=14.8, 1.6 Hz, 1H, CH2COO), 2.19 (dd, J=5.0, 5.0 Hz, 1H), 2.16 (s, 3H, CH=C(CH3)), 1.94 (ddd, J=15.2, 8.3, 3.5 Hz, 1H, CH2CHO), 1.73–1.23 (m, 7H), 1.27 (s, 3H, C(CH3)), 1.10 (d, J=7.0 Hz, 3H, CH(CH3)), 1.08 (d, J=6.8 Hz, 3H, CH(CH3)), 0.97–0.84 (m, 3H, C(CH2)2), 0.78–0.70 (m, 1H, C(CH2)2); 13C NMR (150.9 MHz, CDCl3) d 218.1, 171.0, 165.2, 152.6, 135.5, 119.7, 116.9, 76.4, 73.5, 68.5, 61.8, 60.9, 41.6, 39.4, 34.7, 34.5, 32.9, 32.6, 30.7, 21.6, 19.7, 19.0, 16.1, 15.8, 15.7, 13.9, 10.7, 9.2; FAB HRMS (NBA) m/e 506.2589, calcd for C27H39NO6S (M+H+) 506.2576. 313: Rf=0.37 (silica gel, 80% EtOAc in hexanes); 1H NMR (600 MHz, CDCl3) d 6.99 (s, 1H, SCH=C), 6.53 (s, 1H, CH=CCH3), 5.75 (d, J=7.5 Hz, 1H, O=COCH ), 4.12 (d, J=9.3 Hz, 1H), 3.66 (m, 1H), 3.58 (d, J=9.0 Hz, 1H), 3.43 (s, 1H, OH), 3.35 (s, 1H, OH), 2.88–2.79 (m, 1H), 2.74 (dd, J=16.1, 5.7 Hz, 1H, CH2COO), 2.70 (s, 3H, N=C(CH3)S), 2.57 (d, J=16.1 Hz, 1H, CH2COO), 2.10 (s, 3H, CH=C(CH3)), 2.10–1.84 (m, 2H), 1.62–1.01 (m, 11H), 1.31 (s, 3H, C(CH3)), 1.14 (d, J=6.8 Hz, 3H, CH(CH3)), 1.03 (d, J=6.7 Hz, 3H, CH(CH3)), 0.75–0.70 (m, 1HI C(CH2)2); 13C NMR (150.9 MHz, CDCl3) d 218.5, 171.4, 165.2, 152.4, 135.6, 120.1, 116.7, 76.8, 74.1, 69.8, 61.6, 60.4, 43.4, 39.3, 34.4, 34.2, 32.9, 33.2, 32.2, 31.6, 23.2, 20.8, 19.0, 17.1, 15.5, 15.3, 13.9, 11.4, 10.9; FAB HRMS (NBA) m/e 506.2583, M+H+ calcd for C27H39No6S 506.2576.

Synthesis of Aldehydes 320, 321 and 329 as Illustrated in FIG. 49

The synthesis of aldehydes 320, 321 and 329 are simple aldhehydses synthesized exactly as In conditions found for standard epothilone aldehydes 7 (FIG. 3), and aldehyde 221 (vida supra); all reactions are carried out using the transformations shown and standard conditions known well to one of ordinary skill in the art and therefore no further elaboration will be disclosed here.

Preparation of Aldehyde 320 as Illustrated in FIG. 49

A)(R)-3-bromo-2-methyl-1-propylt-butyldimethylsilyl ether 314. A solution of (R)-3-bromo-2-methyl-1-propanol (Aldrich) (6.50 g, 42.4 mmol, 1.0 equiv.) in DMF (30 mL) at 0° C. was treated with L-butylchlorodimethylsilane (8.23 g, 54.6 mmol 1.3 equiv.) and imidazole (4.32 g, 63.6 mmol, 1.5 equiv.). After stirring for 90 min at 0° C., the reaction mixture was diluted with Et20 (250 mL) and poured in a 1 M HCl, q. solution (150 mL). The organic phase was separated, washed with a 1 M HCl eq. solution (2×150 mL), brine (150 mL), dried over MgSO4 and concentrated in vacuo. Flash chromatography (silica gel, 4% Et2O in hexane) afforded 11.2 g (99% yield) of pure compound as a colorless oil.

B) (R)-3-iodo-2-methyl-1-propyl t-butyldimethylsilyl ether 315. A solution of 1001 (11.2 g, 42.0 mmol, 1.0 equiv.) in acetone (200 mL) was treated with sodium iodide (18.9 g, 126 mmol, 3.0 equiv.) and refluxed for 15 h. The reaction mixture was then diluted with a 1:1 (v/v) solution of Et2O/hexane (400 mL) and poured in a H2 0 (250 mL). The organic phase was separated, washed with brine (2×250 mL), dried over MgSO4 and concentrated in vacuo. Flash chromatography (silica gel, 4% Et2o in hexane) afforded 12.7 g (96% yield) of pure product as a colorless oil.

C) Olefin 318. A 0.01 M Li 2CUC14 solution in THF was prepared by mixing LiCl (85 mg, 2.0 mmol, 2.0 equiv.) and CUC12 (136 mg, 1.0 mmol, 1.0 equiv.) in THF (100 ML). Compound 315 (12.7 g, 40.44 mmol, 1.0 equiv.) was dissolved in THF (25 mL), cooled to 0° C. and treated with a solution of 3-butenylmagnesium bromide (0.5 M in THF, 100 mL, 50.0 mmol, 1.25 equiv.), followed by the Li 2 cucl 4 solution (40.0 mL, 0.40 mmol, 0.01 equiv.). The reaction mixture was stirred at 0° C. for 1 h then diluted with Et 20 (500 mL) and poured in a 1 M HCl,,q. (250 mL). The organic phase was separated, washed with brine (2×250 mL) dried over MgSO4 and concentrated in vacuo. Flash chromatography (silica gel, 4% Et 20 in hexane) afforded 9.3 g (93% yield) of olefin 318 as a colorless oil.

Synthesis of Aldehyde 320 as Illustrated in FIG. 49

Ozonolysis of olefin 318 solution of olefin 318 (4.0 g, 16.4 mmol) and was cooled to −78° C. A gentle stream of ozone was passed through this solution until it turned deep blue. The reaction mixture was then allowed to warm up to room temperature and excess ozone was discharged by sparging argon through the solution. The reaction mixture was then treated with Me2S (20 mL), Et3N (10 mL) and MEOH (20 mL). This mixture was stirred at 23° C. for 1 h then diluted with Et2O (300 mL) and poured in a 1M HCl@q. (250 mL). The organic phase was separated, washed with 1 M HCl. (2×250 mL), dried over MgSO4 and concentrated in vacuo. Flash chromatography (silica gel, 8% ether in hexane) afforded 3.9 g (96% yield) of a pure colorless oil.

Synthesis of Resins 333 Wittig Reaction of Ylide Resin 148 with Aldehydes 330 (320, 321, 329) as Illustrated in FIG. 50

A solution of the corresponding aldehyde 330 (10.22 mmol, 2.0 equiv) in THF (25 mL) was cooled at −78° C. and added to the resin (5.11 Mol, 1.0 equiv.) via canula. The resulting suspension was shaken at 23° C. for 3 h and the supernatant was filtered off. The polymer was washed with THF (100 ml), MEOH (100 mL), CH2Cl2, (100 mL), MEOH (100 mL), CH2Cl2 (100 mL), Et2O (2×100 mL). The resin was dried under high vaccum to a constant weight.

Synthesis of Resins 334. Desilylation of Resin 333 with HF.Pyridine Complex as Illustrated in FIG. 50

Resins 333 (5.05 mmol, 1.0 equiv.) were suspended in THF (135 mL) and treated at 0° C. with HF.Pyridine complex (15 mL). The mixture was allowed to warm to 23° C. and shaken for 12 h. The suspension was poured into a frit and the polymer was filtered, washed with THF (100 mL), CH2Cl2 (100 mL), MEOH (100 mL), CH2C21 (100 mL), Et2O (2×100 mL) and dried under high vaccum to give resin 334.

Synthesis of Resins 335. Swern Oxidation of Resin 334 as Illustrated in FIG. 50

To an Oxalyl Chloride (20.0 mmol, 4.0 equiv.) solution in CHC12 (50 mL) at −78 ° C., was added dropwise DMSO (40.0 mmol, 8.0 equiv). The solution was stirred at -78° C. for 1 h and canulated into a suspension of the appropriate resin 334 (5.0 mmol, 1.0 equiv.) in CH2Cl2, previously cooled to −78° C. The resulting mixture was stirred for an additional hour and treated with Et3N (62.5 mmol, 12.5 equiv.), allowed to warm to 23° C. and stirred for 1 h. The mixture was filtered and the polymer washed successively with methylene chloride (250 mL) MEOH (250 mL), methylene chloride (250 mL) Et2O (2×300 mL) dried under high vaccum to afford the corresponding resins 330.

Synthesis of Resins 336. Aldol Reaction of Resins 335 with Ketoacids 331 as Illustrated in FIG. 50

Enolate formation. To a precooled solution of LDA (6.60 mmol, 4.4 equiv.) obtained by treating Diisopropyl amine (6.60 mmol, 4.4 equiv.) in THF (25 mL) at 0° C. with n-butyllithium (1.6 M solution in THF, 6.60 mmol, 4.4 equiv.) was added a solution of the corresponding ketoacid 1501 (synthesis reported previously) (3.0 mmol, 2.0 equiv.) in THF (25 mL) at −78° C. via canula. The solution was allowed to warm to −40° C. and stirred for 1 h.

Aldol reaction. A suspension of the corresponding resin 335 (1.50 mmol, 1.0 equiv.), ZnCl2 (1.0 M solution in Et2O, 3.0 mmol, 2.0 equiv. ) in THF (25 mL), was treated at −78° C. with the enolate solution described above. The suspension was allowed to warm to −40° C., stirred for 2 h, quenched with saturated NH4Cl2 (8 ML) and neutralised at 23° C. with ACOH (13.2 mmol, 8.8 equiv). The mixture was poured into a frit, the polymer was washed with THF (100 mL), Et2O (100 mL), CHCl2 (100 mL), H20 (100 mL), MEOH (100 mL), CH2cl2 (100 mL), 1% TFA v/v in methylene chloride (3×75 mL), methylene chloride (2×100 mL), Et2O (2×100 mL) and dried under vaccum to afford resins 336.

Synthesis of Resins 337. Esterifications of Resin 336 with alcohols 332 as Illustrated in FIG. 50

A mixture of the appropriate resin 337 (0.46 mmol, 1.0 equiv.), the corresponding alcohol 332 (general procedure same than used for the synthesis of the natural alcohol) (2.31 mmol, 5.0 equiv.), 4-DmAp (2.31 mmol, 5.0 equiv.) and DCC (2.31 mmol, 5.0 equiv.) in CH2Cl2 (10 mL) was shaken al 23° C. for 15 h. The polymer was filtered, washed with CH2cl, (2×50 mL), MEOH (2×50 mL), CH2Cl2 (2×50 mL), Et,O (2×50 mL) and dried under vaccum to afford the corresponding resins 338.

Synthesis of 339–342: Metathesis of resins 107 as Illustrated in FIG. 50

A suspension of the appropriate resin 338 (50.0 mg) in methylene chloride (40 ML) was treated with bis(tricyclohexylphosphine)benzylidine ruthenium di chloride (RuCl2(=CHPh)2(PCy3)2 (20 mg) and stirred at 23° C. for 48 h. The polymer was filtered and the filtrate was evaporated to give mixtures of compounds 338 which were separated by preparative thin layer chromatography to give compounds 339, 340, 341, and 342.

Synthesis of Compounds 343–346 as Illustrated in FIG. 50
Desilylation of Protected Compounds 108–111.

Standard desilation conditions exactly as described vida supra.

Synthesis of Alcohol 350 as Illustrated in FIG. 52

Allylmagnesium bromide (1.3 equiv) was added dropwise over 45 min to a solution of (Ipc)$_2$BOMe (1.3 equiv) in ether (0.2 M) at 0° C., and the resulting pale gray slurry allowed to warm to 25° C. over 1 h. The ether was removed under reduced pressure and pentane added to the residual solid. The slurry was stirred at 25° C. for 10 min and then the solids were allowed to settle over 30 min. The clear supernatant solution was then carefully transferred to a separate flask via cannula. This process was repeated four times, and the resulting solution was then added dropwise over 1 h to a solution of aldehyde 2 (1.0 equiv) in ether at −100° C. After 1 h at −100° C., methanol was added and the mixture allowed to warm over 40 min. Saturated aqueous NaHCO$_3$ and 50% aqueous H$_2$O$_2$ were then added and the mixture left to warm to 25° C. overnight. The layers were separated, the aqueous phase re-extracted with EtOAc and the combined organic phases washed with saturated aqueous NH$_4$Cl. Drying (Na$_2$SO$_4$) and concentration under reduced pressure gave a residue, which was purified by flash column chromatography (silica gel, 20% ether in hexanes) to give the desired alcohol 350 (91%).

Synthesis of Lactone 351 as Illustrated in FIG. 52

To a solution of alcohol 350 (2.0 equiv), 1,3-dicyclohexylcarbodiimide (DCC, 1.2 equiv) and 4-dimethylaminopyridine (4-DMAP, 1.2 equiv) in toluene (0.1 M) was added a mixture of C-6,7-diastereomeric keto acids 348 (1.0 equiv) at 25° C. After 12 h the reaction was complete, as indicated by TLC. The reaction mixture was then passed through a short plug of silica gel, eluted with toluene and concentrated under reduced pressure. The crude material was submitted to flash column chromatography (silica gel, 5% EtOAc in hexanes) to yield pure ester 351 (49%, plus 33% of its (6S, 7R)-diastereomer).

Synthesis of Macrolactones 352 and 353 as Illustrated in FIG. 52

To a solution of ester 351 (1.0 equiv) in CH$_2$Cl$_2$ (0.001 M) was added bis(tricyclohexylphosphine)benzylidine ruthenium dichloride (RuCl$_2$(=CHPh) (PCy$_3$)$_2$, 0.2 equiv) and the reaction mixture allowed to stir at 25° C. for 12 h. After completion of the reaction (established by TLC), the solvent was removed under reduced pressure and the crude products purified by flash chromatography (silica gel, 20% EtOAc in hexanes) to give cis-macrolactone 352 (42%) and trans-macrolactone 353 (23%).

Synthesis of cis-Diol 354 as Illustrated in FIG. 52

To a solution of cis-silyl ether 352 (1.0 equiv) in THF (8.2 mL) at 25° C. was added HFpyr (10 equiv) and the resulting solution stirred at the same temperature for 27 h. The mixture was then added carefully to saturated aqueous sodium bicarbonate and EtOAc, and the resulting two-phase mixture stirred at 25° C. for 2 h. The layers were then separated and the organic layer washed with saturated aqueous sodium bicarbonate and brine. Drying over magnesium sulfate and purification by flash chromatography (silica gel, 20 E 50% EtOAc in hexanes) afforded the desired diol 354 in 84% yield.

Synthesis of trans-Diol 355 as Illustrated in FIG. 52

A solution of trans-silyl ether 353 (1.0 equiv) in THF (5.2 mL) was treated with HFpyr. (10 equiv), according to the procedure described for the deprotection of cis-silyl ether 352, to give after flash column chromatography (silica gel, 20 to 50% EtOAc in hexanes) trans-diol 355 in 85% yield.

Synthesis of 2-(Hydroxymethyl)-4-(tri-n-butylstannyl)-thiazole 363 as Illustrated in FIG. 53a To a solution of 2,5-dibromothiazole (358; 1.0 equiv) in anhydrous ether (0.1 M) was added n-BuLi (1.1 equiv) at −78° C., and the resulting solution was stirred at the same temperature for 30 min, before DMF (1.2 equiv) and hexamethylphosphoramide (HMPA, 1.1 equiv) were added at the same time. After being stirred at −78° C. for 30 min., the reaction mixture was slowly warmed up to room temperature over a period of 2 h. Hexane (2.0 mL) was added and the resulting mixture passed through a short silica cake with 30% ethyl acetate in hexanes. The solvents were evaporated to give the crude aldehyde 359 (72% yield), which was used in the next step without further purification.

To the solution of the crude aldehyde 359 in methanol (0.1 M) was added sodium borohydride (2.0 equiv) at 25° C., and the resulting mixture was stirred at the same temperature for 30 min. EtOAc and hexanes were added, and the mixture passed through a short silica cake with ethyl acetate. The solvents were then evaporated and the crude product was purified by flash chromatography (20 To 50% ethyl acetate in hexanes) to give 2-hydroxymethyl-4-bromothiazole 360 in 88% yield.

To a solution alcohol 360 (1.0 equiv) in methylene chloride (0.1 M) at 25° C. was added imidazole (2.0 equiv), followed by tert-butyldimethylchlorosilane (1.5 equiv). After 30 min, the reaction was quenched with methanol, and the mixture was passed through silica with methylene chloride. Evaporation of solvents gave the silyl ether 361 in 96% yield.

To a solution of 361 (1.0 equiv) in ether (0.1 M) was added n-BuLi (1.2 equiv) at −78° C., and the resulting mixture was stirred at this temperature for 10 min. Tri-n-butyltin chloride (1.2 equiv) was then added, and the reaction mixture was stirred at −78° C. for a further 10 min and then warmed up to 25° C. over a period of 1 h. The reaction mixture was diluted with hexanes and passed through silica with 20% EtOAc in hexanes. The crude product was purified by flash chromatography (silica gel pre-treated with triethylamine, 5% Et,O in hexanes) to afford stannane 362 in 85% yield.

To a solution of silyl ether 362 (1.0 equiv) in THF (0.1 M) was added TBAF (1.0 M in THF, 1.2 equiv) at 25° C. and the reaction mixture was stirred for 20 min at this temperature. Hexanes were added, and the mixture was passed through silica with EtOAc. Evaporation of solvents gave alcohol 363 in 95% yield.

Synthesis of Compounds 364–367 as Illustrated in FIG. 53a.

Compounds 364–367 were exactly prepared according to Dondoni et al. *Synthesis*, 1986, 757–760.

Synthesis of 2-(ω-Acetoxy-pentyl)-4-(trimethylstannyl)-thiazole 371 as Illustrated in FIG. 53a.

To a solution of 2,4-dibromothiazole (358; 1.0 equiv) in i-Pr$_2$NH (0.5 M) was added 4-pentyn-1-ol (2.0 equiv), tetrakis(triphenylphosphine)palladium(0) (0.05 equiv) and CuI (0.1 equiv). The reaction mixture was then heated at 70° C. for 2 h and after cooling to 25° C. the solvents were removed under reduced pressure. Purification by flash column chromatography (silica gel, 10% – 75% EtOAc in hexanes) provided the desired alcohol 368 in 83% yield.

A solution of alcohol 368 (1.0 equiv) and PtO$_2$ (0.1 equiv) in EtOH (0.1 M) was stirred at 25° C. under an atmosphere of hydrogen for 4 h, until the disappearance of starting material was Indicated by 1H NMR. Subsequent filtration through a short plug of silica, washing with EtOAc, and removal of the solvents under reduced pressure afforded the desired alcohol 369 (100%).

A solution of alcohol 369 in pyridine-acetic anhydride (1:1; 0.1 M) was stirred at 25° C. for 2 h, after which TLC indicated completion of the reaction. The reagents were then removed under reduced pressure. Purification by flash column chromatography (silica gel, 10%æ40% ether in hexanes) gave the desired acetate 370 in 90% yield.

A solution of acetate 370 (1.0 equiv) in degassed toluene (0.1 M), was treated with hexamethyldilin (10 equiv) and tetrakis(triphenylphosphine)palladium(0) (0.1 equiv). The mixture was then heated to 100° C. for 3 h, after which TLC indicated disappearance of the aryl bromide. The reaction mixture was cooled to 25° C. and purified by flash column chromatography (silica gel, 50% ether in hexanes containing NEt$_3$) to afford the desired stannane 371 in 93% yield.

Synthesis of 2-Piperidinyl-4-(trimethylstannyl) thiazole 373 as Illustrated in FIG. 53a.

2,4-Dibromothiazole (358; 1.0 equiv) was dissolved in piperidine (0.5 M) and the reaction was warmed to 50° C. for 8 h, upon which completion of the reaction was indicated by TLC. The mixture was poured into water and extracted with ether (2x). Drying (MgSO$_4$) and evaporation of the solvents gave 2-piperidinyl-4-bromothiazole 372, which was isolated after flash column chromatography (silica gel, 5% EtOAc in hexanes) in 100% yield.

2-Piperidinyl-4-bromothiazole (372, 1.0 equiv) was taken up in degassed toluene (0.1 M), and hexamethylditin (10 equiv) and tetrakis(triphenylphosphine)palladium(0) (0.1 equiv) were added. The mixture was then heated to 80° C. for 3 h, after which TLC indicated disappearance of the aryl bromide. The reaction mixture was poured into saturated aqueous NaHCO$_3$ solution and extracted with ether, washed with water and with saturated aqueous NaCi solution (120 mL). The organic extract was dried (Na$_2$SO$_4$) and the solvents and the excess hexamethylditin were removed under reduced pressure. Flash column chromatography (silica gel, 5% NEt$_3$ in hexanes) provided 2-piperidinyl-4-(trimethylstannyl)thiazole 373 in 100% yield.

Synthesis of 2-Thiomethyl-4-(trimethylstannyl) thiazole 375 as Illustrated in FIG. 53a.

2,4-Dibromothiazole (358; 1.0 equiv) was dissolved in ethanol (0.1 M) and treated with sodium thiomethoxide (3.0 equiv). The reaction mixture was stirred at 25° C. for 3 h, upon which completion of the reaction was Indicated by $^1$H NMR. The mixture was poured into water and extracted with ether (2x). Drying (MgSO$_4$) and evaporation of the solvents gave 2-thiomethyl-4-bromothiazole 374, which was Isolated, after flash column chromatography (silica gel, 5% EtOAc in hexanes), in 92% yield.

2-Thiomethyl-4-bromothiazole (374) was taken up in degassed toluene (0.1 M), and was then treated hexamethylditin (10 equiv) and tetrakis(triphenylphosphine) palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt, in hexanes), 2-thiophenyl-4-(trimethylstannyl)thiazole (375; 100%).

Synthesis of Compounds 376–377 and 378–379 as Illustrated in FIG. 53a and 53b.

Compounds 376–377 are commercially available from Aldrich. Compounds 378–379 are exactly prepared according to Dondoni et al. *Synthesis*, 1986, 757; Reynaud et al. *Bull. Soc. Chim. Fr.* 1962, 1735.

Synthesis of 2-Thiophenyl-4-(trimethylstannyl) thiazole 381 as Illustrated in FIG. 53b.

2,4-Dibromothiazole (358; 1.0 equiv) was dissolved in ethanol (0.1 M) and treated with thiophenol (3.0 equiv) and solid sodium hydroxide (3.0 equiv). The reaction mixture was heated at 45° C. for 4 h, upon which completion of the reaction was Indicated by TLC. The mixture was poured into water and extracted with ether (2x). Drying (MgSO$_4$) and evaporation of the solvents gave 2-thiophenyl-4-bromothiazole 380, which was Isolated after flash column chromatography (silica gel, 5% EtOAc in hexanes) in 84% yield.

2-Thiophenyl-4-bromothiazole (380; 1.0 equiv) was taken up in degassed toluene (0.1 M), and was then treated hexamethylditin (10 equiv) and tetrakis(triphenylphosphine) palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt₃ in hexanes), 2-thiophenyl-4-(trimethylstannyl)thiazole (381; 100%).

Synthesis of 2-Ethyl-4-(trimethylstannyl)thiazole 384 as Illustrated in FIG. 53b.

A solution of 2,4-dibromothiazole (358; 1.0 equiv), tributyl(vinyl)tin (1.1 equiv) and tetrakis(triphenylphosphine)palladium(0) (0.1 equiv) in degassed toluene (0.1 M) were heated at 110° C. for 20 min, after which completion of the reaction was shown by TLC. The reaction mixture was poured into saturated aqueous NaHCO₃—NaCl solution and extracted with ether (2×). The organic extract was dried (Na₂SO₄), and the solvents were removed under reduced pressure to yield, after purification by preparative thin layer chromatography (silica gel, 5% EtOAc in hexanes), 2-vinyl-4-bromothiazole 382 in 96% yield.

Vinylthizaole 382 (1.0 equiv) was taken up in ethanol (0.1 M) and treated with Adam's catalyst (PTO₂, 0.05 equiv) and hydrogen (1 atm) for 4 h at 25° C., in accordance with the procedure describing the hydrogenation of compound 368, to yield, after purification by preparative thin layer chromatography (silica gel, 5% EtOAc in hexanes), 2-ethyl-4-bromothiazole 383 in 100% yield.

2-Ethyl-4-bromothiazole (383; 1.0 equiv) was taken up in degassed toluene (0.1 M), and was then treated hexamethylditin (10 equiv) and tetrakis(triphenylphosphine)palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt, in hexanes), 2-ethyl-4-(trimethylstannyl)thiazole (384) in 100% yield.

Synthesis of 2-Dimethylamino-4-tremthylstannylthiazole 386 as Illustrated in FIG. 53b.

2,4-Dibromothiazole (358; 1.0 equiv) was dissolved in DMF (0.1 M) and heated at 150–160 ° C. for 8 h, upon which completion of the reaction was indicated by TLC. The mixture was poured into water and extracted with ether (2×). Drying (MgSO₄) and evaporation of the solvents gave 2-dimethylamino-4-bromothiazole 385, which was isolated after flash column chromatography (silica gel, 5% EtOAc in hexanes) in 89% yield.

2-Dimethylamino-4-bromothiazole (385; 1.0 equiv.) was taken up in degassed toluene (0.1 M), and was then treated hexamethylditin (10 equiv) and tetrakis(triphenylphosphine)palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt₃ in hexanes), 2-dimethylamino-4-(trimethylstannyl)thiazole (386; 100%).

Synthesis of 2-Acetoxymethyl-4-(trimethylstannyl)thiazole 388 as Illustrated in FIG. 53b.

Alcohol 360 (1.0 equiv) was taken up in pyridine-acetic anhydride (1:1; 0.2 M) at 25° C. and stirred at this temperature for 3 h, in accordance with the procedure for the formation of acetate 370, to give, after purification by flash column chromatography (silica gel, 5% EtOAc in hexanes), 2-acetoxymethyl-4-bromothiazole (387) in 95% yield.

2-Acetoxymethyl-4-bromothiazole (387) was taken up in degassed toluene (0.1 M), and was then treated hexamethylditin (10 equiv) and tetrakis(triphenylphosphine)palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt, in hexanes), 2-dacetoxymethyl-4-(trimethylstannyl)thiazole (388; 100%).

Synthesis of 2-Fluoromethyl-4-(trimethylstannyl)thiazole 390 as Illustrated in FIG. 53b.

A solution of alcohol 360 in CH₂Cl₂ (0.1 M) was added via syringe to a cold (–78° C.) solution of diethylaminosulfur trifluoride (DAST, 1.1 equiv) in CH₂Cl₂(0.1 M). The reaction was allowed to warm slowly to 25° C., and was then quenched by addition of saturated aqueous NaHCO₃ solution. The organic layer was separated and washed with saturated aqueous NaCl solution. After drying (MgSO₄) and evaporation of the solvent under reduced pressure, purification by flash column chromatography (silica gel, 5% EtOAc in hexanes) resulted in 2-fluoromethyl-4-bromothiazole (389) in 88% yield.

2-Fluoromethyl-4-bromothiazole (389; 1.0 equiv) was taken up in degassed toluene (0.1 M), and was then treated hexamethylditin (10 equiv) and tetrakis(triphenylphosphine)palladium(0) (0.1 equiv) at 80° C. for 3 h according to the procedure described for the synthesis of 2-piperidinyl-4-(trimethylstannyl)thiazole (373), to yield, after flash column chromatography (silica gel, 5% NEt₃ in hexanes), 2-fluoromethyl-4-(trimethylstannyl)thiazole (390) in 100% yield.

Synthesis of 1-Methyl-2-(trimethylstannyl)imidazole 391 as Illustrated in FIG. 53b.

To a solution of 1-methylimidazole (1.0 equiv) in ether (0.1 M) was added n-BuLi (1.2 equiv) at –78° C., and the resulting mixture was stirred at this temperature for 10 min. Trimethyltin chloride (1.2 equiv) was then added, and the reaction mixture was stirred at –78° C. for 10 more min and then warmed up to 25° C. over a period of 1 h. The reaction mixture was diluted with hexanes and passed through silica with 20% EtOAc in hexanes. The crude product was purified by flash chromatography (silica gel pre-treated with triethylamine, 5% Et₂O in hexanes) to afford stannane 391 in 85% yield.

General Procedure for Stille Coupling with Epothilone Analogs as Illustrated in FIG. 52 and Compounds Found in FIGS. 54–55

General Procedure A

A solution of vinyl iodide (1.0 equiv, cis- or trans-compound), aryl stannane (2.0 equiv) and tetrakis(triphenylphosphine)palladium(0) (0.1 equiv) in degassed toluene (0.1 M) was heated at 100° C. for 30–40 min. The reaction mixture was poured into saturated aqueous NaHCO₃—NaCl solution and extracted with EtOAc. The organic extract was dried (Na₂SO₄), and the solvents were removed under reduced pressure to yield, after purification by preparative thin layer chromatography (250 μm silica gel plate, 75% ether in hexanes), the corresponding epothilone analogs (see Table for yields).

General Procedure B

A solution of vinyl iodide (1.0 equiv, cis- or trans-compound), aryl stannane (2.0 equiv) and palladium(II) bis(benzonitrile) dichloride (0.1 equiv) in degassed DMF (0.1 M) was stirred at 25° C. for 10 h. The reaction mixture was poured into saturated aqueous NaHCO₃—NaCl solution and extracted with EtOAc (2×). The organic extract was dried (Na₂SO₄), and the solvents were removed under reduced pressure to yield after purification by preparative thin layer chromatography (250 μm silica gel plate, 75% ether in hexanes) the corresponding epothilone analogs (see Table for yields).

Synthesis of Epoxide 356B from 356A as Illustrated in FIG. 56

Conditions exactly as that of the conversion from 110 to 111 as shown in FIG. 14 (vida supra).

Synthesis of Alcohol 392 as Illustrated in FIG. 58

Trityl deprotection Method A

To a stirred solution of trityl ether 264(1 equiv.) in $CH_2Cl_2$/MeOH (1:1, 0.1 M) at 0° C. was added camphor sulfonic acid (1 equiv.) and the mixture allowed to warm to room temperature. After stirring for 2 hours, $Et_3N$ (1.5 equiv.) was added and solvent removed in vacuo. Flash chromatography afforded the product 392 as a colorless oil (70%).

Method B

To a stirred solution of trityl ether 264 (1 equiv.) in MeOH/$CH_2Cl_2$ (10:1, 0.1M) was added PPTS (1 equiv.). The reaction was stirred for 72 hours before solvent was removed in vacuo. Filtration through a plug of silica gel gave the product 392 as a colorless oil (60%).

Method C

To the trityl ether 264 (1 equiv.) at 0° C. was added a mixture of ether:formic acid (1:1, 0.2M). After stirring for 1 hour, the reaction was quenched with saturated aqueous sodium bicarbonate. The layers were separated and the aqueous phase extracted with ether. The combined organic extracts were dried ($MgSO_4$), filtered and concentrated in vacuo. Flash chromatography gave the product 392 as a colorless oil (65%).

Synthesis of Compound 393 as Illustrated in FIG. 58

Fluorination of Allylic Alcohol 392.

To a stirred solution of allylic alcohol 393 (1 equiv.) in $CH_2Cl_2$ at −78° C. was added diethylamino sulfurtrifluoride (DAST, 1 equiv.). The reaction was then allowed to warm slowly to room temperature before being quenched with saturated aqueous sodium bicarbonate solution. The layers were separated and the aqueous phase extracted with $CH_2Cl_2$. The combined organic extracts were dried ($MgSO_4$), filtered and concentrated in vacuo. Flash chromatography gave the fluoride 393 as a colorless oil (30%).

Synthesis of Compound 394 as Illustrated in FIG. 58

Compound 394 was prepared using conditions exactly as described for the conversion of 121 to 71 (vida supra) in FIG. 18.

Synthesis of Compound 395 as Illustrated in FIG. 58

Compound 395 was prepared using conditions exactly as described for the conversion of 71 to 2 (vida supra) in FIG. 16.

Synthesis of Compound 396 as Illustrated in FIG. 58

Chlorination of allylic alcohol 392.

To a solution of allylic alcohol 392 in $CCl_4$ (0.1M) was added $PPh_3$ (2.5 equiv.). The reaction was then heated to reflux for 18 hours. After cooling to room temperature, the solvent was removed in vacuo and the resulting residue filtered through a plug of silica gel to provide the chloride 396 as a colorless oil (90%).

Synthesis of Compound 397 as Illustrated in FIG. 58

Compound 397 was prepared using conditions exactly as described for the conversion of 121 to 71 (vida supra) in FIG. 18.

Synthesis of Compound 398 as Illustrated in FIG. 58

Compound 398 was prepared using conditions exactly as described for the conversion of 71 to 2 (vida supra) in FIG. 16.

Synthesis of Compound 399 as Illustrated in FIG. 59

O-alkylation of Allylic Alcohol 392.

To a suspension of sodium hydride (1.2 equiv.) in THF (0.1M) was added a solution of the allylic alcohol 392 in THF. After stirring for 30 minutes, a solution of the alkyl halide in THF (1.0M; alkyl halide can be selected from the group consisting of iodmethane, iodoethane, 2-iodopropane, 1-iodobutane, 1-iodopropane, benzyl iodide and allyl iodide; commercially available from Aldrich/Sigma) was added and the resulting mixture was stirred until TLC indicated completion of the reaction. Saturated aqueous ammonium chloride solution was added and the layers were separated. The aqueous phase was extracted with ether and the combined organic extracts were dried ($MgSO_4$), filtered and concentrated in vacuo. Flash chromatography gave the ether product 399.

Synthesis of Triol 400 as Illustrated in FIG. 59

Compound 399 (1 equiv.) was treated with a 30% solution of Hfpyridine in THF. After stirring for 24 hours, the reaction was quenched by pouring into saturated sodium bicarbonate solution. The layers were separated and the aqueous phase extracted with ether. The combined organic extracts were dried ($MgSO_4$), filtered and concentrated in vacuo. Flash chromatography gave 400 (78%).

Synthesis of Compound 401 as Illustrated in FIG. 59

Compound 398 was prepared using conditions exactly as described for the conversion of 71 to 2 (vida supra) in FIG. 16.

Synthesis of Epoxide 403 as Illustrated in FIG. 59

To a solution of 9.55 g (53.6 mmol) of alcohol 402 and 0.25 equiv of D-(+)diisopropyl tartrate in 0.1 Molar of dichloromethane was added. The solution was cooled to −30° C. and 0.2 equiv of freshly distilled titanium tetraisopropoxide was added. The clear solution was stirred at −20° C. for 30 min, and an aliquot was quenched for capillary GLC analysis. After an additional 5 min of stirring at −20° C., 2.0 equiv of a 1.5 Molar solution of ter-butyl hydroperoxide in 2,2,4-timethylpentane was added over 10 min. The resulting mixture was stirred at 20° C. for 3h after which the reaction was quenched by pouring into saturated sodium bicarbonate solution. The layers were separated and the aqueous phase extracted with ether. The combined organic extracts were dried ($MgSO_4$), filtered and concentrated in vacuo. Flash chromatography gave 403.

Synthesis of Esters 404

Method 1.

To a stirred solution of 403 (1 equiv.) in THF (0.1M) was added triethylamine (1.1 equiv.) and the required anhydride (1.1 equiv. ((RCO)$_2$O) selected from the group consisting of acetic anhydride, chloroacetic anhydride, propionic anhydride, trifluoroacetic anhydride, isobutyric anhydride; commercially available from Aldrich/Sigma). After stirring for 2 hours, the reaction was quenched with saturated aqueous sodium bicarbonate solution. The layers were separated and the aqueous phase extracted with ether. The combined orgainc extracts were dried (MgSO$_4$), filtered and concentrated in vacuo. Flash chromatography gave 403.

Synthesis of Esters 404. Method 2 as Illustrated in FIG. 60

To a stirred solution of 403 (1 equiv) in CH$_2$Cl$_2$ (0.1M) was added triethylamine (1.1 equiv.) and the required acid chloride (1.1 equiv. selected from the group consisting of pivaloyl chloride, cyclopropanecarbonyl chloride, cyclohexanecarbonyl chloride, acryloyl chloride, benzoyl chloride, 2-furoyl chloride, N-benzoyl-(2R,3S)-3-phenylisoserine, cinnamoyl chloride, phenylacetyl chloride, 2-thiophenesulfonyl chloride; commercially available from Aldrich/Sigma). After stirring for 2 hours, the reaction was quenched with saturated aqueous sodium bicarbonate solution. The layers were separated and the aqueous phase extracted with ether. The combined orgainc extracts were dried (MgSO$_4$), filtered and concentrated in vacuo. Flash chromatography gave 404.

Synthesis of Thioether 405 as Illustrated in FIG. 60

To a stirred solution of allylic alcohol 392 (1 equiv.) in THF (0.1M) was added the required disulfide (2 equiv.) followed by tribytul phosphite (2 equiv.). After stirring for 4 hours the reaction was quenched with brine and the layers were separated. The aqueous phase was extracted with ether and the combined organic extracts were dried (MgSO$_4$), filtered and concentrated in vacuo. Flash chromatography gave the thioether 405.

Synthesis of Compound 406 as Illustrated in FIG. 60

Compound 406 was prepared using conditions exactly as described for the conversion of 121 to 71 (vida supra) in FIG. 18.

Synthesis of Compound 407 as Illustrated in FIG. 60

Compound 407 was prepared using conditions exactly as described for the conversion of 71 to 2 (vida supra) in FIG. 16.

Synthesis of Compound 408. Tosylation of Allylic Alcohol 392 as Illustrated in FIG. 61

To a stirred solution of allylic alcohol 392 (1 equiv) in CH$_2$Cl$_2$ (0.1M) at 0° C. was added Et$_3$N (4.0 equiv) followed by tosyl chloride (2.0 equiv.). The reaction mixture was warmed to room temperature and stirred until complete as determined by TLC. Saturated ammonium chloride solution was added and the layers were separated. The aqueous phase was extracted with ether and the combined organic extracts were dried, (MgSO$_4$), filtered and concentrated in vacuo. Flash chromatography gave the tosylate 408.

Synthesis of Azide 409 as Illustrated in FIG. 61

To a stirred solution of tosylate (1 equiv) 408 in DMF was added sodium azide. The reaction was stirred for xx hours. Saturated ammonium chloride solution was added and the layers were separated. The aqueous phase was extracted with ether and the combined organic extracts were dried (MgSO$_4$), filtered and evaporated in vacuo. Flash chromatography then provided the azide 409.

Synthesis of Diol 410 as Illustrated in FIG. 61

Azide (1 equiv.) 409 was treated with a 30% solution of Hfpyridine in THF. After stirring for 24 hours, the reaction was quenched by pouring into saturated sodium bicarbonate solution. The layers were separated and the aqueous phase extracted with ether. The combined organic extracts were dried (MgSO$_4$), filtered and concentrated in vacuo. Flash chromatography gave 410.

Synthesis of Amine 411 as Illustrated in FIG. 61

To a stirred solution of azide 411 (1 equiv.) in a mixed solvent system of THF:H$_2$O (1:1, 0.1M) was PPh$_3$. The reaction was stirred for 4 hours before being poured into saturated brine. The layers were separated and the aqueous phase extracted with ether. The combined orgainc extracts were dried (MgSO$_4$), filtered and concentrated in vacuo. Flash chromatography gave 411.

Synthesis of Amides 412 as Illustrated in FIG. 61

Method 1.

To a stirred solution of amine 411 (1 equiv.) in THF (0.1M) was added triethylamine (1.2 equiv.) and the required anhydride (1.1 equiv. ((RCO)$_2$O) selected from the group consisting of acetic anhydride, chloroacetic anhydride, propionic anhydride, trifluoroacetic anhydride, isobutyric anhydride; commercially available from Aldrich/Sigma). After stirring for 4 hours, the reaction was quenched with saturated aqueous sodium bicarbonate solution. The layers were separated and the aqueous phase extracted with ether. The combined orgainc extracts were dried (MgSO$_4$), filtered and concentrated in vacuo. Flash chromatography gave 412.

Amides 412

Method 2.

To a stirred solution of amine 411 (1 equiv) in CH$_2$Cl$_2$ (0.1M) was added triethylamine (1.2 equiv.) and the required acid chloride (1.1 equiv.) and the required acid chloride (1.1 equiv. selected from the group consisting of pivaloyl chloride, cyclopropanecarbonyl chloride, cyclohexanecarbonyl chloride, acryloyl chloride, benzoyl chloride, 2-furoyl chloride, N-benzoyl-(2R,3S)-3-phenylisoserine, cinnamoyl chloride, phenylacetyl chloride, 2-thiophenesulfonyl chloride; commercially available from Aldrich/Sigma). After stirring for 4 hours, the reaction was quenched with saturated aqueous sodium bicarbonate solution. The layers were separated and the aqueous phase extracted with ether. The combined orgainc extracts were dried (MgSO$_4$), filtered and concentrated in vacuo. Flash chromatography gave 412.

Synthesis of Compound 413 as Illustrated in FIG. 61

Compound 413 was prepared using conditions exactly as described for the conversion of 71 to 2 (vida supra) in FIG. 16.

Synthesis of Aldehyde 414. Oxidation of Alcohol 403 as Illustrated in FIG. 62

To a solution of alcohol 403 (1.0 equiv.) in CH$_2$Cl$_2$ (0.1M) was added at −78° C. TEMPO (2,2,6,6-tetramethyl-1-piperidinyloxy, free radical.) (0.008 M solution in CH$_2$Cl$_2$, 1.5 equiv), KBr (0.2 M aqueous solution, 0.1 equiv), and NaOCl (0.035 M solution in 5% aqueous NaHCO$_3$, 1.0 equiv). After stirring for 0.5 h, the organic layer was dried (MgSO$_4$), filtered and concentrated under reduced pressure. Purification by preparative chromatography provided aldehyde 414 (75%).

Synthesis of Carboxylic Acid 415. Oxidation of Aldehyde 414 as Illustrated in FIG. 62

Aldehyde 414 (1 equiv.), $^t$BuOH (0.1M), isobutylene (3.0 equiv.), H$_2$O (0.02M), NaClO$_2$ (3.0 equiv.) and NaH$_2$PO$_4$ (3 equiv.) were combined and stirred at room temperature for 1 h. The reaction mixture was concentrated under reduced pressure and the residue was subjected to flash column chromatography to afford carboxylic acid 415.

Synthesis of Ester 416. Coupling of Acid 415 with Different Alcohols and Amines as Illustrated in FIG. 62

A solution of acid 415 (1.0 equiv), 4-(dimethylamino) pyridine (4-DMAP, 0.1 equiv) and alcohol or amine selected from the group consisting of methanol, t-butanol, i-propanol, phenol, benzyl alcohol, furfurylamine N-benzoyl-(2R,3S)-3-phenylisoserine, dimethyl amine, diethyl amine, benzyl amine (1.0 equiv) in CH$_2$Cl$_2$ (0.3 M) was cooled to 0° C. and then treated with 1-ethyl-(3-dimethylaminopropyl)-3-carbodiimide hydrochloride (EDC, 1.2 equiv). The reaction mixture was stirred at 0° C. for 2 h and then at 25° C. for 5 h. The solution was concentrated to dryness in vacuo, and the residue was taken up in EtOAc (10 mL) and water (10 mL). The organic layer was separated, washed with saturated NH$_4$Cl solution (10 mL) and water (10 mL) and dried (MgSO$_4$). Evaporation of the solvents followed by flash column chromatography resulted in pure ester 416.

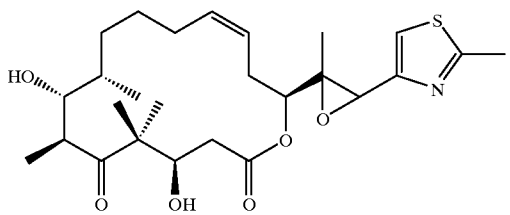

What is claimed:

1. An epothilone analog represented by the following structure: